US010398782B2

(12) United States Patent
Gao et al.

(10) Patent No.: US 10,398,782 B2
(45) Date of Patent: Sep. 3, 2019

(54) MIC-1 COMPOUNDS AND USES THEREOF

(71) Applicant: Novo Nordisk A/S, Bagsvaerd (DK)

(72) Inventors: Xiang Gao, Beijing (CN); Xujia Zhang, Beijing (CN); Hongtao Guan, Shanghai (CN); Henning Thoegersen, Farum (DK); Kristian Sass-Oerum, Copenhagen V (DK); Lars Fogh Iversen, Holte (DK); Per Noergaard, Humlebaek (DK); Sebastian Beck Joergensen, Virum (DK); Kristian Tage Hansen, Slangerup (DK); Yi Wang, Beijing (CN); Kilian Waldemar Conde Frieboes, Maaloev (DK); Birgit Wieczorek, Copenhagen N (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/986,961

(22) Filed: May 23, 2018

(65) Prior Publication Data
US 2018/0339057 A1 Nov. 29, 2018

(30) Foreign Application Priority Data

May 23, 2017 (WO) ............... PCT/CN2017/085576
Nov. 28, 2017 (WO) ............... PCT/CN2017/113335

(51) Int. Cl.
*A61P 3/00* (2006.01)
*A61K 38/00* (2006.01)
*A61K 38/19* (2006.01)
*A61K 47/64* (2017.01)
*C07K 14/50* (2006.01)
*C07K 14/52* (2006.01)
*C07K 14/475* (2006.01)
*G01N 33/68* (2006.01)

(52) U.S. Cl.
CPC ............. *A61K 47/64* (2017.08); *A61K 38/19* (2013.01); *A61P 3/00* (2018.01); *C07K 14/475* (2013.01); *C07K 14/50* (2013.01); *C07K 14/52* (2013.01); *G01N 33/68* (2013.01); *A61K 38/00* (2013.01)

(58) Field of Classification Search
None
See application file for complete search history.

(56) References Cited

U.S. PATENT DOCUMENTS

| 7,083,650 | B2 | 8/2006 | Moscowitz |
| 9,161,966 | B2 | 10/2015 | Matern et al. |
| 9,272,019 | B2 | 3/2016 | Shaw et al. |
| 2004/0063635 | A1 | 4/2004 | Yu et al. |
| 2009/0004181 | A1 | 1/2009 | Breit |
| 2009/0221477 | A1 | 9/2009 | Artymiuk et al. |
| 2010/0239554 | A1* | 9/2010 | Schellenberger .... C07K 14/001 424/94.3 |
| 2011/0172146 | A1 | 7/2011 | Schellenberger et al. |
| 2016/0030585 | A1 | 2/2016 | Barnes et al. |
| 2018/0339057 | A1 | 11/2018 | Gao et al. |

FOREIGN PATENT DOCUMENTS

| JP | 2008506635 A | 3/2008 | |
| JP | 2008507292 A | 3/2008 | |
| WO | 0179271 A1 | 10/2001 | |
| WO | 0179443 A2 | 10/2001 | |
| WO | 2005099746 A1 | 10/2005 | |
| WO | 2009/023270 A2 | 2/2009 | |
| WO | WO-2010084169 A2 * | 7/2010 | ............. C07K 14/50 |
| WO | 12138919 A2 | 10/2012 | |
| WO | 2013113008 A1 | 8/2013 | |
| WO | 2013148117 A1 | 10/2013 | |
| WO | 2014120619 A2 | 8/2014 | |
| WO | 2015/017710 A1 | 2/2015 | |
| WO | 2015027082 A1 | 2/2015 | |
| WO | 2015197446 A1 | 12/2015 | |
| WO | 2015200078 A1 | 12/2015 | |
| WO | 2016102562 A1 | 6/2016 | |
| WO | 2016149501 A2 | 9/2016 | |
| WO | 2017055612 A1 | 4/2017 | |
| WO | 2017055613 A2 | 4/2017 | |
| WO | 2017055614 A1 | 4/2017 | |
| WO | 2017109706 A1 | 6/2017 | |
| WO | 2017202936 A1 | 11/2017 | |

OTHER PUBLICATIONS

Bootcov et al., "MIC-1, a Novel Macrophage Inhibitory Cytokine, is a Divergent Member of the TGF-? Superfamily," Proc. Natl. Acad. Sci. USA, Oct. 1997, vol. 94, pp. 11514-11519.
Johnen et al, "Tumor-Induced Anorexia and Weight Loss are Mediated by the TGF-? Superfamily Cytokine MIC-1," Nature Medicine, Nov. 2007, vol. 13, No. 11, pp. 1333-1340.
Macia et al, "Macrophage Inhibitory Cytokine 1 (MIC-1/GDF15) Decreases Food Intake, Body Weight and Improves Glucose Tolerance in Mice on Normal & Obesogenic Data," PLoS One, Apr. 2012, vol. 7, No. 4, e34868.
Yun Ho Kim et al., "Comparing the Effect on Protein Stability of Methionine Oxidation Versus Mutagenesis: Steps Toward Engineering Oxidative Resistance in Proteins and the Possibility of Oxidation During Processing or Storage," Protein Engineering, 2001, vol. 14, pp. 343-347.

(Continued)

*Primary Examiner* — Christina Bradley
(74) *Attorney, Agent, or Firm* — Leon Y. Lum

(57) ABSTRACT

The invention relates to MIC-1 compounds. More specifically it relates to compounds comprising a MIC-1 polypeptide with an N-terminal amino acid extension and a protractor wherein the amino acid extension comprises 3 to 36 amino acid residues and where the MIC-1 polypeptide and the N-terminal amino acid extension together have a calculated pI lower than 6.5. The compounds of the invention have MIC-1 activity. The invention also relates to pharmaceutical compositions comprising such compounds and pharmaceutically acceptable excipients, as well as the medical use of the compounds.

28 Claims, 6 Drawing Sheets
Specification includes a Sequence Listing.

(56) References Cited

OTHER PUBLICATIONS

Arai R. et al., Design of the linkers which effectively separate domains of a bifunctional fusion protein, Protein Engineering, 2001, vol. 14, No. 8, pp. 529-532.

Bauskin A. R. et al., The propeptide of macrophage inhibitory cytokine (MIC-1), a TGF-beta superfamily member, acts as a quality control determinant for correctly folded MIC-1, The EMBO Journal, 2000, vol. 19, No. 10, pp. 2212-2220.

Bootcov M. R. et al., MIC-1, a novel macrophage inhibitory cytokine, is a divergent member of the TGF-b superfamily, Proceedings of the National Academy of Sciences, 1997, vol. 94, pp. 11514-11519.

Chen X. et al., Fusion protein linkers: property, design and functionality, Advanced Drug Delivery Reviews, 2012, vol. 65, No. 10, pp. 1357-1369.

Lu Z. et al., Change of body weight and macrophage inhibitory cytokine-1 during chemotherapy in advanced gastric cancer: what is their clinical significance?, Public Library of Science One, 2014, vol. 9, No. 2, p. e88553.

Robinson et al "Structure-dependent nonenzymatic deamidation of glutaminyl and asparaginyl pentapeptides" J. Peptide Res 2004 vol. 63 No. 5 pp. 426-436.

Bootcov et al., "MIC-1, a Novel Macrophage Inhibitory Cytokine, is a Divergent Member of the TGF-beta Superfamily," Proc Natl Acad Sci USA, 1997, vol. 94, pp. 11514-11519.

Johnen et al., "Tumor-Induced Anorexia and Weight Loss are Mediated by the TGF-beta Superfamily Cytokine MIC-1," Nat Med, 2007, vol. 13, pp. 1333-1340.

Macia et al., "Macrophage Inhibitory Cytokine 1 (MIC-1/GDF15) Decreases Food Intake, Body Weight and Improves Glucose Tolerance in Mice on Normal & Obesogenic Diets (Anti-Obesity Effects of MIC-1 in Mice)," PLoS ONE, 2012, vol. 7, No. 4, p. e34868.

William R Strohl, "Fusion Proteins for Half-Life Extension of Biologics as a Strategy to Make Biobetters," Biodrugs, 2015, vol. 29, No. 4, pp. 215-239.

Macia et al., "Macrophage Inhibitory Cytokine 1 (MIC-1/GDF15) Decreases Food Intake, Body Weight and Improves Glucose Tolerance in Mice on Normal & Obesogenic Diets," PLOS ONE, Apr. 13, 2012, vol. 7, e34868, pp. 1-8.

Marqusee et al., "Unusually stable helix formation in short alanine-based peptides," Proceedings of the National Academy of Sciences of the United States of America, 1989, vol. 86, pp. 5286-5290.

Tsai et al., "TGF-b Superfamily Cytokine MIC-1/GDF15 Is a Physiological Appetite and Body Weight Regulator," PLOS ONE, Feb. 28, 2013, vol. 8, e55174, pp. 1-10.

Yeh et al., "Design of yeast-secreted albumin derviatives for human therapy: Biological and avtiviral properties of a serum albumin-CD4 genetic conjugate," Proceedings of the National Academy of Sciences of the United States of America, Mar. 1992, vol. 89, pp. 1904-1908.

* cited by examiner

MIC-1 COMPOUNDS AND USES THEREOF

CROSS-REFERENCE TO RELATED APPLICATIONS

This application claims priority to International Applications PCT/CN2017/085576, filed May 23, 2017 and PCT/CN2017/113335 filed Nov. 28, 2017; the contents of all above-named applications are incorporated herein by reference.

TECHNICAL FIELD OF THE INVENTION

The present invention relates to MIC-1 compounds and their pharmaceutical use.

INCORPORATION-BY-REFERENCE OF THE SEQUENCE LISTING

The Sequence Listing, entitled "170039US01_SL_ST25", is 201 kilobytes, was created on May 18, 2018 and is incorporated herein by reference.

BACKGROUND OF THE INVENTION

Macrophage Inhibitory Cytokine-1 (MIC-1) was first described in 1997 (Bootcov et al, Proc. Natl. Acad. Sci. October 1997) based on experiments showing increased expression in activated macrophages. MIC-1 has subsequently been identified by others and given several additional names such as placental transforming growth factor beta (PTGF-β), placental bone morphogenetic protein, growth differentiation factor-15 (GDF15), prostate derived factor (PDF), non-steroidal anti-inflammatory drug-activated gene (NAG-1) and PL74. MIC-1 is a distant member of the TGF-beta super family, a family of peptide hormones involved in cell growth and differentiation. MIC-1 circulates as a cysteine-rich homodimer with a molecular mass of 24.5 kDa. Human wild-type MIC-1 has a short half-life, meaning that treatment with wt-MIC-1 requires daily administration to maintain efficacy.

Accumulating evidence support the therapeutic utility of MIC-1 in metabolic disorders such as obesity and diabetes. Data from patients with advanced cancer showed that weight loss correlated with circulating levels of MIC-1 (Johnen et al, Nat Med., November, 2007). Transgenic mice overexpressing MIC-1 gain less weight and body fat both on a normal low fat diet and on a high fat diet (Macia et al, PLoS One, April, 2012). Also, transgenic mice overexpressing MIC-1 fed both on a low and high fat diet, respectively, had improved glucose tolerance compared with wild type animals on a comparable diet.

WO 2005099746 concerns a method of modulating appetite and/or body weight by administering a MIC-1 modulating agent.

SUMMARY OF INVENTION

The present invention relates to MIC-1 compounds comprising a MIC-1 polypeptide with an N-terminal amino acid extension and a protractor attached to the amino acid extension. In one aspect, the MIC-1 compounds of the invention comprise a MIC-1 polypeptide with an N-terminal amino acid extension and a protractor attached to the amino acid extension, wherein the amino acid extension comprises 3 to 200 amino acid residues, and the MIC-1 polypeptide with the amino acid extension has a calculated pI lower than 6.5.

In some embodiments, the MIC-1 compounds of the invention have an N-terminal amino acid extension with one Cysteine residue, wherein the protractor is attached to the Cysteine residue. In these embodiments the protractor comprises, or consists of at least one of each of Chem. 1, Chem. 2, Chem. 3 and Chem. 4;

wherein Chem. 1 is selected from the group consisting of:

| | |
|---|---|
| HOOC—$(CH_2)_x$—CO—*, | Chem. 1A: |
| HO—$S(=O)_2$—$(CH_2)_x$—CO—*, | Chem. 1B: |
| HOOC-benzene-O—$(CH_2)_y$—CO—*, and | Chem. 1C: |
| (1H-tetrazol-5-yl)-$(CH_2)_x$—CO—*, | Chem. 1D: | wherein x is an integer in the range of 12-20,
wherein y is an integer in the range of 5-15;
wherein Chem. 2 is selected from the group consisting of:

| | |
|---|---|
| *—(NH—CH(COOH)—$(CH_2)m$-CO$)_k$*, | Chem. 2A: |
| *—(NH—$S(=O)_2$—$(CH_2)m$-CO$)_k$*, and | Chem. 2B: |
| *—(NH—(CH2)$m$-cyclohexane-CO$)_k$—*, | Chem. 2C: | wherein m of Chem. 2 is an integer in the range of 1-5, and
k of Chem. 2 is an integer in the range of 0-4;
wherein Chem. 3 is

*(NH—$(CH_2)_2$—[O—$(CH_2)_2]_k$—O—$[CH_2]_n$—CO—*$)_l$, wherein k of Chem. 3 is an integer in the range of 1-10,
n is an integer in the range of 1-5, and
l is an integer in the range of 0-5;
wherein Chem. 4 is selected from

| | |
|---|---|
| *—NH—$(CH_2)_m$—NH—CO—$CH_2$—*, | Chem. 4A: |
| *—NH—CH(COOH)—$(CH_2)_m$—NH—CO—$CH_2$—*, | Chem. 4B: |
| *—NH—(CH2)$m$-CH(COOH)—NH—CO—CH2-*, and | Chem. 4C: |

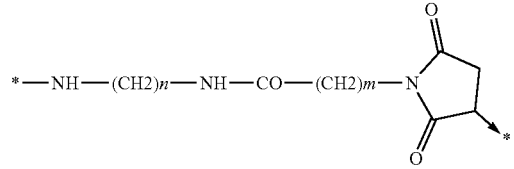

Chem. 4D:
wherein m of Chem. 4 is an integer in the range of 1-5,
and n is an integer in the range 2-6; and
wherein Chem. 1, Chem. 2, Chem. 3, and Chem. 4 are interconnected via amide bonds, connecting the *—NH end of a Chem. to the CO—* end of another Chem., and wherein Chem. 4 is connected to the sulphur atom of the Cysteine residue of the amino acid extension.

An asterisk (*) in a chemical formula designates a point of attachment.

In some embodiments, the MIC-1 compounds of the invention comprise an N-terminal extension that has surplus of acidic amino acid residues (Aspartic acid and/or Glutamic acid) of at least 3, 4, 5 or 6 compared to the number of basic amino acid residues (Lysine, Arginine and/or Histidine).

In some embodiments of the invention the MIC-1 compounds comprise N-terminal extensions composed of amino acid residues selected among the group consisting of A, C, E, G, P, S, T, Q, N and D, wherein the amino acid extension comprises at least three E and/or D amino acid residues.

In some embodiments the MIC-1 compounds of the invention comprise an MIC-1 polypeptide that display at least 85%, 90%, 95% or 98% sequence identity to MIC-1 of SEQ ID NO:1.

In some embodiments the MIC-1 compounds of the invention comprise an MIC-1 polypeptide that comprises a deletion of the first three residues (MIC-1-A1-3) or a deletion of Asparagine 3 (des-N3) compared to MIC-1 of SEQ ID NO: 1.

In a particular embodiment of the invention the MIC-1 compound comprises a MIC-1 polypeptide and an N-terminal amino acid extension with an amino acid sequence according to SEQ ID NO: 87, 90, 92, 93, 94, 97, 98, 99, 100, 101, 102, 108, 109, 111, 112, 113, 114, 115, 116, 117, 164, 288, 289, 290, 291 or 292.

In one aspect, the MIC-1 compounds of the invention have retained MIC-1 receptor potency and in vivo efficacy on lowering food intake and body weight. These MIC-1 compounds can therefore be used for treatment of metabolic disorders such as obesity, diabetes, cardiovascular diseases like dyslipidaemia and arteriosclerosis and other disorders such as steatohepatitis and diabetic nephropathy.

In one aspect, the invention provides a pharmaceutical composition comprising the MIC-1 compound of the invention or a pharmaceutically acceptable salt, amide or ester thereof, and one or more pharmaceutically acceptable excipients.

In one aspect, the invention provides a MIC-1 compound for use in the prevention and/or treatment of a metabolic disorder, wherein the metabolic disorder is obesity, type 2 diabetes, dyslipidemia, or diabetic nephropathy.

In one aspect, the invention provides a MIC-1 compound for use in the prevention and/or treatment of dyslipidaemia, arteriosclerosis, non-alcoholic steatohepatitis, or diabetic nephropathy.

In one aspect, the MIC-1 compounds of the invention have a protracted plasma exposure, i.e. a prolonged half-life compared to human wild type MIC-1.

In one aspect the MIC-1 compounds of the invention have improved solubility. In one aspect, the MIC-1 compounds of the invention have improved chemical stability.

BRIEF DESCRIPTION OF DRAWINGS

FIG. 3 b) The effects of the extended 12mers on the expression level. In addition, the lowest data point in the group of 3.6 is the MIC-1 polypeptide containing M57L. In this figure, "1.6 latter" represents TSTEEG, "2.6" represents TSESAT, "3.6" represents TSTEPS and "4.6" represents SEPATS.

DETAILED DESCRIPTION

Figure 1:
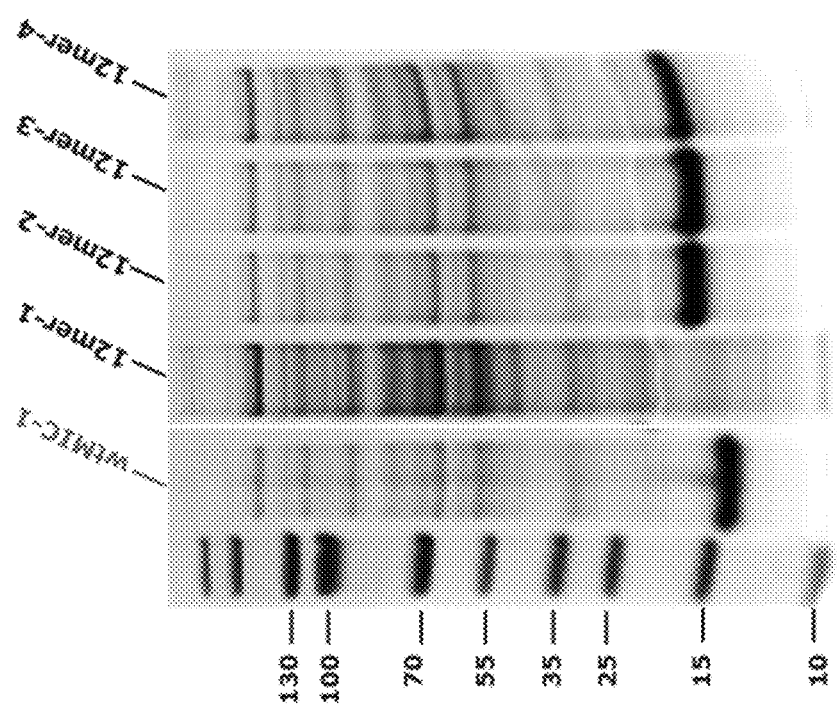
FIG. 1: The expression of MIC-1 polypeptides with N-extensions with single 12-mer building blocks. All cells were grown in TB at 37° C. and proteins were induced to express by adding 0.5 mM IPTG after OD600 reached 1.0. Cells were harvested after overnight and the expression level was checked by loading the total lysate on SDS-PAGE. Wild type human MIC-1 (MIC-1) was loaded as the positive control.

The invention relates to MIC-1 compounds comprising a MIC-1 polypeptide with an N-terminal amino acid extension and a protractor attached to the amino acid extension.

In one aspect, the MIC-1 compounds of the invention comprise a MIC-1 polypeptide an N-terminal amino acid extension and a protractor attached to the amino acid extension, wherein the amino acid extension comprises 3 to 200 amino acid residues, and the MIC-1 polypeptide and the amino acid extension together have a calculated pI lower than 6.5.

The MIC-1 compounds of the invention are biologically active. For example, they are potent, retain full efficacy compared to MIC-1 and also, they have a protracted plasma exposure profile, i.e. have a pronged half-life. The particular combination of potency and long half-life is desirable.

MIC-1

The term "MIC-1" as used herein means Macrophage Inhibitory Cytokine-1 (MIC-1), also known as Growth Differentiation Factor 15 (GDF-15), placental bone morphogenetic protein (PLAB) and nonsteroidal anti-inflammatory drug-activated gene (NAG-1). MIC-1 is synthesized as a 62 kDa intracellular homodimer precursor protein which subsequently is cleaved by a furin-like protease into a 24.5 kDa homodimer. The sequence of the full length wild type human MIC-1 is available from the UNIPROT database with accession no. Q99988. The 308 amino acid precursor sequence includes a signal peptide (amino acids 1-29), a propeptide (amino acids 30-196) and a MIC-1 monomer sequence (amino acids 197-308). The 112 amino acid MIC-1 monomer sequence is included herein as SEQ ID NO:1. MIC-1 monomer contains nine cysteine residues which give rise to the formation of 4 intrachain disulphide bonds and one interchain disulphide bond to create a covalently linked 24.5 kDa homodimer. A naturally occurring mutation corresponding to H6D in the MIC-1 monomer sequence (SEQ ID NO:1) has been described.

The term "MIC-1 compound", as used herein, refers to a compound comprising a MIC-1 polypeptide, an N-terminal amino acid extension, and a protractor. The MIC-1 compound is typically in the form of a homodimer.

The terms "MIC-1 polypeptide" as used herein refer to the human MIC-1 monomer sequence of SEQ ID NO:1 or an analogue thereof. Numerical references to particular MIC-1 residues, if not stated otherwise, refer to the 112 amino acid monomer sequence (i.e., residue 1 is Alanine (A1), and residue 112 is Isoleucine (I112).

The term "MIC-1 analogue", or "analogue of MIC-1" as used herein refers to a MIC-1 polypeptide, which is an amino acid variant of the monomer MIC-1 sequence of SEQ ID NO: 1. In other words, a MIC-1 analogue is a MIC-1 polypeptide in which a number of amino acid residues have been changed when compared to human MIC-1 (SEQ ID NO: 1). These changes may represent, independently, one or more amino acid substitutions, additions, and/or deletions.

MIC-1 analogues may be described by reference to the amino acid residue which is changed, the number of the amino acid residue (i.e. the corresponding position in the MIC-1 monomer sequence (SEQ ID NO:1)), and the change (e.g. the amino acid residue change to).

In one aspect, the MIC-1 analogue is a functional variant of the MIC-1 of SEQ ID NO: 1. In one aspect of the invention, the MIC-1 analogues display at least 85%, 90% or 95% sequence identity to MIC-1 of SEQ ID NO: 1. As an example of a method for determination of the sequence identity between two analogues the two peptides H6D MIC-1 and MIC-1 of SEQ ID NO:1 are aligned. The sequence identity of the H6D MIC-1 analogue relative to MIC-1 of SEQ ID NO:1 is given by the number of aligned identical residues divided by the total number of aligned residues in MIC-1 of SEQ ID NO:1. Accordingly, in the example the sequence identity in percentage is (112-1)/112× 100. In the determination of the sequence identity of a MIC-1 analogue, the N-terminal amino acid extension is not included. A suitable alignment program can be tested with a suitable alignment program "needle", which is a Needleman-Wunsch alignment. The algorithm for this alignment program is described in Needleman, S. B. and Wunsch, C. D., (1970), Journal of Molecular Biology, 48: 443-453.

In another aspect of the invention, the MIC-1 analogues comprise less than 15, 10 or 5, amino acid modifications (substitutions, deletions, additions (including insertions) and any combination thereof) relative to human MIC-1 of SEQ ID NO: 1. The term "amino acid modification" used throughout this application is used in the meaning of a modification to an amino acid as compared to monomer MIC-1 (SEQ ID NO:1). This modification can be the result of a deletion of an amino acid, addition of an amino acid, substitution of one amino acid with another or a substituent covalently attached to an amino acid of the peptide.

Substitutions:

In one aspect amino acids may be substituted by conservative substitution. The term "conservative substitution" as used herein denotes that one or more amino acids are replaced by another, biologically similar residue. Examples include substitution of amino acid residues with similar characteristics, e.g. small amino acids, acidic amino acids, polar amino acids, basic amino acids, hydrophobic amino acids and aromatic amino acids.

In one aspect amino acids may be substituted by non-conservative substitution. The term "non-conservative substitution" as used herein denotes that one or more amino acids are replaced by another amino acid having different characteristics. Examples include substitution of a basic amino acid residue with an acidic amino acid residue, substitution of a polar amino acid residue with an aromatic amino acid residue, etc. In one aspect, the non-conservative substitution is substitution of a coded amino acid to another coded amino acid having different characteristics. In one aspect, the MIC-1 analogues may comprise substitutions of one or more unnatural and/or non-amino acids, e.g., amino acid mimetics, into the sequence of MIC-1.

In one aspect of the invention, the asparagine in the position corresponding to position 3 of monomer MIC-1 sequence (SEQ ID NO:1) is substituted to Serine (N3S), Glutamic acid (N3E), Alanine (N3A), or Glutamine (N3Q).

In one aspect of the invention, the asparagine in the position corresponding to position 3 of human MIC-1 monomer sequence (SEQ ID NO:1) is substituted to Glutamic acid (N3E).

In one aspect of the invention, the arginine in the position corresponding to position 2 of human MIC-1 monomer sequence (SEQ ID NO: 1) has been substituted to alanine (R2A), and the asparagine in the position corresponding to position 3 of human MIC-1 monomer sequence (SEQ ID NO:1) has been substituted to Glutamic acid (N3E).

In one aspect of the invention, the arginine in the position corresponding to position 2 of human MIC-1 monomer sequence (SEQ ID NO: 1) has been substituted to Glutamic acid (R2E), and the asparagine in the position corresponding to position 3 of human MIC-1 monomer sequence (SEQ ID NO:1) has been substituted to Serine (N3S).

Deletions and Truncations:

In one aspect, the MIC-1 analogues of the invention may have one or more amino acid residues deleted from the amino acid sequence of MIC-1 (SEQ ID NO:1), alone or in combination with one or more insertions or substitutions.

MIC-1 analogues with amino acid deletions may be described by "des", reference to the amino acid residue which is deleted, and followed by the number of the deleted amino acid (i.e. the corresponding position in the monomer MIC-1 (SEQ ID NO:1)). In some embodiments of the invention, the asparagine in the position corresponding to position 3 of human monomer MIC-1 (SEQ ID NO:1) is deleted (MIC-1 des-N3, SEQ ID NO:2). In some embodiments of the invention, the alanine in the position corresponding to position 1 of human monomer MIC-1 (SEQ ID NO:1) is deleted (MIC-1, des-A1).

MIC-1 analogues with a truncation of one or more amino acid residues at the N or C terminal may be described by "MIC-1-Δ" and reference to the number(s) of the deleted amino acid residues (i.e. the corresponding position in the monomer MIC-1 (SEQ ID NO:1)). In some embodiments of the invention, the first three residues (A1, R2, N3) at the N terminal are deleted (MIC-1-Δ1-3, SEQ ID NO:3).

Insertions:

In one aspect, the MIC-1 analogues of the invention have one or more amino acid residues inserted into the amino acid sequence of human MIC-1, alone or in combination with one or more deletions and/or substitutions.

In one aspect, the MIC-1 analogues of the invention include insertions of one or more unnatural amino acids and/or non-amino acids into the sequence of MIC-1.

The term "protein" or "polypeptide", as e.g. used herein, refers to a compound which comprises a series of amino acids interconnected by amide (or peptide) bonds. Amino acids are molecules containing an amine group and a carboxylic acid group, and, optionally, one or more additional groups, often referred to as a side chain.

The term "amino acid" includes coded (or proteinogenic or natural) amino acids (amongst those the 20 standard amino acids), as well as non-coded (or non-proteinogenic or non-natural) amino acids. Coded amino acids are those which are naturally incorporated into proteins. The standard amino acids are those encoded by the genetic code. Non-coded amino acids are either not found in proteins, or not produced by standard cellular machinery (e.g., they may have been subject to post-translational modification). In what follows, all amino acids of the MIC-1 proteins for which the optical isomer is not stated is to be understood to mean the L-isomer (unless otherwise specified).

As is apparent from the above, amino acid residues may be identified by their full name, their one-letter code, and/or their three-letter code. These three ways are fully equivalent. For the reader's convenience, the single and three letter amino acid codes are provided below:

Glycine: G and Gly; Proline: P and Pro; Alanine: A and Ala; Valine: V and Val; Leucine: L and Leu; Isoleucine: I and Ile; Methionine: M and Met; Cysteine: C and Cys; Phenylalanine: F and Phe; Tyrosine: Y and Tyr; Tryptophan: W and Trp; Histidine: H and His; Lysine: K and Lys; Arginine: R and Arg; Glutamine: Q and Gln; Asparagine: N and Asn; Glutamic Acid: E and Glu; Aspartic Acid: D and Asp; Serine: S and Ser; and Threonine: T and Thr.

N-Terminal Amino Acid Extension

The MIC-1 compounds of the invention comprise an N-terminal amino acid extension.

The term "N-terminal amino acid extension" as used herein, means that the N-terminal of the MIC-1 polypeptide is attached to the C-terminal of the N-terminal amino acid extension via a peptide bond. The terms "N-terminal amino acid extension", "N-terminal extension", and "N-extension" herein means the same thing and are used interchangeably. In one embodiment, the compound of the invention comprises human MIC-1 monomer sequence (SEQ ID NO: 1) with an amino acid extension attached at the N-terminal, i.e. the Alanine at position 1 (A1) via a peptide bond.

In some embodiments of the invention, the N-terminal amino acid extension is up to 200 amino acid residues long. In a particular embodiment of the invention the N-terminal amino acid extension has from 3 to 36 amino acid residues.

In one aspect of the invention, the N-terminal amino acid extension has a surplus of acidic amino acid residues (Aspartic acid and/or Glutamic acid) of at least 3, 4, 5 or 6 compared to the number of basic amino acid residues (Lysine, Arginine and/or Histidine). A "surplus" of acidic amino acid residues means that the number of acidic residues exceeds the number of basic residues. A defined value of the surplus of acidic amino acid residues is calculated as the number of acidic residues minus the number of basic residues.

Methionine is the initial amino acid for protein expression in prokaryotic cells (e.g. bacteria, for instance, *E. coli*). In some embodiments of the invention, the initial Methionine is removed from the protein during the protein expression. Therefore, the initial Methionine is not included in the sequence of the N-extension of MIC-1 compound. However, a person skilled in the art knows that the start codon, coding the initial Methionine, is required for the protein translation initiation and should be incorporated right in front of the nucleotide sequence for protein expression without exception.

Meanwhile, it can be understood that those MIC-1 compounds with N-extensions having the initial Methionine also fall into the scope of the invention.

Protractor

The MIC-1 compounds of the invention comprise a protractor. The protractor is covalently attached to a specific amino acid residue of the MIC-1 polypeptide or N-terminal amino acid extension.

The term "protractor" relates to the properties of conveying extended plasma exposure ("half-life extending moiety") and is herein understood to refer to a chemical group attached to an amino acid site chain functionalities such as —SH, —OH, —COOH, —CONH2, —NH2 that can increase in vivo circulatory half-life of MIC-1 when conjugated to the MIC-1. Examples of protractors include but are not limited to: fatty acids and derivatives thereof, Hydroxy Alkyl Starch (HAS) e.g. Hydroxy Ethyl Starch (HES), Poly Ethylen Glycol (PEG), Poly (Glyx-Sery)n (HAP), Hyaluronic acid (HA), Heparosan polymers (HEP), Phosphorylcholine-based polymers (PC polymer), Fleximers, Dextran, Poly-sialic acids (PSA), an Fc domain, Transferrin, Albumin, Elastin like peptides, unstructured and repeated amino sequences (e.g. XTEN polymers), Albumin binding peptides, a CTP peptide, and any combination thereof.

In some embodiments of the invention, the protractor is capable of forming non-covalent associations with albumin, thereby increasing the blood/plasma exposure time of the MIC-1 compound, and also having the effect of protracting the time of action of the MIC-1 compound, due to the fact that the association of the MIC-1 compound and albumin is only slowly disintegrated to release the active pharmaceutical ingredient.

In some embodiments, the fatty acid comprising protractors of the invention are capable of forming non-covalent associations with albumin and thereby prolonging plasma half-life of the MIC-1 compound compared to human wide type MIC-1.

In some embodiments of the invention, the protractor is covalently attached to a cysteine residue of the N-terminal amino acid extension of the MIC-1 polypeptide. In an embodiment, the protractor comprises a haloacetamide group, which reacts with the thiol group of a cysteine residue, under formation of a covalent sufur-carbon bond (this process being referred to as Cys-alkylation) which is also referred to as a thio-ether bond. In another embodiment, the protractor comprises a maleimide group, which reacts with the thiol group of a cysteine residue, under formation of a covalent sulfur-carbon bond.

In some embodiments of the invention, the protractor is covalently attached the N-terminal amino acid of the N-terminal amino acid extension.

Fatty Acid Comprising Protractor

In an aspect of the invention, the protractor comprises, or consists of, at least one of each of Chem. 1, Chem. 2, Chem. 3, and Chem. 4:

wherein Chem. 1 is selected from the group consisting of:

| | |
|---|---|
| HOOC—(CH$_2$)$_x$—CO—*, | Chem. 1A: |
| HO—S(=O)$_2$—(CH$_2$)$_x$—CO—*, | Chem. 1B: |
| HOOC-benzene-O—(CH$_2$)$_y$—CO—*, and | Chem. 1C: |
| (1H-tetrazol-5-yl)-(CH$_2$)$_x$—CO—*, | Chem. 1D: | wherein x is an integer in the range of 12-20,
wherein y is an integer in the range of 5-15;
wherein Chem. 2 is selected from the group consisting of:

| | |
|---|---|
| *—NH—CH(COOH)—(CH$_2$)$_m$—CO—*, | Chem. 2A: |
| *—NH—S(=O)$_2$—(CH$_2$)$_m$—CO—*, and | Chem. 2B: |
| *—NH—(CH$_2$)$m$-cyclohexane-CO—*, | Chem. 2C: | wherein m of Chem. 2 is an integer in the range of 1-5;
wherein Chem. 3 is

*NH—(CH$_2$)$_2$—[O—(CH$_2$)$_2$]$_k$—O—[CH$_2$]$_n$—CO—*, wherein k of Chem. 3 is an integer in the range of 1-10,
n is an integer in the range of 1-5; and wherein Chem. 4 is selected from

*—NH—(CH$_2$)$_m$—NH—CO—CH$_2$—*,  (Chem. 4A:)

*—NH—CH(COOH)—(CH$_2$)$_m$—NH—CO—CH$_2$—*,  (Chem. 4B:)

*—NH—(CH2)$m$-CH(COOH)—NH—CO—CH2-*, and  (Chem. 4C:)

Chem. 4D:

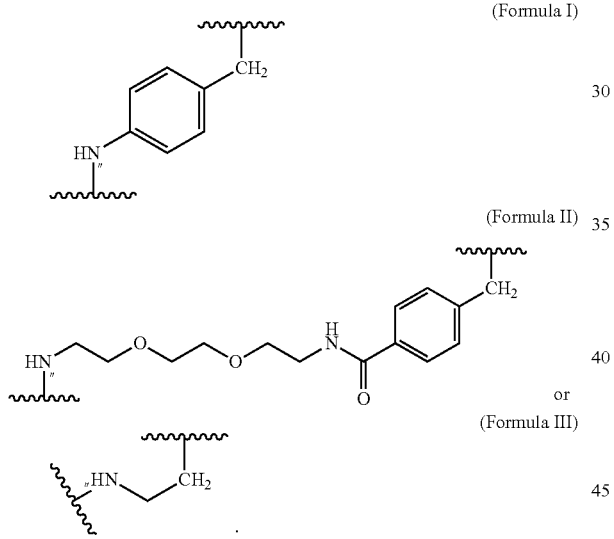

wherein m of Chem. 4 is an integer in the range of 1-5 and n is an integer in the range of 2-6 or wherein Chem. 4 is selected from the group consisting of Formula I, II or III:

(Formula I)

(Formula II)

or (Formula III)

wherein Chem. 1, Chem. 2, Chem. 3, and Chem. 4 are interconnected via amide bonds, connecting the *—NH end of a Chem. to the CO—* end of another Chem.

In some embodiments, the protractor of the invention comprises one Chem. 1, one Chem. 4, and one or more of Chem. 2 and Chem. 3. As a non-limiting example, the protractor consists of one Chem. 1 element, two Chem. 2 elements, two Chem. 3 elements, and one Chem. 4 element.

The elements Chem. 2 and Chem. 3 both hold a —NH— and CO— end allowing them to be linked by amide bonds to each other and to either —CO— or —NH— of Chem. 1 or Chem. 4. Chem. 4 has a —NH— end (capable of forming an amide bond with Chem. 2 or Chem. 3). Chem. 4 further has either a —NH—CO—CH$_2$— end, which in the unreacted form is a haloacetamide capable of reacting with the thiol group of a cysteine residue, or a (—N*—CO—CH2-CH**—CO)-end, the parenthesis representing a cyclic structure, which in the unreacted form is a maleimide capable of reacting with the thiol group of the cysteine; or an aldehyde capable of reacting with the N-terminal amino group in a reductive alkylation reaction.

The length of the carbon chain of Chem. 1 defined by x or y may vary from 12-20 for x and 5-15 for y. Shorter or longer versions may be favoured for different types of protractors. In a particular embodiment of Chem. 1A, *—(CH$_2$)$_x$—* refers to straight alkylene in which x is an integer in the range of 12-20, such as 14-18 or such as 16.

This Chem. 1 may be briefly referred to as C18 diacid, i.e. a fatty di-carboxylic acid with 18 carbon atoms. When x=16 the structure of this linker element corresponds to HOOC—(CH$_2$)$_{16}$—CO—*.  (Chem. 1a:)

In further embodiments Chem. 1 is selected from the group consisting of:

HOOC—(CH$_2$)$_{16}$—CO—*,  (Chem. 1a:)

HO—S(=O)$_2$—(CH$_2$)$_{15}$—CO—*  (Chem. 1b:)

HOOC-benzene-O—(CH$_2$)$_9$—CO—*, and  (Chem. 1c:)

(1H-tetrazol-5-yl)-(CH$_2$)$_{15}$—CO—*,  (Chem. 1d:)

In further embodiments Chem. 2 is selected from the group consisting of:

*—NH—CH(COOH)—(CH$_2$)$_2$—CO—*,  (Chem. 2a:)

*—NH—S(=O)$_2$—(CH$_2$)$_3$—CO—* and  (Chem. 2b:)

*—NH—CH$_2$-cyclohexane-CO—*.  (Chem. 2c:)

In an aspect of the invention, protractor is attached to a Cysteine residue; and the protractor comprises, or consists of, at least one of each of Chem. 1, Chem. 2, Chem. 3 and Chem. 4;

wherein Chem. 1 is selected from the group consisting of:

HOOC—(CH$_2$)$_x$—CO—*,  (Chem. 1A:)

HO—S(=O)$_2$—(CH$_2$)$_x$—CO—*,  (Chem. 1B:)

HOOC-benzene-O—(CH$_2$)$_y$—CO—*, and  (Chem. 1C:)

(1H-tetrazol-5-yl)-(CH$_2$)$_x$—CO—*,  (Chem. 1D:)

wherein x is an integer in the range of 12-20,
wherein y is an integer in the range of 5-15;
wherein Chem. 2 is selected from the group consisting of:

*—(NH—CH(COOH)—(CH$_2$)$_m$—CO)$_k$*,  (Chem. 2A:)

*—(NH—S(=O)$_2$—(CH$_2$)$_m$—CO)$_k$*, and  (Chem. 2B:)

*—(NH—(CH$_2$)$_m$-cyclohexane-CO)$_k$—*,  (Chem. 2C:)

wherein m of Chem. 2 is an integer in the range of 1-5, and
k is an integer in the range of 0-4;
wherein Chem. 3 is

*(NH—(CH$_2$)$_2$—[O—(CH$_2$)$_2$]$_k$—O—[CH$_2$]$_n$—CO—*)$_l$, wherein k of Chem. 3 is an integer in the range of 1-10,
n is an integer in the range of 1-5, and
l is an integer in the range of 0-5;
wherein Chem. 4 is selected from

*—NH—(CH$_2$)$_m$—NH—CO—CH$_2$—*, and  (Chem. 4A:)

*—NH—CH(COOH)—(CH$_2$)$_m$—NH—CO—CH$_2$—*,  (Chem. 4B:)

wherein m of Chem. 4 is an integer in the range of 1-5; and wherein Chem. 1, Chem. 2, Chem. 3, and Chem. 4 are interconnected via amide bonds, connecting the *—NH end of a Chem. to the CO—* end of another Chem., and wherein the $CH_2$—* end of Chem. 4 is connected to the sulphur atom of the Cysteine residue of the amino acid extension.

In an aspect of the invention, the protractor is attached to an N-terminal amino acid, and comprises, or consists of, at least one of each of Chem. 1, Chem. 2, Chem. 3 and Chem. 4;

wherein Chem. 1 is selected from the group consisting of:

HOOC—$(CH_2)_x$—CO—*,      Chem. 1A:

HO—$S(=O)_2$—$(CH_2)_x$—CO—*,      Chem. 1B:

HOOC-benzene-O—$(CH_2)_y$—CO—*, and      Chem. 1C:

(1H-tetrazol-5-yl)-$(CH_2)_x$—CO—*      Chem. 1D:

wherein x is an integer in the range of 12-20,
wherein y is an integer in the range of 5-15;
wherein Chem. 2 is selected from the group consisting of:

*—(NH—CH(COOH)—$(CH_2)_m$—CO)$_k$*,      Chem. 2A:

*—(NH—$S(=O)_2$—$(CH_2)_m$—CO)$_k$*, and      Chem. 2B:

*—(NH—$(CH_2)_m$-cyclohexane-CO)$_k$—*,      Chem. 2C:

wherein m of Chem. 2 is an integer in the range of 1-5, and
k is an integer in the range of 0-4;
wherein Chem. 3 is

*(NH—$(CH_2)_2$—[O—$(CH_2)_2$]$_k$—O—$[CH_2]_n$—CO—*)$_l$, wherein k of Chem. 3 is an integer in the range of 1-10, n is an integer in the range of 1-5, and l is an integer in the range of 0-5;
wherein Chem. 4 is selected from the group consisting of Formula I, II or III:

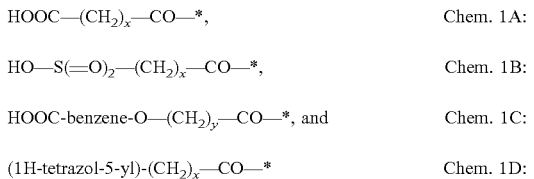

(Formula I)

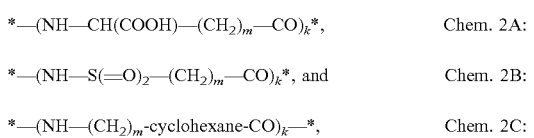

(Formula II)

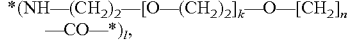

or (Formula III)

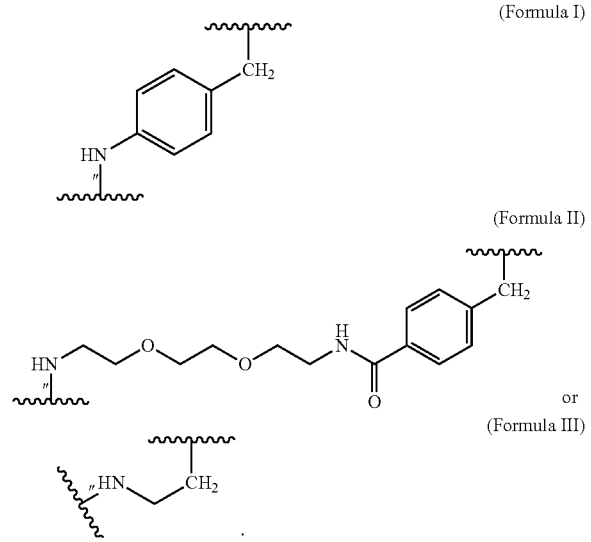

wherein Chem. 1, Chem. 2, Chem. 3, and Chem. 4 are interconnected via amide bonds, connecting the *—NH end of a Chem. to the CO—* end of another Chem., and wherein the $CH_2$—* end of Chem. 4 is connected to the alpha-amino group of the N-terminal of the amino acid extension.

The nomenclature is as is usual in the art, for example in the above formulas *—CO—* refers to carbonyl (*—C(=O)—*). Benzene refers to the ring structure which in Chem. 1C is substituted at C1 and C3 or C4 by —O—$(CH_2)_x$—* and —COOH, respectively. HO—$S(=O)_2$-* describes a sulfonic acid group.

The compounds/protractors of the invention may exist in different stereoisomeric forms having the same molecular formula and sequence of bonded atoms, but differing only in the three-dimensional orientation of their atoms in space. The stereoisomerism of the exemplified compounds/protractors of the invention is indicated in the experimental section, in the names as well as the structures, using standard nomenclature. Unless otherwise stated the invention relates to all stereoisomeric forms of the claimed compounds/protractors.

Isoelectric Point (pI)

The calculated pI of the MIC-1 polypeptide with an N-terminal amino acid extension is defined as the pH at which the net calculated charge of the MIC-1 polypeptide with the N-extension is zero. The calculated charge of the MIC-1 polypeptide with the N-extension as a function of pH is obtained using the pKa values of the amino acid residues described in Table 1 and the method described by B. Skoog and A. Wichman (Trends in Analytical Chemistry, 1986, vol. 5, pp. 82-83). The side chain pKa of cysteine (Cys) is only included in the charge calculation for cysteines with a free sulfhydryl group. As an example the calculated pI value of human wild type MIC-1 as the homodimer is 8.8.

As described herein, pI calculations on MIC-1 polypeptides with N-extensions are made on homodimers.

TABLE 1 pKa of amino acid residues used for calculating pI. The pKa values are those described in "Correlation of Electrophoretic Mobilities from Capillary Electrophoresis with Physicochemical Properties of Proteins and Peptides by Rickard EC, Strohl MM, Nielsen RG. Analytical Biochemistry 1991, vol 197, pp 197-207".

|     | N-terminus | C-Terminus | Side chain |
|-----|------------|------------|------------|
| Asp | 8.6        | 2.75       | 3.5        |
| Asn | 7.3        | 2.75       | —          |
| Thr | 8.2        | 3.2        | —          |
| Ser | 7.3        | 3.2        | —          |
| Glu | 8.2        | 3.2        | 4.5        |
| Gln | 7.7        | 3.2        | —          |
| Pro | 9          | 3.2        | —          |
| Gly | 8.2        | 3.2        | —          |
| Ala | 8.2        | 3.2        | —          |
| Val | 8.2        | 3.2        | —          |
| Cys | 7.3        | 2.75       | 10.3       |
| Met | 9.2        | 3.2        | —          |
| Ile | 8.2        | 3.2        | —          |
| Leu | 8.2        | 3.2        | —          |
| Tyr | 7.7        | 3.2        | 10.3       |
| Phe | 7.7        | 3.2        | —          |
| Lys | 7.7        | 3.2        | 10.3       |
| His | 8.2        | 3.2        | 6.2        |
| Trp | 8.2        | 3.2        | —          |
| Arg | 8.2        | 3.2        | 12.5       |

Functional Properties

In one aspect, the MIC-1 compounds of the invention have good biophysical properties.

The MIC-1 compounds of the invention are biologically active. For example they are potent, binds to and activate the MIC-1 receptor complex. Also MIC-1 compounds exhibit protracted plasma exposure defined as longer half-life. For example MIC-1 compounds have a markedly longer plasma half-life when administered i.v. to rat and/or mini pigs compared to MIC-1 (SEQ ID 1). The particular combination of retained receptor potency and long plasma half-life may be highly desirable.

In Vitro Activity

In one aspect, the compounds of the invention have retained MIC-1 receptor potency relative to human MIC-1 (SEQ ID NO:1). Receptor potency and efficacy can be measured in mammalian cells transfected with human MIC-1 receptor (hGFRAL, GDNF family receptor alpha like) and its signalling co-receptor hRET (proto-oncogene tyrosine-protein kinase receptor Ret). MIC-1 compounds activation of the receptor complex is measured by phosphorylation of extracellular signal-regulated kinases (ERKs) as described in Example 6.

As described herein receptor potency and efficacy is measured on MIC-1 compounds as homodimers.

In Vivo Biological Activity

In one aspect the compounds of the invention are potent in vivo, which may be determined as is known in the art in any suitable animal model.

The non-obese Sprague Dawley rat is one example of a suitable animal model, and the changes in food intake may be determined in such rats in vivo, e.g. as described in Example 14. In one aspect the compounds of the invention inhibits in vivo food intake in non-obese Sprague Dawley rats.

In Vivo Plasma Half-Life

In one aspect the MIC-1 compounds of the invention are protracted and have an extended in vivo plasma half-life, which can be determined in a suitable pharmacokinetic in vivo study.

Extended plasma exposure may be determined as plasma half-life (T½) after i.v. administration to animals such as rats or mini pigs.

In some embodiments, the MIC-1 compounds of the invention have a plasma half-life after i.v. administration to rat of at least 10 hour, more preferably between 25-50 hours, or most preferably at least 50 hours, determined as described in Example 16.

In some embodiments, the MIC-1 compounds of the invention have a plasma half-life after i.v. administration to mini pigs of at least 50 hours, more preferably between 50-200 hours, even more preferably at least 200 hours or most preferably at least 300 hours, determined as described in Example 17.

According to a third aspect, the compounds of the invention are protracted and at the same time retain in vivo potency. The particular combination of retained potency and long plasma half-life may be highly desirable.

Solubility

The human wild type MIC-1 is a hydrophobic protein, with a calculated pI 8.8 based on the homodimer. Consequently, wild type MIC-1 can only be solubilized to around 0.5 mg/ml in neutral pH aqueous buffer systems. The low solubility of MIC-1 significantly hampers its pharmaceutical formulation properties and therapeutic use, so developing a MIC-1 compound with improved solubility would greatly improve the therapeutic utility.

In one aspect, the MIC-1 polypeptides with an N-extension of the invention have improved solubility (i.e. are more soluble) relative to human MIC-1 of SEQ ID NO: 1.

As described herein, solubility is measured as described in Example 4.

In certain embodiments, the MIC-1 polypeptides with an N-extension of the invention have a solubility of at least 1 mg/ml in Tris buffer at pH 8.0. In other embodiments, the MIC-1 polypeptides with an N-extension of the invention have a solubility of at least 5 mg/ml, at least 10 mg/ml, at least 30 mg/ml, or at least 40 mg/ml in Tris buffer at pH 8.0.

Adding a protractor to make a MIC-1 compound do not markedly alter the improved solubility of measured for the corresponding MIC-1 polypeptides with an N-extension (Example 12).

As described herein, solubility is measured on MIC-1 compounds and MIC-1 polypeptides with an N-extension as homodimers.

Stability

The human wild type MIC-1 sequence is chemically unstable and several residues of the amino acid sequence could be modified during storage, including deamidation on Asparagine at position 3 (N3) and oxidation of methionines M43, M57 and M86. Chemical instability of certain residues could impact pharmaceutical properties so developing chemical stable MIC-1 compounds would be another important part of making a MIC-1 therapeutic compound.

In one aspect, the compounds of the invention have improved chemical stability relative to human MIC-1 of SEQ ID NO:1.

The term "chemical stability" refers to chemical changes in the polypeptide structure leading to formation of chemical degradation products potentially having a reduced biological activity, decreased solubility, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

In some embodiments of the invention, certain residues of the MIC-1 monomer sequence (SEQ ID NO:1) is modified, e.g. by substitution to increase the chemical stability of the MIC-1 compounds. To avoid deamidation, N3 is deleted or substituted with other amino acids, e.g. E or Q. To decrease oxidation, Methionine is substituted with other amino acids, e.g. E or L.

Immunogenicity

In one aspect, the MIC-1 compounds of the invention have low immunogenicity risk.

Production Processes

MIC-1 polypeptides with an N-terminal amino acid extension of the present invention may be produced by means of recombinant protein technology known to persons skilled in the art. In general, nucleic acid sequences encoding the proteins of interest or functional variants thereof are modified to encode the desired MIC-1 polypeptide with an N-extension. This modified sequence is then inserted into an expression vector, which is in turn transformed or transfected into the expression host cells.

The nucleic acid construct encoding the MIC-1 polypeptide with an N-extension may suitably be of genomic, cDNA or synthetic origin. Amino acid sequence alterations are accomplished by modification of the genetic code by well-known techniques.

The DNA sequence encoding the MIC-1 polypeptide with an N-extension is usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the MIC-1 polypeptide with an N-extension is operably linked to additional segments required for transcription of the DNA. The term, "operably linked" indicates that the segments are arranged so that they function in concert for their intended purposes, e.g. transcription initiates in a promoter and proceeds through the DNA sequence coding for the polypeptide until it terminates within a terminator.

Thus, expression vectors for use in expressing the MIC-1 polypeptide with an N-extension will comprise a promoter capable of initiating and directing the transcription of a cloned gene or cDNA. The promoter may be any DNA sequence, which shows transcriptional activity in the host cell of choice and may be derived from genes encoding proteins either homologous or heterologous to the host cell.

Additionally, expression vectors for expression of the MIC-1 polypeptide with an N-extension will also comprise a terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Expression of the MIC-1 polypeptide with an N-extension can be aimed for either intracellular expression in the cytosol of the host cell or be directed into the secretory pathway for extracellular expression into the growth medium.

Intracellular expression is the default pathway and requires an expression vector with a DNA sequence comprising a promoter followed by the DNA sequence encoding the MIC-1 polypeptide with an N-extension followed by a terminator.

To direct the sequence of the MIC-1 polypeptide with an N-extension into the secretory pathway of the host cells, a secretory signal sequence (also known as signal peptide or a pre sequence) is needed as an extension of the MIC-1 sequence. A DNA sequence encoding the signal peptide is joined to the 5' end of the DNA sequence encoding the MIC-1 polypeptide with an N-extension in the correct reading frame. The signal peptide may be that normally associated with the protein or may be from a gene encoding another secreted protein.

The procedures used to ligate the DNA sequences coding for the MIC-1 polypeptide with an N-extension, the promoter, the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N.Y., 1989).

The host cell into which the DNA sequence encoding the MIC-1 polypeptide with an N-extension is introduced may be any cell that is capable of expressing the MIC-1 polypeptide with an N-extension either intracellularly or extracellularly. The MIC-1 polypeptide with an N-extension may be produced by culturing a host cell containing a DNA sequence encoding the MIC-1 polypeptide with an N-extension and capable of expressing the MIC-1 polypeptide with an N-extension in a suitable nutrient medium under conditions permitting the expression of the MIC-1 polypeptide with an N-extension. Non-limiting examples of host cells suitable for expression of MIC-1 polypeptide with N-extension are: *Escherichia coli, Saccharomyces cerevisiae*, as well as human embryonic kidney (HEK), Baby Hamster Kidney (BHK) or Chinese hamster ovary (CHO) cell lines. If posttranslational modifications are needed, suitable host cells include yeast, fungi, insects and higher eukaryotic cells such as mammalian cells.

Once the MIC-1 polypeptide with an N-extension has been expressed in a host organism it may be recovered and purified to the required quality by conventional techniques. Non-limiting examples of such conventional recovery and purification techniques are centrifugation, solubilization, filtration, precipitation, ion-exchange chromatography, immobilized metal affinity chromatography (IMAC), Reversed phase—High Performance Liquid Chromatography (RP-HPLC), gel-filtration and freeze drying.

Examples of recombinant expression and purification of MIC-1 proteins may be found in e.g. Cordingley et al., J. Virol. 1989, 63, pp 5037-5045; Birch et al., Protein Expr Purif., 1995, 6, pp 609-618 and in WO2008/043847.

Examples of microbial expression and purification of MIC-1 proteins may be found in e.g. Chich et al, Anal. Biochem, 1995, 224, pp 245-249 and Xin et al., Protein Expr. Purif. 2002, 24, pp 530-538.

Specific examples of methods of preparing a number of the MIC-1 polypeptides with an N-extension of the invention are included in the experimental part.

Inclusion Body and Protein Expression

MIC-1 polypeptides with an N-terminal amino acid extension can be expressed in bacteria such as *E. coli*. In the context of the present invention, large scale protein production of the MIC-1 polypeptides with an N-extension could take of using Inclusion Bodies (IB) as this represent an advantageous approach to controlling process recovery, protein purity, protease degradation and general protein stability. This becomes particular important for large scale protein production. Of critical importance for the quality of IB is the balance of MIC-1 polypeptides with an N-extension solubility partly controlled by the calculated pI and IB formation.

Mode of Administration

The route of administration may be any route which effectively transports a compound of this invention to the desired or appropriate place in the body, such as parenterally, for example, subcutaneously, intramuscularly or intravenously. Alternatively, a compound of this invention can be administered orally, pulmonary, rectally, transdermally, buccally, sublingually, or nasally.

The amount of a compound of this invention to be administered, the determination of how frequently to administer a compound of this invention, and the election of which compound or compounds of this invention to administer, optionally together with another pharmaceutically active agent, is decided in consultation with a practitioner who is familiar with the treatment of obesity and related disorders.

Pharmaceutical Compositions

Pharmaceutical compositions comprising a compound of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19th edition (1995), and any later editions).

Combination Treatment

The treatment with a compound according to the present invention may also be combined with one or more pharmacologically active substances, e.g., selected from antiobesity agents, appetite regulating agents, and agents for the treatment and/or prevention of complications and disorders resulting from or associated with obesity.

Pharmaceutical Indications

In one aspect, the present invention relates to a compound of the invention, for use as a medicament.

In particular embodiments, the compound of the invention may be used for the following medical treatments:

(i) Prevention and/or treatment of eating disorders, such as obesity, e.g. by decreasing food intake, reducing body weight, suppressing appetite and/or inducing satiety.

(ii) Prevention and/or treatment of hyperglycemia, insulin resistance and/or impaired glucose tolerance.

(iii) Prevention and/or treatment of dyslipidaemia.

In some embodiments the invention relates to a method for weight management. In some embodiments the invention relates to a method for reduction of appetite. In some embodiments the invention relates to a method for reduction of food intake.

Generally, all subjects suffering from obesity are also considered to be suffering from overweight. In some embodiments the invention relates to a method for treatment or prevention of obesity. In some embodiments the invention relates to use of the MIC-1 compounds of the invention for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/height in meters$^2$. A human subject suffering from obesity has a BMI of ≥30; this subject may also be referred to as obese. In some embodiments the human subject suffering from obesity has a BMI of ≥35 or a BMI in the range of ≥30 to <40. In some embodiments the obesity is severe obesity or morbid obesity, wherein the human subject has a BMI of ≥40.

In some embodiments the invention relates to a method for treatment or prevention of overweight, optionally in the presence of at least one weight-related comorbidity. In some embodiments the invention relates to use of the MIC-1 compounds of the invention for treatment or prevention of overweight, optionally in the presence of at least one weight-related comorbidity.

In some embodiments the subject suffering from overweight is human, such as an adult human or a paediatric human (including infants, children, and adolescents). In some embodiments a human subject suffering from overweight has a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the MIC-1 compounds of the invention for reduction of body weight. A human to be subjected to reduction of body weight according to the present invention has a BMI of ≥25, such as a BMI of ≥27 or a BMI of ≥30. In some embodiments the human to be subjected to reduction of body weight according to the present invention has a BMI of ≥35 or a BMI of ≥40.

In some embodiments the invention relates to a method for treatment or prevention of cardiovascular diseases like arteriosclerosis and other disorders such as steatohepatitis, and diabetic nephropathy.

The articles "a" and "an" are used herein to refer to one or to more than one (i.e., to at least one) of the grammatical object of the article. By way of example, "a MIC-1 polypeptide" means one MIC-1 polypeptide or more than one MIC-1 polypeptide.

An asterisk (*) in a chemical formula designates a point of attachment.

Particular Embodiments

The invention is further described by the following non-limiting embodiments of the invention:

1. A MIC-1 compound comprising a MIC-1 polypeptide with an N-terminal amino acid extension and a protractor, wherein the protractor is attached to the amino acid extension.

2. The MIC-1 compound according to embodiment 1, wherein the compound is a homodimer.

3. The MIC-1 compound according to embodiments 1 or 2, wherein the N-terminal amino acid extension comprises a cysteine residue, and wherein the protractor is attached to the amino acid extension at the Cysteine residue.

4. The MIC-1 compound according to embodiment 3, wherein the protractor comprises, or consists of, at least one of each of Chem. 1, Chem. 2, Chem. 3 and Chem. 4; wherein Chem. 1 is selected from the group consisting of:

| | |
|---|---|
| HOOC—(CH$_2$)$_x$—CO—*, | Chem. 1A: |
| HO—S(=O)$_2$—(CH$_2$)$_x$—CO—*, | Chem. 1B: |
| HOOC-benzene-O—(CH$_2$)$_y$—CO—*, and | Chem. 1C: |
| (1H-tetrazol-5-yl)-(CH$_2$)$_x$—CO—* | Chem. 1D: | wherein x is an integer in the range of 12-20,
wherein y is an integer in the range of 5-15;
wherein Chem. 2 is selected from the group consisting of:

| | |
|---|---|
| *—(NH—CH(COOH)—(CH$_2$)$_m$—CO)$_k$*, | Chem. 2A: |
| *—(NH—S(=O)$_2$—(CH$_2$)$_m$—CO)$_k$*, and | Chem. 2B: |
| *—(NH—(CH$_2$)$_m$-cyclohexane-CO)$_k$—*, | Chem. 2C: | wherein m of Chem. 2 is an integer in the range of 1-5, and k is an integer in the range of 0-4;
wherein Chem. 3 is

*(NH—(CH$_2$)$_2$—[O—(CH$_2$)$_2$]$_k$—O—[CH$_2$]$_n$—CO—*)$_l$, wherein k of Chem. 3 is an integer in the range of 1-10,
n is an integer in the range of 1-5, and
l is an integer in the range of 0-5;
wherein Chem. 4 is selected from

| | |
|---|---|
| *—NH—(CH$_2$)$_m$—NH—CO—CH$_2$—*, and | Chem. 4A: |
| *—NH—CH(COOH)—(CH$_2$)$_m$—NH—CO—CH$_2$—*, | Chem. 4B: |
| *—NH—(CH2)$m$-CH(COOH)—NH—CO—CH2-*, and | Chem. 4C: |

Chem. 4D:

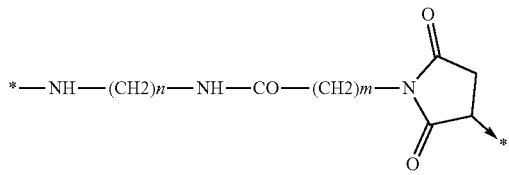

wherein m of Chem. 4 is an integer in the range of 1-5 and n is an integer in the range of 2-6; and
wherein Chem. 1, Chem. 2, Chem. 3, and Chem. 4 are interconnected via amide bonds, connecting the *—NH end of a Chem. to the CO—* end of another Chem., and wherein the $CH_2$—* end of Chem. 4 is connected to a sulfur atom of the Cysteine residue of the amino acid extension.

5. The MIC-1 compound according to embodiments 1 or 2, and wherein the protractor is attached to the N-terminal amino acid of the amino acid extension.

6. The MIC-1 compound according to embodiment 5, wherein the protractor comprises, or consists of, at least one of each of Chem. 1, Chem. 2, Chem. 3 and Chem. 4; wherein Chem. 1 is selected from the group consisting of:

 Chem. 1A:

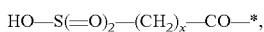 Chem. 1B:

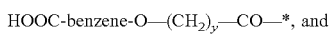 Chem. 1C:

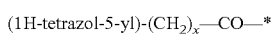 Chem. 1D:

wherein x is an integer in the range of 12-20,
wherein y is an integer in the range of 5-15;
wherein Chem. 2 is selected from the group consisting of:

 Chem. 2A:

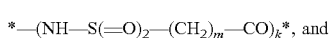 Chem. 2B:

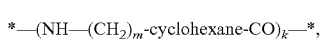 Chem. 2C:

wherein m of Chem. 2 is an integer in the range of 1-5, and k is an integer in the range of 0-4;
wherein Chem. 3 is

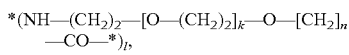

wherein k of Chem. 3 is an integer in the range of 1-10, n is an integer in the range of 1-5, and l is an integer in the range of 0-5;
wherein Chem. 4 is selected from the group consisting of Formula I, II or III:

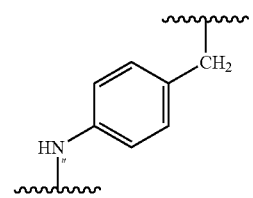
(Formula I)

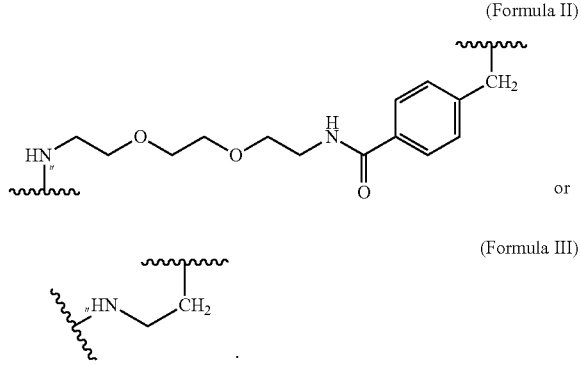
(Formula II) or (Formula III)

wherein Chem. 1, Chem. 2, Chem. 3, and Chem. 4 are interconnected via amide bonds, connecting the *—NH end of a Chem. to the CO—* end of another Chem., and wherein the $CH_2$—* end of Chem. 4 is connected to amino group of the N-terminal of the amino acid extension.

7. The MIC-1 compound according to any one of embodiments 4 and 6, wherein Chem. 1 is selected from the group consisting of:

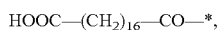 Chem. 1a:

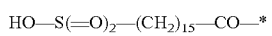 Chem. 1b:

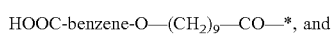 Chem. 1c:

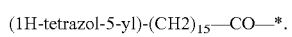 Chem. 1d:

8. The MIC-1 compound according to any one of embodiments 4, 6 and 7 wherein Chem. 2 is selected from the group consisting of:

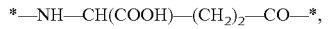 Chem. 2a:

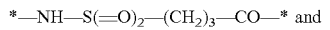 Chem. 2b:

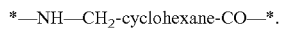 Chem. 2c:

9. The MIC-1 compound according to any one of embodiments 4, 6 and 7, wherein Chem. 2-Chem. 3 is the following Formula IV:

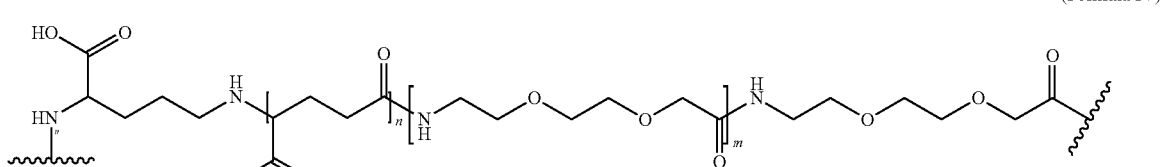
(Formula IV)

where n is of 0-3 and m is 0-3

10. The MIC-1 compound according to any one of embodiments 4 and 7-9, wherein Chem. 4 is selected from the group consisting of:

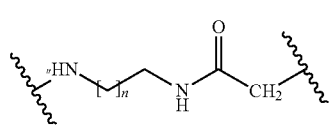   Chem. 4a:

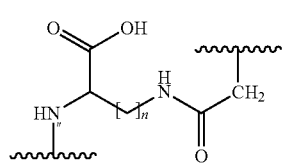   Chem. 4b:

11. The MIC-1 compound according to any one of embodiments 4 and 7-9, wherein Chem. 4 is selected from the group consisting of Formula V, VI or VII:

(Formula V)

(Formula VI)

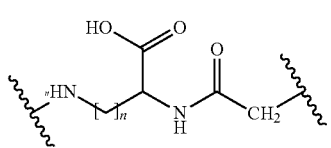   (Formula VII)

where n is 1-4.

12. The MIC-1 compound according to any one of embodiments 4 and 7-9, wherein Chem. 4 is the following Formula VIII:

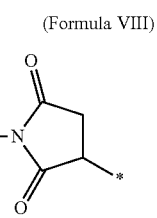   (Formula VIII)

where p is 1-5, and q is 1-5.

13. The MIC-1 compound according to any one of embodiments 1-3 and 5, wherein the protractor is selected from the group consisting of Formula IX, Formula X, Formula XI, Formula XII and Formula XIII:

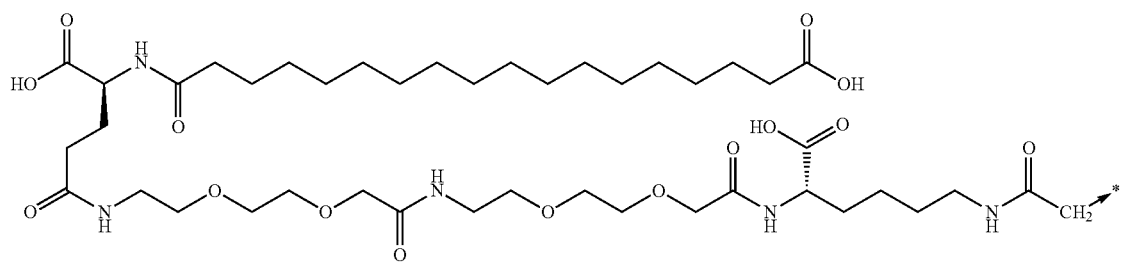   (Formula IX)

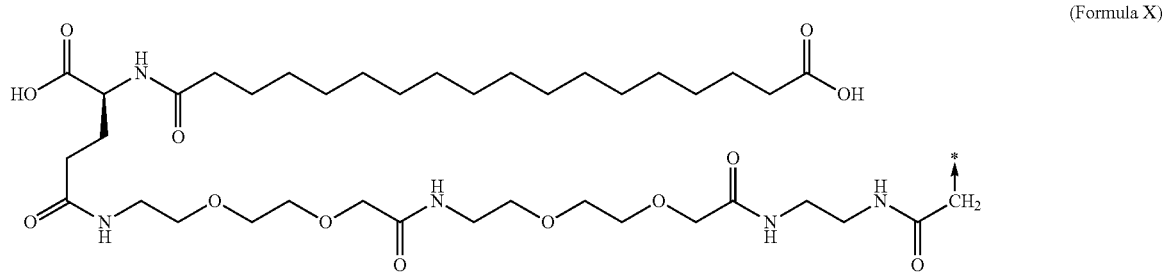   (Formula X)

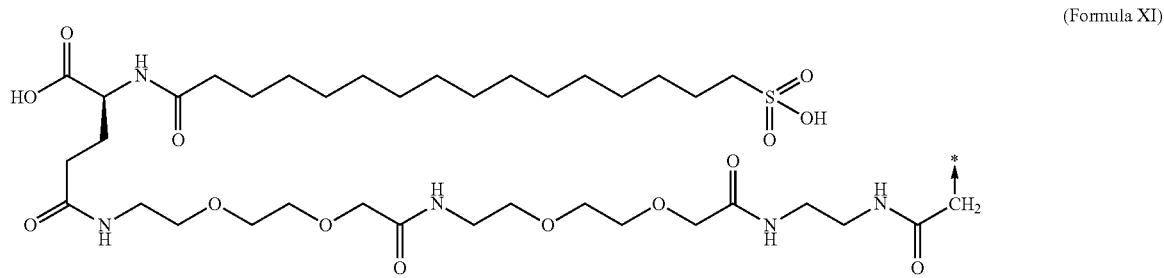   (Formula XI)

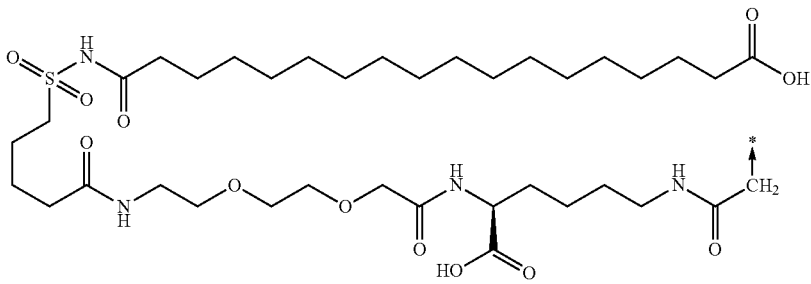
(Formula XII)

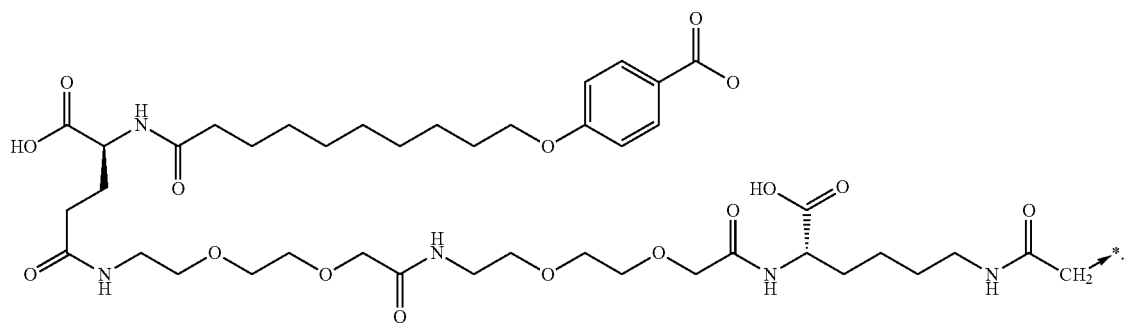
(Formula XIII)

14. The MIC-1 compound according to any one of embodiments 1-3 and 5, wherein the protractor is selected from the group consisting of: Biocompatible fatty acids and derivatives thereof, Hydroxy Alkyl Starch (HAS) e.g. Hydroxy Ethyl Starch (HES), Poly Ethylen Glycol (PEG), Poly (Glyx-Sery)n (HAP), Hyaluronic acid (HA), Heparosan polymers (HEP), Phosphorylcholine-based polymers (PC polymer), Fleximers, Dextran, Poly-sialic acids (PSA), an Fc domain, Transferrin, Albumin, Elastin like peptides, XTEN polymers, Albumin binding peptides, a CTP peptide, and any combination thereof.

15. The MIC-1 compound according to any one of the preceding embodiments, wherein the MIC-1 polypeptide with the amino acid extension has a calculated pI lower than 6.5.

16. The MIC-1 compound according to embodiment 15, wherein the calculated pI is lower than 6.1.

17. The MIC-1 compound according to embodiment 15, wherein the calculated pI is lower than 6.0.

18. The MIC-1 compound according to embodiment 15, wherein the calculated pI is lower than 6.4, 6.3, 6.2, 6.1, 6.0, 5.9, 5.8, 5.7, 5.6, 5.5, 5.4, 5.3, or 5.2, 5.1, or 5.0, 4.9, 4.8, 4.7, 4.6, 4.5, 4.4, 4.3, 4.2, 4.1 or 4.0.

19. The MIC-1 compound according to embodiment 15, wherein the calculated pI is higher than 4.7.

20. The MIC-1 compound according to embodiment 15, wherein the calculated pI is higher than 4.8.

21. The MIC-1 compound according to embodiment 15, wherein the calculated pI is higher than 4.9.

22. The MIC-1 compound according to embodiment 15, wherein the calculated pI is higher than 5.0.

23. The MIC-1 compound according to embodiment 15, wherein the calculated pI is higher than 5.1.

24. The MIC-1 compound according to embodiment 15, wherein the calculated pI is in the range of 6.5-3.0, 6.5-3.5, 6.5-4.0, 6.1-3.0, 6.1-3.5, 6.1-4.0, 6.1-4.7, 6.1-4.9, 6.1-5.0, 6.1-5.1, 6.0-3.0, 6.0-3.5, 6.0-4.0, 5.9-3.0, 5.9-3.5, 5.9-4.0, 5.9-5.0, 5.9-5.1, 5.8-3.0, 5.8-3.5, 5.8-4.0, 5.8-5.1, 5.8-5.2, 5.5-3.0, 5.5-3.5, 5.5-4.0, or 5.0-4.0.

25. The MIC-1 compound according embodiment 15, wherein the calculated pI is in the range of 5.8-5.2.

26. The MIC-1 compound according to any of the preceding embodiments, wherein the amino acid extension comprises 3 to 200 amino acid residues.

27. The MIC-1 compound according to any of the preceding embodiments, wherein the amino acid extension is in the range of 3-100, 3-50, 3-40, 3-30, 5-100, 5-50, 5-40, 5-30, 10-100, 10-50, 10-40, 10-30, 3-36, 3-30, 3-25, 3-24, 3-12, 4-36, 4-30, 4-24, 4-12, 5-36, 5-30, 5-24, 5-12, 6-36, 6-30, 6-24, 6-12, 7-36, 7-30, 7-24, 7-12, 8-36, 8-30, 8-24, 8-12, 30-36, 32-36, 30-34, or 30-32 amino acid residues in length.

28. The MIC-1 compound according to any of the preceding embodiments, wherein the amino acid extension is in the range of 3-36 or 30-32 amino acid residues in length.

29. The MIC-1 compound according to any of the preceding embodiments, wherein the amino acid extension has a surplus of acidic amino acid residues (Aspartic acid or Glutamic acid) of at least 3, 4, 5, 6, 7, 8, 9 or 10 compared to the number of basic amino acid residues (Lysine, Arginine or Histidine).

30. The MIC-1 compound according to any of the preceding embodiments, wherein the amino acid extension comprise at least 10%, 15%, 20%, 25%, 30%, 40%, 50%, 60%, 70% or 75% surplus of acidic amino acid residues (Aspartic acid or Glutamic acid) compared to number of basic amino acid residues (Lysine or Arginine or Histidine).

31. The MIC-1 compound according to embodiment 30, wherein the amino acid extension comprise at least 10% acidic amino acid residues.

32. The MIC-1 compound according to embodiment 30, wherein the amino acid extension comprise at least 15% acidic amino acid residues.

33. The MIC-1 compound according to embodiment 11, wherein the amino acid extension comprise at least 25% acidic amino acid residues.

34. The MIC-1 compound according to any one of embodiments 1-33, wherein the amino acid extension is composed of amino acid residues selected among the group consisting of A, C, E, G, P, S, T, Q, N and D and wherein the amino acid extension comprises at least three E and/or D amino acid residues.

35. The MIC-1 compound according to embodiment 34, wherein the amino acid extension is composed of amino acid residues A, C, E, G, P, S and T.

36. The MIC-1 compound according to embodiment 35, wherein the amino acid extension comprises at least three E and at least one P.

37. The MIC-1 compound according to embodiment 36, wherein the amino acid extension comprises at least 6 Ser, 4 Pro, 4 Gly, 4 Thr, 4 Glu and 2 Ala.

38. The MIC-1 compound according to embodiment 37, wherein the amino acid extension comprises two of sequences selected from the group consisting of SPAGSPTSTEEG, TSESATPESGPG, TSTEPSEGSAPG and SEPATSGSETPG, and wherein one of the amino acid of the amino acid extension is replaced with Cysteine.

39. The MIC-1 compound according to embodiment 38, wherein the amino acid extension further comprises 6-8 consecutive amino acids of SPAGSPTSTEEG, TSESATPESGPG, TSTEPSEGSAPG or SEPATSGSETPG, such as the first 6-8 amino acid residues, the last 6-8 residues or the internal 6-8 residues, and wherein one of the amino acid of the amino acid extension is replaced with Cysteine.

40. The MIC-1 compound according to any one of embodiments 3-39, wherein Cysteine locates in any position of the N-terminal amino acid extension.

41. The MIC-1 compound according to embodiment 40, wherein the distance between the Cysteine residue of the N-terminal extension and the N-terminal amino acid of the MIC-1 polypeptide is at least 1, 3, 5, 10, 15, 19, 23, 26, 29, or 32 amino acids (including Cysteine residue of the N-terminal extension, but not including N-terminal amino acid of MIC-1 polypeptide).

42. The MIC-1 compound according to embodiment 40, wherein the distance between Cysteine residue of the N-terminal extension and the N-terminal amino acid of the MIC-1 polypeptide is at least 10, 11, 12, 13, 14, 15, 16, 17, 18, 19, 20, 21, 22, 23, 24, 25, 26, 27, 28, 29, 30, 31 or 32 amino acids (including Cysteine residue of the N-terminal extension, but not including N-terminal amino acid of MIC-1 polypeptide).

43. The MIC-1 compound according to embodiment 42, wherein the distance between Cysteine residue of the N-terminal extension and the N-terminal amino acid of the MIC-1 polypeptide is 26-29 amino acids (including Cysteine residue of the N-terminal extension, but not including N-terminal amino acid of MIC-1 polypeptide).

44. The MIC-1 compound according to any one of the preceding embodiments, wherein the amino acid extension starts with S.

45. The MIC-1 compound according to any one of the preceding embodiments, wherein the amino acid extension starts with SE.

46. The MIC-1 compound according to any one of the preceding embodiments, wherein the amino acid extension starts with SEP.

47. The MIC-1 compound according to any one of the preceding embodiments, wherein the amino acid extension comprises one or more of the following sequences

```
                                            (SEQ ID NO: 223)
SEPATCGSETPGTSESATPESGPGTSTEPS, (SEQ ID NO: 224)
SEPATSGCETPGTSESATPESGPGTSTEPS, (SEQ ID NO: 225)
SEPCTSGSETPGTSESATPESGPGTSTEPSEG, (SEQ ID NO: 240)
SEPCTSGSETPGTSESATPESGPGTSTEPS, (SEQ ID NO: 241)
SEPCTSGSETPGTSESATPESGPGTSTE, (SEQ ID NO: 242)
SEPCTSGSETPGTSESATPESGPG, (SEQ ID NO: 243)
SEPCTSGSETPGTSESATPES, (SEQ ID NO: 244)
SEPCTSGSETPG, (SEQ ID NO: 245)
SEPCTSGSETPGSPAGSPTSTEEGSPAGSP, (SEQ ID NO: 246)
SEPCTSGSETPGTSESATPESGPGSPAGSP, (SEQ ID NO: 247)
SEPCTSGSETPGTSTEPESGSAPGSPAGSP, (SEQ ID NO: 248)
SEPCTSGSETPGSPAGSPTSTEEGTSESAT, (SEQ ID NO: 249)
SEPCTSGSETPGTSESATPESGPGTSESAT, (SEQ ID NO: 250)
SEPCTSGSETPGTSTEPESGSAPGTSESAT, (SEQ ID NO: 251)
SEPCTSGSETPGSPAGSPTSTEEGTSTEPE, (SEQ ID NO: 252)
SEPCTSGSETPGTSESATPESGPGTSTEPE, (SEQ ID NO: 253)
SEPCTSGSETPGTSTEPESGSAPGTSTEPE, (SEQ ID NO: 254)
SEPCTSGSETPGSPAGSPTSTEEGSEPATS, (SEQ ID NO: 255)
SEPCTSGSETPGTSESATPESGPGSEPATS, (SEQ ID NO: 256)
SEPCTSGSETPGTSTEPESGSAPGSEPATS, (SEQ ID NO: 257)
SEPCTSGSETPGSPAGSPTSTEEGTSTEEG, (SEQ ID NO: 258)
SEPCTSGSETPGTSESATPESGPGTSTEEG, (SEQ ID NO: 259)
SEPCTSGSETPGTSTEPESGSAPGTSTEEG, (SEQ ID NO: 260)
SEPCTSGSETPGSPAGSPTSTEEGPESGPG, (SEQ ID NO: 261)
SEPCTSGSETPGTSESATPESGPGPESGPG, (SEQ ID NO: 262)
SEPCTSGSETPGTSTEPESGSAPGPESGPG, (SEQ ID NO: 263)
SEPCTSGSETPGSPAGSPTSTEEGSGSAPG,
```

-continued

SEPCTSGSETPGTSESATPESGPGSGSAPG, (SEQ ID NO: 264)

SEPCTSGSETPGTSTEPESGSAPGSGSAPG, (SEQ ID NO: 265)

SEPCTSGSETPGSPAGSPTSTEEGGSETPG, (SEQ ID NO: 266)

SEPCTSGSETPGTSESATPESGPGGSETPG, (SEQ ID NO: 267)

SEPCTSGSETPGTSTEPESGSAPGGSETPG, (SEQ ID NO: 268)

SEPCTSGSETPGSPAGSPTSTEEGTSESATPESGPG, (SEQ ID NO: 269)

SEPCTSGSETPGSPAGSPTSTEEGSPAGSPTSTEEG, (SEQ ID NO: 270)

SEPCTSGSETPGSPAGSPTSTEEGTSTEPESGSAPG, (SEQ ID NO: 271)

SEPCTSGSETPGTSESATPESGPGSPAGSPTSTEEG, (SEQ ID NO: 272)

SEPCTSGSETPGTSESATPESGPGTSESATPESGPG, (SEQ ID NO: 273)

SEPCTSGSETPGTSESATPESGPGTSTEPESGSAPG, (SEQ ID NO: 274)

SEPCTSGSETPGTSESATPESGPGSEPATSGSETPG, (SEQ ID NO: 275)

SEPCTSGSETPGTSTEPESGSAPGSPAGSPTSTEEG, (SEQ ID NO: 276)

SEPCTSGSETPGTSTEPESGSAPGTSESATPESGPG, (SEQ ID NO: 277)

SEPCTSGSETPGTSTEPESGSAPGTSTEPESGSAPG, (SEQ ID NO: 278)

SEPCTSGSETPGTSTEPESGSAPGSEPATSGSETPG, (SEQ ID NO: 279)

SEPCTSGSETPGSEPATSGSETPGSPAGSPTSTEEG, (SEQ ID NO: 280)

SEPCTSGSETPGSEPATSGSETPGTSESATPESGPG, (SEQ ID NO: 281)

SEPCTSGSETPGSEPATSGSETPGTSTEPESGSAPG, (SEQ ID NO: 282)

SEPCTSGSETPGSEPATSGSETPGSEPATSGSETPG, (SEQ ID NO: 283)

GPCEGPSEGPSEGPSEGPSEGPSEGPSE, (SEQ ID NO: 284)

GECPGEQPGEQPGEQPGEQPGEQPGEQP, (SEQ ID NO: 285)

PACEEEDDPDGGGSGGGSGGGS, (SEQ ID NO: 286)

PDECTEEETEGGGSGGGSGGGS, (SEQ ID NO: 287)

SEPATCGSETPGTSESATPESGPGTSTEPSEG, (SEQ ID NO: 226)

SEPATSCSETPGTSESATPESGPGTSTEPSEG, (SEQ ID NO: 227)

SEPACSGSETPGTSESATPESGPGTSTEPSEG, (SEQ ID NO: 229)

SEPATSGCETPGTSESATPESGPGTSTEPSEG, (SEQ ID NO: 230)

SEPATSGSECPGTSESATPESGPGTSTEPSEG, (SEQ ID NO: 231)

SEPATSGSETPCTSESATPESGPGTSTEPSEG, (SEQ ID NO: 232)

SEPATSGSETPGTCESATPESGPGTSTEPSEG, (SEQ ID NO: 233)

SEPATSGSETPGTSECATPESGPGTSTEPSEG, (SEQ ID NO: 234)

SEPATSGSETPGTSESACPESGPGTSTEPSEG, (SEQ ID NO: 235)

SEPATSGSETPGTSESATPECGPGTSTEPSEG, (SEQ ID NO: 236)

SEPATSGSETPGTSESATPESCPGTSTEPSEG, (SEQ ID NO: 237)

SEPATSGSETPGTSESATPESGPGTSCEPSEG, (SEQ ID NO: 238)

SEPATSGSETPGTSESATPESGPGTSTEPCEG. (SEQ ID NO: 239)

48. The MIC-1 compound according to any one of embodiments 1-2 and 5-33 wherein the amino acid extension is composed of amino acid residues selected among the group consisting of A, E, G, P, S, T, D, N, and Q wherein the amino acid extension comprises at least three E and/or D amino acid residues.

49. The MIC-1 compound according to any of the preceding embodiments, wherein the amino acid extension is composed of amino acid residues selected among the group consisting of A, E, G, P, S, T, Q and D, wherein the amino acid extension comprises at least three E and/or D amino acid residues.

50. The MIC-1 compound according to embodiment 48 or 49, wherein the amino acid extension comprises at least three E and at least one P.

51. The MIC-1 compound according to embodiment 50, wherein the amino acid extension further comprises S, G, T and A.

52. The MIC-1 compound according to embodiment 51, wherein the amino acid extension comprises 6 Ser, 4 Pro, 4 Gly, 4 Thr, 4 Glu and 2 Ala.

53. The MIC-1 compound according to embodiment 51, wherein the amino acid extension comprises two of sequences selected from the group consisting of SPAGSPTSTEEG, TSESATPESGPG, TSTEPSEGSAPG and SEPATSGSETPG.

54. The MIC-1 compound according to embodiment 53, wherein the amino acid extension further comprises 6-8 consecutive amino acids of SPAGSPTSTEEG, TSESATPESGPG, TSTEPSEGSAPG or SEPATSGSETPG, such as the first 6-8 amino acid residues, the last 6-8 residues or the internal 6-8 residues.

55. The MIC-1 compound according to any one of embodiments 48 to 54, wherein the amino acid extension starts with S.

56. The MIC-1 compound according embodiment 55, wherein the amino acid extension starts with SE.

57. The MIC-1 compound according to embodiment 56, wherein the amino acid extension starts with SEP.

58. The MIC-1 compound according to any one of embodiments 1-2 and 5-33, wherein the amino acid extension comprises one or more of the following sequences SPAGSP (SEQ ID NO:4), TSESAT (SEQ ID NO:5), TSTEPE (SEQ ID NO:6), SEPATS (SEQ ID NO:7), TSTEEG (SEQ ID NO:8), PESGPG (SEQ ID NO:9), SGSAPG (SEQ ID NO:10), GSETPG (SEQ ID NO:11), SEPATSGSETPGSPAGSPTSTEEG (SEQ ID NO:12), SEPATSGSETPGTSESATPESGPG (SEQ ID NO:13), SEPATSGSETPGTSTEPESGSAPG (SEQ ID NO:14), SEPATSGSETPGSPAGSPTSTEEGSPAGSP (SEQ ID NO:15), SEPATSGSETPGTSESATPESGPGSPAGSP (SEQ ID NO:16), SEPATSGSETPGTSTEPESGSAPGSPAGSP (SEQ ID NO:17), SEPATSGSETPGSPAGSPTSTEEGTSESAT (SEQ ID NO:18), SEPATSGSETPGTSESATPESGPGTSESAT (SEQ ID NO:19), SEPATSGSETPGTSTEPESGSAPGTSESAT (SEQ ID NO:20), SEPATSGSETPGSPAGSPTSTEEGTSTEPE (SEQ ID NO:21), SEPATSGSETPGTSESATPESGPGTSTEPE (SEQ ID NO:22), SEPATSGSETPGTSTEPESGSAPGTSTEPE (SEQ ID NO:23), SEPATSGSETPGSPAGSPTSTEEGSEPATS (SEQ ID NO:24), SEPATSGSETPGTSESATPESGPGSEPATS (SEQ ID NO:25), SEPATSGSETPGTSTEPESGSAPGSEPATS (SEQ ID NO:26), SEPATSGSETPGSPAGSPTSTEEGTSTEEG (SEQ ID NO:27), SEPATSGSETPGTSESATPESGPGTSTEEG (SEQ ID NO:28), SEPATSGSETPGTSTEPESGSAPGTSTEEG (SEQ ID NO:29), SEPATSGSETPGSPAGSPTSTEEGPESGPG (SEQ ID NO:30), SEPATSGSETPGTSESATPESGPGPESGPG (SEQ ID NO:31), SEPATSGSETPGTSTEPESGSAPGPESGPG (SEQ ID NO:32), SEPATSGSETPGSPAGSPTSTEEGSGSAPG (SEQ ID NO:33), SEPATSGSETPGTSESATPESGPGSGSAPG (SEQ ID NO:34), SEPATSGSETPGTSTEPESGSAPGSGSAPG (SEQ ID NO:35), SEPATSGSETPGSPAGSPTSTEEGGSETPG (SEQ ID NO:36), SEPATSGSETPGTSESATPESGPGGSETPG (SEQ ID NO:37), SEPATSGSETPGTSTEPESGSAPGGSETPG (SEQ ID NO:38), SEPATSGSETPGTSESATPESGPGTSTEPS (SEQ ID NO:70), SEPATSGSETPGTSESATPESGPGTSTEPSEG (SEQ ID NO:71), SEPATSGSETPGSPAGSPTSTEEGTSESATPESGPG (SEQ ID NO:39), SEPATSGSETPGSPAGSPTSTEEGSPAGSPTSTEEG (SEQ ID NO:40), SEPATSGSETPGSPAGSPTSTEEGTSTEPESGSAPG (SEQ ID NO:41), SEPATSGSETPGTSESATPESGPGSPAGSPTSTEEG (SEQ ID NO:42), SEPATSGSETPGTSESATPESGPGTSESATPESGPG (SEQ ID NO:43), SEPATSGSETPGTSESATPESGPGTSTEPESGSAPG (SEQ ID NO:44), SEPATSGSETPGTSESATPESGPGSEPATSGSETPG (SEQ ID NO:45), SEPATSGSETPGTSTEPESGSAPGSPAGSPTSTEEG (SEQ ID NO:46), SEPATSGSETPGTSTEPESGSAPGTSESATPESGPG (SEQ ID NO:47), SEPATSGSETPGTSTEPESGSAPGTSTEPESGSAPG (SEQ ID NO:48), SEPATSGSETPGTSTEPESGSAPGSEPATSGSETPG (SEQ ID NO:49), SEPATSGSETPGSEPATSGSETPGSPAGSPTSTEEG (SEQ ID NO:50), SEPATSGSETPGSEPATSGSETPGTSESATPESGPG (SEQ ID NO: 51), SEPATSGSETPGSEPATSGSETPGTSTEPESGSAPG (SEQ ID NO:52), SEPATSGSETPGSEPATSGSETPGSEPATSGSETPG (SEQ ID NO:53), GEPS (SEQ ID NO:118), GPSE (SEQ ID NO:119), GPES (SEQ ID NO: 120), GSPE (SEQ ID NO:121), GSEP (SEQ ID NO:122), GEPQ (SEQ ID NO:123), GEQP (SEQ ID NO: 124), GPEQ (SEQ ID NO: 125), GPQE (SEQ ID NO:126), GQEP (SEQ ID NO: 127) or GQPE (SEQ ID NO:128), PEDEETPEQE (SEQ ID NO:129), PDEGTEEETE (SEQ ID NO:130), PAAEEEDDPD (SEQ ID NO: 131), AEPDEDPQSED (SEQ ID NO:132), AEPDEDPQSE (SEQ ID NO:133), AEPEEQEED (SEQ ID NO:134), AEPEEQEE (SEQ ID NO:135), GGGS (SEQ ID NO:136), GSGS (SEQ ID NO: 137), GGSS (SEQ ID NO: 138) and SSSG (SEQ ID NO: 139).

59. The MIC-1 compound according to any one of embodiments 1-2 and 5-33, wherein the amino acid extension comprises one or more of the following sequences SPAGSP (SEQ ID NO:4), TSESAT (SEQ ID NO:5), TSTEPE (SEQ ID NO:6), SEPATS (SEQ ID NO:7), TSTEEG (SEQ ID NO:8), PESGPG (SEQ ID NO:9), SGSAPG (SEQ ID NO:10), GSETPG (SEQ ID NO:11), SEPATSGSETPGSPAGSPTSTEEG (SEQ ID NO:12), SEPATSGSETPGTSESATPESGPG (SEQ ID NO:13), SEPATSGSETPGTSTEPESGSAPG (SEQ ID NO:14), SEPATSGSETPGSPAGSPTSTEEGSPAGSP (SEQ ID NO:15), SEPATSGSETPGTSESATPESGPGSPAGSP (SEQ ID NO:16), SEPATSGSETPGTSTEPESGSAPGSPAGSP (SEQ ID NO: 17), SEPATSGSETPGSPAGSPTSTEEGTSESAT (SEQ ID NO:18), SEPATSGSETPGTSESATPESGPGTSESAT (SEQ ID NO:19), SEPATSGSETPGTSTEPESGSAPGTSESAT (SEQ ID NO:20), SEPATSGSETPGSPAGSPTSTEEGTSTEPE (SEQ ID NO:21), SEPATSGSETPGTSESATPESGPGTSTEPE (SEQ ID NO:22), SEPATSGSETPGTSTEPESGSAPGTSTEPE (SEQ ID NO:23), SEPATSGSETPGSPAGSPTSTEEGSEPATS (SEQ ID NO:24), SEPATSGSETPGTSESATPESGPGSEPATS (SEQ ID NO:25), SEPATSGSETPGTSTEPESGSAPGSEPATS (SEQ ID NO:26), SEPATSGSETPGSPAGSPTSTEEGTSTEEG (SEQ ID NO:27), SEPATSGSETPGTSESATPESGPGTSTEEG (SEQ ID NO:28), SEPATSGSETPGTSTEPESGSAPGTSTEEG (SEQ ID NO:29), SEPATSGSETPGSPAGSPTSTEEGPESGPG (SEQ ID NO:30), SEPATSGSETPGTSESATPESGPGPESGPG (SEQ ID NO:31), SEPATSGSETPGTSTEPESGSAPGPESGPG (SEQ ID NO:32), SEPATSGSETPGSPAGSPTSTEEGSGSAPG (SEQ ID NO:33), SEPATSGSETPGTSESATPESGPGSGSAPG (SEQ ID NO:34), SEPATSGSETPGTSTEPESGSAPGSGSAPG (SEQ ID NO:35), SEPATSGSETPGSPAGSPTSTEEGGSETPG (SEQ ID NO:36), SEPATSGSETPGTSESATPESGPGGSETPG (SEQ ID NO:37), SEPATSGSETPGTSTEPESGSAPGGSETPG (SEQ ID NO:38), SEPATSGSETPGSPAGSPTSTEEGTSESATPESGPG (SEQ ID NO:39), SEPATSGSETPGSPAGSPTSTEEGSPAGSPTSTEEG (SEQ ID NO:40), SEPATSGSETPGSPAGSPTSTEEGTSTEPESGSAPG (SEQ ID NO:41), SEPATSGSETPGTSESATPESGPGSPAGSPTSTEEG (SEQ ID NO:42), SEPATSGSETPGTSESATPESGPGTSESATPESGPG (SEQ ID NO:43), SEPATSGSETPGTSESATPESGPGTSTEPESGSAPG (SEQ ID NO:44), SEPATSGSETPGTSESATPESGPGSEPATSGSETPG (SEQ ID NO:45), SEPATSGSETPGTSTEPESGSAPGSPAGSPTSTEEG (SEQ ID NO:46), SEPATSGSETPGTSTEPESGSAPGTSESATPESGPG (SEQ ID NO:47), SEPATSGSETPGTSTEPESGSAPGTSTEPESGSAPG (SEQ ID NO:48), SEPATSGSETPGTSTEPESGSAPGSEPATSGSETPG (SEQ ID NO:49), SEPATSGSETPGSEPATSGSETPGSPAGSPTSTEEG (SEQ ID NO:50), SEPATSGSETPGSEPATSGSETPGTSESATPESGPG (SEQ ID NO: 51), SEPATSGSETPGSEPATSGSETPGTSTEPESGSAPG (SEQ ID NO:52), SEPATSGSETPGSEPATSGSETPGSEPATSGSETPG (SEQ ID NO:53), GEPQ (SEQ ID NO:123), GEPS (SEQ ID NO:118), GGGS (SEQ ID NO:136), GSGS (SEQ ID NO:137), GGSS (SEQ ID NO:138), and SSSG (SEQ ID NO: 139).

60. The MIC-1 compound according to any one of embodiments 1-2 and 5-33, wherein the amino acid extension comprises any combination of any 2-6 of the following sequences SPAGSP (SEQ ID NO:4), TSESAT (SEQ ID NO:5), TSTEPE (SEQ ID NO:6), SEPATS (SEQ ID NO:7), TSTEEG (SEQ ID NO:8), PESGPG (SEQ ID NO:9), SGSAPG (SEQ ID NO:10), GSETPG (SEQ ID NO:11), GEPQ (SEQ ID NO: 123), GEPS (SEQ ID NO:118), GGGS (SEQ ID NO:136), GSGS (SEQ ID NO:137), GGSS (SEQ ID NO:138), and SSSG (SEQ ID NO:139).

61. The MIC-1 compound according to any one of embodiments 1-2 and 5-33, wherein the amino acid extension comprises one or more of the following sequences GEPS (SEQ ID NO:118), GPSE (SEQ ID NO:119), GPES (SEQ ID NO:120), GSPE (SEQ ID NO:121), GSEP (SEQ ID NO: 122), GEPQ (SEQ ID NO:123), GEQP (SEQ ID NO:124), GPEQ (SEQ ID NO:125), GPQE (SEQ ID NO:126), GQEP (SEQ ID NO: 127), GQPE (SEQ ID NO: 128), GGGS (SEQ ID NO: 136), GSGS (SEQ ID NO:137), GGSS (SEQ ID NO: 138), and SSSG (SEQ ID NO: 139).

62. The MIC-1 compound according to embodiment 61, wherein the amino acid extension comprises any combination of 2-9 of the following sequences GEPS (SEQ ID NO: 118), GPSE (SEQ ID NO:119), GPES (SEQ ID NO:120), GSPE (SEQ ID NO:121), GSEP (SEQ ID NO:122), GEPQ (SEQ ID NO:123), GEQP (SEQ ID NO:124), GPEQ (SEQ ID NO: 125), GPQE (SEQ ID NO: 126), GQEP (SEQ ID NO:127), GQPE (SEQ ID NO:128), GGGS (SEQ ID NO:136), GSGS (SEQ ID NO: 137), GGSS (SEQ ID NO: 138), and SSSG (SEQ ID NO: 139).

63. The MIC-1 compound according to any one of embodiments 1-2 and 5-33, wherein the amino acid extension comprises one or more of the following sequences GEPS (SEQ ID NO:118), GPSE (SEQ ID NO:119), GPES (SEQ ID NO:120), GSPE (SEQ ID NO:121), GSEP (SEQ ID NO: 122), GGGS (SEQ ID NO:136), GSGS (SEQ ID NO:137), GGSS (SEQ ID NO:138), and SSSG (SEQ ID NO:139).

64. The MIC-1 compound according to embodiment 63, wherein the amino acid extension comprises any combination of 2-9 of the following sequences GEPS (SEQ ID NO:118), GPSE (SEQ ID NO:119), GPES (SEQ ID NO:120), GSPE (SEQ ID NO:121), GSEP (SEQ ID NO:122), GGGS (SEQ ID NO:136), GSGS (SEQ ID NO: 137), GGSS (SEQ ID NO:138), and SSSG (SEQ ID NO:139).

65. The MIC-1 compound according to embodiment 64, wherein the amino acid extension comprises one or more of the following sequences GEPSGEPSGEPSGEPSGEPS (SEQ ID NO:140), GPSEGPSEGPSEGPSEGPSE (SEQ ID NO:141), GPESGPESGPESGPESGPES (SEQ ID NO:142), GSPEGSPEGSPEGSPEGSPE (SEQ ID NO:143), and GSEPGSEPGSEPGSEPGSEP (SEQ ID NO: 144).

66. The MIC-1 compound according to any one of embodiments 1-2 and 5-33, wherein the amino acid extension comprises one or more of the following sequences GEPQ (SEQ ID NO:123), GEQP (SEQ ID NO:124), GPEQ (SEQ ID NO:125), GPQE (SEQ ID NO:126), GQEP (SEQ ID NO: 127), GQPE (SEQ ID NO:128), GGGS (SEQ ID NO: 136), GSGS (SEQ ID NO:137), GGSS (SEQ ID NO:138), and SSSG (SEQ ID NO: 139).

67. The MIC-1 compound according to embodiment 66, wherein the amino acid extension comprises any combination of 2-9 of the following sequences GEPQ (SEQ ID NO: 123), GEQP (SEQ ID NO: 124), GPEQ (SEQ ID NO:125), GPQE (SEQ ID NO:126), GQEP (SEQ ID NO:127), GQPE (SEQ ID NO:128), GGGS (SEQ ID NO:136), GSGS (SEQ ID NO:137), GGSS (SEQ ID NO: 138), and SSSG (SEQ ID NO:139).

68. The MIC-1 compound according to embodiment 67, wherein the amino acid extension comprises one or more of the following sequences GEPQGEPQGEPQGEPQGEPQ (SEQ ID NO:145), GEQPGEQPGEQPGEQPGEQP (SEQ ID NO: 146), GPEQGPEQGPEQGPEQGPEQ (SEQ ID NO: 147), GPQEGPQEGPQEGPQEGPQE (SEQ ID NO: 148), GQEPGQEPGQEPGQEPGQEP (SEQ ID NO: 149), and GQPEGQPEGQPEGQPEGQPE (SEQ ID NO:150).

69. The MIC-1 compound according to any of the embodiments 1-2 and 5-33, wherein the amino acid extension comprises one or more of the following sequences PEDEETPEQE (SEQ ID NO:129), PDEGTEEETE (SEQ ID NO:130), PAAEEEDDPD (SEQ ID NO:131), AEPDEDPQSED (SEQ ID NO:132), AEPDEDPQSE (SEQ ID NO:133), AEPEEQEED (SEQ ID NO:134), and AEPEEQEE (SEQ ID NO: 135), GGGS (SEQ ID NO:136), GSGS (SEQ ID NO:137), GGSS (SEQ ID NO: 138) and SSSG (SEQ ID NO:139).

70. The MIC-1 compound according to any of the embodiments 1-2 and 5-33, wherein the amino acid extension comprises any combination of two to three of the following sequences PEDEETPEQE (SEQ ID NO:129), PDEGTEEETE (SEQ ID NO:130), PAAEEEDDPD (SEQ ID NO:131), AEPDEDPQSED (SEQ ID NO: 132), AEPDEDPQSE (SEQ ID NO:133), AEPEEQEED (SEQ ID NO: 134), AEPEEQEE (SEQ ID NO: 135) and AEEAEEAEEAEEAEE.

71. The MIC-1 compound according to any of the embodiments 1-2 and 5-33, wherein the amino acid extension comprises one or more of the following sequences SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:161, SEQ ID NO:162, SEQ ID NO: 181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194 and SEQ ID NO:195.

72. The MIC-1 compound according to any one of preceding embodiments, wherein the amino acid extension comprises 1-3 alanine amino acid residues N-terminally.

73. The MIC-1 compound according to any one of preceding embodiments, wherein the amino acid extension comprises 1-4 Glycine and Serine amino acid residues C-terminally.

74. The MIC-1 compound according to any one of preceding embodiments, wherein the amino acid extension comprises a (Gly-Ser)n or a (Ser-Gly)n sequence C-terminally, wherein n is an integer between 1-8.

75. The MIC-1 compound according to any one of preceding embodiments, wherein the amino acid extension comprises GGGS (SEQ ID NO:136), GSGS (SEQ ID NO: 137), GGSS (SEQ ID NO:138) or SSSG (SEQ ID NO:139)C-terminally.

76. The MIC-1 compound according to any of the preceding embodiments, wherein the MIC-1 polypeptide displays at least 80%, 85%, 90%, 91%, 92%, 93%, 94%, 95%, 96%, 97%, 98% or 99% sequence identity to wild type MIC-1 (SEQ ID NO:1).

77. The MIC-1 compound according to embodiment 70, wherein the MIC-1 polypeptide displays at least 95% sequence identity to wild type MIC-1 (SEQ ID NO: 1).

78. The MIC-1 compound according to any one of embodiments 1-70, wherein the MIC-1 polypeptide has a maximum of 10, 9, 8, 7, 6, 5, 4, 3, 2 or 1 amino acid modifications compared to MIC-1 of SEQ ID NO: 1.

79. The MIC-1 compound according to any one of embodiments 1-72, wherein the MIC-1 polypeptide has a maximum of 7, 6, 5, 4, 3 or 2 amino acid modifications compared to MIC-1 of SEQ ID NO:1.
80. The MIC-1 compound according to any one of the preceding embodiments wherein the MIC-1 polypeptide comprises one or more of the following substitutions P11E, H18E, R21E, A30E, M43L, M43E, A47E, R53E, A54E, M57E, M57L, H66E, R67E, L68E, K69E, A75E, A81E, P85E, M86F, M86L, Q90E, T92E, L105E, K107E, K69R, K107R and K91R compared to wild type MIC-1 (SEQ ID NO:1).
81. The MIC-1 compound according to any one of the preceding embodiments wherein the MIC-1 polypeptide comprises one or more of the following substitutions R2S, R2A, R2E, N3S, N3E, N3A, N3T, N3P, N3G, N3V, N3H, N3Y or N3Q compared to MIC-1 of SEQ ID NO:1.
82. The MIC-1 compound according to any one of the preceding embodiments wherein the MIC-1 polypeptide comprises a deletion of N3 (des-N3) compared to MIC-1 of SEQ ID NO: 1.
83. The MIC-1 compound according to any one of the preceding embodiments wherein the MIC-1 polypeptide comprises a M57E or M57L substitution compared to MIC-1 of SEQ ID NO:1.
84. The MIC-1 compound according to any one of the preceding embodiments wherein the MIC-1 polypeptide comprises a M86L or M86F substitution compared to MIC-1 of SEQ ID NO:1.
85. The MIC-1 compound according to embodiment 84 wherein the MIC-1 polypeptide further comprises a Q90E or T92E substitution compared to MIC-1 of SEQ ID NO: 1.
86. The MIC-1 compound according to any one of the preceding embodiments wherein the MIC-1 polypeptide comprises a H66E substitution compared to MIC-1 of SEQ ID NO:1.
87. The MIC-1 compound according to any one of the preceding embodiments wherein the MIC-1 polypeptide comprises a R67E substitution compared to MIC-1 of SEQ ID NO: 1.
88. The MIC-1 compound according to any one of the preceding embodiments wherein the MIC-1 polypeptide comprises a deletion of the first 3, 4, 5 or 6 residues compared to MIC-1 of SEQ ID NO:1.
89. The MIC-1 compound according to any one of the preceding embodiments wherein the MIC-1 polypeptide comprises a deletion of the first 3 residues compared to MIC-1 of SEQ ID NO:1.
90. The MIC-1 compound according to any one of embodiments 1-75, wherein the MIC-1 polypeptide has a sequence according to SEQ ID NO:154 (M43L/des-N3).
91. The MIC-1 compound according to any one of embodiments 1-75, wherein the MIC-1 polypeptide has a sequence according to SEQ ID NO:155 (M43L/Δ1-3).
92. The MIC-1 compound according to any one of embodiments 1-75, wherein the MIC-1 polypeptide has a sequence according to SEQ ID NO:156 (M57E/H66E/des-N3).
93. The MIC-1 compound according to any one of embodiments 1-75, wherein the MIC-1 polypeptide has a sequence according to SEQ ID NO:157 (M57L/Δ1-3).
94. Compound according to any one of embodiments 1-75, wherein the MIC-1 polypeptide has a sequence according to SEQ ID NO:158 (M57L/des-N3).
95. The MIC-1 compound according to any one of embodiments 1-75, wherein the MIC-1 polypeptide has a according to SEQ ID NO:159 (M86L/Δ1-3).
96. The MIC-1 compound according to any one of embodiments 1-75, wherein the MIC-1 polypeptide has a sequence according to SEQ ID NO:160 (M86L/des-N3) or SEQ ID NO:222 (M57L, M86L/des-N3).
97. The MIC-1 compound according to any one of embodiments 1-75, wherein the MIC-1 polypeptide has a sequence according to SEQ ID NO:1.
98. The MIC-1 compound according to any one of preceding embodiments, wherein the MIC-1 polypeptide and the N-terminal amino acid extension together comprises an amino acid sequence according to SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 164,

```
                                               (SEQ ID NO: 288)
SEPCTSGSETPGTSESATPESGPGTSTEPSEGARGDHCPLGPGRCCRLHT

VRASLEDLGWADWVLSPREVQVTMCIGACPSQFRAANMHAQIKTSLHRLK

PDTVPAPCCVPASYNPMVLIQKTDTGVSLQTYDDLLAKDCHCI, (SEQ ID NO: 289)
SEPATSCSETPGTSESATPESGPGTSTEPSEGARGDHCPLGPGRCCRLHT

VRASLEDLGWADWVLSPREVQVTMCIGACPSQFRAANLHAQIKTSLHRLK

PDTVPAPCCVPASYNPLVLIQKTDTGVSLQTYDDLLAKDCHCI, (SEQ ID NO: 290)
SEPCTSGSETPGTSESATPESGPGTSTEPSEGARGDHCPLGPGRCCRLHT

VRASLEDLGWADWVLSPREVQVTMCIGACPSQFRAANLHAQIKTSLHRLK

PDTVPAPCCVPASYNPLVLIQKTDTGVSLQTYDDLLAKDCHCI, (SEQ ID NO: 291)
SEPATCGSETPGTSESATPESGPGTSTEPSEGARGDHCPLGPGRCCRLHT

VRASLEDLGWADWVLSPREVQVTMCIGACPSQFRAANMHAQIKTSLHRLK

PDTVPAPCCVPASYNPMVLIQKTDTGVSLQTYDDLLAKDCHCI, (SEQ ID NO: 292)
SEPATSGSETPGTSESACPESGPGTSTEPSEGARGDHCPLGPGRCCRLHT

VRASLEDLGWADWVLSPREVQVTMCIGACPSQFRAANLHAQIKTSLHRLK

PDTVPAPCCVPASYNPLVLIQKTDTGVSLQTYDDLLAKDCHCI, (SEQ ID NO: 293)
SEPATSGSETPGTSESATPESGPGTSTEPCEGARGDHCPLGPGRCCRLHT

VRASLEDLGWADWVLSPREVQVTMCIGACPSQFRAANLHAQIKTSLHRLK

PDTVPAPCCVPASYNPLVLIQKTDTGVSLQTYDDLLAKDCHCI, (SEQ ID NO: 294)
SEPATSGSETPGSEPATSGSETPGGDHCPLGPGRCCRLHTVRASLEDLGW

ADWVLSPREVQVTMCIGACPSQFRAANEHAQIKTSLERLKPDTVPAPCCV

PASYNPMVLIQKTDTGVSLQTYDDLLAKDCHCI, (SEQ ID NO: 295)
SEPATSGSETPGTSESATPESGPGTSTEPSEGARGDHCPLGPGRCCRLHT

VRASLEDLGWADWVLSPREVQVTMCIGACPSQFRAANLHAQIKTSLHRLK

PDTVPAPCCVPASYNPMVLIQKTDTGVSLQTYDDLLAKDCHCI,
```

(SEQ ID NO: 296)
SEPATSGSETPGTSESATPESGPGTSTEPSARGDHCPLGPGRCCRLHTVR
ASLEDLGWADWVLSPREVQVTMCIGACPSQFRAANLHAQIKTSLHRLKPD
TVPAPCCVPASYNPLVLIQKTDTGVSLQTYDDLLAKDCHCI, (SEQ ID NO: 297)
SEPATSGSETPGTSESATPESGPGTSTEPSEGARGDHCPLGPGRCCRLHT
VRASLEDLGWADWVLSPREVQVTMCIGACPSQFRAANMHAQIKTSLHRLK
PDTVPAPCCVPASYNPMVLIQKTDTGVSLQTYDDLLAKDCHCI, (SEQ ID NO: 298)
SEPATSGSETPGTSESATPESGPGTSTEPSARGDHCPLGPGRCCRLHTVR
ASLEDLGWADWVLSPREVQVTMCIGACPSQFRAANMHAQIKTSLHRLKPD
TVPAPCCVPASYNPMVLIQKTDTGVSLQTYDDLLAKDCHCI, (SEQ ID NO: 299)
SEPATSGSETPGSEPATSGSETPGTSTEPSARGDHCPLGPGRCCRLHTVR
ASLEDLGWADWVLSPREVQVTMCIGACPSQFRAANMHAQIKTSLHRLKPD
TVPAPCCVPASYNPMVLIQKTDTGVSLQTYDDLLAKDCHCI, (SEQ ID NO: 300)
SAPATSGSATPGSAPATSGSATPGGDHCPLGPGRCCRLHTVRASLEDLGW
ADWVLSPREVQVTMCIGACPSQFRAANMHAQIKTSLHRLKPDTVPAPCCV
PASYNPMVLIQKTDTGVSLQTYDDLLAKDCHCI, (SEQ ID NO: 301)
SEPCTSGSETPGTSESATPESGPGTSTEPSARGDHCPLGPGRCCRLHTVR
ASLEDLGWADWVLSPREVQVTMCIGACPSQFRAANMHAQIKTSLHRLKPD
TVPAPCCVPASYNPMVLIQKTDTGVSLQTYDDLLAKDCHCI, (SEQ ID NO: 302)
SEPATCGSETPGTSESATPESGPGTSTEPSARGDHCPLGPGRCCRLHTVR
ASLEDLGWADWVLSPREVQVTMCIGACPSQFRAANMHAQIKTSLHRLKPD
TVPAPCCVPASYNPMVLIQKTDTGVSLQTYDDLLAKDCHCI, (SEQ ID NO: 303)
SEPATSGCETPGTSESATPESGPGTSTEPSEGARGDHCPLGPGRCCRLHT
VRASLEDLGWADWVLSPREVQVTMCIGACPSQFRAANLHAQIKTSLHRLK
PDTVPAPCCVPASYNPLVLIQKTDTGVSLQTYDDLLAKDCHCI, (SEQ ID NO: 304)
SEPATSGSECPGTSESATPESGPGTSTEPSEGARGDHCPLGPGRCCRLHT
VRASLEDLGWADWVLSPREVQVTMCIGACPSQFRAANLHAQIKTSLHRLK
PDTVPAPCCVPASYNPLVLIQKTDTGVSLQTYDDLLAKDCHCI, (SEQ ID NO: 305)
SEPATSGSETPCTSESATPESGPGTSTEPSEGARGDHCPLGPGRCCRLHT
VRASLEDLGWADWVLSPREVQVTMCIGACPSQFRAANLHAQIKTSLHRLK
PDTVPAPCCVPASYNPLVLIQKTDTGVSLQTYDDLLAKDCHCI, (SEQ ID NO: 306)
SEPATSGSETPGTCESATPESGPGTSTEPSEGARGDHCPLGPGRCCRLHT
VRASLEDLGWADWVLSPREVQVTMCIGACPSQFRAANLHAQIKTSLHRLK
PDTVPAPCCVPASYNPLVLIQKTDTGVSLQTYDDLLAKDCHCI, (SEQ ID NO: 307)
SEPATSGSETPGTSECATPESGPGTSTEPSEGARGDHCPLGPGRCCRLHT
VRASLEDLGWADWVLSPREVQVTMCIGACPSQFRAANLHAQIKTSLHRLK
PDTVPAPCCVPASYNPLVLIQKTDTGVSLQTYDDLLAKDCHCI, (SEQ ID NO: 308)
SEPATSGSETPGTSESATPECGPGTSTEPSEGARGDHCPLGPGRCCRLHT
VRASLEDLGWADWVLSPREVQVTMCIGACPSQFRAANLHAQIKTSLHRLK
PDTVPAPCCVPASYNPLVLIQKTDTGVSLQTYDDLLAKDCHCI, (SEQ ID NO: 309)
SEPATSGSETPGTSESATPESCPGTSTEPSEGARGDHCPLGPGRCCRLHT
VRASLEDLGWADWVLSPREVQVTMCIGACPSQFRAANLHAQIKTSLHRLK
PDTVPAPCCVPASYNPLVLIQKTDTGVSLQTYDDLLAKDCHCI, (SEQ ID NO: 310)
SEPATSGSETPGTSESATPESGPGTSCEPSEGARGDHCPLGPGRCCRLHT
VRASLEDLGWADWVLSPREVQVTMCIGACPSQFRAANLHAQIKTSLHRLK
PDTVPAPCCVPASYNPLVLIQKTDTGVSLQTYDDLLAKDCHCI, (SEQ ID NO: 311)
EEAEADDDDKESGDHCPLGPGRCCRLHTVRASLEDLGWADWVLSPREVQV
TMCIGACPSQFRAANMHAQIKTSLHRLKPDTVPAPCCVPASYNPMVLIQK
TDTGVSLQTYDDLLAKDCHCI,
or (SEQ ID NO: 312)
SEPATSGSETPGTSESATPESGPGTSTEPSEGARGDHCPLGPGRCCRLHT
VRASLEDLGWADWVLSPREVQVTMCIGACPSQFRAANLHAQIKTSLHRLR
PDTVPAPCCVPASYNPLVLIQRTDTGVSLQTYDDLLARDCHCI.

99. MIC-1 compound according to embodiment 1 with one of the following Formulas:

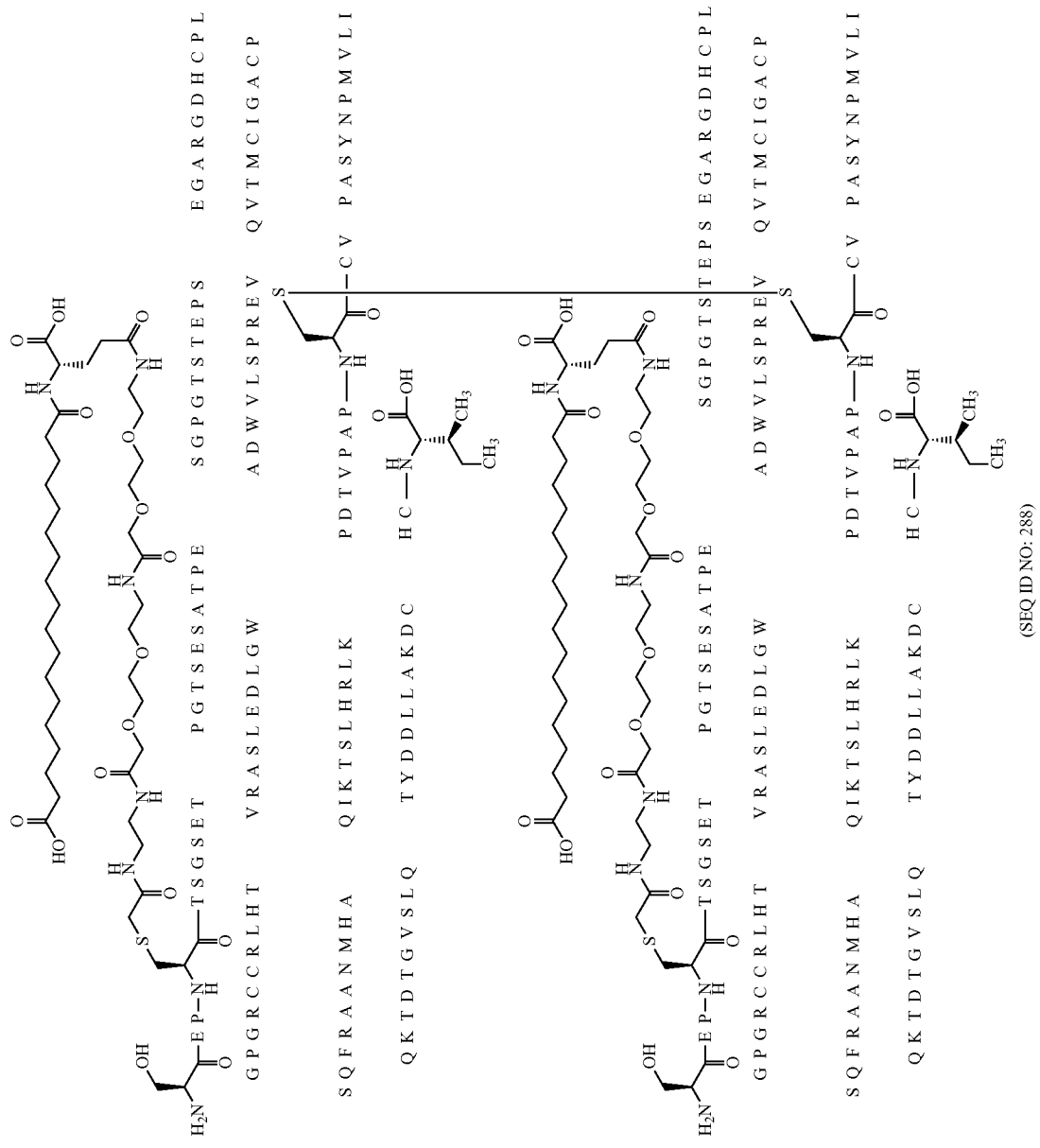

-continued
(Formula 02)
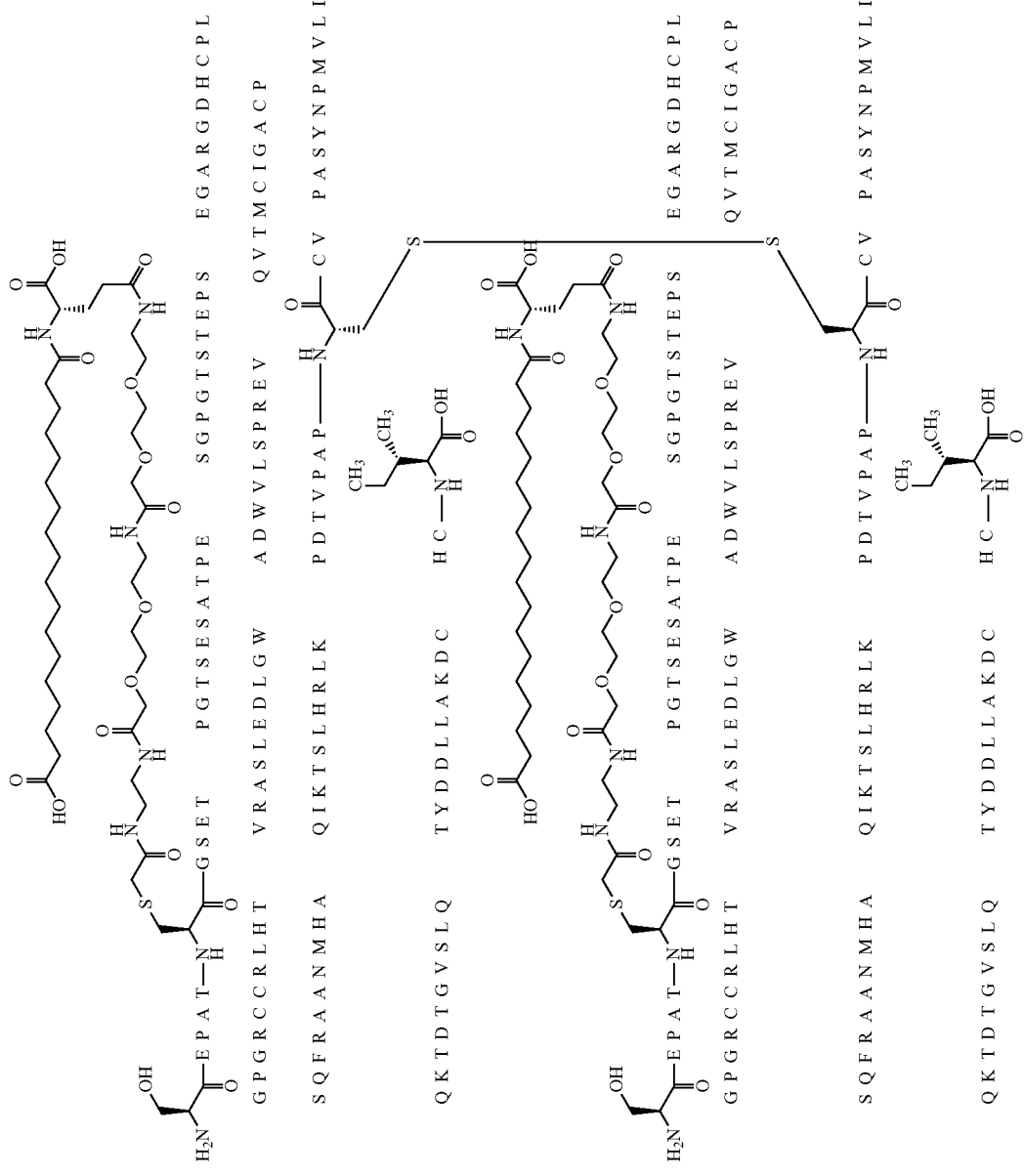
(SEQ ID NO: 291)

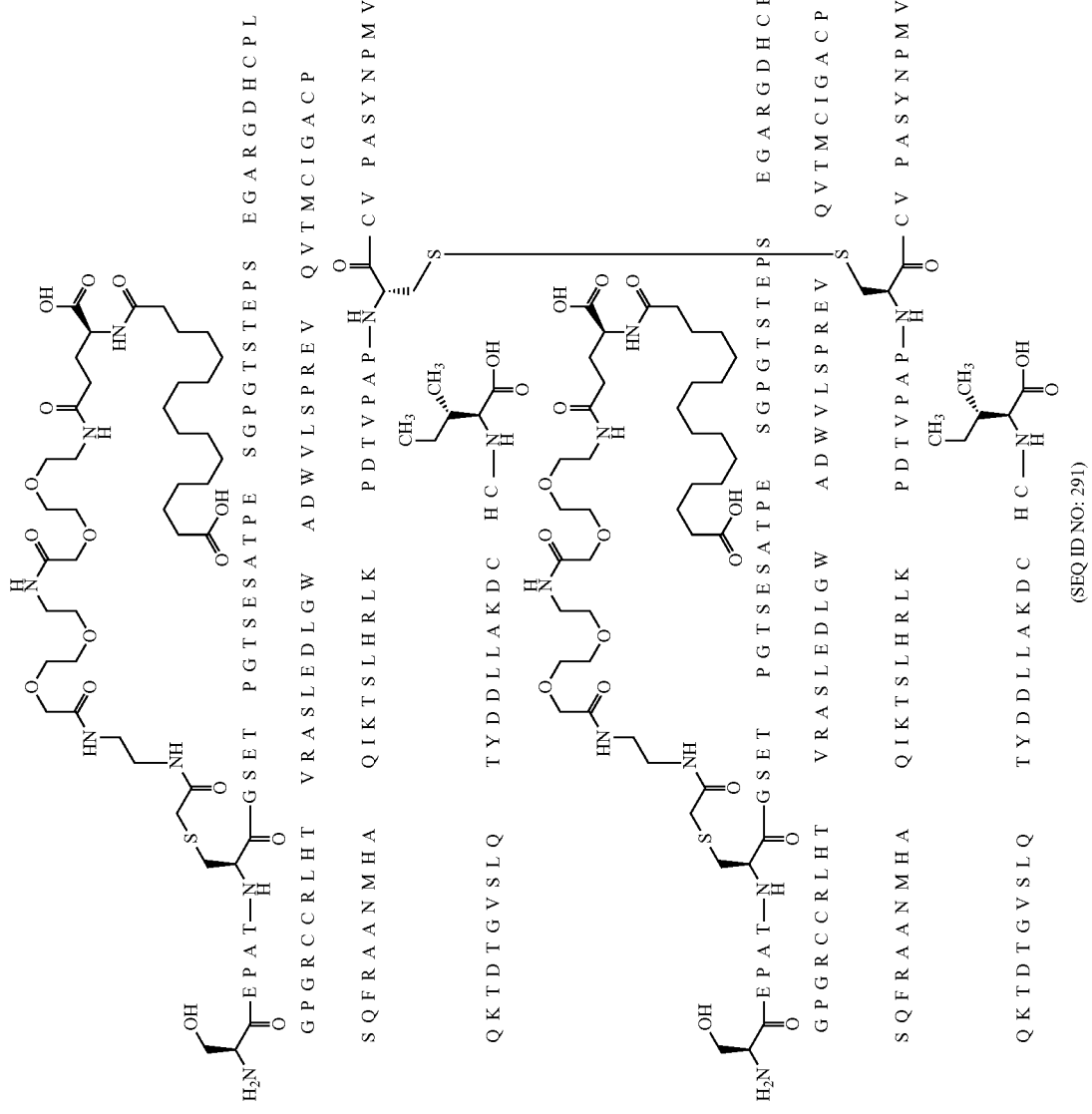
(Formula 03)
(SEQ ID NO: 291)

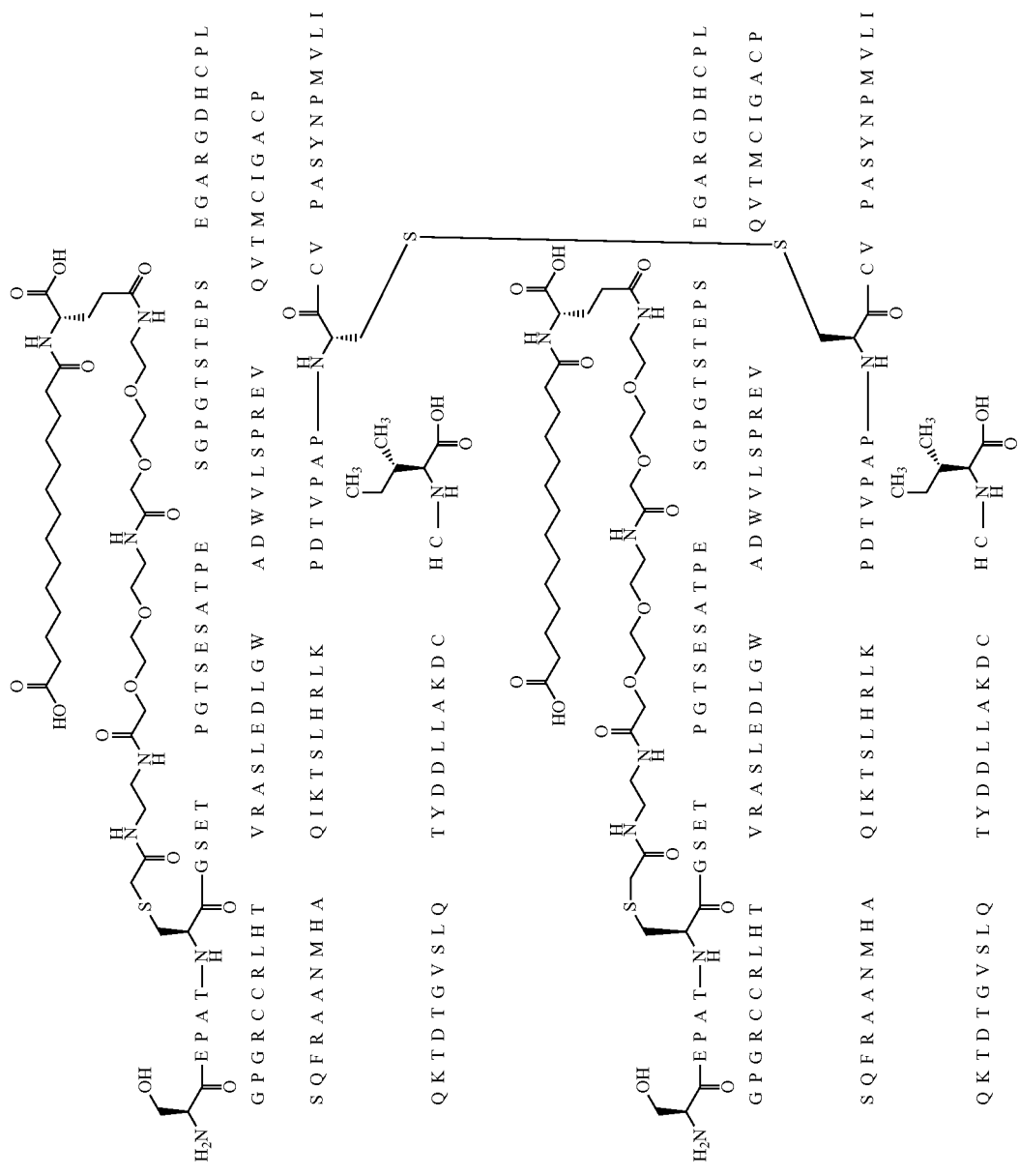
(Formula 04)
(SEQ ID NO: 291)

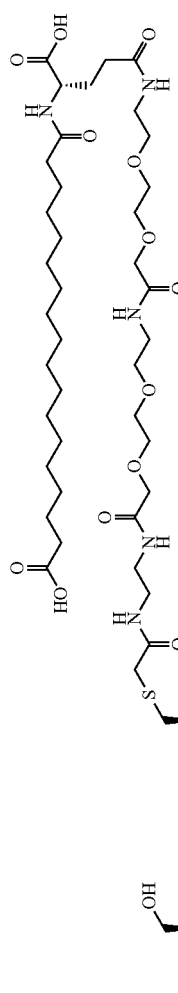

-continued
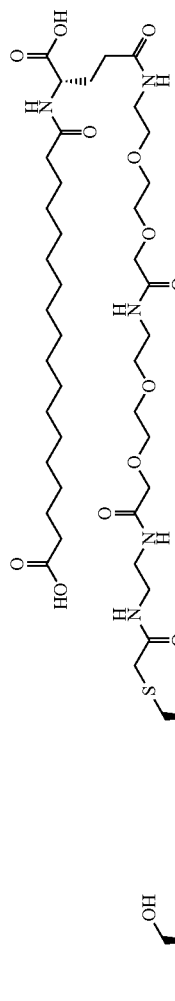
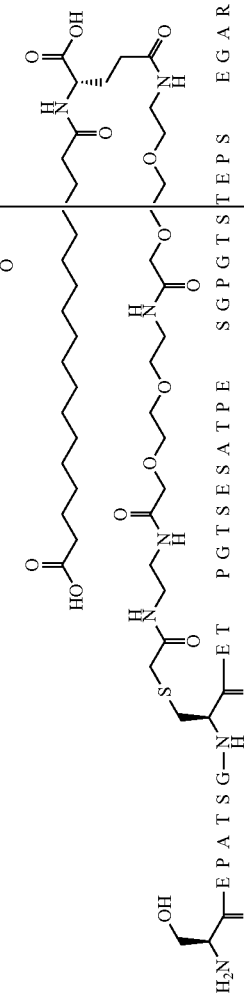
(Formula 06)
(SEQ ID NO: 303)

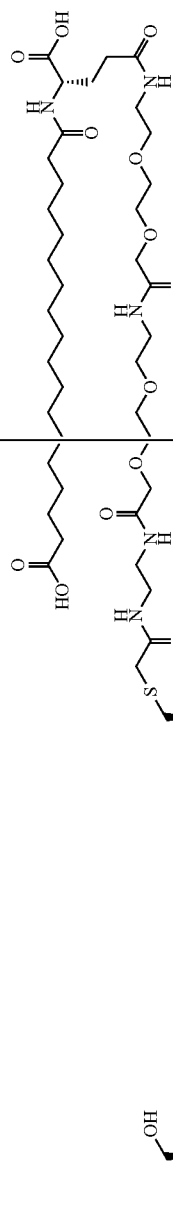
(Formula 07)
(SEQ ID NO: 292)

-continued
(Formula 08)
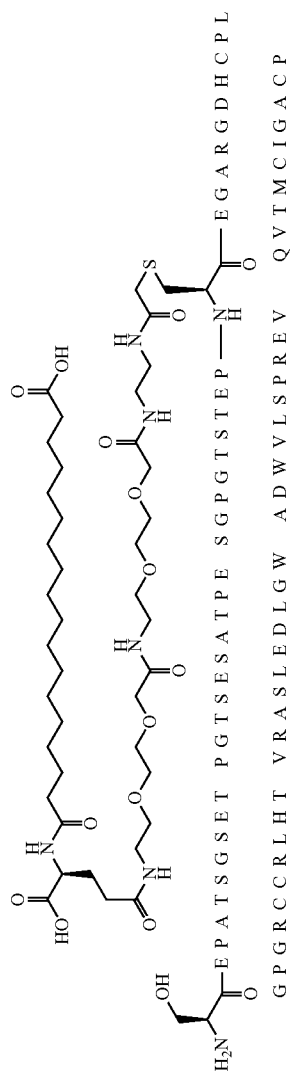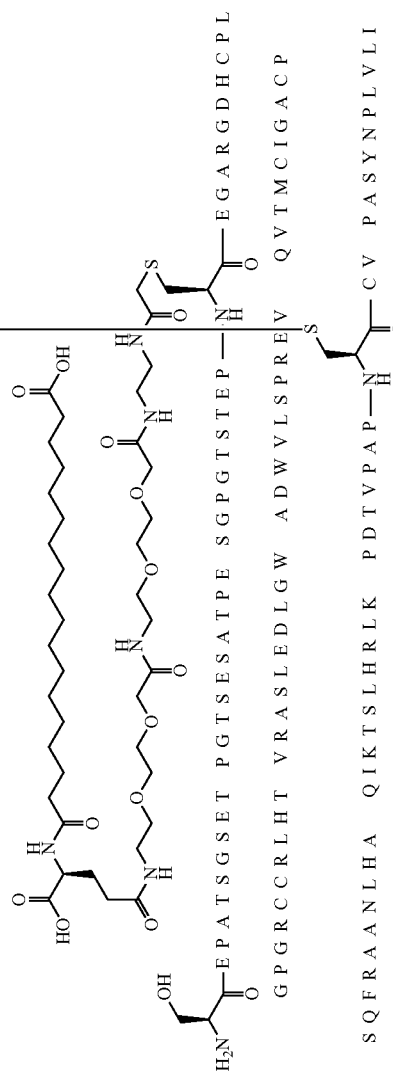
(SEQ ID NO: 293)

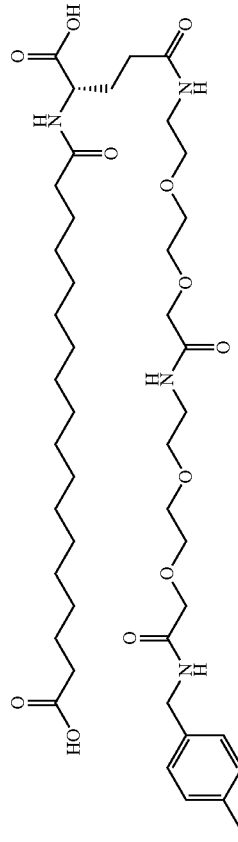

(Formula 10)

(SEQ ID NO: 164)

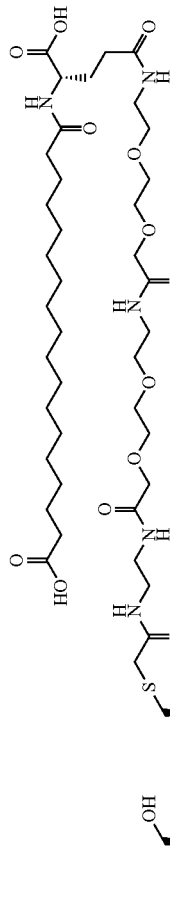
(Formula 11) (SEQ ID NO: 290)

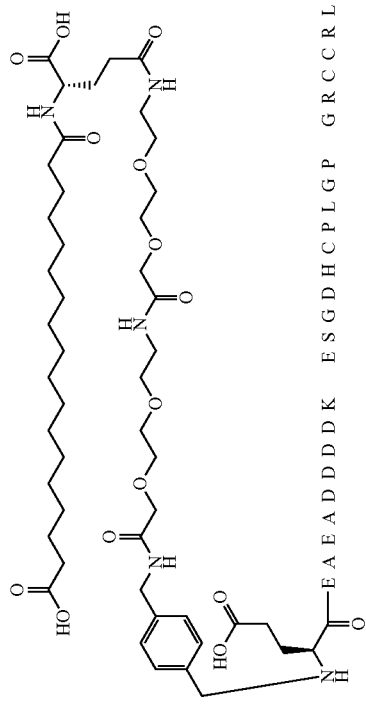

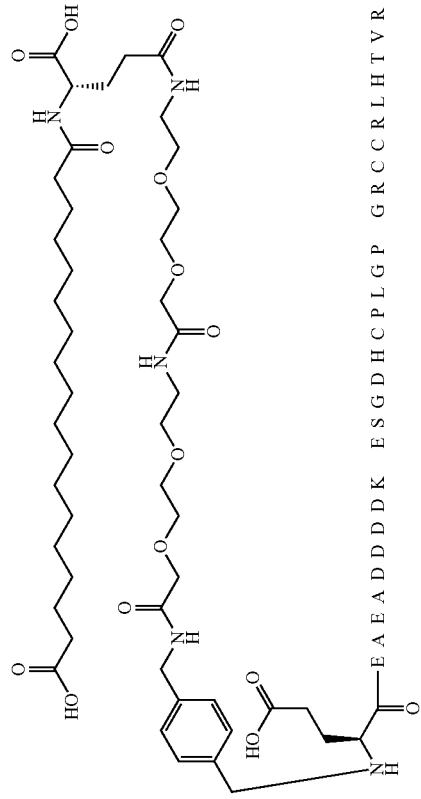
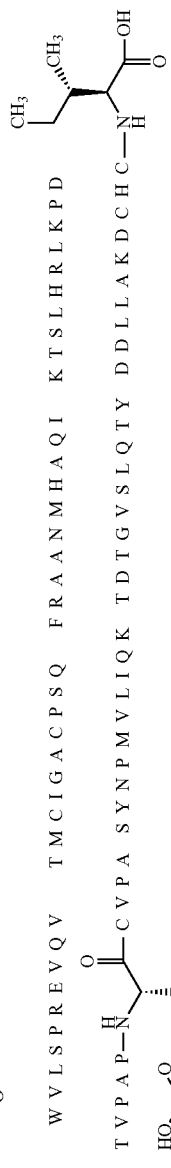
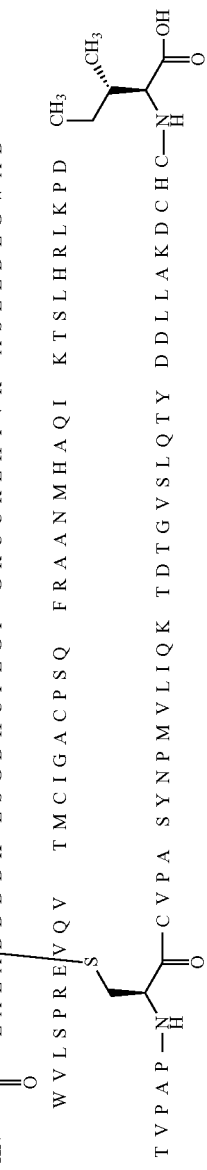
(Formula 13)
(SEQ ID NO: 311)

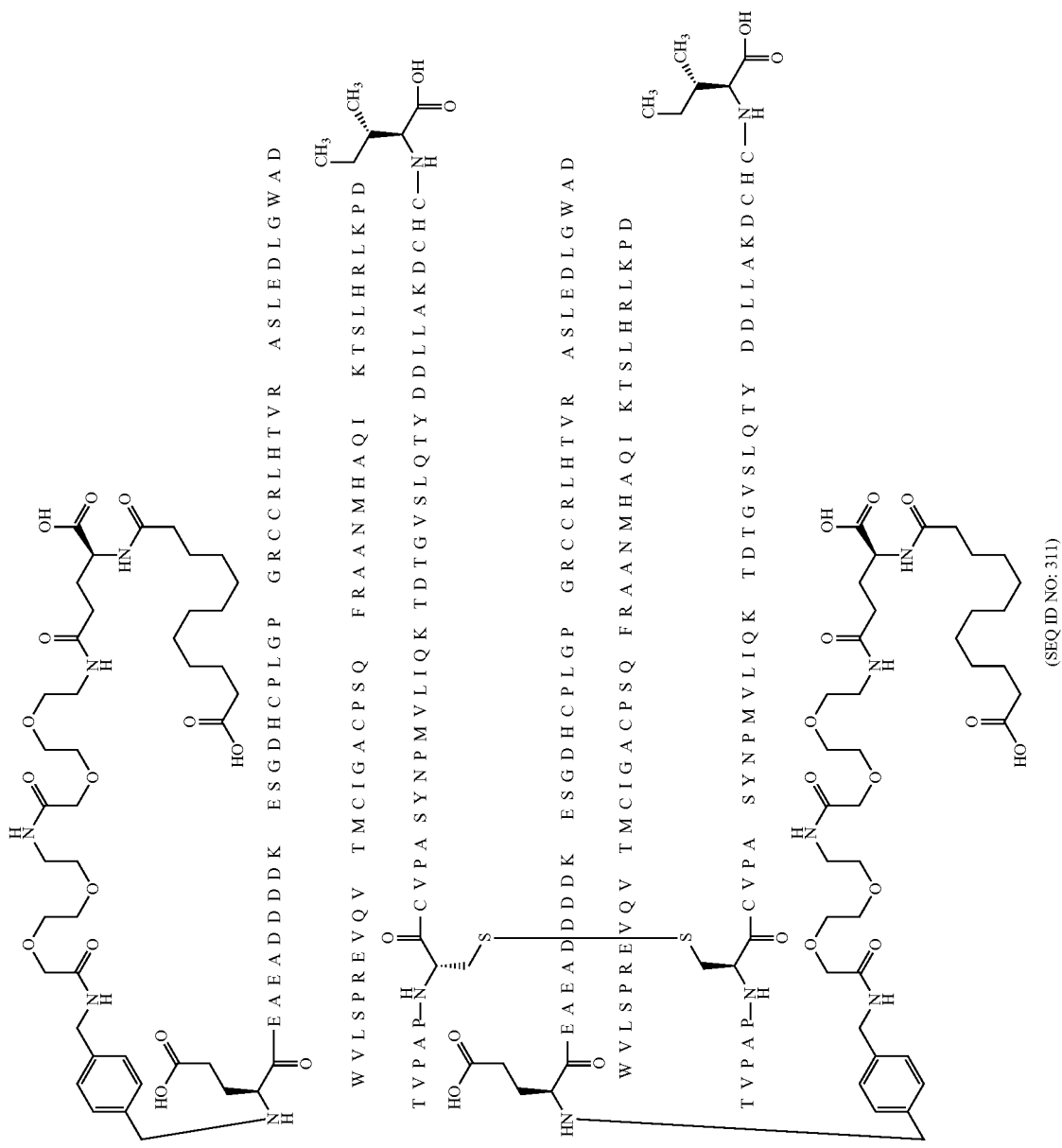

(Formula 15)
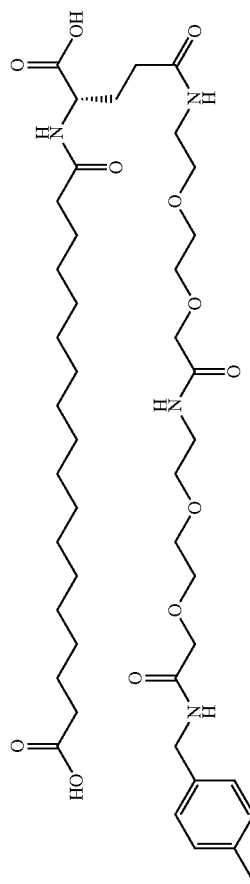
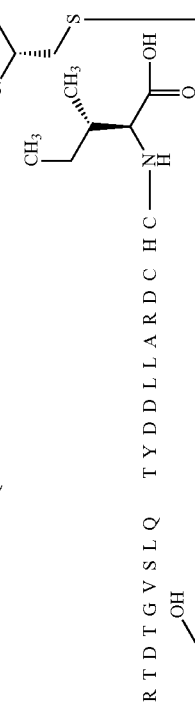
EPATSGSET PGTSESATPE SGPGTSTEPS EGARGDHCPL
GPGRCCRLHT VRASLEDLGW ADWVLSPREV QVTMCIGACP
SQFRAANLHA QIKTSLHRLK PDTVPAP
QRTDTGVSLQ TYDDLLARDC HC
EPATSGSET PGTSESATPE SGPGTSTEPS EGARGDHCPL
GPGRCCRLHT VRASLEDLGW ADWVLSPREV QVTMCIGACP (Formula 16)
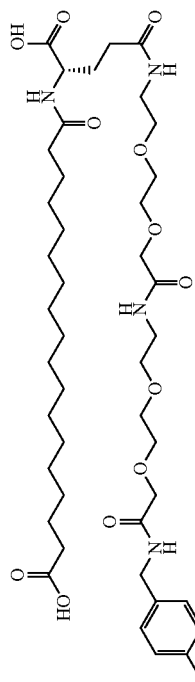
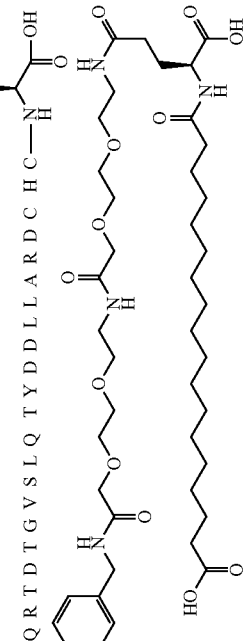
(SEQ ID NO: 312)

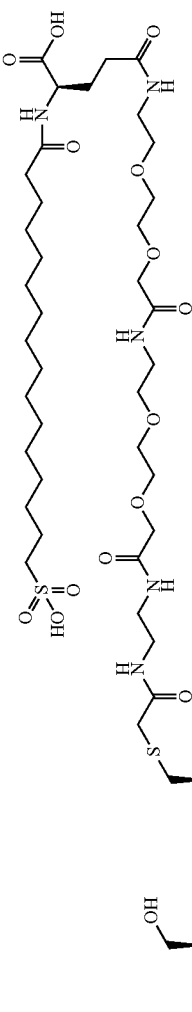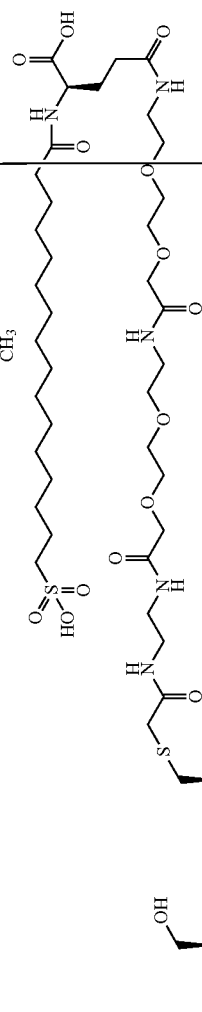
(Formula 17)
(SEQ ID NO: 288)

-continued
(Formula 18)
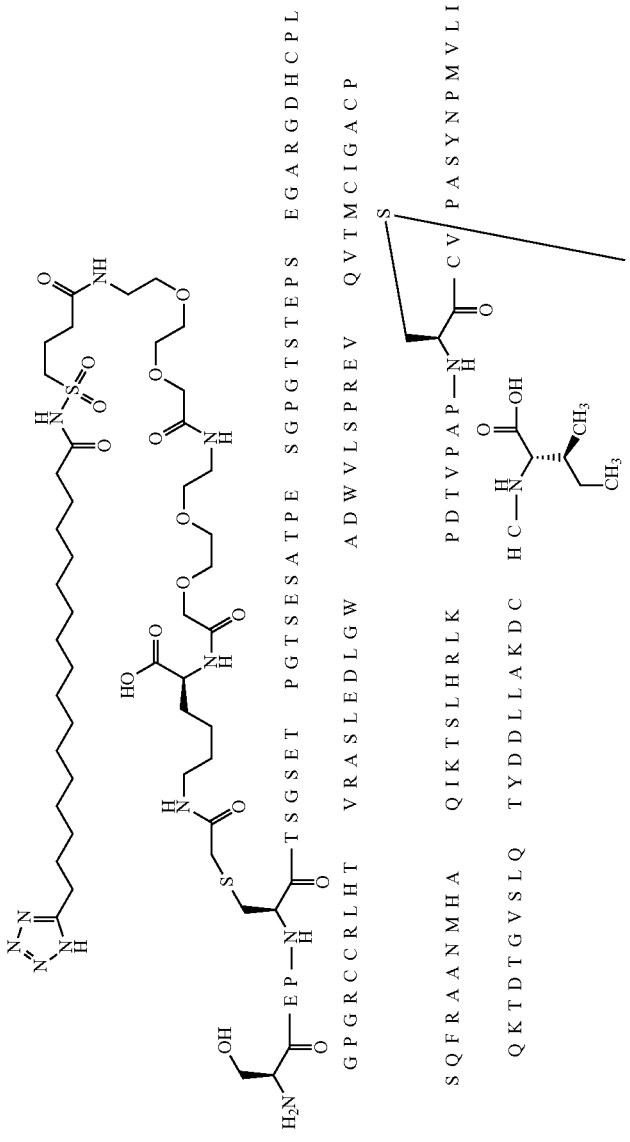

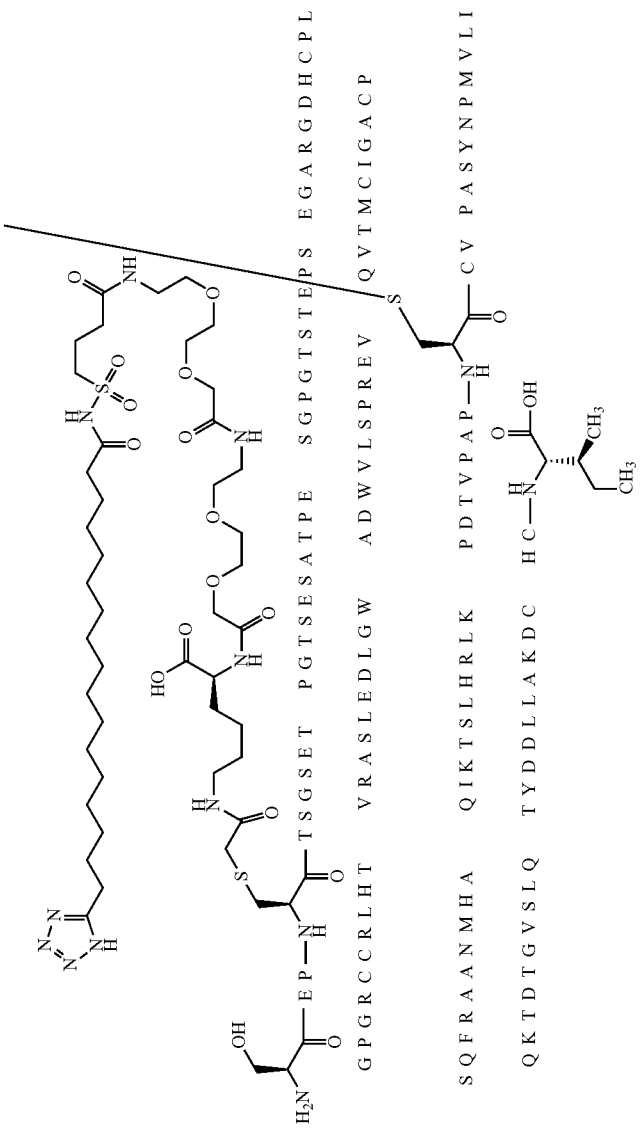
(SEQ ID NO: 288)

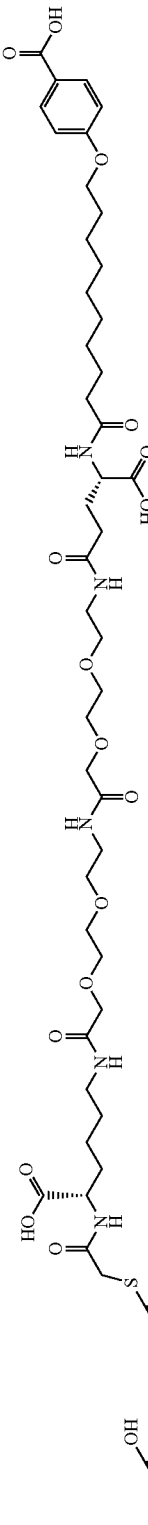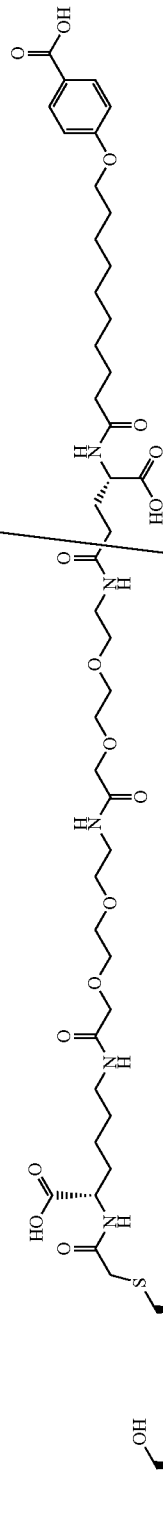
(Formula 19)
(SEQ ID NO: 288)

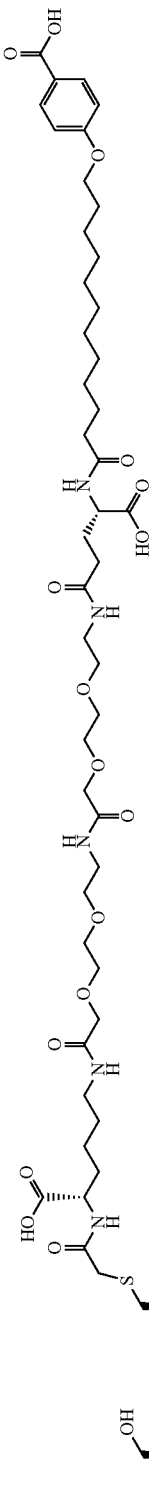

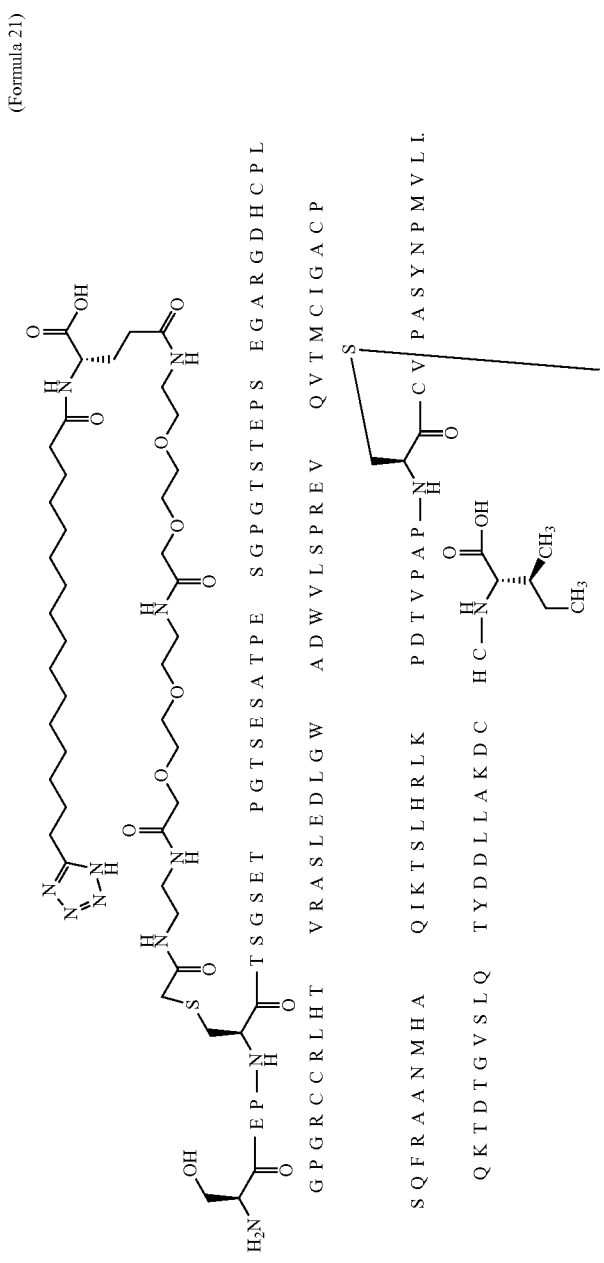
(Formula 21)

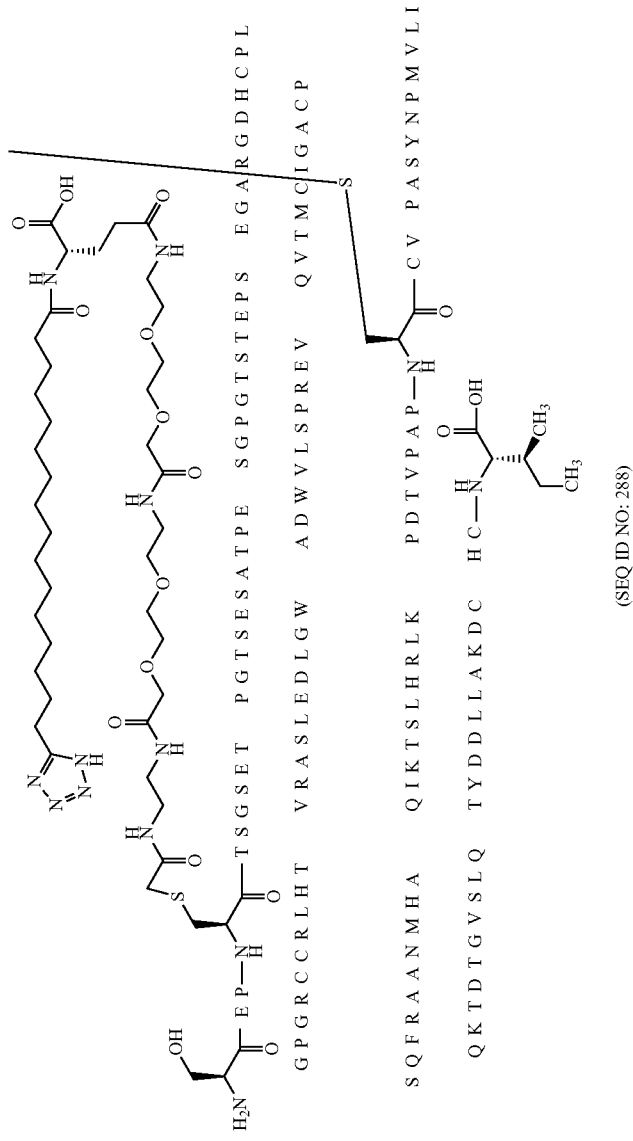
(SEQ ID NO: 288)

100. The MIC-1 compound according to any one of the preceding embodiments, showing 5 extended plasma half-life compared with MIC-1 of SEQ ID NO:1.
101. The MIC-1 compound according to any one of the preceding embodiments, showing improved plasma half-life compared with MIC-1 of SEQ ID NO:1 as measured by administrating the compound to rat i.v. and estimate the terminal half-life from changes in plasma concentration of compound over time.
102. The MIC-1 compound according to any one of the preceding embodiments, showing maintained potency compared with MIC-1 of SEQ ID NO:1.
103. The MIC-1 compound according to any one of the preceding embodiments, showing retained efficacy compared with MIC-1 of SEQ ID NO: 1 as measured by administrating compound to rat s.c. and measure changes in daily food intake.
104. The MIC-1 compound according to any one of the preceding embodiments, wherein the MIC-1 polypeptide with an amino acid extension has acceptable solubility compared with MIC-1 of SEQ ID NO:1.
105. The MIC-1 compound according to any one of embodiments 1-99, wherein the MIC-1 polypeptide with an amino acid extension has a solubility of 0.5, 1.0, 5.0, 10, 30 or 50 mg/ml as measured at pH 8.0 in a Tris buffer system.
106. The MIC-1 compound according to embodiments 1 or 2, wherein the MIC-1 polypeptide comprises a deletion of N3 (des-N3) compared to MIC-1 of SEQ ID NO: 1, wherein the amino acid extension has the following sequence SEPCTSGSETPGTSESATPESGPGTSTEPSEG (SEQ ID NO: 225), and wherein the protractor has the following formula:

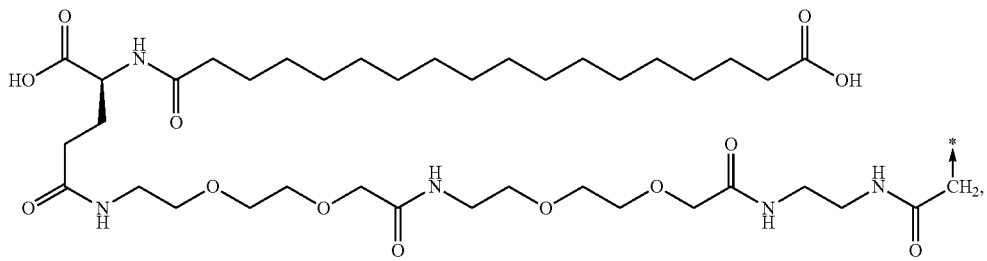

(Formula X)

and wherein the protractor is attached to the Cysteine of the amino acid extension.
107. Compound according to embodiments 1 or 2, wherein the MIC-1 polypeptide with an N-terminal amino acid extension has the sequence according to SEQ ID NO: 288, and the protractor has the following formula:

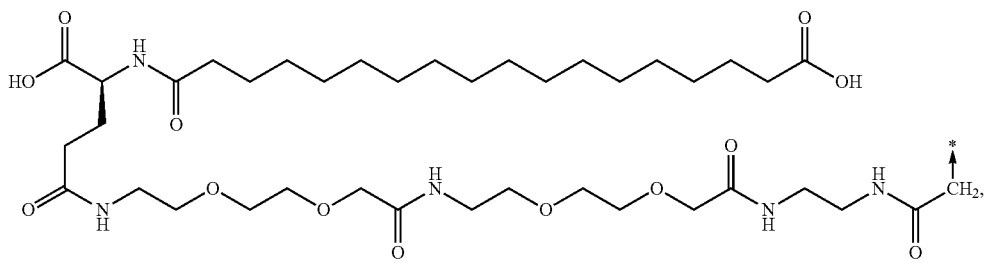

(Formula X)

and wherein the protractor is attached to the Cysteine of the amino acid extension.
108. MIC-1 compound according to any one of embodiments 1-107 or a pharmaceutically acceptable salt, amide or ester thereof.
109. The MIC-1 compound according to any of the preceding embodiments, wherein the compound has improved in vivo efficacy on lowering food intake and/or lowering body weight compared with MIC-1 of SEQ ID NO: 1.
110. MIC-1 compound according to any one of embodiments 1-109 and 132-152 for use as a medicament.
111. MIC-1 compound according to any one of embodiments 1-109 and 132-152 for use in the prevention and/or treatment of a metabolic disorder.
112. MIC-1 compound according to embodiment 111 for use in the prevention and/or treatment of a metabolic disorder, wherein the metabolic disorder is obesity, type 2 diabetes, dyslipidemia, or diabetic nephropathy.
113. MIC-1 compound according to any one of embodiments 1-109 and 132-152 for use in the prevention and/or treatment of eating disorders, such as obesity.
114. MIC-1 compound according to embodiment 113 for use in the prevention and/or treatment of obesity by decreasing food intake, reducing body weight, suppressing appetite and/or inducing satiety.
115. MIC-1 compound according to any one of embodiments 1-109 and 132-152 for use in the prevention and/or treatment of a cardiovascular disease.
116. MIC-1 compound according to embodiment 115 for use in the prevention and/or treatment of dyslipidaemia, arteriosclerosis, steatohepatitis, or diabetic nephropathy.
117. Pharmaceutical composition comprising the MIC-1 compound according to any one of embodiments 1-109 and 132-152 or a pharmaceutically acceptable salt, amide or ester thereof, and one or more pharmaceutically acceptable excipients.

118. The use of a MIC-1 compound according to any one of embodiments 1-109 and 132-152 in the manufacture of a medicament for the prevention and/or treatment of a metabolic disorder, wherein the metabolic disorder is obesity, type 2 diabetes, dyslipidemia, or diabetic nephropathy.

119. The use of a MIC-1 compound according to any one of embodiments 1-109 and 132-152 in the manufacture of a medicament for the prevention and/or treatment of eating disorders.

120. The use of a MIC-1 compound according to any one of embodiments 1-109 and 132-152 in the manufacture of a medicament for the prevention and/or treatment of obesity.

121. The use of a MIC-1 compound according to any one of embodiments 1-109 and 132-152 in the manufacture of a medicament for the prevention and/or treatment of obesity by decreasing food intake, reducing body weight, suppressing appetite and/or inducing satiety.

122. The use of a MIC-1 compound according to any one of embodiments 1-109 and 132-152 in the manufacture of a medicament for the prevention and/or treatment of a cardiovascular disease.

123. The use of a MIC-1 compound according to any one of embodiments 1-109 and 132-152 in the manufacture of a medicament for the prevention and/or treatment of dyslipidaemia, arteriosclerosis, steatohepatitis, or diabetic nephropathy.

124. Method of treating and/or preventing a metabolic disorder by administering a pharmaceutically active amount of a MIC-1 compound according to any one of embodiments 1-109 and 132-152, wherein the metabolic disorder is obesity, type 2 diabetes, dyslipidemia, or diabetic nephropathy.

125. Method of treating and/or preventing eating disorders by administering a pharmaceutically active amount of a MIC-1 compound according to any one of embodiments 1-109 and 132-152.

126. Method of treating and/or preventing obesity by administering a pharmaceutically active amount of a MIC-1 compound according to any one of embodiments 1-109 and 132-152.

127. Method of treating and/or preventing obesity by decreasing food intake, reducing body weight, suppressing appetite and/or inducing satiety by administering a pharmaceutically active amount of a MIC-1 compound according to any one of embodiments 1-109 and 132-152.

128. Method of treating and/or preventing a cardiovascular disease by administering a pharmaceutically active amount of a MIC-1 compound according to any one of embodiments 1-109 and 132-152.

129. Method of treating and/or preventing dyslipidaemia, arteriosclerosis, steatohepatitis, or diabetic nephropathy by administering a pharmaceutically active amount of a MIC-1 compound according to any one of embodiments 1-109 and 132-152.

130. Polynucleotide molecule encoding a MIC-1 compound according to any one of embodiments 1-109 and 132-152.

131. Method of treating and/or preventing overweight by decreasing food intake, reducing body weight, suppressing appetite and/or inducing satiety by administering a pharmaceutically active amount of a MIC-1 compound according to any one of embodiments 1-109 and 132-152.

132. MIC-1 compound according to Formula 01 (SEQ ID NO:288):

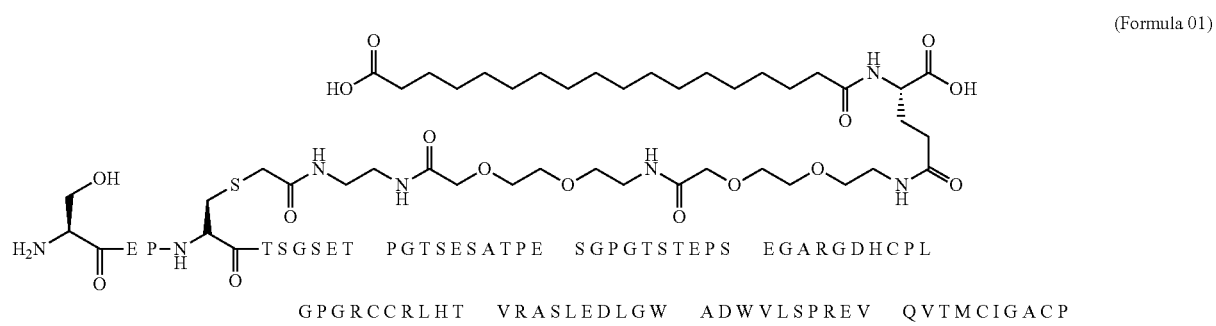

(Formula 01)

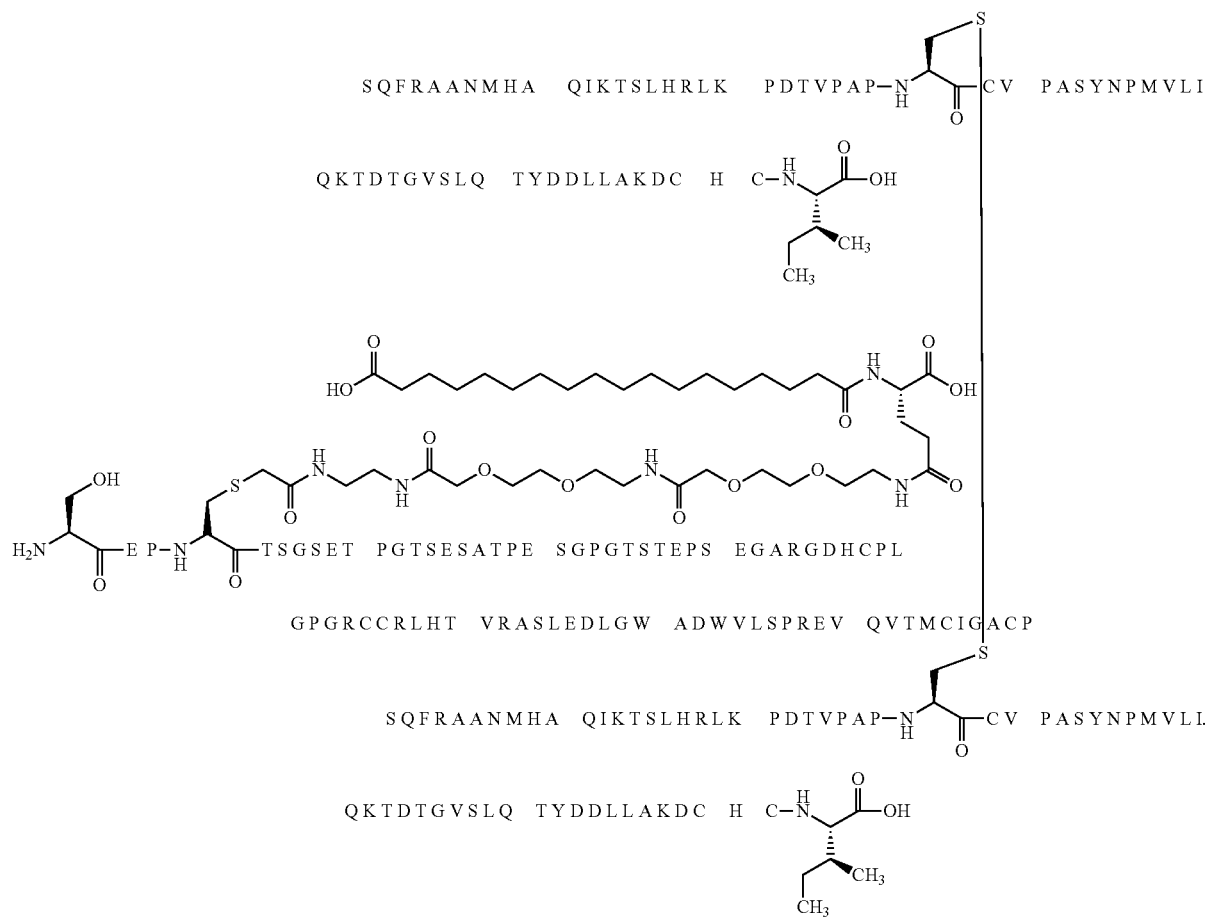
(SEQ ID NO: 288)
133. MIC-1 compound according to Formula 02 (SEQ ID NO:291):
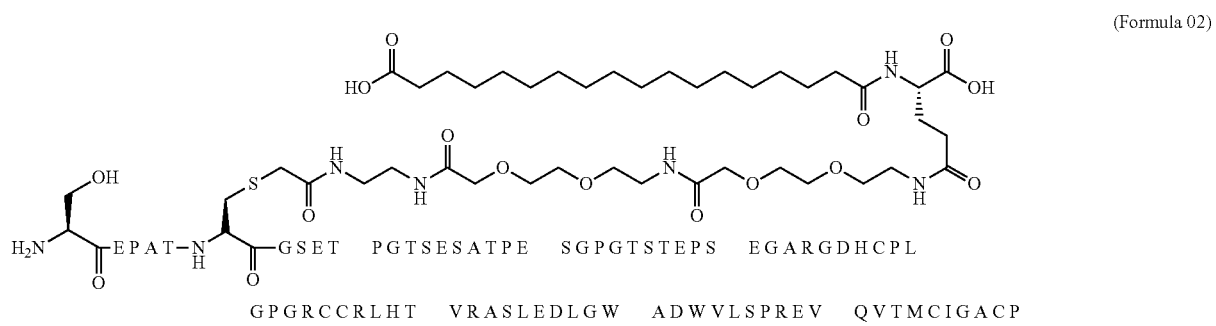
(Formula 02)

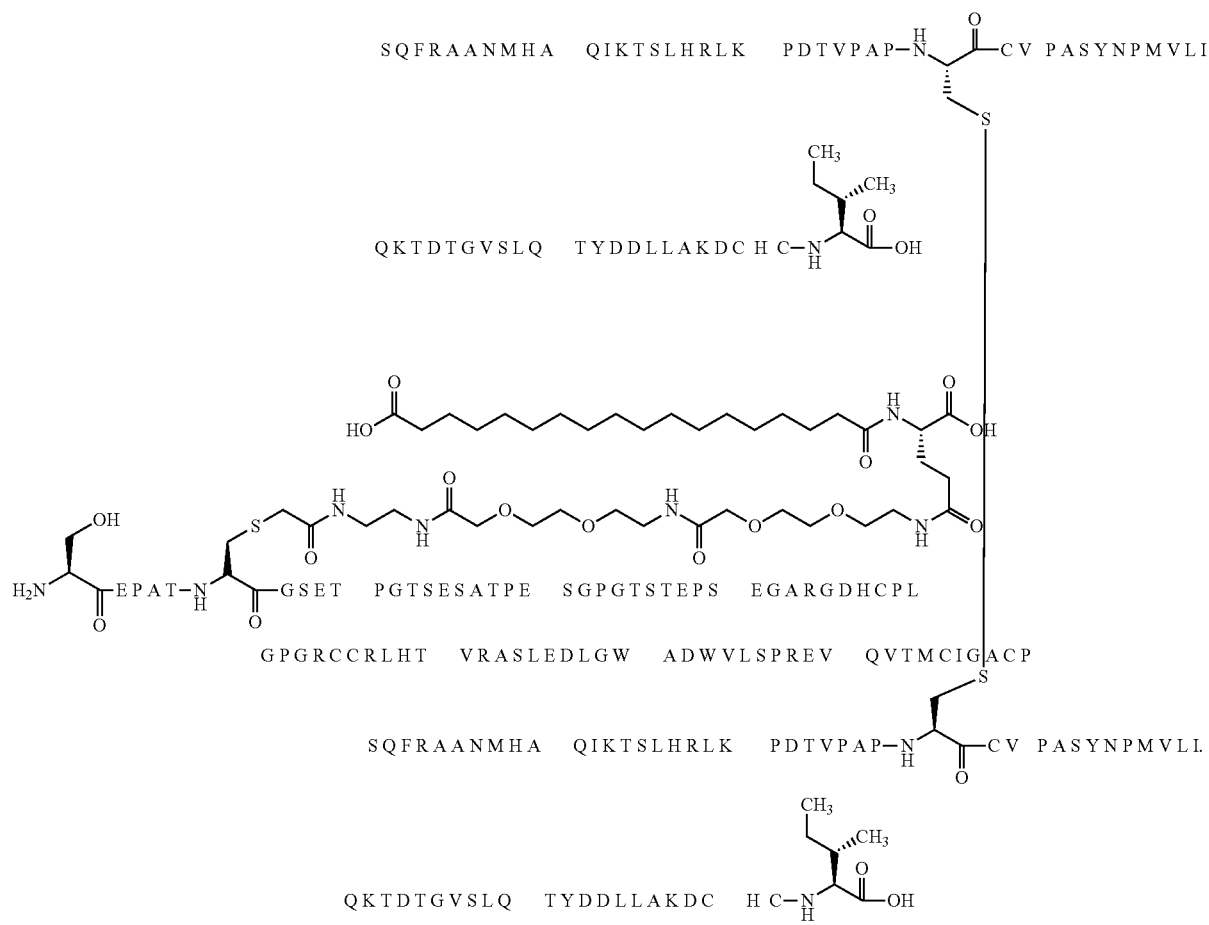
(SEQ ID NO: 291)
134. MIC-1 compound according to Formula 03 (SEQ ID NO:291):
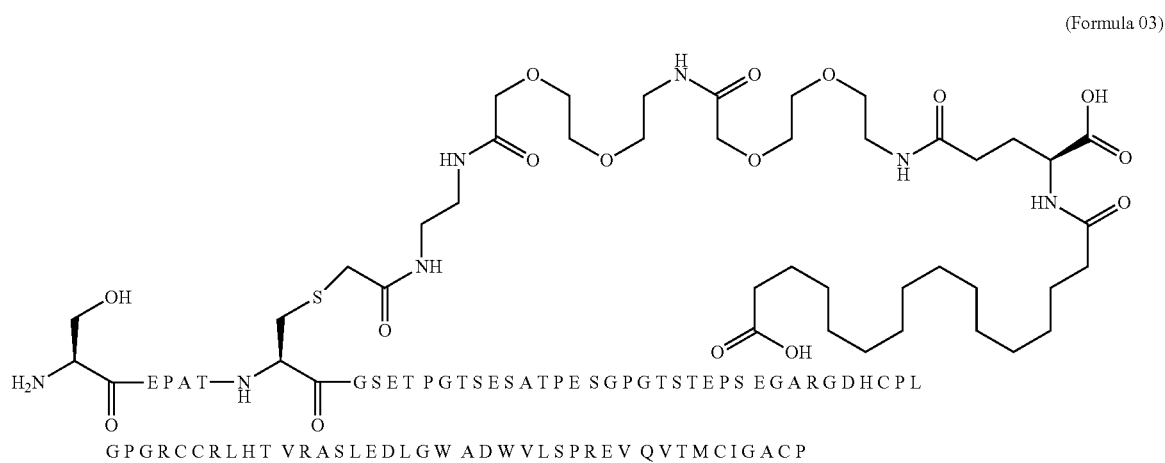
(Formula 03)

(SEQ ID NO: 291)
135. MIC-1 compound according to Formula 04 (SEQ ID NO: 291):
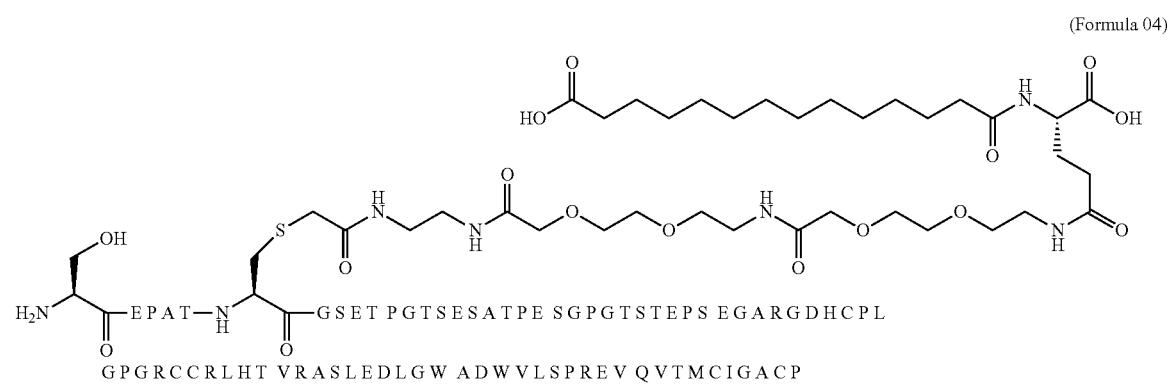
(Formula 04)

-continued
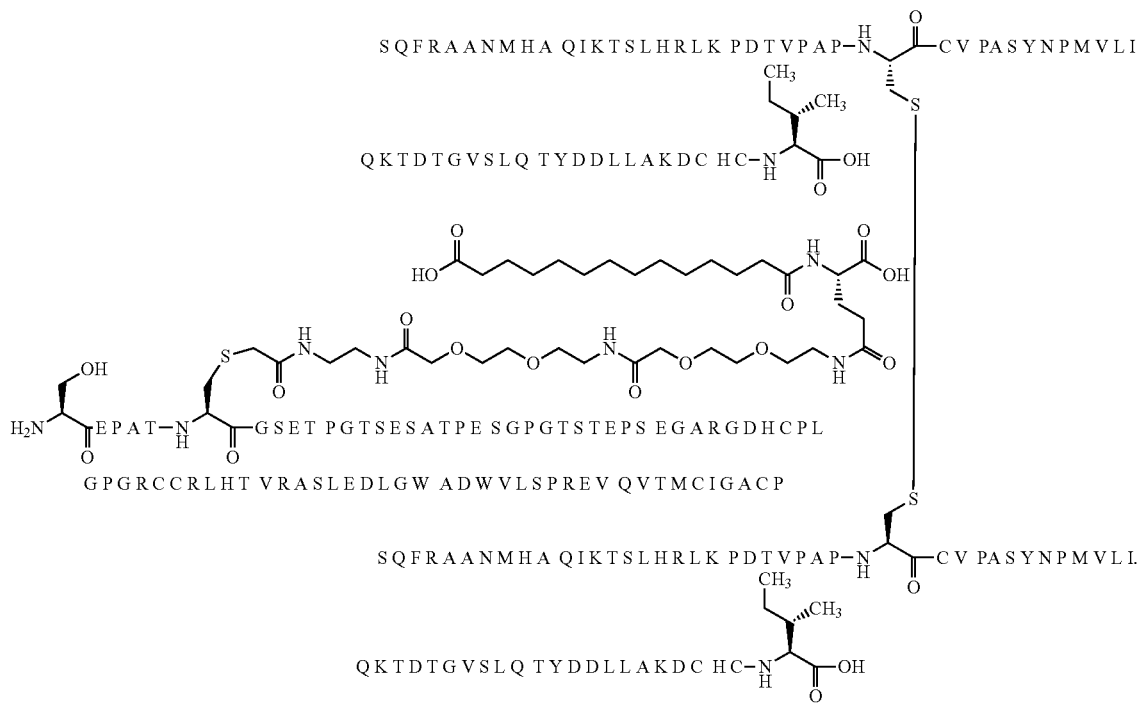
(SEQ ID NO: 291)
136. MIC-1 compound according to Formula 05 (SEQ ID NO:289):
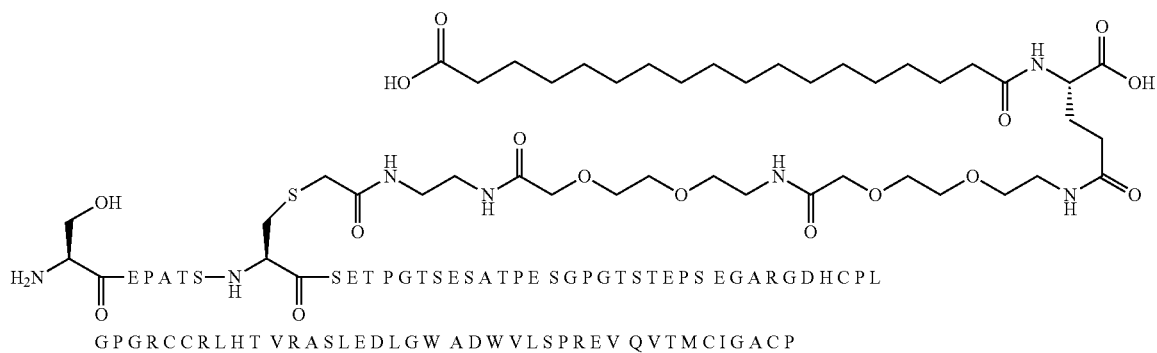
(Formula 05)

(SEQ ID NO: 289)
137. MIC-1 compound according to Formula 06 (SEQ ID NO: 303):
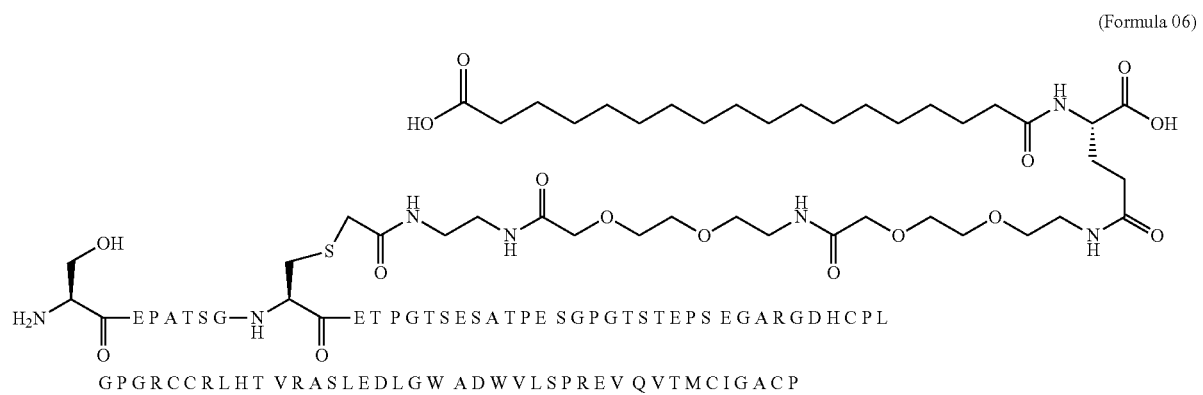
(Formula 06)

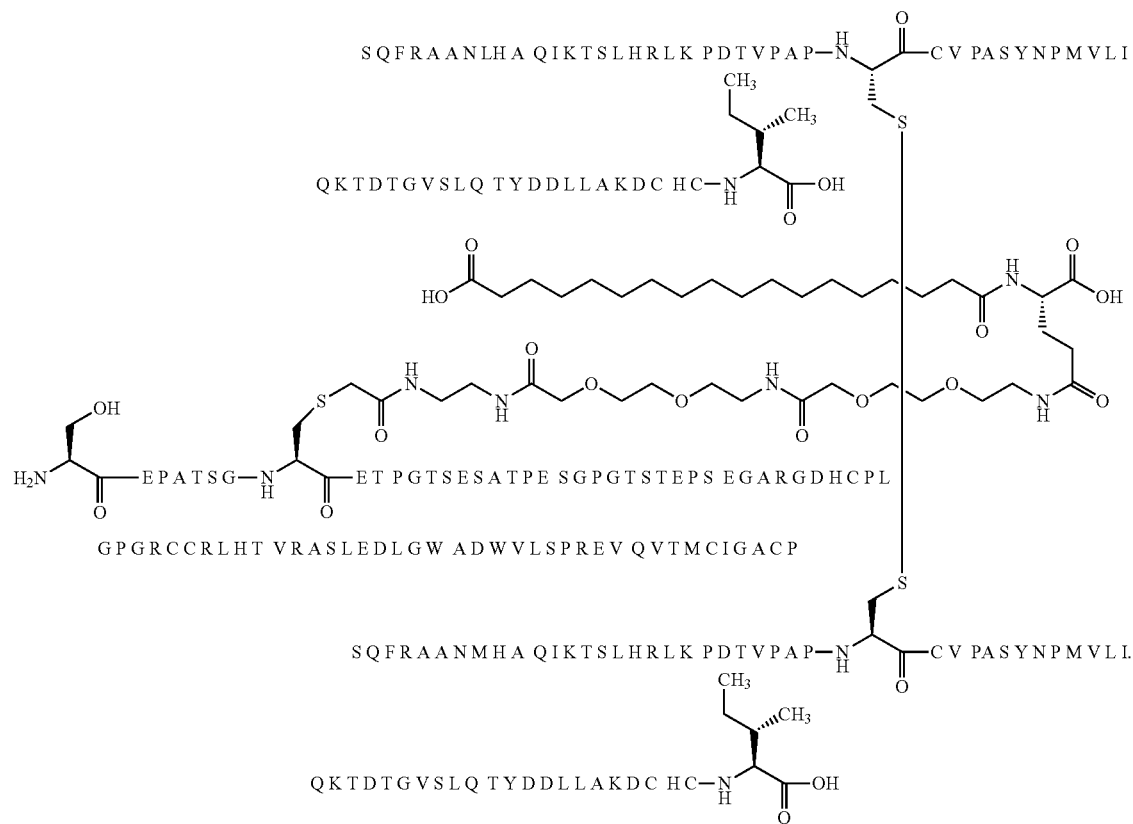
(SEQ ID NO: 303)
138 MIC-1 compound according to Formula 07 (SEQ ID NO:292):
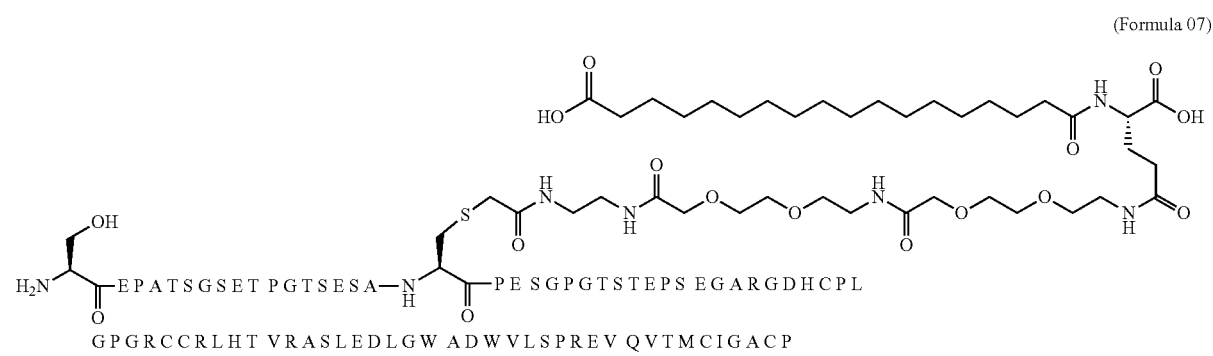
(Formula 07)

(SEQ ID NO: 292)
139. MIC-1 compound according to Formula 08 (SEQ ID NO: 293):
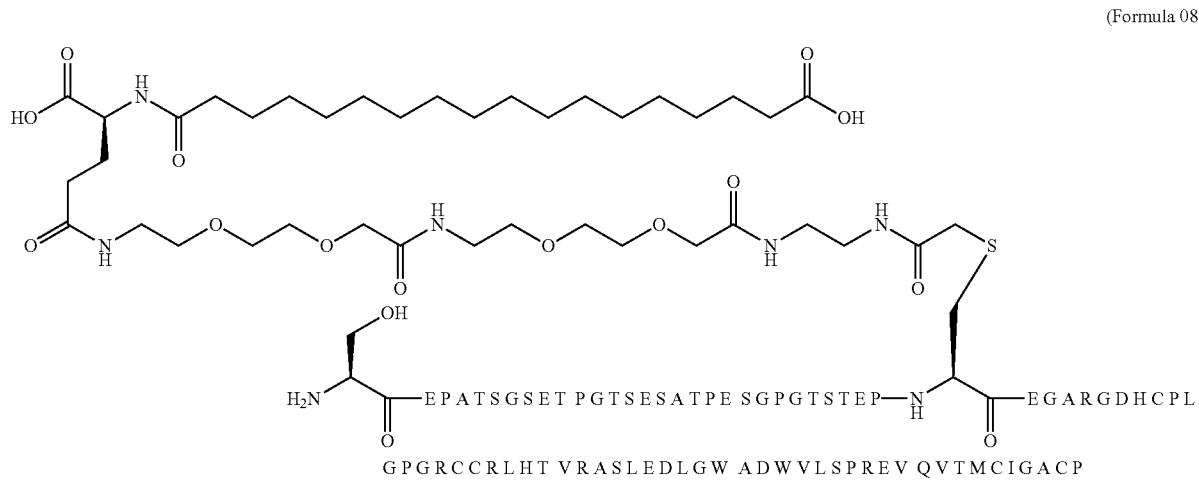
(Formula 08)

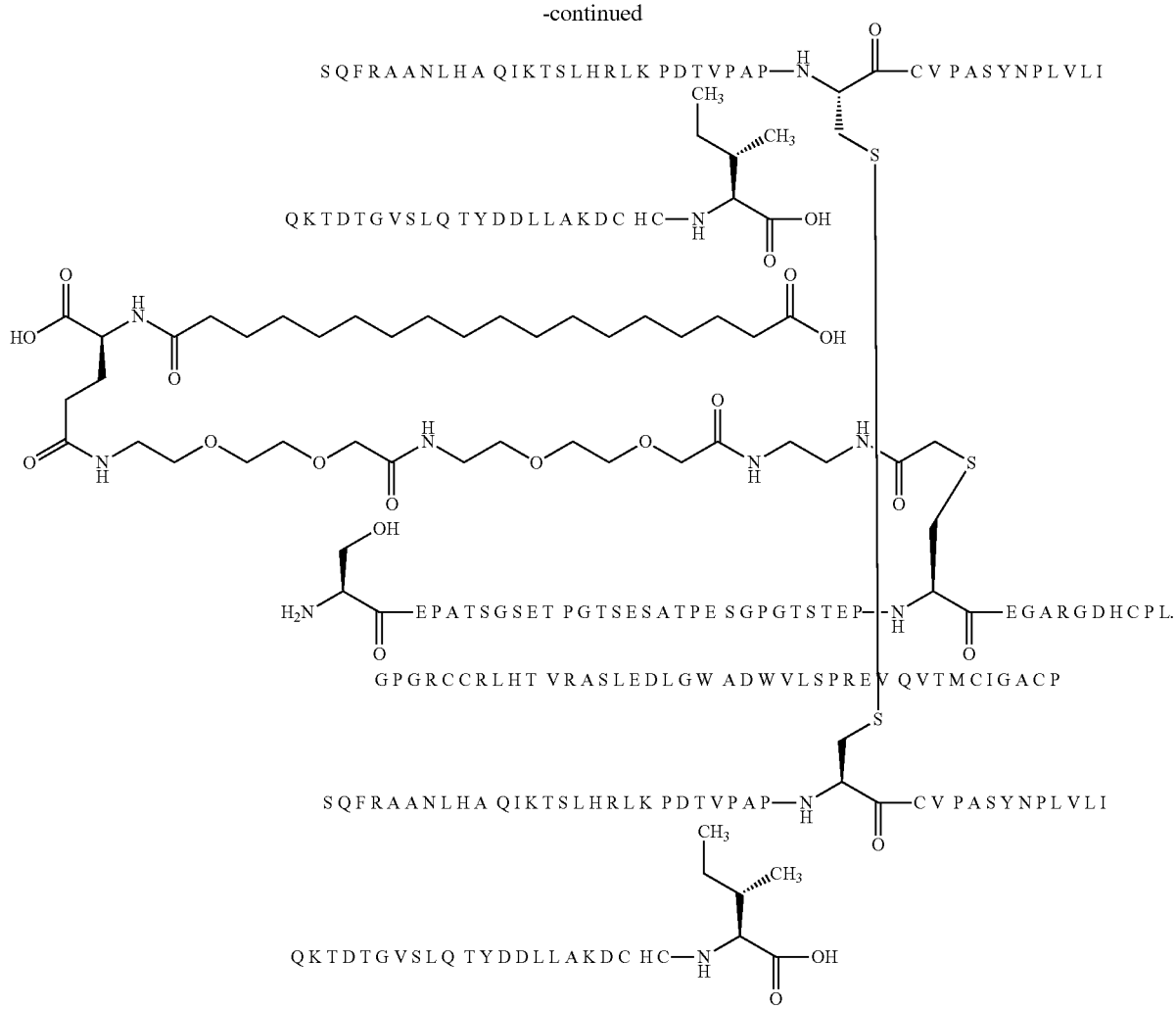
(SEQ ID NO: 293)
140. MIC-1 compound according to Formula 09 (SEQ ID NO: 164):
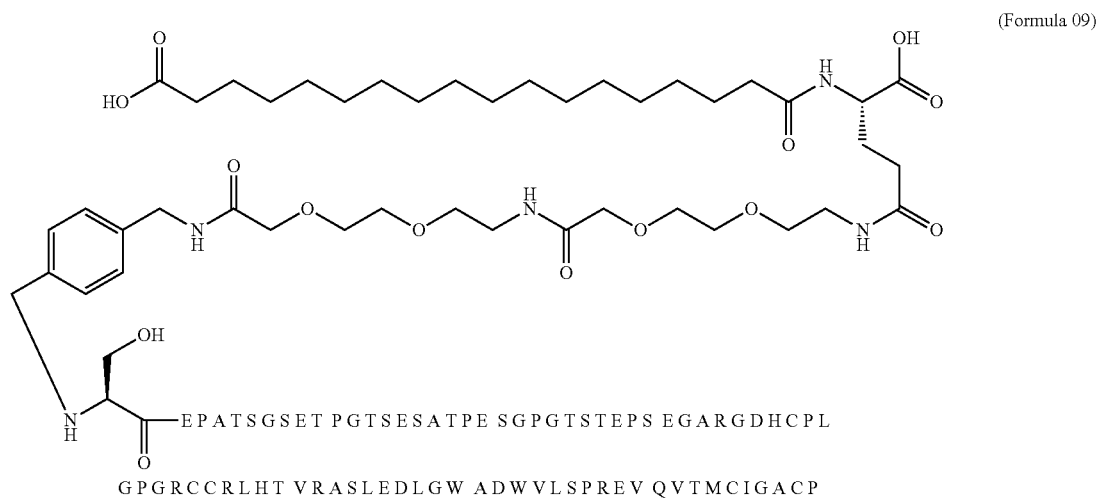
(Formula 09)

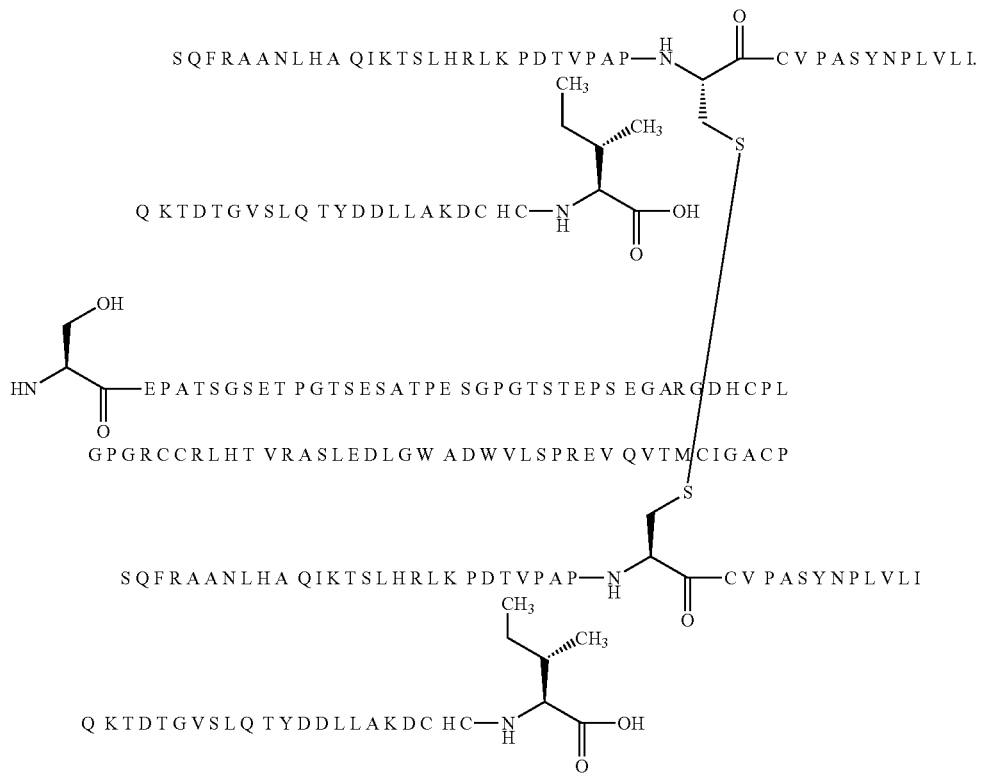
(SEQ ID NO: 164)
141. MIC-1 compound according to Formula 10 (SEQ ID NO: 164):
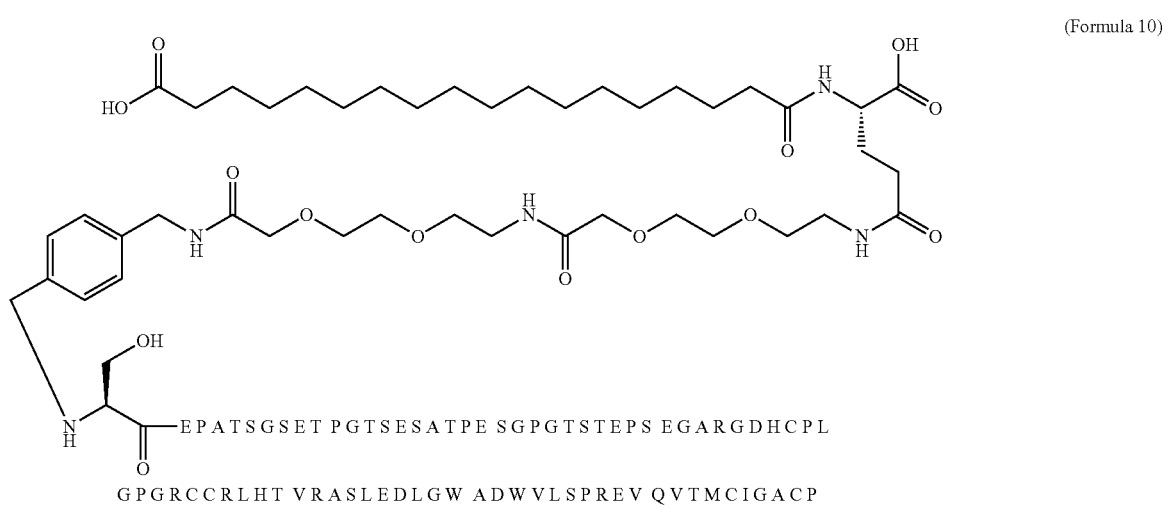
(Formula 10)

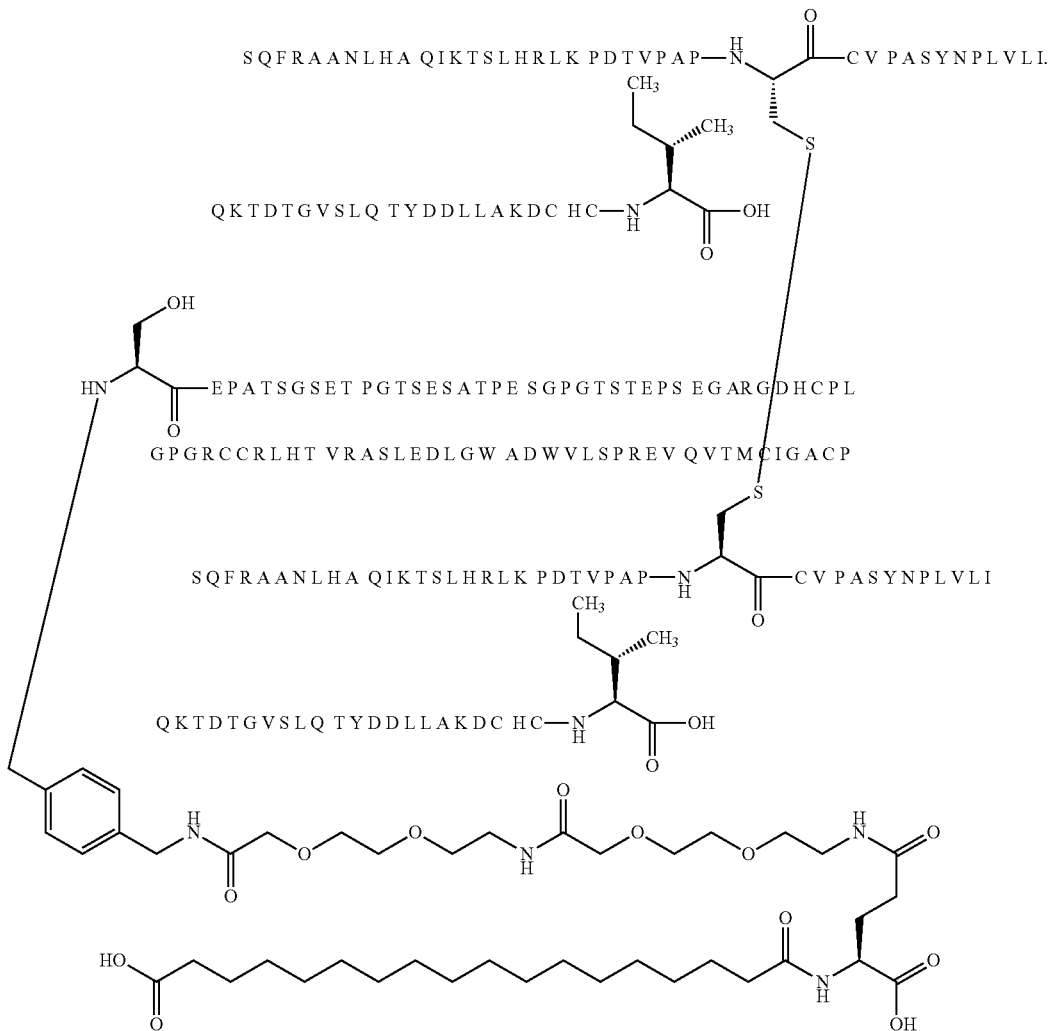
(SEQ ID NO: 164)
142. MIC-1 compound according to Formula 11 (SEQ ID NO:290):
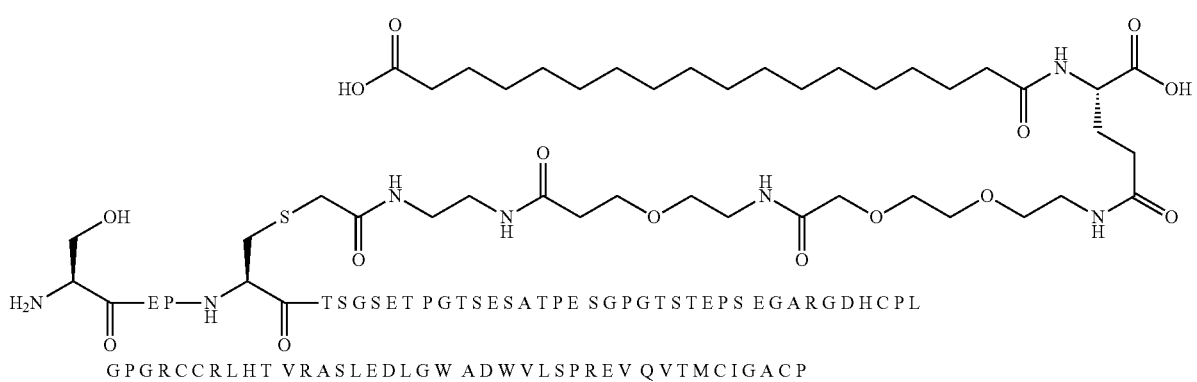
(Formula 11)

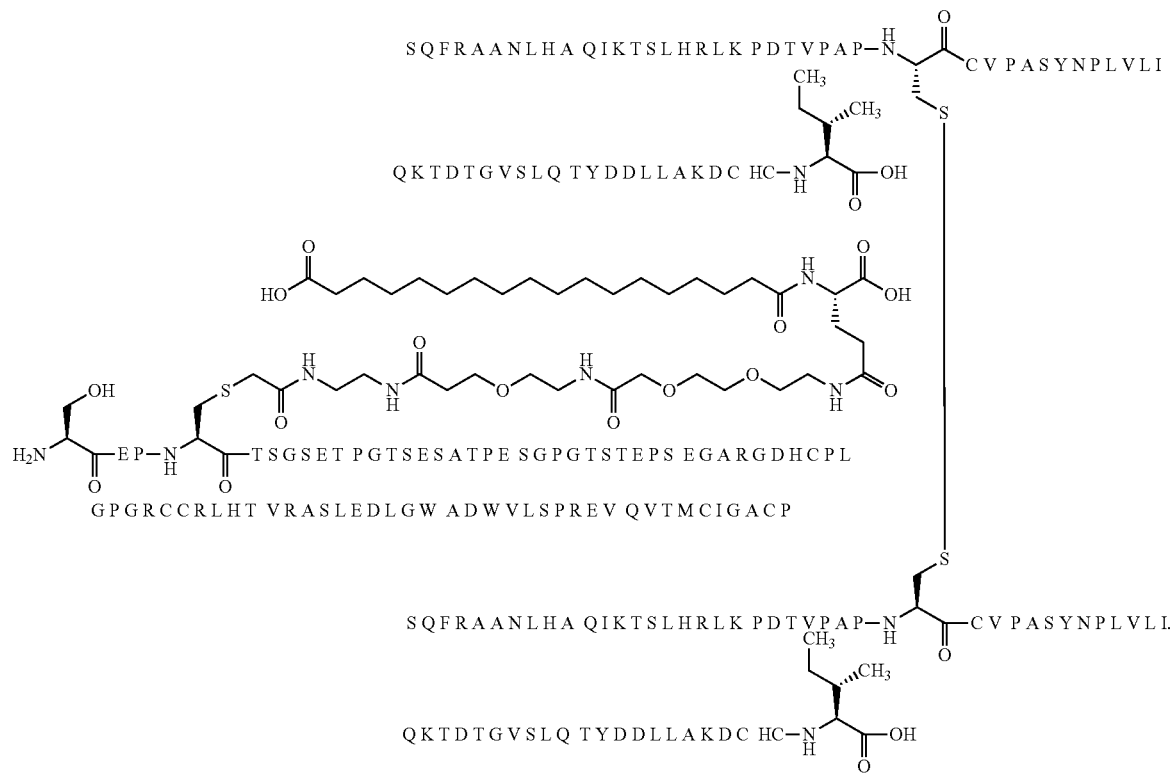
(SEQ ID NO: 290)
143. MIC-1 compound according to Formula 12 (SEQ ID NO: 311):
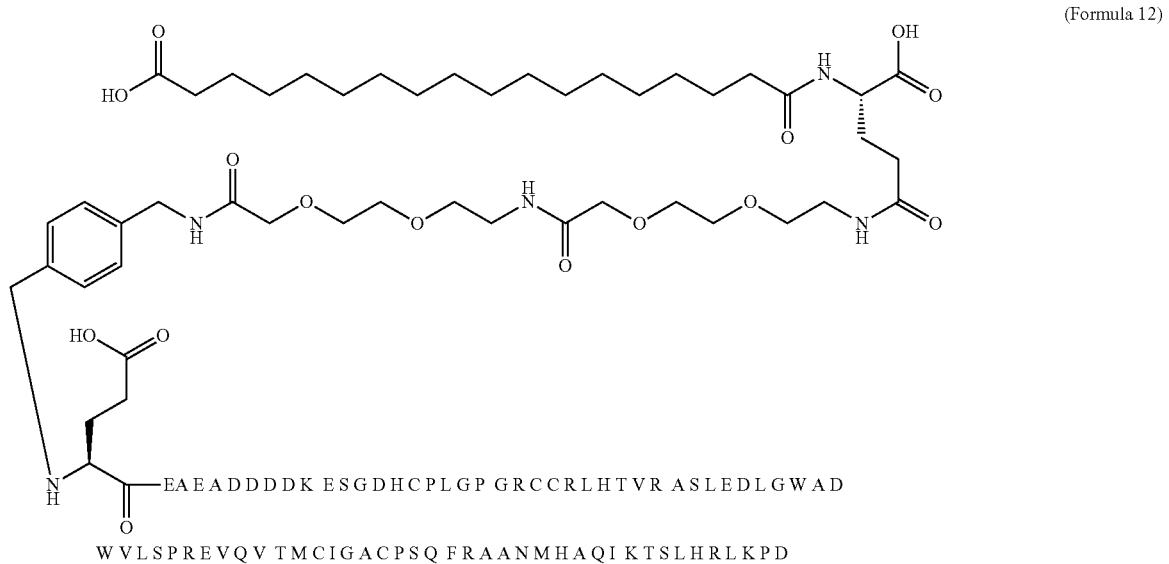
(Formula 12)

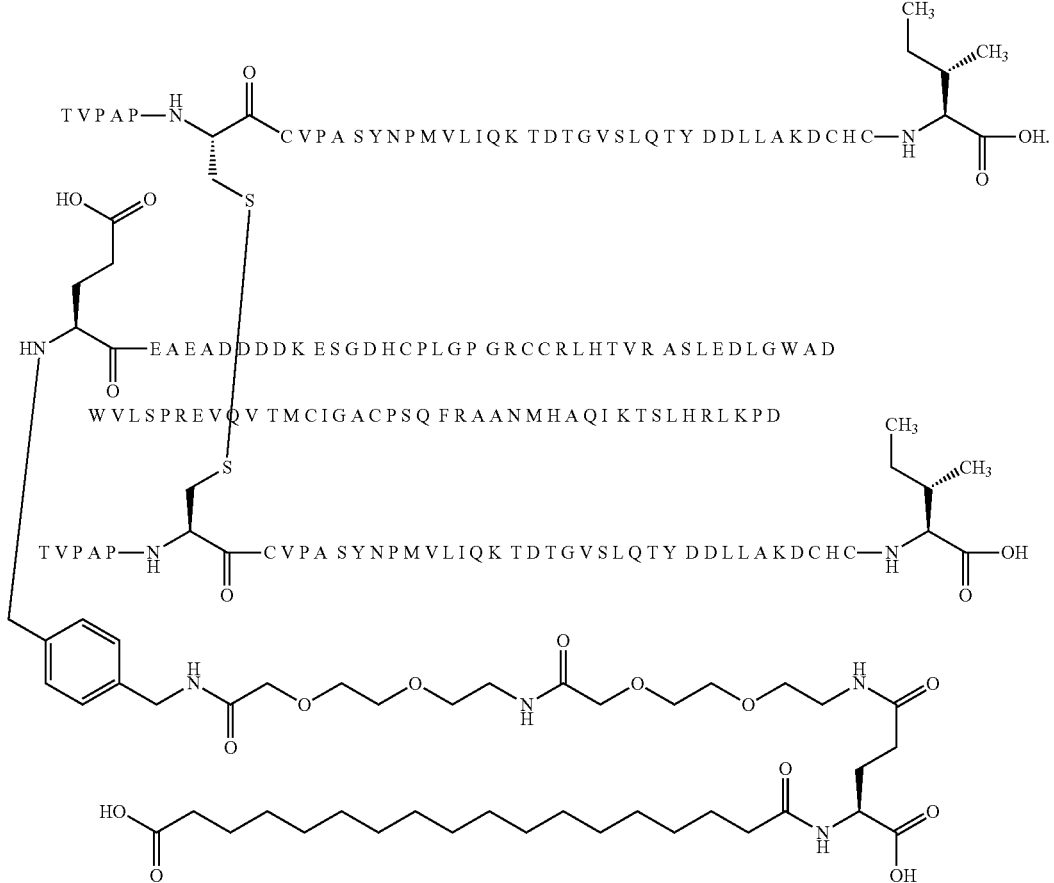
(SEQ ID NO: 311)
144. MIC-1 compound according to Formula 13 (SEQ ID NO: 311):
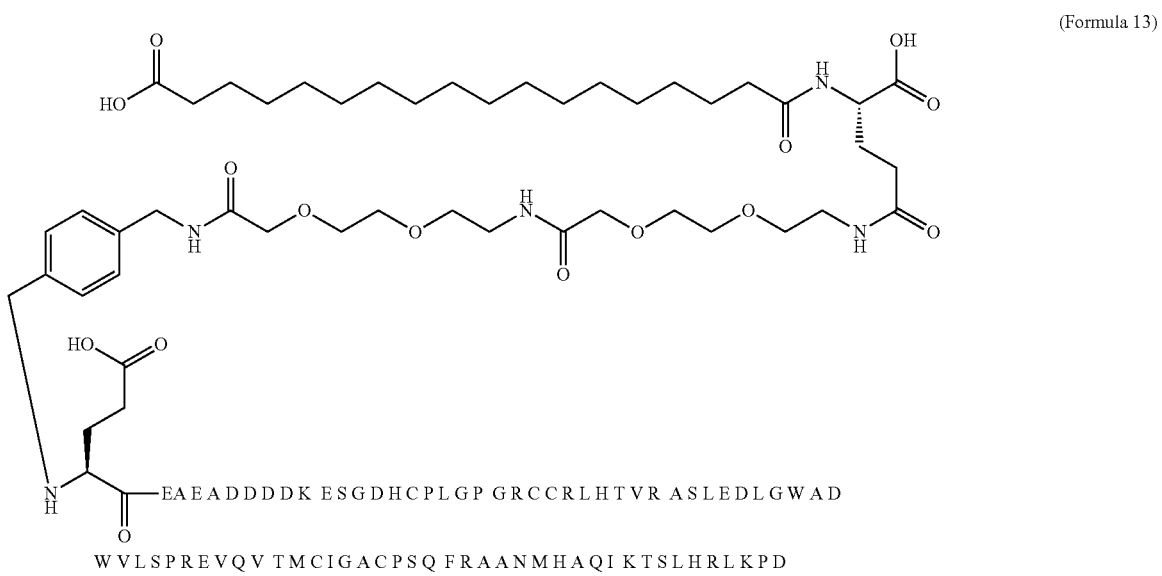

-continued
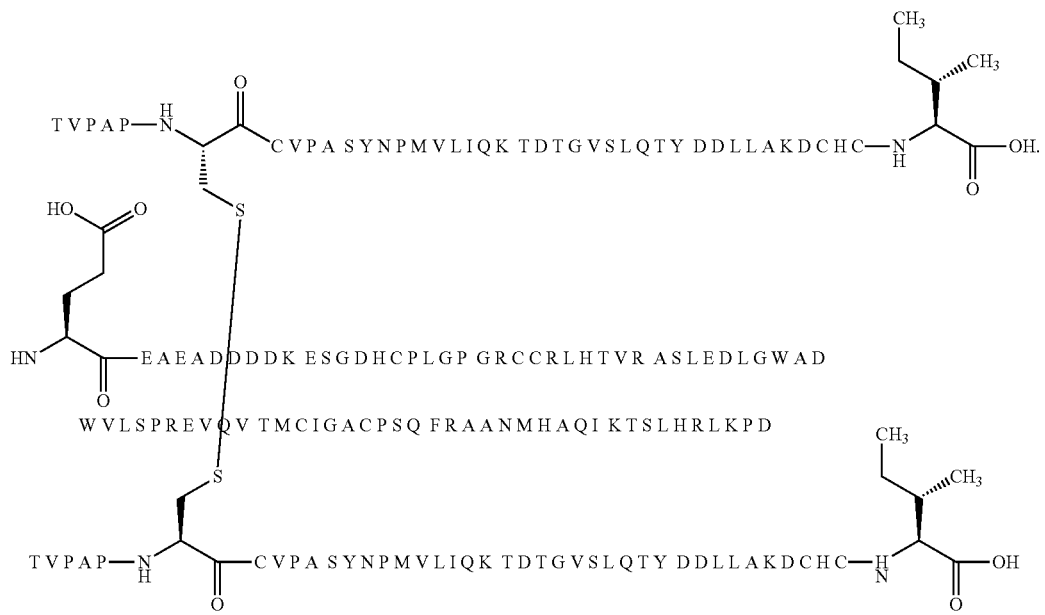
(SEQ ID NO: 311)
145. MIC-1 compound according to Formula 14 (SEQ ID NO: 311):
(Formula 14)
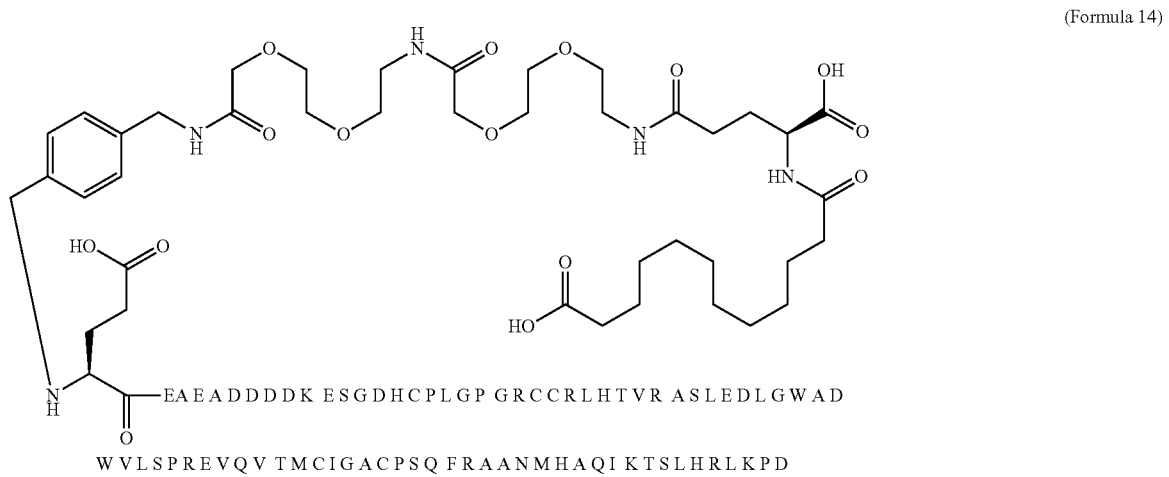

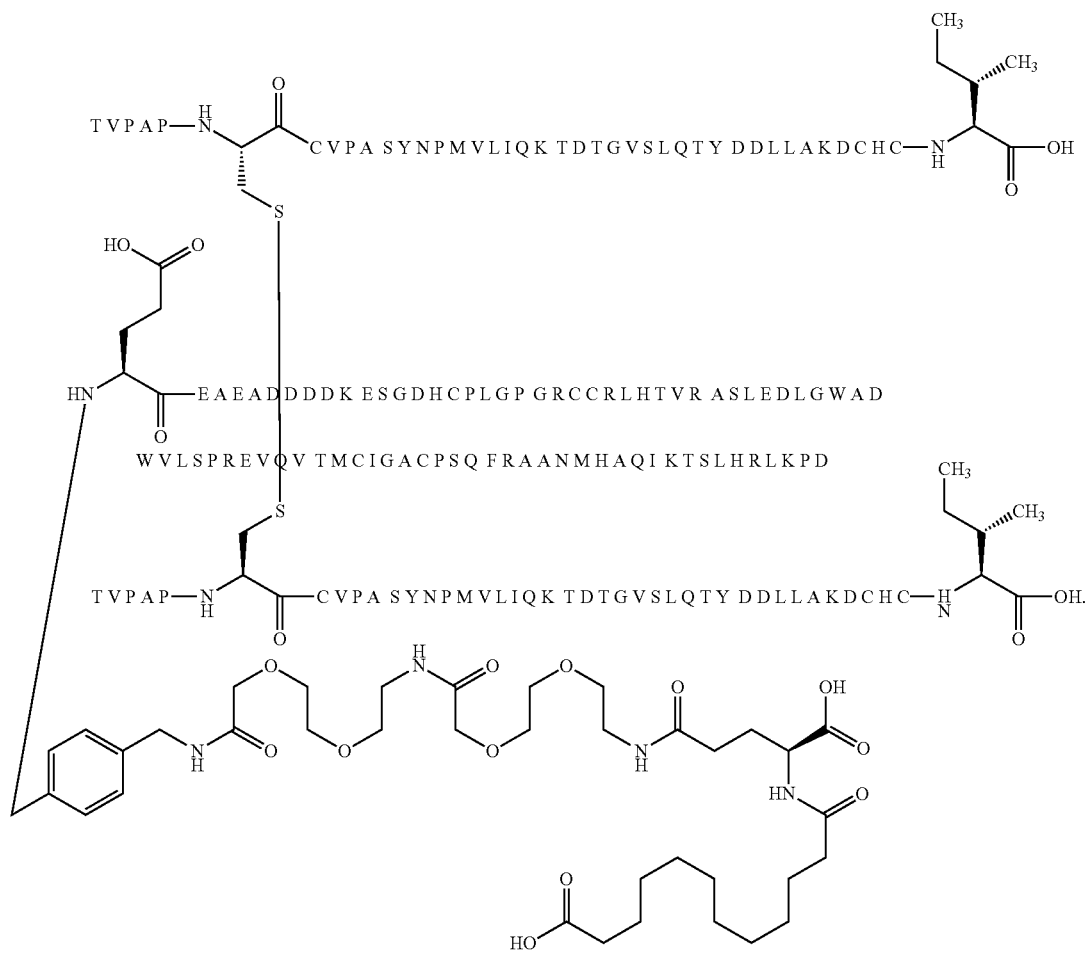
(SEQ ID NO: 311)
146. MIC-1 compound according to Formula 15 (SEQ ID NO: 312):
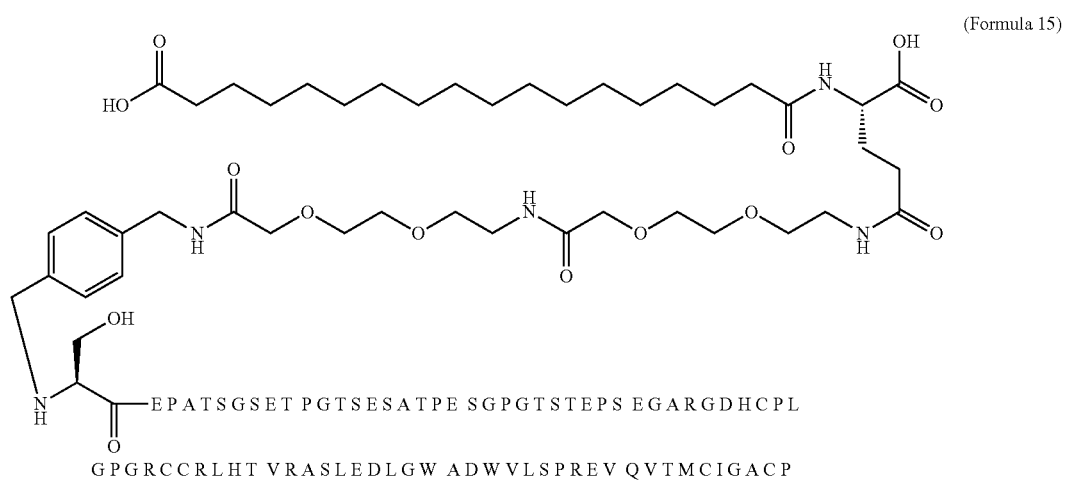

(SEQ ID NO: 312)
147. MIC-1 compound according to Formula 16 (SEQ ID NO: 312):
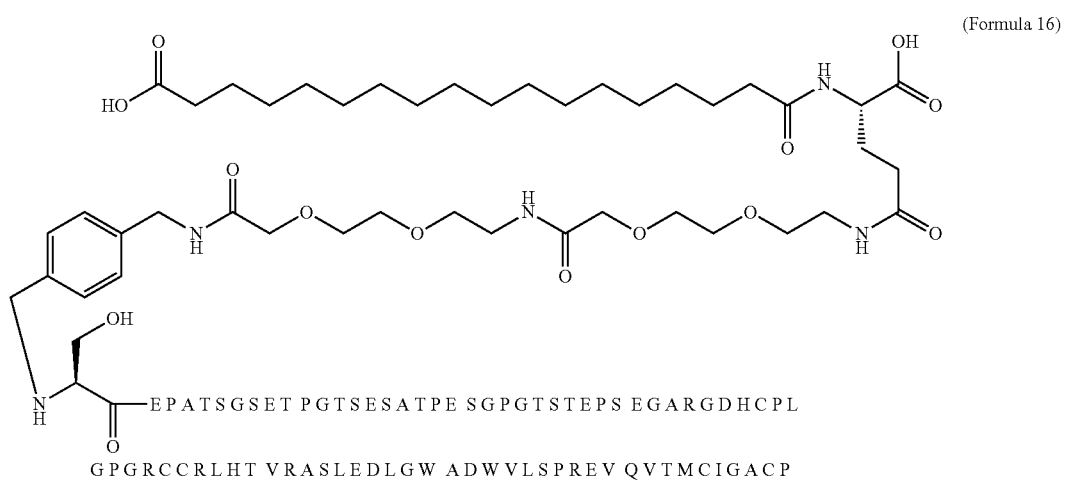
(Formula 16)

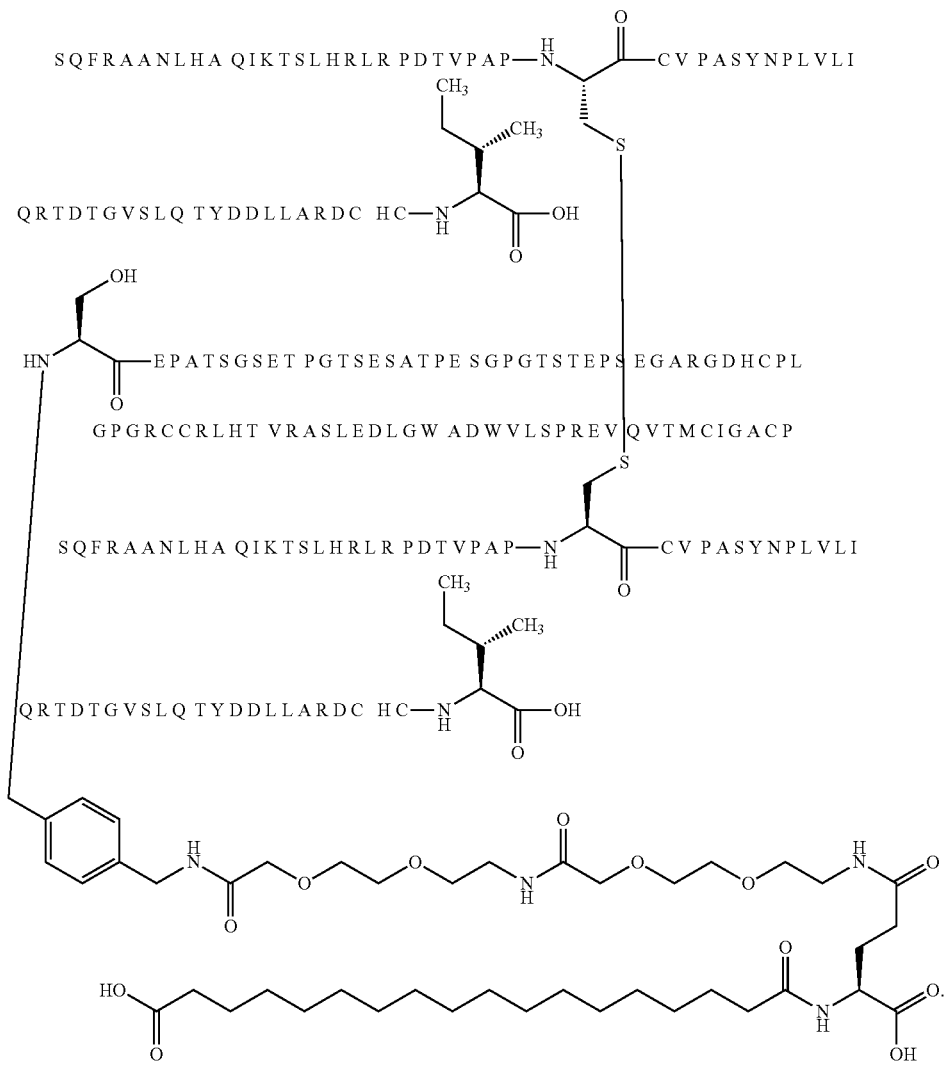
(SEQ ID NO: 312)
148. MIC-1 compound according to Formula 17 (SEQ ID NO:288):
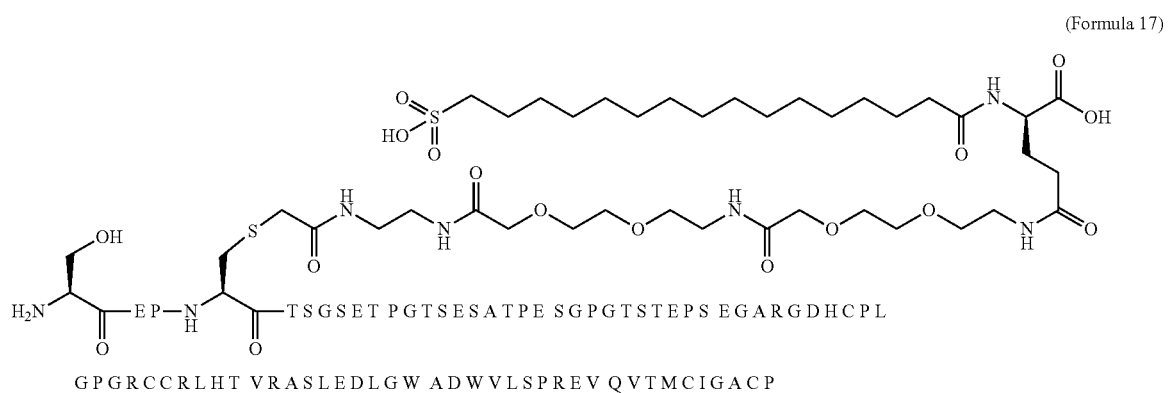
(Formula 17)

-continued
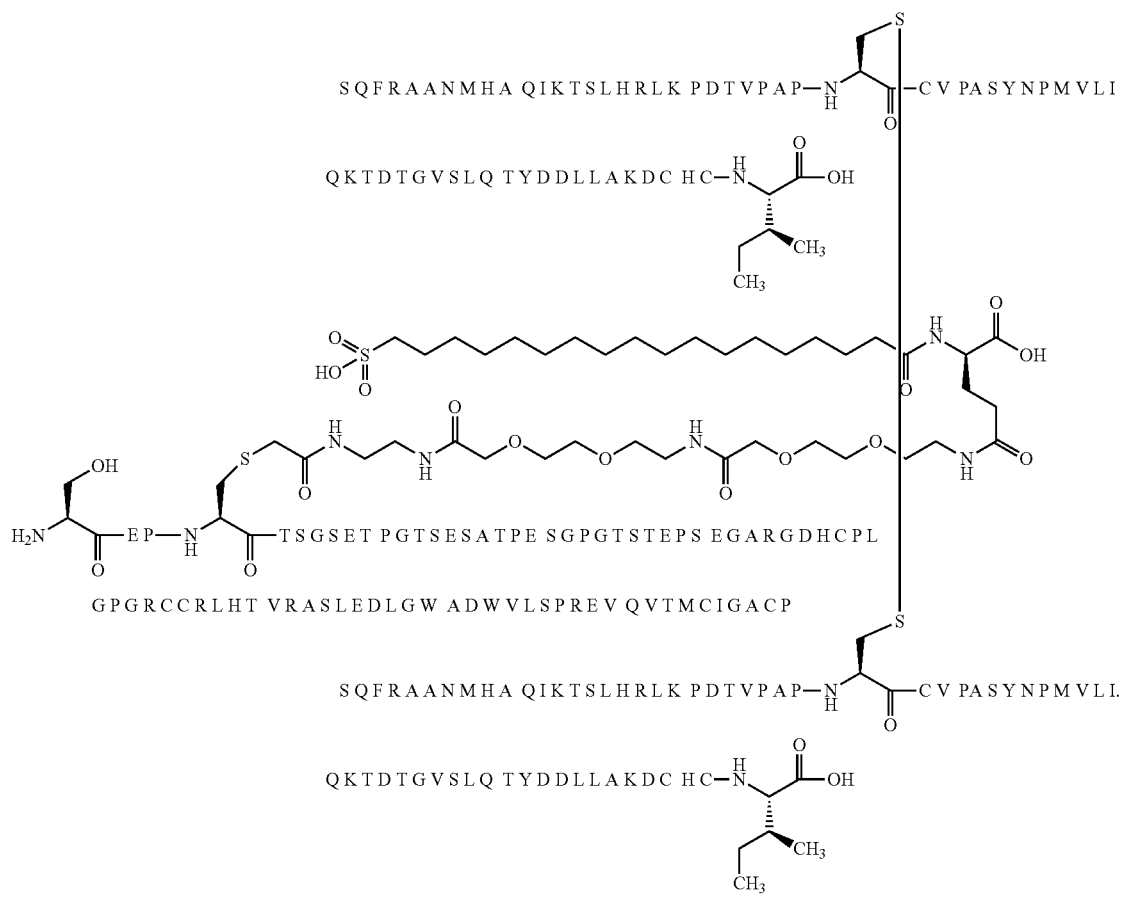
(SEQ ID NO: 288)
149. MIC-1 compound according to Formula 18 (SEQ ID NO:288):
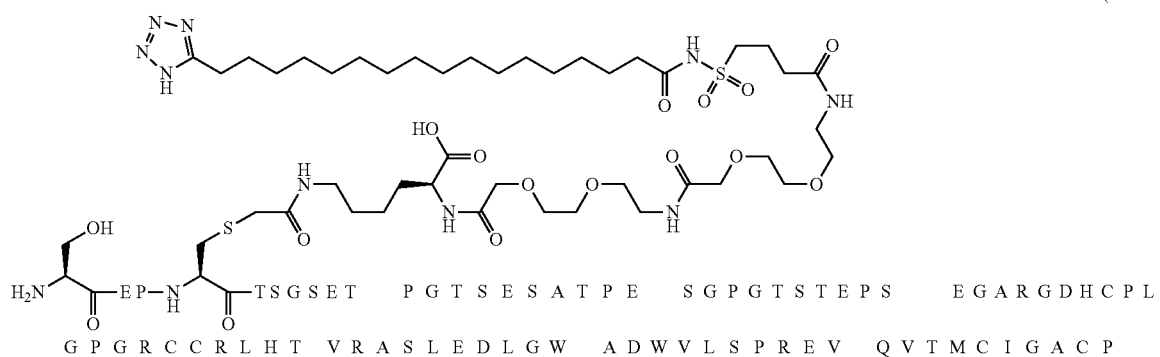
(Formula 18)

-continued
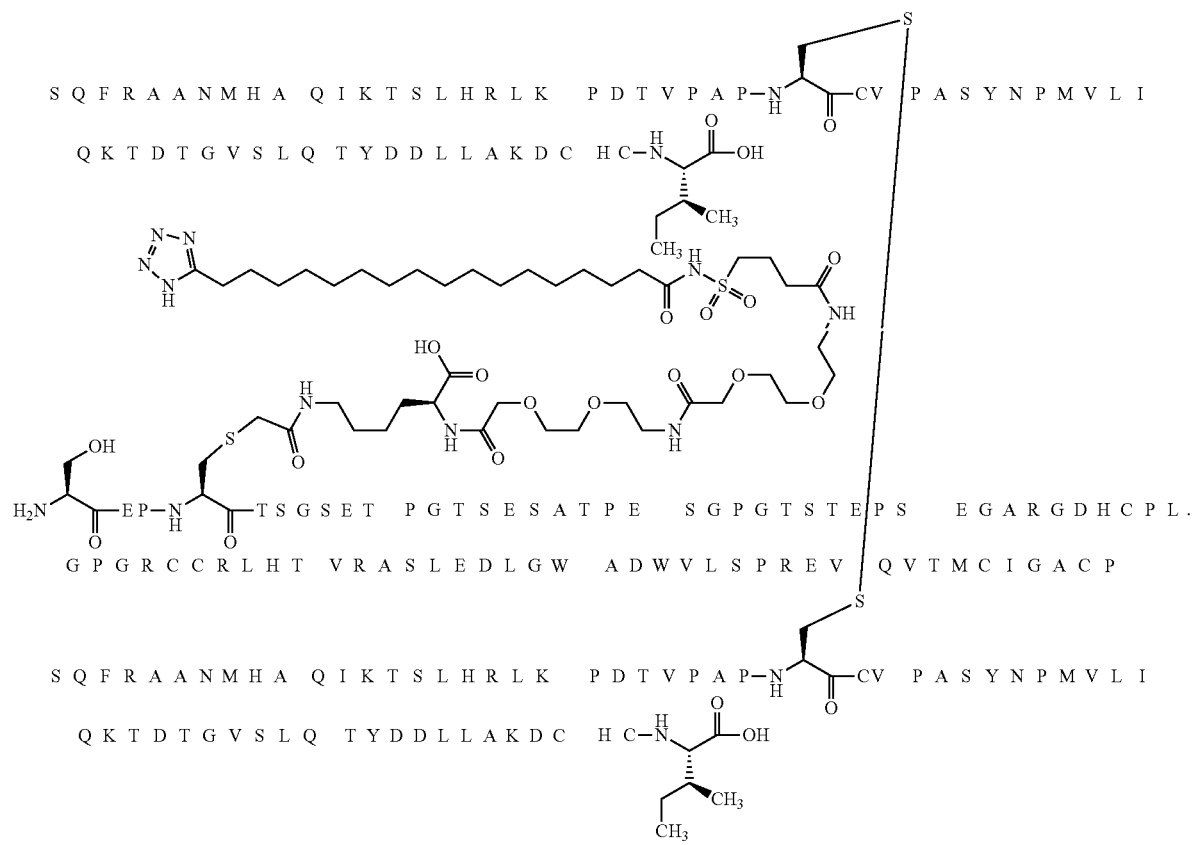
(SEQ ID NO: 288)
150. MIC-1 compound according to Formula 19 (SEQ ID NO:288):

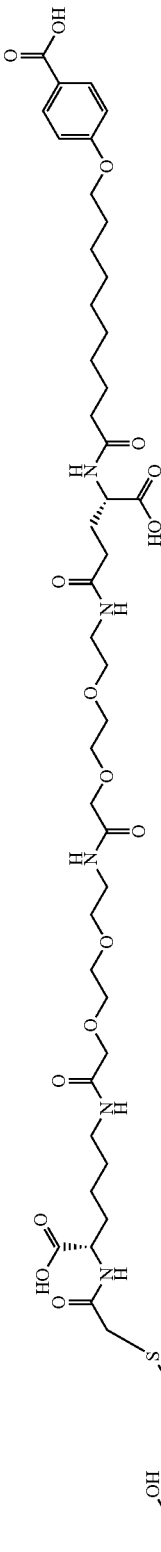
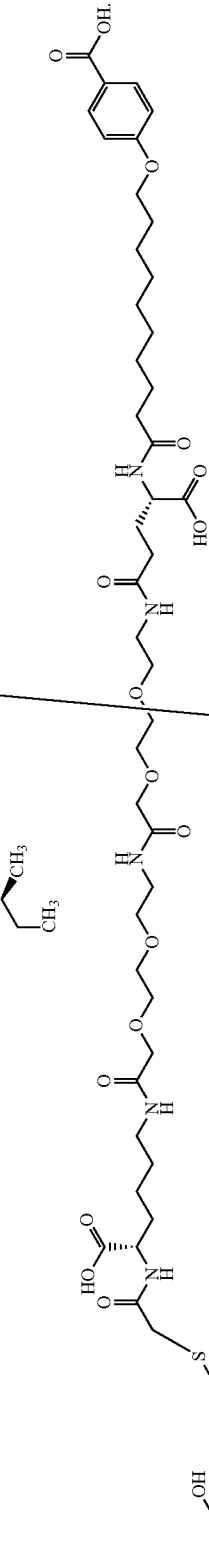
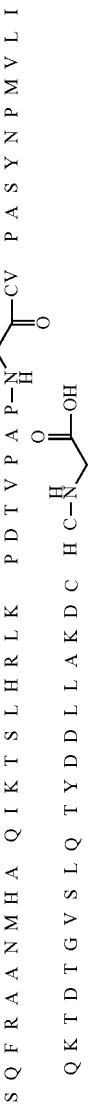
(Formula 19)
(SEQ ID NO: 288)

151. MIC-1 compound according to Formula 20 (SEQ ID NO:288):

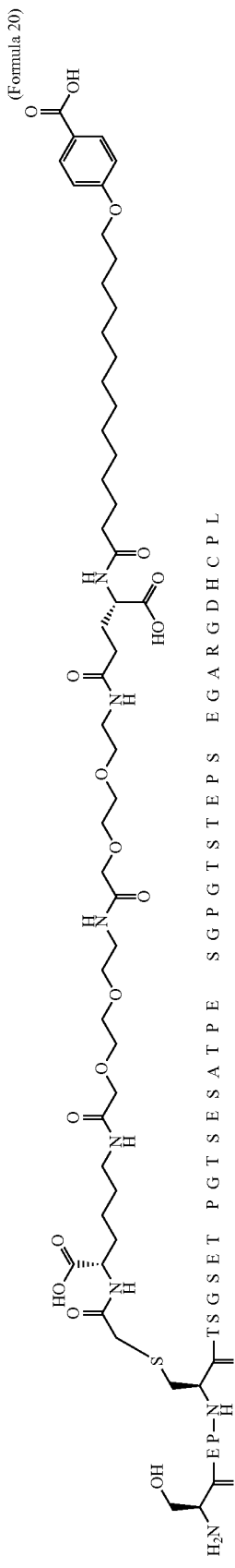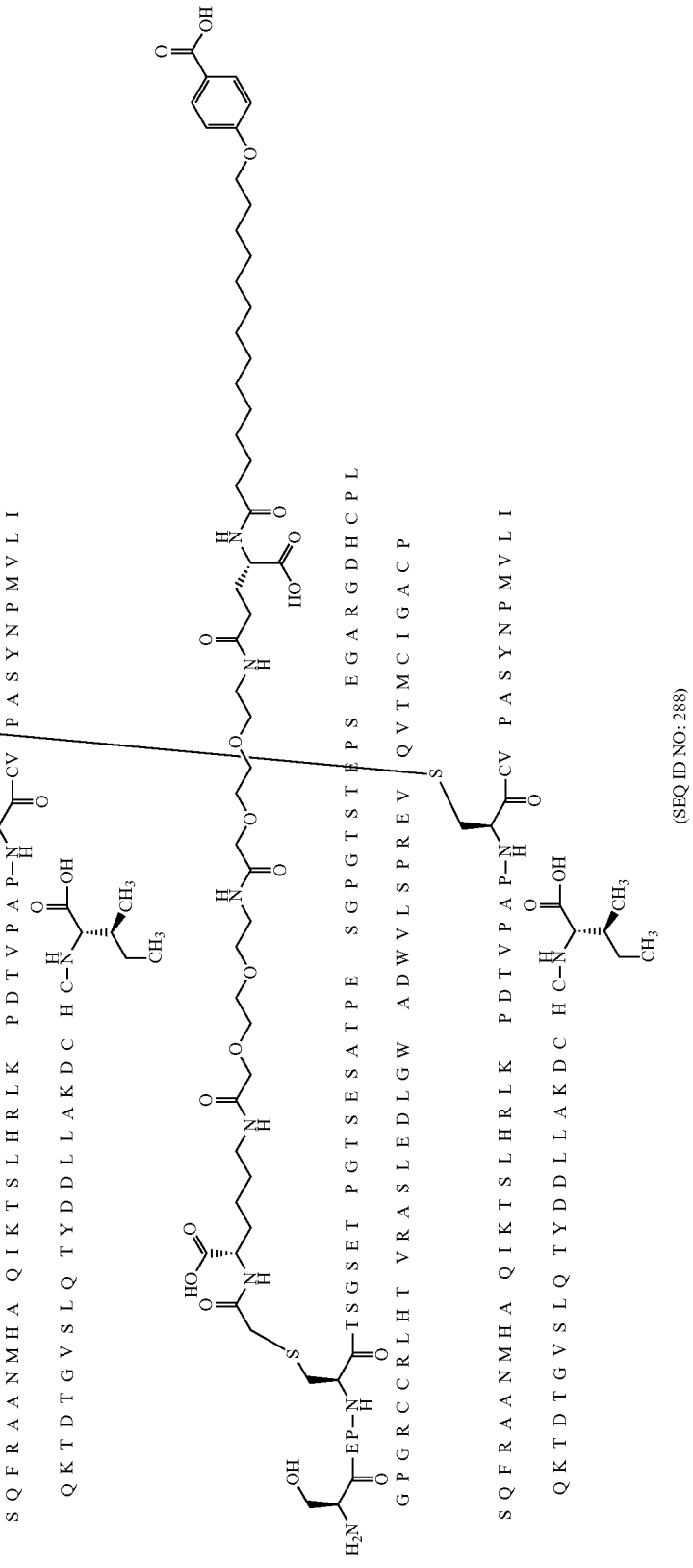
(Formula 20)
(SEQ ID NO: 288)

152. MIC-1 compound according to Formula 21 (SEQ ID NO:288):

(Formula 21)

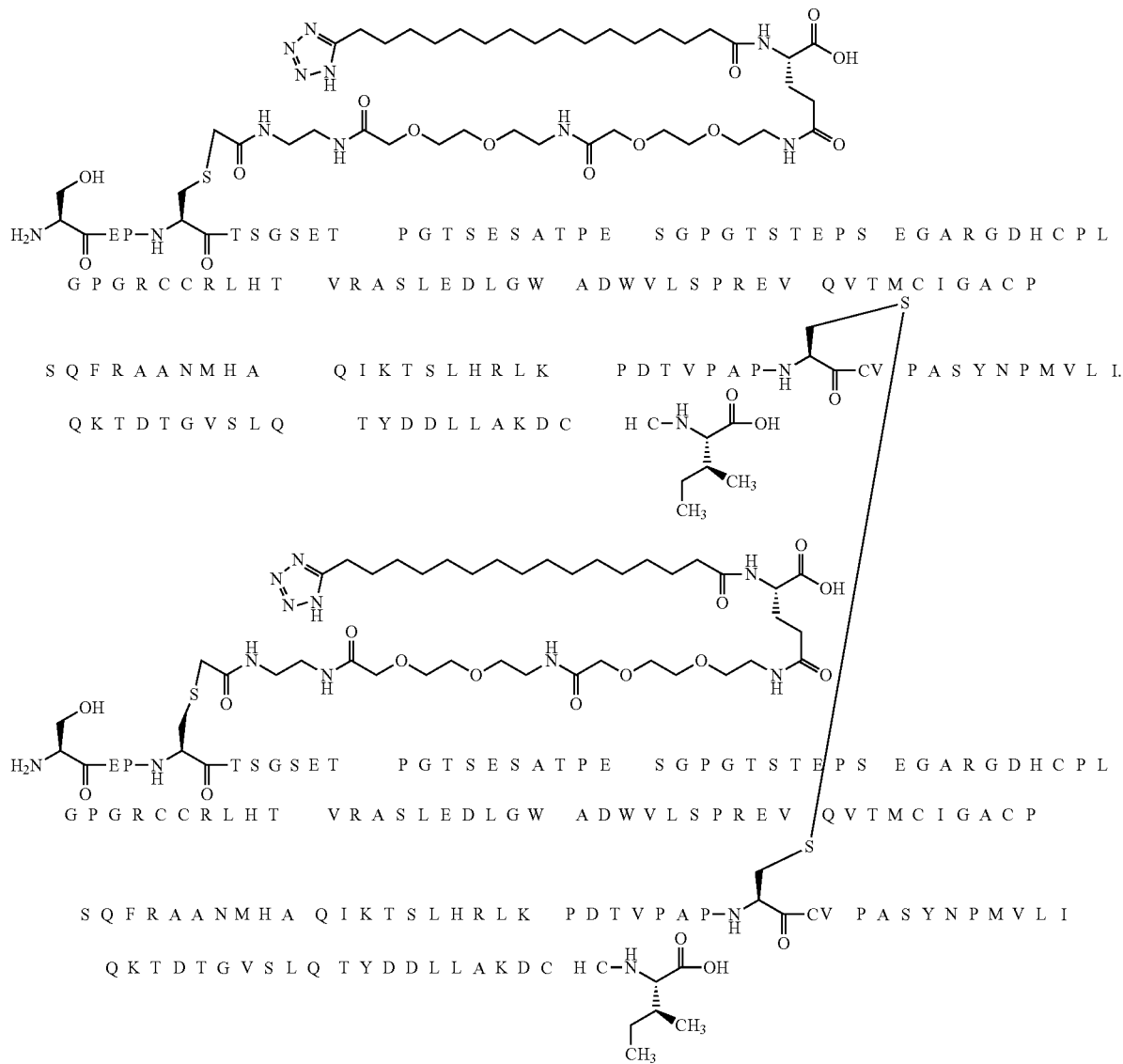

(SEQ ID NO: 288)

EXAMPLES

List of Abbreviations

"Main peak" refers to the peak in a purification chromatogram which has the highest UV intensity in milliabsorbance units and which contains the fusion protein.

HPLC is High performance liquid chromatography.

SDS-PAGE is Sodium dodecyl sulfate Polyacrylamide gel electrophoresis.

IMAC is immobilized metal affinity chromatography.

SEC is size exclusion chromatography.

MS is mass spectrometry.

In this description, Greek letters may be represented by their symbol or the corresponding written name, for example: α=alpha; β=beta; ε=epsilon; γ=gamma; ω=omega; Δ=delta; etc. Also, the Greek letter of μ may be represented by "u", e.g. in μl=ul, or in μM=uM.

MIC-1 Polypeptides with Improved Solubility

In an aspect of the invention, MIC-1 polypeptides were designed to have increased solubility.

In an aspect of the invention, this was achieved by adding an N-terminal "acidic" amino acid extension to the MIC-1 polypeptide.

In an aspect of the invention, solubility was enhanced and stability was improved by modification of the amino acid sequence of the MIC-1 polypeptide. For example, modification was done within the amino acid sequence of the MIC-1 polypeptide (in-sequence mutation).

MIC-1 polypeptides with an N-terminal amino acid extension can be expressed in bacteria such as E. coli. In the context of the present invention, large scale protein production of the MIC-1 polypeptides with an N-extension could take of using Inclusion Bodies (IB) as this represent an advantageous approach to controlling process recovery, protein purity, protease degradation and general protein stability. This becomes particular important for large scale protein production. Of critical importance for the quality of IB is the balance between improved solubility and IB formation of MIC-1 polypeptides with an N-extension.

N-Extension Design:

In the design of the N-terminal amino acid_extension, F, I, L, M, V, W and Y were excluded, since they could contribute to protein aggregation. H, K, and R were also excluded, since they could cause undesired binding on cell membrane. A, C, E, G, P, S, T, D, N, and Q are preferred for the N-extension sequence. E and D are particularly preferred since they increase the solubility by decreasing pI value of the compound. C could provide a —SH group which can be used for protraction purpose, such as fatty acid conjugation and PEGylation. Particularly, for some N-extensions, one or two additional Alanine(s), Glycine(s) or Serine(s) were added at the very N-terminal to increase the initial Methionine removing efficiency when MIC-1 polypeptides with N-extension were expressed in *E. coli*.

Various N-terminal amino acid_extensions were designed. Some N-extensions comprise sequences originating from human proteins (humanized sequences); some comprise artificially designed sequence(s) (e.g. GS, SG, AEE, AES, GEPQ (SEQ ID NO:123), GEPS (SEQ ID NO:118)); some comprise several repeats of the humanized sequences or artificial sequences; some comprise a combination of the above. Several 6-residue sequences (6-mers) were designed. N-extensions could comprise one or more of a 6-mers, part of a 6-mers (e.g., 1-5 residues of a 6-mers), or a combination of the above. The amino acid residues of the artificial sequences (including 6-mers) and the humanized sequences could be arranged in any order.

Some representative 6-mers and combinations of 6-mers are listed in Table 2, and other examples of N-extension are listed in Table 3.

TABLE 2

6-mers and combinations of 6-mers 6-mers:
6-mer-1: SPAGSP (SEQ ID NO: 4)
6-mer-2: TSESAT (SEQ ID NO: 5)
6-mer-3: TSTEPE (SEQ ID NO: 6)
6-mer-4: SEPATS (SEQ ID NO: 7)
6-mer-5: TSTEEG (SEQ ID NO: 8)
6-mer-6: PESGPG (SEQ ID NO: 9)
6-mer-7: SGSAPG (SEQ ID NO: 10)
6-mer-8: GSETPG (SEQ ID NO: 11)

Combinations: SEPATSGSETPGSPAGSPTSTEEG (SEQ ID NO: 12)
SEPATSGSETPGTSESATPESGPG (SEQ ID NO: 13)
SEPATSGSETPGTSTEPESGSAPG (SEQ ID NO: 14)
SEPATSGSETPGSPAGSPTSTEEGSPAGSP (SEQ ID NO: 15)
SEPATSGSETPGTSESATPESGPGSPAGSP (SEQ ID NO: 16)
SEPATSGSETPGTSTEPESGSAPGSPAGSP (SEQ ID NO: 17)
SEPATSGSETPGSPAGSPTSTEEGTSESAT (SEQ ID NO: 18)
SEPATSGSETPGTSESATPESGPGTSESAT (SEQ ID NO: 19)
SEPATSGSETPGTSTEPESGSAPGTSESAT (SEQ ID NO: 20)
SEPATSGSETPGSPAGSPTSTEEGTSTEPE (SEQ ID NO: 21)
SEPATSGSETPGTSESATPESGPGTSTEPE (SEQ ID NO: 22)
SEPATSGSETPGTSTEPESGSAPGTSTEPE (SEQ ID NO: 23)
SEPATSGSETPGSPAGSPTSTEEGSEPATS (SEQ ID NO: 24)
SEPATSGSETPGTSESATPESGPGSEPATS (SEQ ID NO: 25)
SEPATSGSETPGTSTEPESGSAPGSEPATS (SEQ ID NO: 26)
SEPATSGSETPGSPAGSPTSTEEGTSTEEG (SEQ ID NO: 27)
SEPATSGSETPGTSESATPESGPGTSTEEG (SEQ ID NO: 28)
SEPATSGSETPGTSTEPESGSAPGTSTEEG (SEQ ID NO: 29)
SEPATSGSETPGSPAGSPTSTEEGPESGPG (SEQ ID NO: 30)
SEPATSGSETPGTSESATPESGPGPESGPG (SEQ ID NO: 31)
SEPATSGSETPGTSTEPESGSAPGPESGPG (SEQ ID NO: 32)
SEPATSGSETPGSPAGSPTSTEEGSGSAPG (SEQ ID NO: 33)
SEPATSGSETPGTSESATPESGPGSGSAPG (SEQ ID NO: 34)
SEPATSGSETPGTSTEPESGSAPGSGSAPG (SEQ ID NO: 35)
SEPATSGSETPGSPAGSPTSTEEGGSETPG (SEQ ID NO: 36)
SEPATSGSETPGTSESATPESGPGGSETPG (SEQ ID NO: 37)
SEPATSGSETPGTSTEPESGSAPGGSETPG (SEQ ID NO: 38)
SEPATSGSETPGSPAGSPTSTEEGTSESATPESGPG (SEQ ID NO: 39)
SEPATSGSETPGSPAGSPTSTEEGSPAGSPTSTEEG (SEQ ID NO: 40)
SEPATSGSETPGSPAGSPTSTEEGTSTEPESGSAPG (SEQ ID NO: 41)
SEPATSGSETPGTSESATPESGPGSPAGSPTSTEEG (SEQ ID NO: 42)
SEPATSGSETPGTSESATPESGPGTSESATPESGPG (SEQ ID NO: 43)
SEPATSGSETPGTSESATPESGPGTSTEPESGSAPG (SEQ ID NO: 44)
SEPATSGSETPGTSESATPESGPGSEPATSGSETPG (SEQ ID NO: 45)
SEPATSGSETPGTSTEPESGSAPGSPAGSPTSTEEG (SEQ ID NO: 46)
SEPATSGSETPGTSTEPESGSAPGTSESATPESGPG (SEQ ID NO: 47)
SEPATSGSETPGTSTEPESGSAPGTSTEPESGSAPG (SEQ ID NO: 48)
SEPATSGSETPGTSTEPESGSAPGSEPATSGSETPG (SEQ ID NO: 49)
SEPATSGSETPGSEPATSGSETPGSPAGSPTSTEEG (SEQ ID NO: 50)
SEPATSGSETPGSEPATSGSETPGTSESATPESGPG (SEQ ID NO: 51)
SEPATSGSETPGSEPATSGSETPGTSTEPESGSAPG (SEQ ID NO: 52)
SEPATSGSETPGSEPATSGSETPGSEPATSGSETPG (SEQ ID NO: 53)

TABLE 3

Examples of N-extensions

| SEQ ID NO | Residue number | Sequence of N-extension |
|---|---|---|
| SEQ ID NO: 54 | 6 | AEEAES |
| SEQ ID NO: 55 | 3 | AES |
| SEQ ID NO: 56 | 9 | (AEE)$_2$AES |
| SEQ ID NO: 57 | 20 | (GEPS)$_5$ |
| SEQ ID NO: 58 | 24 | SPAGSPTSTEEGTSESATPESGPG |
| SEQ ID NO: 59 | 21 | (AEE)$_6$AEEAES |
| SEQ ID NO: 60 | 18 | (AEE)$_5$AES |
| SEQ ID NO: 61 | 12 | (AEE)$_3$AES |
| SEQ ID NO: 62 | 26 | AASPAGSPTSTEEGTSESATPESGPG |
| SEQ ID NO: 63 | 24 | TSESATPESGPGTSESATPESGPG |
| SEQ ID NO: 64 | 26 | AASPAGSPTSTEEGTSESATPESGPG |
| SEQ ID NO: 65 | 22 | AAPEDEETPEQEGSGSGSGSGS |
| SEQ ID NO: 66 | 12 | AAPEDEETPEQE |
| SEQ ID NO: 67 | 22 | AAPDEGTEEETEGSGSGSGSGS |
| SEQ ID NO: 68 | 24 | SEPATSGSETPGSEPATSGSETPG |
| SEQ ID NO: 69 | 25 | A(GPEQGQEP)$_3$ |
| SEQ ID NO: 70 | 30 | SEPATSGSETPGTSESATPESGPGTSTEPS |
| SEQ ID NO: 71 | 32 | SEPATSGSETPGTSESATPESGPGTSTEPSEG |
| SEQ ID NO: 72 | 24 | (GEPS)$_6$ |
| SEQ ID NO: 161 | 36 | (GEPS)$_9$ |
| SEQ ID NO: 162 | 36 | (GPEQ)$_9$ |
| SEQ ID NO: 163 | 25 | AGPEQGQEPGEPQGQEPQPGEPEGQ |

In-Sequence Mutations:

Certain internal residues of MIC-1 (SEQ ID NO:1) were modified, e.g. by substitution. For example, to increase the solubility of MIC-1 compounds, a hydrophobic residue of MIC-1 could be substituted with a hydrophilic residue, preferably by with an acidic residue; a positive charged residue could be substituted with an acidic residue, etc. To decrease oxidation, methionine could be substituted with other amino acids, e.g. E, F or L.

In-sequence mutations for increasing solubility include but are not limited to: P11E, H18E, R21E, A30E, A47E, R53E, A54E, M57E, H66E, R67E, L68E, K69E, A75E, A81E, P85E, Q90E, T92E, L105E and K107E.

In-sequence mutations for decreasing oxidation include but are not limited to: M43L, M43E, M57E, M57L, M86F and M86L.

In-sequence mutations for increasing chemical stability include but are not limited to N3S, N3E, N3A, N3T, N3P, N3G, N3V, N3H, N3Y and N3Q.

In-sequence mutations for conjugation include but are not limited to K69R, K107R and K91R.

Other in-sequence mutations include but are not limited to a deletion of N3 (des-N3) and/or a deletion of the first 3 residues.

pI Calculation

The calculated pI of a MIC-1 polypeptide with an N-terminal amino acid extension is defined as the pH at which the net calculated charge of the MIC-1 polypeptide with a N-terminal amino acid extension is zero. The calculated charge of the MIC-1 polypeptide with the N-terminal amino acid extension as a function of pH is obtained using the pKa values of the amino acid residues described in Table 1 and the method described by B. Skoog and A. Wichman (Trends in Analytical Chemistry, 1986, vol. 5, pp. 82-83). The side chain pKa of cysteine (Cys) is only included in the charge calculation for cysteines with a free sulfhydryl group. The N-extension may contain one cysteine mutation. As an example the calculated pI value of human wild type MIC-1 is 8.8 as the homodimer. The calculated pI values of MIC-1 polypeptide are shown in Table 4.

Herein, and throughout this document, pI calculations on the MIC-1 polypeptide with an N-terminal amino acid extension, if not stated otherwise, are made on homodimers.

TABLE 4

Calculated pI values

| | MIC-1 (SEQ ID NO: 1) | MIC-1- des-N3 | MIC-1- Δ1-3 | MIC-1 - Δ1-3 (M57E) | MIC-1- Δ1-3 (M57E, H66E) | MIC-1- Δ1-3 (M57E, R67E) | MIC-1- Δ1-3 (M57E, H66E and R67E) |
|---|---|---|---|---|---|---|---|
| Any combinations of four of 6mers 1-8$^\infty$ | 6.1 | 6.1 | 5.8 | 5.5 | 5.0 | 5.0 | 4.7 |
| Any combinations of five 6mers 1-8$^\infty$ | 5.8 | 5.8 | 5.5 | 5.2 | 4.8 | 4.8 | 4.6 |
| (GEPQ*)$_5$ or (GEPS*)$_5$$^\infty$ | 5.8 | 5.8 | 5.5 | 5.2 | 4.8 | 4.8 | 4.6 |

TABLE 4-continued

| | Calculated pI values | | | | | | |
|---|---|---|---|---|---|---|---|
| | MIC-1 (SEQ ID NO: 1) | MIC-1-des-N3 | MIC-1-Δ1-3 | MIC-1 -Δ1-3 (M57E) | MIC-1-Δ1-3 (M57E, H66E) | MIC-1-Δ1-3 (M57E, R67E) | MIC-1-Δ1-3 (M57E, H66E and R67E) |
| (GEPQ*)$_6$[∞] | 5.5 | 5.5 | 5.2 | 5.2 | 4.7 | 4.7 | 4.5 |
| Humanized sequences in examples[∞] | 4.5~5.5 | 4.5~5.5 | 4.2~5.3 | 4.2~5.2 | 4.2~5.1 | 4.2~5.1 | 4.2~5.0 |

*The amino acid residues of "GEPQ" or "GEPS" may be arranged in any order
[∞]One Cys in the N-terminal extension change pI by less than ± 0.1.

Materials and Methods

General Methods of Preparation

Example-1: Expression and Fermentation of the MIC-1 Polypeptide or the MIC-1 Polypeptide with an N-Terminal Extension The cDNA of MIC-1 polypeptide or MIC-1 polypeptide with an N-terminal extension was sub-cloned into a pET11b derived vector. Overexpression of MIC-1f polypeptide or MIC-1 polypeptide with an N-terminal extension as inclusion bodies was induced in *E. coli* by 0.5 mM isopropyl β-d-thiogalactoside (IPTG) when the cell density reached an OD600 of 1.0. After continuous growth in TB for 20h at 37° C., the cells were harvested and samples for both LC/MS and UPLC were prepared to confirm the molecular weight.

Fermentation was carried out on fed-batch process in chemical defined medium as supplement. Fermentation yield largely depended on different polypeptide, which varied from 1 g/L to 8 g/L from polypeptide to polypeptide.

Example-2: Purification and Refolding

The MIC-1 polypeptide or MIC-1 polypeptide with an N-terminal extension were further purified as follows:

Slurry (20% w/v) of *E. coli* in 10 mM Tris buffer pH 8.0 was sonicated (3 seconds on/off intervals on ice for 5 minutes) and the MIC-1 polypeptide or MIC-1 polypeptide with an N-terminal extension was pelleted by centrifugation (10,000×g, for 30 minutes). The inclusion bodies were re-solubilised by 8 M urea in 20 mM Tris pH 8.0, and debris removed by centrifugation (10,000×g, for 30 minutes). The MIC-1 polypeptide or MIC-1 polypeptide with an N-terminal extension in the resulting supernatant was collected and diluted into the refolding buffer (50 mM Tris, pH 8.5 and 10% DMF or 10% DMSO) to the final concentration of 0.1 mg/ml. The refolding process lasted for 48 hours in the cold room. The resulting solution was filtered by 0.4 μm filter and loaded onto Hydrophobic Interaction column or anion exchange chromatography (50 mM Tris pH 8.0, 0-500 mM NaCl) using Q Sepharose Fast Flow resin (GE Healthcare), as generally described in *Protein Purification*. Principles and Practice Series: Springer Advanced Texts in Chemistry Scopes, Robert K. 3rd ed., 1994 (Chapters 6 and 8). In some instances, further purification was done by size exclusion chromatography using a HiLoad 26/60 Superdex pg 75 column (GE Healthcare) operated with 50 mM Tris pH 8.0 and 200 mM NaCl. For storage, the MIC-1 polypeptide or MIC-1 polypeptide with an N-terminal extension was transferred to DPBS, and stored frozen. MIC-1 polypeptides or MIC-1 polypeptides with an N-terminal extension and their maximal solubility at pH8 in Tris buffer are shown in Table 5.

TABLE 5

MIC-1 polypeptides or MIC-1 polypeptides with an N-terminal extension and their maximal solubility at pH 8 in Tris buffer tested according to Example 4

| SEQ ID NO | Structure | Calculated pI | Max. solubility (mg/ml) |
|---|---|---|---|
| SEQ ID NO: 1 | MIC-1 (SEQ ID NO: 1) | 8.8 | 0.3 |
| SEQ ID NO: 73 | MIC-1(R2A, N3E) | 6.8 | 0.9 |
| SEQ ID NO: 74 | MIC-1(R2A, N3E, A54E) | 6.4 | 1.0 |
| SEQ ID NO: 75 | MIC-1(R2A, N3E, A81E) | 6.4 | N.D.* |
| SEQ ID NO: 76 | MIC-1(R2A, N3E, H18E) | 6.2 | 1.7 |
| SEQ ID NO: 77 | MIC-1(R2A, N3E, K69E) | 6.1 | 2.2 |
| SEQ ID NO: 78 | MIC-1(R2A, N3E, K107E) | 6.1 | 1.9 |
| SEQ ID NO: 79 | MIC-1(R2A, N3E, L68E) | 6.4 | 3.9 |
| SEQ ID NO: 80 | MIC-1(R2A, N3E, A47E) | 6.4 | 1.0 |
| SEQ ID NO: 81 | MIC-1(R2A, N3E, L105E) | 6.4 | N.D. |
| SEQ ID NO: 82 | MIC-1(R2A, N3E, M57E) | 6.4 | 1.7 |
| SEQ ID NO: 83 | MIC-1(R2A, N3E, P85E) | 6.4 | N.D. |
| SEQ ID NO: 84 | MIC-1(R2A, N3E, P11E) | 6.4 | 1.6 |
| SEQ ID NO: 85 | MIC-1(R2A, N3E, R21E) | 6.1 | 1.8 |
| SEQ ID NO: 86 | MIC-1(R2A, N3E, R53E) | 6.1 | 1.9 |
| SEQ ID NO: 87 | MIC-1(R2A, N3E, R67E) | 6.1 | 1.8 |

TABLE 5-continued

MIC-1 polypeptides or MIC-1 polypeptides with an N-terminal extension
and their maximal solubility at pH 8 in Tris buffer tested according to Example 4

| SEQ ID NO | Structure | Calculated pI | Max. solubility (mg/ml) |
|---|---|---|---|
| SEQ ID NO: 88 | MIC-1(R2A, N3E, A30E) | 6.4 | 1.5 |
| SEQ ID NO: 89 | AEEAES-MIC-1-Δ1-3 | 6.1 | N.D. |
| SEQ ID NO: 90 | AES-MIC-1-Δ1-3 | 6.8 | 0.9 |
| SEQ ID NO: 91 | (AEE)$_2$AES-MIC-1-Δ1-3 | 5.5 | N.D. |
| SEQ ID NO: 92 | (GEPS)$_5$-MIC-1(SEQ ID NO: 1) | 5.8 | 35.1 |
| SEQ ID NO: 93 | SPAGSPTSTEEGTSESATPESGPG-MIC-1(SEQ ID NO: 1) | 6.1 | 44.5 |
| SEQ ID NO: 94 | (AEE)$_6$AES-MIC-1(SEQ ID NO: 1) | 4.5 | 39.0 |
| SEQ ID NO: 95 | (AEE)$_5$AES-MIC-1-Δ1-3 | 4.6 | 35.0 |
| SEQ ID NO: 96 | (AEE)$_3$AES-MIC-1-Δ1-3 | 5.0 | 36.0 |
| SEQ ID NO: 97 | AASPAGSPTSTEEGTSESATPESGPG-MIC-1(SEQ ID NO: 1) | 6.1 | N.D. |
| SEQ ID NO: 98 | TSESATPESGPGTSESATPESGPG-MIC-1(R2A, N3E) | 5.5 | N.D. |
| SEQ ID NO: 99 | AASPAGSPTSTEEGTSESATPESGPG-MIC-1-Δ1-3 | 5.8 | N.D. |
| SEQ ID NO: 100 | AAPEDEETPEQEGSGSGSGSGS-MIC-1-Δ1-3 | 5.2 | 35.7 |
| SEQ ID NO: 101 | AAPEDEETPEQE-MIC-1-Δ1-3 | 5.2 | N.D. |
| SEQ ID NO: 102 | AAPDEGTEEETEGSGSGSGSGS-MIC-1-Δ1-3 | 5.2 | N.D. |
| SEQ ID NO: 103 | SEPATSGSETPGTSTEPSEGSAPG-MIC-1-Δ1-3 | 5.8 | N.D. |
| SEQ ID NO: 104 | (SEPATSGSETPG)$_2$-MIC-1-Δ1-3 | 5.8 | 35.4 |
| SEQ ID NO: 105 | (SEPATSGSETPG)$_2$-MIC-1-Δ1-3(M57E) | 5.5 | 37.1 |
| SEQ ID NO: 106 | (SEPATSGSETPG)$_2$-MIC-1-Δ1-3(M57L) | 5.8 | 32.5 |
| SEQ ID NO: 107 | A(GPEQGQEP)$_3$-MIC-1-Δ1-3 | 5.2 | 32.2 |
| SEQ ID NO: 108 | SEPATSGSETPGTSESATPESGPG TSTEPS-MIC-1-Δ1-3 | 5.5 | 40.0 |
| SEQ ID NO: 109 | SEPATSGSETPG TSESATPESGPG TSTEPSEG-MIC-1-Δ1-3 | 5.2 | 40.0 |
| SEQ ID NO: 110 | (SEPATSGSETPG)$_2$-MIC-1-Δ1-3(M86L) | 5.8 | N.D. |
| SEQ ID NO: 111 | (SEPATSGSETPG)$_2$-MIC-1-Δ1-3(M57L, M86L) | 5.8 | 31.1 |
| SEQ ID NO: 112 | (SEPATSGSETPG)$_2$-MIC-1-Δ1-3(M57E, H66E) | 5.0 | N.D. |
| SEQ ID NO: 113 | (SEPATSGSETPG)$_2$-MIC-1-Δ1-3(M57E, R67E) | 5.0 | N.D. |
| SEQ ID NO: 114 | (SEPATSGSETPG)$_2$-MIC-1-Δ1-3(M57E, R67E, M86L) | 5.0 | N.D. |
| SEQ ID NO: 115 | SEPATSGSETPG TSESATPESGPGTSTEPSG-MIC-1-Δ1-3(M57L, M86L) | 5.5 | N.D. |
| SEQ ID NO: 116 | (GEPS)$_6$-MIC-1-Δ1-3 | 5.2 | N.D. |
| SEQ ID NO: 117 | (SEPATSGSETPG)$_2$-MIC-1-des-N3 | 6.1 | N.D. |

*N.D.: Not determined

Example-3: pH-Dependent Solubility of MIC-1 Polypeptide with an N-Terminal Extension The purpose of this experiment was to screen for a MIC-1 polypeptide with an N-extension with improved solubility, and determine the optimal pH window for formulation.

MIC-1 polypeptides with N-terminal extensions were dissolved in a mixture of water and ethanol (60% water and 40% ethanol) with a concentration range between 3 mg/ml to 10 mg/ml. The solvent was evaporated with SpeedVac (Concentrator Plus, Eppendorf) for 6 hours to obtain pellet of the MIC-1 polypeptide with N-terminal extension.

Below buffers were used for this pH-dependent solubility curve assay: acetate buffer (pH 3 to pH 6); Tris buffer (pH 7 to pH 9); CAPS buffer (pH 10 to pH 11).

Buffers were added into each well of the 96-well plate together with the MIC-1 polypeptides with N-terminal extensions. The amount used may not be exactly the same but all targeting a theoretical concentration within 12-18 mg/ml. The concentration of MIC-1 polypeptide with N-terminal extension in the supernatant was determined by UPLC (Table 6). Based on the results, solubility of the MIC-1 polypeptide with N-terminal extension of the invention was significantly improved between pH 6-9 compared with wtMIC-1. The optimal pH window of the MIC-1 polypeptides with an N-extension falls into the pH range that is preferred for formulation, e.g. pH 6.5-8.5.

TABLE 6 pH-dependent solubility test of MIC-1 polypeptides with an N-terminal extension (mg/ml)

| SEQ ID NO | Structure | pH | | | | | | | | |
|---|---|---|---|---|---|---|---|---|---|---|
| | | 3.0 | 4.0 | 5.0 | 6.0 | 7.0 | 8.0 | 9.0 | 10.0 | 11.0 |
| SEQ ID NO: 1 | MIC-1 (SEQ ID NO: 1) | 12.8 | 2.0 | 0.2 | 0.3 | 0.2 | 0.3 | 0.6 | 3.6 | 13.9 |
| SEQ ID NO: 74 | MIC-1(R2A, N3E, A54E) | 13.3 | 1.3 | 0.4 | 0.6 | 0.5 | 1.0 | 1.5 | 3.6 | 15.5 |
| SEQ ID NO: 76 | MIC-1(R2A, N3E, H18E) | 14.5 | 3.4 | 0.4 | 0.4 | 0.9 | 1.7 | 3.0 | 14.3 | 13.6 |
| SEQ ID NO: 79 | MIC-1(R2A, N3E, L68E) | 13.6 | 1.4 | 1.4 | 1.7 | 3.2 | 3.9 | 3.9 | 4.0 | 12.1 |
| SEQ ID NO: 80 | MIC-1(R2A, N3E, A47E) | 13.4 | 2.5 | 0.5 | 0.6 | 0.9 | 1.0 | 1.0 | 2.9 | 10.8 |
| SEQ ID NO: 85 | MIC-1(R2A, N3E, R21E) | 14.9 | 1.6 | 0.5 | 0.5 | 1.4 | 1.8 | 1.7 | 2.5 | 12.9 |
| SEQ ID NO: 88 | MIC-1(R2A, N3E, A30E) | 13.9 | 1.7 | 0.8 | 0.8 | 1.4 | 1.5 | 2.1 | 2.4 | 13.7 |
| SEQ ID NO: 90 | AES-MIC-1-Δ1-3 | 12.5 | 2.3 | 0.6 | 0.7 | 1.2 | 0.9 | 1.0 | 3.6 | 8.9 |
| SEQ ID NO: 93 | SPAGSPTSTEEGTSESATPESGPG-MIC-1(SEQ ID NO: 1) | 12.9 | 1.5 | 1.2 | 1.4 | 5.1 | 12.8 | 13.0 | 13.0 | 13.5 |
| SEQ ID NO: 94 | (AEE)$_6$AES-MIC-1-Δ1-3 | 7.3 | 0.2 | 2.9 | 9.5 | 11.6 | 15.3 | 15.1 | 15.0 | 14.8 |
| SEQ ID NO: 95 | (AEE)$_5$AES-MIC-1-Δ1-3 | 11.9 | 0.3 | 1.6 | 5.7 | 9.4 | 15.8 | 15.7 | 14.9 | 15.0 |
| SEQ ID NO: 100 | AAPEDEETPEQEGSGSGSGSGS-MIC-1-Δ1-3 | 11.2 | 3.2 | 2.1 | 5.1 | 8.3 | 15.0 | 15.3 | 15.0 | 15.6 |
| SEQ ID NO: 104 | (SEPATSGSETPG)$_2$-MIC-1-Δ1-3 | 12.2 | 0.7 | 0.3 | 1.0 | 4.6 | 16.4 | 16.9 | 16.0 | 16.2 |
| SEQ ID NO: 105 | (SEPATSGSETPG)$_2$-MIC-1-Δ1-3(M57E) | 7.2 | 1.2 | 0.8 | 3.8 | 11.5 | 15.6 | 15.2 | 14.9 | 16.2 |
| SEQ ID NO: 106 | (SEPATSGSETPG)$_2$-MIC-1-Δ1-3(M57L) | 10.1 | 0.2 | 0.3 | 1.6 | 4.3 | 15.6 | 16.1 | 16.1 | 16.8 |

Example 4: Maximal Solubility of MIC-1 Polypeptides with an N-Terminal Extension at pH 8

In order to test the maximal solubility, the MIC-1 polypeptides with an N-terminal extension were dissolved in a mixture of water and ethanol (60% water and 40% ethanol) with a concentration range between 3 mg/ml to 10 mg/ml. Then the solution (150 µL each well) was aliquot into a 96-well plate (Corning). The solvent was evaporated with SpeedVac (Concentrator Plus, Eppendorf) for 6 hours to obtain pellet of the MIC-1 polypeptide with an N-terminal extension. Tris buffer (pH 8.0, without excipients) was added into each well of the 96-well plate. The amount of buffer added to the well was less than the amount needed for solving the whole pellet in the well, so that maximal concentration was achieved. The plate was shaken on a plate shaker at 800 rpm (MixMate, Eppendorf) for 2 hours. The pellet was spun down at 3600 g for 5 min. The supernatants were transferred to a 96-deep-well plate and diluted 20 times with 40% ethanol. Then all of the samples were subject to UPLC (Acquity, Waters), plate reader (Infinite M200 pro, Tecan) and UV spectrometer (NanoDrop 8000, Thermo Scientific) to determine the concentration (Table 7)

Based on the results, solubility of the MIC-1 polypeptides with an N-terminal extension of the invention was significantly improved at pH 8.0. Especially, the MIC-1 polypeptides with an N-terminal extension achieved solubility of more than 30 mg/ml at pH 8.0.

TABLE 7

Max solubility test of MIC-1 polypeptides with an N-terminal extension at pH 8.0

| SEQ IN NO | Structure | Solubility (mg/ml) |
| --- | --- | --- |
| SEQ ID NO: 96 | (AEE)₃AES-MIC-1-Δ1-3 | 36.0 |
| SEQ ID NO: 95 | (AEE)₅AES-MIC-1-Δ1-3 | 35.0 |
| SEQ ID NO: 94 | (AEE)₆AES-MIC-1(SEQ ID NO: 1) | 39.0 |
| SEQ ID NO: 93 | SPAGSPTSTEEGTSESATPESGPG-MIC-1 | 44.5 |
| SEQ ID NO: 92 | (GEPS)₅-MIC-1(SEQ ID NO: 1) | 35.1 |
| SEQ ID NO: 100 | AAPEDEETPEQEGSGSGSGSGS-MIC-1-Δ1-3 | 35.7 |
| SEQ ID NO: 79 | MIC-1(R2A,N3E,L68E) | 3.9 |
| SEQ ID NO: 85 | MIC-1(R2A,N3E,R21E) | 1.8 |
| SEQ ID NO: 88 | MIC-1(R2A,N3E,A30E) | 1.5 |
| SEQ ID NO: 74 | MIC-1(R2A,N3E,A54E) | 1.0 |
| SEQ ID NO: 76 | MIC-1(R2A,N3E,H18E) | 1.7 |
| SEQ ID NO: 77 | MIC-1(R2A,N3E,K69E) | 2.2 |
| SEQ ID NO: 80 | MIC-1(R2A,N3E,A47E) | 1.0 |
| SEQ ID NO: 90 | AES-MIC-1-Δ1-3 | 0.9 |
| SEQ ID NO: 78 | MIC-1(R2A,N3E,K107E) | 1.9 |
| SEQ ID NO: 82 | MIC-1(R2A,N3E,M57E) | 1.7 |
| SEQ ID NO: 84 | MIC-1(R2A,N3E,P11E) | 1.6 |
| SEQ ID NO: 86 | MIC-1(R2A,N3E,R53E) | 1.9 |
| SEQ ID NO: 87 | MIC-1(R2A,N3E,R67E) | 1.8 |
| SEQ ID NO: 104 | (SEPATSGSETPG)₂-MIC-1-Δ1-3 | 35.4 |
| SEQ ID NO: 105 | (SEPATSGSETPG)₂-MIC-1-Δ1-3(M57E) | 37.1 |
| SEQ ID NO: 106 | (SEPATSGSETPG)₂-MIC-1-Δ1-3(M57L) | 32.5 |
| SEQ ID NO: 107 | A(GPEQGQEP)₃-MIC-1-Δ1-3 | 32.2 |
| SEQ ID NO: 108 | SEPATSGSETPGTSESATPESGPGTSTEPS-MIC-1-Δ1-3 | 40.0 |
| SEQ ID NO: 109 | SEPATSGSETPGTSESATPESGPG TSTEPSEG-MIC-1-Δ1-3 | 40.0 |
| SEQ ID NO: 111 | (SEPATSGSETPG)₂-MIC-1-Δ1-3(M57L, M86L) | 31.1 |
| SEQ ID NO: 73 | MIC-1(R2A, N3E) | 0.9 |
| SEQ ID NO: 164 | SEPATSGSETPGTSESATPESGPGTSTEPSEG-MIC-1-des-N3 (M57L, M86L) | 40.0 |
| SEQ ID NO: 1 | MIC-1(SEQ ID NO: 1) | 0.3 |

The improved solubility of MIC-1 polypeptides with an N-extension was retained in the MIC-1 compounds, i.e. adding a protractor did not significantly lower the solubility (Example 12).

General Methods of In Vitro Activity Screening

Example 5: Establishment of BHK21-hGFRAL-IRES-hRET Cell Line

The purpose of this example was to establish a cell based in vitro assay for testing MIC-1 activity. Mammalian cells were transfected and stably expressed full length MIC-1 receptor (hGFRAL) and its full signaling co-receptor hRET51.

Plasmids expressing full length hGFRAL and full length hRET51 were constructed by inserting synthesized DNA nucleotides encoding full length hGFRAL and full length hRET51 into mammalian expression vector pEL. IRES (internal ribosome entry site) is a commonly used linker between two DNA sequences, so that the two DNA sequences can be simultaneously translated into mRNA. pEL vector backbone was provided by Taihegene CRO company.

Two millions of BHK21 cells were seeded in a 10 cm petri dish and cultured for overnight in culture medium (DMEM+ 10% FBS+1% PS). Cells were transfected with pEL-hG-FRAL-IRES-hRET plasmids. Transfected cells were split into new 10 cm dishes at different densities and grew in selection medium (DMEM+10% FBS+1% PS+1 mg/ml G418) for more than 2 weeks to get single clones. The single clones were transferred to 6 well plates and cultured to 100% confluence. mRNA expression of hGFRAL and hRET was measured by qPCR. Successfully transfected clones were picked up and tested for MIC-1 binding.

Example 6: MIC-1 Cell-Based In Vitro Activity Assay wtMIC-1 and MIC-1 polypeptides with an N-terminal extension induced both phosphorylation of ERK1/2 in BHK21-hGFRAL-IRES-hRET stable cells (Table 8). It can be concluded from the results that the ternary complex of MIC-1, GFRAL and RET phosphorylates RET protein tyrosine kinase to induce in vivo activities of MIC-1 through signal pathways comprising ERK/MAPK pathway by phosphorylation of ERK1/2.

Results from screening MIC-1 polypeptides with an N-terminal extension using BHK21-hGFRAL-IRES-hRET is shown in Table 8. MIC-1 polypeptides with N-extensions only or MIC-1 analogues with in-sequence mutations only achieved in vitro activity equal to or even higher than wtMIC-1. Also, combination of N-extension and in-sequence mutations can also achieve similar activity.

TABLE 8

In vitro activity

| SEQ IN NO | Structure | pERK EC50 (nM) | Emax (%) |
|---|---|---|---|
| SEQ ID NO: 1 | MIC-1(SEQ ID NO: 1) | 0.3 | 100% |
| SEQ ID NO: 73 | MIC-1(R2A, N3E) | 0.3 | 100% |
| SEQ ID NO: 74 | MIC-1(R2A,N3E,A54E) | 0.3 | 100% |
| SEQ ID NO: 75 | MIC-1(R2A,N3E,A81E) | 0.3 | 100% |
| SEQ ID NO: 76 | MIC-1(R2A,N3E,H18E) | 0.5 | 100% |
| SEQ ID NO: 77 | MIC-1(R2A,N3E,K69E) | 0.5 | 100% |
| SEQ ID NO: 78 | MIC-1(R2A,N3E,K107E) | 0.3 | 100% |
| SEQ ID NO: 79 | MIC-1(R2A,N3E,L68E) | 0.8 | 100% |
| SEQ ID NO: 80 | MIC-1(R2A,N3E,A47E) | 0.4 | 100% |
| SEQ ID NO: 81 | MIC-1(R2A,N3E,L105E) | 0.7 | 100% |
| SEQ ID NO: 82 | MIC-1(R2A,N3E,M57E) | 0.3 | 70% |
| SEQ ID NO: 83 | MIC-1(R2A,N3E,P85E) | 0.6 | 100% |
| SEQ ID NO: 84 | MIC-1(R2A,N3E,P11E) | 0.4 | 100% |
| SEQ ID NO: 85 | MIC-1(R2A,N3E,R21E) | 0.6 | 100% |
| SEQ ID NO: 86 | MIC-1(R2A,N3E,R53E) | 0.4 | 100% |
| SEQ ID NO: 87 | MIC-1(R2A,N3E,R67E) | 0.5 | 100% |
| SEQ ID NO: 88 | MIC-1(R2A,N3E,A30E) | 0.7 | 100% |
| SEQ ID NO: 89 | AEEAES-MIC-1-Δ1-3 | 0.3 | 100% |

TABLE 8-continued

In vitro activity

| SEQ IN NO | Structure | pERK EC50 (nM) | Emax (%) |
|---|---|---|---|
| SEQ ID NO: 90 | AES-MIC-1-Δ1-3 | 0.3 | 100% |
| SEQ ID NO: 91 | (AEE)$_2$AES-MIC-1-Δ1-3 | 0.4 | 100% |
| SEQ ID NO: 92 | (GEPS)$_5$-MIC-1(SEQ ID NO: 1) | 0.5 | 100% |
| SEQ ID NO: 93 | SPAGSPTSTEEGTSESATPESGPG-MIC-1(SEQ ID NO: 1) | 0.4 | 100% |
| SEQ ID NO: 94 | (AEE)$_6$AES-MIC-1 | 0.8 | 100% |
| SEQ ID NO: 95 | (AEE)$_5$AES-MIC-1-Δ1-3 | 0.5 | 100% |
| SEQ ID NO: 96 | (AEE)$_3$AES-MIC-1-Δ1-3 | 0.5 | 100% |
| SEQ ID NO: 97 | AASPAGSPTSTEEGTSESATPESGPG-MIC-1(SEQ ID NO: 1) | 0.4 | 100% |
| SEQ ID NO: 98 | TSESATPESGPGTSESATPESGPG-MIC-1(R2A,N3E) | 0.3 | 100% |
| SEQ ID NO: 99 | AASPAGSPTSTEEGTSESATPESGPG-MIC-1-Δ1-3 | 0.7 | 100% |
| SEQ ID NO: 100 | AAPEDEETPEQEGSGSGSGSGS-MIC-1-Δ1-3 | 0.5 | 100% |
| SEQ ID NO: 101 | AAPEDEETPEQE-MIC-1-Δ1-3 | 0.5 | 100% |
| SEQ ID NO: 102 | AAPDEGTEEETEGSGSGSGSGS-MIC-1-Δ1-3 | 0.5 | 100% |
| SEQ ID NO: 103 | SEPATSGSETPGTSTEPESGSAPG-MIC-1-Δ1-3 | 0.7 | 100% |
| SEQ ID NO: 104 | (SEPATSGSETPG)$_2$-MIC-1-Δ1-3 | 0.4 | 100% |
| SEQ ID NO: 105 | (SEPATSGSETPG)$_2$-MIC-1-Δ1-3(M57E) | 0.6 | 60% |
| SEQ ID NO: 106 | (SEPATSGSETPG)$_2$-MIC-1-Δ1-3(M57L) | 0.6 | 100% |
| SEQ ID NO: 107 | A(GPEQGQEP)$_3$-MIC-1-Δ1-3 | 0.8 | 100% |
| SEQ ID NO: 108 | SEPATSGSETPGTSESATPESGPGTSTEPS-MIC-1-Δ1-3 | 0.4 | 100% |
| SEQ ID NO: 109 | SEPATSGSETPGTSESATPESGPGTSTEPSEG-MIC-1-Δ1-3 | 0.4 | 100% |
| SEQ ID NO: 110 | (SEPATSGSETPG)$_2$-MIC-1-Δ1-3(M86L) | 0.4 | 100% |
| SEQ ID NO: 111 | (SEPATSGSETPG)$_2$-MIC-1-Δ1-3(M57L,M86L) | 0.4 | 100% |

In Vivo Efficacy

Example 7: Effect of MIC-1 Polypeptides with an N-Terminal Extension on Food Intake in Lean Sprague Dawley Rats The in vivo efficacy of MIC-1 polypeptides with an N-terminal extension was measured in 9-11 weeks old lean male Sprague Dawley rats. Animals were injected once daily with a dose of 8 nmol/kg body weight 1-2 hrs before the onset of the dark period. Compounds were administrate subcutaneously (1-4 ml/kg) in appropriate buffered solution. Changes in food intake were measured by automatic food monitoring systems (BioDAQ system and HM2 system for rat). In the BioDAQ system animals were single housed; and in the HM2 system animals were in group housed with up to 3 animals per cage. Each compound was tested in n=4-8 animals. Animals were acclimatized for at least 7 days prior to the experiment. Collected data are expressed as daily food intake (24 hour food intake) measured from the onset of each daily 12 hour dark phase to the next day dark phase. Daily changes in food intake in response to administrated compound were calculated by subtracting the average daily food intake of the vehicle group from the average daily food intake of the treatment group. Changes were considered significant if p<0.1 using a two-tailed student's t-test. Results are expressed as the "maximum reduction" in food intake compared with vehicle (percentage) recorded during the study period. Data are also expressed as the "accumulated reduction" in food intake which as the sum of significant (p<0.1) daily reductions in food intake (percentage) during the study period.

TABLE 9

Effect of daily doses (8 nmol/kg) of MIC-1 polypeptides with an N-extension on food intake in lean SD rats.

| SEQ ID NO | Structure | Maximum Efficacy (%) | Accumulated Efficacy (%) |
|---|---|---|---|
| SEQ ID NO: 1 | MIC-1(SEQ ID NO: 1) | 68 | 361 |
| SEQ ID NO: 77 | MIC-1(R2A,N3E,K69E) | 46 | 247 |
| SEQ ID NO: 82 | MIC-1(R2A,N3E,M57E) | 72 | 395 |
| SEQ ID NO: 92 | (GEPS)$_5$-MIC-1(SEQ ID NO: 1) | 84 | 469 |
| SEQ ID NO: 97 | AASPAGSPTSTEEGTSESATPESGPG-MIC-1(SEQ ID NO: 1) | 90 | 456 |
| SEQ ID NO: 98 | TSESATPESGPGTSESATPESGPG-MIC-1(R2A,N3E) | 90 | 503 |
| SEQ ID NO: 100 | AAPEDEETPEQEGSGSGSGSGS-MIC-1-Δ1-3 | 84 | 446 |
| SEQ ID NO: 101 | AAPEDEETPEQE-MIC-1-Δ1-3 | 75 | 408 |
| SEQ ID NO: 102 | AAPDEGTEEETEGSGSGSGSGS-MIC-1-Δ1-3 | 82 | 423 |
| SEQ ID NO: 103 | SEPATSGSETPGTSTEPESGSAPG-MIC-1-Δ1-3 | 82 | 452 |
| SEQ ID NO: 104 | (SEPATSGSETPG)$_2$-MIC-1-Δ1-3 | 93 | 509 |
| SEQ ID NO: 105 | (SEPATSGSETPG)$_2$-MIC-1-Δ1-3(M57E) | 97 | 532 |
| SEQ ID NO: 106 | (SEPATSGSETPG)$_2$-MIC-1-Δ1-3(M57L) | 99 | 532 |
| SEQ ID NO: 107 | A(GPEQGQEP)$_3$-MIC-1-Δ1-3 | 81 | 395 |
| SEQ ID NO: 108 | SEPATSGSETPGTSESATPESGPGTSTEPS-MIC-1-Δ1-3 | 80 | 448 |
| SEQ ID NO: 165 | A(GPEQGQEPGEPQGQEPQPGEPEGQ)-MIC-1-Δ1-3 | 78 | 382 |
| SEQ ID NO: 109 | SEPATSGSETPGTSESATPESGPGTSTEPS EG-MIC-1-Δ1-3 | 82 | 445 |
| SEQ ID NO: 110 | (SEPATSGSETPG)$_2$-MIC-1-Δ1-3 (M86L) | 70 | 398 |
| SEQ ID NO: 111 | (SEPATSGSETPG)$_2$-MIC-1-Δ1-3 (M57L/M86L) | 85 | 462 |
| SEQ ID NO: 112 | (SEPATSGSETPG)$_2$-MIC-1-Δ1-3 (M57E/H66E) | 80 | 369 |
| SEQ ID NO: 113 | (SEPATSGSETPG)$_2$-MIC-1-Δ1-3 (M57E/R67E) | 67 | 266 |

Note:
* means the dose of administration is 4 nmol/kg body weight.

The inventors surprisingly found that these MIC-1 polypeptides with an N-extension not only increased the solubility molecules but also resulted in efficacy equal to or even better than wtMIC-1 (Table 9). For instance compounds according to SEQ ID NO: 105 and SEQ ID NO:106 had a maximum and accumulated in vivo efficacy which was 40-50% greater than wtMIC-1 with subcutaneous dosing. The increase in efficacy was furthermore associated with an increase in solubility as compounds according to SEQ ID NO:92, SEQ ID NO:104, SEQ ID NO:105 and SEQ ID NO: 106 all had elevated solubility and a significant greater in vivo efficacy compared with wtMIC-1. This correlation seems not to be explained by changes in the in vitro Emax as all compounds in table 8, except compound according to SEQ ID NO:105, had an Emax comparable with wtMIC-1. In fact, compound SEQ ID NO:105 had a lower Emax than wtMIC-1 and was still more efficacious than wtMIC-1 in vivo. Also, the in vitro potencies were comparable between compounds as none of the compounds had an EC50 which differed from wtMIC-1. Thus, the association between increased in vivo efficacies and increased solubility is surprising and cannot be simply be explained by changes in increased receptor activation in vitro.

Example 8: MIC-1 Expression and Initial Met Removal Efficiency of Different 12-Mer Blocks In the human body, N-Formyl-Methionine is recognized by the immune system as foreign material, or as an alarm signal released by damaged cells, and stimulates the body to fight against potential infection (Pathologic Basis of Veterinary Disease5: Pathologic Basis of Veterinary Disease, By James F. Zachary, M. Donald McGavin). In addition, Methionine is an instable residue that could be easily oxidized. Therefore, the N-Met cleavage efficiency is very important to MIC-1 expression.

There are 4 different types of 12mers, and all of them are comprised of 3 Ser, 2 Pro, 2 Gly, 2 Thr, 2 Glu and 1 Ala. However, the 12 residues in each repeat are arranged in different ways.

Little is known about the effects of different 12mers on the expression level and the N-Met cleavage efficiency. Thus, systematically investigation of MIC-1 polypeptides initiating with single and double 12mers respectively is quite necessary.

The cDNA of MIC-1 polypeptide with N-terminal extension was sub-cloned into a pET11b derived vector. Overexpression of MIC-1 polypeptides with an N-terminal extension as inclusion bodies or soluble protein was induced in *E. coli* by 0.5 mM isopropyl 3-d-thiogalactoside (IPTG) when the cell density reached an OD600 of 1.0. After continuous growth in TB for 20h at 37° C., the cells were harvested and sonicated in buffer A (20 mM Tris, pH 8.0). The resulting mixture was centrifugated at 10,000 g for 20 min and analysed by LC/MS and SDS-PAGE to confirm the molecular weight.

Fermentation was carried out on fed-batch process in chemical defined medium as supplement. Fermentation yield largely depended on different compounds, which varied from 1 g/L to 8 g/L from compound to compound.

Compounds designed for the single-12mer test and the result are shown in Table 10 and FIG. 1.

TABLE 10

Initial Met removal efficiency of single 12-mer building blocks

| N-extension | N-aa sequence | MIC-1 polypeptide | N-Met cleavage efficiency (%) |
|---|---|---|---|
| 12mer-1 | SPAGSPTSTEEG (SEQ ID NO: 166) | MIC-1 Δ1-3 | N/A |
| 12mer-2 | TSESATPESGPG (SEQ ID NO: 167) | | 0 |
| 12mer-3 | TSTEPSEGSAPG (SEQ ID NO: 168) | | 0 |
| 12mer-4 | SEPATSGSETPG (SEQ ID NO: 169) | | 100 |

N/A: means MIC-1 with the N-terminal extension did not express in *E. coli*.

Figure 2:
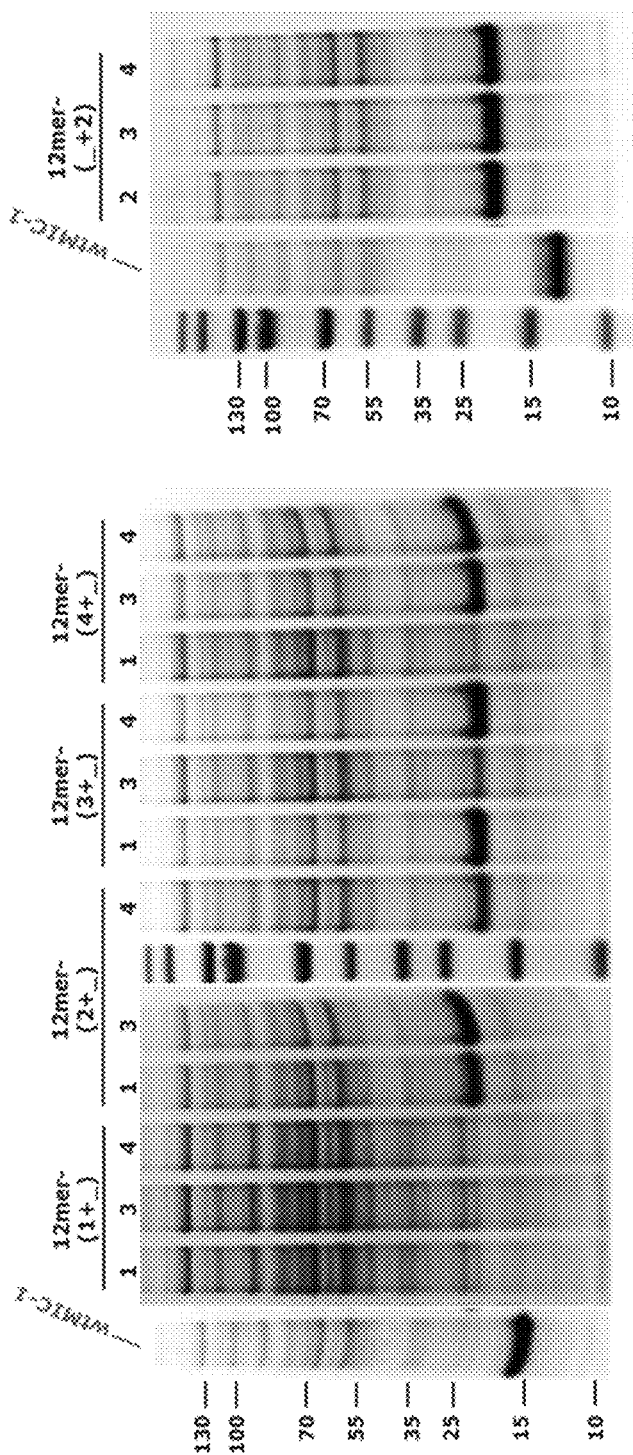
FIG. 2: The expression of MIC-1 polypeptides with N-extensions with double 12-mer building blocks. All cells were grown in TB at 37° C. and proteins were induced to express by adding 0.5 mM IPTG after OD600 reached 1.0. Cells were harvested after overnight and the expression level was checked by loading the total lysate on SDS-PAGE. MIC-1 was loaded as the positive control.

Compounds bearing double 12mers are listed in Table 11, and the results are shown as well (see Table 11 and FIG. 2).

TABLE 11

Initial Met removal efficiency of double 12-mers building blocks

| SEQ ID NO | N-extension | N-aa sequence | MIC-1 polypeptide | N-Met cleavage efficiency (%) |
|---|---|---|---|---|
| N/A | 12mer-(1 + 1) | SPAGSPTSTEEG-SPAGSPTSTEEG (SEQ ID NO: 170) | MIC-1 Δ1-3 | N/A |
| N/A | 12mer-(1 + 3) | SPAGSPTSTEEG-TSTEPSEGSAPG (SEQ ID NO: 171) | | N/A |
| N/A | 12mer (1 + 4) | SPAGSPTSTEEG-SEPATSGSETPG (SEQ ID NO: 172) | | N/A |
| N/A | 12mer-(2 + 1) | TSESATPESGPG-SPAGSPTSTEEG (SEQ ID NO: 173) | | 58.1 |
| N/A | 12mer-(2 + 2) | TSESATPESGPG-TSESATPESGPG (SEQ ID NO: 174) | | 30.0 |
| N/A | 12mer-(2 + 3) | TSESATPESGPG-TSTEPSEGSAPG (SEQ ID NO: 175) | | 58.5 |
| N/A | 12mer-(2 + 4) | TSESATPESGPG-SEPATSGSETPG (SEQ ID NO: 176) | | 64.5 |
| N/A | 12mer-(3 + 1) | TSTEPSEGSAPG-SPAGSPTSTEEG (SEQ ID NO: 177) | | 10.0 |
| N/A | 12mer-(3 + 2) | TSTEPSEGSAPG-TSESATPESGPG (SEQ ID NO: 178) | | 1.0 |
| N/A | 12mer-(3 + 3) | TSTEPESGSAPG-TSTEPESGSAPG (SEQ ID NO: 179) | | 26.4 |
| N/A | 12mer-(3 + 4) | TSTEPSEGSAPG-SEPATSGSETPG (SEQ ID NO: 180) | | 10.5 |
| N/A | 12mer-(4 + 1) | SEPATSGSETPG-SPAGSPTSTEEG (SEQ ID NO: 12) | | N/A |

TABLE 11-continued

Initial Met removal efficiency of double 12-mers building blocks

| SEQ ID NO | N-extension | N-aa sequence | MIC-1 polypeptide | N-Met cleavage efficiency (%) |
|---|---|---|---|---|
| SEQ ID NO: 182 | 12mer- (4 + 2) | SEPATSGSETPG-TSESATPESGPG (SEQ ID NO: 13) | | 100 |
| SEQ ID NO: 103 | 12mer- (4 + 3) | SEPATSGSETPG-TSTEPSEGSAPG (SEQ ID NO: 14) | | 100 |
| SEQ ID NO: 104 | 12mer- (4 + 4) | SEPATSGSETPG-SEPATSGSETPG (SEQ ID NO: 181) | | 100 |

N/A: means MIC-1 polypeptide with N-terminal extension did not express in E. coli.

In conclusion, N-extensions starting with the 12mer-1 block could not be expressed in E. coli. For the other 12mer blocks, protein expression was achieved but only 12mer-4 as the initial sequence resulted in complete methionine cleavage. In addition, the N-met cleavage efficiency of 12mer-2 series is better than that of 12mer-3 series.

Figure 3B:
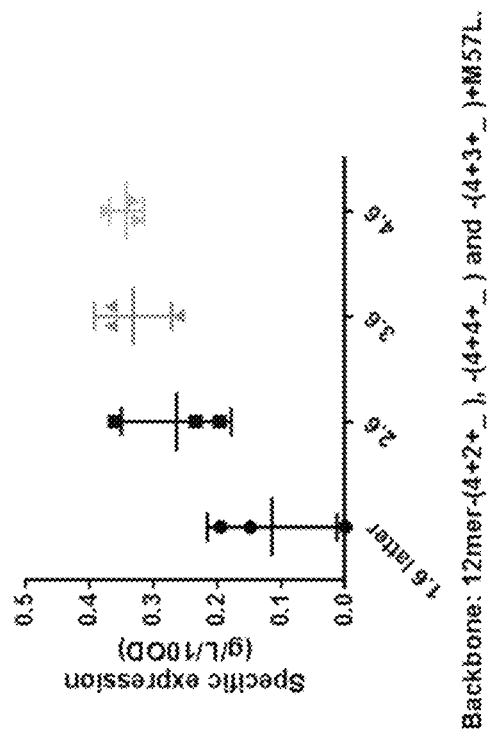
FIG. 3 a) Comparison of expression levels among MIC-1 polypeptides with N-extensions initiating with 12mer-(4+2+_), -(4+4+_) and -(4+3+_). It should be noticed that the group bearing 12mer-(4+3_) and the construct indicated by the dot contain M57L in the MIC-1 polypeptide sequence.
Figure 3A:
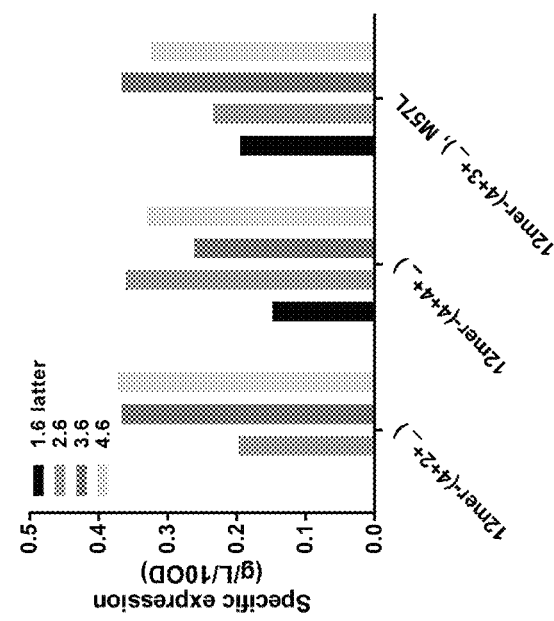
Figure 4:
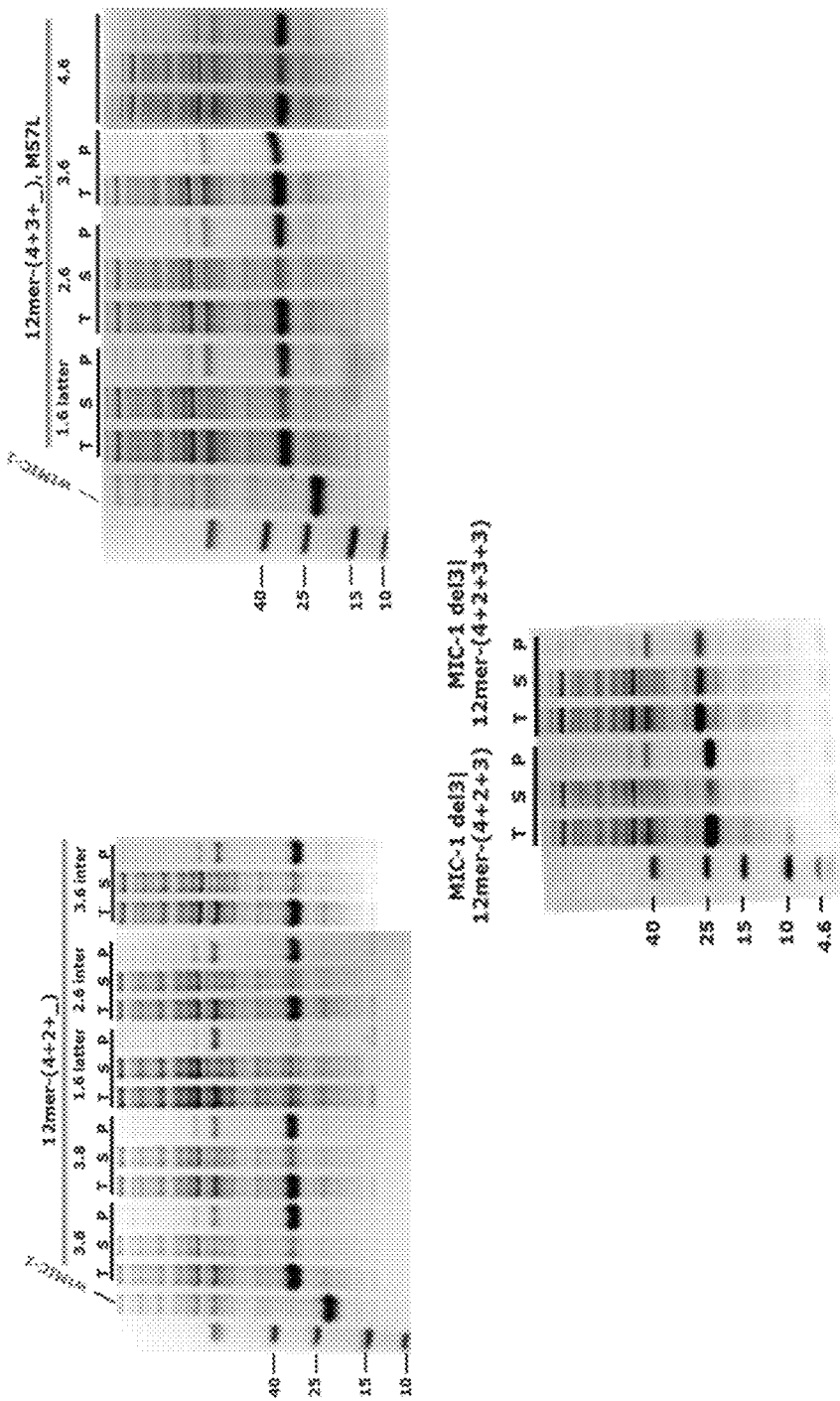
FIG. 4: SDS-PAGE of representatives bearing 12mer-(4+2+_), 12mer-(4+3+_)+M57L, 12mer-(three repeats) and 12mer-(four repeats). T: total protein, S: soluble fraction, P: cell pellet (inclusion body).

Example 9: Expression Level and Inclusion Body Ratio of MIC-1 Polypeptide with 2* or 2.5*12 mer N-Extension (1) Expression of MIC-1 Polypeptide with 2.5*12 mer N-Extension See Example 8 for protein production method. The results are shown in Table 12, FIG. 3 and FIG. 4.

TABLE 12

Constructs and protein production for 2.5*12mer test

| SEQ ID NO | N-extension | N-aa sequence | MIC-1 polypeptide | UPLC Shaker Flask (g/L/100D) | UPLC Fermenter (g/L/100D) |
|---|---|---|---|---|---|
| SEQ ID NO: 200 | 12mer- (4 + 2 + 1.6 latter) | SEPATSGSETPG TSESATPESGPG TSTEEG (SEQ ID NO: 28) | MIC-1 Δ1-3 | N.D. | |
| SEQ ID NO: 201 | 12mer- (4 + 2 + 2.6) | SEPATSGSETPG TSESATPESGPG TSESAT (SEQ ID NO: 19) | | 0.197 | |
| SEQ ID NO: 202 | 12mer- (4 + 2 + 2.6 inter) | SEPATSGSETPG TSESATPESGPG ESATPE (SEQ ID NO: 183) | | 0.206 | |
| SEQ ID NO: 108 | 12mer- (4 + 2 + 3.6) | SEPATSGSETPG TSESATPESGPG TSTEPS (SEQ ID NO: 70) | | 0.367 | 0.374 |
| SEQ ID NO: 203 | 12mer- (4 + 2 + 3.6 inter) | SEPATSGSETPG TSESATPESGPG STEPSE (SEQ ID NO: 184) | | 0.243 | |
| SEQ ID NO: 109 | 12mer- (4 + 2 + 3.8) | SEPATSGSETPG TSESATPESGPG TSTEPSEG (SEQ ID NO: 71) | | 0.273 | 0.162 |
| SEQ ID NO: 204 | 12mer- (4 + 2 + 4.6) | SEPATSGSETPG TSESATPESGPG SEPATS (SEQ ID NO: 25) | | 0.373 | |
| SEQ ID NO: 205 | 12mer- (4 + 3 + 1.6 latter) | SEPATSGSETPG TSTEPSEGSAPG TSTEEG (SEQ ID NO: 185) | MIC-1 Δ1-3, M57L | 0.195 | |

TABLE 12-continued

Constructs and protein production for 2.5*12mer test

| SEQ ID NO | N-extension | N-aa sequence | MIC-1 polypeptide | UPLC Shaker Flask (g/L/100D) | UPLC Fermenter (g/L/100D) |
|---|---|---|---|---|---|
| SEQ ID NO: 206 | 12mer-(4 + 3 + 2.6) | SEPATSGSETPG TSTEPSEGSAPG TSESAT (SEQ ID NO: 186) | | 0.234 | |
| SEQ ID NO: 207 | 12mer-(4 + 3 + 3.6) | SEPATSGSETPG TSTEPSEGSAPG TSTEPS (SEQ ID NO: 187) | | 0.367 | |
| SEQ ID NO: 208 | 12mer-(4 + 3 + 4.6) | SEPATSGSETPG TSTEPSEGSAPG SEPATS (SEQ ID NO: 188) | | 0.324 | |
| SEQ ID NO: 209 | 12mer-(4 + 4 + 1.6 latter) | SEPATSGSETPG SEPATSGSETPG TSTEEG (SEQ ID NO: 189) | MIC-1 Δ1-3, M57L | 0.148 | |
| SEQ ID NO: 210 | 12mer-(4 + 4 + 2.6) | SEPATSGSETPG SEPATSGSETPG TSESAT (SEQ ID NO: 190) | MIC-1 Δ1-3 | 0.361 | |
| SEQ ID NO: 211 | 12mer-(4 + 4 + 2.6 inter) | SEPATSGSETPG SEPATSGSETPG ESATPE (SEQ ID NO: 191) | | N.D. | |
| SEQ ID NO: 212 | 12mer-(4 + 4 + 3.6) | SEPATSGSETPG SEPATSGSETPG TSTEPS (SEQ ID NO: 192) | MIC-1 Δ1-3, M57L | 0.262 | |
| SEQ ID NO: 213 | 12mer-(4 + 4 + 3.6 inter2) | SEPATSGSETPG SEPATSGSETPG STEPSE (SEQ ID NO: 193) | MIC-1 Δ1-3 | 0.262 N.D. | |
| SEQ ID NO: 214 | 12mer-(4 + 4 + 4.6) | SEPATSGSETPG SEPATSGSETPG SEPATS (SEQ ID NO: 194) | | 0.330 | |

Notes:
".6" means the first 6aa of 12mers,
"latter" means the last 6aa of 12mers,
"inter" means the internal 6aa from 12mers.
"N.D." means "not detected".

Although the extended 12mer (6aa) locate 24aa away from the N-terminal, the expression levels of MIC-1 polypeptide with an N-terminal extension vary a lot among different groups. It is clear that the fragment from 12mer-1 is not suitable for expression, which is consistent with previous results. The average expression levels of 12mer-(4+_+3.6) and -(4+_+4.6) are relatively higher than others.

(2) Inclusion Body Ratio of MIC-1 Polypeptide with 2* or 2.5*12 mer N-Extension

For large scale protein production, inclusion body is usually considered as a good choice mainly due to its better up-scaling properties, which mainly include: high expression level, simple recovery step and high purity, protease-resistant and good process stability.

MIC-1 polypeptides with an N-terminal extension could be expressed either inclusion body or soluble form, which is mainly dependent on compounds' pI and extension length. The results are shown in Table 13 and FIG. 4.

TABLE 13

Solubility in cell cytosol and their pI values

| SEQ ID NO | N-extension | Sequences of N-extension | MIC-1 polypeptide | Inclusion body ratio★ | PI values |
|---|---|---|---|---|---|
| SEQ ID NO: 104 | 12mer-(4 + 4) | SEPATSGSETPG SEPATSGSETPG (SEQ ID NO: 181) | MIC-1 Δ1-3 | 100% | 5.8 |

TABLE 13-continued

Solubility in cell cytosol and their pI values

| SEQ ID NO | N-extension | Sequences of N-extension | MIC-1 polypeptide | Inclusion body ratio★ | PI values |
|---|---|---|---|---|---|
| SEQ ID NO: 108 | 12mer-(4 + 2 + 3.6) | SEPATSGSETPG TSESATPESGPG TSTEPS (SEQ ID NO: 70) | | 100% | 5.5 |
| SEQ ID NO: 109 | 12mer-(4 + 2 + 3.8) | SEPATSGSETPG TSESATPESGPG TSTEPSEG (SEQ ID NO: 71) | | 90% | 5.2 |
| SEQ ID NO: 215 | 12mer-(4 + 2)- GPEQGPEQ | SEPATSGSETPG TSESATPESGPG GPEQGPEQ (SEQ ID NO: 195) | | 90% | 5.2 |
| SEQ ID NO: 216 | 12mer-(4 + 2)- GEPSGEPS | SEPATSGSETPG TSESATPESGPG GEPSGEPS (SEQ ID NO: 196) | | 95% | 5.2 |
| SEQ ID NO: 112 | 12mer-(4 + 4) M57E, H66E | SEPATSGSETPG SEPATSGSETPG (SEQ ID NO: 181) | | 70% | 5.0 |
| SEQ ID NO: 113 | 12mer-(4 + 4) M57E, R67E | SEPATSGSETPG SEPATSGSETPG (SEQ ID NO: 181) | | 70% | 5.0 |
| SEQ ID NO: 217 | 12mer-(three repeats) | SEPATSGSETPG TSESATPESGPG TSTEPSEGSAPG (SEQ ID NO: 197) | MIC-1-des- N3 | 85% | 5.4 |
| SEQ ID NO: 218 | 12mer-(four repeats) | SEPATSGSETPG TSESATPESGPG TSTEPSEGSAPG TSTEPSEGSAPG (SEQ ID NO: 198) | MIC-1-des- N3 | 30% | 5.1 |
| SEQ ID NO: 219 | 12mer-(five repeats) | SPAGSPTSTEEG TSESATPESGPG TSTEPSEGSAPG SPAGSPTSTEEG TSTEPSEGSAPG (SEQ ID NO: 199) | MIC-1 | 0% | 4.8 |
| SEQ ID NO: 220 | 12mer-(4 + 4) M57E, H66E, R67E | SEPATSGSETPG SEPATSGSETPG (SEQ ID NO: 181) | MIC-1 Δ1-3 | 0% | 4.7 |
| SEQ ID NO: 221 | 12mer-(4 + 2 + 3.6) M57E, R67E | SEPATSGSETPG TSESATPESGPG TSTEPS (SEQ ID NO: 70) | | 0% | 4.7 |

Note:
★The number here is estimated by SDS-PAGE.

Figure 5:
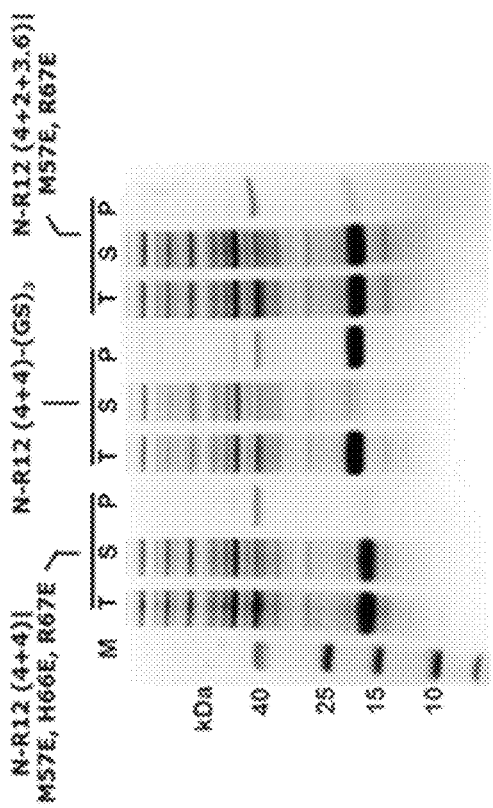
FIG. 5: MIC-1 polypeptides with in-sequence mutations. In this figure, the MIC-1 polypeptide sequence is MIC-1 A1-3. T: total protein, S: soluble fraction, P: cell pellet (inclusion body).

The solubility of MIC-1 polypeptides with in-sequence mutations are shown in Table 14 and FIG. 5 (the MIC-1 polypeptide sequence is MIC-1 A1-3).

TABLE 14

Solubility of MIC-1 polypeptide with in-sequence mutations

| N-extension | In-sequence M | Solubility in cell |
|---|---|---|
| SEPATSGSETPG | M57E | IBs |
| SEPATSGSETPG | M57E/H66E | Partially soluble |
| (12mer-(4 + 4)) (SEQ ID NO: 181) | M57E/H66E/R67E | Fully soluble |
| SEPATSGSETPG TSESATPESGPG-TSTEPS (12mer-(4 + 2 + 3.6)) (SEQ ID NO: 70) | M57E | N.D. |
| | M57E/H66E | Fully soluble |
| | M57E/H66E/R67E | Fully soluble |

MIC-1 polypeptides initiating with 12mer- (4+2+_), -(4+ 4+_) and -(4+3+_) were investigated with their ability to express inclusion body. It was shown that the inclusion body ratio is >90% when pI>5.1. In addition, MIC-1 polypeptides with in-sequence mutations M57E/H66E mainly expressed soluble fractions.

Example 9: Production of MIC-1 Polypeptides with an N-Terminal Extension Including a Cys Mutation To increase the half-life of MIC-1 polypeptides with an N-terminal extension, different fatty acid chains that were used for protraction were conjugated to the N-terminal extension through alkylation mediated by Cysteine introduced by site-directed mutation. The position for the Cys mutation has been systematically mapped and resulting MIC-1 polypeptides with an N-terminal extension were refolded and purified according to the methods described in Example 8.

1. Introduce a Cys Mutation to the N-Terminal Extension for Protraction

Total of 20 different cysteine mutants were generated by site-directed mutations using PCR method and constructs are listed as Table 15.

TABLE 15

Constructs having the Cys mutation at different positions

| Constructs (SEQ ID NO) | N-term. extension | Cys mutation | MIC-1 polypeptide | Inclusion body ratio★ | pI values |
|---|---|---|---|---|---|
| SEQ ID NO: 301 | SEPATCGSETPG-TSESATPESGPG-TSTEPS (SEQ ID NO: 223) | S(-25)C | MIC-1, des-N3 | 100% | 5.7 |
| SEQ ID NO: 302 | SEPATSGCETPG-TSESATPESGPG-TSTEPS(SEQ ID NO: 224) | S(-23)C | | 100% | 5.7 |
| SEQ ID NO: 288 | SEPCTSGSETPG-TSESATPESGPG-TSTEPSEG(SEQ ID NO: 225) | A(-29)C | | 100% | 5.4 |
| SEQ ID NO: 291 | SEPATCGSETPG-TSESATPESGPG-TSTEPSEG(SEQ ID NO: 226) | S(-27)C | | 100% | 5.4 |
| — | SEPATSCSETPG-TSESATPESGPG-TSTEPSEG(SEQ ID NO: 227) | G(-26)C | | 100% | 5.4 |
| — | SEPCTSGSETPG-TSESATPESGPG-TSTEPSEG(SEQ ID NO: 225) | A(-29)C | MIC-1, des-N3, M57L | 100% | 5.4 |
| — | SEPATSCSETPG-TSESATPESGPG-TSTEPSEG(SEQ ID NO: 227) | G(-26)C | | 100% | 5.4 |
| — | SEPCTSGSETPG-TSESATPESGPG-TSTEPSEG(SEQ ID NO: 228) | A(-29)C | MIC-1, des-N3, M57L, M86L | 100% | 5.4 |
| — | SEPACSGSETPG-TSESATPESGPG-TSTEPSEG(SEQ ID NO: 229) | T(-28)C | | 100% | 5.4 |
| SEQ ID NO: 289 | SEPATSCSETPG-TSESATPESGPG-TSTEPSEG(SEQ ID NO: 227) | G(-26)C | | 100% | 5.4 |
| SEQ ID NO: 303 | SEPATSGCETPG-TSESATPESGPG-TSTEPSEG(SEQ ID NO: 230) | S(-25)C | | 100% | 5.4 |

TABLE 15-continued

Constructs having the Cys mutation at different positions

| Constructs (SEQ ID NO) | N-term. extension | Cys mutation | MIC-1 polypeptide | Inclusion body ratio★ | pI values |
|---|---|---|---|---|---|
| SEQ ID NO: 304 | SEPATSGSECPG-TSESATPESGPG-TSTEPSEG(SEQ ID NO: 231) | T(-23)C | | 100% | 5.4 |
| SEQ ID NO: 305 | SEPATSGSETPC-TSESATPESGPG-TSTEPSEG(SEQ ID NO: 232) | G(-21)C | | 100% | 5.4 |
| SEQ ID NO: 306 | SEPATSGSETPG-TCESATPESGPG-TSTEPSEG(SEQ ID NO: 233) | S(-19)C | | 100% | 5.4 |
| SEQ ID NO: 307 | SEPATSGSETPG-TSECATPESGPG-TSTEPSEG(SEQ ID NO: 234) | S(-17)C | | 100% | 5.4 |
| SEQ ID NO: 292 | SEPATSGSETPG-TSESACPESGPG-TSTEPSEG(SEQ ID NO: 235) | T(-15)C | | 100% | 5.4 |
| SEQ ID NO: 308 | SEPATSGSETPG-TSESATPECGPG-TSTEPSEG(SEQ ID NO: 236) | S(-12)C | | 100% | 5.4 |
| SEQ ID NO: 309 | SEPATSGSETPG-TSESATPESCPG-TSTEPSEG(SEQ ID NO: 237) | G(-11)C | | 100% | 5.4 |
| SEQ ID NO: 310 | SEPATSGSETPG-TSESATPESGPG-TSCEPSEG(SEQ ID NO: 238) | T(-6)C | | 100% | 5.4 |
| SEQ ID NO: 293 | SEPATSGSETPG-TSESATPESGPG-TSTEPCEG(SEQ ID NO: 239) | S(-3)C | | 100% | 5.4 |
| SEQ ID NO: 316 | GEQPCEQPGEQPGEQPGEQPGEQPGEQP (SEQ ID NO: 317) | G(-24)C | MIC-1 | 100% | 5.3 |

N.A. = Not available.
★The number in bracket (of the Column Cys mutation) means the distance between Cys and the N-terminal amino acid of MIC-1 polypeptide.

It shows that the expression level of MIC-1 polypeptide with an N-terminal extension with a Cys mutation is similar to those without Cys mutation.

2. Refolding and Purification of MIC-1 Polypeptide with an N-Terminal Extension Including a Cys Mutation WtMIC-1 homo-dimer contains total of 9 pairs of disulphide bonds and in theory, introducing a new cysteine will disturb the original disulphide bond matching by disulphide bond scrambling, which could further decrease refolding yield. While in our experiments, it is surprising to find that these Cys mutants listed were tested in the same refolding buffer used for wtMIC-1 refolding and showed similar refolding yield (~50% to 60%) as wtMIC-1 or solubility-engineered MIC-1 polypeptide with an N-terminal extension described.

3. pH-Dependent Solubility and Maximal Solubility of MIC-1 Polypeptide with an N-Terminal Extension Including a Cys Mutation The pH-dependent solubility and maximal solubility were determined by the same method as described in Example 4. The results are shown in Table 16 and Table 17.

TABLE 16 pH-dependent solubility test of MIC-1 polypeptide with an N-terminal extension including a Cys mutation

| SEQ ID NO | Structure | pH | | | | | | | | |
|---|---|---|---|---|---|---|---|---|---|---|
| | | 3.0 | 4.0 | 5.0 | 6.0 | 7.0 | 8.0 | 9.0 | 10.0 | 11.0 |
| SEQ ID NO: 288 | SEPCTSGSETPGTSESATPESGPGTSTEPSEG-MIC-1-Δ3 | 8.81 | 4.22 | 1.34 | 5.18 | 13.52 | 15.65 | 15.1 | 15.84 | 15.97 |

TABLE 16-continued pH-dependent solubility test of MIC-1 polypeptide with an N-terminal extension including a Cys mutation

| SEQ ID NO | Structure | pH 3.0 | 4.0 | 5.0 | 6.0 | 7.0 | 8.0 | 9.0 | 10.0 | 11.0 |
|---|---|---|---|---|---|---|---|---|---|---|
| SEQ ID NO: 289 | SEPATSCSETPGTSESATPESGPGTSTEPSEG-MIC-1 (M57L, M86L) | 7.91 | 5.12 | 1.37 | 5.91 | 13.59 | 15.62 | 15.15 | 15.83 | 16.47 |
| SEQ ID NO: 316 | GEQPCEQPGEQPGEQPGEQPGEQPGEQP-MIC-1 | 6.24 | 3.14 | 2.54 | 4.71 | 9.43 | 13.24 | 14.21 | 15.21 | 15.2 |

TABLE 17

Maximal solubility determination test of MIC-1 polypeptide with an N-terminal extension including a Cys mutation

| SEQ ID NO | Structure | Max. solubility (mg/ml) |
|---|---|---|
| SEQ ID NO: 288 | SEPCTSGSETPGTSESATPESGPGTSTEPSEG-MIC-1-Δ3 | 36.1 |
| SEQ ID NO: 289 | SEPATSCSETPGTSESATPESGPGTSTEPSEG-MIC-1 (M57L, M86L) | 38.4 |
| SEQ ID NO: 316 | GEQPCEQPGEQPGEQPGEQPGEQPGEQP-MIC-1 | 32.1 |

It can be seen that a Cys mutation does not impact the improved solubility obtained by adding an N-terminal amino acid extension to a MIC-1 polypeptide.

Example 10: Preparation of Protractors for MIC-1 Compounds

Example 10.1: Preparation of 17-[(S)-1-carboxy-3-(2-{2-[(2-{2-[(4-formylbenzylcarbamoyl)methoxy]ethoxy}ethylcarbamoyl)-methoxy]ethoxy}ethylcarbamoyl)propylcarbamoyl]heptadecanoic acid t-Bu-N-(4-Formylbenzyl) carbamate (100 mg) was treated with TFA/DCM (1:1) for 1h. The mixture was concentrated in vacuo and co-concentrated with toluene (twice). The residue was dissolved in THF (2.5 ml) and a solution of 17-((S)-1-carboxy-3-{2-[2-({2-[2-(2,5-dioxopyrrolidin-1-yloxycarbonylmethoxy)-ethoxy]ethylcarbamoyl}methoxy)ethoxy]ethylcarbamoyl}propylcarbamoyl)heptadecanoic acid (320 mg, prepared as described previously in WO2009/083549) in THF (5 ml) was added. DIPEA (0.5 ml) was added slowly. After 130 min, the mixture was concentrated in vacuo. The residue was dissolved in EtOAc and 1N HCl. The organic layer was extracted with 1N HCl and brine. The organic layer was dried ($Na_2SO_4$) and concentrated in vacuo to give the title compound as a white solid, which was used without further purification. Yield 234 mg (72%)

LCMS2: Theoretical mass: 851.0 Found: 851.5 (M+1).

(Formula A)

Example 10.2 (C16): Preparation of 16-[[(1S)-4-[2-[2-[2-[2-[2-[2-[(2-bromoacetyl)amino]ethyl-amino]-2-oxo-ethoxy]ethoxy]ethylamino]-2-oxo-ethoxy]ethoxy]ethylamino]-1-carboxy-4-oxo-butyl]amino]-16-oxo-hexadecanoic acid mL), dichloromethane (2×250 mL) and N,N-dimethylformamide (3×250 mL). Fmoc group was removed by treatment with 20% piperidine in dimethylformamide (1×5 min, 1×10 min, 1×30 min, 3×250 mL). Resin was washed with N,N-dimethylformamide (3×250 mL), 2-propanol (2×250 mL) and dichloromethane (300 mL, 2×250 mL). Solution of

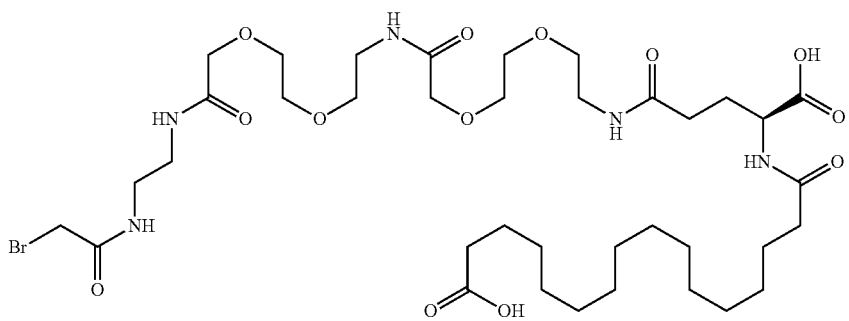

(Formula B)

Solid Phase Synthetic Protocol:

A solution of N-(benzyloxycarbonyloxy)succinimide (ZOSu, 100 g, 401 mmol) in dichloromethane (500 mL) was added dropwise over 2 hours to a solution of ethylenediamine (1, 189 mL, 2.81 mol) in dichloromethane (750 mL). After 30 minutes the suspension was filtered and solids washed with dichloromethane. The filtrate was evaporated to dryness and the residue diluted with toluene (1.00 L) and water (0.50 L). The resulting mixture was filtered and the filtrate was separated to afford two phases. The aqueous phase contained the product; therefore it was extracted with dichloromethane (2×250 mL). All organic phases were combined, dried over anhydrous sodium sulfate, filtered and concentrated in vacuo. The residue was diluted with toluene (750 mL) and extracted with 2 M aqueous hydrochloric acid (500 mL) and 1 M aqueous hydrochloric acid (100 mL). Acidic aqueous phases were combined and basified with a solution of sodium hydroxide (60.0 g, 1.50 mol) in water (90 mL). The resulting mixture was extracted with dichloromethane (4×200 mL), dried over anhydrous sodium sulfate, filtered, concentrated in vacuo and diluted with hexanes (200 mL). 4 M Solution of hydrogen chloride in ether (100 mL, 400 mmol) was added to the solution, the resulting suspension was concentrated in vacuo and diluted with hexanes (1.00 L). The precipitated solid was filtered, washed with hexanes and dried in vacuo to give (2-amino-ethyl)-carbamic acid benzyl ester hydrochloride as white powder. Yield: 62.62 g (68%).

RF (SiO$_2$, dichloromethane/methanol 4:1): 0.25 (free base).

1H NMR spectrum (300 MHz, AcOD-d4, 80° C., dH): 7.42-7.26 (m, 5H); 5.16 (s, 2H); 3.60 (t, J=5.7 Hz, 2H); 3.32 (t, J=5.7 Hz, 2H).

2-Chlorotrityl resin 100-200 mesh 1.7 mmol/g (3, 40.1 g, 68.1 mmol) was left to swell in dry dichloromethane (250 mL) for 20 minutes. A solution of {2-[2-(9H-fluoren-9-ylmethoxycarbonylamino)-ethoxy]-ethoxy}-acetic acid (Fmoc-Ado-OH, 17.5 g, 45.4 mmol) and N,N-diisopropylethylamine (30.1 mL, 173 mmol) in dry dichloromethane (50 mL) was added to resin and the mixture was shaken for 5 hours. Resin was filtered and treated with a solution of N,N-diisopropylethylamine (15.8 mL, 90.8 mmol) in methanol/dichloromethane mixture (4:1, 250 mL, 2×5 min). Then resin was washed with N,N-dimethylformamide (2×250 {2-[2-(9H-fluoren-9-ylmethoxycarbonylamino)-ethoxy]-ethoxy}-acetic acid (Fmoc-Ado-OH, 26.3 g, 68.1 mmol), O-(6-chloro-benzotriazol-1-yl)-N,N,N',N'-tetramethyluronium tetrafluoroborate (TCTU, 24.2 g, 68.1 mmol) and N,N-diisopropylethylamine (21.4 mL, 123 mmol) in N,N-dimethylformamide (140 mL) was added to resin and mixture was shaken for 1 hour. Resin was filtered and washed with N,N-dimethylformamide (2×250 mL), dichloromethane (2×250 mL) and N,N-dimethylformamide (250 mL). Fmoc group was removed by treatment with 20% piperidine in dimethylformamide (1×5 min, 1×10 min, 1×30 min, 3×250 mL). Resin was washed with N,N-dimethylformamide (3×250 mL), 2-propanol (2×250 mL) and dichloromethane (300 mL, 2×250 mL). Solution of (S)-2-(9H-fluoren-9-ylmethoxycarbonylamino)-pentanedioic acid 1-tert-butyl ester (Fmoc-Glu-OtBu, 29.0 g, 68.1 mmol), O-(6-chloro-benzotriazol-1-yl)-N,N,N',N'-tetramethyluronium tetrafluoroborate (TCTU, 24.2 g, 68.1 mmol) and N,N-diisopropylethylamine (21.4 mL, 123 mmol) in N,N-dimethylformamide (140 mL) was added to resin and mixture was shaken for 1 hour. Resin was filtered and washed with N,N-dimethylformamide (2×250 mL), dichloromethane (2×250 mL) and N,N-dimethylformamide (250 mL). Fmoc group was removed by treatment with 20% piperidine in dimethylformamide (1×5 min, 1×10 min, 1×30 min, 3×250 mL). Resin was washed with N,N-dimethylformamide (3×250 mL), 2-propanol (2×250 mL) and dichloromethane (300 mL, 2×250 mL). Solution of 16-(tert-butoxy)-16-oxohexadecanoic acid (23.3 g, 68.1 mmol), O-(6-chloro-benzotriazol-1-yl)-N,N,N',N'-tetramethyluronium tetrafluoroborate (TCTU, 24.2 g, 68.1 mmol) and N,N-diisopropylethylamine (21.4 mL, 123 mmol) in N,N-dimethylformamide/dichloromethane mixture (4:1, 200 mL) was added to resin. Resin was shaken for 1 hour, filtered and washed with N,N-dimethylformamide (3×250 mL), dichloromethane (2×250 mL), methanol (2×250 mL) and dichloromethane (350, 6×250 mL). The product was cleaved from resin by treatment with 2,2,2-trifluoethanol (250 mL) for 18 hours. Resin was filtered off and washed with dichloromethane (2×250 mL), 2-propanol/dichloromethane mixture (1:1, 2×250 mL), 2-propanol (250 mL) and dichloromethane (3×250 mL). Solutions were combined; solvent evaporated and crude product was purified by flash column chromatography (Silicagel 60, 0.040-0.060 mm; eluent: dichloromethane/methanol 1:0-9:1). Pure (S)-22-(tert-butoxycarbonyl)-41,41-dimethyl-10,19,24,39-tetraoxo-3,6,12,15,40-pentaoxa-9,18,23-triazadotetracontanoic acid was dried in vacuo and obtained as pale yellow thick yellow oil.

Yield: 30.88 g (83%).

RF (SiO2, dichloromethane/methanol 4:1): 0.30.

1H NMR spectrum (300 MHz, CDCl3, dH): 7.36 (t, J=5.7 Hz, 1H); 7.02 (t, J=5.4 Hz, 1H); 6.55 (d, J=7.7 Hz, 1H); 4.46 (m, 1H); 4.18 (s, 2H); 4.02 (s, 2H); 3.83-3.36 (m, 16H); 2.44-2.12 (m, 7H); 2.02-1.86 (m, 1H); 1.60 (m, 4H); 1.47 (s, 9H); 1.45 (s, 9H); 1.36-1.21 (m, 20H).

LC-MS method 4:
Purity: 100%
Rt (Kinetex 4.6 mm×50 mm, acetonitrile/water 50:50 to 100:0+0.1% FA): 3.60 min.
Found m/z, z=1: 818.7 (M+H)+

2-(7-Aza-1H-benzotriazole-1-yl)-1,1,3,3-tetramethyluronium hexafluorophosphate (HATU, 11.4 g, 30.1 mmol) and triethylamine (8.77 mL, 62.9 mmol) were subsequently added to a solution of (S)-22-(tert-butoxycarbonyl)-41,41-dimethyl-10,19,24,39-tetraoxo-3,6,12,15,40-pentaoxa-9,18,23-triazadotetracontanoic acid (22.4 g, 27.4 mmol) in dry dichloromethane (110 mL). Triethylamine (5.72 mL, 41.0 mmol) was added to a suspension of (2-amino-ethyl)-carbamic acid benzyl ester hydrochloride (6.94 g, 30.1 mmol) in dry dichloromethane (165 mL) and the resulting mixture was added to the above solution. The mixture was stirred at room temperature overnight, and then it was evaporated to dryness. The residue was re-dissolved in ethyl acetate (500 mL); washed with 1 M aqueous hydrochloric acid (2×200 mL), 5% aqueous solution of sodium carbonate (2×200 mL, very slow separation of phases), 1 M aqueous hydrochloric acid (8×200 mL) and brine; dried over anhydrous sodium sulfate and evaporated to dryness in vacuo. The residue was purified by flash column chromatography (Silicagel 60, 0.040-0.060 mm; eluent: dichloromethane/methanol 95:5) to afford 15-[(S)-3-(2-{2-[(2-{2-[(2-benzyloxycarbonylamino-ethylcarbamoyl)-methoxy]-ethoxy}-ethylcarbamoyl)-methoxy]-ethoxy}-ethylcarbamoyl)-1-tert-butoxycarbonyl-propylcarbamoyl]-pentadecanoic acid tert-butyl ester as pale yellow thick oil.

Yield: 23.84 g (88%)

RF (SiO2, dichloromethane/methanol 9:1): 0.35

1H NMR spectrum (300 MHz, CDCl3, dH): 7.39-7.26 (m, 6H); 7.19 (t, J=6.3 Hz, 1H); 6.91 (t, J=5.7 Hz, 1H); 6.52 (d, J=7.5 Hz, 1H); 5.83 (t, J=5.5 Hz, 1H); 5.09 (s, 2H); 4.41 (ddd, J=12.3, 4.6 and 4.3 Hz, 1H); 3.99 (s, 2H); 3.97 (s, 2H); 3.71-3.30 (m, 20H); 2.33-2.08 (m, 7H); 1.97-1.83 (m, 1H); 1.67-1.51 (m, 4H); 1.45 (s, 9H); 1.44 (s, 9H); 1.35-1.20 (m, 20H).

LCMS method 4
Purity: 100%
Rt (Kinetex 4.6 mm×50 mm, acetonitrile/water 50:50 to 100:0+0.1% FA): 4.18 min
Found m/z, z=1: 994.9 (M+H)+

Palladium on carbon (10%, 1.27 g, 1.20 mmol) was added to a solution of the above compound (23.8 g, 24.0 mmol) in methanol (350 mL) and the resulting mixture was hydrogenated at normal pressure for 4 hours. The catalyst was filtered off and the filtrate evaporated to dryness. The residue was evaporated several times from dichloromethane in order to remove residues of methanol and dried in vacuo to yield tert-butyl (S)-1-amino-25-(tert-butoxycarbonyl)-4,13,22,27-tetraoxo-6,9,15,18-tetraoxa-3,12,21,26-tetraazadotetracontan-42-oate as thick colourless oil.

Yield: 20.50 g (99%).

RF (SiO2, dichloromethane/methanol 9:1): 0.05.

1H NMR spectrum (300 MHz, CDCl3, dH): 7.54 (t, J=5.7 Hz, 1H); 7.41 (t, J=5.6 Hz, 1H); 7.14 (t, J=5.5 Hz, 1H); 6.68 (d, J=7.5 Hz, 1H); 5.25 (bs, 2H); 4.39 (td, J=8.3 and 4.2 Hz, 1H); 4.01 (s, 4H); 3.74-3.39 (m, 18H); 2.96 (t, J=5.7 Hz, 2H); 2.34-2.06 (m, 7H); 1.97-1.83 (m, 1H); 1.68-1.50 (m, 4H); 1.45 (s, 9H); 1.43 (s, 9H); 1.37-1.19 (m, 20H).

LCMS method 4 Purity: 100%
Rt (Kinetex 4.6 mm×50 mm, acetonitrile/water 50:50 to 100:0+0.1% FA): 1.43 min
Found m/z, z=1: 860.8 (M+H)+

N,N-Diisopropylethylamine (4.98 mL, 28.6 mmol) was added to a solution of the above amine (6, 20.5 g, 23.8 mmol) in dry dichloromethane (290 mL) at -30° C. under argon. Bromoacetyl bromide (2.48 mL, 28.6 mmol) was added dropwise and the resulting solution was stirred at -30° C. for additional 3 hours. The cooling bath was removed, the mixture was stirred at room temperature for 1 hour, and then the solvent was removed in vacuo. The residue was re-dissolved in ethyl acetate (450 mL) and washed with 5% aqueous solution of citric acid (300 mL). The phases were separated within 1 hour. The organic layer was washed with water (300 mL) and the resulting emulsion was left to separate overnight to give 3 phases. The clear aqueous layer was removed and the residual 2 phases were shaken with saturated aqueous solution of potassium bromide (100 mL) was added. The phases were left to separate overnight, the aqueous one was then removed and the organic one dried over anhydrous sodium sulfate. The solvent was removed in vacuo and the residue was purified by flash column chromatography (Silicagel 60, 0.040-0.060 mm; eluent: dichloromethane/methanol 95:5) to afford tert-butyl (S)-1-bromo-28-(tert-butoxycarbonyl)-2,7,16,25,30-pentaoxo-9,12,18,21-tetraoxa-3,6,15,24,29-pentaazapentatetracontan-45-oate as colorless solid.

Yield: 19.46 g (83%).

RF (SiO2, dichloromethane/methanol 9:1): 0.25

1H NMR spectrum (300 MHz, CDCl3, dH): 7.46 (m, 1H); 7.33 (t, J=5.9 Hz, 1H); 7.21 (t, J=5.1 Hz, 1H); 6.92 (t, J=5.2 Hz, 1H); 6.50 (d, J=7.5 Hz, 1H); 4.41 (ddd, J=12.2, 4.5 and 4.2 Hz, 1H); 4.01 (s, 4H), 3.85 (s, 2H); 3.75-3.40 (m, 20H), 2.36-2.08 (m, 7H); 1.99-1.84 (m, 1H); 1.68-1.51 (m, 4H); 1.46 (s, 9H); 1.44 (s, 9H); 1.38-1.19 (m, 20H)

LCMS method 4
Purity: 100%
Rt (Kinetex 4.6 mm×50 mm, acetonitrile/water 50:50 to 100:0+0.1% FA): 3.51 min.
Found: m/z, z=1: 980.9, 982.9 (M+H)+

The above compound (19.5 g, 19.8 mmol) was dissolved in trifluoroacetic acid (120 mL) and the resulting solution was stirred at room temperature for 1.5 hours. Trifluoroacetic acid was removed in vacuo and the residue was evaporated from dichloromethane (6×200 mL). Diethyl ether (200 mL) was added to the oily residue and the mixture was stirred overnight to give a suspension. Solid product was filtered, washed with diethyl ether and hexanes and dried in vacuo to afford the title product 15-{(S)-1-carboxy-3-[2-(2-{[2-(2-{[2-(2-Bromoacetylamino)ethylcarbamoyl]methoxy}-ethoxy)ethyl-carbamoyl]methoxy}ethoxy)ethyl-carbamoyl]propylcarbamoyl}pentadecanoic acid as white powder.

Yield: 16.74 g (97%).

1H NMR spectrum (300 MHz, AcOD-d4, dH): 4.61 (dd, J=8.8 and 4.8 Hz, 1H); 4.12 (s, 2H), 4.10 (s, 2H); 3.96 (s, 2H); 3.77-3.39 (m, 20H), 2.49-2.18 (m, 7H); 2.16-1.04 (m, 1H); 1.71-1.56 (m, 4H), 1.30 (bs, 20H)

LCMS method 4:
Purity: 100%
Rt (Kinetex 4.6 mm×50 mm, acetonitrile/water 50:50 to 100:0+0.1% FA): 3.51 min
Theoretical m/z, z=1: 869.8, Found: m/z, z=1: 868.7, 870.7

Example 10.3 (C14): Preparation of 14-[[(1S)-4-[2-[2-[2-[2-[2-[2-[(2-bromoacetyl)amino]ethylamino]-2-oxo-ethoxy]ethoxy]ethylamino]-2-oxo-ethoxy]ethoxy]ethylamino]-1-carboxy-4-oxo-butyl]amino]-14-oxo-tetradecanoic acid

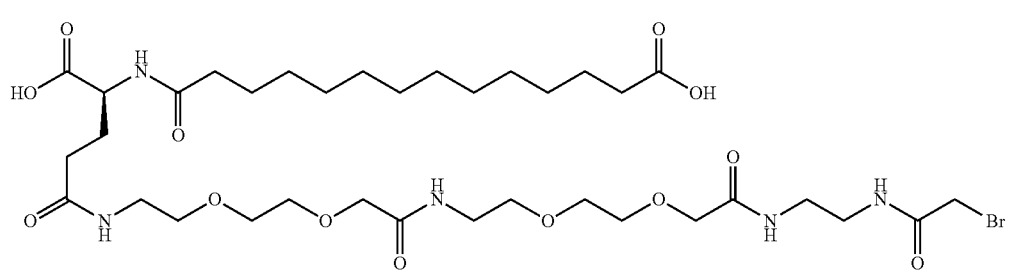

13-{(S)-1-carboxy-3-[2-(2-{2-(2-{[2-(2-Bromoacetylamino)ethylcarbamoyl]methoxy}-ethoxy)ethyl-carbamoyl]methoxy}ethoxy)ethylcarbamoyl]propylcarbamoyl}tridecanoic acid was prepared by the same method as described in Example 10.2 resulting in a thick yellow oil.
1H NMR spectrum (300 MHz, AcOD-d4, dH): 4.61 (dd, J=8.9 and 4.9 Hz, 1H); 4.13 (s, 2H); 4.11 (s, 2H); 3.96 (s, 2H); 3.77-3.40 (m, 20H); 2.49-2.18 (m, 7H); 2.16-2.07 (m, 1H); 1.70-1.56 (m, 4H); 1.31 (bs, 16H).
LCMS method 4:
Purity: 100% (ELSD)
Rt (Kinetex, 4.6 mm×50 mm, acetonitrile/water 20:80 to 100:0+0.1% FA): 2.94 min
Theoretical m/z, z=1: 841.9, Found: m/z, z=1: 841.7, 843.7

Example 10.4 (C18): Preparation of 18-[[(1S)-4-[2-[2-[2-[2-[2-[2-[(2-bromoacetyl)amino]ethylamino]-2-oxo-ethoxy]ethoxy]ethylamino]-2-oxo-ethoxy]ethoxy]ethylamino]-1-carboxy-4-oxo-butyl]amino]-18-oxo-octadecanoic acid Solution Phase Synthetic Protocol:

Step 1: benzyl 18-[[(1S)-4-[2-[2-[2-[2-[2-[2-(2-aminoethylamino)-2-oxo-ethoxy]ethoxy]ethyl-amino]-2-oxo-ethoxy]ethoxy]ethylamino]-1-benzyloxycarbonyl-4-oxo-butyl]amino]-18-oxo-octadecanoate To a solution of ethylenediamine (8.5 ml) in DCM (80 ml) and triethylamine (5.2 ml) at 0° C. was added a solution of benzyl 18-[[(1S)-1-benzyloxycarbonyl-4-[2-[2-[2-[2-[2-[2-(2,5-dioxopyrrolidin-1-yl)oxy-2-oxo-ethoxy]ethoxy]ethyl-amino]-2-oxo-ethoxy]ethoxy]ethylamino]-4-oxo-butyl]

(Formula C)

amino]-18-oxo-octadecanoate (26 g), prepared as described in WO10029159, in DCM (320 ml) dropwise over 75 min. After stirring for 2 h the precipitate was filtered off. To the filtrate was added water (200 ml) and isopropanol (50 ml). The mixture was extracted. The organic layer was dried using MgSO4. The MgSO4 was removed by filtration and the filtrate was dried in vacuo to give the title compound 20.07 g (81%) LCMS: Theoretical mass: 956.2; Found m/z, z=1: 957.0

Step2: benzyl 18-[[(1S)-1-benzyloxycarbonyl-4-[2-[2-[2-[2-[2-[2-[(2-chloroacetyl)amino]ethyl-amino]-2-oxo-ethoxy]ethoxy]ethylamino]-2-oxo-ethoxy]ethoxy]ethylamino]-4-oxo-butyl]amino]-18-oxo-octadecanoate Chloroacetic acid (0.19 g) was dissolved in DCM (15 ml). N-hydroxysuccinimide (0.22 g) and EDAC HCl (0.42 g) was added. After stirring for 2.5h benzyl 18-[[(1S)-4-[2-[2-[2-[2-[2-[2-(2-aminoethylamino)-2-oxo-ethoxy]ethoxy]ethylamino]-2-oxo-ethoxy]ethoxy]ethylamino]-1-benzyloxycarbonyl-4-oxo-butyl]amino]-18-oxo-octadecanoate (1.5 g) in DCM (5 ml) was added. After stirring over night at RT the (Formula D)

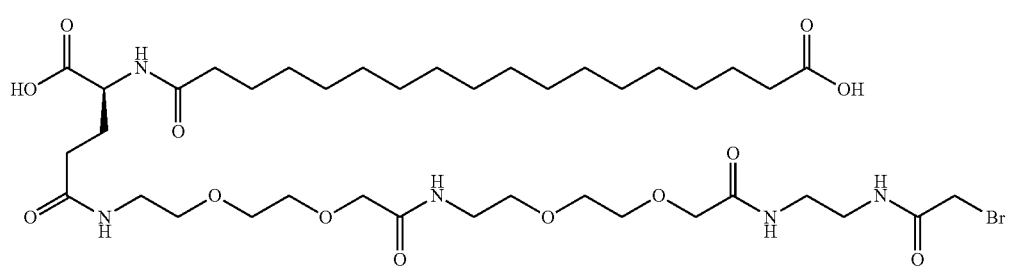

mixture was extracted with 1M HCl (2×20 ml) and water/brine 2:1 (30 ml). The organic layer was dried (MgSO4), filtered and concentrated in vacuo to give a clear oil, 1.37 g (84%) LCMS: Theoretical mass: 1032.7; Found m/z, z=1: 1033.1

Step 3: 18-[[(1S)-1-Carboxy-4-[2-[2-[2-[2-[2-[2-[2-[(2-chloroacetyl)amino]ethylamino]-2-oxo-ethoxy]ethoxy]ethylamino]-2-oxo-ethoxy]ethoxy]ethylamino]-4-oxo-butyl]amino]-18-oxo-octadecanoic acid To a solution of benzyl 18-[[(1S)-1-benzyloxycarbonyl-4-[2-[2-[2-[2-[2-[2-[2-[(2-chloroacetyl)amino]ethylamino]-2-oxo-ethoxy]ethoxy]ethylamino]-2-oxo-ethoxy]ethoxy]ethylamino]-4-oxo-butyl]amino]-18-oxo-octadecanoate (10.5 g) in acetone (140 ml) was added 10% PD/C (1.0 g) after Nitrogen aeration. After hydrogenation for 6h, the mixture was heated to 40-50° C. before filtration. The precipitate in the cold filtrate was isolated and washed with acetone and dried to give the title compound, 7.42 g (85%).

Step 4: 8-[[(1S)-4-[2-[2-[2-[2-[2-[2-[2-[(2-Bromoacetyl)amino]ethylamino]-2-oxo-ethoxy]ethoxy]ethylamino]-2-oxo-ethoxy]ethoxy]ethylamino]-1-carboxy-4-oxo-butyl]amino]-18-oxo-octadecanoic acid To a suspension of 18-[[(1S)-1-Carboxy-4-[2-[2-[2-[2-[2-[2-[2-[(2-chloroacetyl)amino]ethylamino]-2-oxo-ethoxy]ethoxy]ethylamino]-2-oxo-ethoxy]ethoxy]ethylamino]-4-oxo-butyl]amino]-18-oxo-octadecanoic acid in acetone (60 ml) was added sodium bromide (5 eq, 1.21 g). The mixture was stirred at RT in the dark. After 2h more sodium bromide (10 eq, 2.41 g) was added. After 2 days more sodium bromide (5 eq, 1.21 g) was added. After 5 days the mixture was concentrated. To half the residue was added DCM (30 ml), 10% ascorbic acid (20 ml) and water 30 ml. To the emulsion was added isopropanol (50 ml) and water (30 ml). The organic phase was separated and washed twice with a mixture of 10% ascorbic acid (20 ml) and isopropanol (10 ml). The organic layer was dried (MgSO4), filtered and concentrated to give a solid oil, which was crystalised in acetone and isolated by filtration to give the title compound contaminated with starting material, 0.80 g (72%).

LCMS: Theoretical mass: 896.9. Found m/z, z=1: 898.9 (M+1)

Example 10.5 (C12): Preparation of 12-[[(1S)-1-carboxy-4-[2-[2-[2-[2-[2-[2-[(4-formylphenyl)methylamino]-2-oxo-ethoxy]ethoxy]ethylamino]-2-oxo-ethoxy]ethoxy]ethylamino]-4-oxo-butyl]amino]-12-oxo-dodecanoic acid (Formula E)

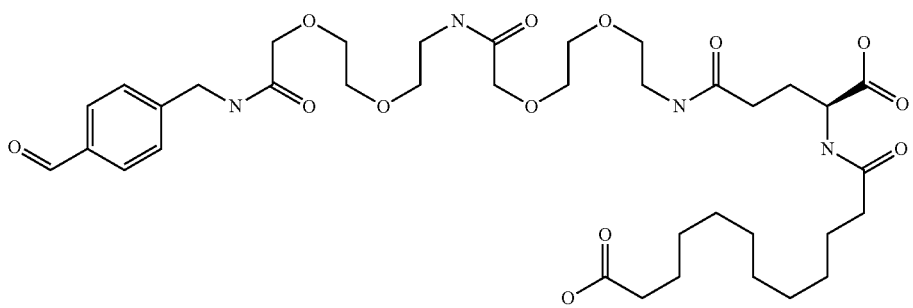

The compound was prepared by the same method as described as for example 10.1.

1H NMR spectrum (300 MHz, CDCl3, dH): 7.39-7.29 (m, 1H); 7.03-6.93 (m, 1H); 6.59-6.51 (m, 1H); 4.49-4.37 (m, 1H); 4.15 (s, 2H); 4.01 (s, 2H); 3.78-3.39 (m, 16H); 2.36-2.10 (m, 7H); 2.01-1.85 (m, 1H); 1.68-1.50 (m, 4H); 1.48-1.41 (m, 18H); 1.34-1.22 (m, 12H).

Example 10.6: Preparation of (2S)-5-[2-[2-[2-[2-[2-[2-[(2-bromoacetyl)amino]ethylamino]-2-oxoethoxy]ethoxy]ethylamino]-2-oxoethoxy]ethoxy]ethylamino]-5-oxo-2-(16-sulfohexadecanoylamino)pentanoic acid (Formula F)

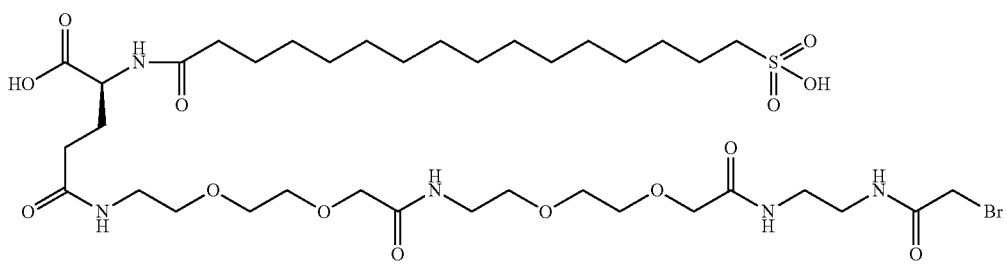

2-Chlorotrityl resin 100-200 mesh 1.5 mmol/g (18.0 g, 27.0 mmol) was left to swell in dry dichloromethane (160 mL) for 20 minutes. A solution of {2-[2-(9H-fluoren-9-ylmethoxycarbonylamino)-ethoxy]-ethoxy}-acetic acid (Fmoc-OEG-OH, 6.94 g, 18.0 mmol) and N,N-diisopropylethylamine (12.5 mL, 72.0 mmol) in dry dichloromethane (100 mL) was added to resin and the mixture was shaken overnight. Resin was filtered and treated with a solution of N,N-diisopropylethylamine (4.12 mL, 23.7 mmol) in methanol/dichloromethane mixture (4:1, 2×5 min, 2×100 mL). Then resin was washed with N,N-dimethylformamide (2×100 mL), dichloromethane (2×100 mL) and N,N-dimethylformamide (3×100 mL). Fmoc group was removed by treatment with 20% piperidine in N,N-dimethylformamide (1×5 min, 1×30 min, 2×100 mL). Resin was washed with N,N-dimethylformamide (3×100 mL), 2-propanol (2×100 mL) and dichloromethane (3×100 mL). Solution of {2-[2-(9H-fluoren-9-ylmethoxycarbonylamino)-ethoxy]-ethoxy}-acetic acid (Fmoc-OEG-OH, 10.4 g, 27.0 mmol), 5-chloro-1-((dimethylamino)(dimethyliminio)methyl)-1H-benzo[d][1,2,3]triazole 3-oxide tetrafluoroborate (TCTU, 9.60 g, 27.0 mmol) and N,N-diisopropylethylamine (8.50 mL, 48.6 mmol) in N,N-dimethylformamide (100 mL) was added to resin and mixture was shaken for 2 hours. Resin was filtered and washed with N,N-dimethylformamide (2×100 mL), dichloromethane (2×100 mL) and N,N-dimethylformamide (3×100 mL). Fmoc group was removed by treatment with 20% piperidine in N,N-dimethylformamide (1×5 min, 1×30 min, 2×100 mL). Resin was washed with N,N-dimethylformamide (3×100 mL), 2-propanol (2×100 mL) and dichloromethane (3×100 mL). Solution of (S)-2-(9H-fluoren-9-ylmethoxycarbonylamino)-pentanedioic acid 1-tert-butyl ester (Fmoc-gGlu-OtBu, 11.5 g, 27.0 mmol), 5-chloro-1-((dimethylamino)(dimethyliminio)methyl)-1H-benzo[d][1,2,3]triazole 3-oxide tetrafluoroborate (TCTU, 9.60 g, 27.0 mmol) and N,N-diisopropylethylamine (8.50 mL, 48.6 mmol) in N,N-dimethylformamide (100 mL) was added to resin and mixture was shaken for 2 hours. Resin was filtered and washed with N,N-dimethylformamide (2×100 mL), dichloromethane (2×100 mL) and N,N-dimethylformamide (2×100 mL). Fmoc group was removed by treatment with 20% piperidine in N,N-dimethylformamide (1×5 min, 1×30 min, 2×100 mL). Resin (2) was washed with N,N-dimethylformamide (3×100 mL), 2-propanol (2×100 mL) and dichloromethane (3×100 mL). Resin was divided into 4 equal parts and this synthesis was continued with one quarter of the original amount (4.50 mmol). Solution of sodium 16-sulfo-hexadecanoic acid (3, 6.16 g, 17.2 mmol, preparation is described in the procedure for synthesis of compound REaD-22296, Batch No. 195-257-1), (benzotriazol-1-yloxy)tripyrrolidinophosphonium hexafluorophosphate (PyBOP, 8.95 g, 17.2 mmol) and N,N-diisopropylethylamine (6.00 mL, 34.0 mmol) in dimethyl sulfoxide (180 mL) was added to resin and mixture was shaken for 4 hours. Resin was filtered and washed with N,N-dimethylformamide (2×100 mL), N,N-dimethylformamide/water (2:1, 2×100 mL), dimethylsulfoxide (2×100 mL), water (2×100 mL) and N,N-dimethylformamide (3×100 mL). The product was cleaved from resin by treatment with 1,1,1,3,3,3-hexafluoro-2-propanol (80 mL) for 2 hours. Resin was filtered off and washed with dichloromethane (4×100 mL). Solutions were combined, volatiles evaporated and crude (S)-22-(tert-butoxycarbonyl)-10,19,24-trioxo-39-sulfo-3,6,12,15-tetraoxa-9,18,23-triazanonatriacontanoic acid (4) was used for the next step without further purification.

Yield: quantitative (based on ELSD).
LC-MS purity: 96%.
LC-MS Rt (Kinetex C18, 4.6 mm×100 mm, acetonitrile/water 20:80 to 100:0+0.1% FA): 3.07 min.
LC-MS m/z: 812.9 (M+H)$^+$.

1-((Dimethylamino)(dimethyliminio)methyl)-1H-[1,2,3]triazolo[4,5-b]pyridine 3-oxide hexafluorophosphate(V) (HATU, 1.87 g, 4.92 mmol) and triethylamine (3.43 mL, 24.6 mmol) were subsequently added to a solution of (S)-22-(tert-butoxycarbonyl)-10,19,24-trioxo-39-sulfo-3,6,12,15-tetraoxa-9,18,23-triazanonatriacontanoic acid (4.5 mmol) in dry dichloromethane (40 mL). Triethylamine (1.82 mL, 13.1 mmol) was added to a suspension of (2-amino-ethyl)-carbamic acid benzyl ester hydrochloride (5, 1.93 g, 8.37 mmol) in dry dichloromethane (20 mL) and the resulting mixture was added to the above solution. The mixture was stirred overnight at room temperature. After 16 hours, another portion of 1-((dimethylamino)(dimethyliminio)methyl)-1H-[1,2,3]triazolo[4,5-b]pyridine 3-oxide hexafluorophosphate(V) (HATU, 0.38 g, 1 mmol), triethylamine (2.00 mL, 14.3 mmol) and (2-amino-ethyl)-carbamic acid benzyl ester hydrochloride (5, 0.40 g, 1.70 mmol) were added and the mixture was stirred for another 2 hours. The solution was washed with 1 M aqueous hydrochloric acid (2×100 mL) and brine (50 mL), dried over anhydrous sodium sulfate and evaporated to dryness. Crude (S)-29-(tert-butoxycarbonyl)-3,8,17,26,31-pentaoxo-1-phenyl-2,10,13,19,22-pentaoxa-4,7,16,25,30-pentaazahexatetracontane-46-sulfonic acid (6) was used for the next step without further purification.

Yield: quantitative (based on ELSD).
LC-MS purity: 83% (ELSD).
LC-MS Rt (Kinetex C18, 4.6 mm×50 mm, acetonitrile/water 20:80 to 100:0+0.1% FA): 3.35 min.
LC-MS m/z: 989.1 (M+H)$^+$.

Palladium on carbon (10%, 0.22 g, 0.20 mmol) was added to a solution of the above compound (4.50 mmol) in methanol (100 mL) and the resulting mixture was hydrogenated at normal pressure for 16 hours and then in sonicator for 1 hour at 40° c. The catalyst was filtered off over Celite™ and the filtrate was evaporated to dryness under reduced pressure. The residue was purified by preparative HPLC (Column DeltaPak C18, 15 m; 50×500 mm; acetonitrile/water 30:70 during 80 min+0.05% TFA) and freeze-dried to afford (S)-1-amino-25-(tert-butoxycarbonyl)-4,13,22,27-tetraoxo-6,9, 15,18-tetraoxa-3, 12,21,26-tetraazadotetracontane-42-sulfonic acid (7) as colorless solid.

Yield: 1.95 g (45% from 1).
LC-MS purity: 98% (ELSD).
LC-MS Rt (Kinetex C18, 4.6 mm×50 mm, acetonitrile/water 20:80 to 100:0+0.1% FA): 2.87 min.
LC-MS m/z: 854.7 (M+H)$^+$.

2,4,6-Collidine (1.60 mL, 12.0 mmol) was added to a solution of the above amine (7, 2.06 g, 2.11 mmol) in anhydrous N,N-dimethylformamide (20 mL) at 0° C. under argon. 2-Bromoacetic anhydride (0.68 g, 2.61 mmol) was added and the resulting solution was stirred at 0° c. for 1 hour. Reaction mixture was then evaporated to dryness under reduced pressure and the residue was triturated with diethyl ether (2×10 mL). Remaining compound (S)-1-bromo-28-(tert-butoxycarbonyl)-2,7,16,25,30-pentaoxo-9,12,18,21-tetraoxa-3,6,15,24,29-pentaazapentatetracontane-45-sulfonic acid (8) was used for the next step without further purification.

Yield: quantitative (based on ELSD).
LC-MS purity: 95% (ELSD).
LC-MS Rt (Kinetex C18, 4.6 mm×50 mm, acetonitrile/water 20:80 to 100:0+0.1% FA): 3.04 min.
LC-MS m/z: 976.9 (M+H)$^+$.

The above compound (8, 2.00 mmol) was dissolved in dichloromethane (20 mL), water (2 mL) and trifluoroacetic acid (25 mL) and the resulting solution was stirred for 2 hours. Trifluoroacetic acid was removed under reduced pressure and the residue was co-evaporated with dichloromethane (3×80 mL). The residue was purified by preparative HPLC (Column DeltaPak C18, 15 m; 50×500 mm; acetonitrile/water 30:70 during 70 min+0.05% TFA) and freeze-dried to afford (S)-1-bromo-2,7,16,25-tetraoxo-28-(16-sulfohexadecanamido)-9,12,18,21-tetraoxa-3,6,15,24-tetraazanonacosan-29-oic acid (9) as white solid.

Yield: 1.92 g (98% over 2 steps).

1H NMR spectrum (300 MHz, AcOD-d4, 80 C, dH): 4.68-4.58 (m, 1H); 4.20-4.08 (m, 4H); 3.94 (s, 2H); 3.82-3.64 (m, 12H); 3.60-3.46 (m, 8H); 3.20-3.10 (m, 2H); 2.51 (t, J=7.2 Hz, 2H); 2.37 (t, J=7.3 Hz, 2H); 2.26 (bs, 1H); 1.92-1.80 (m, 2H); 1.73-1.62 (m, 2H); 1.55-1.44 (m, 2H); 1.43-1.29 (m, 21H).

LC-MS purity: 95% (ELSD).

LC-MS Rt (Kinetex C18, 4.6 mm×50 mm, acetonitrile/water 20:80 to 100:0+0.1% FA): 2.73 min.

LC-MS m/z: 920.9 (M+H)+.

Example 10.7: Preparation of (2S)-6-[(2-bromoacetyl)amino]-2-[[2-[2-[2-[[2-[2-[2-[4-[17-(1H-tetrazol-5-yl)heptadecanoylsulfamoyl]butanoylamino]ethoxy]ethoxy]acetyl]amino]ethoxy]ethoxy]acetyl]amino]hexanoic acid Wang Fmoc-Lys(Mtt) resin 0.29 mmol/g (17.24 g, 5.0 mmol) was left to swell and washed in DMF (60 mL) for 7×5 minutes. Fmoc group was removed by treatment with 20% piperidine in N,N-dimethylformamide (2×60 mL, 2×15 min). Resin was washed with N,N-dimethylformamide (6×60 mL). Fmoc-OEG-OH was weight out for two reactions (2×20 mmol 15.416 g). Dissolved in 120 mL DMF with Oxyma (0.3M) and split out in volume of 2×53 mL. A solution of Fmoc-OEG-OH and Oxyma in DMF (53.2 mL, 0.3 M) was mixed with DIC (26.6 mL, 0.6M) in DMF. The AA was activated over 10 min then added to the resin and the mixture was shaken for 8 hours.

The resin was drained and washed with N,N-dimethylformamide (4×60 mL). Fmoc group was removed by treatment with 20% piperidine in N,N-dimethylformamide (2×60 mL, 2×15 min). Resin was washed with N,N-dimethylformamide (6×60 mL) A solution of Fmoc-OEG-OH and Oxyma in DMF (53.2 mL, 0.3 M) was mixed with DIC (26.6 mL, 0.6M) in DMF. The AA was activated over 10 min then added to the resin and the mixture was shaken for 8 hours. The resin was drained and washed with N,N-dimethylformamide (4×60 mL) and then with acetonitrile (2×60 mL 2×8h).

The above resin, 0.27 mmol/g (2.46 g, 0.66 mmol) was swelled in DMF (12 mL, 3×5 min). Fmoc group was removed by treatment with 20% piperidine in N,N-dimethylformamide (2×12 mL, 1×15 min+1×30 min). The Resin was washed with N,N-dimethylformamide (2×15 mL), DCM (2×15 mL), DMF (2×15 mL).

A solution of 4-[17-(1H-tetrazol-5-yl)heptadecanoylsulfamoyl]butanoic acid (0.966 g, 1.98 mmol), Oxyma (0.281 g, 1.98 mmol) and DIC (0.309 mL) in N,N-dimethylformamide (15 mL) was made and left for approximately 10 min in order to activate the amino acid. The mixture was then added to the reaction-tube and shaken overnight.

The Resin was drained and washed with N,N-dimethylformamide (2×15 mL), DCM (5×15 mL). The MTT group was cleaved by 1,1,1,3,3,3-hexafluoro-2-propanol/DCM/Triisopropylsilane 80/18/2, 3×20 ml, (3×20 min with DCM wash between each treatment) and then washed with 4×20 mL DCM. Bromoacetic acid (1.10 g, 7.92 mmol) and DIC (0.62 mL, 3.96 mmo) in 10 mL DMF were added to the resin and shaken for 1 h. The resin was washed with N,N-dimethylformamide (3×20 mL) and dichloromethane (5×20 mL).

The product was cleaved from the resin with TFA (98%), water (2%), 20 mL for 1h and 20 mL for ½h. The resin was washed with 20 mL DCM. The solvents were evaporated to give a yellow oil. The oil was dissolved in EtOAc (50 mL) and washed with water 2×100 mL). White solid precipitated in the EtOAc layer. The amount of EtOAc was reduced in vacuum and filtered. The precipitate was washed with EtOAc and dried on the filter giving 270 mg of white solid.

LC-MS m/z: 1026.39 (M+H)+.

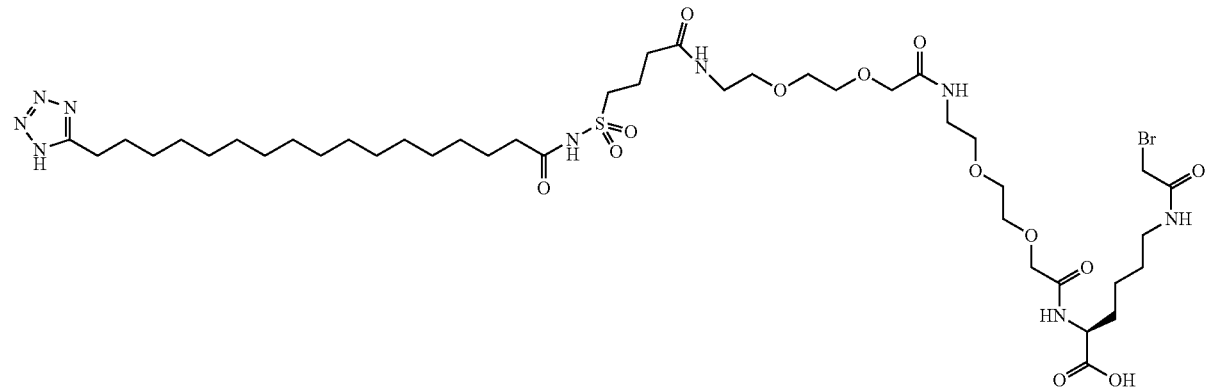

(Formula G)

Example 10.8: Preparation of 4-[10-[[(1S)-4-[2-[2-[2-[2-[2-[2-[2-[[(5S)-5-[(2-bromoacetyl)amino]-5-carboxypentyl]amino]-2-oxoethoxy]ethoxy]ethylamino]-2-oxoethoxy]ethoxy]ethylamino]-1-carboxy-4-oxobutyl]amino]-10-oxodecoxy]benzoic acid (Formula H)

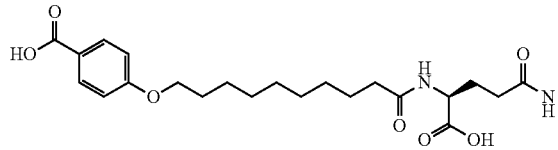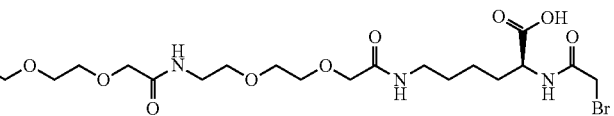

2-Chlorotrityl resin 100-200 mesh 1.5 mmol/g (1, 2.70 g, 4.05 mmol) was left to swell in dry dichloromethane (40 mL) for 30 minutes. A solution of {2-[2-(9H-fluoren-9-ylmethoxycarbonylamino)-ethoxy]-ethoxy}-acetic acid (Fmoc-OEG-OH, 1.04 g, 2.70 mmol) and N,N-diisopropylethylamine (1.82 mL, 10.3 mmol) in dry dichloromethane (40 mL) was added to resin and the mixture was shaken overnight. Resin was filtered and treated with a solution of N,N-diisopropylethylamine (0.94 mL, 5.40 mmol) in methanol/dichloromethane mixture (4:1, 2×5 min, 2×40 mL). Then resin was washed with N,N-dimethylformamide (4×40 mL), dichloromethane (4×40 mL) and N,N-dimethylformamide (4×40 mL). Fmoc group was removed by treatment with 20% piperidine in N,N-dimethylformamide (1×10 min, 1×30 min, 2×40 mL). Resin was washed with N,N-dimethylformamide (3×40 mL), 2-propanol (2×40 mL), dichloromethane (3×40 mL) and N,N-dimethylformamide (3×40 mL). Solution of {2-[2-(9H-fluoren-9-ylmethoxycarbonylamino)-ethoxy]-ethoxy}-acetic acid (Fmoc-OEG-OH, 3.18 g, 8.20 mmol), 5-chloro-1-((dimethylamino)(dimethyliminio)methyl)-1H-benzo[d][1,2,3]triazole 3-oxide tetrafluoroborate (TCTU, 2.93 g, 8.20 mmol) and N,N-diisopropylethylamine (2.87 mL, 16.4 mmol) in N,N-dimethylformamide (40 mL) was added to resin and mixture was shaken for 1 hour. Resin was filtered and washed with N,N-dimethylformamide (4×40 mL), dichloromethane (4×40 mL) and N,N-dimethylformamide (4×40 mL). Fmoc group was removed by treatment with 20% piperidine in N,N-dimethylformamide (1×10 min, 1×30 min, 2×40 mL). Resin was washed with N,N-dimethylformamide (3×40 mL), 2-propanol (2×40 mL), dichloromethane (3×40 mL) and N,N-dimethylformamide (3×40 mL). Solution of (S)-2-(9H-fluoren-9-ylmethoxycarbonylamino)-pentanedioic acid 1-tert-butyl ester (Fmoc-L-Glu-OtBu, 3.50 g, 8.20 mmol), 5-chloro-1-((dimethylamino)(dimethyliminio)methyl)-1H-benzo[d][1,2,3]triazole 3-oxide tetrafluoroborate (TCTU, 2.93 g, 8.20 mmol) and N,N-diisopropylethylamine (2.87 mL, 16.4 mmol) in N,N-dimethylformamide (40 mL) was added to resin and mixture was shaken for 1 hour. Resin was filtered and washed with N,N-dimethylformamide (4×40 mL), dichloromethane (4×40 mL) and N,N-dimethylformamide (4×40 mL). Fmoc group was removed by treatment with 20% piperidine in N,N-dimethylformamide (1×10 min, 1×30 min, 2×40 mL). Resin was washed with N,N-dimethylformamide (3×40 mL), 2-propanol (2×40 mL), dichloromethane (3×40 mL) and N,N-dimethylformamide (3×40 mL). Solution of 10-(4-(tert-butoxycarbonyl)phenoxy)decanoic acid (CNB, 3.00 g, 8.20 mmol), 5-chloro-1-((dimethylamino)(dimethyliminio)methyl)-1H-benzo[d][1,2,3]triazole 3-oxide tetrafluoroborate (TCTU, 2.93 g, 8.20 mmol) and N,N-diisopropylethylamine (2.87 mL, 16.4 mmol) in N,N-dimethylformamide (40 mL) was added to resin and mixture was shaken for 1 hour. Resin was filtered and washed with N,N-dimethylformamide (4×40 mL), dichloromethane (4×40 mL), N,N-dimethylformamide (4×40 mL) and dichloromethane (10×40 mL).

The product was cleaved from the resin by the treatment with 2,2,2-trifluoroethanol (40 mL) overnight. Resin was filtered off and washed with dichloromethane (4×40 mL). The solvent was evaporated to dryness to afford pure (S)-22-(tert-butoxycarbonyl)-33-(4-(tert-butoxycarbonyl)phenoxy)-10,19,24-trioxo-3,6,12,15-tetraoxa-9,18,23-triazatriacontanoic acid as yellow oil.

Yield: 2.26 g (100%).

1H NMR spectrum (300 MHz, CDCl3, dH): 7.95-7.87 (m, 2H); 7.41-7.32 (m, 1H); 7.05-6.95 (m, 1H); 6.92-6.82 (m, 2H); 6.61 (d, J=7.7 Hz, 1H); 4.49-4.37 (m, 1H); 4.15 (s, 2H); 4.04-3.95 (m, 4H); 3.76-3.36 (m, 17H); 2.39-2.09 (m, 5H); 2.04-1.85 (m, 1H); 1.84-1.70 (m, 2H); 1.67-1.52 (m, 10H); 1.50-1.39 (m, 11H); 1.37-1.24 (m, 8H).

LC-MS purity: 100% (ELSD).

LC-MS Rt (Kinetex C18, 4.6 mm×50 mm, acetonitrile/water 50:50 to 100:0+0.1% FA): 4.49 min.

LC-MS m/z: 841.2 (M+H)$^+$.

Wang-Fmoc-Lys(Mtt)-OH resin 0.33 mmol/g (3, 4.15 g, 1.37 mmol) was left to swell in dichloromethane (50 mL) for 30 minutes. Mtt group was removed by treatment with 80% 1,1,1,3,3,3-hexafluoropropan-2-ol in dichloromethane (2×5 min, 2×10 min, 1×15 min, 1×30 min, 6×50 mL). Resin 3 was washed with dichloromethane (4×70 mL), 10% N,N-diisopropylethylamine in dichloromethane (1×50 mL) and dichloromethane (2×50 mL).

A solution of (S)-22-(tert-butoxycarbonyl)-33-(4-(tert-butoxycarbonyl)phenoxy)-10,19,24-trioxo-3,6,12,15-tetraoxa-9,18,23-triazatritriacontanoic acid (2, 2.30 g, 2.73 mmol), 5-chloro-1-((dimethylamino)(dimethyliminio)methyl)-1H-benzo[d][1,2,3]triazole 3-oxide tetrafluoroborate (TCTU, 0.97 g, 2.73 mmol) and N,N-diisopropylethylamine (1.20 mL, 6.85 mmol) in N,N-dimethylformamide (50 mL) was added to resin and mixture was shaken overnight. Resin was filtered and washed with N,N-dimethylformamide (4×50 mL), dichloromethane (4×50 mL) and N,N-dimethylformamide (4×50 mL). Fmoc group was removed by treatment with 20% piperidine in N,N-dimethylformamide (1×10 min, 1×30 min, 2×50 mL). Resin was washed with N,N-dimethylformamide (3×50 mL), 2-propanol (2×50 mL), dichloromethane (3×50 mL) and N,N-dimethylformamide (3×50 mL). A solution of bromoacetic acid (0.76 g, 5.48 mmol), N,N'-diisopropylcarbodiimide (DIC, 0.85 mL, 5.48 mmol), 2,4,6-collidine (0.91 mL, 5.48 mmol) in N,N-dimethylformamide (50 mL) was added to resin and mixture was shaken for 1 hour. Resin was filtered and washed with N,N-dimethylformamide (4×50 mL), dichloromethane (4×50 mL), N,N-dimethylformamide (4×50 mL) and dichloromethane (10×40 mL). The product (4) was cleaved from the resin by the treatment with trifluoroacetic acid/dichloromethane mixture (2:1, 30 mL) for 3 hours. Resin was filtered off and washed with dichloromethane (4×40 mL). The solvent was evaporated to dryness to afford pure (2S,29S)-29-(2-bromoacetamido)-2-(10-(4-carboxyphenoxy)decanamido)-5,14,23-trioxo-9,12,18,21-tetraoxa-6,15,24-triazatriacontanedioic acid (4) as yellow oil.

Yield: 1.33 g (100%).

1H NMR spectrum (300 MHz, DMSO-d6+DCl, dH): 7.93-7.76 (m, 2H); 7.05-6.89 (m, 2H); 4.16-4.05 (m, 3H); 4.05-3.93 (m, 2H); 3.93-3.79 (m, 5H); 3.60-3.48 (m, 9H); 3.46-3.32 (m, 4H); 3.30-3.21 (m, 2H); 3.21-3.12 (m, 2H); 3.10-3.00 (m, 2H); 2.19-1.77 (m, 6H); 1.77-1.49 (m, 7H); 1.48-1.22 (m, 12H).

LC-MS purity: 95% (ELSD).

LC-MS Rt (Kinetex C18, 4.6 mm×50 mm, acetonitrile/water 20:80 to 100:0+0.1% FA): 3.02 min.

LC-MS m/z: 977.3 (M+H)$^+$.

Example 10.9: Preparation of 4-[12-[[(1S)-4-[2-[2-[2-[2-[2-[2-[[(6S)-6-[(2-bromoacetyl)amino]-6-carboxyhexyl]amino]-2-oxoethoxy]ethoxy]ethylamino]-2-oxoethoxy]ethoxy]ethylamino]-1-carboxy-4-oxobutyl]amino]-12-oxododecoxy]benzoic acid Resin was washed with N,N-dimethylformamide (3×40 mL), 2-propanol (2×40 mL), dichloromethane (3×40 mL) and N,N-dimethylformamide (3×40 mL). Solution of (S)-2-(9H-fluoren-9-ylmethoxycarbonylamino)-pentanedioic acid 1-tert-butyl ester (Fmoc-L-Glu-OtBu, 3.40 g, 7.90 mmol), 5-chloro-1-((dimethylamino)(dimethyliminio)methyl)-1H-benzo[d][1,2,3]triazole 3-oxide tetrafluoroborate (TCTU, 2.82 g, 7.90 mmol) and N,N-diisopropylethylamine (2.76 mL, 15.0 mmol) in N,N-dimethylformamide (40 mL) was added to resin and mixture was shaken for 1 hour. Resin was filtered and washed with N,N-dimethylformamide (4×40 mL), dichloromethane (4×40 mL) and N,N-dimethylformamide (4×40 mL). Fmoc group was removed by treatment with 20% piperidine in N,N-dimethylformamide (1×10 min, 1×30 min, 2×40 mL). Resin was washed with N,N-dimethylformamide (3×40 mL), 2-propanol (2×40 mL), dichloromethane (3×40 mL) and N,N-dimethylformamide (3×40 mL). Solution of 12-(4-(tert-butoxycarbonyl)phenoxy)dodecanoic acid (CUB, 3.12 g, 7.90 mmol), 5-chloro-1-((dimethylamino)(dimethyliminio)methyl)-1H-benzo[d][1,2,3]triazole 3-oxide tetrafluoroborate (TCTU, 2.82 g, 7.90 mmol) and N,N-diisopropylethylamine (2.76 mL, 15.0 mmol) in N,N-dimethylformamide (40 mL) was added to resin and mixture was shaken for 1 hour. Resin was filtered and washed with N,N-dimethylformamide (4×40 mL), dichloromethane (4×40 mL), N,N-dimethylformamide (4×40 mL) and dichloromethane (10×40 mL).

(Formula K)

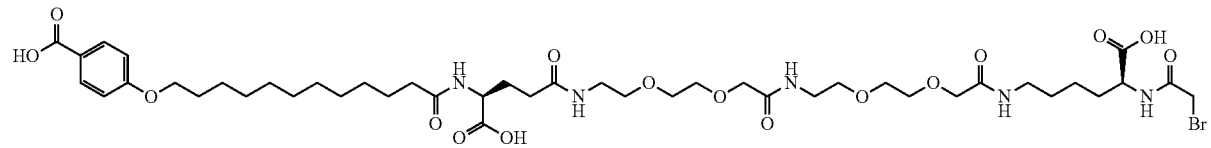

2-Chlorotrityl chloride resin 100-200 mesh 1.5 mmol/g (2.60 g, 3.90 mmol) was left to swell in dry dichloromethane (40 mL) for 30 minutes. A solution of {2-[2-(9H-fluoren-9-ylmethoxycarbonylamino)-ethoxy]-ethoxy}-acetic acid (Fmoc-OEG-OH, 1.02 g, 2.60 mmol) and N,N-diisopropylethylamine (1.75 mL, 10.0 mmol) in dry dichloromethane (40 mL) was added to resin and the mixture was shaken overnight. Resin was filtered and treated with a solution of N,N-diisopropylethylamine (0.90 mL, 5.20 mmol) in methanol/dichloromethane mixture (4:1, 2×5 min, 2×40 mL). Then resin was washed with N,N-dimethylformamide (4×40 mL), dichloromethane (4×40 mL) and N,N-dimethylformamide (4×40 mL). Fmoc group was removed by treatment with 20% piperidine in N,N-dimethylformamide (1×10 min, 1×30 min, 2×40 mL). Resin was washed with N,N-dimethylformamide (3×40 mL), 2-propanol (2×40 mL), dichloromethane (3×40 mL) and N,N-dimethylformamide (3×40 mL). Solution of {2-[2-(9H-fluoren-9-ylmethoxycarbonylamino)-ethoxy]-ethoxy}-acetic acid (Fmoc-OEG-OH, 3.06 g, 7.90 mmol), 5-chloro-1-((dimethylamino)(dimethyliminio)methyl)-1H-benzo[d][1,2,3]triazole 3-oxide tetrafluoroborate (TCTU, 2.82 g, 7.90 mmol) and N,N-diisopropylethylamine (2.76 mL, 15.0 mmol) in N,N-dimethylformamide (40 mL) was added to resin and mixture was shaken for 1 hour. Resin was filtered and washed with N,N-dimethylformamide (4×40 mL), dichloromethane (4×40 mL) and N,N-dimethylformamide (4×40 mL). Fmoc group was removed by treatment with 20% piperidine in N,N-dimethylformamide (1×10 min, 1×30 min, 2×40 mL).

The product was cleaved from the resin by the treatment with 2,2,2-trifluoroethanol (40 mL) overnight. Resin was filtered off and washed with dichloromethane (4×40 mL). The solvent was evaporated to dryness to afford pure (S)-22-(tert-butoxycarbonyl)-35-(4-(tert-butoxycarbonyl)phenoxy)-10,19,24-trioxo-3,6,12,15-tetraoxa-9,18,23-triazapentatriacontanoic acid as yellow oil.

Yield: 1.93 g (86%).

LC-MS purity: 100% (ELSD).

LC-MS Rt (Kinetex C18, 4.6 mm×50 mm, acetonitrile/water 20:80 to 100:0+0.1% FA): 4.88 min.

LC-MS m/z: 869.2 (M+H)$^+$.

Wang-Fmoc-Lys(Mtt)-OH resin 0.33 mmol/g (3.40 g, 1.11 mmol) was left to swell in dichloromethane (50 mL) for 30 minutes. Mtt group was removed by treatment with 80% 1,1,1,3,3,3-hexafluoropropan-2-ol in dichloromethane (2×5 min, 2×10 min, 1×15 min, 1×30 min, 6×50 mL). Resin was washed with dichloromethane (4×70 mL), 10% N,N-diisopropylethylamine in dichloromethane (1×50 mL) and dichloromethane (2×50 mL).

A solution of (S)-22-(tert-butoxycarbonyl)-35-(4-(tert-butoxycarbonyl)phenoxy)-10,19,24-trioxo-3,6,12,15-tetraoxa-9,18,23-triazapentatriacontanoic acid (1.93 g, 2.22 mmol), 5-chloro-1-((dimethylamino)(dimethyliminio)methyl)-1H-benzo[d][1,2,3]triazole 3-oxide tetrafluoroborate (TCTU, 0.79 g, 2.22 mmol) and N,N-diisopropylethylamine (0.86 mL, 6.66 mmol) in N,N-dimethylformamide (50 mL) was added to resin and mixture was shaken overnight. Resin was filtered and washed with N,N-dimethylformamide (4×50 mL), dichloromethane (4×50 mL) and N,N-dimethylformamide (4×50 mL). Fmoc group was removed by treatment with 20% piperidine in N,N-dimethylformamide (1×10 min, 1×30 min, 2×50 mL). Resin was washed with N,N-dimethylformamide (3×50 mL), 2-propanol (2×50 mL), dichloromethane (3×50 mL) and N,N-dimethylformamide (3×50 mL). A solution of bromoacetic acid (0.62 g, 4.44 mmol), N,N'-diisopropylcarbodiimide (DIC, 0.69 mL, 4.44 mmol) and 2,4,6-collidine (0.59 mL, 4.44 mmol) in N,N-dimethylformamide (50 mL) was added to resin and mixture was shaken for 1 hour. Resin was filtered and washed with N,N-dimethylformamide (4×50 mL), dichloromethane (4×50 mL), N,N-dimethylformamide (4×50 mL) and dichloromethane (10×40 mL). The product was cleaved from the resin by the treatment with trifluoroacetic acid/dichloromethane mixture (2:1, 30 mL) for 3 hours. Resin was filtered off and washed with dichloromethane (4×40 mL). The solvent was evaporated to dryness to afford pure (2S, 29S)-29-(2-bromoacetamido)-2-(12-(4-carboxyphenoxy)dodecanamido)-5,14,23-trioxo-9,12,18,21-tetraoxa-6,15,24-triazatriacontanedioic acid as yellow oil.

Yield: 1.10 g (99%).

1H NMR spectrum (300 MHz, DMSO-d6+DCI, dH): 7.93-7.74 (m, 2H); 7.06-6.86 (m, 2H); 4.20-3.93 (m, 5H); 3.92-3.78 (m, 6H); 3.54 (s, 9H); 3.46-2.94 (m, 12H); 2.19-1.84 (m, 5H); 1.81-1.52 (m, 6H); 1.51-1.23 (m, 15H).

LC-MS purity: 97% (ELSD).

LC-MS Rt (Kinetex C18, 4.6 mm×50 mm, acetonitrile/water 20:80 to 100:0+0.1% FA): 3.20 min.

LC-MS m/z: 1005.3 (M+H)+.

Example 10.10: Preparation of (2S)-5-[2-[2-[2-[2-[2-[2-[2-[(2-bromoacetyl)amino]ethylamino]-2-oxoethoxy]ethoxy]ethylamino]-2-oxoethoxy]ethoxy]ethylamino]-5-oxo-2-[16-(1H-tetrazol-5-yl)hexadecanoylamino]pentanoic acid Yield: 4.73 g (69%).

RF (SiO2, ethyl acetate): 0.35.

1H NMR spectrum (300 MHz, AcOD-d4, dH): 3.02 (t, J=7.7 Hz, 2H); 2.86 (s, 4H); 2.62 (t, J=7.3 Hz, 2H); 1.90-1.63 (m, 4H); 1.30 (bs, 22H).

2-Chlorotrityl resin bound Fmoc-gGlu(tBu)-OEG-OEG- (11.5 mmol, preparation is described in the procedure for synthesis of the protractor of Example 10.6) was left to swell in dichloromethane (100 mL) for 20 minutes. Resin was washed with N,N-dimethylformamide (2×100 mL). Fmoc group was removed by treatment with 20% piperidine in N,N-dimethylformamide (1×5 min, 1×30 min, 2×100 mL). Resin was washed with N,N-dimethylformamide (3×100 mL), 2-propanol (2×100 mL) and dichloromethane (8×100 mL). The product was cleaved from resin by treatment with 1,1,1,3,3,3-hexafluoro-2-propanol in dichloromethane (2:8, 80 mL) for 2 hours. Resin was filtered off and washed with dichloromethane (2×80 mL). Solutions were combined; solvents evaporated to obtain product (4) as brownish oil. The crude product contained 2 equivalents of 1,1,1,3,3,3-hexafluoro-2-propanol.

Yield: 9.49 g (99%, counted for adduct with 2 equivalents of HFIP).

1H NMR spectrum (300 MHz, CDCl3, dH): 7.72-7.64 (m, 1H); 7.59-7.50 (m, 1H); 4.00 (s, 2H); 3.94 (s, 2H); 3.94-3.85 (m, 1H); 3.71-3.32 (m, 16H); 2.56-2.45 (m, 2H); 2.42-2.26 (m, 1H); 2.16-2.02 (m, 1H); 1.49 (s, 9H).

To a solution of the above acid (6.10 g, 7.93 mmol) in tetrahydrofuran (50 mL) and 2,5-dioxopyrrolidin-1-yl 16-(1H-tetrazol-5-yl)hexadecanoate (2, 3.33 g, 7.93 mmol) was added N,N-diisopropylethylamine (6.91 mL, 39.6 mmol) and the reaction mixture was stirred overnight. Then the solvent was removed under reduced pressure and the residue purified by flash column chromatography (Silicagel 60, 0.040-0.063 mm; eluent: dichloromethane/methanol/acetic acid 15:1:0.2 to 5:1:0.2). Residual acetic acid was removed by freeze-drying from acetonitrile/water mixture 1:1 giving pure (5) as off-white solid.

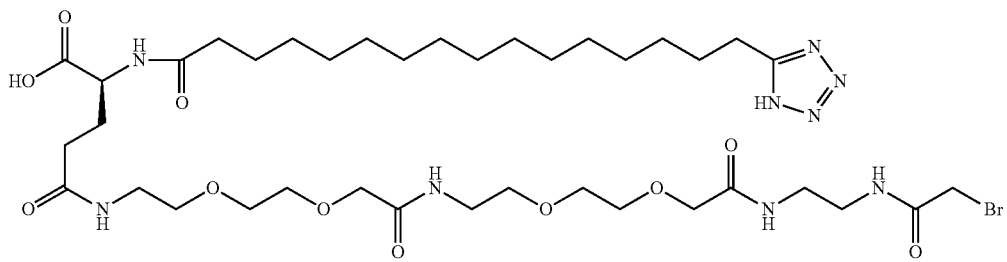

(Formula J)

1-Ethyl-3-(3-dimethylaminopropyl)carbodiimide hydrochloride (EDCHCI, 6.25 g, 32.6 mmol) was added to a stirred solution of 16-(1H-tetrazol-5-yl)hexadecanoic acid (1, 5.28 g, 16.3 mmol) and N-hydroxysuccinic imide (HOSu, 3.75 g, 32.6 mmol) in N,N-dimethylformamide (70 mL) and mixture was stirred overnight. The reaction mixture was diluted with 1 M aqueous solution of hydrochloric acid (400 mL). The crude product was extracted with ethyl acetate (4×400 mL) and the organic phase was dried over anhydrous sodium sulfate. After filtration the solvent was removed under reduced pressure. 2-Propanol (100 mL) was added to the oily residue and the precipitated white solid was filtered off. The pure product (2) was obtained by recrystallization from 2-propanol (70 mL) as white microcrystalline solid.

Yield: 1.39 g (22%).

1H NMR spectrum (300 MHz, DMSO-d6, dH): 8.13-8.07 (m, 1H); 8.01-7.93 (m, 1H); 7.74-7.68 (m, 1H); 4.11-3.99 (m, 1H); 3.88 (s, 2H); 3.82 (s, 2H); 3.62-3.49 (m, 8H); 3.49-3.37 (m, 4H); 3.33-3.15 (m, 4H); 2.73-2.65 (m, 2H); 2.18-2.03 (m, 4H); 1.94-1.81 (m, 1H); 1.80-1.67 (m, 1H); 1.66-1.53 (m, 2H); 1.53-1.41 (m, 2H); 1.38 (s, 9H); 1.23 (s, 22H).

To a solution of the above compound (1.39 g, 1.73 mmol), 1-((dimethylamino)(dimethyliminio)methyl)-1H-[1,2,3]triazolo[4,5-b]pyridine 3-oxide hexafluorophosphate(V) (HATU, 657 mg, 1.73 mmol) and N,N-diisopropylethylamine (1.21 mL, 6.90 mmol) in N,N-dimethylformamide (30 mL) was added benzyl (2-aminoethyl)carbamate (6, 400 mg, 1.73 mmol) and the reaction mixture was stirred overnight. Then the solvent was removed under reduced pressure and the residue was purified by flash column chromatography (Silicagel 60, 0.040-0.063 mm; eluent: ethyl acetate/methanol/acetic acid 15:1:0.2 to dichloromethane/methanol/acetic acid 15:1:0.2) giving pure product (7) as brownish sticky solid.

Yield: 1.63 g (97%).

1H NMR spectrum (300 MHz, AcOD-d4, dH): 7.35 (bs, 5H); 5.25-5.12 (m, 2H); 4.50-4.42 (m, 1H); 4.14 (s, 2H); 4.09 (s, 2H); 3.79-3.30 (m, 20H); 3.02 (t, J=7.6 Hz, 2H); 2.46-2.27 (m, 4H); 2.26-2.09 (m, 1H); 2.05-1.92 (m, 1H); 1.88-1.72 (m, 2H); 1.72-1.53 (m, 2H); 1.47 (s, 9H); 1.29 (bs, 22H).

To a solution of the above compound (1.63 g, 1.67 mmol) in methanol was added palladium on carbon (10%, 0.25 g, 0.23 mmol) under hydrogen blanket and the reaction mixture was vigorously stirred for 2 hours. Then the reaction mixture was filtered through a short pad of diatomite and washed with methanol. The solvent was removed under reduced pressure giving pure product (8) as white solid foam.

Yield: 1.32 g (94%).

1H NMR spectrum (300 MHz, AcOD-d4, dH): 4.50-4.42 (m, 1H); 4.16-4.10 (m, 4H); 3.71-3.61 (m, 14H); 3.59-3.51 (m, 2H); 3.51-3.45 (m, 2H); 3.40-3.32 (m, 2H); 3.02 (t, J=7.6 Hz, 2H); 2.45-2.28 (m, 4H); 2.27-2.12 (m, 1H); 2.05-1.93 (m, 1H); 1.89-1.74 (m, 2H); 1.70-1.58 (m, 2H); 1.47 (s, 9H); 1.30 (bs, 22H).

The above compound (1.32 g, 1.57 mmol) was dissolved in a mixture of trifluoroacetic acid (90 mL) and water (10 mL). After 90 minutes the volatiles were removed under reduced pressure and the residue was evaporated with toluene (3×50 mL). The residue was dissolved in N,N-dimethylformamide (15 mL) and cooled to 0° c. Bromoacetic anhydride (678 mg, 2.61 mmol) and sodium bicarbonate (2.02 g, 24.0 mmol) were added while stirring and the reaction mixture was allowed to warm up to ambient temperature. After 60 minutes additional bromoacetic anhydride (200 mg, 0.77 mmol) was added to complete the reaction. After 30 minutes the solvent was removed under reduced pressure giving brownish liquid immiscible with dichloromethane, ethyl acetate and water. The residue was placed to separatory funnel and tried to dissolve in ethyl acetate (50 mL) and water (50). It created three phases. Ethyl acetate phase and water phase were removed and the third phase was purified by preparative HPLC (Column labio DeltaPak C18, 15 mm, 50×500 mm, acetonitrile/water 25:75 to 50:50+0.05% TFA). Resulting solution was freeze-dried to give the title product (9) as white solid.

Yield: 210 mg (15%).

1H NMR spectrum (300 MHz, AcOD-d4, dH): 4.64-4.56 (m, 1H); 4.12 (s, 2H); 4.10 (s, 2H); 3.95 (s, 2H); 3.77-3.59 (m, 12H); 3.59-3.37 (m, 8H); 3.02 (t, J=7.6 Hz, 2H); 2.44 (t, J=7.8 Hz, 2H); 2.34 (t, J=8.0 Hz, 2H); 2.28-2.18 (m, 1H); 2.15-2.04 (m, 1H); 1.86-1.70 (m, 2H); 1.70-1.56 (m, 2H), 1.29 (bs, 22H).

LC-MS purity: 100%.

LC-MS Rt (Kinetex C18, 4.6 mm×50 mm, acetonitrile/water 20:80 to 100:0+0.1% FA): 3.35 min.

LC-MS m/z: 908.8 (M+H)$^+$.

Example 11: Preparation of MIC-1 Compounds with Protractors

Example 11.1: Compound 01

SerA-32,GluA-31,ProA-30,S{Beta}-[2-[2-[[2-[2-[2-[[2-[2-[2-[[(4S)-4-carboxy-4-(17-carboxyheptadecanoylamino) butanoyl]amino]ethoxy]ethoxy]acetyl]amino]ethoxy] ethoxy]acetyl]amino]ethylamino]-2-oxoethyl]CysA-29, ThrA-28,SerA-27,GlyA-26,SerA-25,GluA-24,ThrA-23, ProA-22,GlyA-21,ThrA-20,SerA-19,GluA-18,SerA-17, AlaA-16,ThrA-15,ProA-14,GluA-13,SerA-12,GlyA-11, ProA-10,GlyA-9,ThrA-8,SerA-7,ThrA-6,GluA-5,ProA-4, SerA-3,GluA-2,GlyA-1,SerB-32,GluB-31,ProB-30, S{Beta}-[2-[2-[[2-[2-[2-[[2-[2-[2-[[(4S)-4-carboxy-4-(17-carboxyheptadecanoylamino)butanoyl]amino]ethoxy] ethoxy]acetyl]amino]ethoxy]ethoxy]acetyl]amino] ethylamino]-2-oxoethyl]CysB-29,ThrB-28,SerB-27,GlyB-26,SerB-25,GluB-24,ThrB-23,ProB-22,GlyB-21,ThrB-20, SerB-19,GluB-18,SerB-17,AlaB-16,ThrB-15,ProB-14, GluB-13,SerB-12,GlyB-11,ProB-10,GlyB-9,ThrB-8,SerB-7,ThrB-6,GluB-5,ProB-4,SerB-3,GluB-2,GlyB-1,des-AsnA3,AsnB3-MIC-1

(Formula 01)

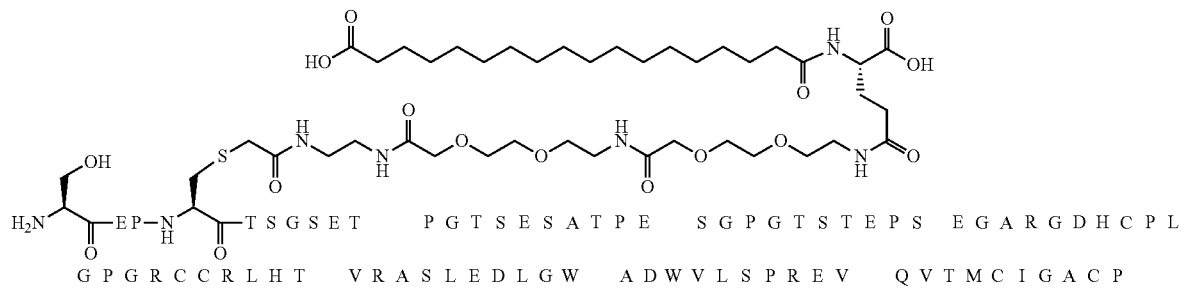

-continued

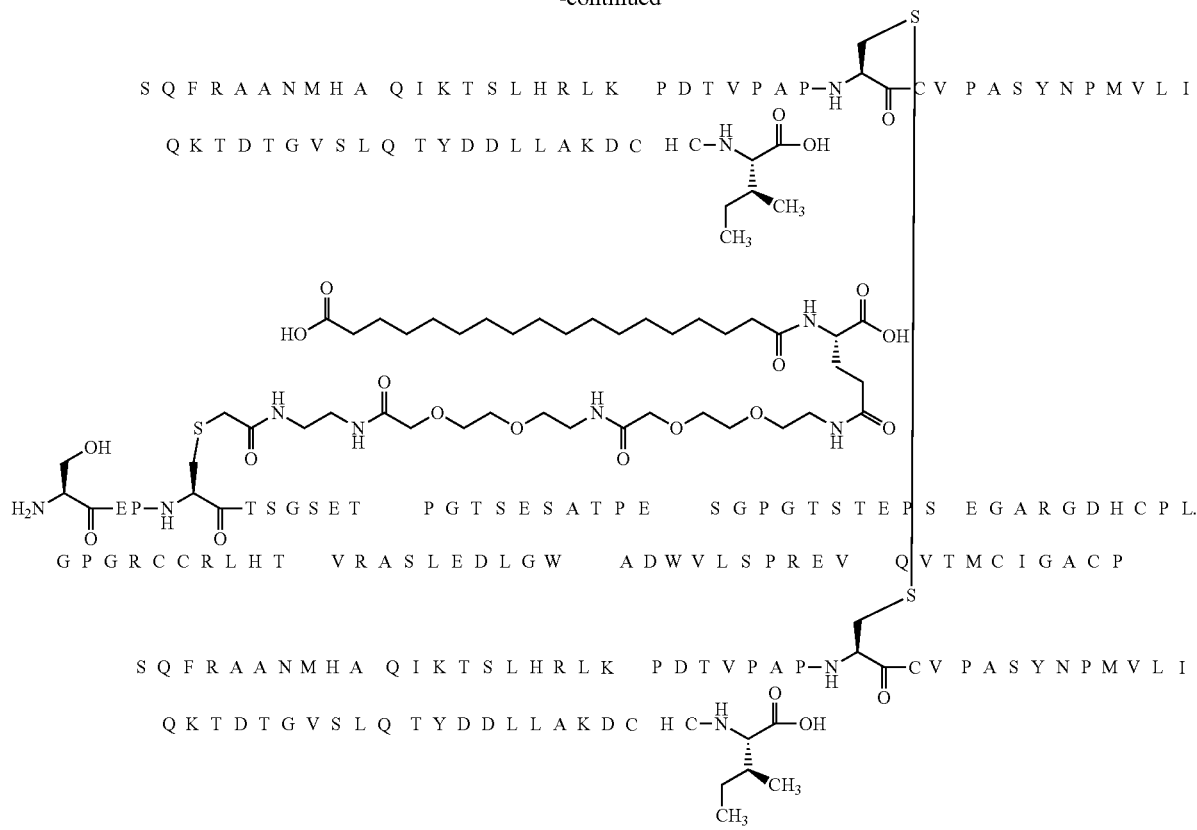

(SEQ ID NO: 288)

30 mg protractor (example 10.4, 8 equivalents) was dissolved in 1.5 mL of sat. NaHCO₃ and added to 108 mg MIC-1 polypeptide with N-extension (SEQ ID NO: 288) in PBS buffer, pH 7.4, 2.1 mg/mL. Added 19 mg bis(p-sulfonatophenyl)phenylphosphine, Kalium salt dihydrate, Sigma-Aldrich 698539 (8 equivalent). After 24h standing at roomtemeperature the protein was purified on a C4 reverse phase column using a 10-50% ethanol/phosphate buffer pH 3.0 gradient. Yield ~20% after purification.

Theoretical mass: 32006.3; Found: 32006.5.

Example 11.2: Compound 02

SerA-32,GluA-31,ProA-30,AlaA-29,ThrA-28,S{Beta}-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethylamino]-2-oxoethyl]CysA-27,GlyA-26,SerA-25,GluA-24,ThrA-23,ProA-22,GlyA-21,ThrA-20,SerA-19,GluA-18,SerA-17,AlaA-16,ThrA-15,ProA-14,GluA-13,SerA-12,GlyA-11,ProA-10,GlyA-9,ThrA-8,SerA-7,ThrA-6,GluA-5,ProA-4,SerA-3,GluA-2,GlyA-1,SerB-32,GluB-31,ProB-30,AlaB-29,ThrB-28,S{Beta}-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethylamino]-2-oxoethyl]CysB-27,GlyB-26,SerB-25,GluB-24,ThrB-23,ProB-22,GlyB-21,ThrB-20,SerB-19,GluB-18,SerB-17,AlaB-16,ThrB-15,ProB-14,GluB-13,SerB-12,GlyB-11,ProB-10,GlyB-9,ThrB-8,SerB-7,ThrB-6,GluB-5,ProB-4,SerB-3,GluB-2,GlyB- des-AsnA3,AsnB3-MIC-1

(Formula 02)

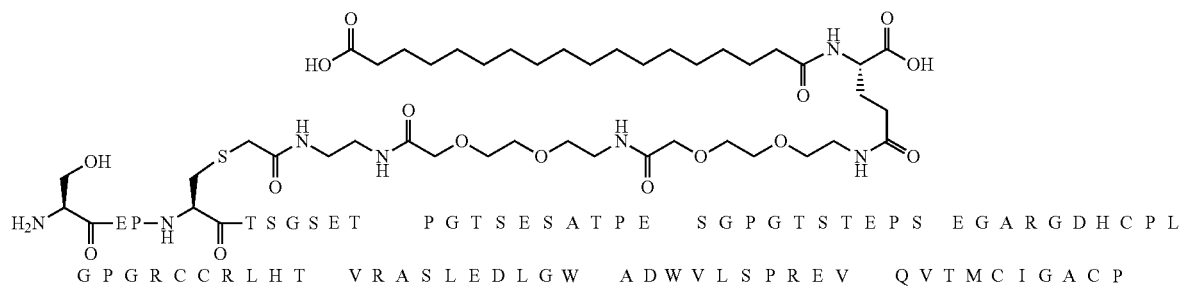

-continued

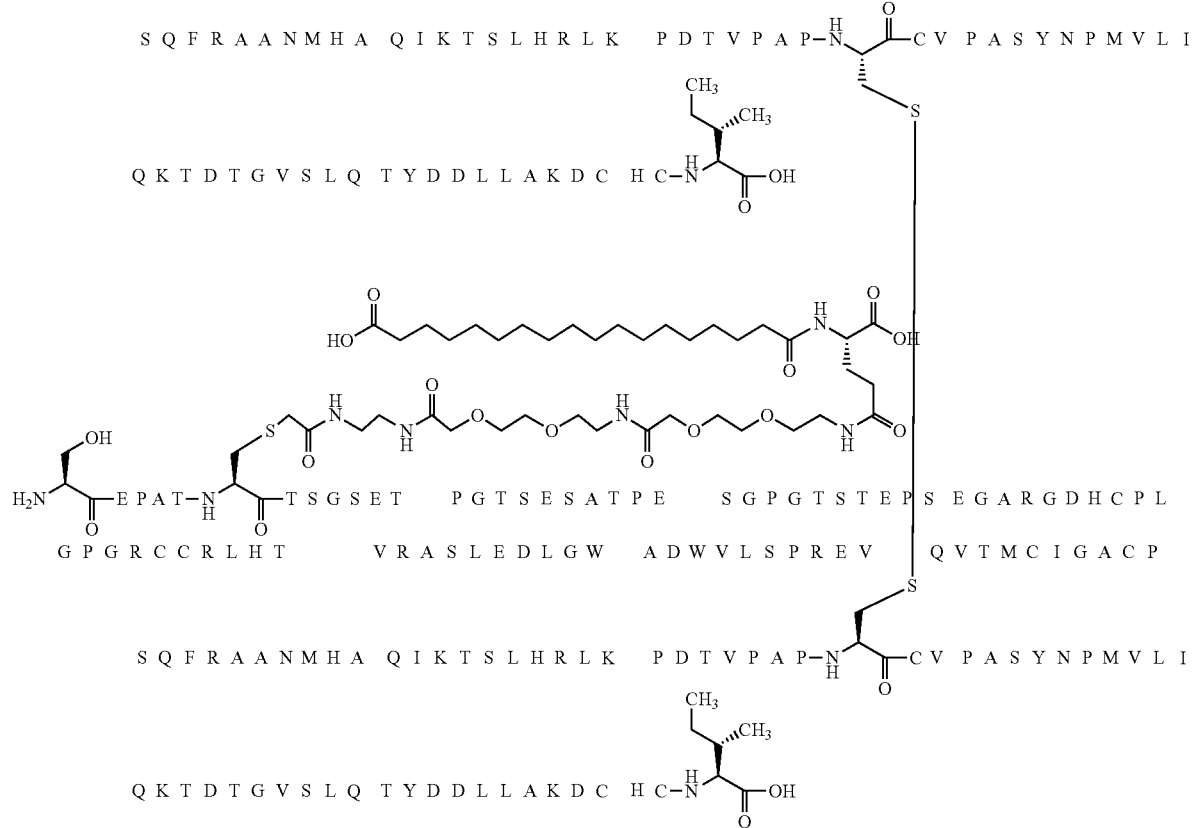

(SEQ ID NO: 291)

Compound 02 was prepared using the procedure described in example 11.1 using MIC-1 polypeptide with N-extension (SEQ ID NO: 291).
Theoretical mass: 31974.3; Found: 31974.0

Example 11.3: Compound 03

SerA-32,GluA-31,ProA-30,AlaA-29,ThrA-28,S{Beta}-[2-[2-[[2-[2-[2-[[2-[2-[2-[[(4S)-4-carboxy-4-(15-carboxy-pentadecanoylamino)butanoyl]amino]ethoxy]ethoxy]acetyl]amino]ethoxy]ethoxy]acetyl]amino]ethylamino]-2-oxoethyl]CysA-27,GlyA-26,SerA-25,GluA-24,ThrA-23,ProA-22,GlyA-21,ThrA-20,SerA-19,GluA-18,SerA-17, AlaA-16,ThrA-15,ProA-14,GluA-13,SerA-12,GlyA-11,ProA-10,GlyA-9,ThrA-8,SerA-7,ThrA-6,GluA-5,ProA-4,SerA-3,GluA-2,GlyA-1,SerB-32,GluB-31,ProB-30,AlaB-29,ThrB-28,S{Beta}-[2-[2-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]ethylamino]-2-oxoethyl]CysB-27,GlyB-26,SerB-25,GluB-24,ThrB-23,ProB-22,GlyB-21,ThrB-20,SerB-19,GluB-18,SerB-17,AlaB-16,ThrB-15,ProB-14,GluB-13,SerB-12,GlyB-11,ProB-10,GlyB-9,ThrB-8,SerB-7,ThrB-6,GluB-5,ProB-4,SerB-3,GluB-2,GlyB-1des-AsnA3,AsnB3-MIC-1

(Formula 03)

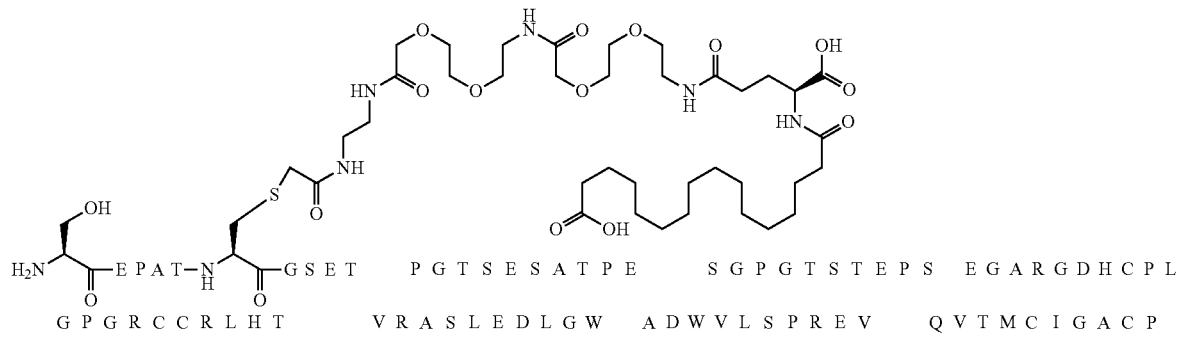

-continued

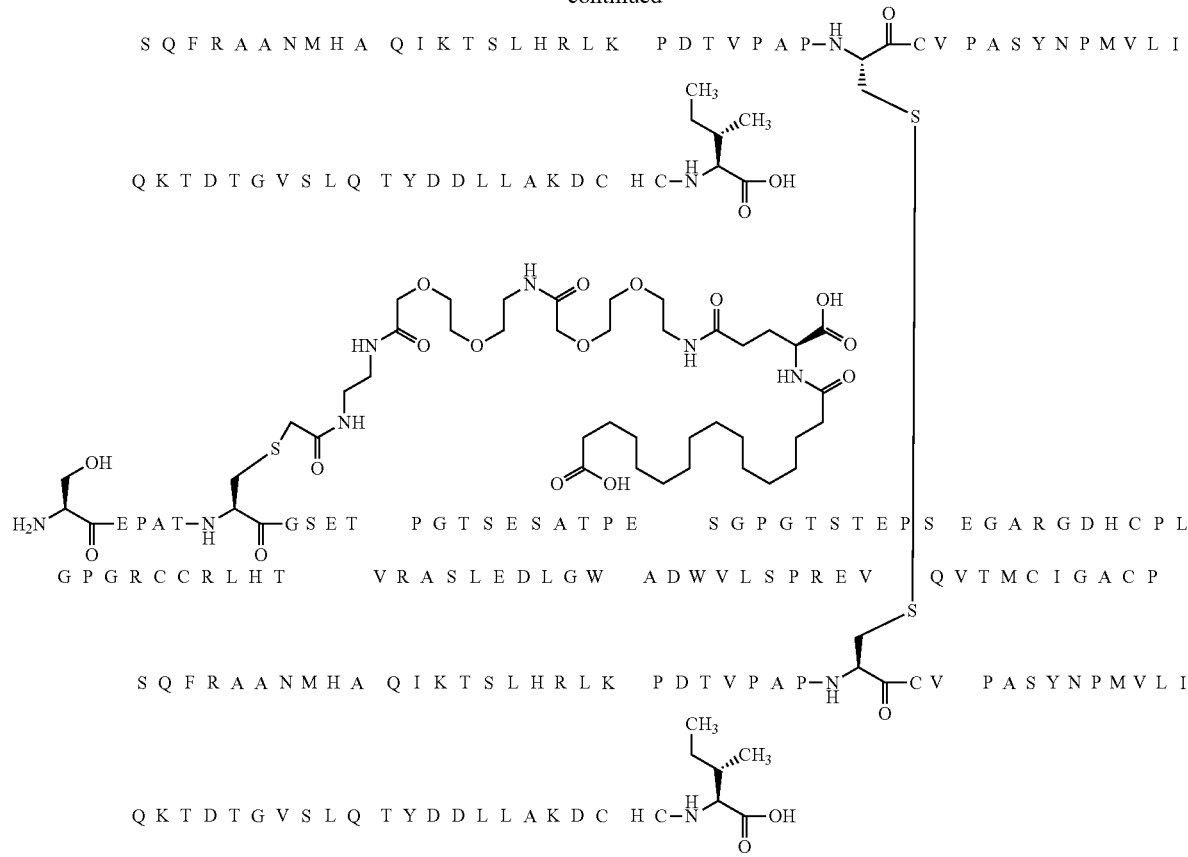

(SEQ ID NO: 291)

Compound 03 was prepared using the procedure described in example 11.1 using the protractor described in example 10.2 and MIC-1 polypeptide with N-extension (SEQ ID NO: 291).

Theoretical mass: 31918.2; Found: 31918.0.

Example 11.4: Compound 04

SerA-32,GluA-31,ProA-30,AlaA-29,ThrA-28,S{Beta}-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethylamino]-2-oxoethyl]CysA-27,GlyA-26,SerA-25,GluA-24,ThrA-23, ProA-22,GlyA-21,ThrA-20,SerA-19,GluA-18,SerA-17, AlaA-16,ThrA-15,ProA-14,GluA-13,SerA-12,GlyA-11, ProA-10,GlyA-9,ThrA-8,SerA-7,ThrA-6,GluA-5,ProA-4, SerA-3,GluA-2,GlyA-1,SerB-32,GluB-31,ProB-30,AlaB-29,ThrB-28,S{Beta}-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethylamino]-2-oxoethyl]CysB-27,GlyB-26,SerB-25,GluB-24,ThrB-23,ProB-22,GlyB-21,ThrB-20,SerB-19,GluB-18, SerB-17,AlaB-16,ThrB-15,ProB-14,GluB-13,SerB-12, GlyB-11,ProB-10,GlyB-9,ThrB-8,SerB-7,ThrB-6,GluB-5, ProB-4,SerB-3,GluB-2,GlyB-1des-AsnA3,AsnB3-MIC-1

(Formula 04)

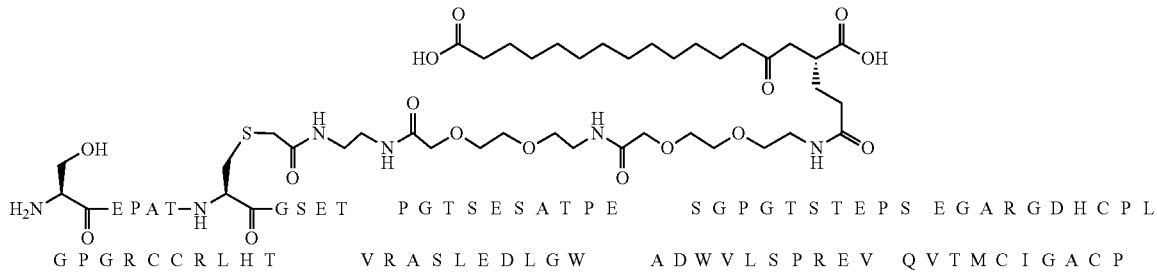

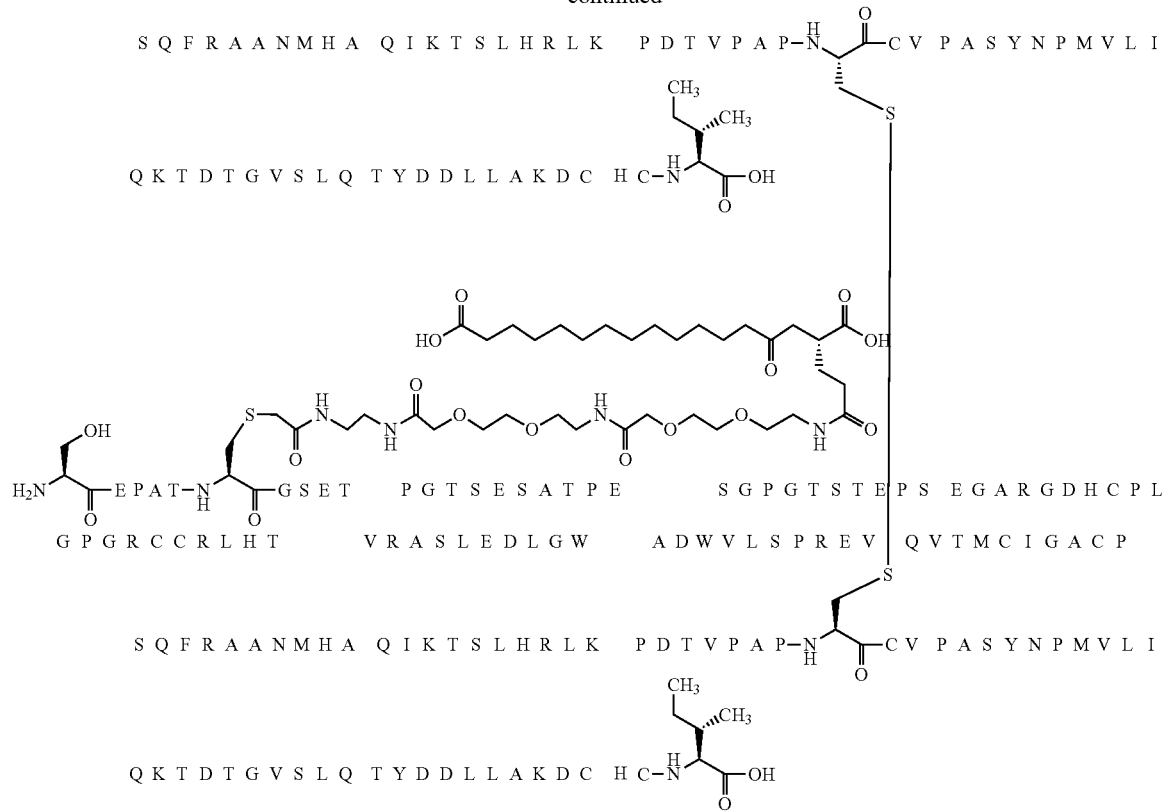

(SEQ ID NO: 291)

Compound 04 was prepared using the procedure described in example 11.1 using the protractor described in example 10.3 and MIC-1 polypeptide with N-extension (SEQ ID NO: 291).

Theoretical mass: 31862.1; Found: 31862.0.

Example 11.5: Compound 05

SerA-32,GluA-31,ProA-30,AlaA-29,ThrA-28,SerA-27, S{Beta}-[2-[2-[[[2-[2-[[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethylamino]-2-oxoethyl]CysA-26,SerA-25,GluA-24,ThrA-23,ProA-22,GlyA-21,ThrA-20,SerA-19,GluA-18,SerA-17,AlaA-16,ThrA-15,ProA-14,GluA-13,SerA-12,GlyA-11,ProA-10,GlyA-9,ThrA-8,SerA-7,ThrA-6,GluA-5,ProA-4,SerA-3,GluA-2,GlyA-1,SerB-32,GluB-31,ProB-30,AlaB-29,ThrB-28,SerB-27,S{Beta}-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethylamino]-2-oxoethyl]CysB-26,SerB-25,GluB-24,ThrB-23,ProB-22,GlyB-21,ThrB-20,SerB-19,GluB-18,SerB-17,AlaB-16,ThrB-15,ProB-14,GluB-13,SerB-12,GlyB-11,ProB-10,GlyB-9,ThrB-8,SerB-7,ThrB-6,GluB-5,ProB-4,SerB-3,GluB-2,GlyB-1[LeuA57,LeuA86,LeuB57,LeuB86],des-AsnA3,AsnB3-MIC-1

(Formula 05)

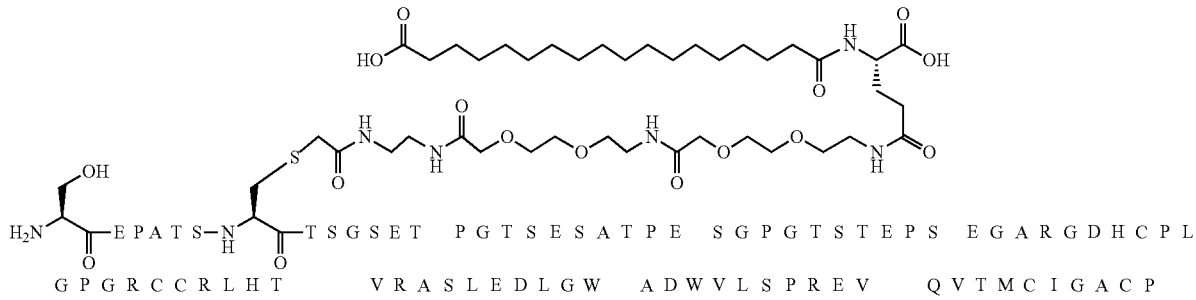

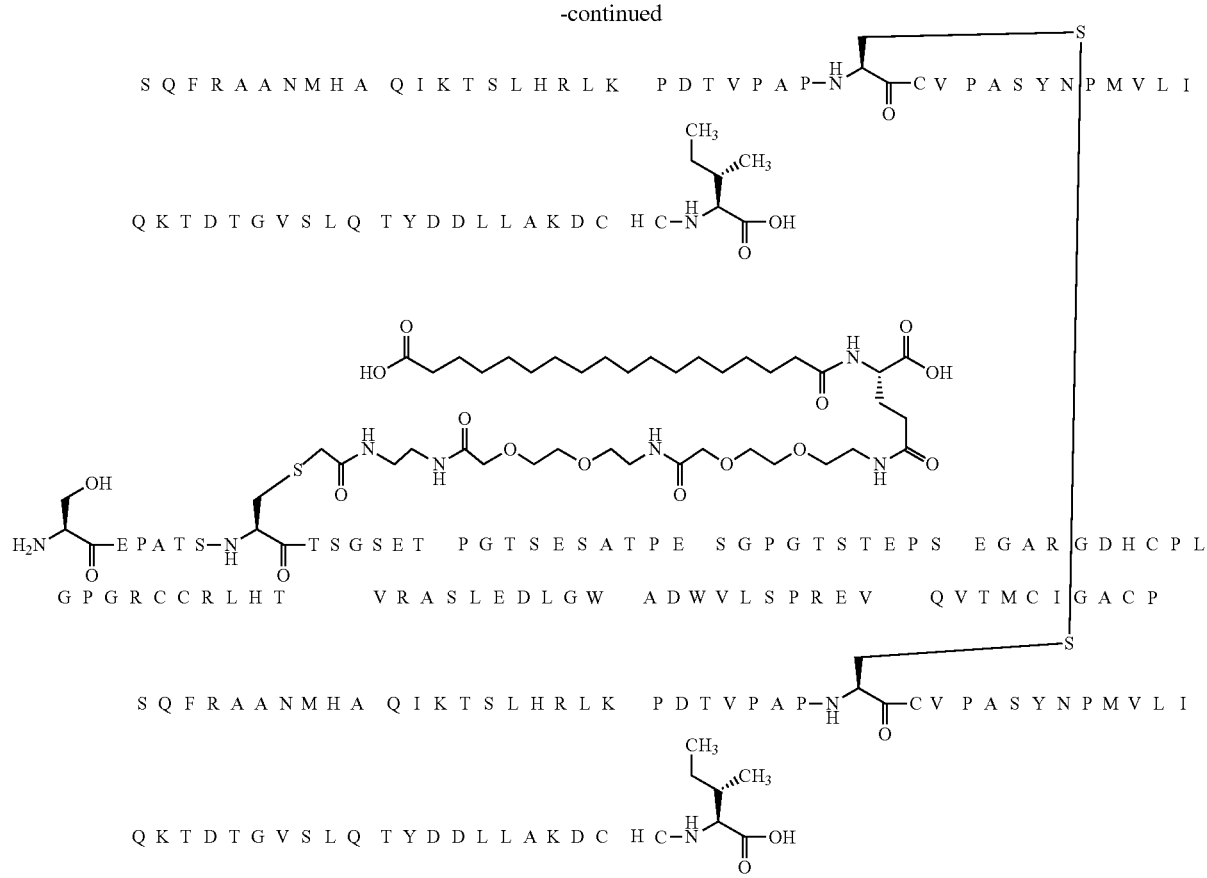

(SEQ ID NO: 289)

Compound 05 was prepared using the procedure described in example 11.1 using the 5 protractor described in example 10.4 and MIC-1 polypeptide with N-extension (SEQ ID NO: 289).

Theoretical mass: 31962.2; Found: 31962.0.

Example 11.6: Compound 06

SerA-32,GluA-31,ProA-30,AlaA-29,ThrA-28,SerA-27, GlyA-26,S{Beta}-[2-[2-[[2-[2-[2-[[2-[2-[2-[[(4S)-4-carboxy-4-(17-carboxyheptadecanoylamino)butanoyl]amino] ethoxy]ethoxy]acetyl]amino]ethoxy]ethoxy]acetyl]amino] ethylamino]-2-oxoethyl]CysA-25,GluA-24,ThrA-23,ProA-22,GlyA-21,ThrA-20,SerA-19,GluA-18,SerA-17,AlaA-16, ThrA-15,ProA-14,GluA-13,SerA-12,GlyA-11,ProA-10, GlyA-9,ThrA-8,SerA-7,ThrA-6,GluA-5,ProA-4,SerA-3, GluA-2,GlyA-1,SerB-32,GluB-31,ProB-30,AlaB-29,ThrB-28,SerB-27,GlyB-26,S{Beta}-[2-[2-[[2-[2-[2-[[2-[2-[2-[[(4S)-4-carboxy-4-(17-carboxyheptadecanoylamino) butanoyl]amino]ethoxy]ethoxy]acetyl]amino]ethoxy] ethoxy]acetyl]amino]ethylamino]-2-oxoethyl]CysB-25, GluB-24,ThrB-23,ProB-22,GlyB-21,ThrB-20,SerB-19, GluB-18,SerB-17,AlaB-16,ThrB-15,ProB-14,GluB-13, SerB-12,GlyB-11,ProB-10,GlyB-9,ThrB-8,SerB-7,ThrB-6, GluB-5,ProB-4,SerB-3,GluB-2,GlyB-1[LeuA57,LeuA86, LeuB57,LeuB86],des-AsnA3,AsnB3-MIC-1

(Formula 06)

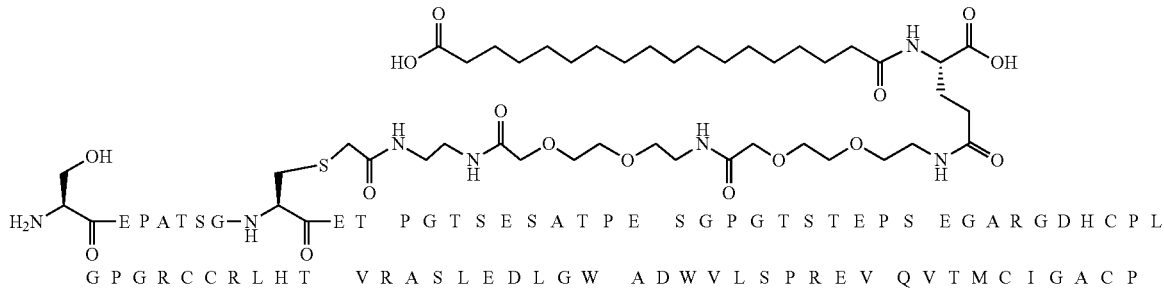

-continued

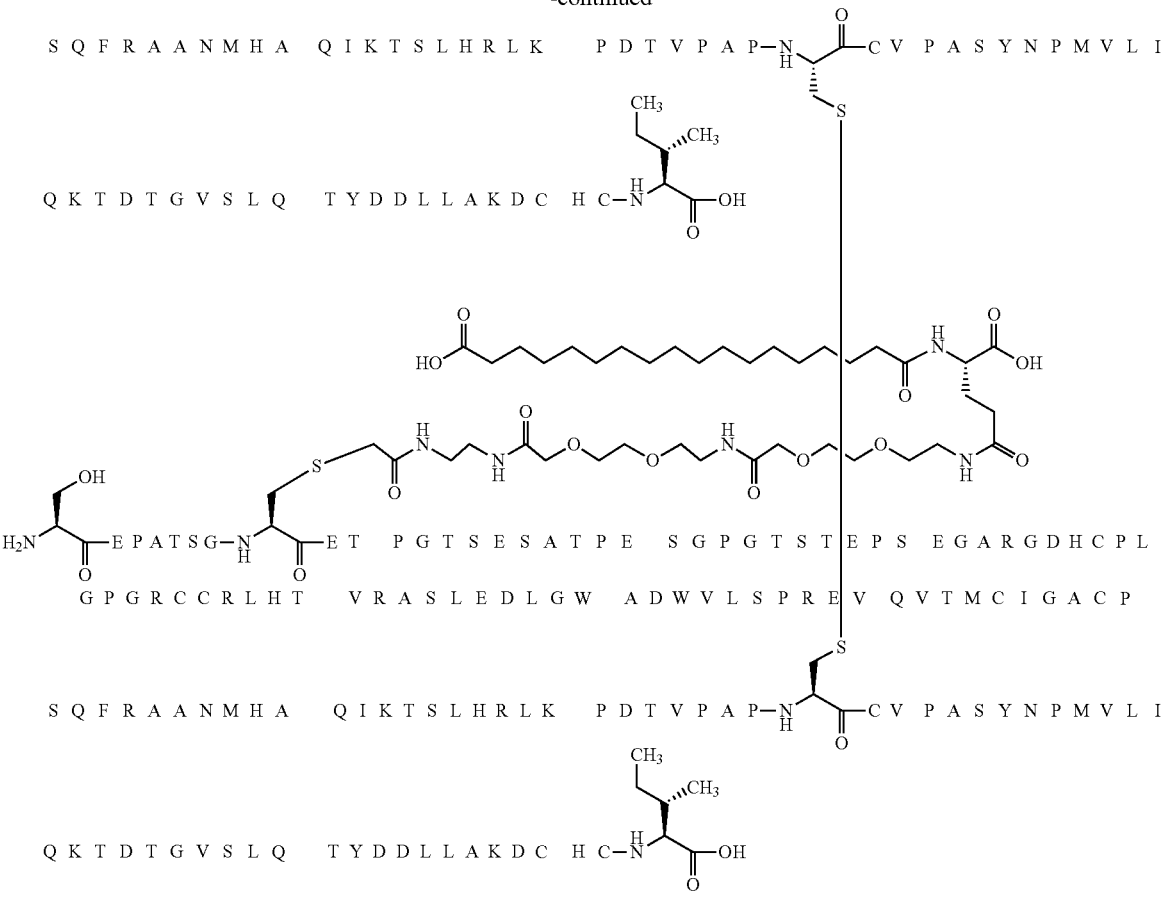

(SEQ ID NO: 303)

Compound 06 was prepared using the procedure described in example 11.1 using the 5 protractor described in example 10.4 and MIC-1 polypeptide with N-extension (SEQ ID NO: 303).

Theoretical mass: 31902.1; Found: 31902.0

Example 11.7: Compound 07

SerA-32,GluA-31,ProA-30,AlaA-29,ThrA-28,SerA-27, GlyA-26,SerA-25,GluA-24,ThrA-23,ProA-22,GlyA-21, ThrA-20,SerA-19,GluA-18,SerA-17,AlaA-16,S{Beta}-[2 [2-[[2-[2-[2-[[2-[2-[2-[[(4S)-4-carboxy-4-(17-carboxyheptadecanoylamino)butanoyl]amino]ethoxy]ethoxy]acetyl] amino]ethoxy]ethoxy]acetyl]amino]ethylamino]-2-oxo-ethyl]CysA-15,ProA-14,GluA-13,SerA-12,GlyA-11,ProA-10,GlyA-9,ThrA-8,SerA-7,ThrA-6,GluA-5,ProA-4,SerA-3, GluA-2,GlyA-1,SerB-32,GluB-31,ProB-30,AlaB-29,ThrB-28,SerB-27,GlyB-26,SerB-25,GluB-24,ThrB-23,ProB-22, GlyB-21,ThrB-20,SerB-19,GluB-18,SerB-17,AlaB-16, S{Beta}-[2-[2-[[2-[2-[2-[[2-[2-[2-[[(4S)-4-carboxy-4-(17-carboxyheptadecanoylamino)butanoyl]amino]ethoxy] ethoxy]acetyl]amino]ethoxy]ethoxy]acetyl]amino] ethylamino]-2-oxoethyl]CysB-15,ProB-14,GluB-13,SerB-12,GlyB-11,ProB-10,GlyB-9,ThrB-8,SerB-7,ThrB-6,GluB-5,ProB-4,SerB-3,GluB-2,GlyB-1[LeuA57,LeuA86, LeuB57,LeuB86],des-AsnA3,AsnB3-MIC-1

(Formula 07)

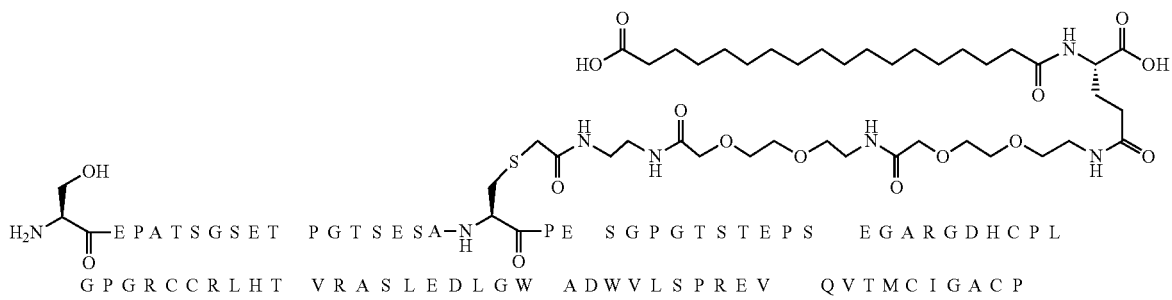

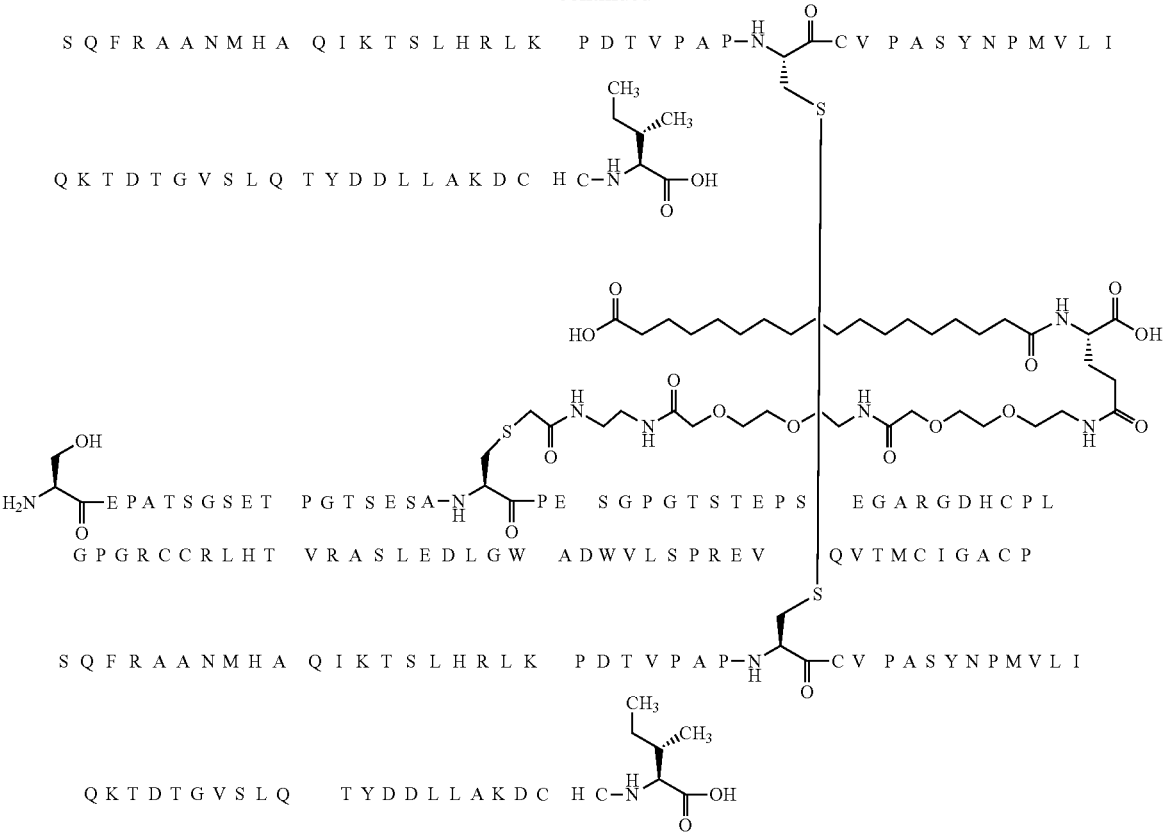

(SEQ ID NO: 292)

Compound 07 was prepared using the procedure described in example 11.1 using the 5 protractor described in example 10.4 and MIC-1 polypeptide with N-extension (SEQ ID NO: 292).

Theoretical mass: 31874.1; Found: 31873.0.

Example 11.8: Compound 08

SerA-32,GluA-31,ProA-30,AlaA-29,ThrA-28,SerA-27, GlyA-26,SerA-25,GluA-24,ThrA-23,ProA-22,GlyA-21, ThrA-20,SerA-19,GluA-18,SerA-17,AlaA-16,ThrA-15, ProA-14,GluA-13,SerA-12,GlyA-11,ProA-10,GlyA-9, ThrA-8,SerA-7,ThrA-6,GluA-5,ProA-4,S{Beta}-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethylamino]-2-oxoethyl]CysA-3,GluA-2,GlyA-1,SerB-32, GluB-31,ProB-30,AlaB-29,ThrB-28,SerB-27,GlyB-26, SerB-25,GluB-24,ThrB-23,ProB-22,GlyB-21,ThrB-20, SerB-19,GluB-18,SerB-17,AlaB-16,ThrB-15,ProB-14, GluB-13,SerB-12,GlyB-11,ProB-10,GlyB-9,ThrB-8,SerB-7,ThrB-6,GluB-5,ProB-4,S{Beta}-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethylamino]-2-oxoethyl]CysB-3, GluB-2,GlyB-1[LeuA57,LeuA86,LeuB57,LeuB86],des-AsnA3,AsnB3-MIC-1

(Formula 08)

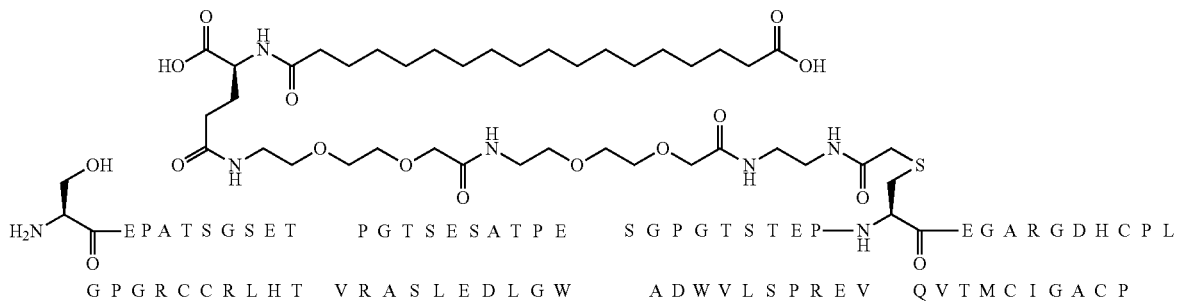

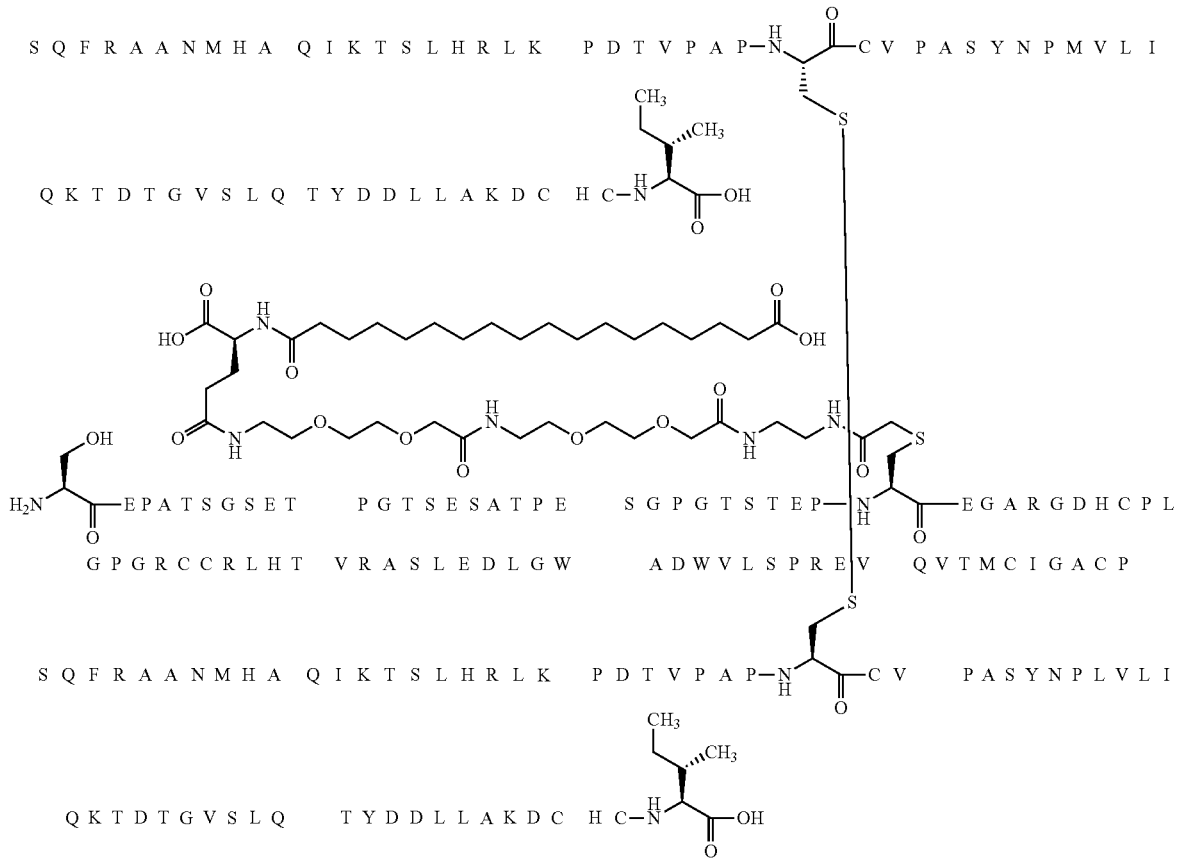

(SEQ ID NO: 293)

Compound 08 was prepared using the procedure described in example 11.1 using the protractor described in example 10.4 and MIC-1 polypeptide with N-extension (SEQ ID NO: 293).

Theoretical mass: 31902.1; Found: 31901.0

Example 11.9 and Example 11.10: Compound 09 and Compound 10 Compound 09

N{B-32}-[4-[[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]methyl]phenyl]methyl-SerA-32,GluA-31,ProA-30,AlaA-29,ThrA-28,SerA-27,GlyA-26,SerA-25,GluA-24,ThrA-23,ProA-22A-21ThrA-220,SerA-19,GluA-18,SerA-17,AlaA-16,ThrA-15,ProA-14,GluA-13,SerA-12,GlyA-11,ProA-10,GlyA-9,ThrA-8,SerA-7,ThrA-6,GluA-5,ProA-4,SerA-3,GluA-2,GlyA-1,SerB-32,GluB-31,ProB-30,AlaB-29,ThrB-28,SerB-27,GlyB-26,SerB-25,GluB-24,ThrB-23,ProB-22,GlyB-21,ThrB-20,SerB-19,GluB-18,SerB-17,AlaB-16,ThrB-15,ProB-14,GluB-13,SerB-12,GlyB-11,ProB-10,GlyB-9,ThrB-8,SerB-7,ThrB-6,GluB-5,ProB-4,SerB-3,GluB-2,GlyB-1[LeuA57,LeuA86,LeuB57,LeuB86],des-AsnA3,AsnB3-MIC-1

Compound 10:

N{A-32}-[4-[[[2-[2-[2-[[2-[2-[2-[[(4S)-4-carboxy-4-(17-carboxyheptadecanoylamino) butanoyl]amino]ethoxy]ethoxy]acetyl]amino]ethoxy]ethoxy]acetyl]amino]methyl]phenyl]methyl,N{B-32}-[4-[[[2-[2-[2-[[2-[2-[2-[[(4S)-4-carboxy-4-(17-carboxyheptadecanoylamino) butanoyl]amino]ethoxy]ethoxy]acetyl]amino]ethoxy]ethoxy]acetyl]amino]methyl]phenyl]methyl-SerA-32,GluA-31,ProA-30,AlaA-29,ThrA-28,SerA-27,GlyA-26,SerA-25,GluA-24,ThrA-23,ProA-22,GlyA-21,ThrA-20,SerA-19,GluA-18,SerA-17,AlaA-16,ThrA-15,ProA-14,GluA-13,SerA-12,GlyA-11,ProA-10,GlyA-9,ThrA-8,SerA-7,ThrA-6,GluA-5,ProA-4,SerA-3,GluA-2,GlyA-1,SerB-32,GluB-31,ProB-30,AlaB-29,ThrB-28,SerB-27,GlyB-26,SerB-25,GluB-24,ThrB-23,ProB-22,GlyB-21,ThrB-20,SerB-19,GluB-18,SerB-17,AlaB-16,ThrB-15,ProB-14,GluB-13,SerB-12,GlyB-11,ProB-10,GlyB-9,ThrB-8,SerB-7,ThrB-6,GluB-5,ProB-4,SerB-3,GluB-2,GlyB-1[LeuA57,LeuA86,LeuB57,LeuB86],des-AsnA3,AsnB3-MIC-1

(Formula 09)

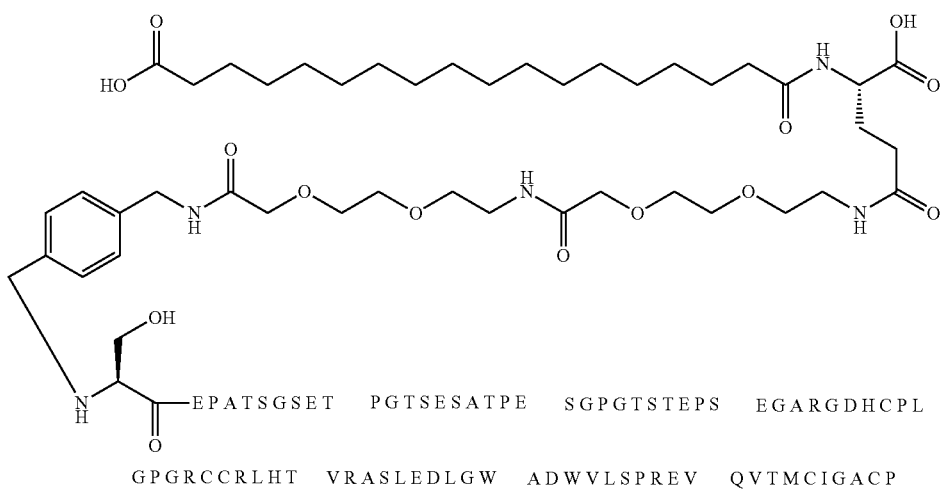

EPATSGSET PGTSESATPE SGPGTSTEPS EGARGDHCPL
GPGRCCRLHT VRASLEDLGW ADWVLSPREV QVTMCIGACP
SQFRAANLHA QIKTSLHRLK PDTVPAP

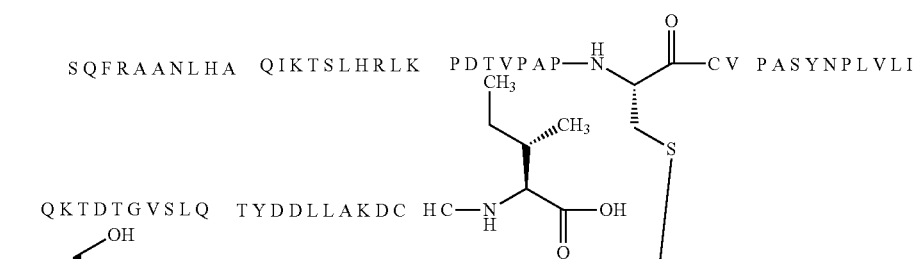

CV PASYNPLVLI

QKTDTGVSLQ TYDDLLAKDC HC

EPATSGSET PGTSESATPE SGPGTSTEPS EGARGDHCPL
GPGRCCRLHT VRASLEDLGW ADWVLSPREV QVTMCIGACP

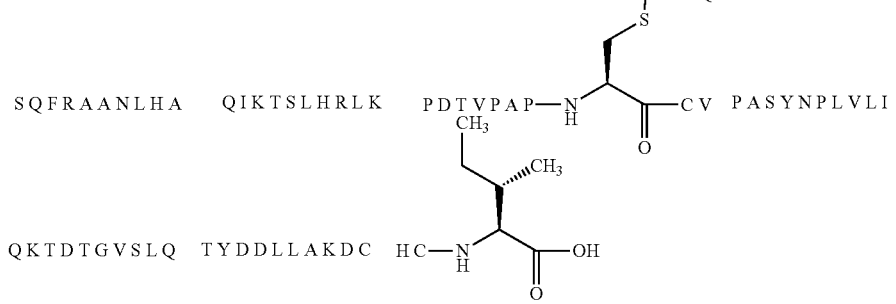

CV PASYNPLVLI

QKTDTGVSLQ TYDDLLAKDC HC (Formula 10)

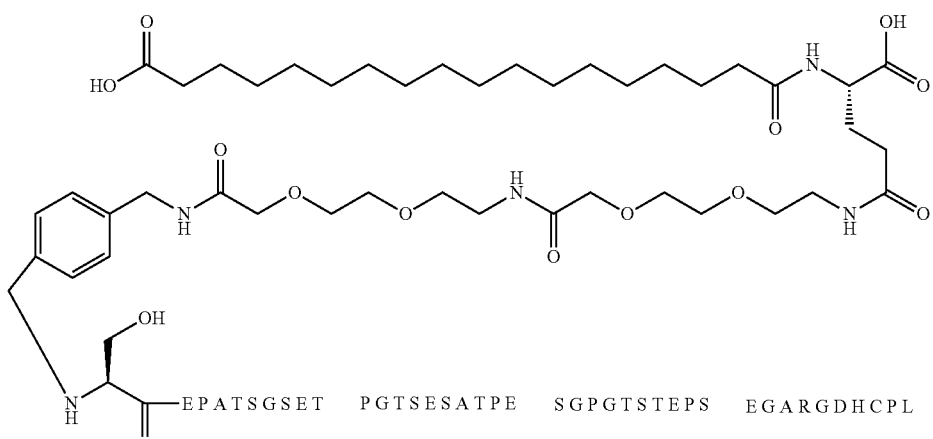

EPATSGSET PGTSESATPE SGPGTSTEPS EGARGDHCPL
GPGRCCRLHT VRASLEDLGW ADWVLSPREV QVTMCIGACP

SQFRAANLHA QIKTSLHRLK PDTVPAP—N(CH₃)—...—CV PASYNPLVLI

QKTDTGVSLQ TYDDLLAKDC HC—NH—...—OH

HN—...—EPATSGSET PGTSESATPE SGPGTSTEPS EGARGDHCPL

GPGRCCRLHT VRASLEDLGW ADWVLSPREV QVTMCIGACP

SQFRAANLHA QIKTSLHRLK PDTVPAP—N(CH₃)—...—CV PASYNPLVLI

QKTDTGVSLQ TYDDLLAKDC HC—NH—...—OH 20 mg of protractor (example 10.1, 8 equivalents) dissolved in 2 mL 40% Hydroxypropyl-beta-cyclodextrin was added to 75 mg of MIC-1 polypeptide with N-extension (SEQ ID NO: 164) in 40 mL PBS buffer, pH 7.4. 100 μL of borane pyridine complex (8M) was added. After 24h standing at room temperature 20 mg of the protractor and 100 μL of borane reagent were added again.

After 48h the mono and dialkylated protein mixture was purified on a C4 reverse phase column using a 10-50% ethanol/phosphate buffer pH 3.0 gradient. Yield ~19% monoalkylated protein (Compound 09) and 6% dialkylated protein (Compound 10) after purification.

Compound 09: Theoretical mass: 31073.0; Found: 31073.5

Compound 10: Theoretical mass: 31908.1; Found: 31908.5

Example 11.11: Compound 11

SerA-32,GluA-31,ProA-30,S{Beta}-[2-[2-[[2-[2-[2-[[2-[2-[2-[[(4S)-4-carboxy-4-(17-carboxyheptadecanoylamino) butanoyl]amino]ethoxy]ethoxy]acetyl]amino]ethoxy] ethoxy]acetyl]amino]ethylamino]-2-oxoethyl]CysA-29, ThrA-28,SerA-27,GlyA-26,SerA-25,GluA-24,ThrA-23, ProA-22,GlyA-21,ThrA-20,SerA-19,GluA-18,SerA-17, AlaA-16,ThrA-15,ProA-14,GluA-13,SerA-12,GlyA-11, ProA-10,GlyA-9,ThrA-8,SerA-7,ThrA-6,GluA-5,ProA-4, SerA-3,GluA-2,GlyA-1,SerB-32,GluB-31,ProB-30, S{Beta}-[2-[2-[[2-[2-[2-[[2-[2-[2-[[(4S)-4-carboxy-4-(17-carboxyheptadecanoylamino)butanoyl]amino]ethoxy] ethoxy]acetyl]amino]ethoxy]ethoxy]acetyl]amino] ethylamino]-2-oxoethyl]CysB-29,ThrB-28,SerB-27,GlyB-26,SerB-25,GluB-24,ThrB-23,ProB-22,GlyB-21,ThrB-20, SerB-19,GluB-18,SerB-17,AlaB-16,ThrB-15,ProB-14, GluB-13,SerB-12,GlyB-11,ProB-10,GlyB-9,ThrB-8,SerB-7,ThrB-6,GluB-5,ProB-4,SerB-3,GluB-2,GlyB-1[LeuA57, LeuA86,LeuB57,LeuB86],des-AsnA3,AsnB3-MIC-1

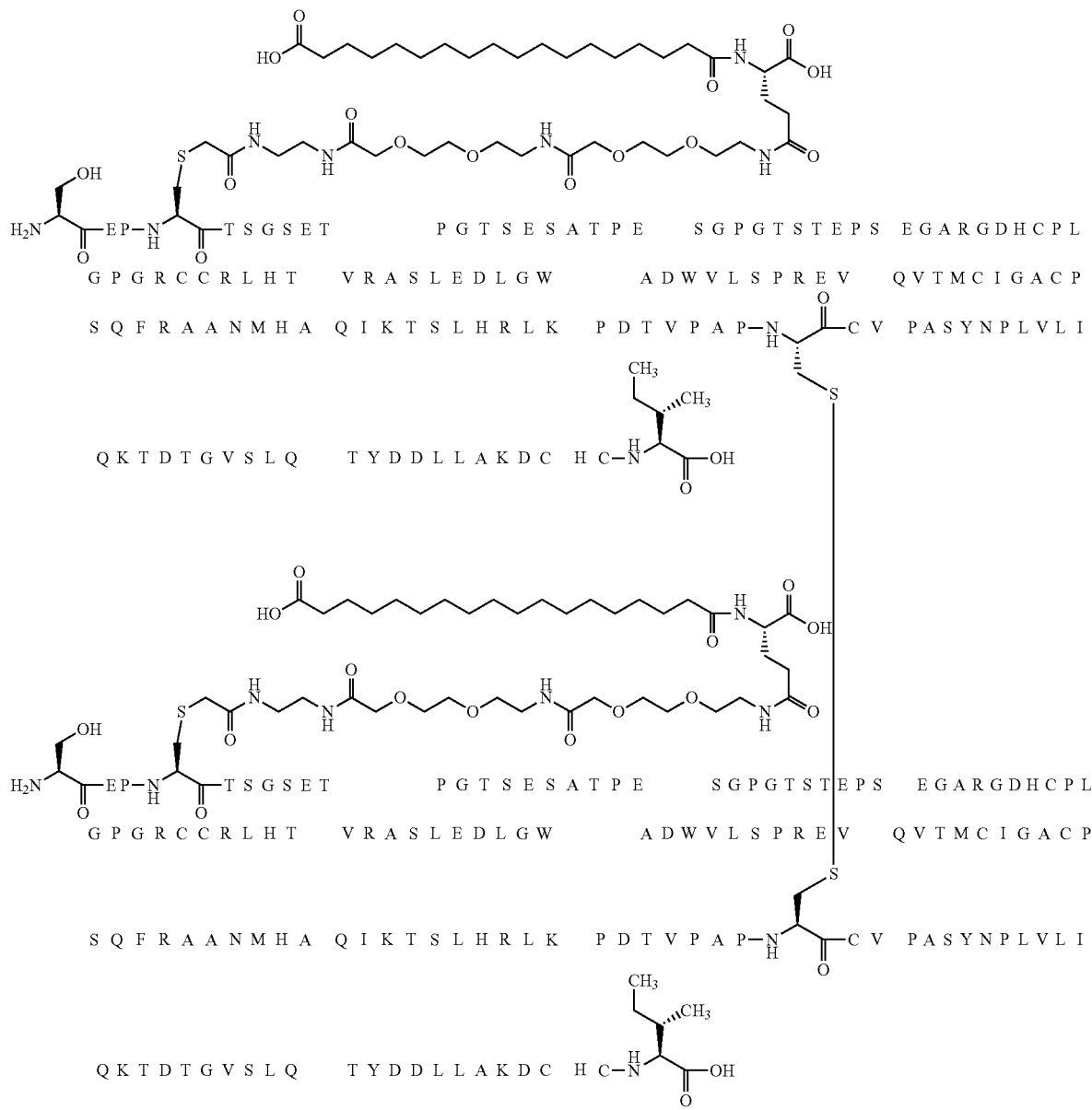

(Formula 11)

(SEQ ID NO: 290)

Compound 11 was prepared using the procedure described in example 11.1 using the protractor described in example 10.4 and MIC-1 polypeptide with N-extension (SEQ ID NO: 290).

Theoretical mass: 31934.1; Found: 31938.5.

Example 11.12 and Example 11.13: Compound 12 and Compound 13

Compound 12:

N{A-9}-[4-[[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]methyl]phenyl]methyl,N{B-9}-[4-[[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]methyl]phenyl]methyl-GluA-9,GluA-8,AlaA-7,GluA-6,AlaA-5,AspA-4,AspA-3,AspA-2,AspA-1,GluB-9,GluB-8,AlaB-7,GluB-6,AlaB-5,AspB-4,AspB-3,AspB-2,AspB-1[LysA1,GluA2,SerA3,LysB1,GluB2,SerB3]-MIC-1

Compound 13:

N{B-9}-[4-[[[2-[2-[2-[[2-[2-[2-[[(4S)-4-carboxy-4-(17-carboxyheptadecanoylamino) butanoyl]amino]ethoxy]ethoxy]acetyl]amino]ethoxy]ethoxy]acetyl]amino]methyl]phenyl]methyl-GluA-9,GluA-8,AlaA-7,GluA-6,AlaA-5,AspA-4,AspA-3,AspA-2,AspA-1,GluB-9,GluB-8,AlaB-7,GluB-6,AlaB-5,AspB-4,AspB-3,AspB-2,AspB-1 [LysA1, GluA2,SerA3,LysB1,GluB2,SerB3]-MIC-1

(Formula 12)
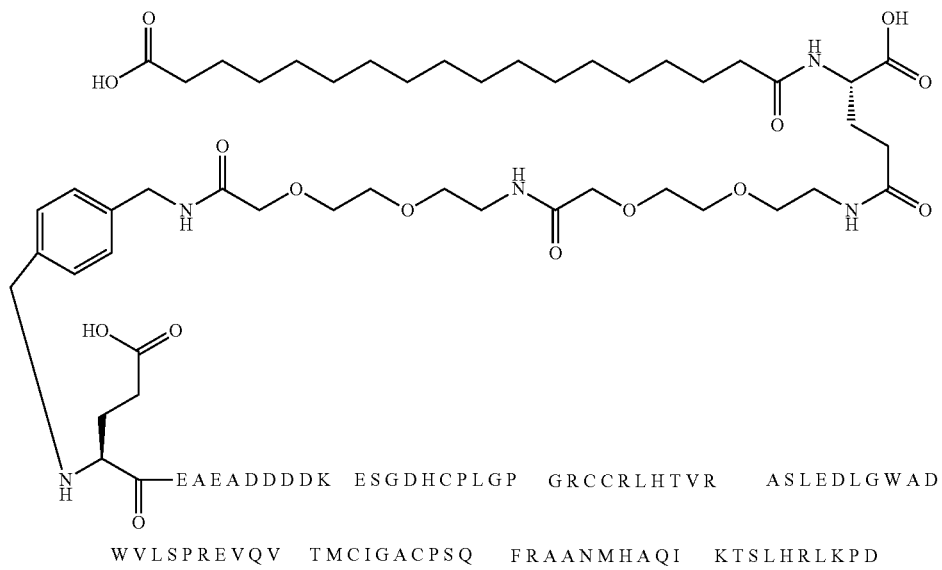
EAEADDDDK ESGDHCPLGP GRCCRLHTVR ASLEDLGWAD
WVLSPREVQV TMCIGACPSQ FRAANMHAQI KTSLHRLKPD
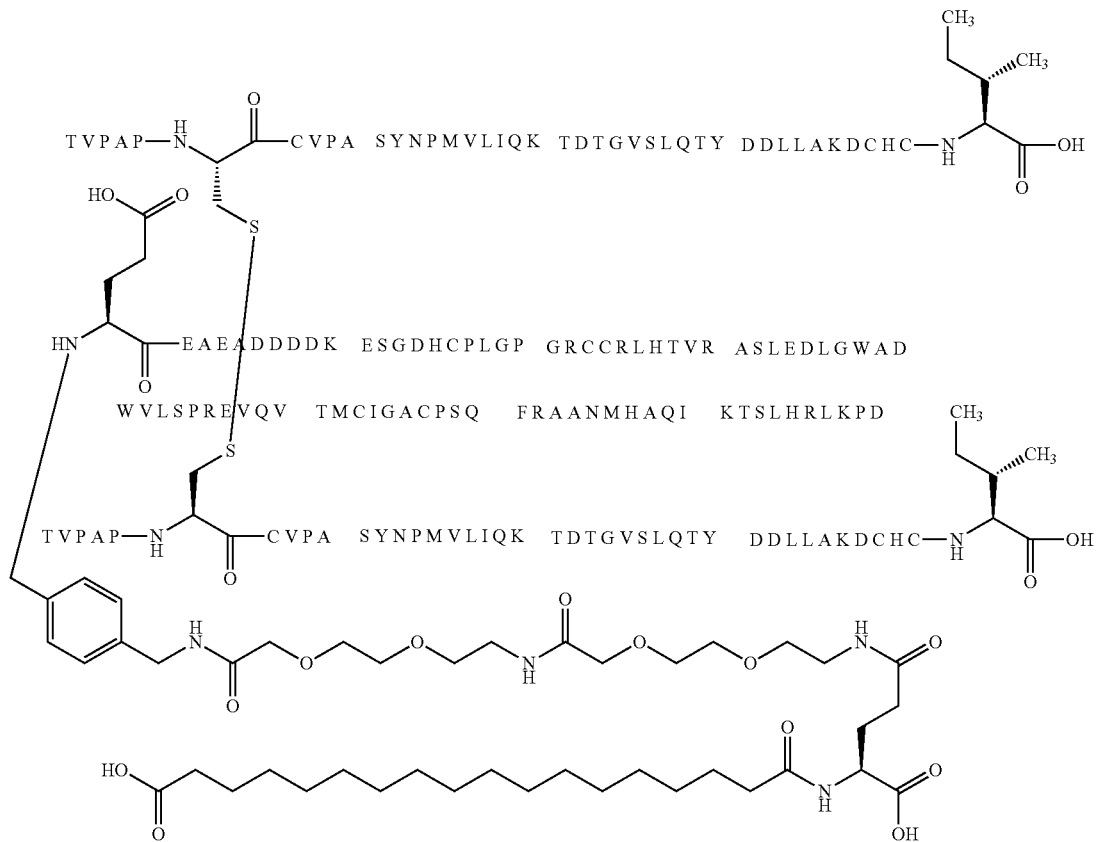

(Formula 13)

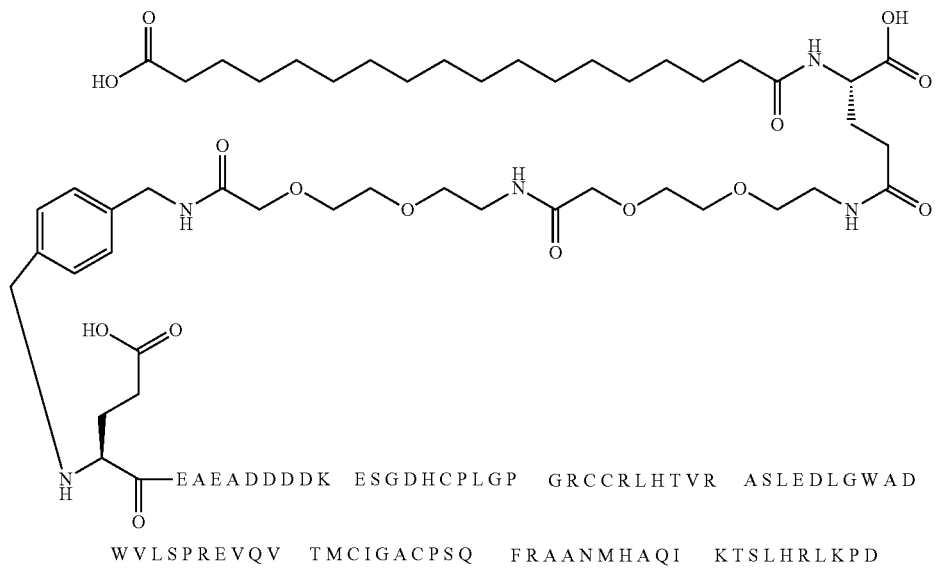

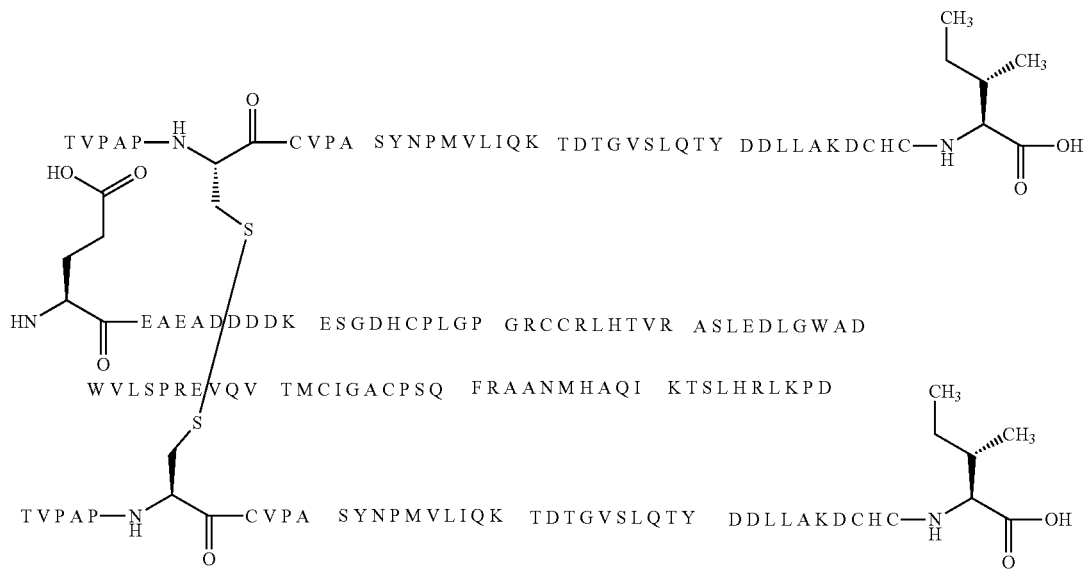

Compounds 12 and 13 were prepared using the procedure described in example 11.10 using the protractor described in example 10.1 and MIC-1 polypeptide with N-extension (SEQ ID NO: 311).

Compound 12: Theoretical mass: 28212.3; Found: 28211.9

Compound 13: Theoretical mass: 27377.2; Found: 27376.8

Example 11.14: Compound 14

N{A-9}-[4-[[[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]amino]methyl]phenyl]methyl,N {B-9}-[4-[[[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]amino]methyl]phenyl]methyl-GluA-9,GluA-8,AlaA-7,GluA-6,AlaA-5,AspA-4,AspA-3,AspA-2,AspA-1,GluB-9,GluB-8,AlaB-7,GluB-6,AlaB-5,AspB-4,AspB-3,AspB-2,AspB-1[LysA1,GluA2,SerA3,LysB1,GluB2,SerB3]-MIC-1

(Formula 14)

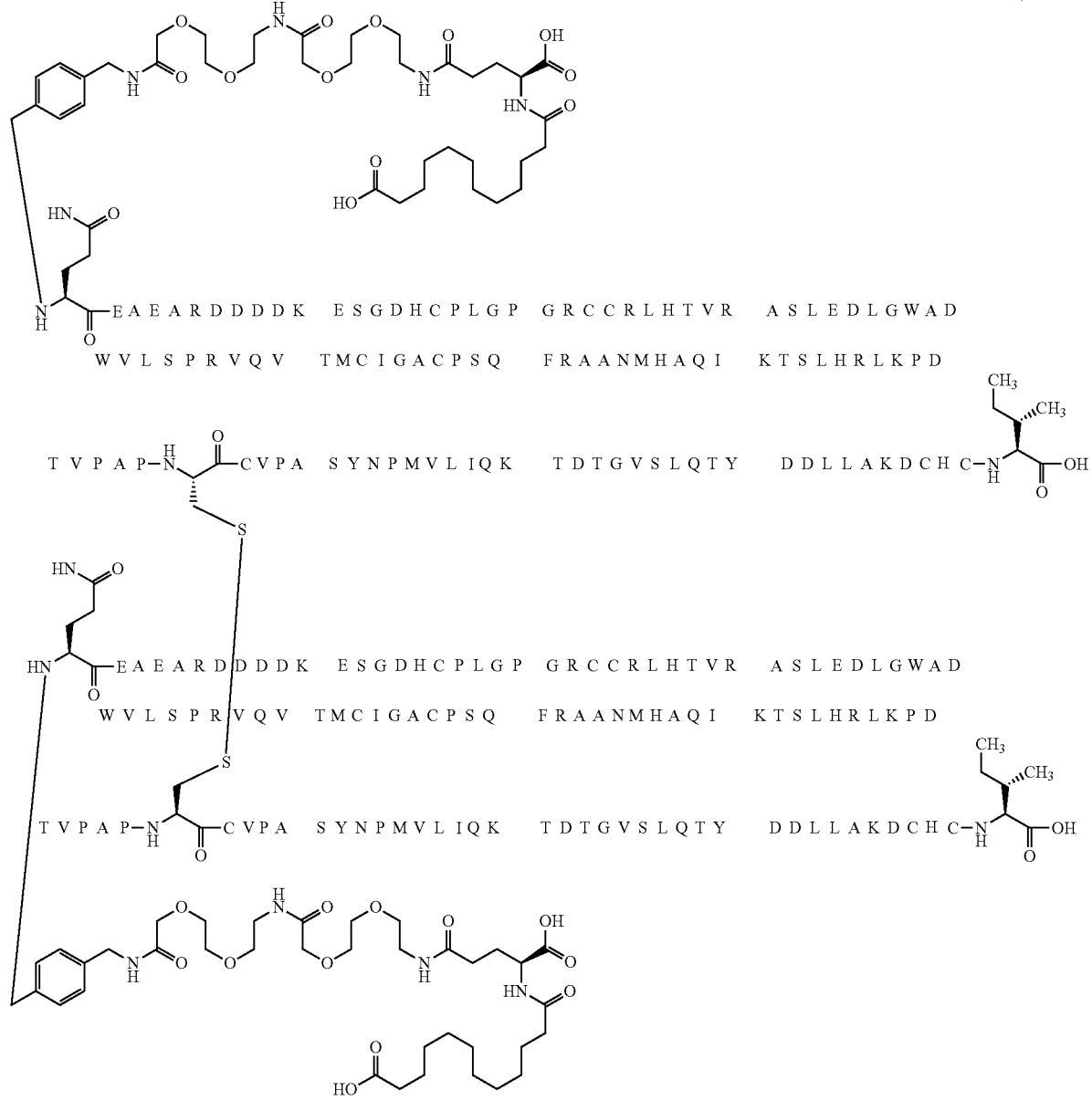

(SEQ ID NO: 311)

Compound 14 was prepared using the procedure described in example 11.10 using the protractor described in example 10.5 and MIC-1 polypeptide with N-extension (SEQ ID NO: 311).

Theoretical mass: 28043.9; Found: 28043.6.

Example 11.15 and Example 11.16: Compound 15 and Compound 16

Compound 15:
N{B-32}-[4-[[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]methyl]phenyl]methyl-SerA-32,GluA-31,ProA-30,AlaA-29,ThrA-28,SerA-27,GlyA-26,SerA-25,GluA-24,ThrA-23,ProA-22 A-21ThrA-220,SerA-19,GluA-18,SerA-17,AlaA-16,ThrA-15,ProA-14,GluA-13,SerA-12,GlyA-11,ProA-10,GlyA-9,ThrA-8,SerA-7,ThrA-6,GluA-5,ProA-4,SerA-3,GluA-2,GlyA-1,SerB-32,GluB-31,ProB-30,AlaB-29,ThrB-28,SerB-27,GlyB-26,SerB-25,GluB-24,ThrB-23,ProB-22,GlyB-21,ThrB-20,SerB-19,GluB-18,SerB-17,AlaB-16,ThrB-15,ProB-14,GluB-13,SerB-12,GlyB-11,ProB-10,GlyB-9,ThrB-8,SerB-7,ThrB-6,GluB-5,ProB-4,SerB-3,GluB-2,GlyB-1[LeuA57,ArgA69, LeuA86,ArgA91,ArgA107, LeuB57,ArgB69, LeuB86,ArgB91,Arg B 107],des-AsnA3,AsnB3-MIC-1

Compound 16:
N{A-32}-[4-[[[2-[2-[2-[[2-[2-[2-[[(4S)-4-carboxy-4-(17-carboxyheptadecanoylamino) butanoyl]amino]ethoxy]ethoxy]acetyl]amino]ethoxy]ethoxy]acetyl]amino]methyl]phenyl]methyl,N{B-32}-[4-[[[2-[2-[2-[[2-[2-[2-[[(4S)-4-carboxy-4-(17-carboxyheptadecanoylamino) butanoyl]

amino]ethoxy]ethoxy]acetyl]amino]ethoxy]ethoxy]acetyl]amino]methyl]phenyl]methyl-SerA-32,GluA-31,ProA-30,AlaA-29,ThrA-28,SerA-27,GlyA-26,SerA-25,GluA-24,ThrA-23,ProA-22 A-21ThrA-220,SerA-19,GluA-18,SerA-17,AlaA-16,ThrA-15,ProA-14,GluA-13,SerA-12,GlyA-11,ProA-10,GlyA-9,ThrA-8,SerA-7,ThrA-6,GluA-5,ProA-4,SerA-3,GluA-2,GlyA-1,SerB-32,GluB-31,ProB-30,AlaB-29,ThrB-28,SerB-27,GlyB-26,SerB-25,GluB-24,ThrB-23,ProB-22,GlyB-21,ThrB-20,SerB-19,GluB-18,SerB-17,AlaB-16,ThrB-15,ProB-14,GluB-13,SerB-12,GlyB-11,ProB-10,GlyB-9,ThrB-8,SerB-7,ThrB-6,GluB-5,ProB-4,SerB-3,GluB-2,GlyB-1 [LeuA57,ArgA69,LeuA86,ArgA91,ArgA107,LeuB57,ArgB69,LeuB86,ArgB91,ArgB107],des-AsnA3,AsnB3-MIC-1

(Formula 15)

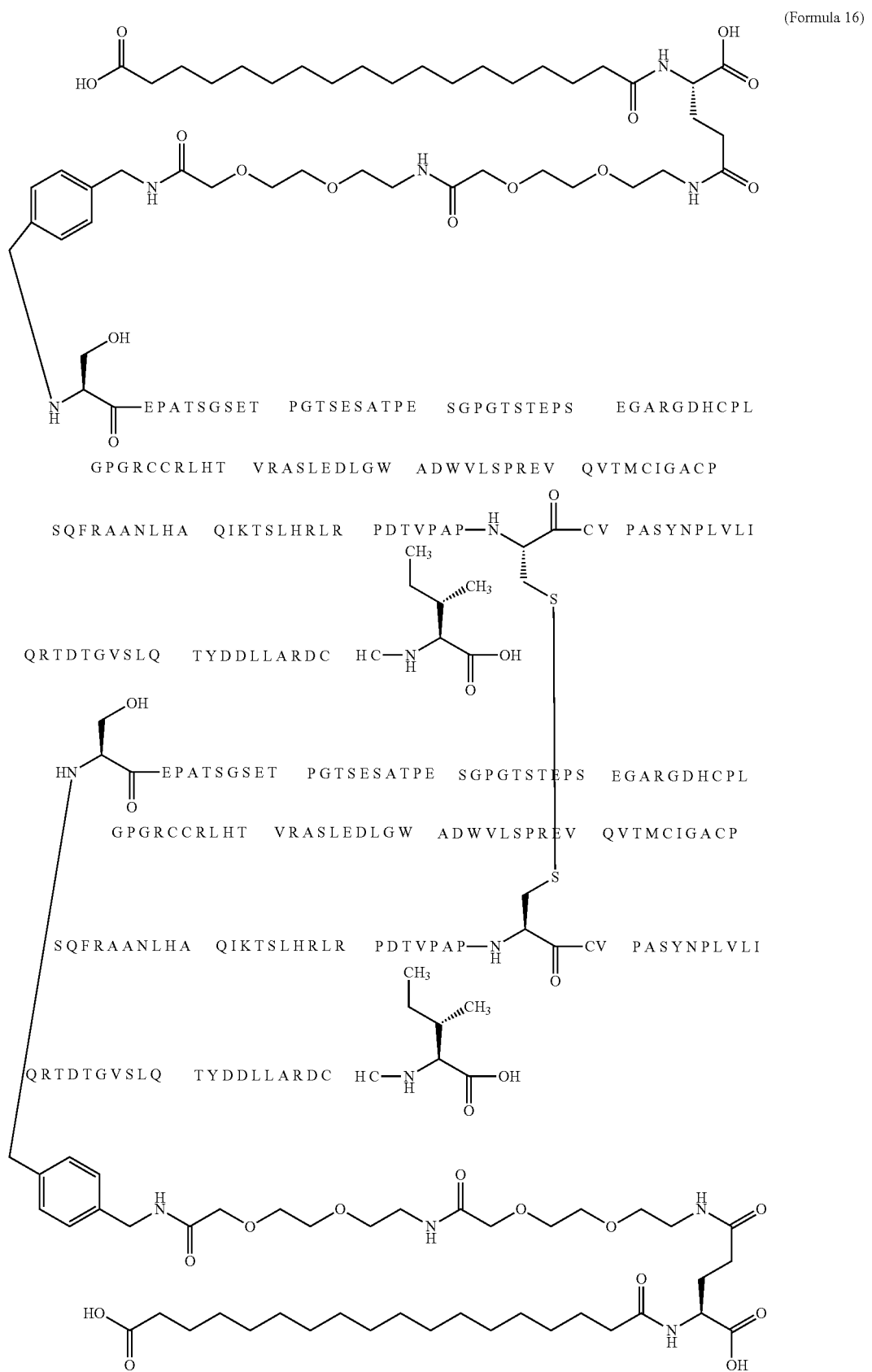

Compounds 15 and 16 were prepared using the procedure described in example 11.10 using the protractor described in example 10.1 and MIC-1 polypeptide with N-extension (SEQ ID NO: 312).

Compounds 15: Theoretical mass: 31241.1; Found: 31242.0.

Compounds 16: Theoretical mass: 32076.0; Found: 32075.0.

Example 11.17: Compound 17

SerA-32,GluA-31,ProA-30,S{Beta}-[2-[2-[[2-[2-[2-[[2-[2-[2-[[(4S)-4-carboxy-4-(16-sulfohexadecanoylamino)butanoyl]amino]ethoxy]ethoxy]acetyl]amino]ethoxy]ethoxy] acetyl]amino]ethylamino]-2-oxoethyl]CysA-29,ThrA-28, SerA-27,GlyA-26,SerA-25,GluA-24,ThrA-23,ProA-22, GlyA-21,ThrA-20,SerA-19,GluA-18,SerA-17,AlaA-16, ThrA-15,ProA-14,GluA-13,SerA-12,GlyA-11,ProA-10, GlyA-9,ThrA-8,SerA-7,ThrA-6,GluA-5,ProA-4,SerA-3, GluA-2,GlyA-1,SerB-32,GluB-31,ProB-30,S{Beta}-[2-[2-[[2-[2-[2-[[2-[2-[2-[[(4S)-4-carboxy-4-(16-sulfohexadecanoylamino)butanoyl]amino]ethoxy]ethoxy] acetyl]amino]ethoxy]ethoxy]acetyl]amino]ethylamino]-2-oxoethyl]CysB-29,ThrB-28,SerB-27,GlyB-26,SerB-25, GluB-24,ThrB-23,ProB-22,GlyB-21,ThrB-20,SerB-19,G u B-18,SerB-17,AlaB-16,ThrB-15,ProB-14,GluB-13,SerB-12,GlyB-11,ProB-10,GlyB-9,ThrB-8,SerB-7,ThrB-6,GluB-5,ProB-4,SerB-3,GluB-2,GlyB-1des-AsnA3,AsnB3-MIC-1

(Formula 17)

(SEQ ID NO: 288)

4 mL 2M TRIS buffer was added to 176 mg of MIC-1 polypeptide with N-extension (SEQ ID NO: 288) in 15 mM citric acid/450 mM sodium chloride, pH 3, 2.2 mg/mL. The protractor described in Example 10.6 was dissolved in saturated sodium hydrogen carbonate to 20 mg/L, 8 equivalents. The protractor was then added to the polypeptide solution. 12.4 mg of bis(p-sulfonatophenyl)phenylphosphine, kalium salt dihydrate, Sigma-Aldrich 698539 dissolved in water (0.1 mg/mL) were added and the reaction mixture was gently shaken for 10s. After 6 hours the compound was purified on a C4 column using a C4 reverse phase column using a 10-50% ethanol/phosphate buffer pH 3.0.

Theoretical mass: 32050.3; Found: 32050.0.

Example 11.18: Compound 18

SerA-32,GluA-31,ProA-30,S{Beta}-[2-[[(5S)-5-carboxy-5-[[2-[2-[2-[[2-[2-[2-[4-[17-(1H-tetrazol-5-yl)heptadecanoylsulfamoyl]butanoylamino]ethoxy]ethoxy]acetyl]amino]ethoxy]ethoxy]acetyl]amino]pentyl]amino]-2-oxoethyl]CysA-29,ThrA-28,SerA-27,GlyA-26,SerA-25, GluA-24,ThrA-23,ProA-22,GlyA-21,ThrA-20,SerA-19, GluA-18,SerA-17,AlaA-16,ThrA-15,ProA-14,GluA-13, SerA-12,GlyA-11,ProA-10,GlyA-9,ThrA-8,SerA-7,ThrA-6,GluA-5,ProA-4,SerA-3,GluA-2,GlyA-1,SerB-32,GluB-31,ProB-30,S{Beta}-[2-[[(5S)-5-carboxy-5-[[2-[2-[2-[[2-[2-[2-[4-[17-(1H-tetrazol-5-yl)heptadecanoylsulfamoyl]butanoylamino]ethoxy]ethoxy]acetyl]amino]ethoxy]ethoxy]acetyl]amino]pentyl]amino]-2-oxoethyl]CysB-29, ThrB-28,SerB-27,GlyB-26,SerB-25,GluB-24,ThrB-23, ProB-22,GlyB-21,ThrB-20,SerB-19,G u B-18,SerB-17, AlaB-16,ThrB-15,ProB-14,GluB-13,SerB-12,GlyB-11, ProB-10,GlyB-9,ThrB-8,SerB-7,ThrB-6,GluB-5,ProB-4, SerB-3,GluB-2,GlyB-1des-AsnA3,AsnB3-MIC-1

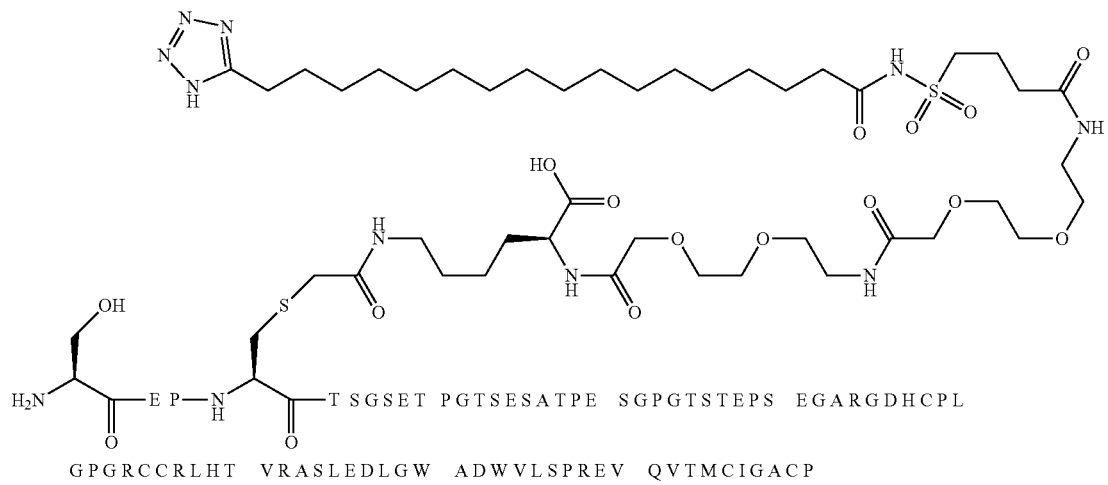

(Formula 18)

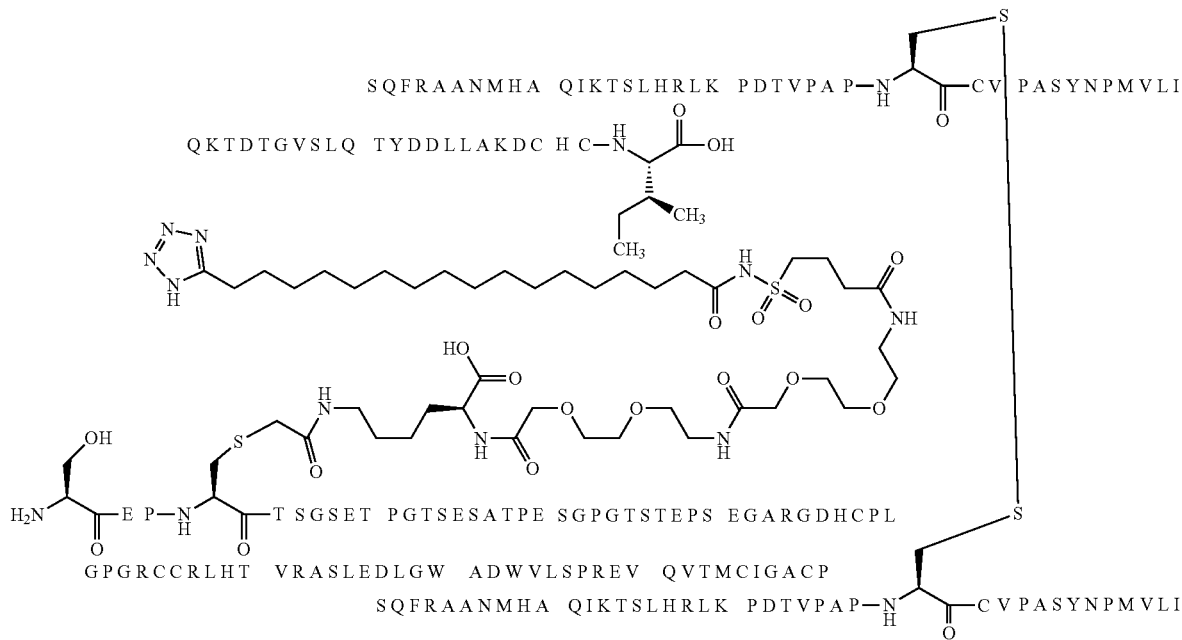

QKTDTGVSLQ TYDDLLAKDC 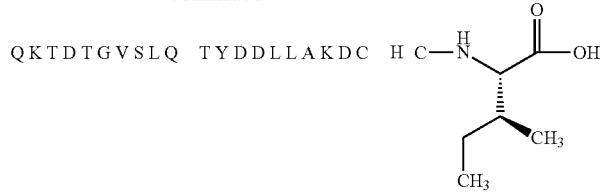

(SEQ ID NO: 288)

Compounds 18 was prepared using the procedure described in Example 11.17 using the 5 protractor described in Example 10.7 and MIC-1 polypeptide with N-extension (SEQ ID NO: 288).

Theoretical mass: 32266.6; Found: 32266.0.

Example 11.19: Compound 19

SerA-32,GluA-31,ProA-30,S{Beta}-[2-[[(1S)-1-carboxy-5-[[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]amino]pentyl]amino]-2-oxoethyl]CysA-29,ThrA-28,SerA-27,GlyA-26, SerA-25,GluA-24,ThrA-23,ProA-22,GlyA-21,ThrA-20, SerA-19,GluA-18,SerA-17,AlaA-16,ThrA-15,ProA-14, GluA-13,SerA-12,GlyA-11,ProA-10,GlyA-9,ThrA-8,SerA-7,ThrA-6,GluA-5,ProA-4,SerA-3,GluA-2,GlyA-1,SerB-32, GluB-31,ProB-30,S{Beta}-[2-[[(1S)-1-carboxy-5-[[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]amino]pentyl]amino]-2-oxoethyl]CysB-29,ThrB-28,SerB-27,GlyB-26,SerB-25, GluB-24,ThrB-23,ProB-22,GlyB-21,ThrB-20,SerB-19, GluB-18,SerB-17,AlaB-16,ThrB-15,ProB-14,GluB-13, SerB-12,GlyB-11,ProB-10,GlyB-9,ThrB-8,SerB-7,ThrB-6, GluB-5,ProB-4,SerB-3,GluB-2,GlyB-1des-AsnA3,AsnB3-MIC-1

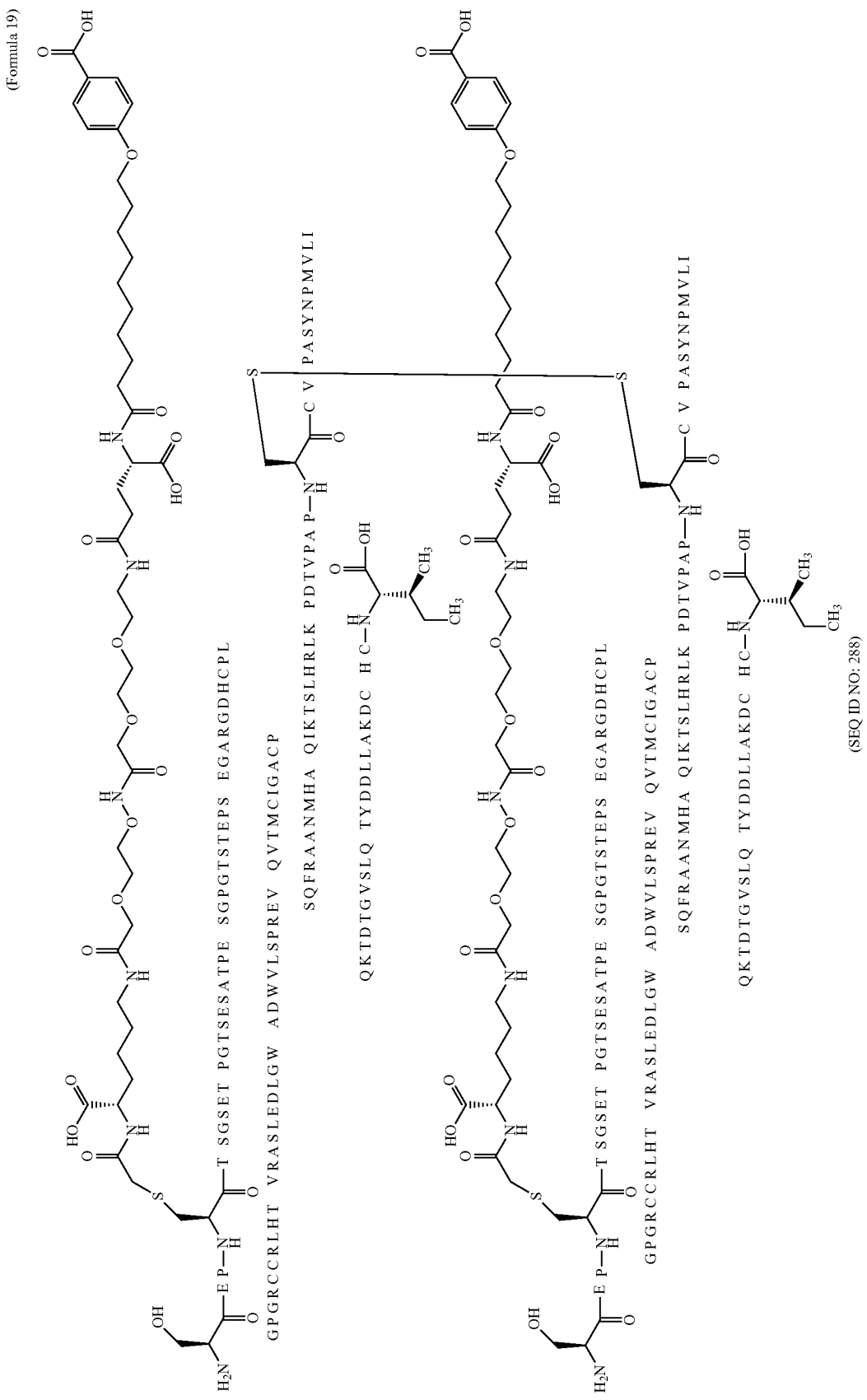

Compounds 19 was prepared using the procedure described in Example 11.17 using the protractor described in Example 10.8 and MIC-1 polypeptide with N-extension (SEQ ID NO: 288).

Theoretical mass: 32166.3; Found: 32166.0.

Example 11.20: Compound 20

SerA-32,GluA-31,ProA-30,S{Beta}-[2-[[(1S)-1-carboxy-5-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]eth oxy]acetyl]amino]pentyl]amino]-2-oxoethyl]CysA-29,ThrA-28,SerA-27,GlyA-26,SerA-25,GluA-24,ThrA-23,ProA-22,GlyA-21,ThrA-20,SerA-19,GluA-18,SerA-17,AlaA-16,ThrA-15,ProA-14,GluA-13,SerA-12,GlyA-11,ProA-10,GlyA-9,ThrA-8,SerA-7,ThrA-6,GluA-5,ProA-4,SerA-3,GluA-2,GlyA-1,SerB-32,GluB-31,ProB-30,S{Beta}-[2-[[(1S)-1-carboxy-5-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]eth oxy]acetyl]amino]pentyl]amino]-2-oxoethyl]CysB-29,ThrB-28,SerB-27,GlyB-26,SerB-25,GluB-24,ThrB-23,ProB-22,GlyB-21,ThrB-20,SerB-19,GluB-18,SerB-17,AlaB-16,ThrB-15,ProB-14,GluB-13,SerB-12,GlyB-11,ProB-10,GlyB-9,ThrB-8,SerB-7,ThrB-6,GluB-5,ProB-4,SerB-3,GluB-2,GlyB-1des-AsnA3,AsnB3-MIC-1

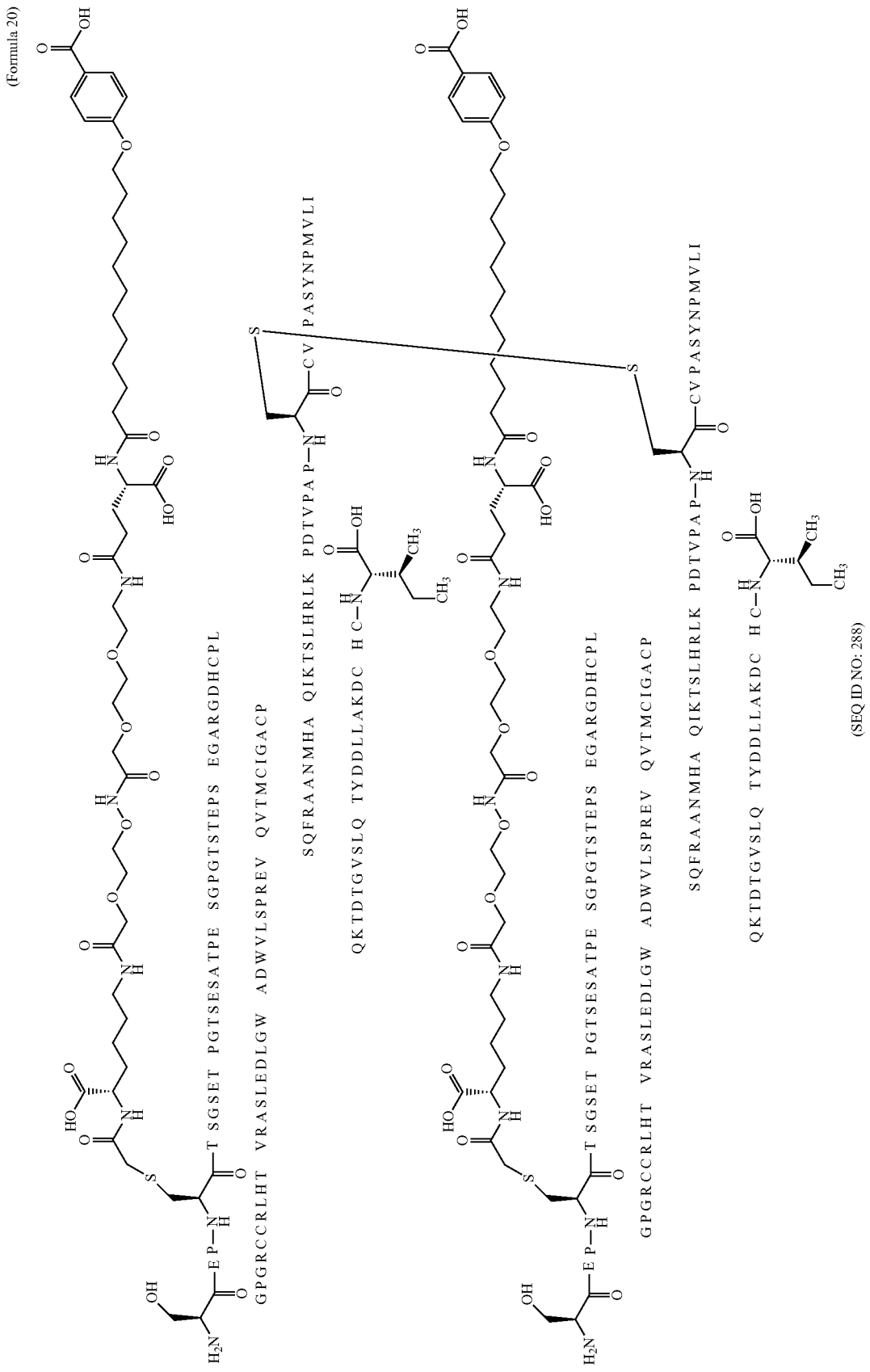

Compounds 20 was prepared using the procedure described in Example 11.17 using the protractor described in Example 10.9 and MIC-1 polypeptide with N-extension (SEQ ID NO: 288).

Theoretical mass: 32222.4; Found: 32222.0.

Example 11.21: Compound 21

SerA-32,GluA-31,ProA-30,S{Beta}-[2-[2-[[2-[2-[2-[[2-[2-[2-[[(4S)-4-carboxy-4-[16-(1H-tetrazol-5-yl)hexadecanoylamino]butanoyl]amino]ethoxy]ethoxy]acetyl]amino] ethoxy]ethoxy]acetyl]amino]ethylamino]-2-oxoethyl] CysA-29,ThrA-28,SerA-27,GlyA-26,SerA-25,GluA-24, ThrA-23,ProA-22,GlyA-21,ThrA-20,SerA-19,GluA-18, SerA-17,AlaA-16,ThrA-15,ProA-14,GluA-13,SerA-12, GlyA-11,ProA-10,GlyA-9,ThrA-8,SerA-7,ThrA-6,GluA-5, ProA-4,SerA-3,GluA-2,GlyA-1,SerB-32,GluB-31,ProB-30, S{Beta}-[2-[2-[[2-[2-[2-[[2-[2-[2-[[(4S)-4-ar-4-carboxy-4-[16-(1H-tetrazol-5-yl)hexadecanoylamino]butanoyl]amino] ethoxy]ethoxy]acetyl]amino]ethoxy]ethoxy]acetyl]amino] ethylamino]-2-oxoethyl]CysB-29,ThrB-28,SerB-27,GlyB-26,SerB-25,GluB-24,ThrB-23,ProB-22,GlyB-21,ThrB-20, SerB-19,GluB-18,SerB-17,AlaB-16,ThrB-15,ProB-14, GluB-13,SerB-12,GlyB-11,ProB-10,GlyB-9,ThrB-8,SerB-7,ThrB-6,GluB-5,ProB-4,SerB-3,GluB-2,GlyB-1des-AsnA3,AsnB3-MIC-1

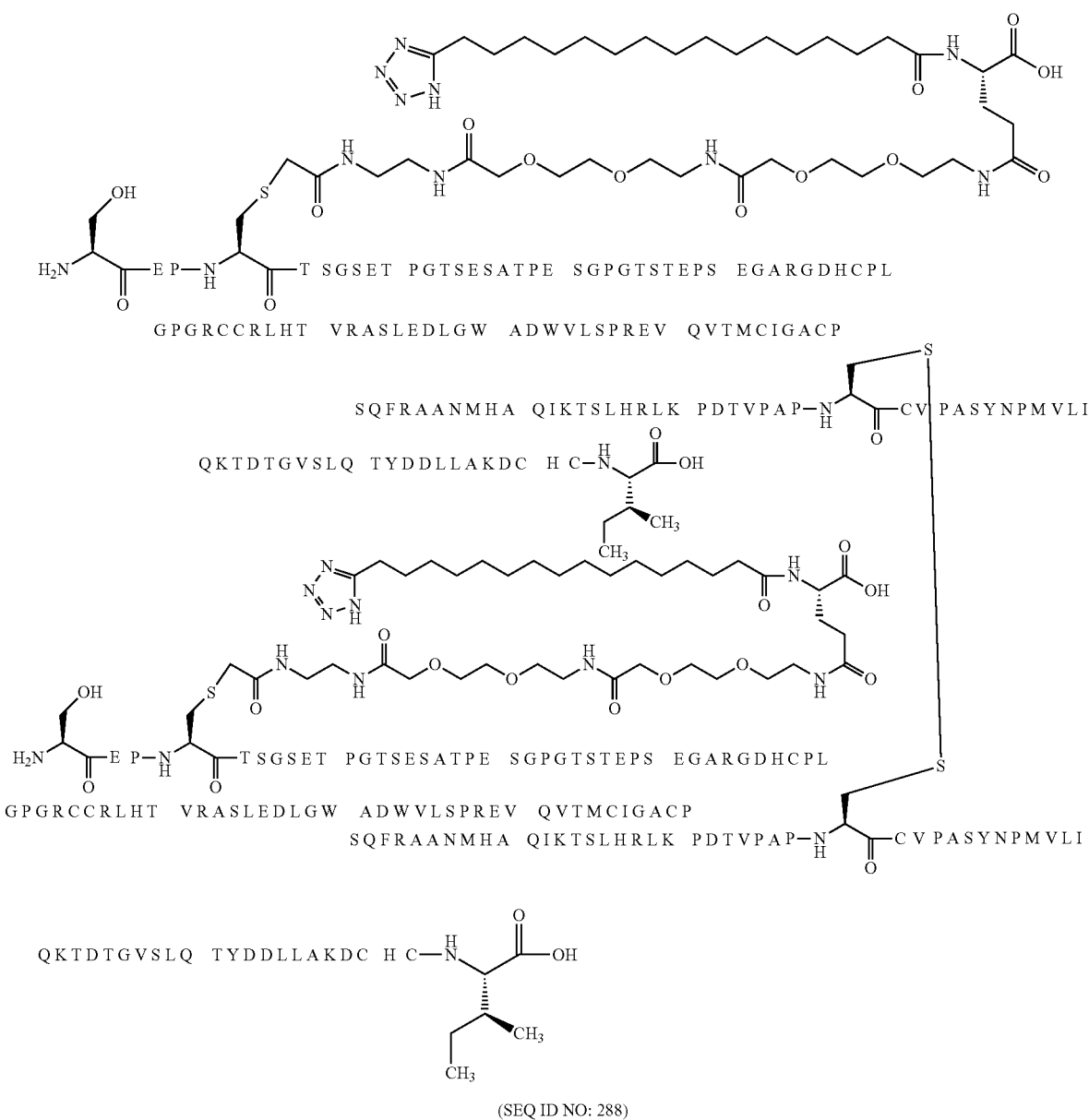

(Formula 21)

(SEQ ID NO: 288)

Compounds 21 was prepared using the procedure described in Example 11.17 using the protractor described in Example 10.10 and MIC-1 polypeptide with N-extension (SEQ ID NO: 288).

Theoretical mass: 32026.3; Found: 32026.0.

The structures of Compounds 01-21 are summarized in Table 18.

TABLE 18

The structures of MIC-1 compounds

| Compound No | N-extension | MIC-1 polypeptide | protractor |
|---|---|---|---|
| Compound 01 | SEPCTSGSETPGTSESATPESGPGTSTEPSEG (SEQ ID NO: 225) | MIC-1, des-N3 (SEQ ID NO: 2) | Formula D (C18) |
| Compound 02 | SEPATCGSETPGTSESATPESGPGTSTEPSEG (SEQ ID NO: 226) | MIC-1, des-N3 (SEQ ID NO: 2) | Formula D (C18) |
| Compound 03 | SEPATCGSETPGTSESATPESGPGTSTEPSEG (SEQ ID NO: 226) | MIC-1, des-N3 (SEQ ID NO: 2) | Formula B (C16) |
| Compound 04 | SEPATCGSETPGTSESATPESGPGTSTEPSEG (SEQ ID NO: 226) | MIC-1, des-N3 (SEQ ID NO: 2) | Formula C (C14) |
| Compound 05 | SEPATSCSETPGTSESATPESGPGTSTEPSEG (SEQ ID NO: 227) | MIC-1, des-N3, M57L, M86L (SEQ ID NO: 222) | Formula D (C18) |
| Compound 06 | SEPATSGCETPGTSESATPESGPGTSTEPSEG (SEQ ID NO: 230) | MIC-1, des-N3, M57L, M86L (SEQ ID NO: 222) | Formula D (C18) |
| Compound 07 | SEPATSGSETPGTSESACPESGPGTSTEPSEG (SEQ ID NO: 235) | MIC-1, des-N3, M57L, M86L (SEQ ID NO: 222) | Formula D (C18) |
| Compound 08 | SEPATSGSETPGTSESATPESGPGTSTEPCEG (SEQ ID NO: 239) | MIC-1, des-N3, M57L, M86L (SEQ ID NO: 222) | Formula D (C18) |
| Compound 09 | SEPATSGSETPGTSESATPESGPGTSTEPSEG (SEQ ID NO: 71) | MIC-1, des-N3, M57L, M86L (SEQ ID NO: 222) | Formula A (C18)* |
| Compound 10 | SEPATSGSETPGTSESATPESGPGTSTEPSEG (SEQ ID NO: 71) | MIC-1, des-N3, M57L, M86L (SEQ ID NO: 222) | Formula A (C18) |
| Compound 11 | SEPCTSGSETPGTSESATPESGPGTSTEPSEG (SEQ ID NO: 225) | MIC-1, des-N3, M57L, M86L (SEQ ID NO: 222) | Formula D (C18) |
| Compound 12 | EEAEADDDDK (SEQ ID NO: 313) | MIC-1, des-A1, R2E, N3S | Formula D (C18) |
| Compound 13 | EEAEADDDDK (SEQ ID NO: 313) | MIC-1, des-A1, R2E, N3S (SEQ ID NO: 314) | Formula D (C18)* |
| Compound 14 | EEAEADDDDK (SEQ ID NO: 313) | MIC-1, des-A1, R2E, N3S (SEQ ID NO: 314) | Formula E (C12) |
| Compound 15 | SEPATSGSETPGTSESATPESGPGTSTEPSEG (SEQ ID NO: 71) | MIC-1, del-N3, M57L, M86L, K69R, K107R, K91R (SEQ ID NO: 315) | Formula A (C18)* |

TABLE 18-continued

The structures of MIC-1 compounds

| Compound No | N-extension | MIC-1 polypeptide | protractor |
|---|---|---|---|
| Compound 16 | SEPATSGSETPGTSE SATPESGPGTSTEPS EG (SEQ ID NO: 71) | MIC-1, del-N3, M57L, M86L, K69R, K107R, K91R (SEQ ID NO: 315) | Formula A (C18) |
| Compound 17 | SEPCTSGSETPGTSE SATPESGPGTSTEPS EG (SEQ ID NO: 225) | MIC-1, des-N3 (SEQ ID NO: 2) | Formula F |
| Compound 18 | SEPCTSGSETPGTSE SATPESGPGTSTEPS EG (SEQ ID NO: 225) | MIC-1, des-N3 (SEQ ID NO: 2) | Formula G |
| Compound 19 | SEPCTSGSETPGTSE SATPESGPGTSTEPS EG (SEQ ID NO: 225) | MIC-1, des-N3 (SEQ ID NO: 2) | Formula H |
| Compound 20 | SEPCTSGSETPGTSE SATPESGPGTSTEPS EG (SEQ ID NO: 225) | MIC-1, des-N3 (SEQ ID NO: 2) | Formula K |
| Compound 21 | SEPCTSGSETPGTSE SATPESGPGTSTEPS EG (SEQ ID NO: 225) | MIC-1, des-N3 (SEQ ID NO: 2) | Formula J |

Note:
*means only one protractor is attached to Compound 09, Compound 13 or Compound 15, i.e. Compound 09, Compound 13 or Compound 15 as a dimer has only one protractor attached to one of its two N-terminal extensions. For the other Compounds, one protractor is attached to each of the two N-terminal extensions of the dimer, i.e. two protractors per dimer Compound.

Example 12: Solubility of MIC-1 Compounds

Samples of MIC-1 compounds was prepared in PBS buffer pH 7.4 followed by an up-concentrating the samples to above 35 mg/ml.

MIC-1 compound samples in PBS were concentrated on a Vivaspin 20 10 kDa MWCO (Sartorius) according to the description in the Vivaspin manual. A Heraus Multifuge X3R centrifuge equipped with swinging-bucket rotor (Thermo Scientific) was used at 4000 rpm (3310×g) to concentrate the MIC-1 compound samples. The concentration was subsequently determined by measuring UV at 280 nm on a Nanodrop 2000 (Thermo Scientific). The measured concentrations are presented in Table 19.

TABLE 19

The solubility of MIC-1 compounds

| MIC-1 compounds | Solubility (mg/ml) |
|---|---|
| Compound 03 | 43 |
| Compound 05 | 36 |
| Compound 01 | 32 |
| Compound 07 | 35 |
| Compound 17 | 41 |
| Compound 19 | 37 |
| Compound 20 | 39 |
| Compound 21 | 31 |

It can be seen that attaching various protractors does not impact the improved solubility obtained by adding an N-terminal amino acid extension to a MIC-1 polypeptide.

Example 13: In Vitro Potency and Binding Activity Assay of MIC-1 Compounds with Protractors Cell Line The stable cell line BHK21-hGFRAL-IRES-hRET was generated at Novo Nordisk with the addition of a vector with the Serum Response Element (SRE) in front of the luciferase reporter (See Example 5). Sequence for human GFRAL and human RET was obtained at Uniprot: UniProtKB—Q6UXV0 (GFRAL_HUMAN) and UniProtKB—P07949 (RET_HUMAN). This cell line was used for the functional luciferase assay as well as for membrane preparation for Scintillation proximity assay (SPA) binding.

Luciferase assay: BHK21 cells stably transfected with hGFRAL, hRET receptors and SRE-Luciferase reporter genes were treated by different concentrations of MIC-1 compounds. Activation of receptors was measured by quantification of luciferase activity and potencies of compounds were calculated by EC50.

SPA binding: Cell membrane of BHK21-hGFRAL-IRES-hRET, SRE-Luciferase cells were isolated treated by 50 pM of 1125 labelled MIC-1 with different concentrations of MIC-1 compounds. Binding potencies of MIC-1 compounds were calculated by IC50 of displacement curves.

Luciferase Assay

Vials with frozen cells were rapidly thawed and the cells moved to a 50 ml corning tube with 10 ml pre-warmed complete medium consisting of DMEM with high glucose and sodium pyrovate, heat inactivated 10% Fetal Bovine Serum, 1% Penicillin-Streptomycin, 1 mg/ml G418-Geneticin and 400 µg/ml Hygromycin. Cells were centrifuged at 1200 rpm and the supernatant was discarded. This washing procedure was repeated once resulting in 2 times washing of the cells. Cells were resuspended in complete media to a concentration of $1.2 \times 10^6$ cells per ml. Cells were seeded $1.2 \times 10^5$ cells per well (100 μl/well) in 96 well Poly-D-Lysine coated assay palates. Cells were let to attach to the bottom surface of the wells for 4-6 hours at +34° C. followed by change of medium to 80 pl starvation medium consisting of RPMI medium with 15 mM HEPES. Cells were left to incubate over night at +34° C. in a humidified milieu with 5% $CO_2$. Test compounds were serial diluted in assay medium consisting of RPMI, 15 mM HEPES and 0.5% ovalbumin with or without 5% human serum albumin (HSA). 20 μl of assay buffer containing test compounds was added to each well resulting in a final concentration of 0.1% ovalbumin, 1% HSA and test compounds ranging from 30000 pM to 3 pM with a blank included. Plates were incubated for 4 hours at +37° C. in a humidified milieu with 5% $CO_2$. After incubation, 100 pll luciferase substrate solutions was added to each well and sealed. The plate was let to incubate for 15 minutes followed by reading of luminescence. An intensity measurement of luminescence was used for calculations of $EC_{50}$ values by nonlinear regression analysis of sigmoidal dose response curves.

SPA Binding

BHK21-hGFRAL-IRES-hRET cells were cultured at +37° C. in a humidified atmosphere with 5% $CO_2$ in complete medium consisting of DMEM with high glucose and sodium pyrovate, heat inactivated 10% Fetal Bovine Serum, 1% Penicillin-Streptomycin, 1 mg/ml G418-Geneticin and 400 ug/ml Hygromycin. Cells were washed twice in ice cold Dulbecco's phosphate-buffered saline (DPBS) and detached mechanically by scraping, transferred in ice cold DPBS into conical centrifuge tubes and centrifuged for 5 min at 1500 rpm at +20° C. Cell pellet was resuspended in a total amount of 10 ml ice cold homogenization buffer A (50 mM Tris, 2.5 mM EDTA, adjust pH7.4 with one EDTA-free protease inhibitor cocktail tablet/50 ml) and homogenized for 20 seconds. The homogenate was centrifuged at 16000 rpm in 20 minutes at +4° C. The supernatant was discarded and the pellet was reconstituted in 10 ml homogenization buffer B (50 mM Tris, 320 mM Sucrose, adjust pH 7.4 with one EDTA-free protease inhibitor cocktail tablet/50 ml) and homogenized for 20 seconds and centrifuged at 16000 rpm in 20 minutes at +4° C. This procedure was repeated one more time. The supernatant was discarded and the pellet was reconstituted in 3 ml homogenization buffer B and homogenized for 10 seconds at low speed. Protein concentration was determined by standard Bradford method and 1.5 mg protein/tube was aliquoted to cryotubes and stored at −80° C. Binding assays were performed in white 96-well plates in a total volume of 200 μl per well. Wheat germ agglutinin SPA beads were reconstituted in assay buffer (50 mM Tris/HCl, 4.5 mM $MgCl_2$, 0.02% Tween 20 and 0.25% Ovalbumin pH 7.4) and mixed with membrane preparation to give a final concentration of 0.5 mg SPA beads and 10 μg total protein per well. Fifty thousand counts per minute per well of the radio ligand human [125I]-MIC-1 (Generated at Novo Nordisk) was added corresponding to a concentration of 50 pM. MIC-1 compounds to be tested were serial diluted in assay buffer to give a final assay concentration ranging from 1 μM to 1 pM. The plate was sealed and incubated at +22° C. for 2 hours in a plate shaker set at 350 rpm and thereafter centrifuged at 1500 rpm for 10 minutes prior to reading of SPA bead light emission. Displacement of radio ligand was measured as reduction of light emission from SPA beads and $IC_{50}$ values were calculated by nonlinear regression analysis of sigmoidal dose-response curves (Table 20).

TABLE 20

Potency and binding activity of MIC-1 compounds

| Compound No/SEQ ID NO | Luciferase NNDK EC50 (pM) | Luciferase + 0.1% HSA NNDK EC50 (pM) | MIC-1 SPA binding IC50 (nM) |
|---|---|---|---|
| SEQ ID NO: 1 | 59 | 36 | 0.67 |
| SEQ ID NO: 164 | 85 | 64 | 119 |
| SEQ ID NO: 288 | 70 | 47 | 6.7 |
| SEQ ID NO: 291 | 80 | 45 | 10 |
| SEQ ID NO: 312 | 42 | 35 | 116 |
| SEQ ID NO: 303 | 57 | 34 | 43 |
| SEQ ID NO: 292 | 125 | 115 | 29 |
| SEQ ID NO: 293 | 217 | 243 | 83 |
| SEQ ID NO: 289 | 35 | 26 | 36 |
| SEQ ID NO: 290 | 100 | 75 | 80 |
| Compound 10 | 71 | 146 | 20 |
| Compound 02 | 123 | 107 | 4.9 |
| Compound 03 | 96 | 106 | 11 |
| Compound 04 | 90 | 58 | 17 |
| Compound 01 | 72 | 59 | 3.8 |
| Compound 15 | 61 | 39 | 39 |
| Compound 16 | 63 | 51 | 11 |
| Compound 06 | 81 | 61 | 21 |
| Compound 05 | 57 | 63 | 23 |
| Compound 08 | 139 | 651 | 56 |
| Compound 11 | 55 | 62 | 29 |
| Compound 07 | 121 | 198 | 29 |
| Compound 17 | 43 | 65 | 4.7 |
| Compound 18 | 66 | 67 | 1.3 |
| Compound 19 | 45 | 62 | 17 |
| Compound 20 | 49 | 77 | 6.5 |
| Compound 21 | 53 | 56 | 1.0 |

As can be seen from Table 20, MIC-1 compounds with fatty acids have similar in vitro potency compared to MIC-1 polypeptides without fatty acids. But in vitro potency would be lower if the Cys mutation is close to N-terminal of MIC-1 polypeptide, such as Cys mutation S(−3)C.

The finding that MIC-1 compounds with fatty acids have similar potency as MIC-1 polypeptides without fatty acids is surprising. In general, adding fatty acids to pharmaceutical biological compounds for protraction results in a decrease in potency and this decrease is in general further enhanced by measuring the potency in the presence of albumin. Therefore, the finding of no reduction in potency of MIC-1 compounds with fatty acid protractors is unexpected.

Example 14: Effect of MIC-1 Compounds on Food Intake and Body Weight in Lean Sprague Dawley Rats The in vivo efficacy of MIC-1 compounds of the invention was measured in 9-11 weeks old lean male Sprague Dawley rats. Animals were injected daily with a dose of 8 nmol/kg body weight 1-2 hrs before the onset of the dark period. Compounds were administrated subcutaneously (1-4 ml/kg) in appropriate buffered solution. Changes in food intake were measured for 7 days using automatic food monitoring systems (BioDAQ system and HM2 system for rat). In the BioDAQ system animals were single housed; and in the HM2 system animals were in group housed with up to 3 animals per cage. On day 8, a tail blood sample was collected 2-3 hrs after administration of compound, and this sample was used for measuring plasma concentrations of administrated compounds. Each compound was tested in n=4-8 animals. Animals were acclimatized for at least 7 days prior to the experiment. Collected food intake data are expressed as daily food intake (24 hour food intake) measured from the onset of each daily 12 hour dark phase to the next day dark phase. Daily changes in food intake in response to administered compound were calculated by subtracting the average daily food intake of the vehicle group from the average daily food intake of the treatment group. Changes were considered significant if p<0.1 using a two-tailed student's t-test. Results are expressed as the "maximum reduction" in food intake compared with vehicle (buffer solution, percentage) recorded during the study period. Data are also expressed as the "accumulated reduction" in food intake which as the sum of significant (p<0.1) daily reductions in food intake (percentage) during the study period. The body weight of the animals was measured at the day of study termination using a calibrated scale. The effect of treatment on the body weight was calculated as the percentage difference in body weight between compound treated animals compared with vehicle treated animals at study termination (Table 21).

TABLE 21

Food intake and body weight reduction in SD rats

| Compound No/SEQ ID NO | Food intake reduction | | Body weight reduction [% compared with vehicle] |
|---|---|---|---|
| | Max efficacy @ 8 nmol/kg [% reduction compared to vehicle] | Acc efficacy, 7 days [% reduction compared to vehicle] | |
| SEQ ID NO: 1 | 67 | 391 | 18.4 |
| Compound 12 | 66 | 342 | 18.5 |
| SEQ ID NO: 300 | 87 | 431 | 23.5 |
| SEQ ID NO: 299 | 92 | 453 | 26.0 |
| SEQ ID NO: 298 | 83 | 446 | 24.2 |
| SEQ ID NO: 297 | 92 | 495 | 26.6 |
| SEQ ID NO: 296 | 86 | 427 | 22.6 |
| SEQ ID NO: 295 | 92 | 533 | 29.5 |
| SEQ ID NO: 311 | 77 | 420 | 23.4 |
| Compound 13 | 75 | 431 | 25.2 |
| Compound 14 | 89 | 484 | 26.1 |
| SEQ ID NO: 164 | 71 | 408 | 23.3 |
| Compound 09 | 54 | 283 | 16.5 |
| Compound 10 | 61 | 288 | 18.4 |
| Compound 02 | 86 | 470 | 27.2 |
| Compound 03 | 86 | 458 | 27.4 |
| Compound 04 | 79 | 497 | 30.2 |
| Compound 07 | 77 | 375 | 20.0 |
| Compound 08 | 70 | 353 | 17.7 |
| Compound 05 | 75 | 405 | 19.9 |
| Compound 01 | 77 | 426 | 23.4 |
| Compound 11 | 58 | 287 | 17.5 |
| Compound 17 | 63 | 371 | 18.6 |
| Compound 18 | 72 | 384 | 21.2 |
| Compound 19 | 68 | 398 | 23.5 |
| Compound 20 | 69 | 374 | 22.5 |
| Compound 21 | 73 | 394 | 23.1 |

It is shown from the experimental data of Table 21 that MIC-1 compounds with or without protractors has an equivalent or better in vivo efficacy in rats when compared with wild type MIC-1 polypeptide. The data also show that these protractors don't have a 5 negative impact on the in vivo efficacy of MIC-1 compounds.

Example 15: Pharmacodynamic (PD) Study in Pigs

The purpose of this experiment was to investigate the effect of the MIC-1 compounds on food intake and body weight in pigs. This was done in a pharmacodynamic (PD) study as described below, in which food intake was measured from 1 to 21 days after administration of a single dose of the MIC-1 compound, as compared to a vehicle-treated control group.

Female Landrace Yorkshire Duroc (LYD) pigs approximately 3 months of age, weighing approximately 30-35 kg were used (n=4-6 per group). The animals were housed in a group for approximately 1 week during acclimatisation to the animal facilities. During the last part of the acclimatisation period the animals were placed in individual pens (2 weeks before dosing) and during the entire experiment for measurement of individual food intake. The food intake measured the last three days before dosing served as baseline.

The animals were fed ad libitum with pig fodder (Svinefoder Danish Top SI 611+3', Danish Agro) at all times both during the acclimatisation and the experimental period. Food intake was monitored on line by logging the weight of fodder continuously using the HMview system (Ellegaard Systems, Faaborg, Denmark). Any notable spillage was collected and weighed, and the automatically measured food intake was corrected for this amount.

Body weight was measured once or twice weekly during the study. The MIC-1 compounds were dissolved in an appropriate buffer at concentrations of approximately 25 or 100 nmol/ml corresponding to doses of 1 or 9 nmol/kg. The buffer solution also served as vehicle.

Animals were dosed with a single subcutaneous dose of the MIC-1 compounds or vehicle on the morning of day 1, and food intake was measured for 21 days after dosing. At the end of the study the animals were euthanised with an i.v. overdose of Euthasol administered through the ear vein catheter.

Food intake was calculated in 24 h intervals (0-24 h, 24-48 h, 48-72 h, 72-96 h up to 20-21 days). In Table 22, the resulting mean food intake is presented as percentage of the mean food intake of the vehicle group in the same time interval.

TABLE 22

Effect on food intake in pigs

| | PD in pig, food intake (% of vehicle) at indicated time intervals | | |
|---|---|---|---|
| | Time interval (days) | | |
| MIC-1 compound | 6-7 | 13-14 | 20-21 |
| Vehicle | 100 | 100 | 100 |
| Compound 05 (1 nmol/kg) | 88 | 100 | 117 |
| Compound 05 (9 nmol/kg) | 36 | 38 | 65 |
| Compound 01 (1 nmol/kg) | 49 | 86 | 103 |
| Compound 01 (9 nmol/kg) | 29 | 22 | 23 |

The data shows that a single s.c. injection of the tested compounds in pigs caused a reduced food intake for up to and even more than 21 days after the injection (for the 9 nmol/kg doses of Compound 01).

Figure 6:
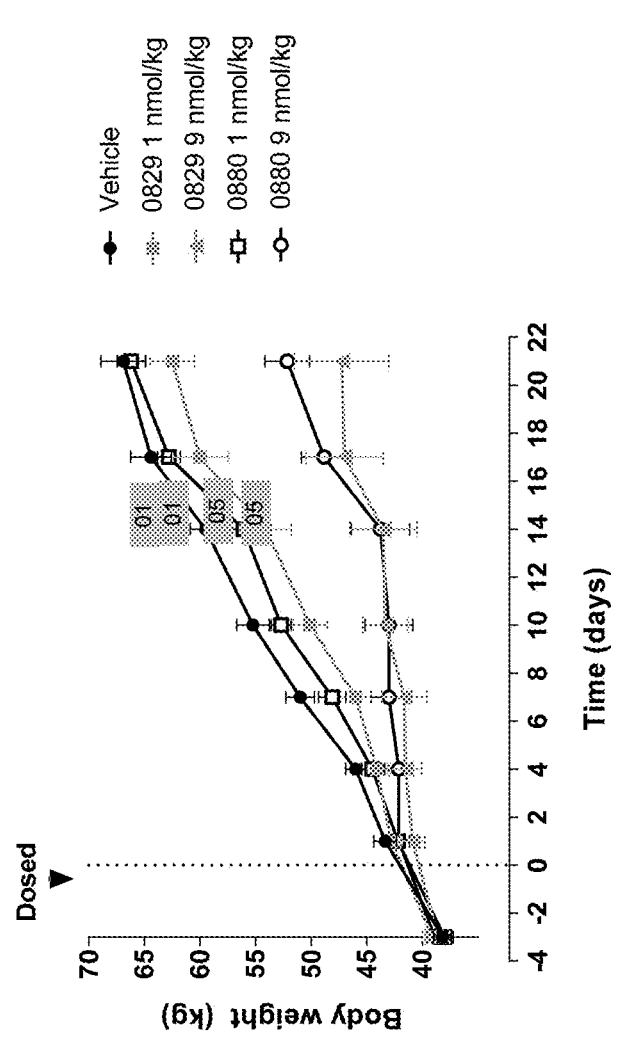
FIG. 6: Body weight change over time during Pharmacodynamic (PD) study in pigs. 01: Compound 01; 05: Compound 05

Body weight was measured during the study and the pigs gained less weight in the groups treated with MIC-1 compounds (Table 23, FIG. 6).

TABLE 23

Change in body weight gain relative to vehicle group

| MIC-1 compounds | PD in pig, Δbody weight (relative to vehicle (%)) Time (days) | | |
|---|---|---|---|
| | 7 | 14 | 21 |
| Vehicle | 0 | 0 | 0 |
| Compound 05 (1 nmol/kg) | −5.7 | −5.7 | −1.1 |
| Compound 05 (9 nmol/kg) | −15.7 | −26.5 | −22.0 |
| Compound 01 (1 nmol/kg) | −9.8 | −9.1 | −6.6 |
| Compound 01 (9 nmol/kg) | −18.4 | −26.9 | −29.4 |

Example 16: Pharmacokinetic Study in Lean SD Rats

The purpose of this study is to determine the terminal half-life (T½), the mean residence time (MRT), the time for maximal plasma levels (Tmax) and the bioavailability (F) time in vivo of the MIC-1 compounds after intravenous and subcutaneous administration to lean Sprague Dawley rats This is done in a pharmacokinetic (PK) study, where the PK parameters of the MIC-1 compounds in question are determined. By T½ is generally meant the period of time it takes to halve a certain plasma concentration, measured after the initial distribution phase with intravenous dosing. By MRT is in general meant the average amount of time that the compound in question stays in the body. By Tmax is in general meant the point in time after subcutaneous administration of the compound in question when the compound in question reaches the highest concentration in the blood plasma during. By F is in general meant the fraction of subcutaneously administered compound which appears in the blood plasma.

The aforementioned PK parameters were measured in 300 g-500 g lean SD rats by injecting the compound into either the tail vein or to the subcutis of the neck followed by collection of blood plasma samples at various time points for exposure analysis. Compounds (4-5 nmol/kg body weight) were administered intravenously (1 ml/kg) in an appropriate buffer solution. The group size of the intravenous group was typically 4 and the groups size of the subcutaneous group was typically 5. The rats were awake during the whole experiment and have access to food and water.

For compounds with a T½ of less than 12 hrs blood samples were collected from the tongue typically at time 5 min, 15 min, 30 min, 60 min, 90 min, 2h, 3h, 4h, 5h, 6h, 8h, 12h, 14h, 22h, 30h, 48h after dosing or at times 0 min, 15 min, 30 min, 60 min, 90 min, 2h, 2½h, 3h, 4h, 5h, 6h, 8h, 24h, 30h, 48h after dosing. For compounds with a T½ of more than 24 hrs blood samples were typically collected from the tongue at time 5 min, 15 min, 30 min, 60 min, 120 min, 360 min, 720 min, 24h, 30h, 48h, 54h, 72h, 96h, 168h, 216h, 264h, 336h after dosing, 200 pl of blood was collected into EDTA tubes and stored on ice for up to 20 minutes. Plasma samples were generated by centrifuging blood samples for 5 minutes at 10000 G at 4° C. The sample was subsequent pipetted into Micronic tubes on dry ice, and kept at −20° C. until analysed for plasma concentration of the respective MIC-1 compound using LOCI or a similar antibody based assay such as ELISA. The individual plasma concentration-time profiles were analysed by a non-compartmental model in Phoenix v. 6.4 software (Pharsight Inc., Mountain View, Calif., USA), and the resulting T½, MRT, Tmax and F determined (Table 24).

TABLE 24

Pharmacokinetic profiles of MIC-1 compounds/polypeptides with N-terminal extension

| Compound No/SEQ ID NO | Dose | ROA | T½ hrs (mean) | MRT hrs (mean) | Tmax hrs (mean) | BA % (mean) |
|---|---|---|---|---|---|---|
| SEQ ID NO: 1 | 4 nmol/kg | IV | 1.7 | 0.53 | NA | NA |
| SEQ ID NO: 92 | 4 nmol/kg | IV | 3.9 | 2.2 | NA | NA |
| SEQ ID NO: 100 | 4 nmol/kg | IV | 4.0 | 3.0 | NA | NA |
| SEQ ID NO: 104 | 4 nmol/kg | IV | 3.8 | 3.2 | NA | NA |
| SEQ ID NO: 105 | 4 nmol/kg | IV | 3.4 | 2.1 | NA | NA |
| SEQ ID NO: 106 | 4 nmol/kg | IV | 3.4 | 1.7 | NA | NA |
| SEQ ID NO: 107 | 4 nmol/kg | IV | 2.8 | 1.4 | NA | NA |
| SEQ ID NO: 108 | 4 nmol/kg | IV | 3.8 | 3.8 | NA | NA |
| SEQ ID O: 294 | 4 nmol/kg | IV | 2.9 | 1.5 | NA | NA |
| SEQ ID NO: 1 | 4 nmol/kg | SC | 1.9 | 4.1 | 2.2 | 70 |
| SEQ ID NO: 106 | 4 nmol/kg | SC | 3.3 | 6.7 | 3.0 | 88 |
| SEQ ID NO: 107 | 4 nmol/kg | SC | 3.4 | 6.8 | 2.8 | 82 |
| SEQ ID NO: 108 | 4 nmol/kg | SC | 4.1 | 8.6 | 3.0 | 90± |
| SEQ ID NO: 294 | 4 nmol/kg | SC | 2.8 | 6.2 | 3.0 | 67 |
| Compound 13 | 5 nmol/kg | IV | 26.3 | 33.1 | NA | NA |
| Compound 12 | 5 nmol/kg | IV | 42.1 | 54.8 | NA | NA |
| Compound 14 | 5 nmol/kg | IV | 2.9 | 2.1 | NA | NA |
| Compound 10 | 4 nmol/kg | IV | 37.0 | 45.7 | NA | NA |
| Compound 02 | 4 nmol/kg | IV | 73.8 | 106.2. | NA | NA |
| Compound 03 | 4 nmol/kg | IV | 62.4 | 89.3 | NA | NA |
| Compound 04 | 4 nmol/kg | IV | 15.6 | 16.8 | NA | NA |
| Compound 06 | 4 nmol/kg | IV | 46.6 | 63.8 | NA | NA |
| SEQ ID NO: 289 | 4 nmol/kg | IV | 5.1 | 2.8 | NA | NA |
| Compound 01 | 4 nmol/kg | IV | 58 | 82 | NA | NA |
| Compound 05 | 4 nmol/kg | IV | 53 | 71 | NA | NA |
| Compound 11 | 4 nmol/kg | IV | 50 | 72 | NA | NA |
| Compound 01 | 4 nmol/kg | SC | 56 | 114 | 50 | 36 |
| Compound 05 | 4 nmol/kg | SC | 53 | 106 | 50 | 35 |
| Compound 11 | 4 nmol/kg | SC | 57 | 116 | 50 | 52 |
| Compound 17 | 4 nmol/kg | SC | 55.8 | 57.2 | 55.5 | 42.3 |
| Compound 18 | 4 nmol/kg | SC | 52.9 | 53.1 | 54.0 | 38.2 |
| Compound 17 | 4 nmol/kg | IV | 68.5 | 90.1 | NA | NA |
| Compound 18 | 4 nmol/kg | IV | 50.8 | 67.4 | NA | NA |

It can be seen that MIC-1 compounds with protractors have much longer T½, MRT and Tmax compared to their non-protracted MIC-1 polypeptides with N-extensions. Protraction of pharmaceutical biological compounds with comparable fatty acid protractors in general results in a terminal half-life rarely exceeding 12 hours in rat. The finding of terminal half-lives of more than 48 hours is unexpected and surprising.

Example 17: Pharmacokinetic Study in Mini Pigs

The purpose of this study was to determine the protraction in vivo of the MIC-1 compound after i.v. administration to minipigs, i.e. the prolongation of their time in the body and thereby their time of action. This was done in pharmacokinetic (PK) studies, where the terminal half-life of the compound in question was determined. By terminal half-life is meant the time it takes to halve a certain plasma concentration in the terminal elimination phase.

Female Göttingen minipigs were obtained from Ellegaard Göttingen Minipigs (Dalmose, Denmark) approximately 8 months of age and weighing approximately 23-25 kg were used in the studies. The minipigs were housed individually (pigs with permanent catheters) in pens with straw as bedding and fed restrictedly once daily with Altromin 9030 minipig diet (Altromin Spezialfutter GmbH & Co. KG).

After three weeks of acclimatisation two permanent central venous catheters were implanted in vena cava caudalis in each animal. The animals were allowed 1 week recovery after the surgery, and were then used for repeated pharmacokinetic studies with a suitable wash-out period between successive dosing.

Intravenous injections (the volume corresponding to 0.17 ml/kg) of the compound was given through one catheter, and blood was sampled at predefined time points for up till 12 days post dosing (preferably from the other catheter).

Blood samples (for example 0.8 ml) were collected in EDTA (8 mM) coated tubes and then centrifuged at 4° C. and 1942 g for 10 minutes. Blood samples were collected at predefined timepoints. In example blood samples were collected at t=predose, 0.0833, 0.25, 0.5, 0.75, 1, 1.5, 2, 3, 4, 6, 8, 10, 12, 24, 30, 48, 72, 96, 120, 168, 192, 216, 240, 264, and 288 hours after dose.

Plasma was pipetted into Micronic tubes on dry ice, and kept at −20° C. until analysed for plasma concentration of the MIC-1 compound using LOCI. Individual plasma concentration-time profiles were analysed by a non-compartmental pharmacokinetic method in Phoenix v. 6.4 (Pharsight Inc., Mountain View, Calif., USA), and the resulting terminal half-lives (harmonic mean) determined.

Results

The following result was obtained (Table 25).

TABLE 25

In vivo study in Gottingen minipigs after intravenous administration

| Compound no. | Minipig iv PK | |
|---|---|---|
| | t½ (hours) | MRT (hours) |
| Compound 02 | 338 | 487 |
| Compound 05 | 290 | 420 |
| Compound 11 | 347 | 489 |

Terminal half-life (t½) is harmonic mean, n = 3

Protraction of pharmaceutical biological compounds with comparable fatty acid protractors in general results in a terminal half-life rarely exceeding 100 hours in mini pig. The finding of a terminal half-life of more than 300 hours is unexpected and surprising.

SEQUENCE LISTING

```
<160> NUMBER OF SEQ ID NOS: 317

<210> SEQ ID NO 1
<211> LENGTH: 112
<212> TYPE: PRT
<213> ORGANISM: Homo Sapiens

<400> SEQUENCE: 1

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 2
<211> LENGTH: 111
<212> TYPE: PRT
<213> ORGANISM: Artificial Sequence
<220> FEATURE:
<223> OTHER INFORMATION: MIC-1 des-N3

<400> SEQUENCE: 2

Ala Arg Gly Asp His Cys Pro Leu Gly Pro Gly Arg Cys Cys Arg Leu
1               5                   10                  15

His Thr Val Arg Ala Ser Leu Glu Asp Leu Gly Trp Ala Asp Trp Val
```

```
                    20                  25                  30

Leu Ser Pro Arg Glu Val Gln Val Thr Met Cys Ile Gly Ala Cys Pro
            35                  40                  45

Ser Gln Phe Arg Ala Ala Asn Met His Ala Gln Ile Lys Thr Ser Leu
        50                  55                  60

His Arg Leu Lys Pro Asp Thr Val Pro Ala Pro Cys Cys Val Pro Ala
65                  70                  75                  80

Ser Tyr Asn Pro Met Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110

<210> SEQ ID NO 3
<211> LENGTH: 109
<212> TYPE: PRT
<213> ORGANISM: Artificial Sequence
<220> FEATURE:
<223> OTHER INFORMATION: MIC-1-Del (1-3)

<400> SEQUENCE: 3

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
            35                  40                  45

Phe Arg Ala Ala Asn Met His Ala Gln Ile Lys Thr Ser Leu His Arg
        50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 4
<211> LENGTH: 6
<212> TYPE: PRT
<213> ORGANISM: Artificial Sequence
<220> FEATURE:
<223> OTHER INFORMATION: N-terminal extension

<400> SEQUENCE: 4

Ser Pro Ala Gly Ser Pro
1               5

<210> SEQ ID NO 5
<211> LENGTH: 6
<212> TYPE: PRT
<213> ORGANISM: Artificial Sequence
<220> FEATURE:
<223> OTHER INFORMATION: N-terminal extension

<400> SEQUENCE: 5

Thr Ser Glu Ser Ala Thr
1               5

<210> SEQ ID NO 6
<211> LENGTH: 6
<212> TYPE: PRT
<213> ORGANISM: Artificial Sequence
```

<220> FEATURE:
<223> OTHER INFORMATION: N-terminal extension

<400> SEQUENCE: 6

Thr Ser Thr Glu Pro Glu
1               5

<210> SEQ ID NO 7
<211> LENGTH: 6
<212> TYPE: PRT
<213> ORGANISM: Artificial Sequence
<220> FEATURE:
<223> OTHER INFORMATION: N-terminal extension

<400> SEQUENCE: 7

Ser Glu Pro Ala Thr Ser
1               5

<210> SEQ ID NO 8
<211> LENGTH: 6
<212> TYPE: PRT
<213> ORGANISM: Artificial Sequence
<220> FEATURE:
<223> OTHER INFORMATION: N-terminal extension

<400> SEQUENCE: 8

Thr Ser Thr Glu Glu Gly
1               5

<210> SEQ ID NO 9
<211> LENGTH: 6
<212> TYPE: PRT
<213> ORGANISM: Artificial Sequence
<220> FEATURE:
<223> OTHER INFORMATION: N-terminal extension

<400> SEQUENCE: 9

Pro Glu Ser Gly Pro Gly
1               5

<210> SEQ ID NO 10
<211> LENGTH: 6
<212> TYPE: PRT
<213> ORGANISM: Artificial Sequence
<220> FEATURE:
<223> OTHER INFORMATION: N-terminal extension

<400> SEQUENCE: 10

Ser Gly Ser Ala Pro Gly
1               5

<210> SEQ ID NO 11
<211> LENGTH: 6
<212> TYPE: PRT
<213> ORGANISM: Artificial Sequence
<220> FEATURE:
<223> OTHER INFORMATION: N-terminal extension

<400> SEQUENCE: 11

Gly Ser Glu Thr Pro Gly
1               5

<210> SEQ ID NO 12
<211> LENGTH: 24
<212> TYPE: PRT
<213> ORGANISM: Artificial Sequence
<220> FEATURE:

```
<223> OTHER INFORMATION: N-terminal extension

<400> SEQUENCE: 12

Ser Glu Pro Ala Thr Ser Gly Ser Glu Thr Pro Gly Ser Pro Ala Gly
1               5                   10                  15

Ser Pro Thr Ser Thr Glu Glu Gly
            20

<210> SEQ ID NO 13
<211> LENGTH: 24
<212> TYPE: PRT
<213> ORGANISM: Artificial Sequence
<220> FEATURE:
<223> OTHER INFORMATION: N-terminal extension

<400> SEQUENCE: 13

Ser Glu Pro Ala Thr Ser Gly Ser Glu Thr Pro Gly Thr Ser Glu Ser
1               5                   10                  15

Ala Thr Pro Glu Ser Gly Pro Gly
            20

<210> SEQ ID NO 14
<211> LENGTH: 24
<212> TYPE: PRT
<213> ORGANISM: Artificial Sequence
<220> FEATURE:
<223> OTHER INFORMATION: N-terminal extension

<400> SEQUENCE: 14

Ser Glu Pro Ala Thr Ser Gly Ser Glu Thr Pro Gly Thr Ser Thr Glu
1               5                   10                  15

Pro Glu Ser Gly Ser Ala Pro Gly
            20

<210> SEQ ID NO 15
<211> LENGTH: 30
<212> TYPE: PRT
<213> ORGANISM: Artificial Sequence
<220> FEATURE:
<223> OTHER INFORMATION: N-terminal extension

<400> SEQUENCE: 15

Ser Glu Pro Ala Thr Ser Gly Ser Glu Thr Pro Gly Ser Pro Ala Gly
1               5                   10                  15

Ser Pro Thr Ser Thr Glu Glu Gly Ser Pro Ala Gly Ser Pro
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: N-terminal extension

<400> SEQUENCE: 16

Ser Glu Pro Ala Thr Ser Gly Ser Glu Thr Pro Gly Thr Ser Glu Ser
1               5                   10                  15

Ala Thr Pro Glu Ser Gly Pro Gly Ser Pro Ala Gly Ser Pro
            20                  25                  30

<210> SEQ ID NO 17
<211> LENGTH: 30
<212> TYPE: PRT
<213> ORGANISM: Artificial Sequence
```

```
<220> FEATURE:
<223> OTHER INFORMATION: N-terminal extension

<400> SEQUENCE: 17

Ser Glu Pro Ala Thr Ser Gly Ser Glu Thr Pro Gly Thr Ser Thr Glu
1               5                   10                  15
Pro Glu Ser Gly Ser Ala Pro Gly Ser Pro Ala Gly Ser Pro
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: N-terminal extension

<400> SEQUENCE: 18

Ser Glu Pro Ala Thr Ser Gly Ser Glu Thr Pro Gly Ser Pro Ala Gly
1               5                   10                  15
Ser Pro Thr Ser Thr Glu Glu Gly Thr Ser Glu Ser Ala Thr
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: N-terminal extension

<400> SEQUENCE: 19

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Glu Ser Ala Thr
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: N-terminal extension

<400> SEQUENCE: 20

Ser Glu Pro Ala Thr Ser Gly Ser Glu Thr Pro Gly Thr Ser Thr Glu
1               5                   10                  15
Pro Glu Ser Gly Ser Ala Pro Gly Thr Ser Glu Ser Ala Thr
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: N-terminal extension

<400> SEQUENCE: 21

Ser Glu Pro Ala Thr Ser Gly Ser Glu Thr Pro Gly Ser Pro Ala Gly
1               5                   10                  15
Ser Pro Thr Ser Thr Glu Glu Gly Thr Ser Thr Glu Pro Glu
            20                  25                  30

<210> SEQ ID NO 22
<211> LENGTH: 30
<212> TYPE: PRT
```

<213> ORGANISM: Artificial Sequence
<220> FEATURE:
<223> OTHER INFORMATION: N-terminal extension

<400> SEQUENCE: 22

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Glu
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: N-terminal extension

<400> SEQUENCE: 23

Ser Glu Pro Ala Thr Ser Gly Ser Glu Thr Pro Gly Thr Ser Thr Glu
1               5                   10                  15

Pro Glu Ser Gly Ser Ala Pro Gly Thr Ser Thr Glu Pro Glu
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: N-terminal extension

<400> SEQUENCE: 24

Ser Glu Pro Ala Thr Ser Gly Ser Glu Thr Pro Gly Ser Pro Ala Gly
1               5                   10                  15

Ser Pro Thr Ser Thr Glu Glu Gly Ser Glu Pro Ala Thr Ser
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: N-terminal extension

<400> SEQUENCE: 25

Ser Glu Pro Ala Thr Ser Gly Ser Glu Thr Pro Gly Thr Ser Glu Ser
1               5                   10                  15

Ala Thr Pro Glu Ser Gly Pro Gly Ser Glu Pro Ala Thr Ser
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: N-terminal extension

<400> SEQUENCE: 26

Ser Glu Pro Ala Thr Ser Gly Ser Glu Thr Pro Gly Thr Ser Thr Glu
1               5                   10                  15

Pro Glu Ser Gly Ser Ala Pro Gly Ser Glu Pro Ala Thr Ser
            20                  25                  30

<210> SEQ ID NO 27
<211> LENGTH: 30

<212> TYPE: PRT
<213> ORGANISM: Artificial Sequence
<220> FEATURE:
<223> OTHER INFORMATION: N-terminal extension

<400> SEQUENCE: 27

Ser Glu Pro Ala Thr Ser Gly Ser Glu Thr Pro Gly Ser Pro Ala Gly
1               5                   10                  15
Ser Pro Thr Ser Thr Glu Glu Gly Thr Ser Thr Glu Glu Gly
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: N-terminal extension

<400> SEQUENCE: 28

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Glu Gly
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: N-terminal extension

<400> SEQUENCE: 29

Ser Glu Pro Ala Thr Ser Gly Ser Glu Thr Pro Gly Thr Ser Thr Glu
1               5                   10                  15
Pro Glu Ser Gly Ser Ala Pro Gly Thr Ser Thr Glu Glu Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: N-terminal extension

<400> SEQUENCE: 30

Ser Glu Pro Ala Thr Ser Gly Ser Glu Thr Pro Gly Ser Pro Ala Gly
1               5                   10                  15
Ser Pro Thr Ser Thr Glu Glu Gly Pro Glu Ser Gly Pro Gly
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: N-terminal extension

<400> SEQUENCE: 31

Ser Glu Pro Ala Thr Ser Gly Ser Glu Thr Pro Gly Thr Ser Glu Ser
1               5                   10                  15
Ala Thr Pro Glu Ser Gly Pro Gly Pro Glu Ser Gly Pro Gly
            20                  25                  30

<210> SEQ ID NO 32

```
<211> LENGTH: 30
<212> TYPE: PRT
<213> ORGANISM: Artificial Sequence
<220> FEATURE:
<223> OTHER INFORMATION: N-terminal extension

<400> SEQUENCE: 32

Ser Glu Pro Ala Thr Ser Gly Ser Glu Thr Pro Gly Thr Ser Thr Glu
1               5                   10                  15
Pro Glu Ser Gly Ser Ala Pro Gly Pro Glu Ser Gly Pro Gly
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: N-terminal extension

<400> SEQUENCE: 33

Ser Glu Pro Ala Thr Ser Gly Ser Glu Thr Pro Gly Ser Pro Ala Gly
1               5                   10                  15
Ser Pro Thr Ser Thr Glu Glu Gly Ser Gly Ser Ala Pro Gly
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: N-terminal extension

<400> SEQUENCE: 34

Ser Glu Pro Ala Thr Ser Gly Ser Glu Thr Pro Gly Thr Ser Glu Ser
1               5                   10                  15
Ala Thr Pro Glu Ser Gly Pro Gly Ser Gly Ser Ala Pro Gly
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: N-terminal extension

<400> SEQUENCE: 35

Ser Glu Pro Ala Thr Ser Gly Ser Glu Thr Pro Gly Thr Ser Thr Glu
1               5                   10                  15
Pro Glu Ser Gly Ser Ala Pro Gly Ser Gly Ser Ala Pro Gly
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: N-terminal extension

<400> SEQUENCE: 36

Ser Glu Pro Ala Thr Ser Gly Ser Glu Thr Pro Gly Ser Pro Ala Gly
1               5                   10                  15
Ser Pro Thr Ser Thr Glu Glu Gly Gly Ser Glu Thr Pro Gly
            20                  25                  30
```

-continued

```
<210> SEQ ID NO 37
<211> LENGTH: 30
<212> TYPE: PRT
<213> ORGANISM: Artificial Sequence
<220> FEATURE:
<223> OTHER INFORMATION: N-terminal extension

<400> SEQUENCE: 37

Ser Glu Pro Ala Thr Ser Gly Ser Glu Thr Pro Gly Thr Ser Glu Ser
1               5                   10                  15

Ala Thr Pro Glu Ser Gly Pro Gly Gly Ser Glu Thr Pro Gly
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: N-terminal extension

<400> SEQUENCE: 38

Ser Glu Pro Ala Thr Ser Gly Ser Glu Thr Pro Gly Thr Ser Thr Glu
1               5                   10                  15

Pro Glu Ser Gly Ser Ala Pro Gly Gly Ser Glu Thr Pro Gly
            20                  25                  30

<210> SEQ ID NO 39
<211> LENGTH: 36
<212> TYPE: PRT
<213> ORGANISM: Artificial Sequence
<220> FEATURE:
<223> OTHER INFORMATION: N-terminal extension

<400> SEQUENCE: 39

Ser Glu Pro Ala Thr Ser Gly Ser Glu Thr Pro Gly Ser Pro Ala Gly
1               5                   10                  15

Ser Pro Thr Ser Thr Glu Glu Gly Thr Ser Glu Ser Ala Thr Pro Glu
            20                  25                  30

Ser Gly Pro Gly
        35

<210> SEQ ID NO 40
<211> LENGTH: 36
<212> TYPE: PRT
<213> ORGANISM: Artificial Sequence
<220> FEATURE:
<223> OTHER INFORMATION: N-terminal extension

<400> SEQUENCE: 40

Ser Glu Pro Ala Thr Ser Gly Ser Glu Thr Pro Gly Ser Pro Ala Gly
1               5                   10                  15

Ser Pro Thr Ser Thr Glu Glu Gly Ser Pro Ala Gly Ser Pro Thr Ser
            20                  25                  30

Thr Glu Glu Gly
        35

<210> SEQ ID NO 41
<211> LENGTH: 36
<212> TYPE: PRT
<213> ORGANISM: Artificial Sequence
<220> FEATURE:
<223> OTHER INFORMATION: N-terminal extension

<400> SEQUENCE: 41
```

Ser Glu Pro Ala Thr Ser Gly Ser Glu Thr Pro Gly Ser Pro Ala Gly
1               5                   10                  15

Ser Pro Thr Ser Thr Glu Glu Gly Thr Ser Thr Glu Pro Glu Ser Gly
                20                  25                  30

Ser Ala Pro Gly
        35

<210> SEQ ID NO 42
<211> LENGTH: 36
<212> TYPE: PRT
<213> ORGANISM: Artificial Sequence
<220> FEATURE:
<223> OTHER INFORMATION: N-terminal extension

<400> SEQUENCE: 42

Ser Glu Pro Ala Thr Ser Gly Ser Glu Thr Pro Gly Thr Ser Glu Ser
1               5                   10                  15

Ala Thr Pro Glu Ser Gly Pro Gly Ser Pro Ala Gly Ser Pro Thr Ser
                20                  25                  30

Thr Glu Glu Gly
        35

<210> SEQ ID NO 43
<211> LENGTH: 36
<212> TYPE: PRT
<213> ORGANISM: Artificial Sequence
<220> FEATURE:
<223> OTHER INFORMATION: N-terminal extension

<400> SEQUENCE: 43

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Glu Ser Ala Thr Pro Glu
                20                  25                  30

Ser Gly Pro Gly
        35

<210> SEQ ID NO 44
<211> LENGTH: 36
<212> TYPE: PRT
<213> ORGANISM: Artificial Sequence
<220> FEATURE:
<223> OTHER INFORMATION: N-terminal extension

<400> SEQUENCE: 44

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Glu Ser Gly
                20                  25                  30

Ser Ala Pro Gly
        35

<210> SEQ ID NO 45
<211> LENGTH: 36
<212> TYPE: PRT
<213> ORGANISM: Artificial Sequence
<220> FEATURE:
<223> OTHER INFORMATION: N-terminal extension

<400> SEQUENCE: 45

Ser Glu Pro Ala Thr Ser Gly Ser Glu Thr Pro Gly Thr Ser Glu Ser
1               5                   10                  15

Ala Thr Pro Glu Ser Gly Pro Gly Ser Glu Pro Ala Thr Gly Ser
            20                  25                  30

Glu Thr Pro Gly
        35

<210> SEQ ID NO 46
<211> LENGTH: 36
<212> TYPE: PRT
<213> ORGANISM: Artificial Sequence
<220> FEATURE:
<223> OTHER INFORMATION: N-terminal extension

<400> SEQUENCE: 46

Ser Glu Pro Ala Thr Ser Gly Ser Glu Thr Pro Gly Thr Ser Thr Glu
1               5                   10                  15

Pro Glu Ser Gly Ser Ala Pro Gly Ser Pro Ala Gly Ser Pro Thr Ser
            20                  25                  30

Thr Glu Glu Gly
        35

<210> SEQ ID NO 47
<211> LENGTH: 36
<212> TYPE: PRT
<213> ORGANISM: Artificial Sequence
<220> FEATURE:
<223> OTHER INFORMATION: N-terminal extension

<400> SEQUENCE: 47

Ser Glu Pro Ala Thr Ser Gly Ser Glu Thr Pro Gly Thr Ser Thr Glu
1               5                   10                  15

Pro Glu Ser Gly Ser Ala Pro Gly Thr Ser Glu Ser Ala Thr Pro Glu
            20                  25                  30

Ser Gly Pro Gly
        35

<210> SEQ ID NO 48
<211> LENGTH: 36
<212> TYPE: PRT
<213> ORGANISM: Artificial Sequence
<220> FEATURE:
<223> OTHER INFORMATION: N-terminal extension

<400> SEQUENCE: 48

Ser Glu Pro Ala Thr Ser Gly Ser Glu Thr Pro Gly Thr Ser Thr Glu
1               5                   10                  15

Pro Glu Ser Gly Ser Ala Pro Gly Thr Ser Thr Glu Pro Glu Ser Gly
            20                  25                  30

Ser Ala Pro Gly
        35

<210> SEQ ID NO 49
<211> LENGTH: 36
<212> TYPE: PRT
<213> ORGANISM: Artificial Sequence
<220> FEATURE:
<223> OTHER INFORMATION: N-terminal extension

<400> SEQUENCE: 49

Ser Glu Pro Ala Thr Ser Gly Ser Glu Thr Pro Gly Thr Ser Thr Glu
1               5                   10                  15

Pro Glu Ser Gly Ser Ala Pro Gly Ser Glu Pro Ala Thr Ser Gly Ser
            20                  25                  30

Glu Thr Pro Gly
        35

<210> SEQ ID NO 50
<211> LENGTH: 36
<212> TYPE: PRT
<213> ORGANISM: Artificial Sequence
<220> FEATURE:
<223> OTHER INFORMATION: N-terminal extension

<400> SEQUENCE: 50

Ser Glu Pro Ala Thr Ser Gly Ser Glu Thr Pro Gly Ser Glu Pro Ala
1               5                   10                  15

Thr Ser Gly Ser Glu Thr Pro Gly Ser Pro Ala Gly Ser Pro Thr Ser
            20                  25                  30

Thr Glu Glu Gly
        35

<210> SEQ ID NO 51
<211> LENGTH: 36
<212> TYPE: PRT
<213> ORGANISM: Artificial Sequence
<220> FEATURE:
<223> OTHER INFORMATION: N-terminal extension

<400> SEQUENCE: 51

Ser Glu Pro Ala Thr Ser Gly Ser Glu Thr Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly
        35

<210> SEQ ID NO 52
<211> LENGTH: 36
<212> TYPE: PRT
<213> ORGANISM: Artificial Sequence
<220> FEATURE:
<223> OTHER INFORMATION: N-terminal extension

<400> SEQUENCE: 52

Ser Glu Pro Ala Thr Ser Gly Ser Glu Thr Pro Gly Ser Glu Pro Ala
1               5                   10                  15

Thr Ser Gly Ser Glu Thr Pro Gly Thr Ser Thr Glu Pro Glu Ser Gly
            20                  25                  30

Ser Ala Pro Gly
        35

<210> SEQ ID NO 53
<211> LENGTH: 36
<212> TYPE: PRT
<213> ORGANISM: Artificial Sequence
<220> FEATURE:
<223> OTHER INFORMATION: N-terminal extension

<400> SEQUENCE: 53

Ser Glu Pro Ala Thr Ser Gly Ser Glu Thr Pro Gly Ser Glu Pro Ala
1               5                   10                  15

Thr Ser Gly Ser Glu Thr Pro Gly Ser Glu Pro Ala Thr Ser Gly Ser
            20                  25                  30

Glu Thr Pro Gly
        35

<210> SEQ ID NO 54
<211> LENGTH: 6
<212> TYPE: PRT
<213> ORGANISM: Artificial Sequence
<220> FEATURE:
<223> OTHER INFORMATION: N-terminal extension

<400> SEQUENCE: 54

Ala Glu Glu Ala Glu Ser
1               5

<210> SEQ ID NO 55
<211> LENGTH: 4
<212> TYPE: PRT
<213> ORGANISM: Artificial Sequence
<220> FEATURE:
<223> OTHER INFORMATION: N-terminal extension

<400> SEQUENCE: 55

Ala Glu Ser Met
1

<210> SEQ ID NO 56
<211> LENGTH: 9
<212> TYPE: PRT
<213> ORGANISM: Artificial Sequence
<220> FEATURE:
<223> OTHER INFORMATION: N-terminal extension

<400> SEQUENCE: 56

Ala Glu Glu Ala Glu Glu Ala Glu Ser
1               5

<210> SEQ ID NO 57
<211> LENGTH: 20
<212> TYPE: PRT
<213> ORGANISM: Artificial Sequence
<220> FEATURE:
<223> OTHER INFORMATION: N-terminal extension

<400> SEQUENCE: 57

Gly Glu Pro Ser Gly Glu Pro Ser Gly Glu Pro Ser Gly Glu Pro Ser
1               5                   10                  15

Gly Glu Pro Ser
            20

<210> SEQ ID NO 58
<211> LENGTH: 24
<212> TYPE: PRT
<213> ORGANISM: Artificial Sequence
<220> FEATURE:
<223> OTHER INFORMATION: N-terminal extension

<400> SEQUENCE: 58

Ser Pro Ala Gly Ser Pro Thr Ser Thr Glu Glu Gly Thr Ser Glu Ser
1               5                   10                  15

Ala Thr Pro Glu Ser Gly Pro Gly
            20

<210> SEQ ID NO 59
<211> LENGTH: 21
<212> TYPE: PRT
<213> ORGANISM: Artificial Sequence
<220> FEATURE:
<223> OTHER INFORMATION: N-terminal extension

```
<400> SEQUENCE: 59

Ala Glu Glu Ala Glu Glu Ala Glu Glu Ala Glu Glu Ala Glu Glu Ala
1               5                   10                  15

Glu Glu Ala Glu Ser
            20

<210> SEQ ID NO 60
<211> LENGTH: 18
<212> TYPE: PRT
<213> ORGANISM: Artificial Sequence
<220> FEATURE:
<223> OTHER INFORMATION: N-terminal extension

<400> SEQUENCE: 60

Ala Glu Glu Ala Glu Glu Ala Glu Glu Ala Glu Glu Ala Glu Glu Ala
1               5                   10                  15

Glu Ser

<210> SEQ ID NO 61
<211> LENGTH: 12
<212> TYPE: PRT
<213> ORGANISM: Artificial Sequence
<220> FEATURE:
<223> OTHER INFORMATION: N-terminal extension

<400> SEQUENCE: 61

Ala Glu Glu Ala Glu Glu Ala Glu Glu Ala Glu Ser
1               5                   10

<210> SEQ ID NO 62
<211> LENGTH: 26
<212> TYPE: PRT
<213> ORGANISM: Artificial Sequence
<220> FEATURE:
<223> OTHER INFORMATION: N-terminal extension

<400> SEQUENCE: 62

Ala Ala Ser Pro Ala Gly Ser Pro Thr Ser Thr Glu Glu Gly Thr Ser
1               5                   10                  15

Glu Ser Ala Thr Pro Glu Ser Gly Pro Gly
            20                  25

<210> SEQ ID NO 63
<211> LENGTH: 24
<212> TYPE: PRT
<213> ORGANISM: Artificial Sequence
<220> FEATURE:
<223> OTHER INFORMATION: N-terminal extension

<400> SEQUENCE: 63

Thr Ser Glu Ser Ala Thr Pro Glu Ser Gly Pro Gly Thr Ser Glu Ser
1               5                   10                  15

Ala Thr Pro Glu Ser Gly Pro Gly
            20

<210> SEQ ID NO 64
<211> LENGTH: 26
<212> TYPE: PRT
<213> ORGANISM: Artificial Sequence
<220> FEATURE:
<223> OTHER INFORMATION: N-terminal extension

<400> SEQUENCE: 64

Ala Ala Ser Pro Ala Gly Ser Pro Thr Ser Thr Glu Glu Gly Thr Ser
```

```
1               5                   10                  15
Glu Ser Ala Thr Pro Glu Ser Gly Pro Gly
            20                  25

<210> SEQ ID NO 65
<211> LENGTH: 22
<212> TYPE: PRT
<213> ORGANISM: Artificial Sequence
<220> FEATURE:
<223> OTHER INFORMATION: N-terminal extension

<400> SEQUENCE: 65

Ala Ala Pro Glu Asp Glu Glu Thr Pro Glu Gln Glu Gly Ser Gly Ser
1               5                   10                  15

Gly Ser Gly Ser Gly Ser
            20

<210> SEQ ID NO 66
<211> LENGTH: 12
<212> TYPE: PRT
<213> ORGANISM: Artificial Sequence
<220> FEATURE:
<223> OTHER INFORMATION: N-terminal extension

<400> SEQUENCE: 66

Ala Ala Pro Glu Asp Glu Glu Thr Pro Glu Gln Glu
1               5                   10

<210> SEQ ID NO 67
<211> LENGTH: 22
<212> TYPE: PRT
<213> ORGANISM: Artificial Sequence
<220> FEATURE:
<223> OTHER INFORMATION: N-terminal extension

<400> SEQUENCE: 67

Ala Ala Pro Asp Glu Gly Thr Glu Glu Thr Glu Gly Ser Gly Ser
1               5                   10                  15

Gly Ser Gly Ser Gly Ser
            20

<210> SEQ ID NO 68
<211> LENGTH: 24
<212> TYPE: PRT
<213> ORGANISM: Artificial Sequence
<220> FEATURE:
<223> OTHER INFORMATION: N-terminal extension

<400> SEQUENCE: 68

Ser Glu Pro Ala Thr Ser Gly Ser Glu Thr Pro Gly Ser Glu Pro Ala
1               5                   10                  15

Thr Ser Gly Ser Glu Thr Pro Gly
            20

<210> SEQ ID NO 69
<211> LENGTH: 25
<212> TYPE: PRT
<213> ORGANISM: Artificial Sequence
<220> FEATURE:
<223> OTHER INFORMATION: N-terminal extension

<400> SEQUENCE: 69

Ala Gly Pro Glu Gln Gly Gln Glu Pro Gly Pro Glu Gln Gly Gln Glu
1               5                   10                  15
```

```
Pro Gly Pro Glu Gln Gly Gln Glu Pro
            20              25
```

<210> SEQ ID NO 70
<211> LENGTH: 30
<212> TYPE: PRT
<213> ORGANISM: Artificial Sequence
<220> FEATURE:
<223> OTHER INFORMATION: N-terminal extension

<400> SEQUENCE: 70

```
Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser
            20                  25                  30
```

<210> SEQ ID NO 71
<211> LENGTH: 32
<212> TYPE: PRT
<213> ORGANISM: Artificial Sequence
<220> FEATURE:
<223> OTHER INFORMATION: N-terminal extension

<400> SEQUENCE: 71

```
Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30
```

<210> SEQ ID NO 72
<211> LENGTH: 24
<212> TYPE: PRT
<213> ORGANISM: Artificial Sequence
<220> FEATURE:
<223> OTHER INFORMATION: N-terminal extension

<400> SEQUENCE: 72

```
Gly Glu Pro Ser Gly Glu Pro Ser Gly Glu Pro Ser Gly Glu Pro Ser
1               5                   10                  15

Gly Glu Pro Ser Gly Glu Pro Ser
            20
```

<210> SEQ ID NO 73
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 73

```
Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95
```

Ser Leu Gln Thr Tyr Asp Asp Leu Leu Ala Lys Asp Cys His Cys Ile
            100                 105                 110

<210> SEQ ID NO 74
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 74

Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Glu Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 75
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 75

Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Glu Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 76
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 76

Ala Ala Glu Gly Asp His Cys Pro Leu Gly Pro Gly Arg Cys Cys Arg
1               5                   10                  15

Leu Glu Thr Val Arg Ala Ser Leu Glu Asp Leu Gly Trp Ala Asp Trp

```
            20                  25                  30
Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 77
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 77

Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Glu Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 78
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 78

Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Glu Asp Cys His Cys Ile
            100                 105                 110
```

<210> SEQ ID NO 79
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 79

```
Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Glu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 80
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 80

```
Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Glu Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 81
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 81

```
Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
```

35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Glu Ala Lys Asp Cys His Cys Ile
            100                 105                 110

<210> SEQ ID NO 82
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 82

Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Glu His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 83
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 83

Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Glu Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 84
<211> LENGTH: 112

<212> TYPE: PRT
<213> ORGANISM: Artificial Sequence
<220> FEATURE:
<223> OTHER INFORMATION: MIC-1 polypeptide

<400> SEQUENCE: 84

Ala Ala Glu Gly Asp His Cys Pro Leu Gly Glu Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 85
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 85

Ala Ala Glu Gly Asp His Cys Pro Leu Gly Pro Gly Arg Cys Cys Arg
1               5                   10                  15

Leu His Thr Val Glu Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 86
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 86

Ala Ala Glu Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Glu Ala Ala Asn Met His Ala Gln Ile Lys Thr Ser

```
                50                  55                  60
Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
                100                 105                 110
```

<210> SEQ ID NO 87
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 87

```
Ala Ala Glu Gly Asp His Cys Pro Leu Gly Pro Gly Arg Cys Cys Arg
  1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
 50                  55                  60

Leu His Glu Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
                100                 105                 110
```

<210> SEQ ID NO 88
<211> LENGTH: 112
<212> TYPE: PRT
<213> ORGANISM: Artificial Sequence
<220> FEATURE:
<223> OTHER INFORMATION: MIC-1 polypeptide

<400> SEQUENCE: 88

```
Ala Ala Glu Gly Asp His Cys Pro Leu Gly Pro Gly Arg Cys Cys Arg
  1               5                  10                  15

Leu His Thr Val Arg Ala Ser Leu Glu Asp Leu Gly Trp Glu Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
                100                 105                 110
```

<210> SEQ ID NO 89
<211> LENGTH: 115
<212> TYPE: PRT
<213> ORGANISM: Artificial Sequence
<220> FEATURE:

<223> OTHER INFORMATION: MIC-1 polypeptide with N-terminal extension

<400> SEQUENCE: 89

```
Ala Glu Glu Ala Glu Ser Gly Asp His Cys Pro Leu Gly Pro Gly Arg
1               5                   10                  15

Cys Cys Arg Leu His Thr Val Arg Ala Ser Leu Glu Asp Leu Gly Trp
            20                  25                  30

Ala Asp Trp Val Leu Ser Pro Arg Glu Val Gln Val Thr Met Cys Ile
        35                  40                  45

Gly Ala Cys Pro Ser Gln Phe Arg Ala Ala Asn Met His Ala Gln Ile
    50                  55                  60

Lys Thr Ser Leu His Arg Leu Lys Pro Asp Thr Val Pro Ala Pro Cys
65                  70                  75                  80

Cys Val Pro Ala Ser Tyr Asn Pro Met Val Leu Ile Gln Lys Thr Asp
                85                  90                  95

Thr Gly Val Ser Leu Gln Thr Tyr Asp Asp Leu Leu Ala Lys Asp Cys
            100                 105                 110

His Cys Ile
        115
```

<210> SEQ ID NO 90
<211> LENGTH: 112
<212> TYPE: PRT
<213> ORGANISM: Artificial Sequence
<220> FEATURE:
<223> OTHER INFORMATION: MIC-1 polypeptide with N-terminal extension

<400> SEQUENCE: 90

```
Ala Glu Ser Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 91
<211> LENGTH: 118
<212> TYPE: PRT
<213> ORGANISM: Artificial Sequence
<220> FEATURE:
<223> OTHER INFORMATION: MIC-1 polypeptide with N-terminal extension

<400> SEQUENCE: 91

```
Ala Glu Glu Ala Glu Glu Ala Glu Ser Gly Asp His Cys Pro Leu Gly
1               5                   10                  15

Pro Gly Arg Cys Cys Arg Leu His Thr Val Arg Ala Ser Leu Glu Asp
            20                  25                  30

Leu Gly Trp Ala Asp Trp Val Leu Ser Pro Arg Glu Val Gln Val Thr
        35                  40                  45

Met Cys Ile Gly Ala Cys Pro Ser Gln Phe Arg Ala Ala Asn Met His
```

```
                50                  55                  60
Ala Gln Ile Lys Thr Ser Leu His Arg Leu Lys Pro Asp Thr Val Pro
 65                  70                  75                  80

Ala Pro Cys Cys Val Pro Ala Ser Tyr Asn Pro Met Val Leu Ile Gln
                 85                  90                  95

Lys Thr Asp Thr Gly Val Ser Leu Gln Thr Tyr Asp Asp Leu Leu Ala
                100                 105                 110

Lys Asp Cys His Cys Ile
            115

<210> SEQ ID NO 92
<211> LENGTH: 132
<212> TYPE: PRT
<213> ORGANISM: Artificial Sequence
<220> FEATURE:
<223> OTHER INFORMATION: MIC-1 polypeptide with N-terminal extension

<400> SEQUENCE: 92

Gly Glu Pro Ser Gly Glu Pro Ser Gly Glu Pro Ser Gly Glu Pro Ser
  1               5                  10                  15

Gly Glu Pro Ser Ala Arg Asn Gly Asp His Cys Pro Leu Gly Pro Gly
                 20                  25                  30

Arg Cys Cys Arg Leu His Thr Val Arg Ala Ser Leu Glu Asp Leu Gly
             35                  40                  45

Trp Ala Asp Trp Val Leu Ser Pro Arg Glu Val Gln Val Thr Met Cys
 50                  55                  60

Ile Gly Ala Cys Pro Ser Gln Phe Arg Ala Ala Asn Met His Ala Gln
 65                  70                  75                  80

Ile Lys Thr Ser Leu His Arg Leu Lys Pro Asp Thr Val Pro Ala Pro
                 85                  90                  95

Cys Cys Val Pro Ala Ser Tyr Asn Pro Met Val Leu Ile Gln Lys Thr
                100                 105                 110

Asp Thr Gly Val Ser Leu Gln Thr Tyr Asp Asp Leu Leu Ala Lys Asp
            115                 120                 125

Cys His Cys Ile
        130

<210> SEQ ID NO 93
<211> LENGTH: 136
<212> TYPE: PRT
<213> ORGANISM: Artificial Sequence
<220> FEATURE:
<223> OTHER INFORMATION: MIC-1 polypeptide with N-terminal extension

<400> SEQUENCE: 93

Ser Pro Ala Gly Ser Pro Thr Ser Thr Glu Glu Gly Thr Ser Glu Ser
  1               5                  10                  15

Ala Thr Pro Glu Ser Gly Pro Gly Ala Arg Asn Gly Asp His Cys Pro
                 20                  25                  30

Leu Gly Pro Gly Arg Cys Cys Arg Leu His Thr Val Arg Ala Ser Leu
             35                  40                  45

Glu Asp Leu Gly Trp Ala Asp Trp Val Leu Ser Pro Arg Glu Val Gln
 50                  55                  60

Val Thr Met Cys Ile Gly Ala Cys Pro Ser Gln Phe Arg Ala Ala Asn
 65                  70                  75                  80

Met His Ala Gln Ile Lys Thr Ser Leu His Arg Leu Lys Pro Asp Thr
                 85                  90                  95
```

Val Pro Ala Pro Cys Cys Val Pro Ala Ser Tyr Asn Pro Met Val Leu
            100                 105                 110

Ile Gln Lys Thr Asp Thr Gly Val Ser Leu Gln Thr Tyr Asp Asp Leu
        115                 120                 125

Leu Ala Lys Asp Cys His Cys Ile
    130                 135

<210> SEQ ID NO 94
<211> LENGTH: 130
<212> TYPE: PRT
<213> ORGANISM: Artificial Sequence
<220> FEATURE:
<223> OTHER INFORMATION: MIC-1 polypeptide with N-terminal extension

<400> SEQUENCE: 94

Ala Glu Glu Ala Glu Glu Ala Glu Glu Ala Glu Glu Ala Glu Glu Ala
1               5                   10                  15

Glu Glu Ala Glu Ser Gly Asp His Cys Pro Leu Gly Pro Gly Arg Cys
            20                  25                  30

Cys Arg Leu His Thr Val Arg Ala Ser Leu Glu Asp Leu Gly Trp Ala
        35                  40                  45

Asp Trp Val Leu Ser Pro Arg Glu Val Gln Val Thr Met Cys Ile Gly
    50                  55                  60

Ala Cys Pro Ser Gln Phe Arg Ala Ala Asn Met His Ala Gln Ile Lys
65                  70                  75                  80

Thr Ser Leu His Arg Leu Lys Pro Asp Thr Val Pro Ala Pro Cys Cys
                85                  90                  95

Val Pro Ala Ser Tyr Asn Pro Met Val Leu Ile Gln Lys Thr Asp Thr
            100                 105                 110

Gly Val Ser Leu Gln Thr Tyr Asp Asp Leu Leu Ala Lys Asp Cys His
        115                 120                 125

Cys Ile
    130

<210> SEQ ID NO 95
<211> LENGTH: 127
<212> TYPE: PRT
<213> ORGANISM: Artificial Sequence
<220> FEATURE:
<223> OTHER INFORMATION: MIC-1 polypeptide with N-terminal extension

<400> SEQUENCE: 95

Ala Glu Glu Ala Glu Glu Ala Glu Glu Ala Glu Glu Ala Glu Glu Ala
1               5                   10                  15

Glu Ser Gly Asp His Cys Pro Leu Gly Pro Gly Arg Cys Cys Arg Leu
            20                  25                  30

His Thr Val Arg Ala Ser Leu Glu Asp Leu Gly Trp Ala Asp Trp Val
        35                  40                  45

Leu Ser Pro Arg Glu Val Gln Val Thr Met Cys Ile Gly Ala Cys Pro
    50                  55                  60

Ser Gln Phe Arg Ala Ala Asn Met His Ala Gln Ile Lys Thr Ser Leu
65                  70                  75                  80

His Arg Leu Lys Pro Asp Thr Val Pro Ala Pro Cys Cys Val Pro Ala
                85                  90                  95

Ser Tyr Asn Pro Met Val Leu Ile Gln Lys Thr Asp Thr Gly Val Ser
            100                 105                 110

Leu Gln Thr Tyr Asp Asp Leu Leu Ala Lys Asp Cys His Cys Ile
        115                 120                 125

<210> SEQ ID NO 96
<211> LENGTH: 121
<212> TYPE: PRT
<213> ORGANISM: Artificial Sequence
<220> FEATURE:
<223> OTHER INFORMATION: MIC-1 polypeptide with N-terminal extension

<400> SEQUENCE: 96

Ala Glu Ala Glu Glu Ala Glu Ala Glu Ser Gly Asp His Cys
1               5                   10                  15

Pro Leu Gly Pro Gly Arg Cys Cys Arg Leu His Thr Val Arg Ala Ser
            20                  25                  30

Leu Glu Asp Leu Gly Trp Ala Asp Trp Val Leu Ser Pro Arg Glu Val
        35                  40                  45

Gln Val Thr Met Cys Ile Gly Ala Cys Pro Ser Gln Phe Arg Ala Ala
    50                  55                  60

Asn Met His Ala Gln Ile Lys Thr Ser Leu His Arg Leu Lys Pro Asp
65                  70                  75                  80

Thr Val Pro Ala Pro Cys Cys Val Pro Ala Ser Tyr Asn Pro Met Val
                85                  90                  95

Leu Ile Gln Lys Thr Asp Thr Gly Val Ser Leu Gln Thr Tyr Asp Asp
            100                 105                 110

Leu Leu Ala Lys Asp Cys His Cys Ile
        115                 120

<210> SEQ ID NO 97
<211> LENGTH: 138
<212> TYPE: PRT
<213> ORGANISM: Artificial Sequence
<220> FEATURE:
<223> OTHER INFORMATION: MIC-1 polypeptide with N-terminal extension

<400> SEQUENCE: 97

Ala Ala Ser Pro Ala Gly Ser Pro Thr Ser Thr Glu Glu Gly Thr Ser
1               5                   10                  15

Glu Ser Ala Thr Pro Glu Ser Gly Pro Gly Ala Arg Asn Gly Asp His
            20                  25                  30

Cys Pro Leu Gly Pro Gly Arg Cys Cys Arg Leu His Thr Val Arg Ala
        35                  40                  45

Ser Leu Glu Asp Leu Gly Trp Ala Asp Trp Val Leu Ser Pro Arg Glu
    50                  55                  60

Val Gln Val Thr Met Cys Ile Gly Ala Cys Pro Ser Gln Phe Arg Ala
65                  70                  75                  80

Ala Asn Met His Ala Gln Ile Lys Thr Ser Leu His Arg Leu Lys Pro
                85                  90                  95

Asp Thr Val Pro Ala Pro Cys Cys Val Pro Ala Ser Tyr Asn Pro Met
            100                 105                 110

Val Leu Ile Gln Lys Thr Asp Thr Gly Val Ser Leu Gln Thr Tyr Asp
        115                 120                 125

Asp Leu Leu Ala Lys Asp Cys His Cys Ile
    130                 135

<210> SEQ ID NO 98
<211> LENGTH: 136
<212> TYPE: PRT
<213> ORGANISM: Artificial Sequence
<220> FEATURE:
<223> OTHER INFORMATION: MIC-1 polypeptide with N-terminal extension

<400> SEQUENCE: 98

Thr Ser Glu Ser Ala Thr Pro Glu Ser Gly Pro Gly Thr Ser Glu Ser
1               5                   10                  15

Ala Thr Pro Glu Ser Gly Pro Gly Ala Ala Glu Gly Asp His Cys Pro
            20                  25                  30

Leu Gly Pro Gly Arg Cys Cys Arg Leu His Thr Val Arg Ala Ser Leu
        35                  40                  45

Glu Asp Leu Gly Trp Ala Asp Trp Val Leu Ser Pro Arg Glu Val Gln
    50                  55                  60

Val Thr Met Cys Ile Gly Ala Cys Pro Ser Gln Phe Arg Ala Ala Asn
65                  70                  75                  80

Met His Ala Gln Ile Lys Thr Ser Leu His Arg Leu Lys Pro Asp Thr
                85                  90                  95

Val Pro Ala Pro Cys Cys Val Pro Ala Ser Tyr Asn Pro Met Val Leu
            100                 105                 110

Ile Gln Lys Thr Asp Thr Gly Val Ser Leu Gln Thr Tyr Asp Asp Leu
        115                 120                 125

Leu Ala Lys Asp Cys His Cys Ile
    130                 135

<210> SEQ ID NO 99
<211> LENGTH: 135
<212> TYPE: PRT
<213> ORGANISM: Artificial Sequence
<220> FEATURE:
<223> OTHER INFORMATION: MIC-1 polypeptide with N-terminal extension

<400> SEQUENCE: 99

Ala Ala Ser Pro Ala Gly Ser Pro Thr Ser Thr Glu Glu Gly Thr Ser
1               5                   10                  15

Glu Ser Ala Thr Pro Glu Ser Gly Pro Gly Gly Asp His Cys Pro Leu
            20                  25                  30

Gly Pro Gly Arg Cys Cys Arg Leu His Thr Val Arg Ala Ser Leu Glu
        35                  40                  45

Asp Leu Gly Trp Ala Asp Trp Val Leu Ser Pro Arg Glu Val Gln Val
    50                  55                  60

Thr Met Cys Ile Gly Ala Cys Pro Ser Gln Phe Arg Ala Ala Asn Met
65                  70                  75                  80

His Ala Gln Ile Lys Thr Ser Leu His Arg Leu Lys Pro Asp Thr Val
                85                  90                  95

Pro Ala Pro Cys Cys Val Pro Ala Ser Tyr Asn Pro Met Val Leu Ile
            100                 105                 110

Gln Lys Thr Asp Thr Gly Val Ser Leu Gln Thr Tyr Asp Asp Leu Leu
        115                 120                 125

Ala Lys Asp Cys His Cys Ile
    130                 135

<210> SEQ ID NO 100
<211> LENGTH: 131
<212> TYPE: PRT
<213> ORGANISM: Artificial Sequence
<220> FEATURE:
<223> OTHER INFORMATION: MIC-1 polypeptide with N-terminal extension

<400> SEQUENCE: 100

Ala Ala Pro Glu Asp Glu Glu Thr Pro Glu Gln Glu Gly Ser Gly Ser
1               5                   10                  15

Gly Ser Gly Ser Gly Ser Gly Asp His Cys Pro Leu Gly Pro Gly Arg
            20                  25                  30

Cys Cys Arg Leu His Thr Val Arg Ala Ser Leu Glu Asp Leu Gly Trp
            35                  40                  45

Ala Asp Trp Val Leu Ser Pro Arg Glu Val Gln Val Thr Met Cys Ile
 50                  55                  60

Gly Ala Cys Pro Ser Gln Phe Arg Ala Ala Asn Met His Ala Gln Ile
 65                  70                  75                  80

Lys Thr Ser Leu His Arg Leu Lys Pro Asp Thr Val Pro Ala Pro Cys
            85                  90                  95

Cys Val Pro Ala Ser Tyr Asn Pro Met Val Leu Ile Gln Lys Thr Asp
            100                 105                 110

Thr Gly Val Ser Leu Gln Thr Tyr Asp Asp Leu Leu Ala Lys Asp Cys
            115                 120                 125

His Cys Ile
    130

<210> SEQ ID NO 101
<211> LENGTH: 121
<212> TYPE: PRT
<213> ORGANISM: Artificial Sequence
<220> FEATURE:
<223> OTHER INFORMATION: MIC-1 polypeptide with N-terminal extension

<400> SEQUENCE: 101

Ala Ala Pro Glu Asp Glu Glu Thr Pro Glu Gln Glu Gly Asp His Cys
 1               5                   10                  15

Pro Leu Gly Pro Gly Arg Cys Cys Arg Leu His Thr Val Arg Ala Ser
            20                  25                  30

Leu Glu Asp Leu Gly Trp Ala Asp Trp Val Leu Ser Pro Arg Glu Val
            35                  40                  45

Gln Val Thr Met Cys Ile Gly Ala Cys Pro Ser Gln Phe Arg Ala Ala
 50                  55                  60

Asn Met His Ala Gln Ile Lys Thr Ser Leu His Arg Leu Lys Pro Asp
 65                  70                  75                  80

Thr Val Pro Ala Pro Cys Cys Val Pro Ala Ser Tyr Asn Pro Met Val
            85                  90                  95

Leu Ile Gln Lys Thr Asp Thr Gly Val Ser Leu Gln Thr Tyr Asp Asp
            100                 105                 110

Leu Leu Ala Lys Asp Cys His Cys Ile
            115                 120

<210> SEQ ID NO 102
<211> LENGTH: 131
<212> TYPE: PRT
<213> ORGANISM: Artificial Sequence
<220> FEATURE:
<223> OTHER INFORMATION: MIC-1 polypeptide with N-terminal extension

<400> SEQUENCE: 102

Ala Ala Pro Asp Glu Gly Thr Glu Glu Thr Glu Gly Ser Gly Ser
 1               5                   10                  15

Gly Ser Gly Ser Gly Ser Gly Asp His Cys Pro Leu Gly Pro Gly Arg
            20                  25                  30

Cys Cys Arg Leu His Thr Val Arg Ala Ser Leu Glu Asp Leu Gly Trp
            35                  40                  45

Ala Asp Trp Val Leu Ser Pro Arg Glu Val Gln Val Thr Met Cys Ile

```
                50                   55                  60

Gly Ala Cys Pro Ser Gln Phe Arg Ala Ala Asn Met His Ala Gln Ile
 65                  70                  75                  80

Lys Thr Ser Leu His Arg Leu Lys Pro Asp Thr Val Pro Ala Pro Cys
                 85                  90                  95

Cys Val Pro Ala Ser Tyr Asn Pro Met Val Leu Ile Gln Lys Thr Asp
                100                 105                 110

Thr Gly Val Ser Leu Gln Thr Tyr Asp Asp Leu Leu Ala Lys Asp Cys
            115                 120                 125

His Cys Ile
        130

<210> SEQ ID NO 103
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 103

Ser Glu Pro Ala Thr Ser Gly Ser Glu Thr Pro Gly Thr Ser Thr Glu
 1               5                  10                  15

Pro Ser Glu Gly Ser Ala Pro Gly Gly Asp His Cys Pro Leu Gly Pro
                20                  25                  30

Gly Arg Cys Cys Arg Leu His Thr Val Arg Ala Ser Leu Glu Asp Leu
            35                  40                  45

Gly Trp Ala Asp Trp Val Leu Ser Pro Arg Glu Val Gln Val Thr Met
        50                  55                  60

Cys Ile Gly Ala Cys Pro Ser Gln Phe Arg Ala Ala Asn Met His Ala
 65                  70                  75                  80

Gln Ile Lys Thr Ser Leu His Arg Leu Lys Pro Asp Thr Val Pro Ala
                 85                  90                  95

Pro Cys Cys Val Pro Ala Ser Tyr Asn Pro Met Val Leu Ile Gln Lys
                100                 105                 110

Thr Asp Thr Gly Val Ser Leu Gln Thr Tyr Asp Asp Leu Leu Ala Lys
            115                 120                 125

Asp Cys His Cys Ile
        130

<210> SEQ ID NO 104
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 104

Ser Glu Pro Ala Thr Ser Gly Ser Glu Thr Pro Gly Ser Glu Pro Ala
 1               5                  10                  15

Thr Ser Gly Ser Glu Thr Pro Gly Gly Asp His Cys Pro Leu Gly Pro
                20                  25                  30

Gly Arg Cys Cys Arg Leu His Thr Val Arg Ala Ser Leu Glu Asp Leu
            35                  40                  45

Gly Trp Ala Asp Trp Val Leu Ser Pro Arg Glu Val Gln Val Thr Met
        50                  55                  60

Cys Ile Gly Ala Cys Pro Ser Gln Phe Arg Ala Ala Asn Met His Ala
 65                  70                  75                  80
```

```
Gln Ile Lys Thr Ser Leu His Arg Leu Lys Pro Asp Thr Val Pro Ala
            85                  90                  95

Pro Cys Cys Val Pro Ala Ser Tyr Asn Pro Met Val Leu Ile Gln Lys
            100                 105                 110

Thr Asp Thr Gly Val Ser Leu Gln Thr Tyr Asp Asp Leu Leu Ala Lys
        115                 120                 125

Asp Cys His Cys Ile
    130

<210> SEQ ID NO 105
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 105

Ser Glu Pro Ala Thr Ser Gly Ser Glu Thr Pro Gly Ser Glu Pro Ala
1               5                   10                  15

Thr Ser Gly Ser Glu Thr Pro Gly Gly Asp His Cys Pro Leu Gly Pro
            20                  25                  30

Gly Arg Cys Cys Arg Leu His Thr Val Arg Ala Ser Leu Glu Asp Leu
        35                  40                  45

Gly Trp Ala Asp Trp Val Leu Ser Pro Arg Glu Val Gln Val Thr Met
    50                  55                  60

Cys Ile Gly Ala Cys Pro Ser Gln Phe Arg Ala Ala Asn Glu His Ala
65                  70                  75                  80

Gln Ile Lys Thr Ser Leu His Arg Leu Lys Pro Asp Thr Val Pro Ala
            85                  90                  95

Pro Cys Cys Val Pro Ala Ser Tyr Asn Pro Met Val Leu Ile Gln Lys
            100                 105                 110

Thr Asp Thr Gly Val Ser Leu Gln Thr Tyr Asp Asp Leu Leu Ala Lys
        115                 120                 125

Asp Cys His Cys Ile
    130

<210> SEQ ID NO 106
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 106

Ser Glu Pro Ala Thr Ser Gly Ser Glu Thr Pro Gly Ser Glu Pro Ala
1               5                   10                  15

Thr Ser Gly Ser Glu Thr Pro Gly Gly Asp His Cys Pro Leu Gly Pro
            20                  25                  30

Gly Arg Cys Cys Arg Leu His Thr Val Arg Ala Ser Leu Glu Asp Leu
        35                  40                  45

Gly Trp Ala Asp Trp Val Leu Ser Pro Arg Glu Val Gln Val Thr Met
    50                  55                  60

Cys Ile Gly Ala Cys Pro Ser Gln Phe Arg Ala Ala Asn Leu His Ala
65                  70                  75                  80

Gln Ile Lys Thr Ser Leu His Arg Leu Lys Pro Asp Thr Val Pro Ala
            85                  90                  95

Pro Cys Cys Val Pro Ala Ser Tyr Asn Pro Met Val Leu Ile Gln Lys
            100                 105                 110
```

```
Thr Asp Thr Gly Val Ser Leu Gln Thr Tyr Asp Asp Leu Leu Ala Lys
        115                 120                 125

Asp Cys His Cys Ile
    130

<210> SEQ ID NO 107
<211> LENGTH: 134
<212> TYPE: PRT
<213> ORGANISM: Artificial Sequence
<220> FEATURE:
<223> OTHER INFORMATION: MIC-1 polypeptide with N-terminal extension

<400> SEQUENCE: 107

Ala Gly Pro Glu Gln Gly Gln Glu Pro Gly Pro Gln Gly Gln Glu
1               5                   10                  15

Pro Gly Pro Glu Gln Gly Gln Glu Pro Gly Asp His Cys Pro Leu Gly
                20                  25                  30

Pro Gly Arg Cys Cys Arg Leu His Thr Val Arg Ala Ser Leu Glu Asp
            35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
        115                 120                 125

Lys Asp Cys His Cys Ile
    130

<210> SEQ ID NO 108
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 108

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Gly Asp
                20                  25                  30

His Cys Pro Leu Gly Pro Gly Arg Cys Cys Arg Leu His Thr Val Arg
            35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Met His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
        115                 120                 125

Asp Asp Leu Leu Ala Lys Asp Cys His Cys Ile
```

130                 135

<210> SEQ ID NO 109
<211> LENGTH: 141
<212> TYPE: PRT
<213> ORGANISM: Artificial Sequence
<220> FEATURE:
<223> OTHER INFORMATION: MIC-1 polypeptide with N-terminal extension

<400> SEQUENCE: 109

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
                20                  25                  30

Gly Asp His Cys Pro Leu Gly Pro Gly Arg Cys Cys Arg Leu His Thr
            35                  40                  45

Val Arg Ala Ser Leu Glu Asp Leu Gly Trp Ala Asp Trp Val Leu Ser
        50                  55                  60

Pro Arg Glu Val Gln Val Thr Met Cys Ile Gly Ala Cys Pro Ser Gln
65                  70                  75                  80

Phe Arg Ala Ala Asn Met His Ala Gln Ile Lys Thr Ser Leu His Arg
                85                  90                  95

Leu Lys Pro Asp Thr Val Pro Ala Pro Cys Cys Val Pro Ala Ser Tyr
            100                 105                 110

Asn Pro Met Val Leu Ile Gln Lys Thr Asp Thr Gly Val Ser Leu Gln
        115                 120                 125

Thr Tyr Asp Asp Leu Leu Ala Lys Asp Cys His Cys Ile
    130                 135                 140

<210> SEQ ID NO 110
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 110

Ser Glu Pro Ala Thr Ser Gly Ser Glu Thr Pro Gly Ser Glu Pro Ala
1               5                   10                  15

Thr Ser Gly Ser Glu Thr Pro Gly Gly Asp His Cys Pro Leu Gly Pro
                20                  25                  30

Gly Arg Cys Cys Arg Leu His Thr Val Arg Ala Ser Leu Glu Asp Leu
            35                  40                  45

Gly Trp Ala Asp Trp Val Leu Ser Pro Arg Glu Val Gln Val Thr Met
        50                  55                  60

Cys Ile Gly Ala Cys Pro Ser Gln Phe Arg Ala Ala Asn Met His Ala
65                  70                  75                  80

Gln Ile Lys Thr Ser Leu His Arg Leu Lys Pro Asp Thr Val Pro Ala
                85                  90                  95

Pro Cys Cys Val Pro Ala Ser Tyr Asn Pro Leu Val Leu Ile Gln Lys
            100                 105                 110

Thr Asp Thr Gly Val Ser Leu Gln Thr Tyr Asp Asp Leu Leu Ala Lys
        115                 120                 125

Asp Cys His Cys Ile
    130

<210> SEQ ID NO 111
<211> LENGTH: 133

```
<212> TYPE: PRT
<213> ORGANISM: Artificial Sequence
<220> FEATURE:
<223> OTHER INFORMATION: MIC-1 polypeptide with N-terminal extension

<400> SEQUENCE: 111

Ser Glu Pro Ala Thr Ser Gly Ser Glu Thr Pro Gly Ser Glu Pro Ala
1               5                   10                  15

Thr Ser Gly Ser Glu Thr Pro Gly Gly Asp His Cys Pro Leu Gly Pro
                20                  25                  30

Gly Arg Cys Cys Arg Leu His Thr Val Arg Ala Ser Leu Glu Asp Leu
            35                  40                  45

Gly Trp Ala Asp Trp Val Leu Ser Pro Arg Glu Val Gln Val Thr Met
        50                  55                  60

Cys Ile Gly Ala Cys Pro Ser Gln Phe Arg Ala Ala Asn Leu His Ala
65                  70                  75                  80

Gln Ile Lys Thr Ser Leu His Arg Leu Lys Pro Asp Thr Val Pro Ala
                85                  90                  95

Pro Cys Cys Val Pro Ala Ser Tyr Asn Pro Leu Val Leu Ile Gln Lys
            100                 105                 110

Thr Asp Thr Gly Val Ser Leu Gln Thr Tyr Asp Asp Leu Leu Ala Lys
        115                 120                 125

Asp Cys His Cys Ile
        130

<210> SEQ ID NO 112
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 112

Ser Glu Pro Ala Thr Ser Gly Ser Glu Thr Pro Gly Ser Glu Pro Ala
1               5                   10                  15

Thr Ser Gly Ser Glu Thr Pro Gly Gly Asp His Cys Pro Leu Gly Pro
                20                  25                  30

Gly Arg Cys Cys Arg Leu His Thr Val Arg Ala Ser Leu Glu Asp Leu
            35                  40                  45

Gly Trp Ala Asp Trp Val Leu Ser Pro Arg Glu Val Gln Val Thr Met
        50                  55                  60

Cys Ile Gly Ala Cys Pro Ser Gln Phe Arg Ala Ala Asn Glu His Ala
65                  70                  75                  80

Gln Ile Lys Thr Ser Leu Glu Arg Leu Lys Pro Asp Thr Val Pro Ala
                85                  90                  95

Pro Cys Cys Val Pro Ala Ser Tyr Asn Pro Met Val Leu Ile Gln Lys
            100                 105                 110

Thr Asp Thr Gly Val Ser Leu Gln Thr Tyr Asp Asp Leu Leu Ala Lys
        115                 120                 125

Asp Cys His Cys Ile
        130

<210> SEQ ID NO 113
<211> LENGTH: 133
<212> TYPE: PRT
<213> ORGANISM: Artificial Sequence
<220> FEATURE:
<223> OTHER INFORMATION: MIC-1 polypeptide with N-terminal extension
```

<400> SEQUENCE: 113

Ser Glu Pro Ala Thr Ser Gly Ser Glu Thr Pro Gly Ser Glu Pro Ala
1               5                   10                  15

Thr Ser Gly Ser Glu Thr Pro Gly Gly Asp His Cys Pro Leu Gly Pro
            20                  25                  30

Gly Arg Cys Cys Arg Leu His Thr Val Arg Ala Ser Leu Glu Asp Leu
        35                  40                  45

Gly Trp Ala Asp Trp Val Leu Ser Pro Arg Glu Val Gln Val Thr Met
    50                  55                  60

Cys Ile Gly Ala Cys Pro Ser Gln Phe Arg Ala Ala Asn Glu His Ala
65                  70                  75                  80

Gln Ile Lys Thr Ser Leu His Glu Leu Lys Pro Asp Thr Val Pro Ala
                85                  90                  95

Pro Cys Cys Val Pro Ala Ser Tyr Asn Pro Met Val Leu Ile Gln Lys
            100                 105                 110

Thr Asp Thr Gly Val Ser Leu Gln Thr Tyr Asp Asp Leu Leu Ala Lys
        115                 120                 125

Asp Cys His Cys Ile
    130

<210> SEQ ID NO 114
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 114

Ser Glu Pro Ala Thr Ser Gly Ser Glu Thr Pro Gly Ser Glu Pro Ala
1               5                   10                  15

Thr Ser Gly Ser Glu Thr Pro Gly Gly Asp His Cys Pro Leu Gly Pro
            20                  25                  30

Gly Arg Cys Cys Arg Leu His Thr Val Arg Ala Ser Leu Glu Asp Leu
        35                  40                  45

Gly Trp Ala Asp Trp Val Leu Ser Pro Arg Glu Val Gln Val Thr Met
    50                  55                  60

Cys Ile Gly Ala Cys Pro Ser Gln Phe Arg Ala Ala Asn Glu His Ala
65                  70                  75                  80

Gln Ile Lys Thr Ser Leu His Glu Leu Lys Pro Asp Thr Val Pro Ala
                85                  90                  95

Pro Cys Cys Val Pro Ala Ser Tyr Asn Pro Leu Val Leu Ile Gln Lys
            100                 105                 110

Thr Asp Thr Gly Val Ser Leu Gln Thr Tyr Asp Asp Leu Leu Ala Lys
        115                 120                 125

Asp Cys His Cys Ile
    130

<210> SEQ ID NO 115
<211> LENGTH: 140
<212> TYPE: PRT
<213> ORGANISM: Artificial Sequence
<220> FEATURE:
<223> OTHER INFORMATION: MIC-1 polypeptide with N-terminal extension

<400> SEQUENCE: 115

Ser Glu Pro Ala Thr Ser Gly Ser Glu Thr Pro Gly Thr Ser Glu Ser
1               5                   10                  15

```
Ala Thr Pro Glu Ser Gly Pro Gly Thr Ser Thr Glu Pro Gly Gly
            20                  25                  30

Asp His Cys Pro Leu Gly Pro Gly Arg Cys Cys Arg Leu His Thr Val
        35                  40                  45

Arg Ala Ser Leu Glu Asp Leu Gly Trp Ala Asp Trp Val Leu Ser Pro
50                  55                  60

Arg Glu Val Gln Val Thr Met Cys Ile Gly Ala Cys Pro Ser Gln Phe
65                  70                  75                  80

Arg Ala Ala Asn Leu His Ala Gln Ile Lys Thr Ser Leu His Arg Leu
                85                  90                  95

Lys Pro Asp Thr Val Pro Ala Pro Cys Cys Val Pro Ala Ser Tyr Asn
            100                 105                 110

Pro Leu Val Leu Ile Gln Lys Thr Asp Thr Gly Val Ser Leu Gln Thr
        115                 120                 125

Tyr Asp Asp Leu Leu Ala Lys Asp Cys His Cys Ile
130                 135                 140
```

<210> SEQ ID NO 116
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 116

```
Gly Glu Pro Ser Gly Glu Pro Ser Gly Glu Pro Ser Gly Glu Pro Ser
1               5                   10                  15

Gly Glu Pro Ser Gly Glu Pro Ser Gly Asp His Cys Pro Leu Gly Pro
            20                  25                  30

Gly Arg Cys Cys Arg Leu His Thr Val Arg Ala Ser Leu Glu Asp Leu
        35                  40                  45

Gly Trp Ala Asp Trp Val Leu Ser Pro Arg Glu Val Gln Val Thr Met
    50                  55                  60

Cys Ile Gly Ala Cys Pro Ser Gln Phe Arg Ala Ala Asn Met His Ala
65                  70                  75                  80

Gln Ile Lys Thr Ser Leu His Arg Leu Lys Pro Asp Thr Val Pro Ala
                85                  90                  95

Pro Cys Cys Val Pro Ala Ser Tyr Asn Pro Met Val Leu Ile Gln Lys
            100                 105                 110

Thr Asp Thr Gly Val Ser Leu Gln Thr Tyr Asp Asp Leu Leu Ala Lys
        115                 120                 125

Asp Cys His Cys Ile
130
```

<210> SEQ ID NO 117
<211> LENGTH: 135
<212> TYPE: PRT
<213> ORGANISM: Artificial Sequence
<220> FEATURE:
<223> OTHER INFORMATION: MIC-1 polypeptide with N-terminal extension

<400> SEQUENCE: 117

```
Ser Glu Pro Ala Thr Ser Gly Glu Thr Pro Gly Ser Glu Pro Ala
1               5                   10                  15

Thr Ser Gly Ser Glu Thr Pro Gly Ala Arg Gly Asp His Cys Pro Leu
            20                  25                  30

Gly Pro Gly Arg Cys Cys Arg Leu His Thr Val Arg Ala Ser Leu Glu
        35                  40                  45
```

Asp Leu Gly Trp Ala Asp Trp Val Leu Ser Pro Arg Glu Val Gln Val
            50                  55                  60

Thr Met Cys Ile Gly Ala Cys Pro Ser Gln Phe Arg Ala Ala Asn Met
 65                  70                  75                  80

His Ala Gln Ile Lys Thr Ser Leu His Arg Leu Lys Pro Asp Thr Val
                 85                  90                  95

Pro Ala Pro Cys Cys Val Pro Ala Ser Tyr Asn Pro Met Val Leu Ile
            100                 105                 110

Gln Lys Thr Asp Thr Gly Val Ser Leu Gln Thr Tyr Asp Asp Leu Leu
            115                 120                 125

Ala Lys Asp Cys His Cys Ile
            130             135

<210> SEQ ID NO 118
<211> LENGTH: 4
<212> TYPE: PRT
<213> ORGANISM: Artificial Sequence
<220> FEATURE:
<223> OTHER INFORMATION: N-terminal extension

<400> SEQUENCE: 118

Gly Glu Pro Ser
1

<210> SEQ ID NO 119
<211> LENGTH: 4
<212> TYPE: PRT
<213> ORGANISM: Artificial Sequence
<220> FEATURE:
<223> OTHER INFORMATION: N-terminal extension

<400> SEQUENCE: 119

Gly Pro Ser Glu
1

<210> SEQ ID NO 120
<211> LENGTH: 4
<212> TYPE: PRT
<213> ORGANISM: Artificial Sequence
<220> FEATURE:
<223> OTHER INFORMATION: N-terminal extension

<400> SEQUENCE: 120

Gly Pro Glu Ser
1

<210> SEQ ID NO 121
<211> LENGTH: 4
<212> TYPE: PRT
<213> ORGANISM: Artificial Sequence
<220> FEATURE:
<223> OTHER INFORMATION: N-terminal extension

<400> SEQUENCE: 121

Gly Ser Pro Glu
1

<210> SEQ ID NO 122
<211> LENGTH: 4
<212> TYPE: PRT
<213> ORGANISM: Artificial Sequence
<220> FEATURE:
<223> OTHER INFORMATION: N-terminal extension

```
<400> SEQUENCE: 122

Gly Ser Glu Pro
1

<210> SEQ ID NO 123
<211> LENGTH: 4
<212> TYPE: PRT
<213> ORGANISM: Artificial Sequence
<220> FEATURE:
<223> OTHER INFORMATION: N-terminal extension

<400> SEQUENCE: 123

Gly Glu Pro Gln
1

<210> SEQ ID NO 124
<211> LENGTH: 4
<212> TYPE: PRT
<213> ORGANISM: Artificial Sequence
<220> FEATURE:
<223> OTHER INFORMATION: N-terminal extension

<400> SEQUENCE: 124

Gly Glu Gln Pro
1

<210> SEQ ID NO 125
<211> LENGTH: 4
<212> TYPE: PRT
<213> ORGANISM: Artificial Sequence
<220> FEATURE:
<223> OTHER INFORMATION: N-terminal extension

<400> SEQUENCE: 125

Gly Pro Glu Gln
1

<210> SEQ ID NO 126
<211> LENGTH: 4
<212> TYPE: PRT
<213> ORGANISM: Artificial Sequence
<220> FEATURE:
<223> OTHER INFORMATION: N-terminal extension

<400> SEQUENCE: 126

Gly Pro Gln Glu
1

<210> SEQ ID NO 127
<211> LENGTH: 4
<212> TYPE: PRT
<213> ORGANISM: Artificial Sequence
<220> FEATURE:
<223> OTHER INFORMATION: N-terminal extension

<400> SEQUENCE: 127

Gly Gln Glu Pro
1

<210> SEQ ID NO 128
<211> LENGTH: 4
<212> TYPE: PRT
<213> ORGANISM: Artificial Sequence
<220> FEATURE:
<223> OTHER INFORMATION: N-terminal extension

<400> SEQUENCE: 128
```

Gly Gln Pro Glu
1

<210> SEQ ID NO 129
<211> LENGTH: 10
<212> TYPE: PRT
<213> ORGANISM: Artificial Sequence
<220> FEATURE:
<223> OTHER INFORMATION: N-terminal extension

<400> SEQUENCE: 129

Pro Glu Asp Glu Glu Thr Pro Glu Gln Glu
1               5                   10

<210> SEQ ID NO 130
<211> LENGTH: 10
<212> TYPE: PRT
<213> ORGANISM: Artificial Sequence
<220> FEATURE:
<223> OTHER INFORMATION: N-terminal extension

<400> SEQUENCE: 130

Pro Asp Glu Gly Thr Glu Glu Thr Glu
1               5                   10

<210> SEQ ID NO 131
<211> LENGTH: 10
<212> TYPE: PRT
<213> ORGANISM: Artificial Sequence
<220> FEATURE:
<223> OTHER INFORMATION: N-terminal extension

<400> SEQUENCE: 131

Pro Ala Ala Glu Glu Asp Asp Pro Asp
1               5                   10

<210> SEQ ID NO 132
<211> LENGTH: 11
<212> TYPE: PRT
<213> ORGANISM: Artificial Sequence
<220> FEATURE:
<223> OTHER INFORMATION: N-terminal extension

<400> SEQUENCE: 132

Ala Glu Pro Asp Glu Asp Pro Gln Ser Glu Asp
1               5                   10

<210> SEQ ID NO 133
<211> LENGTH: 10
<212> TYPE: PRT
<213> ORGANISM: Artificial Sequence
<220> FEATURE:
<223> OTHER INFORMATION: N-terminal extension

<400> SEQUENCE: 133

Ala Glu Pro Asp Glu Asp Pro Gln Ser Glu
1               5                   10

<210> SEQ ID NO 134
<211> LENGTH: 9
<212> TYPE: PRT
<213> ORGANISM: Artificial Sequence
<220> FEATURE:
<223> OTHER INFORMATION: N-terminal extension

<400> SEQUENCE: 134

```
Ala Glu Pro Glu Glu Gln Glu Glu Asp
1               5
```

<210> SEQ ID NO 135
<211> LENGTH: 8
<212> TYPE: PRT
<213> ORGANISM: Artificial Sequence
<220> FEATURE:
<223> OTHER INFORMATION: N-terminal extension

<400> SEQUENCE: 135

```
Ala Glu Pro Glu Glu Gln Glu Glu
1               5
```

<210> SEQ ID NO 136
<211> LENGTH: 4
<212> TYPE: PRT
<213> ORGANISM: Artificial Sequence
<220> FEATURE:
<223> OTHER INFORMATION: N-terminal extension

<400> SEQUENCE: 136

```
Gly Gly Gly Ser
1
```

<210> SEQ ID NO 137
<211> LENGTH: 4
<212> TYPE: PRT
<213> ORGANISM: Artificial Sequence
<220> FEATURE:
<223> OTHER INFORMATION: N-terminal extension

<400> SEQUENCE: 137

```
Gly Ser Gly Ser
1
```

<210> SEQ ID NO 138
<211> LENGTH: 4
<212> TYPE: PRT
<213> ORGANISM: Artificial Sequence
<220> FEATURE:
<223> OTHER INFORMATION: N-terminal extension

<400> SEQUENCE: 138

```
Gly Gly Ser Ser
1
```

<210> SEQ ID NO 139
<211> LENGTH: 4
<212> TYPE: PRT
<213> ORGANISM: Artificial Sequence
<220> FEATURE:
<223> OTHER INFORMATION: N-terminal extension

<400> SEQUENCE: 139

```
Ser Ser Ser Gly
1
```

<210> SEQ ID NO 140
<211> LENGTH: 20
<212> TYPE: PRT
<213> ORGANISM: Artificial Sequence
<220> FEATURE:
<223> OTHER INFORMATION: N-terminal extension

<400> SEQUENCE: 140

```
Gly Glu Pro Ser Gly Glu Pro Ser Gly Glu Pro Ser Gly Glu Pro Ser
```

-continued

```
                 1               5                  10                 15

Gly Glu Pro Ser
             20

<210> SEQ ID NO 141
<211> LENGTH: 20
<212> TYPE: PRT
<213> ORGANISM: Artificial Sequence
<220> FEATURE:
<223> OTHER INFORMATION: N-terminal extension

<400> SEQUENCE: 141

Gly Pro Ser Glu Gly Pro Ser Glu Gly Pro Ser Glu Gly Pro Ser Glu
1               5                   10                  15

Gly Pro Ser Glu
             20

<210> SEQ ID NO 142
<211> LENGTH: 20
<212> TYPE: PRT
<213> ORGANISM: Artificial Sequence
<220> FEATURE:
<223> OTHER INFORMATION: N-terminal extension

<400> SEQUENCE: 142

Gly Pro Glu Ser Gly Pro Glu Ser Gly Pro Glu Ser Gly Pro Glu Ser
1               5                   10                  15

Gly Pro Glu Ser
             20

<210> SEQ ID NO 143
<211> LENGTH: 20
<212> TYPE: PRT
<213> ORGANISM: Artificial Sequence
<220> FEATURE:
<223> OTHER INFORMATION: N-terminal extension

<400> SEQUENCE: 143

Gly Ser Pro Glu Gly Ser Pro Glu Gly Ser Pro Glu Gly Ser Pro Glu
1               5                   10                  15

Gly Ser Pro Glu
             20

<210> SEQ ID NO 144
<211> LENGTH: 20
<212> TYPE: PRT
<213> ORGANISM: Artificial Sequence
<220> FEATURE:
<223> OTHER INFORMATION: N-terminal extension

<400> SEQUENCE: 144

Gly Ser Glu Pro Gly Ser Glu Pro Gly Ser Glu Pro Gly Ser Glu Pro
1               5                   10                  15

Gly Ser Glu Pro
             20

<210> SEQ ID NO 145
<211> LENGTH: 20
<212> TYPE: PRT
<213> ORGANISM: Artificial Sequence
<220> FEATURE:
<223> OTHER INFORMATION: N-terminal extension

<400> SEQUENCE: 145
```

Gly Glu Pro Gln Gly Glu Pro Gln Gly Glu Pro Gln Gly Glu Pro Gln
1               5                   10                  15

Gly Glu Pro Gln
            20

<210> SEQ ID NO 146
<211> LENGTH: 20
<212> TYPE: PRT
<213> ORGANISM: Artificial Sequence
<220> FEATURE:
<223> OTHER INFORMATION: N-terminal extension

<400> SEQUENCE: 146

Gly Glu Gln Pro Gly Glu Gln Pro Gly Glu Gln Pro Gly Glu Gln Pro
1               5                   10                  15

Gly Glu Gln Pro
            20

<210> SEQ ID NO 147
<211> LENGTH: 20
<212> TYPE: PRT
<213> ORGANISM: Artificial Sequence
<220> FEATURE:
<223> OTHER INFORMATION: N-terminal extension

<400> SEQUENCE: 147

Gly Pro Glu Gln Gly Pro Glu Gln Gly Pro Glu Gln Gly Pro Glu Gln
1               5                   10                  15

Gly Pro Glu Gln
            20

<210> SEQ ID NO 148
<211> LENGTH: 20
<212> TYPE: PRT
<213> ORGANISM: Artificial Sequence
<220> FEATURE:
<223> OTHER INFORMATION: N-terminal extension

<400> SEQUENCE: 148

Gly Pro Gln Glu Gly Pro Gln Glu Gly Pro Gln Glu Gly Pro Gln Glu
1               5                   10                  15

Gly Pro Gln Glu
            20

<210> SEQ ID NO 149
<211> LENGTH: 20
<212> TYPE: PRT
<213> ORGANISM: Artificial Sequence
<220> FEATURE:
<223> OTHER INFORMATION: N-terminal extension

<400> SEQUENCE: 149

Gly Gln Glu Pro Gly Gln Glu Pro Gly Gln Glu Pro Gly Gln Glu Pro
1               5                   10                  15

Gly Gln Glu Pro
            20

<210> SEQ ID NO 150
<211> LENGTH: 20
<212> TYPE: PRT
<213> ORGANISM: Artificial Sequence
<220> FEATURE:
<223> OTHER INFORMATION: N-terminal extension

<400> SEQUENCE: 150

```
Gly Gln Pro Glu Gly Gln Pro Glu Gly Gln Pro Glu Gly Gln Pro Glu
1               5                   10                  15

Gly Gln Pro Glu
            20

<210> SEQ ID NO 151
<211> LENGTH: 15
<212> TYPE: PRT
<213> ORGANISM: Artificial Sequence
<220> FEATURE:
<223> OTHER INFORMATION: N-terminal extension

<400> SEQUENCE: 151

Ala Glu Glu Ala Glu Glu Ala Glu Glu Ala Glu Glu Ala Glu Glu
1               5                   10                  15

<210> SEQ ID NO 152
<211> LENGTH: 7
<212> TYPE: PRT
<213> ORGANISM: Artificial Sequence
<220> FEATURE:
<223> OTHER INFORMATION: Linker

<400> SEQUENCE: 152

Gly Gly Ser Ser Ser Gly Ser
1               5

<210> SEQ ID NO 153
<211> LENGTH: 31
<212> TYPE: PRT
<213> ORGANISM: Artificial Sequence
<220> FEATURE:
<223> OTHER INFORMATION: Linker

<400> SEQUENCE: 153

Pro Thr Pro Thr Pro Thr Pro Thr Pro Thr Pro Thr Pro Thr Pro Thr
1               5                   10                  15

Pro Thr Pro Thr Pro Thr Pro Thr Pro Thr Pro Thr Pro Thr Pro
            20                  25                  30

<210> SEQ ID NO 154
<211> LENGTH: 111
<212> TYPE: PRT
<213> ORGANISM: Artificial Sequence
<220> FEATURE:
<223> OTHER INFORMATION: MIC-1 polypeptide

<400> SEQUENCE: 154

Ala Arg Gly Asp His Cys Pro Leu Gly Pro Gly Arg Cys Cys Arg Leu
1               5                   10                  15

His Thr Val Arg Ala Ser Leu Glu Asp Leu Gly Trp Ala Asp Trp Val
            20                  25                  30

Leu Ser Pro Arg Glu Val Gln Val Thr Leu Cys Ile Gly Ala Cys Pro
        35                  40                  45

Ser Gln Phe Arg Ala Ala Asn Met His Ala Gln Ile Lys Thr Ser Leu
    50                  55                  60

His Arg Leu Lys Pro Asp Thr Val Pro Ala Pro Cys Cys Val Pro Ala
65                  70                  75                  80

Ser Tyr Asn Pro Met Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110
```

<210> SEQ ID NO 155
<211> LENGTH: 109
<212> TYPE: PRT
<213> ORGANISM: Artificial Sequence
<220> FEATURE:
<223> OTHER INFORMATION: MIC-1 polypeptide

<400> SEQUENCE: 155

```
Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Leu Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105
```

<210> SEQ ID NO 156
<211> LENGTH: 111
<212> TYPE: PRT
<213> ORGANISM: Artificial Sequence
<220> FEATURE:
<223> OTHER INFORMATION: MIC-1 polypeptide

<400> SEQUENCE: 156

```
Ala Arg Gly Asp His Cys Pro Leu Gly Pro Gly Arg Cys Cys Arg Leu
1               5                   10                  15

His Thr Val Arg Ala Ser Leu Glu Asp Leu Gly Trp Ala Asp Trp Val
            20                  25                  30

Leu Ser Pro Arg Glu Val Gln Val Thr Met Cys Ile Gly Ala Cys Pro
        35                  40                  45

Ser Gln Phe Arg Ala Ala Asn Glu His Ala Gln Ile Lys Thr Ser Leu
    50                  55                  60

Glu Arg Leu Lys Pro Asp Thr Val Pro Ala Pro Cys Cys Val Pro Ala
65                  70                  75                  80

Ser Tyr Asn Pro Met Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110
```

<210> SEQ ID NO 157
<211> LENGTH: 109
<212> TYPE: PRT
<213> ORGANISM: Artificial Sequence
<220> FEATURE:
<223> OTHER INFORMATION: MIC-1 polypeptide

<400> SEQUENCE: 157

```
Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30
```

```
Pro Arg Glu Val Gln Val Thr Met Cys Ile Gly Ala Cys Pro Ser Gln
            35                  40                  45

Phe Arg Ala Ala Asn Leu His Ala Gln Ile Lys Thr Ser Leu His Arg
 50                  55                  60

Leu Lys Pro Asp Thr Val Pro Ala Pro Cys Cys Val Pro Ala Ser Tyr
 65                  70                  75                  80

Asn Pro Met Val Leu Ile Gln Lys Thr Asp Thr Gly Val Ser Leu Gln
                 85                  90                  95

Thr Tyr Asp Asp Leu Leu Ala Lys Asp Cys His Cys Ile
                100                 105
```

<210> SEQ ID NO 158
<211> LENGTH: 111
<212> TYPE: PRT
<213> ORGANISM: Artificial Sequence
<220> FEATURE:
<223> OTHER INFORMATION: MIC-1 polypeptide

<400> SEQUENCE: 158

```
Ala Arg Gly Asp His Cys Pro Leu Gly Pro Gly Arg Cys Cys Arg Leu
 1               5                  10                  15

His Thr Val Arg Ala Ser Leu Glu Asp Leu Gly Trp Ala Asp Trp Val
                 20                  25                  30

Leu Ser Pro Arg Glu Val Gln Val Thr Met Cys Ile Gly Ala Cys Pro
             35                  40                  45

Ser Gln Phe Arg Ala Ala Asn Leu His Ala Gln Ile Lys Thr Ser Leu
 50                  55                  60

His Arg Leu Lys Pro Asp Thr Val Pro Ala Pro Cys Cys Val Pro Ala
 65                  70                  75                  80

Ser Tyr Asn Pro Met Val Leu Ile Gln Lys Thr Asp Thr Gly Val Ser
                 85                  90                  95

Leu Gln Thr Tyr Asp Asp Leu Leu Ala Lys Asp Cys His Cys Ile
            100                 105                 110
```

<210> SEQ ID NO 159
<211> LENGTH: 109
<212> TYPE: PRT
<213> ORGANISM: Artificial Sequence
<220> FEATURE:
<223> OTHER INFORMATION: MIC-1 polypeptide

<400> SEQUENCE: 159

```
Gly Asp His Cys Pro Leu Gly Pro Gly Arg Cys Cys Arg Leu His Thr
 1               5                  10                  15

Val Arg Ala Ser Leu Glu Asp Leu Gly Trp Ala Asp Trp Val Leu Ser
                 20                  25                  30

Pro Arg Glu Val Gln Val Thr Met Cys Ile Gly Ala Cys Pro Ser Gln
            35                  40                  45

Phe Arg Ala Ala Asn Met His Ala Gln Ile Lys Thr Ser Leu His Arg
 50                  55                  60

Leu Lys Pro Asp Thr Val Pro Ala Pro Cys Cys Val Pro Ala Ser Tyr
 65                  70                  75                  80

Asn Pro Leu Val Leu Ile Gln Lys Thr Asp Thr Gly Val Ser Leu Gln
                 85                  90                  95

Thr Tyr Asp Asp Leu Leu Ala Lys Asp Cys His Cys Ile
                100                 105
```

<210> SEQ ID NO 160

```
<211> LENGTH: 111
<212> TYPE: PRT
<213> ORGANISM: Artificial Sequence
<220> FEATURE:
<223> OTHER INFORMATION: MIC-1 polypeptide

<400> SEQUENCE: 160

Ala Arg Gly Asp His Cys Pro Leu Gly Pro Gly Arg Cys Cys Arg Leu
1               5                   10                  15

His Thr Val Arg Ala Ser Leu Glu Asp Leu Gly Trp Ala Asp Trp Val
            20                  25                  30

Leu Ser Pro Arg Glu Val Gln Val Thr Met Cys Ile Gly Ala Cys Pro
        35                  40                  45

Ser Gln Phe Arg Ala Ala Asn Met His Ala Gln Ile Lys Thr Ser Leu
    50                  55                  60

His Arg Leu Lys Pro Asp Thr Val Pro Ala Pro Cys Cys Val Pro Ala
65                  70                  75                  80

Ser Tyr Asn Pro Leu Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110

<210> SEQ ID NO 161
<211> LENGTH: 36
<212> TYPE: PRT
<213> ORGANISM: Artificial Sequence
<220> FEATURE:
<223> OTHER INFORMATION: N-terminal extension

<400> SEQUENCE: 161

Gly Glu Pro Ser Gly Glu Pro Ser Gly Glu Pro Ser Gly Glu Pro Ser
1               5                   10                  15

Gly Glu Pro Ser Gly Glu Pro Ser Gly Glu Pro Ser Gly Glu Pro Ser
            20                  25                  30

Gly Glu Pro Ser
        35

<210> SEQ ID NO 162
<211> LENGTH: 36
<212> TYPE: PRT
<213> ORGANISM: Artificial Sequence
<220> FEATURE:
<223> OTHER INFORMATION: N-terminal extension

<400> SEQUENCE: 162

Gly Glu Pro Gln Gly Glu Pro Gln Gly Glu Pro Gln Gly Glu Pro Gln
1               5                   10                  15

Gly Glu Pro Gln Gly Glu Pro Gln Gly Glu Pro Gln Gly Glu Pro Gln
            20                  25                  30

Gly Glu Pro Gln
        35

<210> SEQ ID NO 163
<211> LENGTH: 25
<212> TYPE: PRT
<213> ORGANISM: Artificial Sequence
<220> FEATURE:
<223> OTHER INFORMATION: N-terminal extension

<400> SEQUENCE: 163

Ala Gly Pro Glu Gln Gly Gln Glu Pro Gly Glu Pro Gln Gly Gln Glu
1               5                   10                  15
```

Pro Gln Pro Gly Glu Pro Gly Gln
          20              25

<210> SEQ ID NO 164
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 164

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
                20                  25                  30

Ala Arg Gly Asp His Cys Pro Leu Gly Pro Gly Arg Cys Cys Arg Leu
            35                  40                  45

His Thr Val Arg Ala Ser Leu Glu Asp Leu Gly Trp Ala Asp Trp Val
        50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                85                  90                  95

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140

<210> SEQ ID NO 165
<211> LENGTH: 134
<212> TYPE: PRT
<213> ORGANISM: Artificial Sequence
<220> FEATURE:
<223> OTHER INFORMATION: MIC-1 polypeptide with N-terminal extension

<400> SEQUENCE: 165

Ala Gly Pro Glu Gln Gly Gln Glu Pro Gly Glu Pro Gln Gly Gln Glu
1               5                   10                  15

Pro Gln Pro Gly Glu Pro Gly Gln Gly Asp His Cys Pro Leu Gly
                20                  25                  30

Pro Gly Arg Cys Cys Arg Leu His Thr Val Arg Ala Ser Leu Glu Asp
            35                  40                  45

Leu Gly Trp Ala Asp Trp Val Leu Ser Pro Arg Glu Val Gln Val Thr
        50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
        115                 120                 125

Lys Asp Cys His Cys Ile
    130

```
<210> SEQ ID NO 166
<211> LENGTH: 12
<212> TYPE: PRT
<213> ORGANISM: Artificial Sequence
<220> FEATURE:
<223> OTHER INFORMATION: N-terminal extension

<400> SEQUENCE: 166

Ser Pro Ala Gly Ser Pro Thr Ser Thr Glu Glu Gly
1               5                   10

<210> SEQ ID NO 167
<211> LENGTH: 12
<212> TYPE: PRT
<213> ORGANISM: Artificial Sequence
<220> FEATURE:
<223> OTHER INFORMATION: N-terminal extension

<400> SEQUENCE: 167

Thr Ser Glu Ser Ala Thr Pro Glu Ser Gly Pro Gly
1               5                   10

<210> SEQ ID NO 168
<211> LENGTH: 12
<212> TYPE: PRT
<213> ORGANISM: Artificial Sequence
<220> FEATURE:
<223> OTHER INFORMATION: N-terminal extension

<400> SEQUENCE: 168

Thr Ser Thr Glu Pro Ser Glu Gly Ser Ala Pro Gly
1               5                   10

<210> SEQ ID NO 169
<211> LENGTH: 12
<212> TYPE: PRT
<213> ORGANISM: Artificial Sequence
<220> FEATURE:
<223> OTHER INFORMATION: N-terminal extension

<400> SEQUENCE: 169

Ser Glu Pro Ala Thr Ser Gly Ser Glu Thr Pro Gly
1               5                   10

<210> SEQ ID NO 170
<211> LENGTH: 24
<212> TYPE: PRT
<213> ORGANISM: Artificial Sequence
<220> FEATURE:
<223> OTHER INFORMATION: N-terminal extension

<400> SEQUENCE: 170

Ser Pro Ala Gly Ser Pro Thr Ser Thr Glu Glu Gly Ser Pro Ala Gly
1               5                   10                  15

Ser Pro Thr Ser Thr Glu Glu Gly
            20

<210> SEQ ID NO 171
<211> LENGTH: 24
<212> TYPE: PRT
<213> ORGANISM: Artificial Sequence
<220> FEATURE:
<223> OTHER INFORMATION: N-terminal extension

<400> SEQUENCE: 171

Ser Pro Ala Gly Ser Pro Thr Ser Thr Glu Glu Gly Thr Ser Thr Glu
1               5                   10                  15
```

Pro Ser Glu Gly Ser Ala Pro Gly
            20

<210> SEQ ID NO 172
<211> LENGTH: 24
<212> TYPE: PRT
<213> ORGANISM: Artificial Sequence
<220> FEATURE:
<223> OTHER INFORMATION: N-terminal extension

<400> SEQUENCE: 172

Ser Pro Ala Gly Ser Pro Thr Ser Thr Glu Glu Gly Ser Glu Pro Ala
1               5                   10                  15

Thr Ser Gly Ser Glu Thr Pro Gly
            20

<210> SEQ ID NO 173
<211> LENGTH: 24
<212> TYPE: PRT
<213> ORGANISM: Artificial Sequence
<220> FEATURE:
<223> OTHER INFORMATION: N-teminal extension

<400> SEQUENCE: 173

Thr Ser Glu Ser Ala Thr Pro Glu Ser Gly Pro Gly Ser Pro Ala Gly
1               5                   10                  15

Ser Pro Thr Ser Thr Glu Glu Gly
            20

<210> SEQ ID NO 174
<211> LENGTH: 24
<212> TYPE: PRT
<213> ORGANISM: Artificial Sequence
<220> FEATURE:
<223> OTHER INFORMATION: N-external extension

<400> SEQUENCE: 174

Thr Ser Glu Ser Ala Thr Pro Glu Ser Gly Pro Gly Thr Ser Glu Ser
1               5                   10                  15

Ala Thr Pro Glu Ser Gly Pro Gly
            20

<210> SEQ ID NO 175
<211> LENGTH: 24
<212> TYPE: PRT
<213> ORGANISM: Artificial Sequence
<220> FEATURE:
<223> OTHER INFORMATION: N-terminal extension

<400> SEQUENCE: 175

Thr Ser Glu Ser Ala Thr Pro Glu Ser Gly Pro Gly Thr Ser Thr Glu
1               5                   10                  15

Pro Ser Glu Gly Ser Ala Pro Gly
            20

<210> SEQ ID NO 176
<211> LENGTH: 24
<212> TYPE: PRT
<213> ORGANISM: Artificial Sequence
<220> FEATURE:
<223> OTHER INFORMATION: N-terminal extension

<400> SEQUENCE: 176

Thr Ser Glu Ser Ala Thr Pro Glu Ser Gly Pro Gly Ser Glu Pro Ala

```
1               5                   10                  15
Thr Ser Gly Ser Glu Thr Pro Gly
            20

<210> SEQ ID NO 177
<211> LENGTH: 24
<212> TYPE: PRT
<213> ORGANISM: Artificial Sequence
<220> FEATURE:
<223> OTHER INFORMATION: N-terminal extension

<400> SEQUENCE: 177

Thr Ser Thr Glu Pro Ser Glu Gly Ser Ala Pro Gly Ser Pro Ala Gly
1               5                   10                  15

Ser Pro Thr Ser Thr Glu Glu Gly
            20

<210> SEQ ID NO 178
<211> LENGTH: 24
<212> TYPE: PRT
<213> ORGANISM: Artificial Sequence
<220> FEATURE:
<223> OTHER INFORMATION: N-terminal extension

<400> SEQUENCE: 178

Thr Ser Thr Glu Pro Ser Glu Gly Ser Ala Pro Gly Thr Ser Glu Ser
1               5                   10                  15

Ala Thr Pro Glu Ser Gly Pro Gly
            20

<210> SEQ ID NO 179
<211> LENGTH: 24
<212> TYPE: PRT
<213> ORGANISM: Artificial Sequence
<220> FEATURE:
<223> OTHER INFORMATION: N-terminal extension

<400> SEQUENCE: 179

Thr Ser Thr Glu Pro Glu Ser Gly Ser Ala Pro Gly Thr Ser Thr Glu
1               5                   10                  15

Pro Glu Ser Gly Ser Ala Pro Gly
            20

<210> SEQ ID NO 180
<211> LENGTH: 24
<212> TYPE: PRT
<213> ORGANISM: Artificial Sequence
<220> FEATURE:
<223> OTHER INFORMATION: N-terminal extension

<400> SEQUENCE: 180

Thr Ser Thr Glu Pro Ser Glu Gly Ser Ala Pro Gly Ser Glu Pro Ala
1               5                   10                  15

Thr Ser Gly Ser Glu Thr Pro Gly
            20

<210> SEQ ID NO 181
<211> LENGTH: 24
<212> TYPE: PRT
<213> ORGANISM: Artificial Sequence
<220> FEATURE:
<223> OTHER INFORMATION: N-terminal extension

<400> SEQUENCE: 181
```

```
Ser Glu Pro Ala Thr Ser Gly Ser Glu Thr Pro Gly Ser Glu Pro Ala
1               5                   10                  15

Thr Ser Gly Ser Glu Thr Pro Gly
            20
```

<210> SEQ ID NO 182
<211> LENGTH: 133
<212> TYPE: PRT
<213> ORGANISM: Artificial Sequence
<220> FEATURE:
<223> OTHER INFORMATION: MIC-1 polypeptide plus N-terminal extension

<400> SEQUENCE: 182

```
Ser Glu Pro Ala Thr Ser Gly Ser Glu Thr Pro Gly Thr Ser Glu Ser
1               5                   10                  15

Ala Thr Pro Glu Ser Gly Pro Gly Gly Asp His Cys Pro Leu Gly Pro
            20                  25                  30

Gly Arg Cys Cys Arg Leu His Thr Val Arg Ala Ser Leu Glu Asp Leu
        35                  40                  45

Gly Trp Ala Asp Trp Val Leu Ser Pro Arg Glu Val Gln Val Thr Met
    50                  55                  60

Cys Ile Gly Ala Cys Pro Ser Gln Phe Arg Ala Ala Asn Met His Ala
65                  70                  75                  80

Gln Ile Lys Thr Ser Leu His Arg Leu Lys Pro Asp Thr Val Pro Ala
                85                  90                  95

Pro Cys Cys Val Pro Ala Ser Tyr Asn Pro Met Val Leu Ile Gln Lys
            100                 105                 110

Thr Asp Thr Gly Val Ser Leu Gln Thr Tyr Asp Asp Leu Leu Ala Lys
        115                 120                 125

Asp Cys His Cys Ile
    130
```

<210> SEQ ID NO 183
<211> LENGTH: 30
<212> TYPE: PRT
<213> ORGANISM: Artificial Sequence
<220> FEATURE:
<223> OTHER INFORMATION: N-terminal extension

<400> SEQUENCE: 183

```
Ser Glu Pro Ala Thr Ser Gly Ser Glu Thr Pro Gly Thr Ser Glu Ser
1               5                   10                  15

Ala Thr Pro Glu Ser Gly Pro Gly Glu Ser Ala Thr Pro Glu
            20                  25                  30
```

<210> SEQ ID NO 184
<211> LENGTH: 30
<212> TYPE: PRT
<213> ORGANISM: Artificial Sequence
<220> FEATURE:
<223> OTHER INFORMATION: N-terminal extension

<400> SEQUENCE: 184

```
Ser Glu Pro Ala Thr Ser Gly Ser Glu Thr Pro Gly Thr Ser Glu Ser
1               5                   10                  15

Ala Thr Pro Glu Ser Gly Pro Gly Ser Thr Glu Pro Ser Glu
            20                  25                  30
```

<210> SEQ ID NO 185
<211> LENGTH: 30
<212> TYPE: PRT

```
<213> ORGANISM: Artificial Sequence
<220> FEATURE:
<223> OTHER INFORMATION: N-terminal extension

<400> SEQUENCE: 185

Ser Glu Pro Ala Thr Ser Gly Ser Glu Thr Pro Gly Thr Ser Thr Glu
1               5                   10                  15

Pro Ser Glu Gly Ser Ala Pro Gly Thr Ser Thr Glu Glu Gly
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: N-terminal extension

<400> SEQUENCE: 186

Ser Glu Pro Ala Thr Ser Gly Ser Glu Thr Pro Gly Thr Ser Thr Glu
1               5                   10                  15

Pro Ser Glu Gly Ser Ala Pro Gly Thr Ser Glu Ser Ala Thr
            20                  25                  30

<210> SEQ ID NO 187
<211> LENGTH: 30
<212> TYPE: PRT
<213> ORGANISM: Artificial Sequence
<220> FEATURE:
<223> OTHER INFORMATION: N-terminal extension

<400> SEQUENCE: 187

Ser Glu Pro Ala Thr Ser Gly Ser Glu Thr Pro Gly Thr Ser Thr Glu
1               5                   10                  15

Pro Ser Glu Gly Ser Ala Pro Gly Thr Ser Thr Glu Pro Ser
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: N-terminal extension

<400> SEQUENCE: 188

Ser Glu Pro Ala Thr Ser Gly Ser Glu Thr Pro Gly Thr Ser Thr Glu
1               5                   10                  15

Pro Ser Glu Gly Ser Ala Pro Gly Ser Glu Pro Ala Thr Ser
            20                  25                  30

<210> SEQ ID NO 189
<211> LENGTH: 30
<212> TYPE: PRT
<213> ORGANISM: Artificial Sequence
<220> FEATURE:
<223> OTHER INFORMATION: N-terminal extension

<400> SEQUENCE: 189

Ser Glu Pro Ala Thr Ser Gly Ser Glu Thr Pro Gly Ser Glu Pro Ala
1               5                   10                  15

Thr Ser Gly Ser Glu Thr Pro Gly Thr Ser Thr Glu Glu Gly
            20                  25                  30

<210> SEQ ID NO 190
<211> LENGTH: 30
```

```
<212> TYPE: PRT
<213> ORGANISM: Artificial Sequence
<220> FEATURE:
<223> OTHER INFORMATION: N-terminal extension

<400> SEQUENCE: 190

Ser Glu Pro Ala Thr Ser Gly Ser Glu Thr Pro Gly Ser Glu Pro Ala
1               5                   10                  15
Thr Ser Gly Ser Glu Thr Pro Gly Thr Ser Glu Ser Ala Thr
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: N-terminal extension

<400> SEQUENCE: 191

Ser Glu Pro Ala Thr Ser Gly Ser Glu Thr Pro Gly Ser Glu Pro Ala
1               5                   10                  15
Thr Ser Gly Ser Glu Thr Pro Gly Glu Ser Ala Thr Pro Glu
            20                  25                  30

<210> SEQ ID NO 192
<211> LENGTH: 30
<212> TYPE: PRT
<213> ORGANISM: Artificial Sequence
<220> FEATURE:
<223> OTHER INFORMATION: N-terminal extension

<400> SEQUENCE: 192

Ser Glu Pro Ala Thr Ser Gly Ser Glu Thr Pro Gly Ser Glu Pro Ala
1               5                   10                  15
Thr Ser Gly Ser Glu Thr Pro Gly Thr Ser Thr Glu Pro Ser
            20                  25                  30

<210> SEQ ID NO 193
<211> LENGTH: 30
<212> TYPE: PRT
<213> ORGANISM: Artificial Sequence
<220> FEATURE:
<223> OTHER INFORMATION: N-terminal extension

<400> SEQUENCE: 193

Ser Glu Pro Ala Thr Ser Gly Ser Glu Thr Pro Gly Ser Glu Pro Ala
1               5                   10                  15
Thr Ser Gly Ser Glu Thr Pro Gly Ser Thr Glu Pro Ser Glu
            20                  25                  30

<210> SEQ ID NO 194
<211> LENGTH: 30
<212> TYPE: PRT
<213> ORGANISM: Artificial Sequence
<220> FEATURE:
<223> OTHER INFORMATION: N-terminal extension

<400> SEQUENCE: 194

Ser Glu Pro Ala Thr Ser Gly Ser Glu Thr Pro Gly Ser Glu Pro Ala
1               5                   10                  15
Thr Ser Gly Ser Glu Thr Pro Gly Ser Glu Pro Ala Thr Ser
            20                  25                  30

<210> SEQ ID NO 195
```

```
<211> LENGTH: 32
<212> TYPE: PRT
<213> ORGANISM: Artificial Sequence
<220> FEATURE:
<223> OTHER INFORMATION: N-terminal extension

<400> SEQUENCE: 195

Ser Glu Pro Ala Thr Ser Gly Ser Glu Thr Pro Gly Thr Ser Glu Ser
1               5                   10                  15
Ala Thr Pro Glu Ser Gly Pro Gly Gly Pro Glu Gln Gly Pro Glu Gln
            20                  25                  30

<210> SEQ ID NO 196
<211> LENGTH: 32
<212> TYPE: PRT
<213> ORGANISM: Artificial Sequence
<220> FEATURE:
<223> OTHER INFORMATION: N-terminal extension

<400> SEQUENCE: 196

Ser Glu Pro Ala Thr Ser Gly Ser Glu Thr Pro Gly Thr Ser Glu Ser
1               5                   10                  15
Ala Thr Pro Glu Ser Gly Pro Gly Gly Glu Pro Ser Gly Glu Pro Ser
            20                  25                  30

<210> SEQ ID NO 197
<211> LENGTH: 36
<212> TYPE: PRT
<213> ORGANISM: Artificial Sequence
<220> FEATURE:
<223> OTHER INFORMATION: N-terminal extension

<400> SEQUENCE: 197

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Glu Gly
            20                  25                  30
Ser Ala Pro Gly
        35

<210> SEQ ID NO 198
<211> LENGTH: 48
<212> TYPE: PRT
<213> ORGANISM: Artificial Sequence
<220> FEATURE:
<223> OTHER INFORMATION: N-terminal extension

<400> SEQUENCE: 198

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Glu Gly
            20                  25                  30
Ser Ala Pro Gly Thr Ser Thr Glu Pro Ser Glu Gly Ser Ala Pro Gly
        35                  40                  45

<210> SEQ ID NO 199
<211> LENGTH: 60
<212> TYPE: PRT
<213> ORGANISM: Artificial Sequence
<220> FEATURE:
<223> OTHER INFORMATION: N-terminal extension

<400> SEQUENCE: 199

Ser Pro Ala Gly Ser Pro Thr Ser Thr Glu Glu Gly Thr Ser Glu Ser
```

```
                1               5                       10                      15
Ala Thr Pro Glu Ser Gly Pro Gly Thr Ser Thr Glu Pro Ser Glu Gly
                20                      25                      30

Ser Ala Pro Gly Ser Pro Ala Gly Ser Pro Thr Ser Thr Glu Glu Gly
        35                      40                      45

Thr Ser Thr Glu Pro Ser Glu Gly Ser Ala Pro Gly
    50                      55                      60

<210> SEQ ID NO 200
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 200

Ser Glu Pro Ala Thr Ser Gly Ser Glu Thr Pro Gly Thr Ser Glu Ser
1               5                       10                      15

Ala Thr Pro Glu Ser Gly Pro Gly Thr Ser Thr Glu Glu Gly Gly Asp
                20                      25                      30

His Cys Pro Leu Gly Pro Gly Arg Cys Cys Arg Leu His Thr Val Arg
        35                      40                      45

Ala Ser Leu Glu Asp Leu Gly Trp Ala Asp Trp Val Leu Ser Pro Arg
    50                      55                      60

Glu Val Gln Val Thr Met Cys Ile Gly Ala Cys Pro Ser Gln Phe Arg
65                      70                      75                      80

Ala Ala Asn Met His Ala Gln Ile Lys Thr Ser Leu His Arg Leu Lys
                85                      90                      95

Pro Asp Thr Val Pro Ala Pro Cys Cys Val Pro Ala Ser Tyr Asn Pro
            100                     105                     110

Met Val Leu Ile Gln Lys Thr Asp Thr Gly Val Ser Leu Gln Thr Tyr
        115                     120                     125

Asp Asp Leu Leu Ala Lys Asp Cys His Cys Ile
    130                     135

<210> SEQ ID NO 201
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 201

Ser Glu Pro Ala Thr Ser Gly Ser Glu Thr Pro Gly Thr Ser Glu Ser
1               5                       10                      15

Ala Thr Pro Glu Ser Gly Pro Gly Thr Ser Glu Ser Ala Thr Gly Asp
                20                      25                      30

His Cys Pro Leu Gly Pro Gly Arg Cys Cys Arg Leu His Thr Val Arg
        35                      40                      45

Ala Ser Leu Glu Asp Leu Gly Trp Ala Asp Trp Val Leu Ser Pro Arg
    50                      55                      60

Glu Val Gln Val Thr Met Cys Ile Gly Ala Cys Pro Ser Gln Phe Arg
65                      70                      75                      80

Ala Ala Asn Met His Ala Gln Ile Lys Thr Ser Leu His Arg Leu Lys
                85                      90                      95

Pro Asp Thr Val Pro Ala Pro Cys Cys Val Pro Ala Ser Tyr Asn Pro
            100                     105                     110
```

```
Met Val Leu Ile Gln Lys Thr Asp Thr Gly Val Ser Leu Gln Thr Tyr
            115                 120                 125

Asp Asp Leu Leu Ala Lys Asp Cys His Cys Ile
    130                 135

<210> SEQ ID NO 202
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 202

Ser Glu Pro Ala Thr Ser Gly Ser Glu Thr Pro Gly Thr Ser Glu Ser
1               5                   10                  15

Ala Thr Pro Glu Ser Gly Pro Gly Ser Ala Thr Pro Glu Gly Asp
            20                  25                  30

His Cys Pro Leu Gly Pro Gly Arg Cys Cys Arg Leu His Thr Val Arg
            35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Met His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
            115                 120                 125

Asp Asp Leu Leu Ala Lys Asp Cys His Cys Ile
    130                 135

<210> SEQ ID NO 203
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 203

Ser Glu Pro Ala Thr Ser Gly Ser Glu Thr Pro Gly Thr Ser Glu Ser
1               5                   10                  15

Ala Thr Pro Glu Ser Gly Pro Gly Ser Thr Glu Pro Ser Glu Gly Asp
            20                  25                  30

His Cys Pro Leu Gly Pro Gly Arg Cys Cys Arg Leu His Thr Val Arg
            35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Met His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
            115                 120                 125

Asp Asp Leu Leu Ala Lys Asp Cys His Cys Ile
    130                 135
```

<210> SEQ ID NO 204
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 204

Ser Glu Pro Ala Thr Ser Gly Ser Glu Thr Pro Gly Thr Ser Glu Ser
1               5                   10                  15

Ala Thr Pro Glu Ser Gly Pro Gly Ser Glu Pro Ala Thr Ser Gly Asp
                20                  25                  30

His Cys Pro Leu Gly Pro Gly Arg Cys Cys Arg Leu His Thr Val Arg
            35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Met His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
        115                 120                 125

Asp Asp Leu Leu Ala Lys Asp Cys His Cys Ile
    130                 135

<210> SEQ ID NO 205
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 205

Ser Glu Pro Ala Thr Ser Gly Ser Glu Thr Pro Gly Thr Ser Thr Glu
1               5                   10                  15

Pro Ser Glu Gly Ser Ala Pro Gly Thr Ser Thr Glu Glu Gly Gly Asp
                20                  25                  30

His Cys Pro Leu Gly Pro Gly Arg Cys Cys Arg Leu His Thr Val Arg
            35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Leu His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
        115                 120                 125

Asp Asp Leu Leu Ala Lys Asp Cys His Cys Ile
    130                 135

<210> SEQ ID NO 206
<211> LENGTH: 139
<212> TYPE: PRT

<213> ORGANISM: Artificial Sequence
<220> FEATURE:
<223> OTHER INFORMATION: MIC-1 polypeptide with N-terminal extension

<400> SEQUENCE: 206

```
Ser Glu Pro Ala Thr Ser Gly Ser Glu Thr Pro Gly Thr Ser Thr Glu
1               5                   10                  15

Pro Ser Glu Gly Ser Ala Pro Gly Thr Ser Glu Ser Ala Thr Gly Asp
            20                  25                  30

His Cys Pro Leu Gly Pro Gly Arg Cys Cys Arg Leu His Thr Val Arg
            35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Leu His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
            115                 120                 125

Asp Asp Leu Leu Ala Lys Asp Cys His Cys Ile
            130                 135
```

<210> SEQ ID NO 207
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 207

```
Ser Glu Pro Ala Thr Ser Gly Ser Glu Thr Pro Gly Thr Ser Thr Glu
1               5                   10                  15

Pro Ser Glu Gly Ser Ala Pro Gly Thr Ser Thr Glu Pro Ser Gly Asp
            20                  25                  30

His Cys Pro Leu Gly Pro Gly Arg Cys Cys Arg Leu His Thr Val Arg
            35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Leu His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
            115                 120                 125

Asp Asp Leu Leu Ala Lys Asp Cys His Cys Ile
            130                 135
```

<210> SEQ ID NO 208
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 208

```
Ser Glu Pro Ala Thr Ser Gly Ser Glu Thr Pro Gly Thr Ser Thr Glu
1               5                   10                  15

Pro Ser Glu Gly Ser Ala Pro Gly Ser Glu Pro Ala Thr Ser Gly Asp
            20                  25                  30

His Cys Pro Leu Gly Pro Gly Arg Cys Cys Arg Leu His Thr Val Arg
            35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Leu His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
            115                 120                 125

Asp Asp Leu Leu Ala Lys Asp Cys His Cys Ile
        130                 135
```

```
<210> SEQ ID NO 209
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 209

Ser Glu Pro Ala Thr Ser Gly Ser Glu Thr Pro Gly Ser Glu Pro Ala
1               5                   10                  15

Thr Ser Gly Ser Glu Thr Pro Gly Thr Ser Thr Glu Glu Gly Gly Asp
            20                  25                  30

His Cys Pro Leu Gly Pro Gly Arg Cys Cys Arg Leu His Thr Val Arg
            35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Leu His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
            115                 120                 125

Asp Asp Leu Leu Ala Lys Asp Cys His Cys Ile
        130                 135
```

```
<210> SEQ ID NO 210
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 210

Ser Glu Pro Ala Thr Ser Gly Ser Glu Thr Pro Gly Ser Glu Pro Ala
1               5                   10                  15

Thr Ser Gly Ser Glu Thr Pro Gly Thr Ser Glu Ser Ala Thr Gly Asp
```

```
            20                  25                  30
His Cys Pro Leu Gly Pro Gly Arg Cys Cys Arg Leu His Thr Val Arg
        35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Met His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
        115                 120                 125

Asp Asp Leu Leu Ala Lys Asp Cys His Cys Ile
            130                 135

<210> SEQ ID NO 211
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 211

Ser Glu Pro Ala Thr Ser Gly Ser Glu Thr Pro Gly Ser Glu Pro Ala
1               5                   10                  15

Thr Ser Gly Ser Glu Thr Pro Gly Glu Ser Ala Thr Pro Glu Gly Asp
            20                  25                  30

His Cys Pro Leu Gly Pro Gly Arg Cys Cys Arg Leu His Thr Val Arg
        35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Met His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
        115                 120                 125

Asp Asp Leu Leu Ala Lys Asp Cys His Cys Ile
            130                 135

<210> SEQ ID NO 212
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 212

Ser Glu Pro Ala Thr Ser Gly Ser Glu Thr Pro Gly Ser Glu Pro Ala
1               5                   10                  15

Thr Ser Gly Ser Glu Thr Pro Gly Thr Ser Thr Glu Pro Ser Gly Asp
            20                  25                  30

His Cys Pro Leu Gly Pro Gly Arg Cys Cys Arg Leu His Thr Val Arg
        35                  40                  45
```

```
Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Leu His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
        115                 120                 125

Asp Asp Leu Leu Ala Lys Asp Cys His Cys Ile
    130                 135

<210> SEQ ID NO 213
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 213

Ser Glu Pro Ala Thr Ser Gly Ser Glu Thr Pro Gly Ser Glu Pro Ala
1               5                   10                  15

Thr Ser Gly Ser Glu Thr Pro Gly Ser Thr Glu Pro Ser Glu Gly Asp
            20                  25                  30

His Cys Pro Leu Gly Pro Gly Arg Cys Cys Arg Leu His Thr Val Arg
        35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80

Ala Ala Asn Met His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
        115                 120                 125

Asp Asp Leu Leu Ala Lys Asp Cys His Cys Ile
    130                 135

<210> SEQ ID NO 214
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 214

Ser Glu Pro Ala Thr Ser Gly Ser Glu Thr Pro Gly Ser Glu Pro Ala
1               5                   10                  15

Thr Ser Gly Ser Glu Thr Pro Gly Ser Glu Pro Ala Thr Ser Gly Asp
            20                  25                  30

His Cys Pro Leu Gly Pro Gly Arg Cys Cys Arg Leu His Thr Val Arg
        35                  40                  45

Ala Ser Leu Glu Asp Leu Gly Trp Ala Asp Trp Val Leu Ser Pro Arg
    50                  55                  60

Glu Val Gln Val Thr Met Cys Ile Gly Ala Cys Pro Ser Gln Phe Arg
65                  70                  75                  80
```

```
Ala Ala Asn Met His Ala Gln Ile Lys Thr Ser Leu His Arg Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
        115                 120                 125

Asp Asp Leu Leu Ala Lys Asp Cys His Cys Ile
    130                 135
```

<210> SEQ ID NO 215
<211> LENGTH: 141
<212> TYPE: PRT
<213> ORGANISM: Artificial Sequence
<220> FEATURE:
<223> OTHER INFORMATION: MIC-1 polypeptide with N-terminal extension

<400> SEQUENCE: 215

```
Ser Glu Pro Ala Thr Ser Gly Ser Glu Thr Pro Gly Thr Ser Glu Ser
1               5                   10                  15

Ala Thr Pro Glu Ser Gly Pro Gly Gly Pro Glu Gln Gly Pro Glu Gln
            20                  25                  30

Gly Asp His Cys Pro Leu Gly Pro Gly Arg Cys Cys Arg Leu His Thr
        35                  40                  45

Val Arg Ala Ser Leu Glu Asp Leu Gly Trp Ala Asp Trp Val Leu Ser
    50                  55                  60

Pro Arg Glu Val Gln Val Thr Met Cys Ile Gly Ala Cys Pro Ser Gln
65                  70                  75                  80

Phe Arg Ala Ala Asn Met His Ala Gln Ile Lys Thr Ser Leu His Arg
                85                  90                  95

Leu Lys Pro Asp Thr Val Pro Ala Pro Cys Cys Val Pro Ala Ser Tyr
            100                 105                 110

Asn Pro Met Val Leu Ile Gln Lys Thr Asp Thr Gly Val Ser Leu Gln
        115                 120                 125

Thr Tyr Asp Asp Leu Leu Ala Lys Asp Cys His Cys Ile
    130                 135                 140
```

<210> SEQ ID NO 216
<211> LENGTH: 141
<212> TYPE: PRT
<213> ORGANISM: Artificial Sequence
<220> FEATURE:
<223> OTHER INFORMATION: MIC-1 polypeptide with N-terminal extension

<400> SEQUENCE: 216

```
Ser Glu Pro Ala Thr Ser Gly Ser Glu Thr Pro Gly Thr Ser Glu Ser
1               5                   10                  15

Ala Thr Pro Glu Ser Gly Pro Gly Gly Glu Pro Ser Gly Glu Pro Ser
            20                  25                  30

Gly Asp His Cys Pro Leu Gly Pro Gly Arg Cys Cys Arg Leu His Thr
        35                  40                  45

Val Arg Ala Ser Leu Glu Asp Leu Gly Trp Ala Asp Trp Val Leu Ser
    50                  55                  60

Pro Arg Glu Val Gln Val Thr Met Cys Ile Gly Ala Cys Pro Ser Gln
65                  70                  75                  80

Phe Arg Ala Ala Asn Met His Ala Gln Ile Lys Thr Ser Leu His Arg
                85                  90                  95

Leu Lys Pro Asp Thr Val Pro Ala Pro Cys Cys Val Pro Ala Ser Tyr
```

```
            100                 105                 110
Asn Pro Met Val Leu Ile Gln Lys Thr Asp Thr Gly Val Ser Leu Gln
        115                 120                 125

Thr Tyr Asp Asp Leu Leu Ala Lys Asp Cys His Cys Ile
    130                 135                 140

<210> SEQ ID NO 217
<211> LENGTH: 147
<212> TYPE: PRT
<213> ORGANISM: Artificial Sequence
<220> FEATURE:
<223> OTHER INFORMATION: MIC-1 polypeptide with N-terminal extension

<400> SEQUENCE: 217

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Ser Ala Pro Gly Ala Arg Gly Asp His Cys Pro Leu Gly Pro Gly Arg
        35                  40                  45

Cys Cys Arg Leu His Thr Val Arg Ala Ser Leu Glu Asp Leu Gly Trp
50                  55                  60

Ala Asp Trp Val Leu Ser Pro Arg Glu Val Gln Val Thr Met Cys Ile
65                  70                  75                  80

Gly Ala Cys Pro Ser Gln Phe Arg Ala Ala Asn Met His Ala Gln Ile
                85                  90                  95

Lys Thr Ser Leu His Arg Leu Lys Pro Asp Thr Val Pro Ala Pro Cys
            100                 105                 110

Cys Val Pro Ala Ser Tyr Asn Pro Met Val Leu Ile Gln Lys Thr Asp
        115                 120                 125

Thr Gly Val Ser Leu Gln Thr Tyr Asp Asp Leu Leu Ala Lys Asp Cys
    130                 135                 140

His Cys Ile
145

<210> SEQ ID NO 218
<211> LENGTH: 159
<212> TYPE: PRT
<213> ORGANISM: Artificial Sequence
<220> FEATURE:
<223> OTHER INFORMATION: MIC-1 polypeptide with N-terminal extension

<400> SEQUENCE: 218

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Ser Ala Pro Gly Thr Ser Thr Glu Pro Ser Glu Gly Ser Ala Pro Gly
        35                  40                  45

Ala Arg Gly Asp His Cys Pro Leu Gly Pro Gly Arg Cys Cys Arg Leu
50                  55                  60

His Thr Val Arg Ala Ser Leu Glu Asp Leu Gly Trp Ala Asp Trp Val
65                  70                  75                  80

Leu Ser Pro Arg Glu Val Gln Val Thr Met Cys Ile Gly Ala Cys Pro
                85                  90                  95

Ser Gln Phe Arg Ala Ala Asn Met His Ala Gln Ile Lys Thr Ser Leu
            100                 105                 110
```

His Arg Leu Lys Pro Asp Thr Val Pro Ala Pro Cys Cys Val Pro Ala
            115                 120                 125

Ser Tyr Asn Pro Met Val Leu Ile Gln Lys Thr Asp Thr Gly Val Ser
        130                 135                 140

Leu Gln Thr Tyr Asp Asp Leu Leu Ala Lys Asp Cys His Cys Ile
145                 150                 155

<210> SEQ ID NO 219
<211> LENGTH: 172
<212> TYPE: PRT
<213> ORGANISM: Artificial Sequence
<220> FEATURE:
<223> OTHER INFORMATION: MIC-1 polypeptide with N-terminal extension

<400> SEQUENCE: 219

Ser Pro Ala Gly Ser Pro Thr Ser Thr Glu Glu Gly Thr Ser Glu Ser
1               5                   10                  15

Ala Thr Pro Glu Ser Gly Pro Gly Thr Ser Thr Glu Pro Ser Glu Gly
            20                  25                  30

Ser Ala Pro Gly Ser Pro Ala Gly Ser Pro Thr Ser Thr Glu Glu Gly
        35                  40                  45

Thr Ser Thr Glu Pro Ser Glu Gly Ser Ala Pro Gly Ala Arg Asn Gly
    50                  55                  60

Asp His Cys Pro Leu Gly Pro Gly Arg Cys Cys Arg Leu His Thr Val
65                  70                  75                  80

Arg Ala Ser Leu Glu Asp Leu Gly Trp Ala Asp Trp Val Leu Ser Pro
                85                  90                  95

Arg Glu Val Gln Val Thr Met Cys Ile Gly Ala Cys Pro Ser Gln Phe
            100                 105                 110

Arg Ala Ala Asn Met His Ala Gln Ile Lys Thr Ser Leu His Arg Leu
        115                 120                 125

Lys Pro Asp Thr Val Pro Ala Pro Cys Cys Val Pro Ala Ser Tyr Asn
    130                 135                 140

Pro Met Val Leu Ile Gln Lys Thr Asp Thr Gly Val Ser Leu Gln Thr
145                 150                 155                 160

Tyr Asp Asp Leu Leu Ala Lys Asp Cys His Cys Ile
                165                 170

<210> SEQ ID NO 220
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 220

Ser Glu Pro Ala Thr Ser Gly Ser Glu Thr Pro Gly Ser Glu Pro Ala
1               5                   10                  15

Thr Ser Gly Ser Glu Thr Pro Gly Gly Asp His Cys Pro Leu Gly Pro
            20                  25                  30

Gly Arg Cys Cys Arg Leu His Thr Val Arg Ala Ser Leu Glu Asp Leu
        35                  40                  45

Gly Trp Ala Asp Trp Val Leu Ser Pro Arg Glu Val Gln Val Thr Met
    50                  55                  60

Cys Ile Gly Ala Cys Pro Ser Gln Phe Arg Ala Ala Asn Met His Ala
65                  70                  75                  80

Gln Ile Lys Thr Ser Leu Glu Glu Leu Lys Pro Asp Thr Val Pro Ala
                85                  90                  95

```
Pro Cys Cys Val Pro Ala Ser Tyr Asn Pro Met Val Leu Ile Gln Lys
            100                 105                 110

Thr Asp Thr Gly Val Ser Leu Gln Thr Tyr Asp Leu Leu Ala Lys
        115                 120                 125

Asp Cys His Cys Ile
    130

<210> SEQ ID NO 221
<211> LENGTH: 139
<212> TYPE: PRT
<213> ORGANISM: Artificial Sequence
<220> FEATURE:
<223> OTHER INFORMATION: MIC-1 polypeptide with N-terminal extension

<400> SEQUENCE: 221

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Gly Asp
            20                  25                  30

His Cys Pro Leu Gly Pro Gly Arg Cys Cys Arg Leu His Thr Val Arg
        35                  40                  45

Ala Ser Leu Glu Asp Leu Gly Trp Ala Asp Trp Val Leu Ser Pro Arg
50                  55                  60

Glu Val Gln Val Thr Met Cys Ile Gly Ala Cys Pro Ser Gln Phe Arg
65                  70                  75                  80

Ala Ala Asn Glu His Ala Gln Ile Lys Thr Ser Leu His Glu Leu Lys
                85                  90                  95

Pro Asp Thr Val Pro Ala Pro Cys Cys Val Pro Ala Ser Tyr Asn Pro
            100                 105                 110

Met Val Leu Ile Gln Lys Thr Asp Thr Gly Val Ser Leu Gln Thr Tyr
        115                 120                 125

Asp Asp Leu Leu Ala Lys Asp Cys His Cys Ile
    130                 135

<210> SEQ ID NO 222
<211> LENGTH: 111
<212> TYPE: PRT
<213> ORGANISM: Artificial Sequence
<220> FEATURE:
<223> OTHER INFORMATION: MIC-1 polypeptide

<400> SEQUENCE: 222

Ala Arg Gly Asp His Cys Pro Leu Gly Pro Gly Arg Cys Cys Arg Leu
1               5                   10                  15

His Thr Val Arg Ala Ser Leu Glu Asp Leu Gly Trp Ala Asp Trp Val
            20                  25                  30

Leu Ser Pro Arg Glu Val Gln Val Thr Met Cys Ile Gly Ala Cys Pro
        35                  40                  45

Ser Gln Phe Arg Ala Ala Asn Leu His Ala Gln Ile Lys Thr Ser Leu
50                  55                  60

His Arg Leu Lys Pro Asp Thr Val Pro Ala Pro Cys Cys Val Pro Ala
65                  70                  75                  80

Ser Tyr Asn Pro Leu Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110
```

```
<210> SEQ ID NO 223
<211> LENGTH: 30
<212> TYPE: PRT
<213> ORGANISM: Artificial Sequence
<220> FEATURE:
<223> OTHER INFORMATION: N-terminal extension

<400> SEQUENCE: 223

Ser Glu Pro Ala Thr Cys Gly Ser Glu Thr Pro Gly Thr Ser Glu Ser
1               5                   10                  15

Ala Thr Pro Glu Ser Gly Pro Gly Thr Ser Thr Glu Pro Ser
            20                  25                  30

<210> SEQ ID NO 224
<211> LENGTH: 30
<212> TYPE: PRT
<213> ORGANISM: Artificial Sequence
<220> FEATURE:
<223> OTHER INFORMATION: N-terminal extension

<400> SEQUENCE: 224

Ser Glu Pro Ala Thr Ser Gly Cys Glu Thr Pro Gly Thr Ser Glu Ser
1               5                   10                  15

Ala Thr Pro Glu Ser Gly Pro Gly Thr Ser Thr Glu Pro Ser
            20                  25                  30

<210> SEQ ID NO 225
<211> LENGTH: 32
<212> TYPE: PRT
<213> ORGANISM: Artificial Sequence
<220> FEATURE:
<223> OTHER INFORMATION: N-terminal extension

<400> SEQUENCE: 225

Ser Glu Pro Cys Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

<210> SEQ ID NO 226
<211> LENGTH: 32
<212> TYPE: PRT
<213> ORGANISM: Artificial Sequence
<220> FEATURE:
<223> OTHER INFORMATION: N-terminal extension

<400> SEQUENCE: 226

Ser Glu Pro Ala Thr Cys Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

<210> SEQ ID NO 227
<211> LENGTH: 32
<212> TYPE: PRT
<213> ORGANISM: Artificial Sequence
<220> FEATURE:
<223> OTHER INFORMATION: N-terminal extension

<400> SEQUENCE: 227

Ser Glu Pro Ala Thr Ser Cys Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30
```

<210> SEQ ID NO 228
<211> LENGTH: 32
<212> TYPE: PRT
<213> ORGANISM: Artificial Sequence
<220> FEATURE:
<223> OTHER INFORMATION: N-terminal extension

<400> SEQUENCE: 228

Ser Glu Pro Cys Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

<210> SEQ ID NO 229
<211> LENGTH: 32
<212> TYPE: PRT
<213> ORGANISM: Artificial Sequence
<220> FEATURE:
<223> OTHER INFORMATION: N-terminal extension

<400> SEQUENCE: 229

Ser Glu Pro Ala Cys Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

<210> SEQ ID NO 230
<211> LENGTH: 32
<212> TYPE: PRT
<213> ORGANISM: Artificial Sequence
<220> FEATURE:
<223> OTHER INFORMATION: N-terminal extension

<400> SEQUENCE: 230

Ser Glu Pro Ala Thr Ser Gly Cys Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

<210> SEQ ID NO 231
<211> LENGTH: 32
<212> TYPE: PRT
<213> ORGANISM: Artificial Sequence
<220> FEATURE:
<223> OTHER INFORMATION: N-terminal extension

<400> SEQUENCE: 231

Ser Glu Pro Ala Thr Ser Gly Ser Glu Cys Pro Gly Thr Ser Glu Ser
1               5                   10                  15

Ala Thr Pro Glu Ser Gly Pro Gly Thr Ser Thr Glu Pro Ser Glu Gly
            20                  25                  30

<210> SEQ ID NO 232
<211> LENGTH: 32
<212> TYPE: PRT
<213> ORGANISM: Artificial Sequence
<220> FEATURE:
<223> OTHER INFORMATION: N-terminal extension

<400> SEQUENCE: 232

Ser Glu Pro Ala Thr Ser Gly Ser Glu Thr Pro Cys Thr Ser Glu Ser
1               5                   10                  15

Ala Thr Pro Glu Ser Gly Pro Gly Thr Ser Thr Glu Pro Ser Glu Gly
            20                  25                  30

<210> SEQ ID NO 233
<211> LENGTH: 32
<212> TYPE: PRT
<213> ORGANISM: Artificial Sequence
<220> FEATURE:
<223> OTHER INFORMATION: N-terminal extension

<400> SEQUENCE: 233

Ser Glu Pro Ala Thr Ser Gly Ser Glu Thr Pro Gly Thr Cys Glu Ser
1               5                   10                  15

Ala Thr Pro Glu Ser Gly Pro Gly Thr Ser Thr Glu Pro Ser Glu Gly
            20                  25                  30

<210> SEQ ID NO 234
<211> LENGTH: 32
<212> TYPE: PRT
<213> ORGANISM: Artificial Sequence
<220> FEATURE:
<223> OTHER INFORMATION: N-terminal extension

<400> SEQUENCE: 234

Ser Glu Pro Ala Thr Ser Gly Ser Glu Thr Pro Gly Thr Ser Glu Cys
1               5                   10                  15

Ala Thr Pro Glu Ser Gly Pro Gly Thr Ser Thr Glu Pro Ser Glu Gly
            20                  25                  30

<210> SEQ ID NO 235
<211> LENGTH: 32
<212> TYPE: PRT
<213> ORGANISM: Artificial Sequence
<220> FEATURE:
<223> OTHER INFORMATION: N-terminal extension

<400> SEQUENCE: 235

Ser Glu Pro Ala Thr Ser Gly Ser Glu Thr Pro Gly Thr Ser Glu Ser
1               5                   10                  15

Ala Cys Pro Glu Ser Gly Pro Gly Thr Ser Thr Glu Pro Ser Glu Gly
            20                  25                  30

<210> SEQ ID NO 236
<211> LENGTH: 32
<212> TYPE: PRT
<213> ORGANISM: Artificial Sequence
<220> FEATURE:
<223> OTHER INFORMATION: N-terminal extension

<400> SEQUENCE: 236

Ser Glu Pro Ala Thr Ser Gly Ser Glu Thr Pro Gly Thr Ser Glu Ser
1               5                   10                  15

Ala Thr Pro Glu Cys Gly Pro Gly Thr Ser Thr Glu Pro Ser Glu Gly
            20                  25                  30

<210> SEQ ID NO 237
<211> LENGTH: 32
<212> TYPE: PRT
<213> ORGANISM: Artificial Sequence
<220> FEATURE:
<223> OTHER INFORMATION: N-terminal extension

<400> SEQUENCE: 237

Ser Glu Pro Ala Thr Ser Gly Ser Glu Thr Pro Gly Thr Ser Glu Ser
1               5                   10                  15

Ala Thr Pro Glu Ser Cys Pro Gly Thr Ser Thr Glu Pro Ser Glu Gly

<210> SEQ ID NO 238
<211> LENGTH: 32
<212> TYPE: PRT
<213> ORGANISM: Artificial Sequence
<220> FEATURE:
<223> OTHER INFORMATION: N-terminal extension

<400> SEQUENCE: 238

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Cys Glu Pro Ser Glu Gly
            20                  25                  30

<210> SEQ ID NO 239
<211> LENGTH: 32
<212> TYPE: PRT
<213> ORGANISM: Artificial Sequence
<220> FEATURE:
<223> OTHER INFORMATION: N-terminal extension

<400> SEQUENCE: 239

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Cys Glu Gly
            20                  25                  30

<210> SEQ ID NO 240
<211> LENGTH: 30
<212> TYPE: PRT
<213> ORGANISM: Artificial Sequence
<220> FEATURE:
<223> OTHER INFORMATION: N-terminal extension

<400> SEQUENCE: 240

Ser Glu Pro Cys Thr Ser Gly Ser Glu Thr Pro Gly Thr Ser Glu Ser
1               5                   10                  15
Ala Thr Pro Glu Ser Gly Pro Gly Thr Ser Thr Glu Pro Ser
            20                  25                  30

<210> SEQ ID NO 241
<211> LENGTH: 28
<212> TYPE: PRT
<213> ORGANISM: Artificial Sequence
<220> FEATURE:
<223> OTHER INFORMATION: N-terminal extension

<400> SEQUENCE: 241

Ser Glu Pro Cys Thr Ser Gly Ser Glu Thr Pro Gly Thr Ser Glu Ser
1               5                   10                  15
Ala Thr Pro Glu Ser Gly Pro Gly Thr Ser Thr Glu
            20                  25

<210> SEQ ID NO 242
<211> LENGTH: 24
<212> TYPE: PRT
<213> ORGANISM: Artificial Sequence
<220> FEATURE:
<223> OTHER INFORMATION: N-terminal extension

<400> SEQUENCE: 242

Ser Glu Pro Cys Thr Ser Gly Ser Glu Thr Pro Gly Thr Ser Glu Ser
1               5                   10                  15

-continued

Ala Thr Pro Glu Ser Gly Pro Gly
            20

<210> SEQ ID NO 243
<211> LENGTH: 21
<212> TYPE: PRT
<213> ORGANISM: Artificial Sequence
<220> FEATURE:
<223> OTHER INFORMATION: N-terminal extension

<400> SEQUENCE: 243

Ser Glu Pro Cys Thr Ser Gly Ser Glu Thr Pro Gly Thr Ser Glu Ser
1               5                   10                  15

Ala Thr Pro Glu Ser
            20

<210> SEQ ID NO 244
<211> LENGTH: 12
<212> TYPE: PRT
<213> ORGANISM: Artificial Sequence
<220> FEATURE:
<223> OTHER INFORMATION: N-terminal extension

<400> SEQUENCE: 244

Ser Glu Pro Cys Thr Ser Gly Ser Glu Thr Pro Gly
1               5                   10

<210> SEQ ID NO 245
<211> LENGTH: 30
<212> TYPE: PRT
<213> ORGANISM: Artificial Sequence
<220> FEATURE:
<223> OTHER INFORMATION: N-terminal extension

<400> SEQUENCE: 245

Ser Glu Pro Cys Thr Ser Gly Ser Glu Thr Pro Gly Ser Pro Ala Gly
1               5                   10                  15

Ser Pro Thr Ser Thr Glu Glu Gly Ser Pro Ala Gly Ser Pro
            20                  25                  30

<210> SEQ ID NO 246
<211> LENGTH: 30
<212> TYPE: PRT
<213> ORGANISM: Artificial Sequence
<220> FEATURE:
<223> OTHER INFORMATION: N-terminal extension

<400> SEQUENCE: 246

Ser Glu Pro Cys Thr Ser Gly Ser Glu Thr Pro Gly Thr Ser Glu Ser
1               5                   10                  15

Ala Thr Pro Glu Ser Gly Pro Gly Ser Pro Ala Gly Ser Pro
            20                  25                  30

<210> SEQ ID NO 247
<211> LENGTH: 30
<212> TYPE: PRT
<213> ORGANISM: Artificial Sequence
<220> FEATURE:
<223> OTHER INFORMATION: N-terminal extension

<400> SEQUENCE: 247

Ser Glu Pro Cys Thr Ser Gly Ser Glu Thr Pro Gly Thr Ser Thr Glu
1               5                   10                  15

Pro Glu Ser Gly Ser Ala Pro Gly Ser Pro Ala Gly Ser Pro
            20                  25                  30

```
<210> SEQ ID NO 248
<211> LENGTH: 30
<212> TYPE: PRT
<213> ORGANISM: Artificial Sequence
<220> FEATURE:
<223> OTHER INFORMATION: N-terminal extension

<400> SEQUENCE: 248

Ser Glu Pro Cys Thr Ser Gly Ser Glu Thr Pro Gly Ser Pro Ala Gly
1               5                   10                  15

Ser Pro Thr Ser Thr Glu Glu Gly Thr Ser Glu Ser Ala Thr
            20                  25                  30

<210> SEQ ID NO 249
<211> LENGTH: 30
<212> TYPE: PRT
<213> ORGANISM: Artificial Sequence
<220> FEATURE:
<223> OTHER INFORMATION: N-terminal extension

<400> SEQUENCE: 249

Ser Glu Pro Cys Thr Ser Gly Ser Glu Thr Pro Gly Thr Ser Glu Ser
1               5                   10                  15

Ala Thr Pro Glu Ser Gly Pro Gly Thr Ser Glu Ser Ala Thr
            20                  25                  30

<210> SEQ ID NO 250
<211> LENGTH: 30
<212> TYPE: PRT
<213> ORGANISM: Artificial Sequence
<220> FEATURE:
<223> OTHER INFORMATION: N-terminal extension

<400> SEQUENCE: 250

Ser Glu Pro Cys Thr Ser Gly Ser Glu Thr Pro Gly Thr Ser Thr Glu
1               5                   10                  15

Pro Glu Ser Gly Ser Ala Pro Gly Thr Ser Glu Ser Ala Thr
            20                  25                  30

<210> SEQ ID NO 251
<211> LENGTH: 30
<212> TYPE: PRT
<213> ORGANISM: Artificial Sequence
<220> FEATURE:
<223> OTHER INFORMATION: N-terminal extension

<400> SEQUENCE: 251

Ser Glu Pro Cys Thr Ser Gly Ser Glu Thr Pro Gly Ser Pro Ala Gly
1               5                   10                  15

Ser Pro Thr Ser Thr Glu Glu Gly Thr Ser Thr Glu Pro Glu
            20                  25                  30

<210> SEQ ID NO 252
<211> LENGTH: 30
<212> TYPE: PRT
<213> ORGANISM: Artificial Sequence
<220> FEATURE:
<223> OTHER INFORMATION: N-terminal extension

<400> SEQUENCE: 252

Ser Glu Pro Cys Thr Ser Gly Ser Glu Thr Pro Gly Thr Ser Glu Ser
1               5                   10                  15

Ala Thr Pro Glu Ser Gly Pro Gly Thr Ser Thr Glu Pro Glu
```

20                  25                  30

<210> SEQ ID NO 253
<211> LENGTH: 30
<212> TYPE: PRT
<213> ORGANISM: Artificial Sequence
<220> FEATURE:
<223> OTHER INFORMATION: N-terminal extension

<400> SEQUENCE: 253

Ser Glu Pro Cys Thr Ser Gly Ser Glu Thr Pro Gly Thr Ser Thr Glu
1               5                   10                  15

Pro Glu Ser Gly Ser Ala Pro Gly Thr Ser Thr Glu Pro Glu
            20                  25                  30

<210> SEQ ID NO 254
<211> LENGTH: 30
<212> TYPE: PRT
<213> ORGANISM: Artificial Sequence
<220> FEATURE:
<223> OTHER INFORMATION: N-terminal extension

<400> SEQUENCE: 254

Ser Glu Pro Cys Thr Ser Gly Ser Glu Thr Pro Gly Ser Pro Ala Gly
1               5                   10                  15

Ser Pro Thr Ser Thr Glu Glu Gly Ser Glu Pro Ala Thr Ser
            20                  25                  30

<210> SEQ ID NO 255
<211> LENGTH: 30
<212> TYPE: PRT
<213> ORGANISM: Artificial Sequence
<220> FEATURE:
<223> OTHER INFORMATION: N-terminal extension

<400> SEQUENCE: 255

Ser Glu Pro Cys Thr Ser Gly Ser Glu Thr Pro Gly Thr Ser Glu Ser
1               5                   10                  15

Ala Thr Pro Glu Ser Gly Pro Gly Ser Glu Pro Ala Thr Ser
            20                  25                  30

<210> SEQ ID NO 256
<211> LENGTH: 30
<212> TYPE: PRT
<213> ORGANISM: Artificial Sequence
<220> FEATURE:
<223> OTHER INFORMATION: N-terminal extension

<400> SEQUENCE: 256

Ser Glu Pro Cys Thr Ser Gly Ser Glu Thr Pro Gly Thr Ser Thr Glu
1               5                   10                  15

Pro Glu Ser Gly Ser Ala Pro Gly Ser Glu Pro Ala Thr Ser
            20                  25                  30

<210> SEQ ID NO 257
<211> LENGTH: 30
<212> TYPE: PRT
<213> ORGANISM: Artificial Sequence
<220> FEATURE:
<223> OTHER INFORMATION: N-terminal extension

<400> SEQUENCE: 257

Ser Glu Pro Cys Thr Ser Gly Ser Glu Thr Pro Gly Ser Pro Ala Gly
1               5                   10                  15

-continued

```
Ser Pro Thr Ser Thr Glu Glu Gly Thr Ser Thr Glu Glu Gly
            20                  25                  30

<210> SEQ ID NO 258
<211> LENGTH: 30
<212> TYPE: PRT
<213> ORGANISM: Artificial Sequence
<220> FEATURE:
<223> OTHER INFORMATION: N-terminal extension

<400> SEQUENCE: 258

Ser Glu Pro Cys Thr Ser Gly Ser Glu Thr Pro Gly Thr Ser Glu Ser
1               5                   10                  15

Ala Thr Pro Glu Ser Gly Pro Gly Thr Ser Thr Glu Glu Gly
            20                  25                  30

<210> SEQ ID NO 259
<211> LENGTH: 30
<212> TYPE: PRT
<213> ORGANISM: Artificial Sequence
<220> FEATURE:
<223> OTHER INFORMATION: N-terminal extension

<400> SEQUENCE: 259

Ser Glu Pro Cys Thr Ser Gly Ser Glu Thr Pro Gly Thr Ser Thr Glu
1               5                   10                  15

Pro Glu Ser Gly Ser Ala Pro Gly Thr Ser Thr Glu Glu Gly
            20                  25                  30

<210> SEQ ID NO 260
<211> LENGTH: 30
<212> TYPE: PRT
<213> ORGANISM: Artificial Sequence
<220> FEATURE:
<223> OTHER INFORMATION: N-terminal extension

<400> SEQUENCE: 260

Ser Glu Pro Cys Thr Ser Gly Ser Glu Thr Pro Gly Ser Pro Ala Gly
1               5                   10                  15

Ser Pro Thr Ser Thr Glu Glu Gly Pro Glu Ser Gly Pro Gly
            20                  25                  30

<210> SEQ ID NO 261
<211> LENGTH: 30
<212> TYPE: PRT
<213> ORGANISM: Artificial Sequence
<220> FEATURE:
<223> OTHER INFORMATION: N-terminal extension

<400> SEQUENCE: 261

Ser Glu Pro Cys Thr Ser Gly Ser Glu Thr Pro Gly Thr Ser Glu Ser
1               5                   10                  15

Ala Thr Pro Glu Ser Gly Pro Gly Pro Glu Ser Gly Pro Gly
            20                  25                  30

<210> SEQ ID NO 262
<211> LENGTH: 30
<212> TYPE: PRT
<213> ORGANISM: Artificial Sequence
<220> FEATURE:
<223> OTHER INFORMATION: N-terminal extension

<400> SEQUENCE: 262

Ser Glu Pro Cys Thr Ser Gly Ser Glu Thr Pro Gly Thr Ser Thr Glu
1               5                   10                  15
```

Pro Glu Ser Gly Ser Ala Pro Gly Pro Glu Ser Gly Pro Gly
            20                  25                  30

<210> SEQ ID NO 263
<211> LENGTH: 30
<212> TYPE: PRT
<213> ORGANISM: Artificial Sequence
<220> FEATURE:
<223> OTHER INFORMATION: N-terminal extension

<400> SEQUENCE: 263

Ser Glu Pro Cys Thr Ser Gly Ser Glu Thr Pro Gly Ser Pro Ala Gly
1               5                   10                  15

Ser Pro Thr Ser Thr Glu Glu Gly Ser Gly Ser Ala Pro Gly
            20                  25                  30

<210> SEQ ID NO 264
<211> LENGTH: 30
<212> TYPE: PRT
<213> ORGANISM: Artificial Sequence
<220> FEATURE:
<223> OTHER INFORMATION: N-terminal extension

<400> SEQUENCE: 264

Ser Glu Pro Cys Thr Ser Gly Ser Glu Thr Pro Gly Thr Ser Glu Ser
1               5                   10                  15

Ala Thr Pro Glu Ser Gly Pro Gly Ser Gly Ser Ala Pro Gly
            20                  25                  30

<210> SEQ ID NO 265
<211> LENGTH: 30
<212> TYPE: PRT
<213> ORGANISM: Artificial Sequence
<220> FEATURE:
<223> OTHER INFORMATION: N-terminal extension

<400> SEQUENCE: 265

Ser Glu Pro Cys Thr Ser Gly Ser Glu Thr Pro Gly Thr Ser Thr Glu
1               5                   10                  15

Pro Glu Ser Gly Ser Ala Pro Gly Ser Gly Ser Ala Pro Gly
            20                  25                  30

<210> SEQ ID NO 266
<211> LENGTH: 30
<212> TYPE: PRT
<213> ORGANISM: Artificial Sequence
<220> FEATURE:
<223> OTHER INFORMATION: N-terminal extension

<400> SEQUENCE: 266

Ser Glu Pro Cys Thr Ser Gly Ser Glu Thr Pro Gly Ser Pro Ala Gly
1               5                   10                  15

Ser Pro Thr Ser Thr Glu Glu Gly Gly Ser Glu Thr Pro Gly
            20                  25                  30

<210> SEQ ID NO 267
<211> LENGTH: 30
<212> TYPE: PRT
<213> ORGANISM: Artificial Sequence
<220> FEATURE:
<223> OTHER INFORMATION: N-terminal extension

<400> SEQUENCE: 267

Ser Glu Pro Cys Thr Ser Gly Ser Glu Thr Pro Gly Thr Ser Glu Ser

```
                1               5                  10                  15
Ala Thr Pro Glu Ser Gly Pro Gly Gly Ser Glu Thr Pro Gly
        20                  25                  30

<210> SEQ ID NO 268
<211> LENGTH: 30
<212> TYPE: PRT
<213> ORGANISM: Artificial Sequence
<220> FEATURE:
<223> OTHER INFORMATION: N-terminal extension

<400> SEQUENCE: 268

Ser Glu Pro Cys Thr Ser Gly Ser Glu Thr Pro Gly Thr Ser Glu
1               5                  10                  15

Pro Glu Ser Gly Ser Ala Pro Gly Gly Ser Glu Thr Pro Gly
        20                  25                  30

<210> SEQ ID NO 269
<211> LENGTH: 36
<212> TYPE: PRT
<213> ORGANISM: Artificial Sequence
<220> FEATURE:
<223> OTHER INFORMATION: N-terminal extension

<400> SEQUENCE: 269

Ser Glu Pro Cys Thr Ser Gly Ser Glu Thr Pro Gly Ser Pro Ala Gly
1               5                  10                  15

Ser Pro Thr Ser Thr Glu Glu Gly Thr Ser Glu Ser Ala Thr Pro Glu
        20                  25                  30

Ser Gly Pro Gly
        35

<210> SEQ ID NO 270
<211> LENGTH: 36
<212> TYPE: PRT
<213> ORGANISM: Artificial Sequence
<220> FEATURE:
<223> OTHER INFORMATION: N-terminal extension

<400> SEQUENCE: 270

Ser Glu Pro Cys Thr Ser Gly Ser Glu Thr Pro Gly Ser Pro Ala Gly
1               5                  10                  15

Ser Pro Thr Ser Thr Glu Glu Gly Ser Pro Ala Gly Ser Pro Thr Ser
        20                  25                  30

Thr Glu Glu Gly
        35

<210> SEQ ID NO 271
<211> LENGTH: 36
<212> TYPE: PRT
<213> ORGANISM: Artificial Sequence
<220> FEATURE:
<223> OTHER INFORMATION: N-terminal extension

<400> SEQUENCE: 271

Ser Glu Pro Cys Thr Ser Gly Ser Glu Thr Pro Gly Ser Pro Ala Gly
1               5                  10                  15

Ser Pro Thr Ser Thr Glu Glu Gly Thr Ser Thr Glu Pro Glu Ser Gly
        20                  25                  30

Ser Ala Pro Gly
        35
```

```
<210> SEQ ID NO 272
<211> LENGTH: 36
<212> TYPE: PRT
<213> ORGANISM: Artificial Sequence
<220> FEATURE:
<223> OTHER INFORMATION: N-terminal extension

<400> SEQUENCE: 272

Ser Glu Pro Cys Thr Ser Gly Ser Glu Thr Pro Gly Thr Ser Glu Ser
1               5                   10                  15

Ala Thr Pro Glu Ser Gly Pro Gly Ser Pro Ala Gly Ser Pro Thr Ser
            20                  25                  30

Thr Glu Glu Gly
        35

<210> SEQ ID NO 273
<211> LENGTH: 36
<212> TYPE: PRT
<213> ORGANISM: Artificial Sequence
<220> FEATURE:
<223> OTHER INFORMATION: N-terminal extension

<400> SEQUENCE: 273

Ser Glu Pro Cys Thr Ser Gly Ser Glu Thr Pro Gly Thr Ser Glu Ser
1               5                   10                  15

Ala Thr Pro Glu Ser Gly Pro Gly Thr Ser Glu Ser Ala Thr Pro Glu
            20                  25                  30

Ser Gly Pro Gly
        35

<210> SEQ ID NO 274
<211> LENGTH: 36
<212> TYPE: PRT
<213> ORGANISM: Artificial Sequence
<220> FEATURE:
<223> OTHER INFORMATION: N-terminal extension

<400> SEQUENCE: 274

Ser Glu Pro Cys Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Ser Ala Pro Gly
        35

<210> SEQ ID NO 275
<211> LENGTH: 36
<212> TYPE: PRT
<213> ORGANISM: Artificial Sequence
<220> FEATURE:
<223> OTHER INFORMATION: N-terminal extension

<400> SEQUENCE: 275

Ser Glu Pro Cys Thr Ser Gly Ser Glu Thr Pro Gly Thr Ser Glu Ser
1               5                   10                  15

Ala Thr Pro Glu Ser Gly Pro Gly Ser Glu Pro Ala Thr Ser Gly Ser
            20                  25                  30

Glu Thr Pro Gly
        35

<210> SEQ ID NO 276
<211> LENGTH: 36
<212> TYPE: PRT
```

<213> ORGANISM: Artificial Sequence
<220> FEATURE:
<223> OTHER INFORMATION: N-terminal extension

<400> SEQUENCE: 276

Ser Glu Pro Cys Thr Ser Gly Ser Glu Thr Pro Gly Thr Ser Thr Glu
1               5                   10                  15

Pro Glu Ser Gly Ser Ala Pro Gly Ser Pro Ala Gly Ser Pro Thr Ser
            20                  25                  30

Thr Glu Glu Gly
        35

<210> SEQ ID NO 277
<211> LENGTH: 36
<212> TYPE: PRT
<213> ORGANISM: Artificial Sequence
<220> FEATURE:
<223> OTHER INFORMATION: N-terminal extension

<400> SEQUENCE: 277

Ser Glu Pro Cys Thr Ser Gly Ser Glu Thr Pro Gly Thr Ser Thr Glu
1               5                   10                  15

Pro Glu Ser Gly Ser Ala Pro Gly Thr Ser Glu Ser Ala Thr Pro Glu
            20                  25                  30

Ser Gly Pro Gly
        35

<210> SEQ ID NO 278
<211> LENGTH: 36
<212> TYPE: PRT
<213> ORGANISM: Artificial Sequence
<220> FEATURE:
<223> OTHER INFORMATION: N-terminal extension

<400> SEQUENCE: 278

Ser Glu Pro Cys Thr Ser Gly Ser Glu Thr Pro Gly Thr Ser Thr Glu
1               5                   10                  15

Pro Glu Ser Gly Ser Ala Pro Gly Thr Ser Thr Glu Pro Glu Ser Gly
            20                  25                  30

Ser Ala Pro Gly
        35

<210> SEQ ID NO 279
<211> LENGTH: 36
<212> TYPE: PRT
<213> ORGANISM: Artificial Sequence
<220> FEATURE:
<223> OTHER INFORMATION: N-terminal extension

<400> SEQUENCE: 279

Ser Glu Pro Cys Thr Ser Gly Ser Glu Thr Pro Gly Thr Ser Thr Glu
1               5                   10                  15

Pro Glu Ser Gly Ser Ala Pro Gly Ser Glu Pro Ala Thr Ser Gly Ser
            20                  25                  30

Glu Thr Pro Gly
        35

<210> SEQ ID NO 280
<211> LENGTH: 36
<212> TYPE: PRT
<213> ORGANISM: Artificial Sequence
<220> FEATURE:
<223> OTHER INFORMATION: N-terminal extension

<400> SEQUENCE: 280

Ser Glu Pro Cys Thr Ser Gly Ser Glu Thr Pro Gly Ser Glu Pro Ala
1               5                   10                  15

Thr Ser Gly Ser Glu Thr Pro Gly Ser Pro Ala Gly Ser Pro Thr Ser
            20                  25                  30

Thr Glu Glu Gly
        35

<210> SEQ ID NO 281
<211> LENGTH: 36
<212> TYPE: PRT
<213> ORGANISM: Artificial Sequence
<220> FEATURE:
<223> OTHER INFORMATION: N-terminal extension

<400> SEQUENCE: 281

Ser Glu Pro Cys Thr Ser Gly Ser Glu Thr Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly
        35

<210> SEQ ID NO 282
<211> LENGTH: 36
<212> TYPE: PRT
<213> ORGANISM: Artificial Sequence
<220> FEATURE:
<223> OTHER INFORMATION: N-terminal extension

<400> SEQUENCE: 282

Ser Glu Pro Cys Thr Ser Gly Ser Glu Thr Pro Gly Ser Glu Pro Ala
1               5                   10                  15

Thr Ser Gly Ser Glu Thr Pro Gly Thr Ser Thr Glu Pro Glu Ser Gly
            20                  25                  30

Ser Ala Pro Gly
        35

<210> SEQ ID NO 283
<211> LENGTH: 36
<212> TYPE: PRT
<213> ORGANISM: Artificial Sequence
<220> FEATURE:
<223> OTHER INFORMATION: N-terminal extension

<400> SEQUENCE: 283

Ser Glu Pro Cys Thr Ser Gly Ser Glu Thr Pro Gly Ser Glu Pro Ala
1               5                   10                  15

Thr Ser Gly Ser Glu Thr Pro Gly Ser Glu Pro Ala Thr Ser Gly Ser
            20                  25                  30

Glu Thr Pro Gly
        35

<210> SEQ ID NO 284
<211> LENGTH: 28
<212> TYPE: PRT
<213> ORGANISM: Artificial Sequence
<220> FEATURE:
<223> OTHER INFORMATION: N-terminal extension

<400> SEQUENCE: 284

```
Gly Pro Cys Glu Gly Pro Ser Glu Gly Pro Ser Glu Gly Pro Ser Glu
1               5                   10                  15

Gly Pro Ser Glu Gly Pro Ser Glu Gly Pro Ser Glu
                20                  25
```

<210> SEQ ID NO 285
<211> LENGTH: 28
<212> TYPE: PRT
<213> ORGANISM: Artificial Sequence
<220> FEATURE:
<223> OTHER INFORMATION: N-terminal extension

<400> SEQUENCE: 285

```
Gly Glu Cys Pro Gly Glu Gln Pro Gly Glu Gln Pro Gly Glu Gln Pro
1               5                   10                  15

Gly Glu Gln Pro Gly Glu Gln Pro Gly Glu Gln Pro
                20                  25
```

<210> SEQ ID NO 286
<211> LENGTH: 22
<212> TYPE: PRT
<213> ORGANISM: Artificial Sequence
<220> FEATURE:
<223> OTHER INFORMATION: N-terminal extension

<400> SEQUENCE: 286

```
Pro Ala Cys Glu Glu Glu Asp Asp Pro Asp Gly Gly Gly Ser Gly Gly
1               5                   10                  15

Gly Ser Gly Gly Gly Ser
                20
```

<210> SEQ ID NO 287
<211> LENGTH: 22
<212> TYPE: PRT
<213> ORGANISM: Artificial Sequence
<220> FEATURE:
<223> OTHER INFORMATION: N-terminal extension

<400> SEQUENCE: 287

```
Pro Asp Glu Cys Thr Glu Glu Thr Glu Gly Gly Gly Ser Gly Gly
1               5                   10                  15

Gly Ser Gly Gly Gly Ser
                20
```

<210> SEQ ID NO 288
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 288

```
Ser Glu Pro Cys Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
                20                  25                  30

Ala Arg Gly Asp His Cys Pro Leu Gly Pro Gly Arg Cys Cys Arg Leu
            35                  40                  45

His Thr Val Arg Ala Ser Leu Glu Asp Leu Gly Trp Ala Asp Trp Val
        50                  55                  60

Leu Ser Pro Arg Glu Val Gln Val Thr Met Cys Ile Gly Ala Cys Pro
65                  70                  75                  80
```

```
Ser Gln Phe Arg Ala Ala Asn Met His Ala Gln Ile Lys Thr Ser Leu
                85                  90                  95

His Arg Leu Lys Pro Asp Thr Val Pro Ala Pro Cys Cys Val Pro Ala
            100                 105                 110

Ser Tyr Asn Pro Met Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140
```

<210> SEQ ID NO 289
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 289

```
Ser Glu Pro Ala Thr Ser Cys Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                85                  90                  95

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140
```

<210> SEQ ID NO 290
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 290

```
Ser Glu Pro Cys Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                85                  90                  95

His Arg Leu Lys Pro Asp Thr Val Pro Ala Pro Cys Cys Val Pro Ala
            100                 105                 110
```

Ser Tyr Asn Pro Leu Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140

<210> SEQ ID NO 291
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 291

Ser Glu Pro Ala Thr Cys Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Met His Ala Gln Ile Lys Thr Ser Leu
                85                  90                  95

His Arg Leu Lys Pro Asp Thr Val Pro Ala Pro Cys Cys Val Pro Ala
            100                 105                 110

Ser Tyr Asn Pro Met Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140

<210> SEQ ID NO 292
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 292

Ser Glu Pro Ala Thr Ser Gly Ser Glu Thr Pro Gly Thr Ser Glu Ser
1               5                   10                  15

Ala Cys Pro Glu Ser Gly Pro Gly Thr Ser Thr Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                85                  90                  95

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
        115                 120                 125

Leu Gln Thr Tyr Asp Asp Leu Leu Ala Lys Asp Cys His Cys Ile

<210> SEQ ID NO 293
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 293

```
Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Cys Glu Gly
            20                  25                  30
Ala Arg Gly Asp His Cys Pro Leu Gly Pro Gly Arg Cys Cys Arg Leu
        35                  40                  45
His Thr Val Arg Ala Ser Leu Glu Asp Leu Gly Trp Ala Asp Trp Val
    50                  55                  60
Leu Ser Pro Arg Glu Val Gln Val Thr Met Cys Ile Gly Ala Cys Pro
65                  70                  75                  80
Ser Gln Phe Arg Ala Ala Asn Leu His Ala Gln Ile Lys Thr Ser Leu
                85                  90                  95
His Arg Leu Lys Pro Asp Thr Val Pro Ala Pro Cys Cys Val Pro Ala
            100                 105                 110
Ser Tyr Asn Pro Leu Val Leu Ile Gln Lys Thr Asp Thr Gly Val Ser
        115                 120                 125
Leu Gln Thr Tyr Asp Asp Leu Leu Ala Lys Asp Cys His Cys Ile
    130                 135                 140
```

<210> SEQ ID NO 294
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 294

```
Ser Glu Pro Ala Thr Ser Gly Ser Glu Thr Pro Gly Ser Glu Pro Ala
1               5                   10                  15
Thr Ser Gly Ser Glu Thr Pro Gly Gly Asp His Cys Pro Leu Gly Pro
            20                  25                  30
Gly Arg Cys Cys Arg Leu His Thr Val Arg Ala Ser Leu Glu Asp Leu
        35                  40                  45
Gly Trp Ala Asp Trp Val Leu Ser Pro Arg Glu Val Gln Val Thr Met
    50                  55                  60
Cys Ile Gly Ala Cys Pro Ser Gln Phe Arg Ala Ala Asn Glu His Ala
65                  70                  75                  80
Gln Ile Lys Thr Ser Leu Glu Arg Leu Lys Pro Asp Thr Val Pro Ala
                85                  90                  95
Pro Cys Cys Val Pro Ala Ser Tyr Asn Pro Met Val Leu Ile Gln Lys
            100                 105                 110
Thr Asp Thr Gly Val Ser Leu Gln Thr Tyr Asp Asp Leu Leu Ala Lys
        115                 120                 125
Asp Cys His Cys Ile
    130
```

<210> SEQ ID NO 295
<211> LENGTH: 143

<212> TYPE: PRT
<213> ORGANISM: Artificial Sequence
<220> FEATURE:
<223> OTHER INFORMATION: MIC-1 polypeptide with N-terminal extension

<400> SEQUENCE: 295

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Glu Gly
                20                  25                  30
Ala Arg Gly Asp His Cys Pro Leu Gly Pro Gly Arg Cys Cys Arg Leu
                35                  40                  45
His Thr Val Arg Ala Ser Leu Glu Asp Leu Gly Trp Ala Asp Trp Val
            50                  55                  60
Leu Ser Pro Arg Glu Val Gln Val Thr Met Cys Ile Gly Ala Cys Pro
65                  70                  75                  80
Ser Gln Phe Arg Ala Ala Asn Leu His Ala Gln Ile Lys Thr Ser Leu
                85                  90                  95
His Arg Leu Lys Pro Asp Thr Val Pro Ala Pro Cys Cys Val Pro Ala
                100                 105                 110
Ser Tyr Asn Pro Met Val Leu Ile Gln Lys Thr Asp Thr Gly Val Ser
                115                 120                 125
Leu Gln Thr Tyr Asp Asp Leu Leu Ala Lys Asp Cys His Cys Ile
            130                 135                 140

<210> SEQ ID NO 296
<211> LENGTH: 141
<212> TYPE: PRT
<213> ORGANISM: Artificial Sequence
<220> FEATURE:
<223> OTHER INFORMATION: MIC-1 polypeptide with N-terminal extension

<400> SEQUENCE: 296

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Ala Arg
                20                  25                  30
Gly Asp His Cys Pro Leu Gly Pro Gly Arg Cys Cys Arg Leu His Thr
                35                  40                  45
Val Arg Ala Ser Leu Glu Asp Leu Gly Trp Ala Asp Trp Val Leu Ser
            50                  55                  60
Pro Arg Glu Val Gln Val Thr Met Cys Ile Gly Ala Cys Pro Ser Gln
65                  70                  75                  80
Phe Arg Ala Ala Asn Leu His Ala Gln Ile Lys Thr Ser Leu His Arg
                85                  90                  95
Leu Lys Pro Asp Thr Val Pro Ala Pro Cys Cys Val Pro Ala Ser Tyr
                100                 105                 110
Asn Pro Leu Val Leu Ile Gln Lys Thr Asp Thr Gly Val Ser Leu Gln
                115                 120                 125
Thr Tyr Asp Asp Leu Leu Ala Lys Asp Cys His Cys Ile
            130                 135                 140

<210> SEQ ID NO 297
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 297

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Met His Ala Gln Ile Lys Thr Ser Leu
                85                  90                  95

His Arg Leu Lys Pro Asp Thr Val Pro Ala Pro Cys Cys Val Pro Ala
            100                 105                 110

Ser Tyr Asn Pro Met Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140

<210> SEQ ID NO 298
<211> LENGTH: 141
<212> TYPE: PRT
<213> ORGANISM: Artificial Sequence
<220> FEATURE:
<223> OTHER INFORMATION: MIC-1 polypeptide with N-terminal extension

<400> SEQUENCE: 298

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Ala Arg
            20                  25                  30

Gly Asp His Cys Pro Leu Gly Pro Gly Arg Cys Cys Arg Leu His Thr
        35                  40                  45

Val Arg Ala Ser Leu Glu Asp Leu Gly Trp Ala Asp Trp Val Leu Ser
    50                  55                  60

Pro Arg Glu Val Gln Val Thr Met Cys Ile Gly Ala Cys Pro Ser Gln
65                  70                  75                  80

Phe Arg Ala Ala Asn Met His Ala Gln Ile Lys Thr Ser Leu His Arg
                85                  90                  95

Leu Lys Pro Asp Thr Val Pro Ala Pro Cys Cys Val Pro Ala Ser Tyr
            100                 105                 110

Asn Pro Met Val Leu Ile Gln Lys Thr Asp Thr Gly Val Ser Leu Gln
        115                 120                 125

Thr Tyr Asp Asp Leu Leu Ala Lys Asp Cys His Cys Ile
    130                 135                 140

<210> SEQ ID NO 299
<211> LENGTH: 141
<212> TYPE: PRT
<213> ORGANISM: Artificial Sequence
<220> FEATURE:
<223> OTHER INFORMATION: MIC-1 polypeptide with N-terminal extension

<400> SEQUENCE: 299

Ser Glu Pro Ala Thr Ser Gly Ser Glu Thr Pro Gly Ser Glu Pro Ala
1               5                   10                  15

```
Thr Ser Gly Ser Glu Thr Pro Gly Thr Ser Thr Glu Pro Ser Ala Arg
            20                  25                  30

Gly Asp His Cys Pro Leu Gly Pro Gly Arg Cys Cys Arg Leu His Thr
            35                  40                  45

Val Arg Ala Ser Leu Glu Asp Leu Gly Trp Ala Asp Trp Val Leu Ser
 50                  55                  60

Pro Arg Glu Val Gln Val Thr Met Cys Ile Gly Ala Cys Pro Ser Gln
 65                  70                  75                  80

Phe Arg Ala Ala Asn Met His Ala Gln Ile Lys Thr Ser Leu His Arg
                85                  90                  95

Leu Lys Pro Asp Thr Val Pro Ala Pro Cys Cys Val Pro Ala Ser Tyr
            100                 105                 110

Asn Pro Met Val Leu Ile Gln Lys Thr Asp Thr Gly Val Ser Leu Gln
            115                 120                 125

Thr Tyr Asp Asp Leu Leu Ala Lys Asp Cys His Cys Ile
            130                 135                 140

<210> SEQ ID NO 300
<211> LENGTH: 133
<212> TYPE: PRT
<213> ORGANISM: Artificial Sequence
<220> FEATURE:
<223> OTHER INFORMATION: MIC-1 polypeptide with N-terminal extension

<400> SEQUENCE: 300

Ser Ala Pro Ala Thr Ser Gly Ser Ala Thr Pro Gly Ser Ala Pro Ala
 1               5                  10                  15

Thr Ser Gly Ser Ala Thr Pro Gly Gly Asp His Cys Pro Leu Gly Pro
            20                  25                  30

Gly Arg Cys Cys Arg Leu His Thr Val Arg Ala Ser Leu Glu Asp Leu
            35                  40                  45

Gly Trp Ala Asp Trp Val Leu Ser Pro Arg Glu Val Gln Val Thr Met
 50                  55                  60

Cys Ile Gly Ala Cys Pro Ser Gln Phe Arg Ala Ala Asn Met His Ala
 65                  70                  75                  80

Gln Ile Lys Thr Ser Leu His Arg Leu Lys Pro Asp Thr Val Pro Ala
                85                  90                  95

Pro Cys Cys Val Pro Ala Ser Tyr Asn Pro Met Val Leu Ile Gln Lys
            100                 105                 110

Thr Asp Thr Gly Val Ser Leu Gln Thr Tyr Asp Asp Leu Leu Ala Lys
            115                 120                 125

Asp Cys His Cys Ile
            130

<210> SEQ ID NO 301
<211> LENGTH: 141
<212> TYPE: PRT
<213> ORGANISM: Artificial Sequence
<220> FEATURE:
<223> OTHER INFORMATION: MIC-1 polypeptide with N-terminal extension

<400> SEQUENCE: 301

Ser Glu Pro Cys Thr Ser Gly Ser Glu Thr Pro Gly Ser Glu Pro Ser
 1               5                  10                  15

Ala Thr Pro Glu Ser Gly Pro Gly Thr Ser Thr Glu Pro Ser Ala Arg
            20                  25                  30

Gly Asp His Cys Pro Leu Gly Pro Gly Arg Cys Cys Arg Leu His Thr
            35                  40                  45
```

```
Val Arg Ala Ser Leu Glu Asp Leu Gly Trp Ala Asp Trp Val Leu Ser
 50                  55                  60

Pro Arg Glu Val Gln Val Thr Met Cys Ile Gly Ala Cys Pro Ser Gln
 65                  70                  75                  80

Phe Arg Ala Ala Asn Met His Ala Gln Ile Lys Thr Ser Leu His Arg
                 85                  90                  95

Leu Lys Pro Asp Thr Val Pro Ala Pro Cys Cys Val Pro Ala Ser Tyr
                100                 105                 110

Asn Pro Met Val Leu Ile Gln Lys Thr Asp Thr Gly Val Ser Leu Gln
            115                 120                 125

Thr Tyr Asp Asp Leu Leu Ala Lys Asp Cys His Cys Ile
130                 135                 140

<210> SEQ ID NO 302
<211> LENGTH: 141
<212> TYPE: PRT
<213> ORGANISM: Artificial Sequence
<220> FEATURE:
<223> OTHER INFORMATION: MIC-1 polypeptide with N-terminal extension

<400> SEQUENCE: 302

Ser Glu Pro Ala Thr Cys Gly Ser Glu Thr Pro Gly Thr Ser Glu Ser
 1               5                  10                  15

Ala Thr Pro Glu Ser Gly Pro Gly Thr Ser Thr Glu Pro Ser Ala Arg
                 20                  25                  30

Gly Asp His Cys Pro Leu Gly Pro Gly Arg Cys Cys Arg Leu His Thr
             35                  40                  45

Val Arg Ala Ser Leu Glu Asp Leu Gly Trp Ala Asp Trp Val Leu Ser
 50                  55                  60

Pro Arg Glu Val Gln Val Thr Met Cys Ile Gly Ala Cys Pro Ser Gln
 65                  70                  75                  80

Phe Arg Ala Ala Asn Met His Ala Gln Ile Lys Thr Ser Leu His Arg
                 85                  90                  95

Leu Lys Pro Asp Thr Val Pro Ala Pro Cys Cys Val Pro Ala Ser Tyr
                100                 105                 110

Asn Pro Met Val Leu Ile Gln Lys Thr Asp Thr Gly Val Ser Leu Gln
            115                 120                 125

Thr Tyr Asp Asp Leu Leu Ala Lys Asp Cys His Cys Ile
130                 135                 140

<210> SEQ ID NO 303
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 303

Ser Glu Pro Ala Thr Ser Gly Cys Glu Thr Pro Gly Thr Ser Glu Ser
 1               5                  10                  15

Ala Thr Pro Glu Ser Gly Pro Gly Thr Ser Thr Glu Pro Ser Glu Gly
                 20                  25                  30

Ala Arg Gly Asp His Cys Pro Leu Gly Pro Gly Arg Cys Cys Arg Leu
             35                  40                  45

His Thr Val Arg Ala Ser Leu Glu Asp Leu Gly Trp Ala Asp Trp Val
 50                  55                  60

Leu Ser Pro Arg Glu Val Gln Val Thr Met Cys Ile Gly Ala Cys Pro
```

```
                65                  70                  75                  80
Ser Gln Phe Arg Ala Ala Asn Leu His Ala Gln Ile Lys Thr Ser Leu
                    85                  90                  95

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
                115                 120                 125

Leu Gln Thr Tyr Asp Asp Leu Leu Ala Lys Asp Cys His Cys Ile
            130                 135                 140

<210> SEQ ID NO 304
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 304

Ser Glu Pro Ala Thr Ser Gly Ser Glu Cys Pro Gly Thr Ser Glu Ser
1               5                   10                  15

Ala Thr Pro Glu Ser Gly Pro Gly Thr Ser Thr Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                    85                  90                  95

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
                115                 120                 125

Leu Gln Thr Tyr Asp Asp Leu Leu Ala Lys Asp Cys His Cys Ile
            130                 135                 140

<210> SEQ ID NO 305
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 305

Ser Glu Pro Ala Thr Ser Gly Ser Glu Thr Pro Cys Thr Ser Glu Ser
1               5                   10                  15

Ala Thr Pro Glu Ser Gly Pro Gly Thr Ser Thr Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                    85                  90                  95
```

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140

<210> SEQ ID NO 306
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 306

Ser Glu Pro Ala Thr Ser Gly Ser Glu Thr Pro Gly Thr Cys Glu Ser
1               5                   10                  15

Ala Thr Pro Glu Ser Gly Pro Gly Thr Ser Thr Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
            85                  90                  95

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140

<210> SEQ ID NO 307
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 307

Ser Glu Pro Ala Thr Ser Gly Ser Glu Thr Pro Gly Thr Ser Glu Cys
1               5                   10                  15

Ala Thr Pro Glu Ser Gly Pro Gly Thr Ser Thr Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
            85                  90                  95

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
        115                 120                 125

```
Leu Gln Thr Tyr Asp Asp Leu Leu Ala Lys Asp Cys His Cys Ile
    130                 135                 140

<210> SEQ ID NO 308
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 308

Ser Glu Pro Ala Thr Ser Gly Ser Glu Thr Pro Gly Thr Ser Glu Ser
1               5                   10                  15

Ala Thr Pro Glu Cys Gly Pro Gly Thr Ser Thr Glu Pro Ser Glu Gly
                20                  25                  30

Ala Arg Gly Asp His Cys Pro Leu Gly Pro Gly Arg Cys Cys Arg Leu
            35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                85                  90                  95

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140

<210> SEQ ID NO 309
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 309

Ser Glu Pro Ala Thr Ser Gly Ser Glu Thr Pro Gly Thr Ser Glu Ser
1               5                   10                  15

Ala Thr Pro Glu Ser Cys Pro Gly Thr Ser Thr Glu Pro Ser Glu Gly
                20                  25                  30

Ala Arg Gly Asp His Cys Pro Leu Gly Pro Gly Arg Cys Cys Arg Leu
            35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                85                  90                  95

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140
```

<210> SEQ ID NO 310
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 310

```
Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Cys Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
 50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                85                  90                  95

His Arg Leu Lys Pro Asp Thr Val Pro Ala Pro Cys Cys Val Pro Ala
            100                 105                 110

Ser Tyr Asn Pro Leu Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140
```

<210> SEQ ID NO 311
<211> LENGTH: 121
<212> TYPE: PRT
<213> ORGANISM: Artificial Sequence
<220> FEATURE:
<223> OTHER INFORMATION: MIC-1 polypeptide with N-terminal extension

<400> SEQUENCE: 311

```
Glu Glu Ala Glu Ala Asp Asp Asp Lys Glu Ser Gly Asp His Cys
1               5                   10                  15

Pro Leu Gly Pro Gly Arg Cys Cys Arg Leu His Thr Val Arg Ala Ser
            20                  25                  30

Leu Glu Asp Leu Gly Trp Ala Asp Trp Val Leu Ser Pro Arg Glu Val
        35                  40                  45

Gln Val Thr Met Cys Ile Gly Ala Cys Pro Ser Gln Phe Arg Ala Ala
 50                  55                  60

Asn Met His Ala Gln Ile Lys Thr Ser Leu His Arg Leu Lys Pro Asp
65                  70                  75                  80

Thr Val Pro Ala Pro Cys Cys Val Pro Ala Ser Tyr Asn Pro Met Val
                85                  90                  95

Leu Ile Gln Lys Thr Asp Thr Gly Val Ser Leu Gln Thr Tyr Asp Asp
            100                 105                 110

Leu Leu Ala Lys Asp Cys His Cys Ile
        115                 120
```

<210> SEQ ID NO 312
<211> LENGTH: 143
<212> TYPE: PRT
<213> ORGANISM: Artificial Sequence
<220> FEATURE:
<223> OTHER INFORMATION: MIC-1 polypeptide with N-terminal extension

<400> SEQUENCE: 312

-continued

```
Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Ala Arg Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                85                  90                  95

His Arg Leu Arg Pro Asp Thr Val Pro Ala Pro Cys Cys Val Pro Ala
            100                 105                 110

Ser Tyr Asn Pro Leu Val Leu Ile Gln Arg Thr Asp Thr Gly Val Ser
            115                 120                 125

Leu Gln Thr Tyr Asp Asp Leu Leu Ala Arg Asp Cys His Cys Ile
            130                 135                 140
```

<210> SEQ ID NO 313
<211> LENGTH: 10
<212> TYPE: PRT
<213> ORGANISM: Artificial Sequence
<220> FEATURE:
<223> OTHER INFORMATION: N-terminal extension

<400> SEQUENCE: 313

```
Glu Glu Ala Glu Ala Asp Asp Asp Asp Lys
1               5                   10
```

<210> SEQ ID NO 314
<211> LENGTH: 111
<212> TYPE: PRT
<213> ORGANISM: Artificial Sequence
<220> FEATURE:
<223> OTHER INFORMATION: MIC-1 polypeptide

<400> SEQUENCE: 314

```
Glu Ser Gly Asp His Cys Pro Leu Gly Pro Gly Arg Cys Cys Arg Leu
1               5                   10                  15

His Thr Val Arg Ala Ser Leu Glu Asp Leu Gly Trp Ala Asp Trp Val
            20                  25                  30

Leu Ser Pro Arg Glu Val Gln Val Thr Met Cys Ile Gly Ala Cys Pro
        35                  40                  45

Ser Gln Phe Arg Ala Ala Asn Met His Ala Gln Ile Lys Thr Ser Leu
    50                  55                  60

His Arg Leu Lys Pro Asp Thr Val Pro Ala Pro Cys Cys Val Pro Ala
65                  70                  75                  80

Ser Tyr Asn Pro Met Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110
```

<210> SEQ ID NO 315
<211> LENGTH: 111
<212> TYPE: PRT
<213> ORGANISM: Artificial Sequence
<220> FEATURE:
<223> OTHER INFORMATION: MIC-1 polypeptide

<400> SEQUENCE: 315

Ala Arg Gly Asp His Cys Pro Leu Gly Pro Gly Arg Cys Cys Arg Leu
1               5                   10                  15

His Thr Val Arg Ala Ser Leu Glu Asp Leu Gly Trp Ala Asp Trp Val
            20                  25                  30

Leu Ser Pro Arg Glu Val Gln Val Thr Met Cys Ile Gly Ala Cys Pro
        35                  40                  45

Ser Gln Phe Arg Ala Ala Asn Leu His Ala Gln Ile Lys Thr Ser Leu
    50                  55                  60

His Arg Leu Arg Pro Asp Thr Val Pro Ala Pro Cys Cys Val Pro Ala
65                  70                  75                  80

Ser Tyr Asn Pro Leu Val Leu Ile Gln Arg Thr Asp Thr Gly Val Ser
                85                  90                  95

Leu Gln Thr Tyr Asp Asp Leu Leu Ala Arg Asp Cys His Cys Ile
            100                 105                 110

<210> SEQ ID NO 316
<211> LENGTH: 140
<212> TYPE: PRT
<213> ORGANISM: Artificial Sequence
<220> FEATURE:
<223> OTHER INFORMATION: MIC-1 polypeptide with N-terminal extension

<400> SEQUENCE: 316

Gly Glu Gln Pro Cys Glu Gln Pro Gly Glu Gln Pro Gly Glu Gln Pro
1               5                   10                  15

Gly Glu Gln Pro Gly Glu Gln Pro Gly Glu Gln Pro Ala Arg Asn Gly
            20                  25                  30

Asp His Cys Pro Leu Gly Pro Gly Arg Cys Cys Arg Leu His Thr Val
        35                  40                  45

Arg Ala Ser Leu Glu Asp Leu Gly Trp Ala Asp Trp Val Leu Ser Pro
    50                  55                  60

Arg Glu Val Gln Val Thr Met Cys Ile Gly Ala Cys Pro Ser Gln Phe
65                  70                  75                  80

Arg Ala Ala Asn Met His Ala Gln Ile Lys Thr Ser Leu His Arg Leu
                85                  90                  95

Lys Pro Asp Thr Val Pro Ala Pro Cys Cys Val Pro Ala Ser Tyr Asn
            100                 105                 110

Pro Met Val Leu Ile Gln Lys Thr Asp Thr Gly Val Ser Leu Gln Thr
        115                 120                 125

Tyr Asp Asp Leu Leu Ala Lys Asp Cys His Cys Ile
    130                 135                 140

<210> SEQ ID NO 317
<211> LENGTH: 28
<212> TYPE: PRT
<213> ORGANISM: Artificial Sequence
<220> FEATURE:
<223> OTHER INFORMATION: N-terminal extension

<400> SEQUENCE: 317

Gly Glu Gln Pro Cys Glu Gln Pro Gly Glu Gln Pro Gly Glu Gln Pro
1               5                   10                  15

Gly Glu Gln Pro Gly Glu Gln Pro Gly Glu Gln Pro
            20                  25

The invention claimed is:
1. A MIC-1 compound, comprising
a MIC-1 polypeptide;
an amino acid extension attached to the N-terminal of the MIC-1 polypeptide; and
a protractor attached to the amino acid extension;
wherein the amino acid extension comprises 3 to 36 amino acid residues;
wherein one of the amino acid residues is a Cys and the remainder of the amino acid residues are selected from the group consisting of Ala, Glu, Gly, Pro, Ser, and Thr;
wherein the distance between the Cys residue and the N-terminal amino acid of the MIC-1 polypeptide is at least 3 amino acids;
wherein the protractor is attached to the amino acid extension at the Cys residue;
wherein the protractor comprises Chem. 1, Chem. 2, Chem. 3, and Chem. 4;
wherein Chem. 1 is selected from the group consisting of:

| | |
|---|---|
| $HOOC—(CH_2)_x—CO—*$, | Chem. 1A: |
| $HO—S(=O)_2—(CH_2)_x—CO—*$, | Chem. 1B: |
| $HOOC\text{-benzene-}O—(CH_2)_y—CO—*$, and | Chem. 1C: |
| $(1H\text{-tetrazol-5-yl})\text{-}(CH_2)_x—CO—*$, | Chem. 1D: | wherein x is an integer in the range of 12-20, and
wherein y is an integer in the range of 5-15;
wherein Chem. 2 is selected from the group consisting of:

| | |
|---|---|
| $*—(NH—CH(COOH)—(CH_2)_m—CO)_k—*$ and | Chem. 2A: |
| $*—(NH—S(=O)_2—(CH_2)_m—CO)_k—*$ | Chem. 2B: | wherein m of Chem. 2 is an integer in the range of 1-5, and
wherein k of Chem. 2 is an integer in the range of 0-4;
wherein Chem. 3 is $*(NH—(CH_2)_2—[O—(CH_2)_2]_k—O—[CH_2]_n—CO—*)_l$,
wherein k of Chem. 3 is an integer in the range of 1-10,
wherein n is an integer in the range of 1-5, and
wherein l is an integer in the range of 0-5;
wherein Chem. 4 is selected from the group consisting of:

| | |
|---|---|
| $*—NH—(CH_2)_m—NH—CO—CH_2—*$, and | Chem. 4A: |
| $*—NH—CH(COOH)—(CH_2)_m—NH—O—CH_2—*$, | Chem. 4B: | wherein m of Chem. 4 is an integer in the range of 1-5;
wherein Chem. 1, Chem. 2, Chem. 3, and Chem. 4 are interconnected via amide bonds;
wherein Chem. 4 at its $CH_2—*$ end is connected to a sulphur atom of the Cys residue of the amino acid extension; and
wherein the MIC-1 polypeptide with the amino acid extension has a calculated pI lower than 6.5.

2. The MIC-1 compound according to claim 1, wherein Chem. 1 is selected from the group consisting of:

| | |
|---|---|
| $HOOC—(CH_2)_{16}—CO—*$, | Chem. 1a: |
| $HO—S(=O)_2—(CH_2)_{15}—CO—*$, and | Chem. 1b: |
| $HOOC\text{-benzene-}O—(CH_2)_9—CO—*$. | Chem. 1c: |

3. The MIC-1 compound according to claim 1, wherein Chem. 2 is selected from the group consisting of:

| | |
|---|---|
| $*—NH—CH(COOH)—(CH_2)_2—CO—*$ and | Chem. 2a: |
| $*—NH—S(=O)_2—(CH_2)_3—CO—*$. | Chem. 2b: |

4. The MIC-1 compound according to claim 1, wherein Chem. 4 is selected from the group consisting of:

| | |
|---|---|
| $*—NH—(CH_2)_2—NH—CO—CH_2—*$ and | Chem. 4a: |
| $*—NH—CH(COOH)—(CH_2)_4—NH—CO—CH_2—*$. | Chem. 4b: |

5. The MIC-1 compound according to claim 1, wherein Chem. 1 is selected from the group consisting of:

| | |
|---|---|
| $HOOC—(CH_2)_{16}—CO—*$, | Chem. 1a: |
| $HO—S(=O)_2—(CH_2)_{15}—CO—*$, and | Chem. 1b: |
| $HOOC\text{-benzene-}O—(CH_2)_9—CO—*$; | Chem. 1c: | wherein Chem. 2 is selected from the group consisting of:

| | |
|---|---|
| $*—NH—CH(COOH)—(CH_2)_2—CO—*$ and | Chem. 2a: |
| $*—NH—S(=O)_2—(CH_2)_3—CO—*$; and | Chem. 2b: | wherein Chem. 4 is selected from the group consisting of:

| | |
|---|---|
| $*—NH—(CH_2)_2—NH—CO—CH_2—*$ and | Chem. 4a: |
| $*—NH—CH(COOH)—(CH_2)_4—NH—CO—CH_2—*$. | Chem. 4b: |

6. The MIC-1 compound according to claim 1, wherein the protractor is selected from the group consisting of Formula IX, Formula X, Formula XI, Formula XII, and Formula XIII:

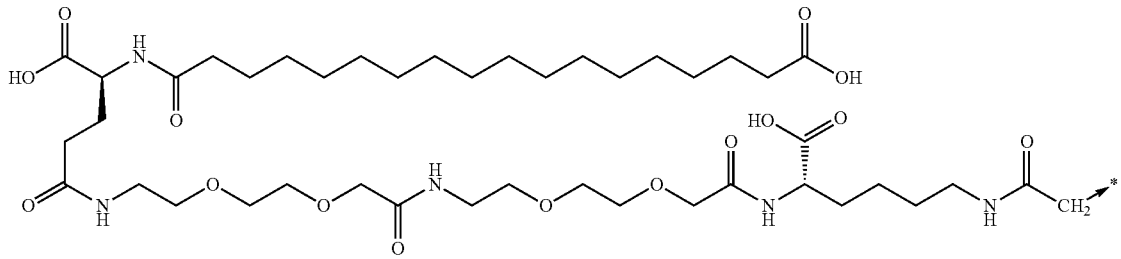

(Formula IX)

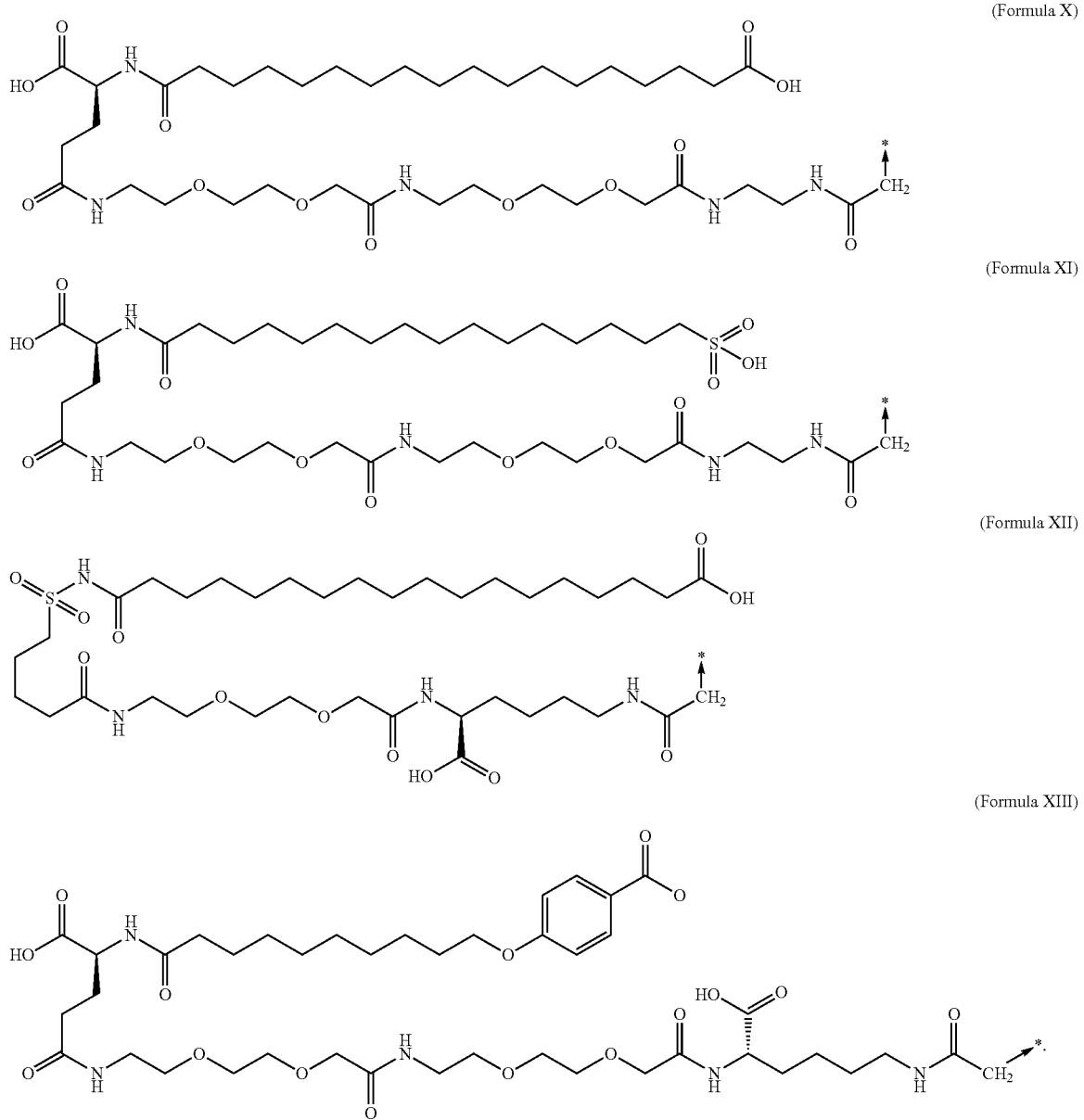

7. The MIC-1 compound according to claim 1, wherein the amino acid extension comprises a sequence selected from the group consisting of:

SEPATCGSETPGTSESATPESGPGTSTEPS,     (SEQ ID NO: 223)

SEPATSGCETPGTSESATPESGPGTSTEPS,     (SEQ ID NO: 224)

SEPCTSGSETPGTSESATPESGPGTSTEPSEG,   (SEQ ID NO: 225)

SEPATCGSETPGTSESATPESGPGTSTEPSEG,   (SEQ ID NO: 226)

SEPATSCSETPGTSESATPESGPGTSTEPSEG,   (SEQ ID NO: 227)

SEPACSGSETPGTSESATPESGPGTSTEPSEG,   (SEQ ID NO: 229)

SEPATSGCETPGTSESATPESGPGTSTEPSEG,   (SEQ ID NO: 230)

SEPATSGSECPGTSESATPESGPGTSTEPSEG,   (SEQ ID NO: 231)

SEPATSGSETPCTSESATPESGPGTSTEPSEG,   (SEQ ID NO: 232)

SEPATSGSETPGTCESATPESGPGTSTEPSEG,   (SEQ ID NO: 233)

SEPATSGSETPGTSECATPESGPGTSTEPSEG,   (SEQ ID NO: 234)

-continued

SEPATSGSETPGTSESACPESGPGTSTEPSEG, (SEQ ID NO: 235)

SEPATSGSETPGTSESATPECGPGTSTEPSEG, (SEQ ID NO: 236)
and

SEPATSGSETPGTSESATPESCPGTSTEPSEG. (SEQ ID NO: 237)

8. The MIC-1 compound according to claim 1, wherein the MIC-1 polypeptide comprises at least one of M57L and M86L, when compared to SEQ ID NO: 1.

9. The MIC-1 compound according to claim 1, wherein the MIC-1 polypeptide comprises a deletion of the first three residues or a deletion of N3 when compared to SEQ ID NO: 1.

10. The MIC-1 compound according to claim 1, wherein the MIC-1 polypeptide comprises (i) at least one of M57L and M86L and (ii) a deletion of the first three residues or a deletion of N3, when compared to SEQ ID NO:1.

11. The MIC-1 compound according to claim 1, wherein the combination of the MIC-1 polypeptide and the amino acid extension comprises an amino acid sequence selected from the group consisting of SEQ ID NO: 100, SEQ ID NO: 104, SEQ ID NO: 106, SEQ ID NO: 107, SEQ ID NO: 108, SEQ ID NO: 109, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 164, SEQ ID NO: 288, SEQ ID NO: 289, SEQ ID NO: 290, SEQ ID NO: 291, and SEQ ID NO: 292.

12. The MIC-1 compound according to claim 1, where the compound is selected from the group consisting of:

(Formula 1)
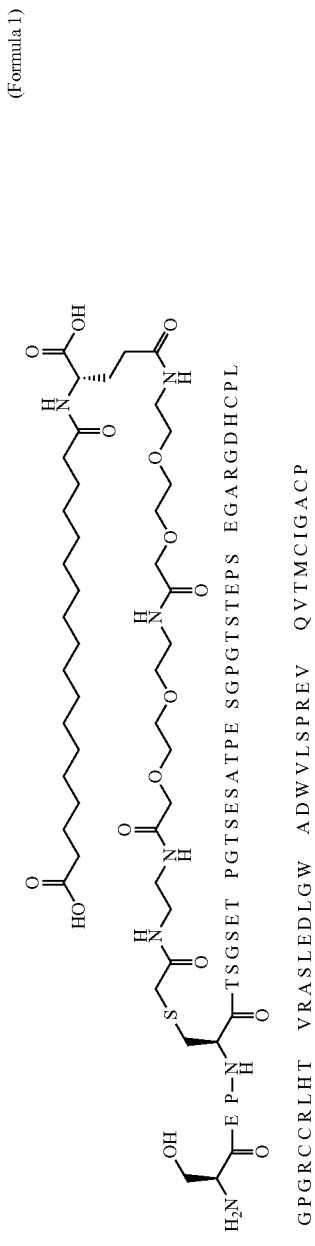
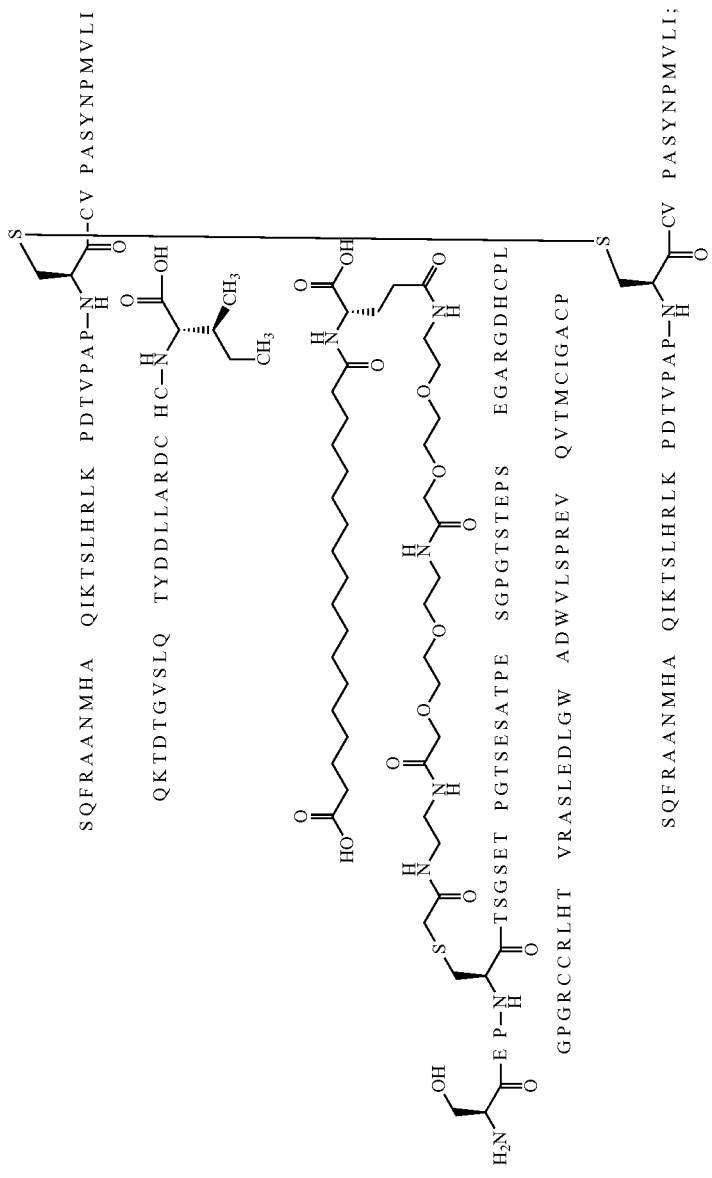

-continued
QKTDTGVSLQ TYDDLLAKDC HC—N—CH
                              |
                              CH₂—CH₃
                              (with COOH, CH₃)
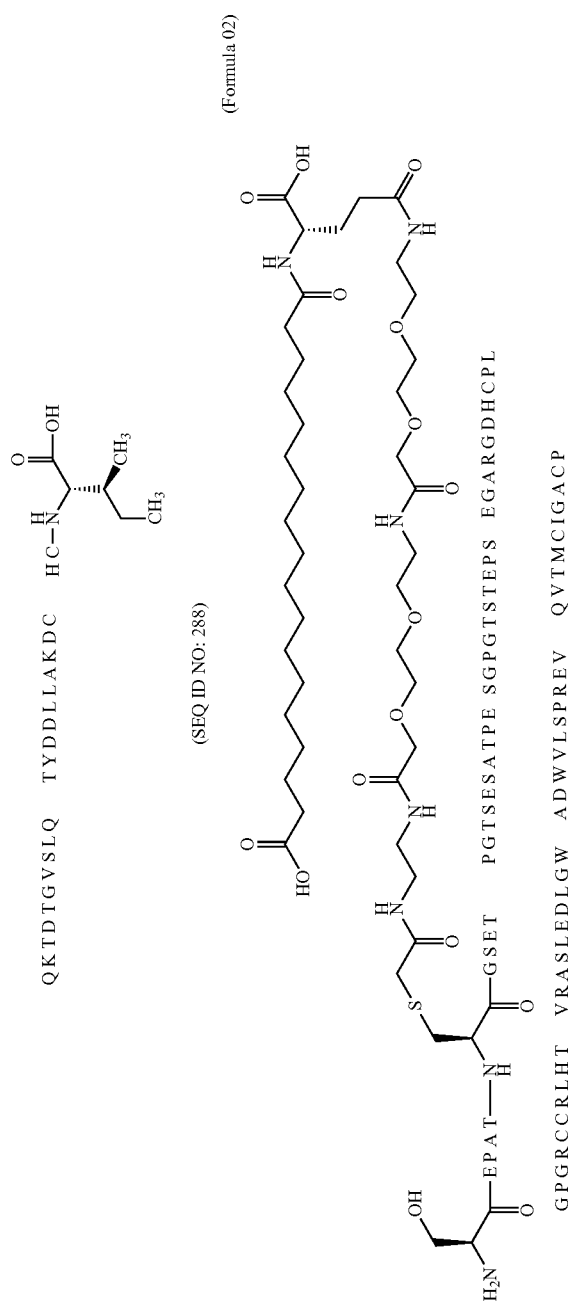
(SEQ ID NO: 288)
GPGRCCRLHT GSET PGTSESATPE SGPGTSTEPS EGARGDHCPL
VRASLEDLGW ADWVLSPREV QVTMCIGACP
(Formula 02)

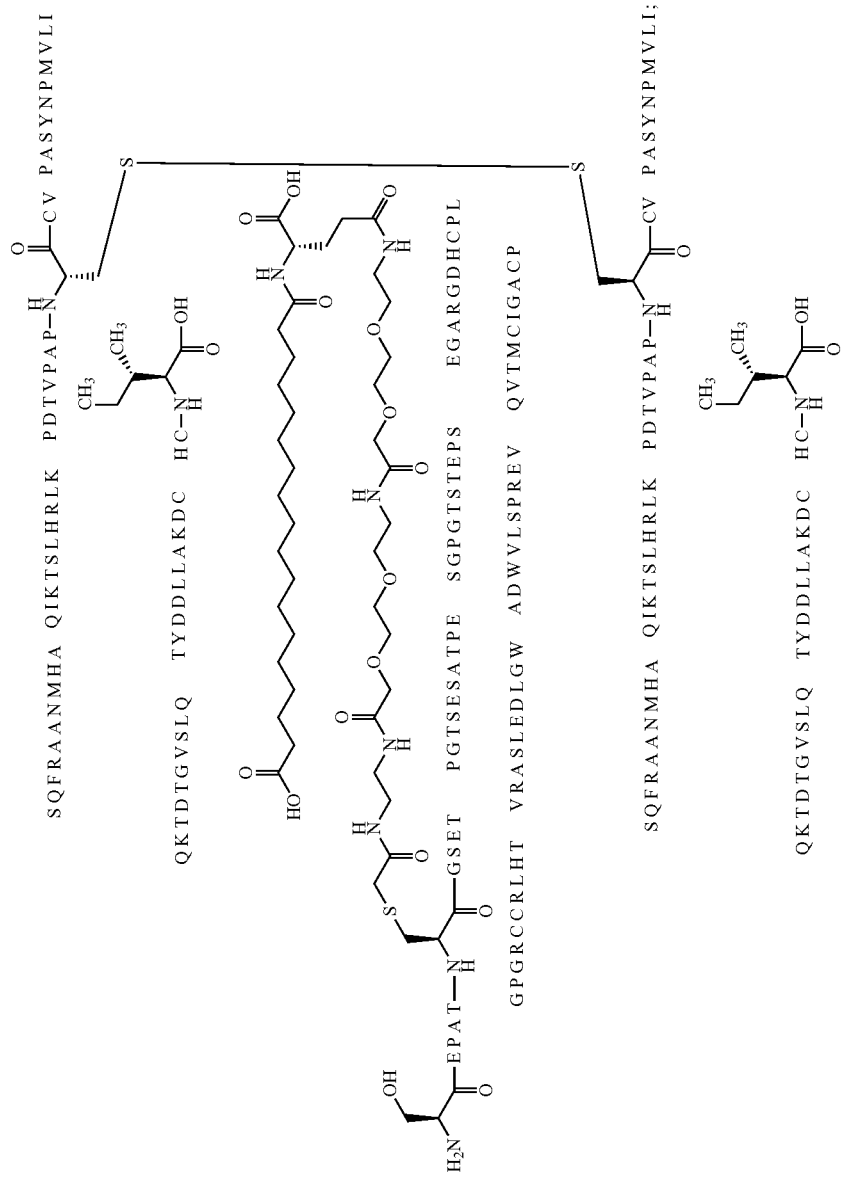

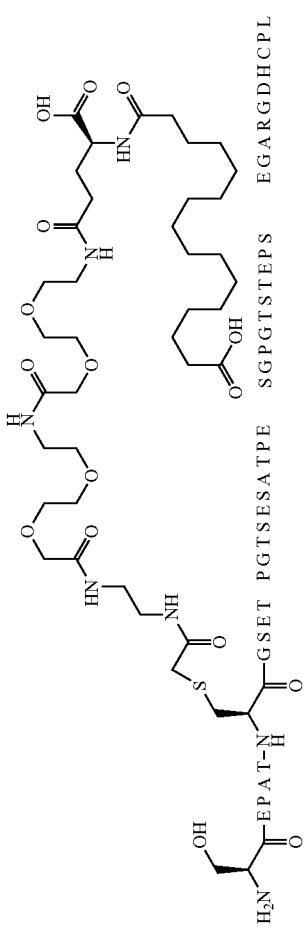
(Formula 03)

-continued
QKTDTGVSLQ TYDDLLAKDC
(SEQ ID NO: 291)

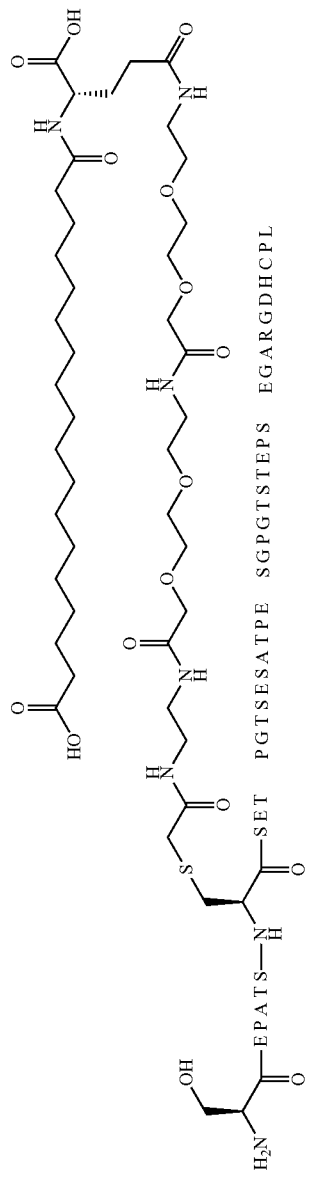
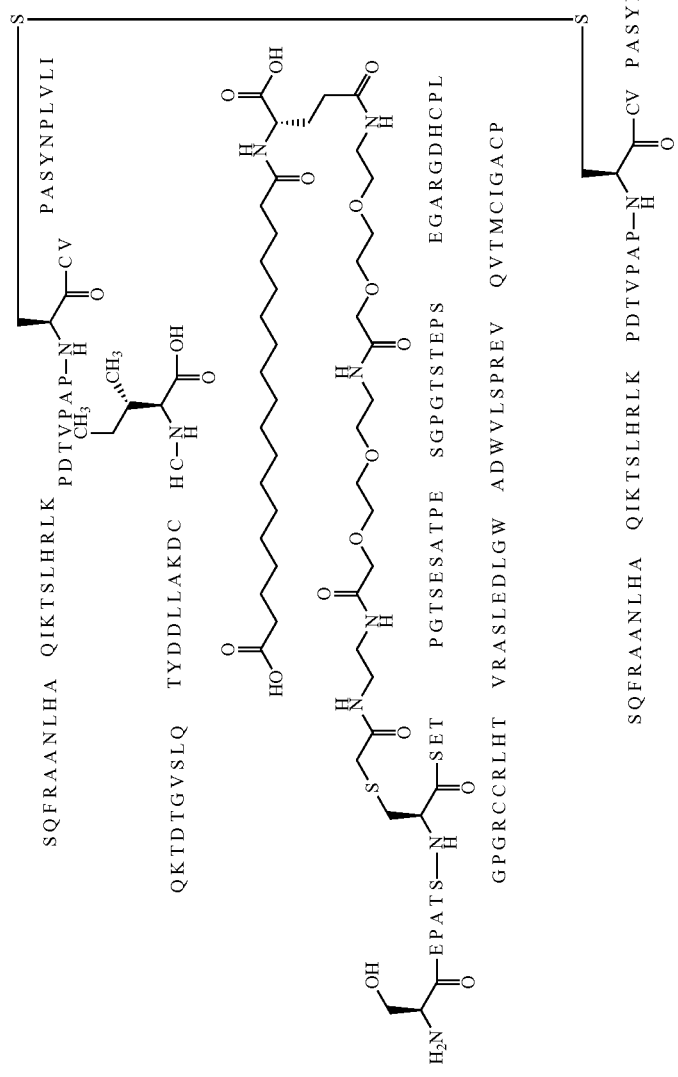

-continued
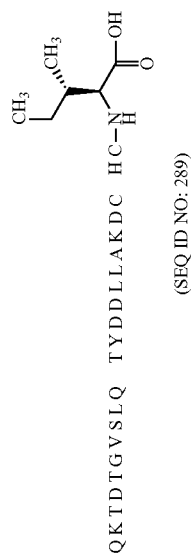
QKTDTGVSLQ TYDDLLAKDC
(SEQ ID NO: 289)

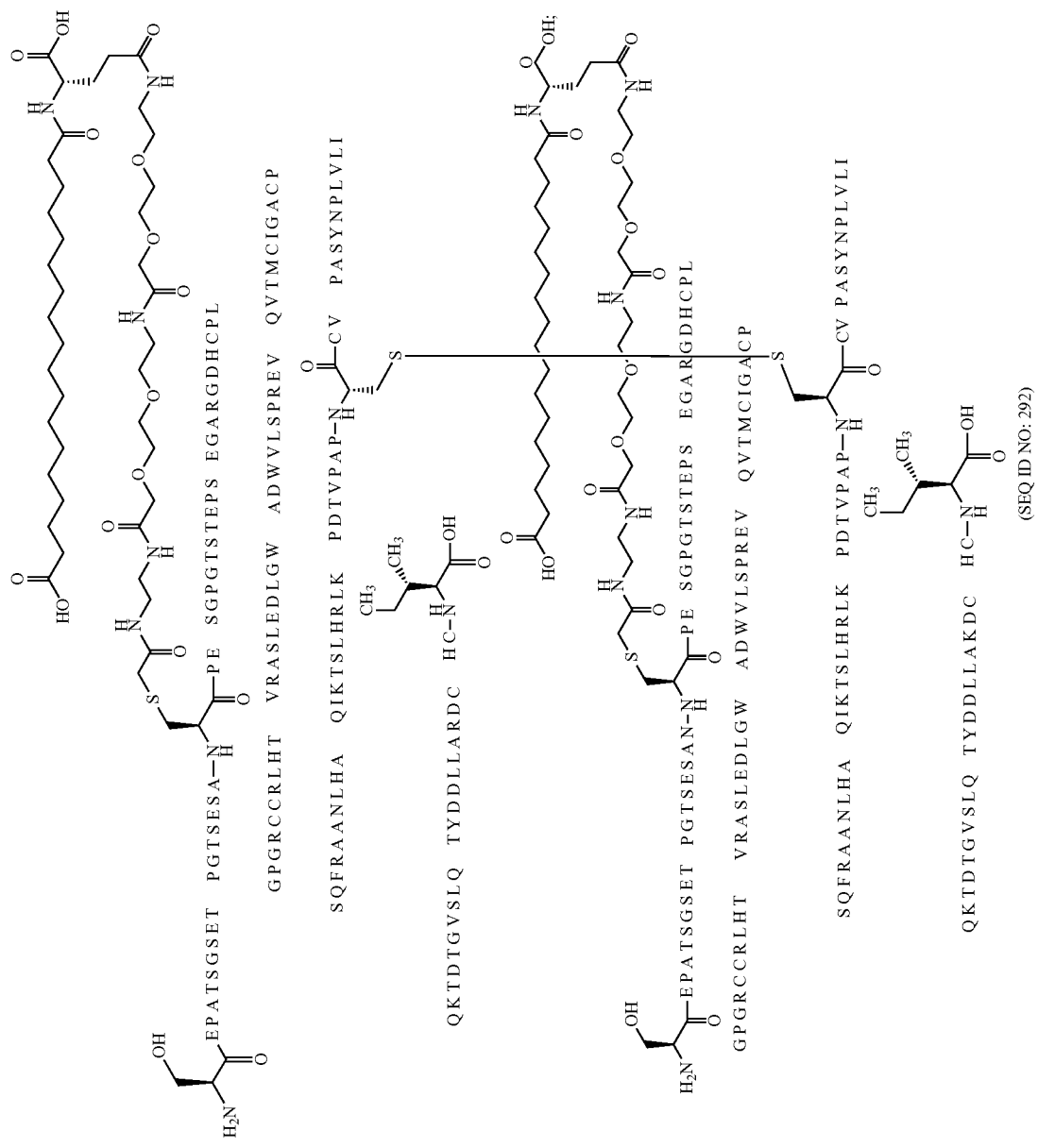

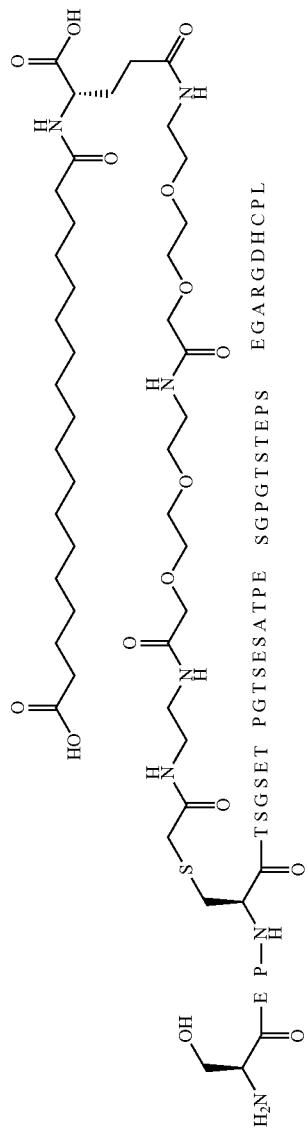

-continued
QKTDTGVSLQ TYDDLLAKDC
(SEQ ID NO: 290)

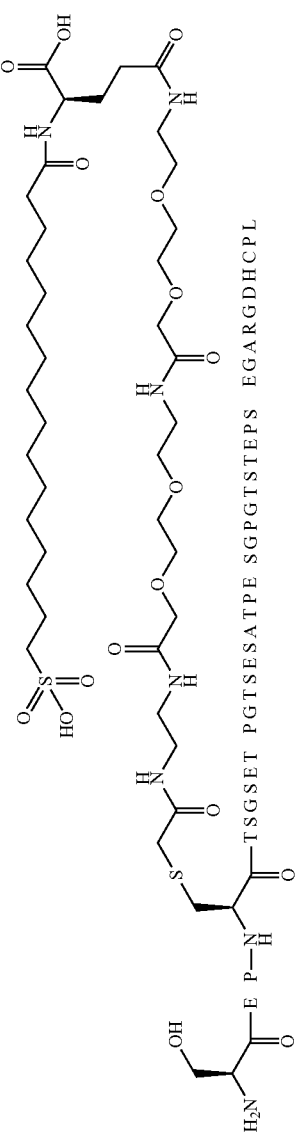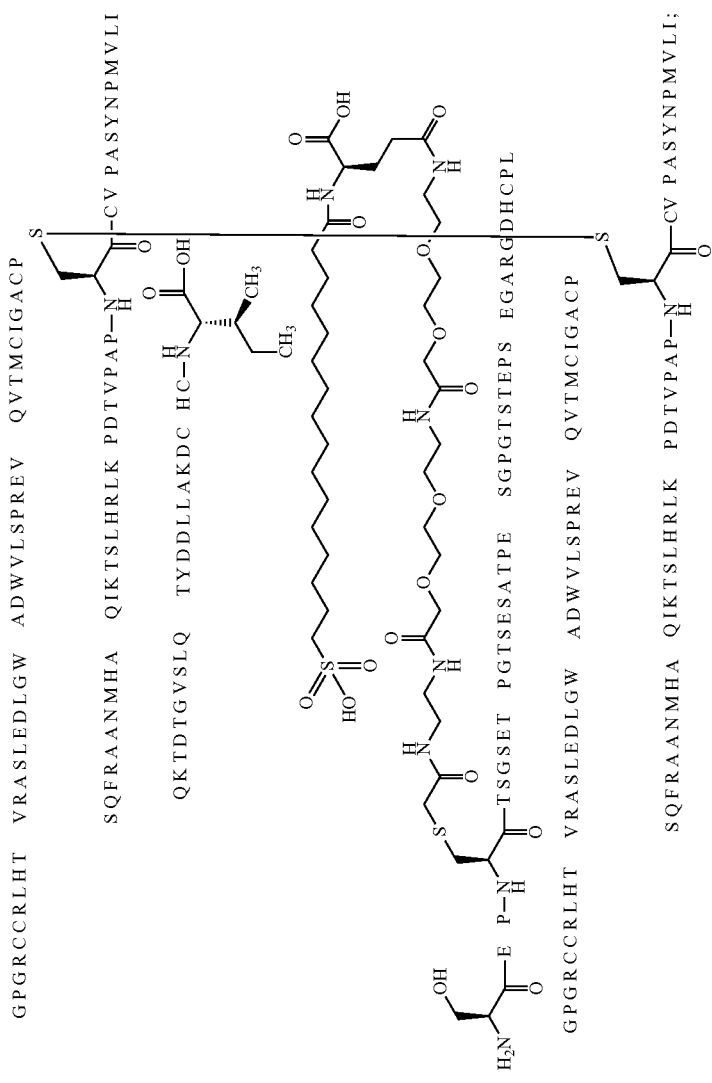

-continued
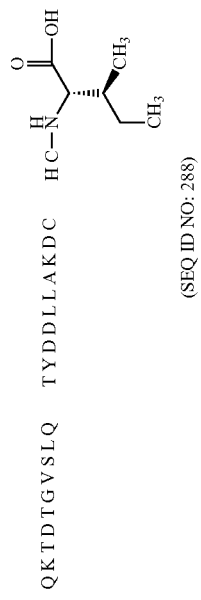
QKTDTGVSLQ TYDDLLAKDC
(SEQ ID NO: 288)

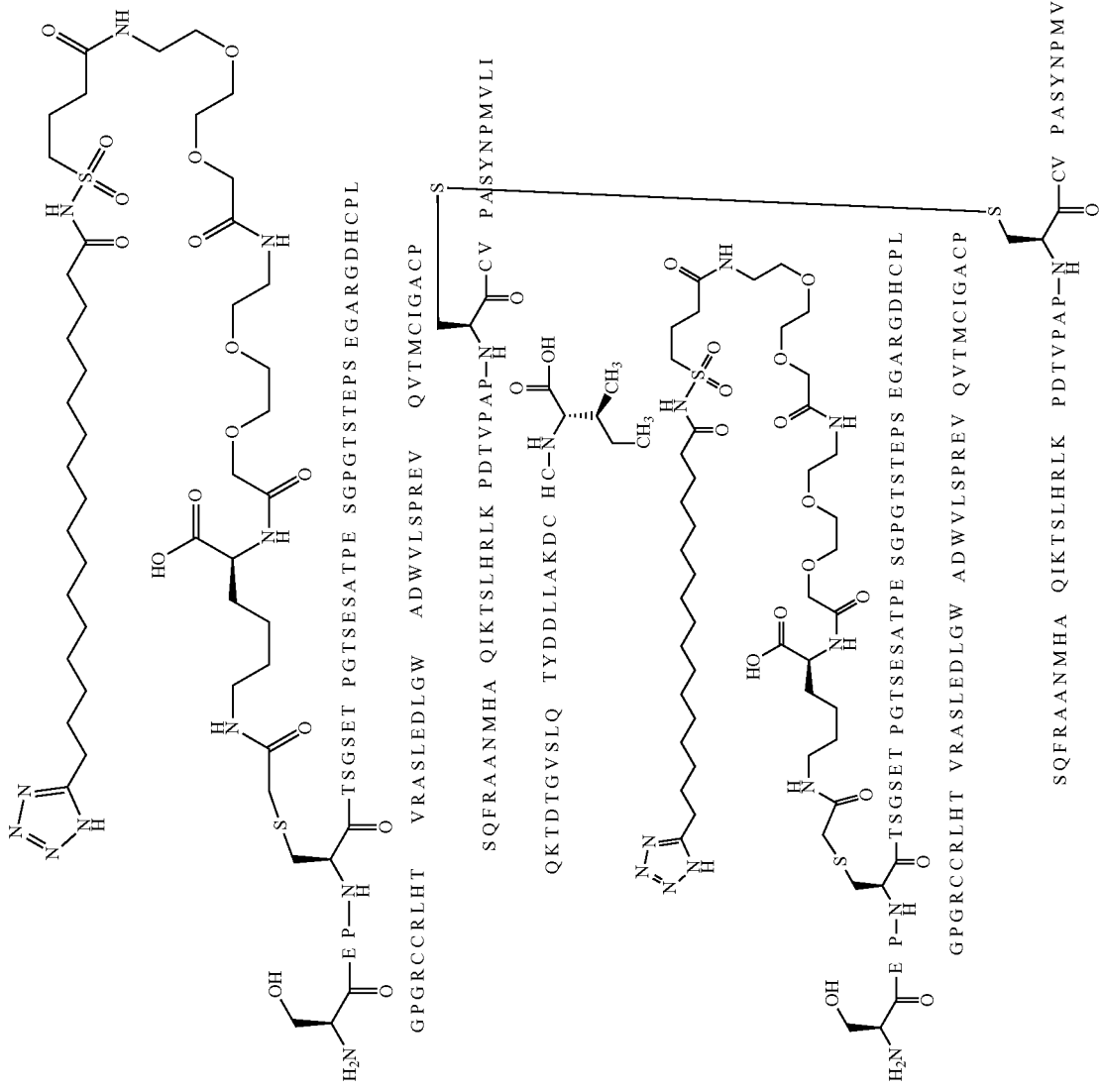
(Formula 18)

-continued
QKTDTGVSLQ TYDDLLAKDC
(SEQ ID NO: 288)

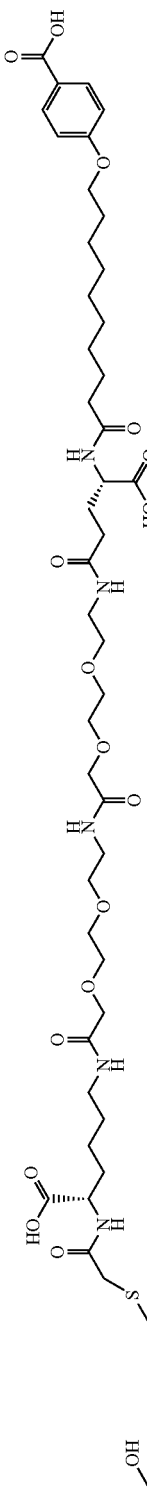

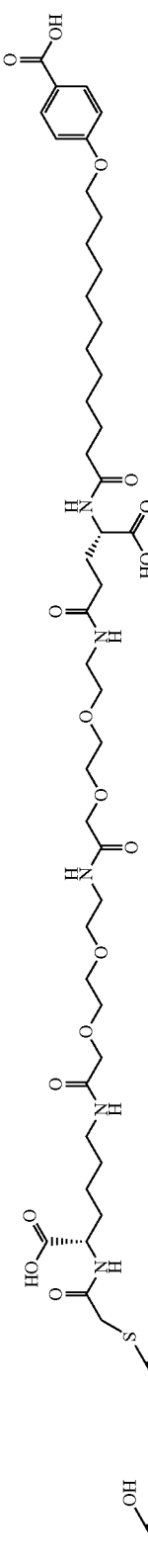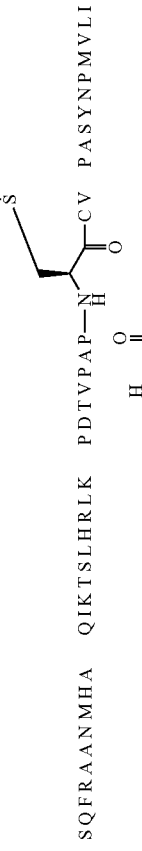
(Formula 20)
(SEQ ID NO: 288)

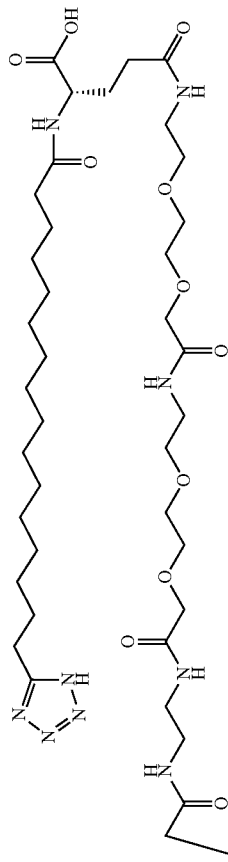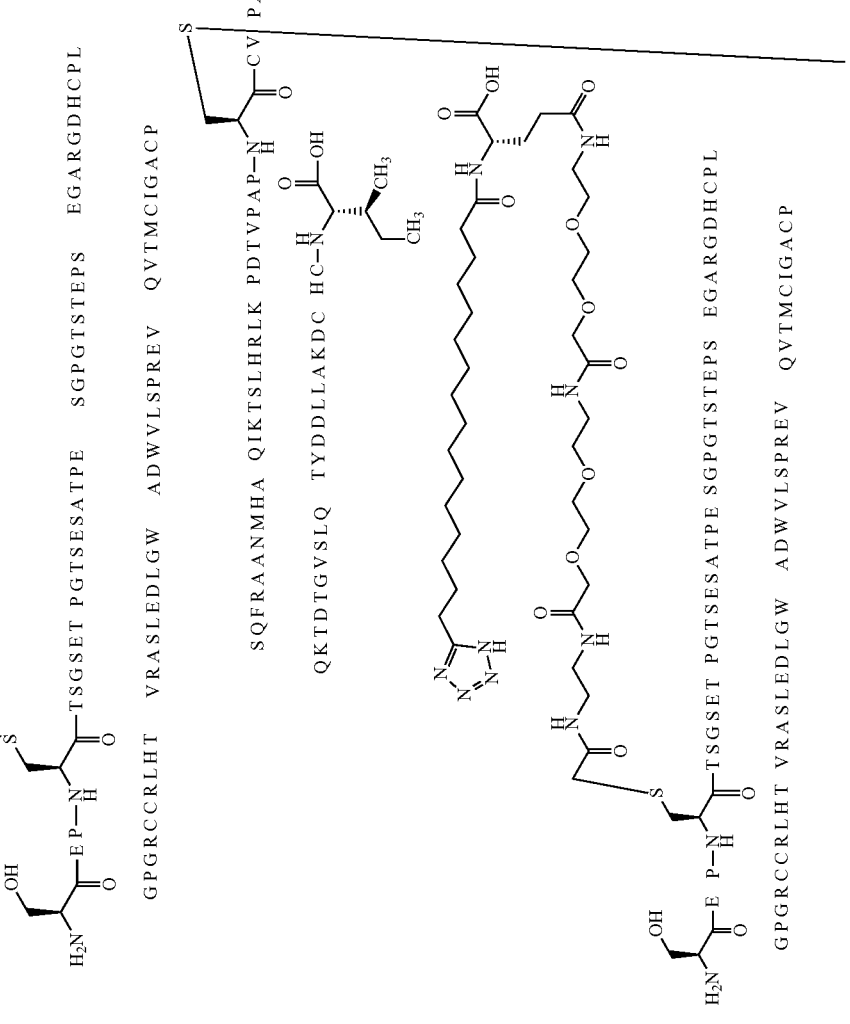

-continued
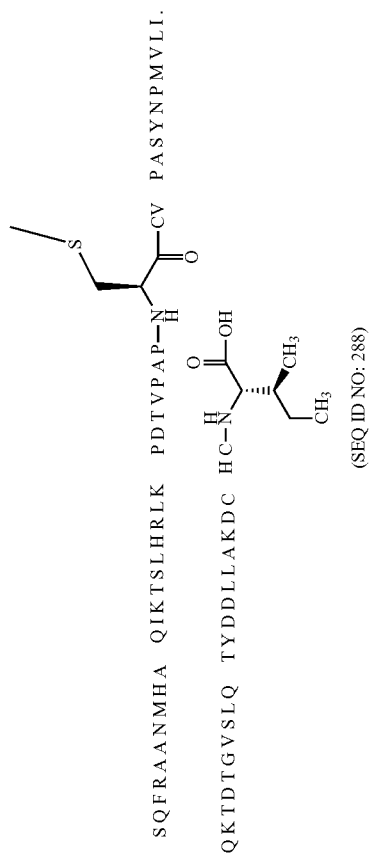
SQFRAANMHA QIKTSLHRLK PDTVPAP-...-CV PASYNPMVLI
QKTDTGVSLQ TYDDLLAKDC
(SEQ ID NO: 288)

13. The MIC-1 compound according to claim 1, wherein the compound is (Formula 01)

SGSET PGTSESATPE SGPGTSTEPS EGARGDHCPL
GPGRCCRLHT VRASLEDLGW ADWVLSPREV QVTMCIGACP

SQFRAANMHA QIKTSLHRLK PDTVPAP—CV PASYNPMVLI
QKTDTGVSLQ TYDDLLAKDC HC

TSGSET PGTSESATPE SGPGTSTEPS EGARGDHCPL
GPGRCCRLHT VRASLEDLGW ADWVLSPREV QVTMCIGACP
SQFRAANMHA QIKTSLHRLK PDTVPAP—C V PASYNPMVLI

QKTDTGVSLQ TYDDLLAKDC HC (SEQ ID NO: 288)

14. The MIC-1 compound according to claim 1, wherein the compound is
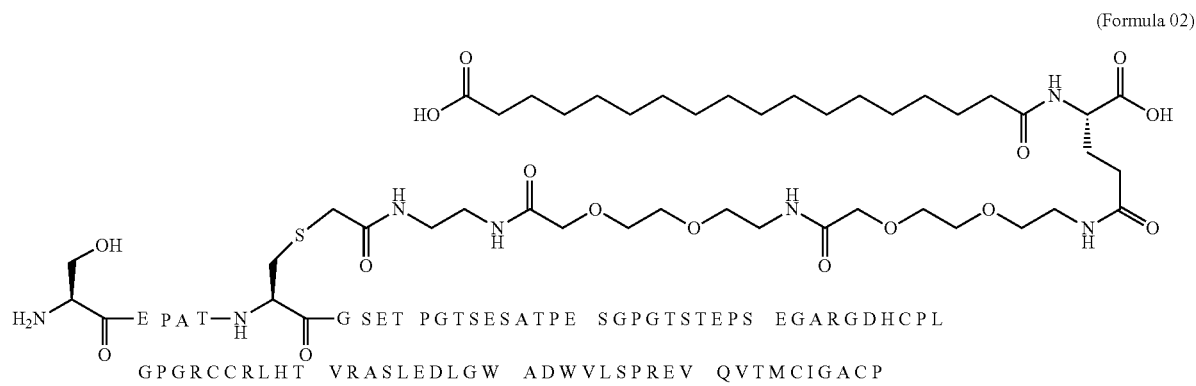
(Formula 02)
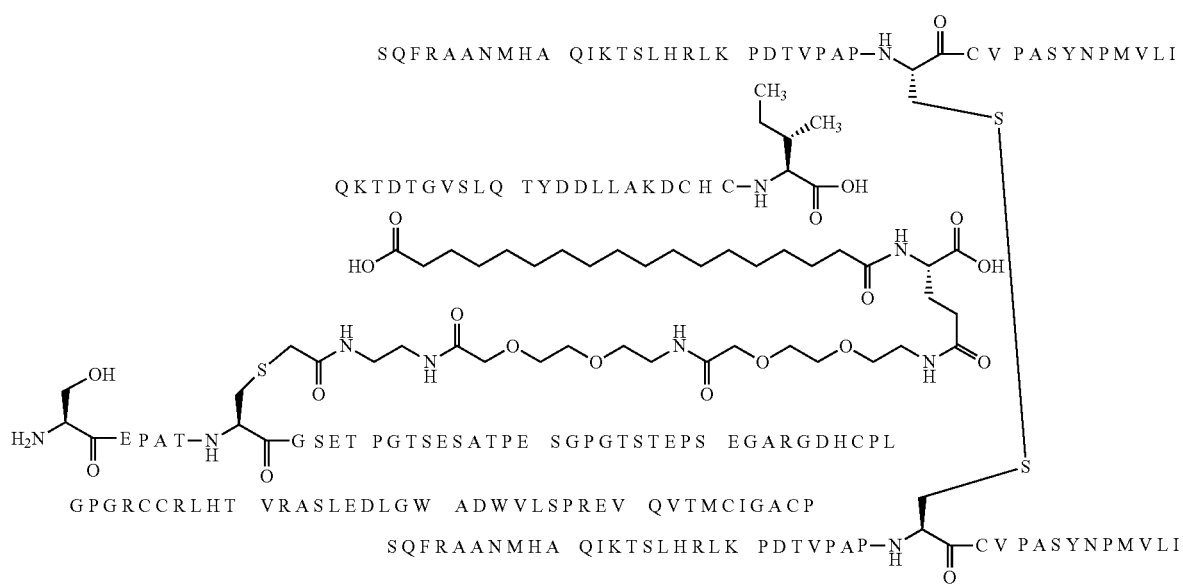
(SEQ ID NO: 291)

15. The MIC-1 compound according to claim 1, wherein the compound is
(Formula 03)
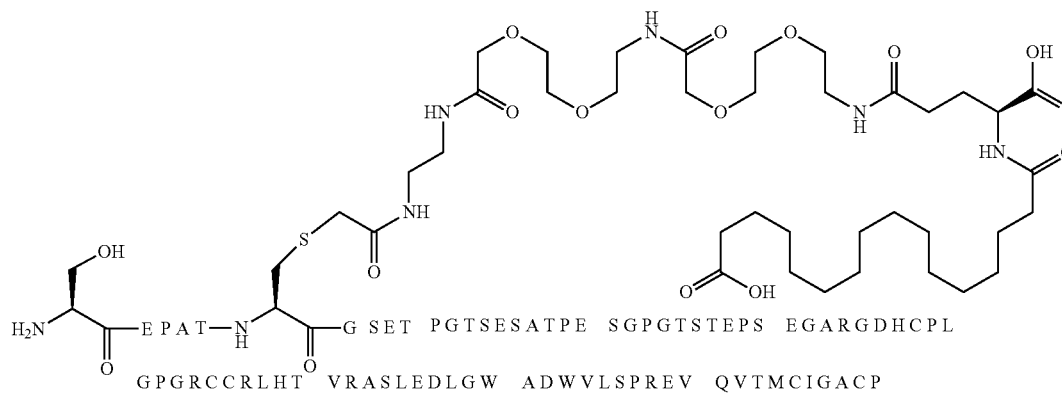
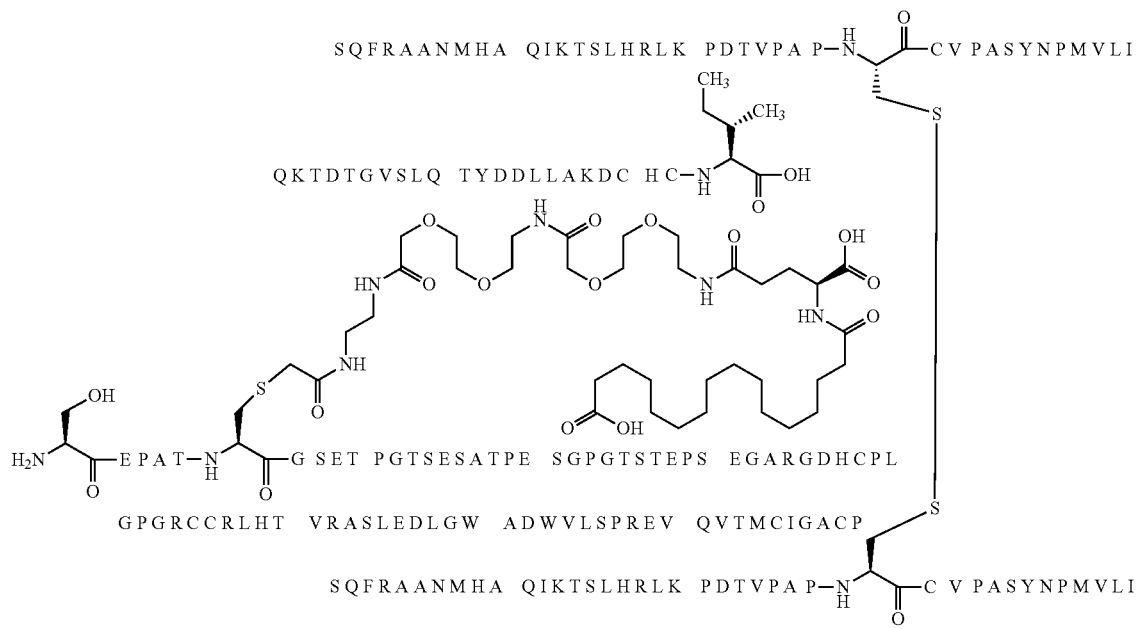
(SEQ ID NO: 291)

16. The MIC-1 compound according to claim 1, wherein the compound is
(Formula 05)
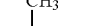
(SEQ ID NO: 289)

17. The MIC-1 compound according to claim 1, wherein the compound is
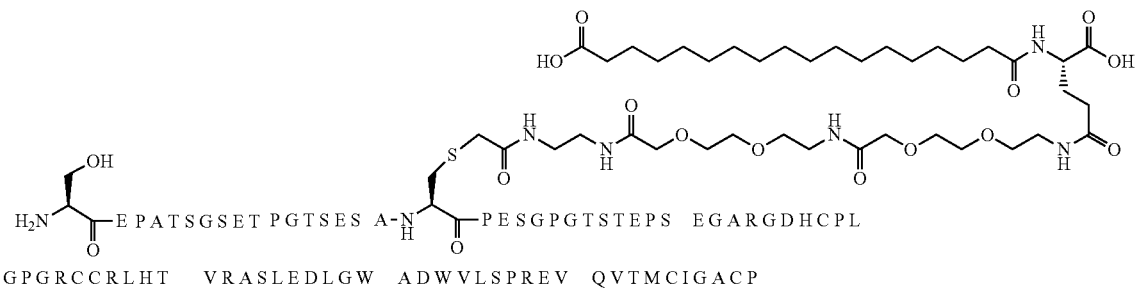
(Formula 07)
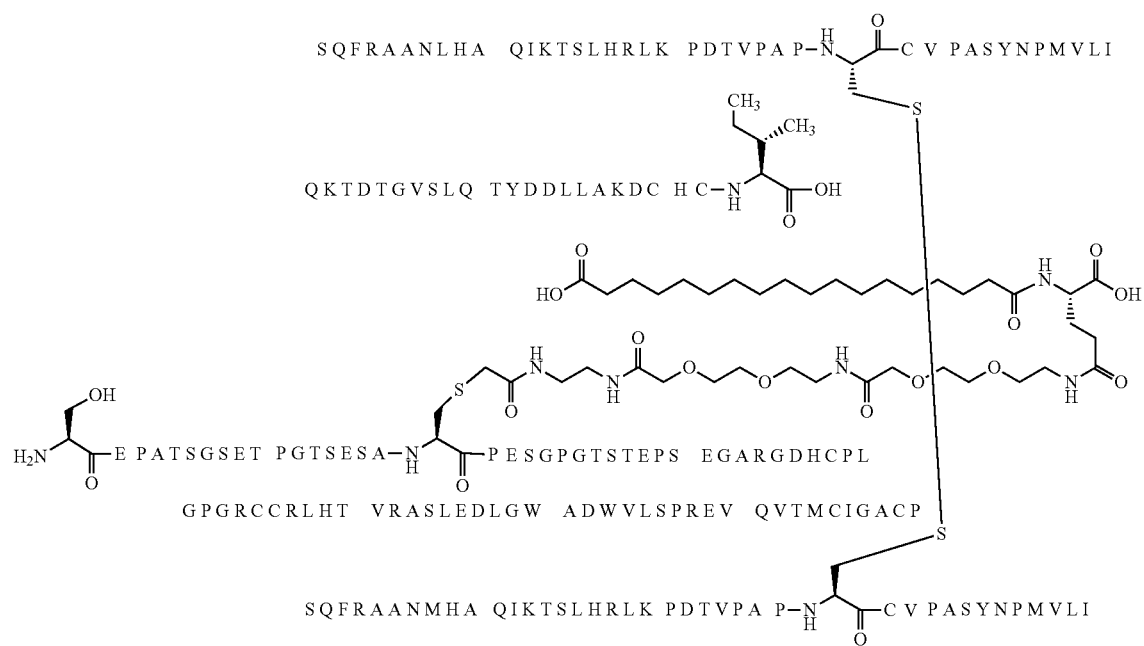
(SEQ ID NO: 292)

18. The MIC-1 compound according to claim 1, wherein the compound is (Formula 11)

[Chemical structure of a dimeric MIC-1 compound with fatty acid-PEG linkers attached via cysteine residues]

GPGRCCRLHT VRASLEDLGW ADWVLSPREV QVTMCIGACP
SQFRAANLHA QIKTSLHRLK PDTVPAP-CV PASYNPMVLI
QKTDTGVSLQ TYDDLLAKDCH C-

GPGRCCRLHT VRASLEDLGW ADWVLSPREV QVTMCIGACP
SQFRAANMHA QIKTSLHRLK PDTVPAP-CV PASYNPMVLI
QKTDTGVSLQ TYDDLLAKDC HC- (SEQ ID NO: 290)

19. The MIC-1 compound according to claim 1, wherein the compound is (Formula 17)

[Chemical structure with sulfonate-terminated fatty acid-PEG linker attached to peptide]

GPGRCCRLHT VRASLEDLGW ADWVLSPREV QVTMCIGACP

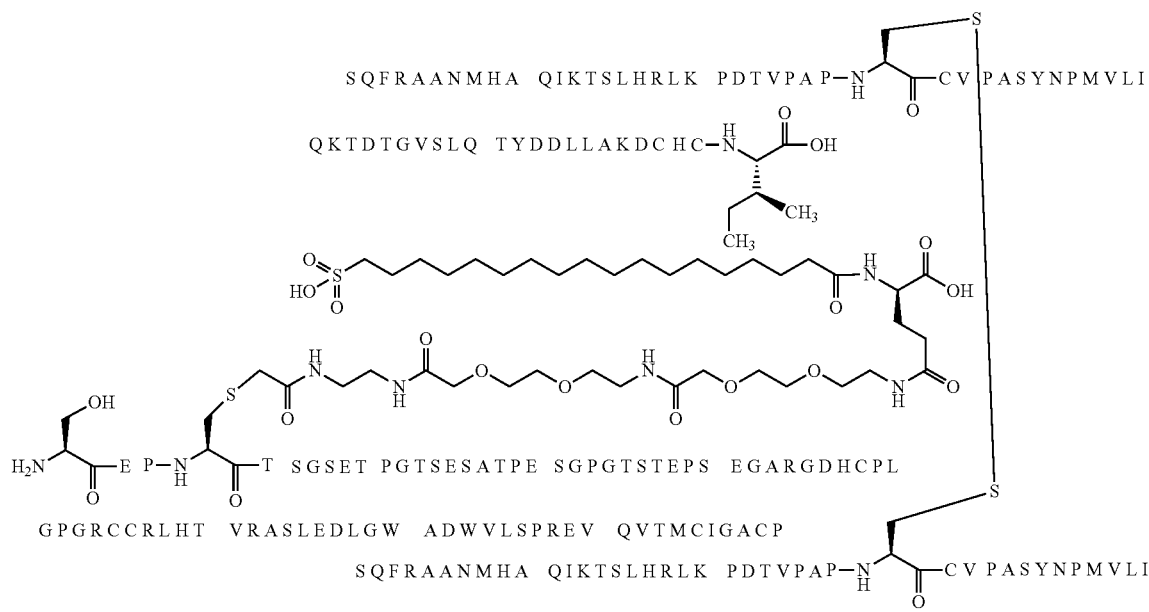
(SEQ ID NO: 288)
20. The MIC-1 compound according to claim 1, wherein the compound is
(Formula 18)
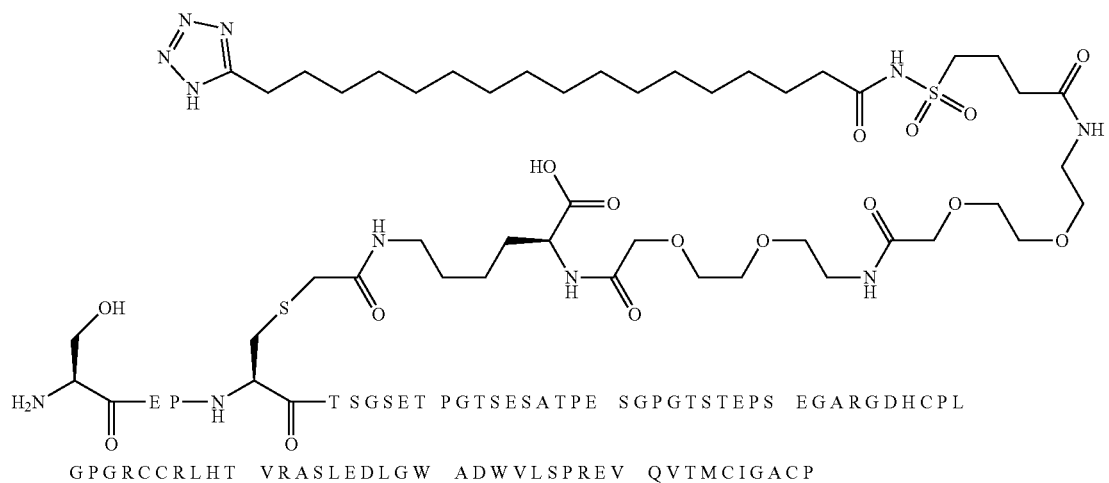

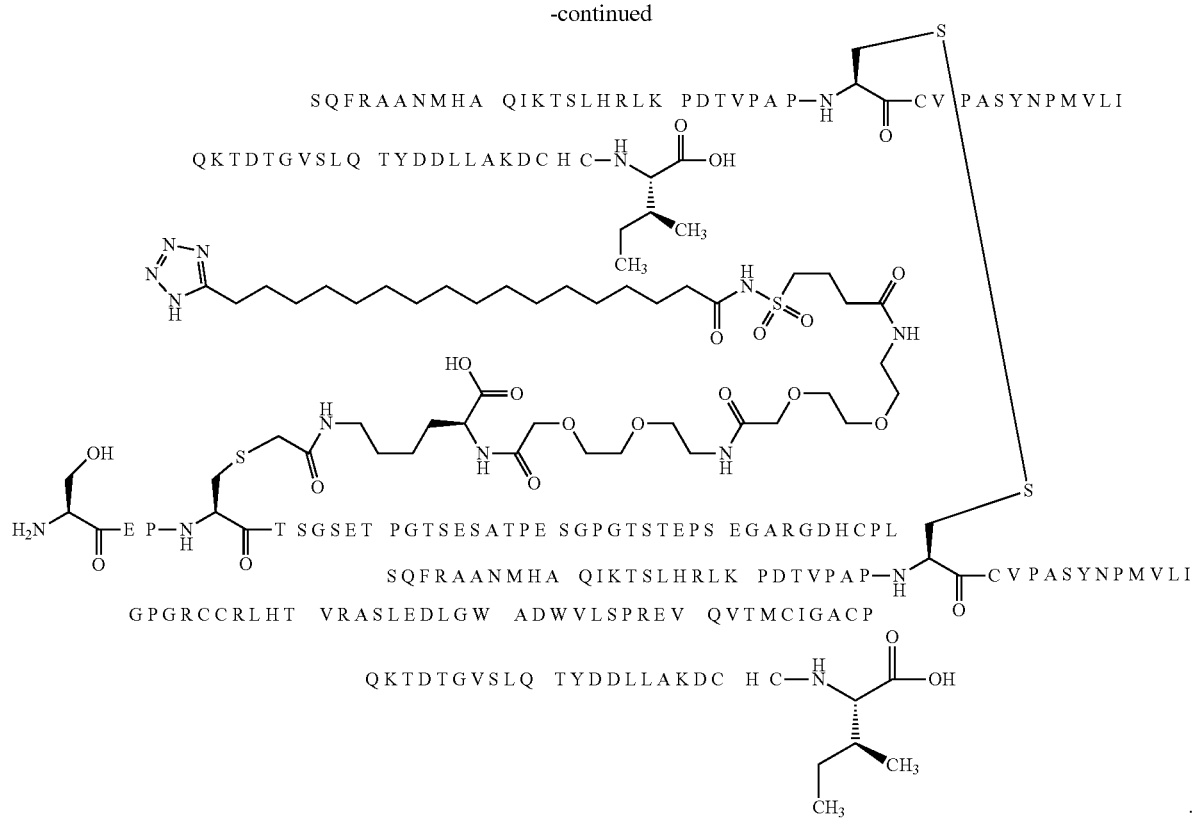
(SEQ ID NO: 288)
21. The MIC-1 compound according to claim 1, wherein the compound is

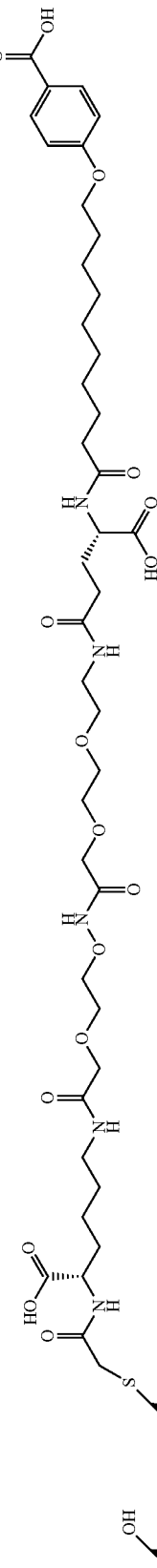
(Formula 19)
(SEQ ID NO: 288)

22. The MIC-1 compound according to claim 1, wherein the compound is

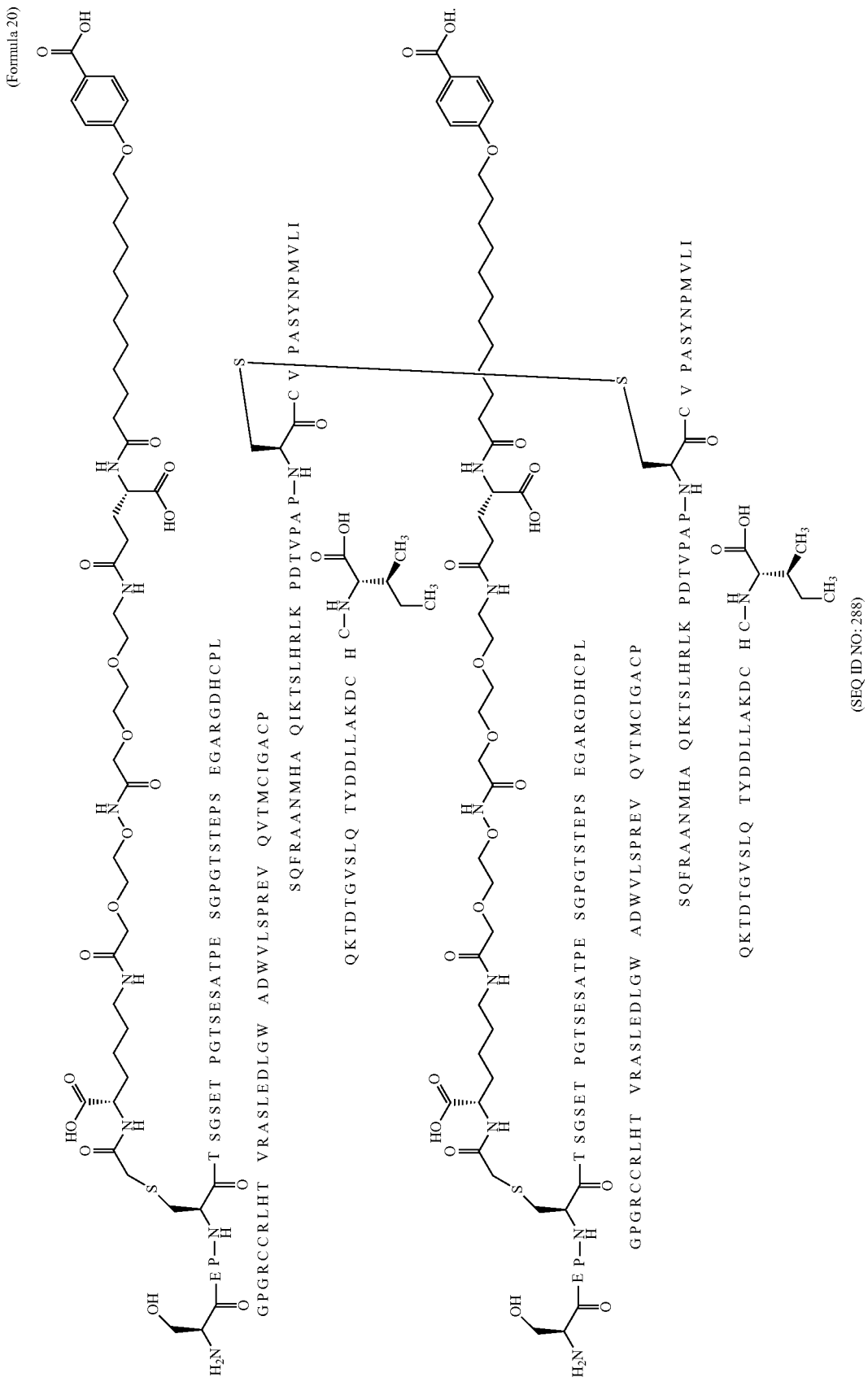

23. The MIC-1 compound according to claim 1, wherein the compound is (Formula 21)

(SEQ ID NO: 288)

24. A method for treating obesity, comprising administering a MIC-1 compound according to claim 1 to a subject in need thereof.

25. The method according to claim 24, wherein Chem. 1 is selected from the group consisting of:

HOOC—(CH$_2$)$_{16}$—CO—*,      Chem. 1a:

HO—S(=O)$_2$—(CH$_2$)$_{15}$—CO—*, and      Chem. 1b:

HOOC-benzene-O—(CH$_2$)$_9$—CO—*;      Chem. 1c:

wherein Chem. 2 is selected from the group consisting of:

*—NH—CH(COOH)—(CH$_2$)$_2$—CO—* and      Chem. 2a:

*—NH—S(=O)$_2$—(CH$_2$)$_3$—CO—*;and      Chem. 2b:

wherein Chem. 4 is selected from the group consisting of:

*—NH—(CH$_2$)$_2$—NH—CO—CH$_2$—* and      Chem. 4a:

*—NH—CH(COOH)—(CH$_2$)$_4$—NH—CO—CH$_2$—*.      Chem. 4b:

26. The method according to claim 24, wherein the amino acid extension comprises a sequence selected from the group consisting of:

(SEQ ID NO: 223)
SEPATCGSETPGTSESATPESGPGTSTEPS, (SEQ ID NO: 224)
SEPATSGCETPGTSESATPESGPGTSTEPS,

-continued

SEPCTSGSETPGTSESATPESGPGTSTEPSEG,
(SEQ ID NO: 225)

SEPATCGSETPGTSESATPESGPGTSTEPSEG,
(SEQ ID NO: 226)

SEPATSCSETPGTSESATPESGPGTSTEPSEG,
(SEQ ID NO: 227)

SEPACSGSETPGTSESATPESGPGTSTEPSEG,
(SEQ ID NO: 229)

SEPATSGCETPGTSESATPESGPGTSTEPSEG,
(SEQ ID NO: 230)

SEPATSGSECPGTSESATPESGPGTSTEPSEG,
(SEQ ID NO: 231)

SEPATSGSETPCTSESATPESGPGTSTEPSEG,
(SEQ ID NO: 232)

SEPATSGSETPGTCESATPESGPGTSTEPSEG,
(SEQ ID NO: 233)

SEPATSGSETPGTSECATPESGPGTSTEPSEG,
(SEQ ID NO: 234)

SEPATSGSETPGTSESACPESGPGTSTEPSEG,
(SEQ ID NO: 235)

SEPATSGSETPGTSESATPECGPGTSTEPSEG,
and
(SEQ ID NO: 236)

SEPATSGSETPGTSESATPESCPGTSTEPSEG.
(SEQ ID NO: 237)

27. The method according to claim 24, wherein the combination of the MIC-1 polypeptide and the amino acid extension comprises an amino acid sequence selected from the group consisting of SEQ ID NO: 100, SEQ ID NO: 104, SEQ ID NO: 106, SEQ ID NO: 107, SEQ ID NO: 108, SEQ ID NO: 109, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 164, SEQ ID NO: 288, SEQ ID NO: 289, SEQ ID NO: 290, SEQ ID NO: 291, and SEQ ID NO: 292.

28. The method according to claim 24, where the MIC-1 compound is selected from the group consisting of:

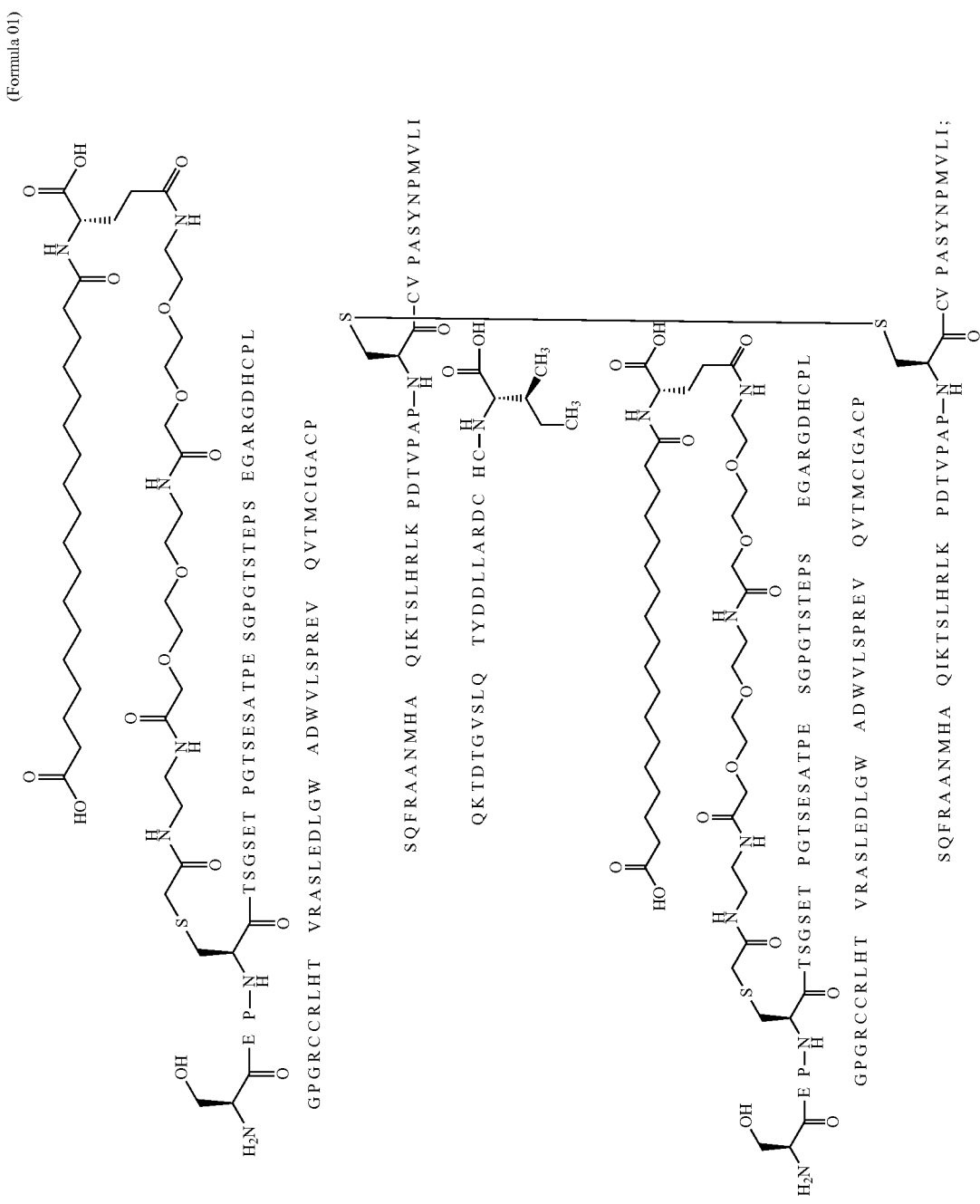
(Formula 01)

-continued
QKTDTGVSLQ TYDDLLAKDC 
(SEQ ID NO: 288)

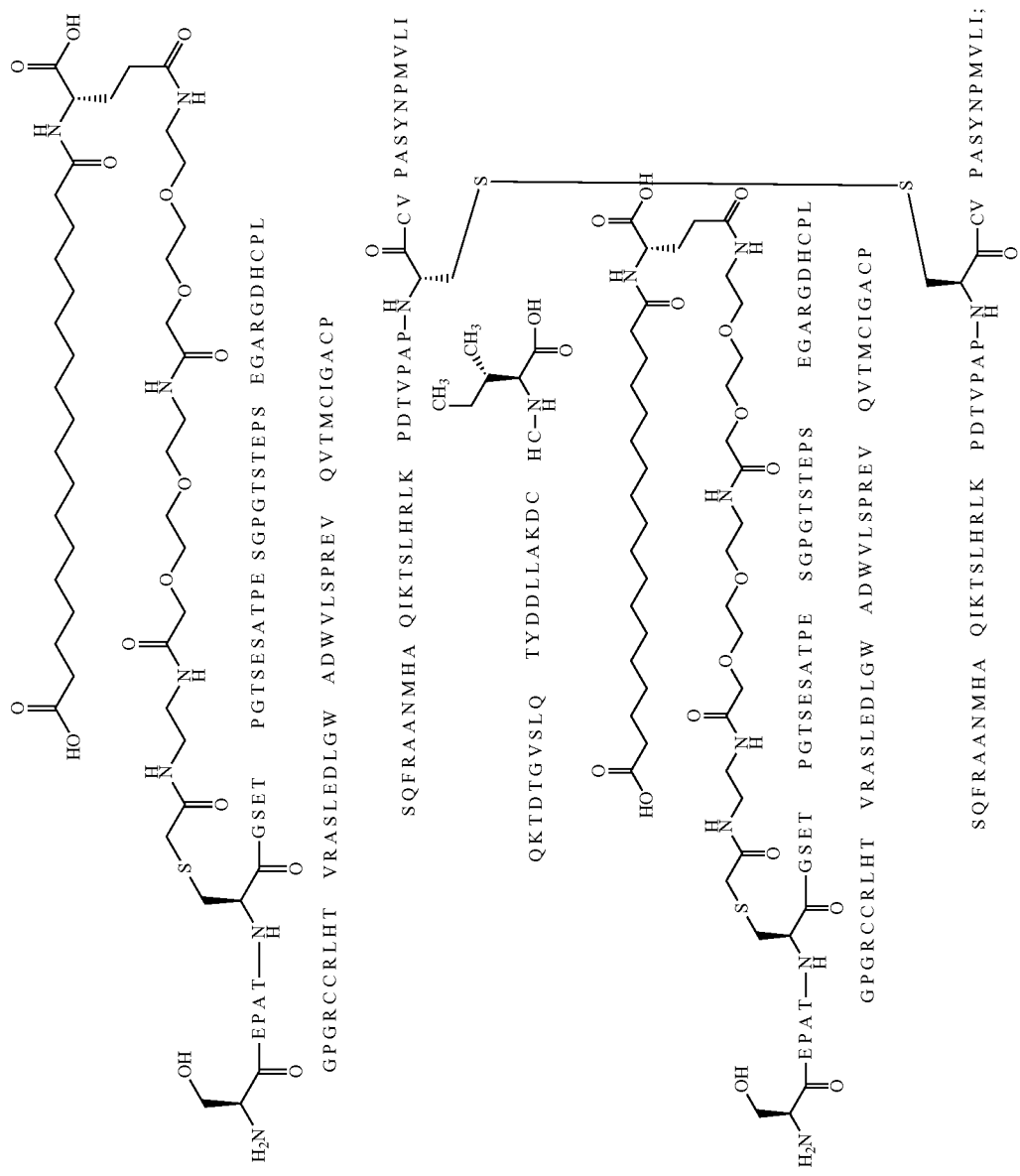

-continued
QKTDTGVSLQ TYDDLLAKDC
(SEQ ID NO: 291)

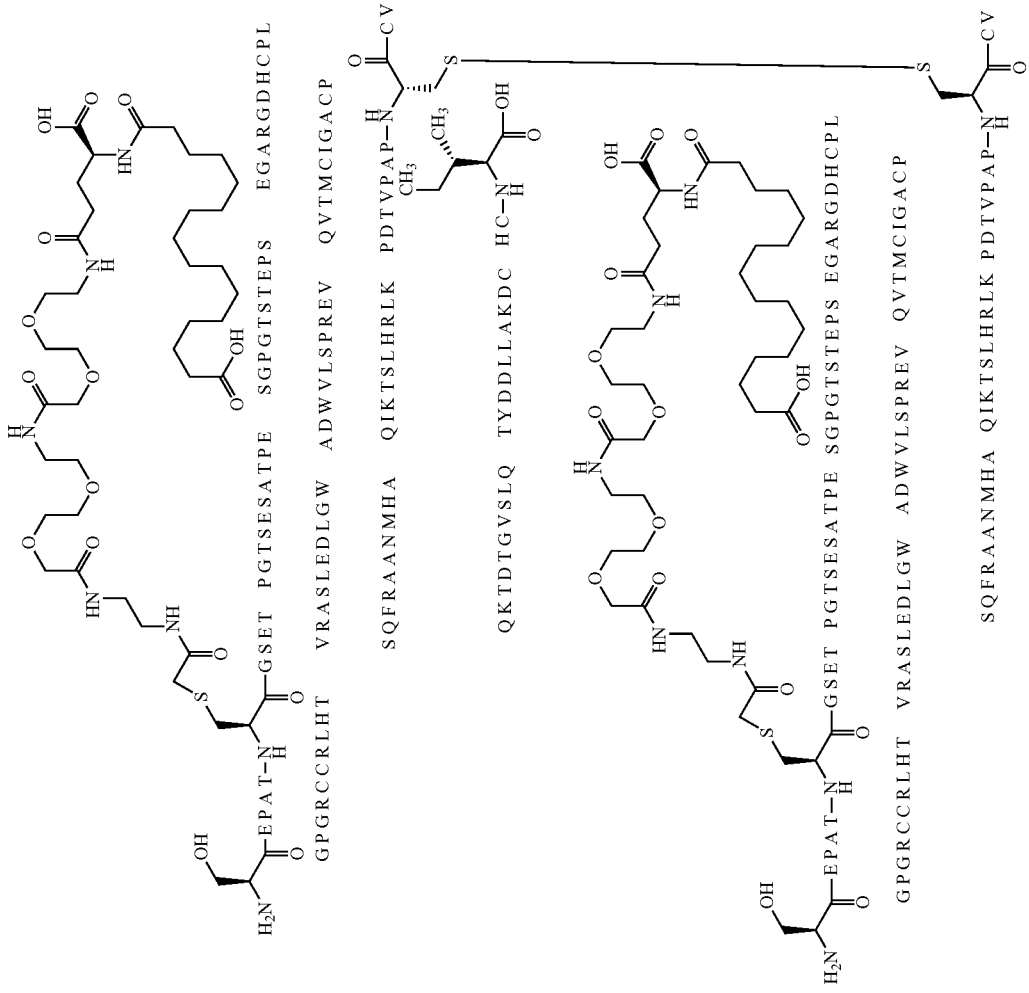
(Formula 03)

-continued
QKTDTGVSLQ TYDDLLAKDC
(SEQ ID NO: 291)

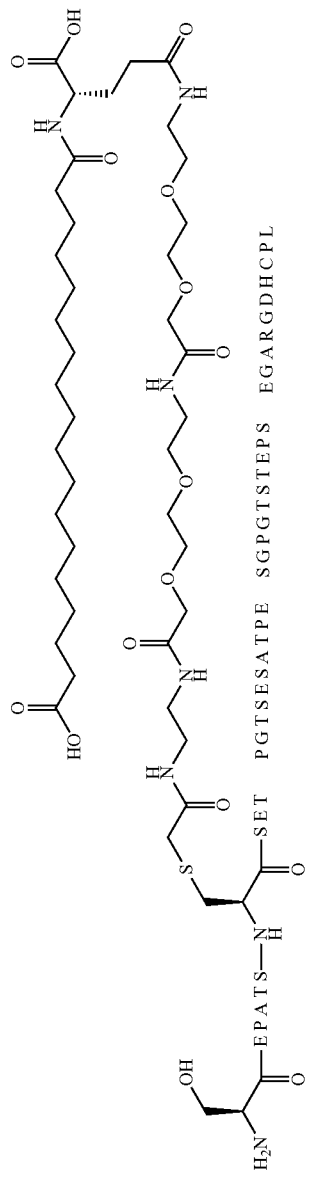
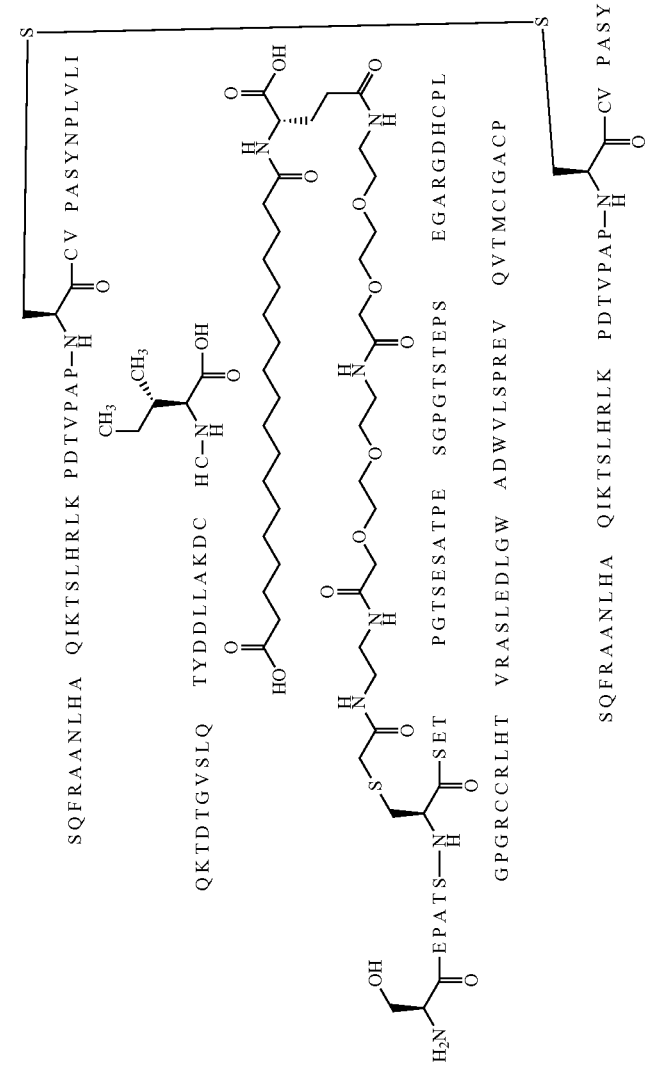

-continued
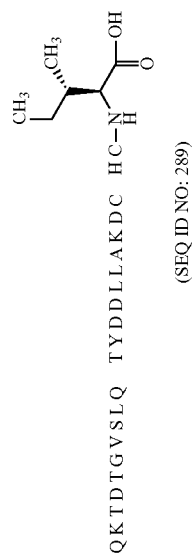
QKTDTGVSLQ TYDDLLAKDC HC-NH
(SEQ ID NO: 289)

-continued (Formula 07)

EPATSGSET PGTSGSET PGTSESA- GPGRCCRLHT VRASLEDLGW ADWVLSPREV QVTMCIGACP

SQFRAANLHA QIKTSLHRLK PDTVPAP-

QKTDTGVSLQ TYDDLLARDC

EPATSGSET PGTSGSET PGTSESAN- GPGRCCRLHT VRASLEDLGW ADWVLSPREV QVTMCIGACP

SQFRAANLHA QIKTSLHRLK PDTVPAP-

QKTDTGVSLQ TYDDLLAKDC (SEQ ID NO: 292)

(Formula 11)

```
H₂N-S E P-N-H-[Cys(S-CH₂-C(O)-NH-...)]-GPGRCCRLHT TSGSET PGTSESATPE SGPGTSTEPS EGARGDHCPL
  (with fatty-diacid-γGlu-PEG-PEG-β-Ala linker attached)
SQFRAANLHA QIKTSLHRLK PDTVPAP-NH-Cys(S-S-)-CV PASYNPLVLI
QKTDTGVSLQ TYDDLLAKDC HC-N-H-[tBu/Ile]-OH H₂N-S E P-N-H-[Cys(S-CH₂-C(O)-NH-...)]-GPGRCCRLHT TSGSET PGTSESATPE SGPGTSTEPS EGARGDHCPL
  (with fatty-diacid-γGlu-PEG-PEG-β-Ala linker attached)
SQFRAANLHA QIKTSLHRLK PDTVPAP-NH-Cys(S-S-)-CV PASYNPLVLI;
QKTDTGVSL -continued
(Formula 17)
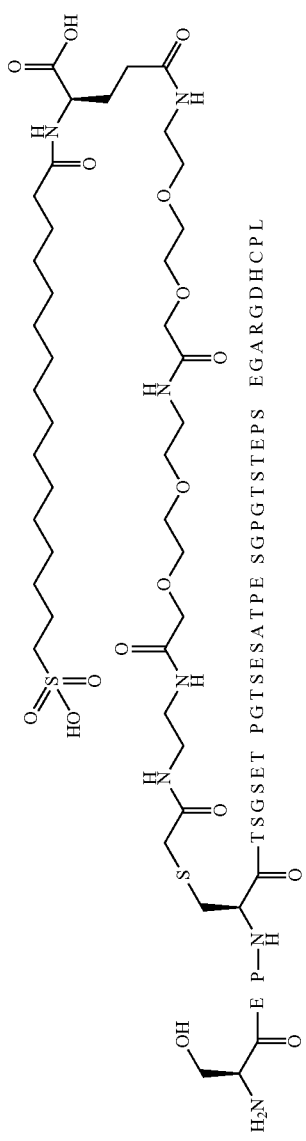
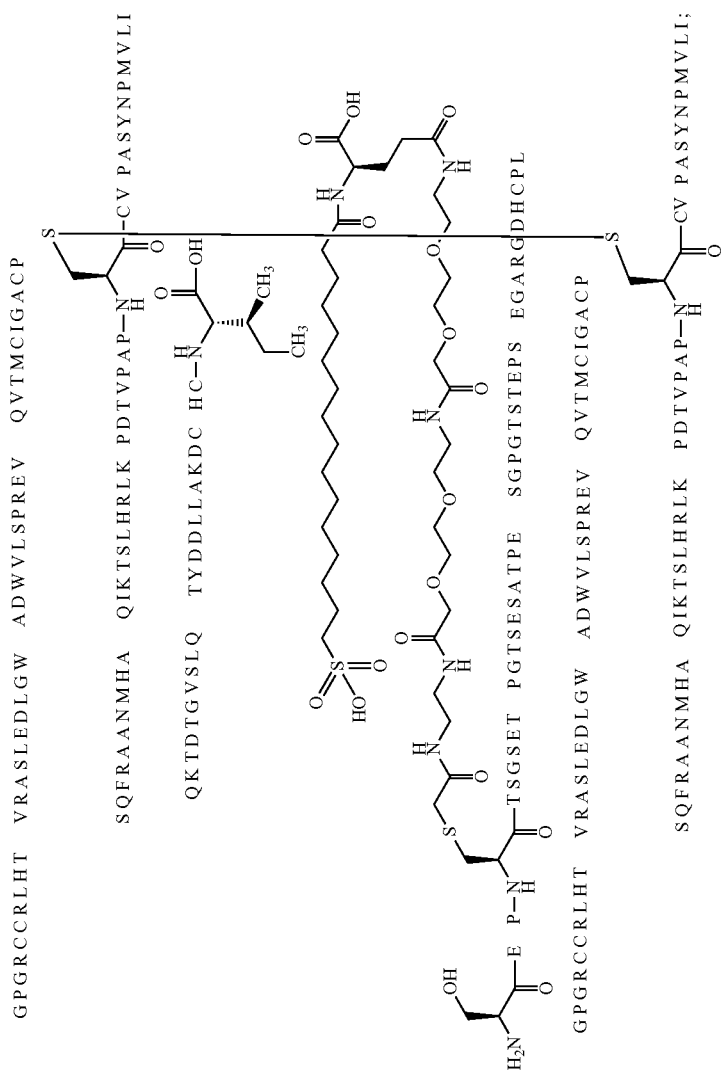

-continued
QKTDTGVSLQ TYDDLLAKDC 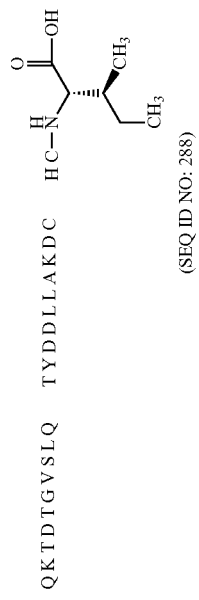
(SEQ ID NO: 288)

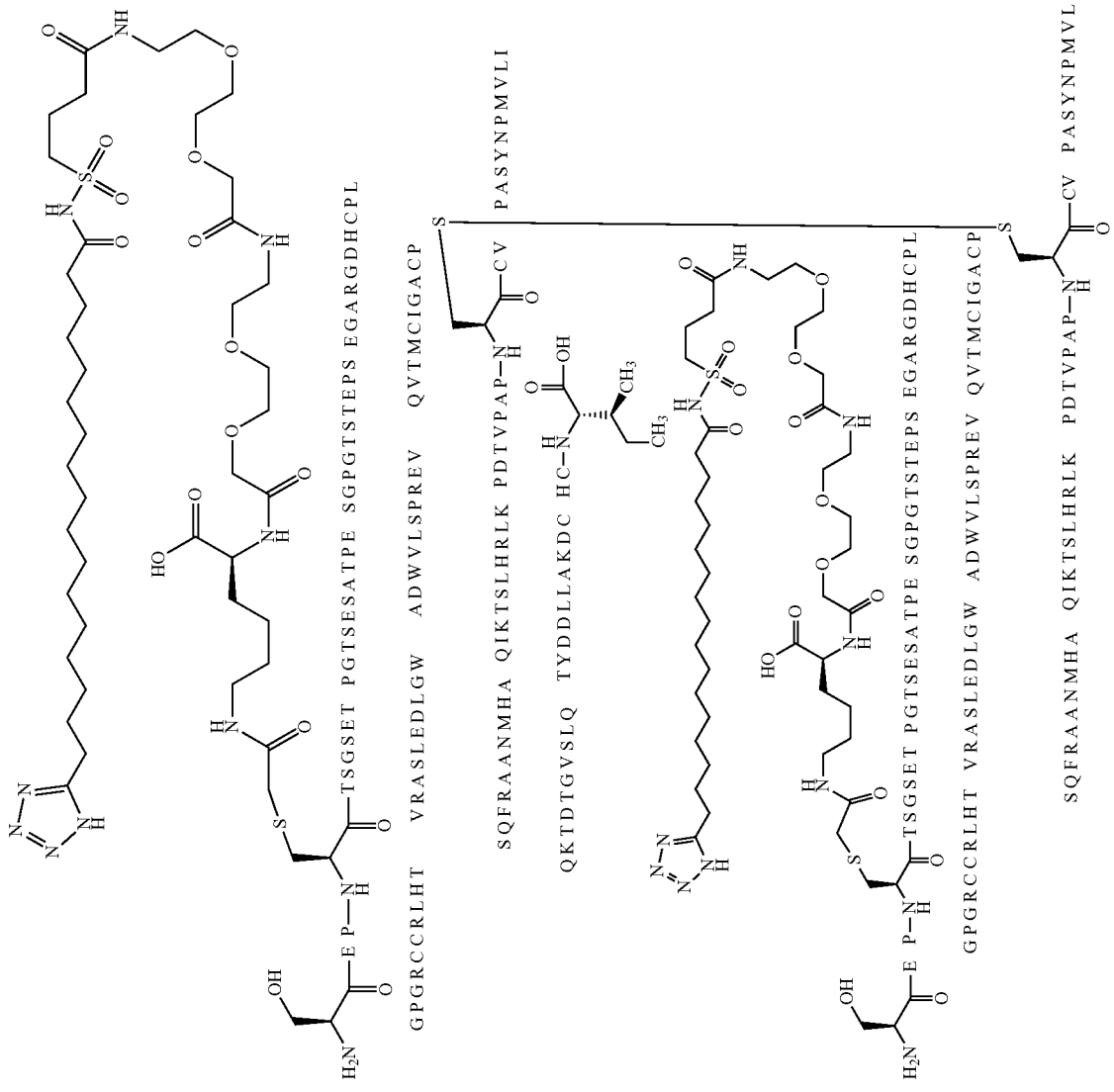

-continued
QKTDTGVSLQ TYDDLLAKDC 
(SEQ ID NO: 288)

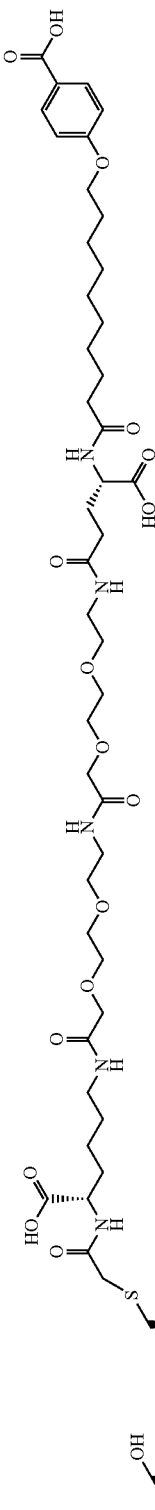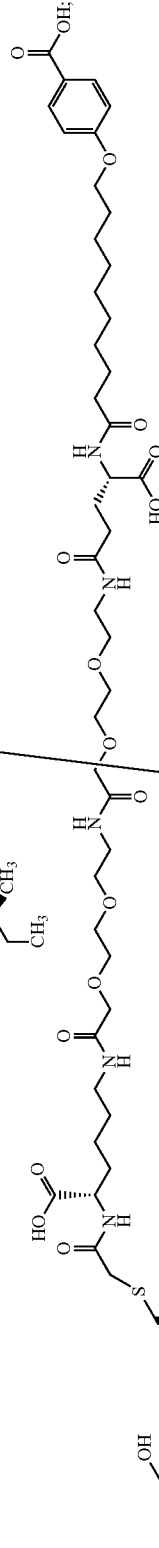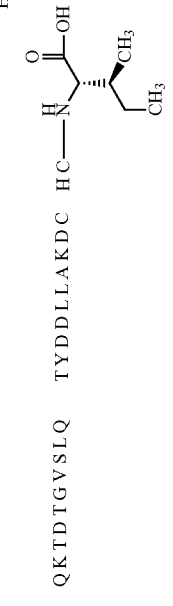
(Formula 19)
(SEQ ID NO: 288)

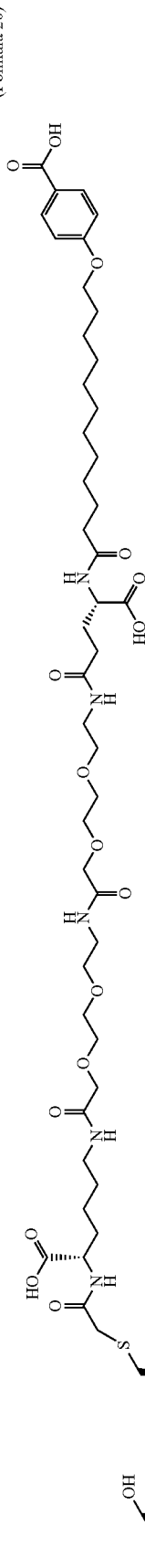
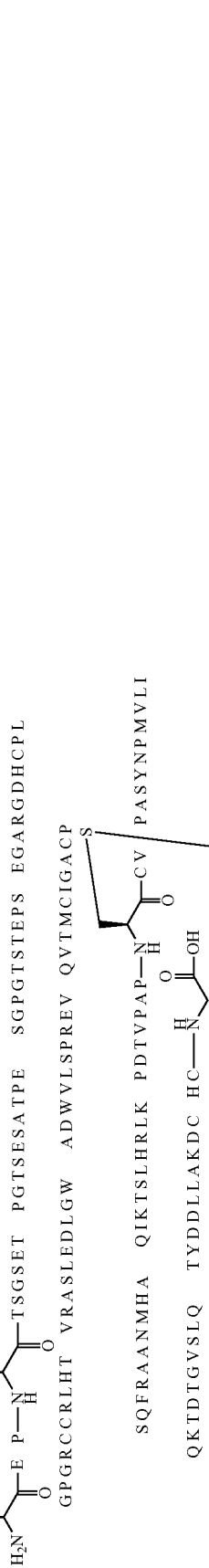
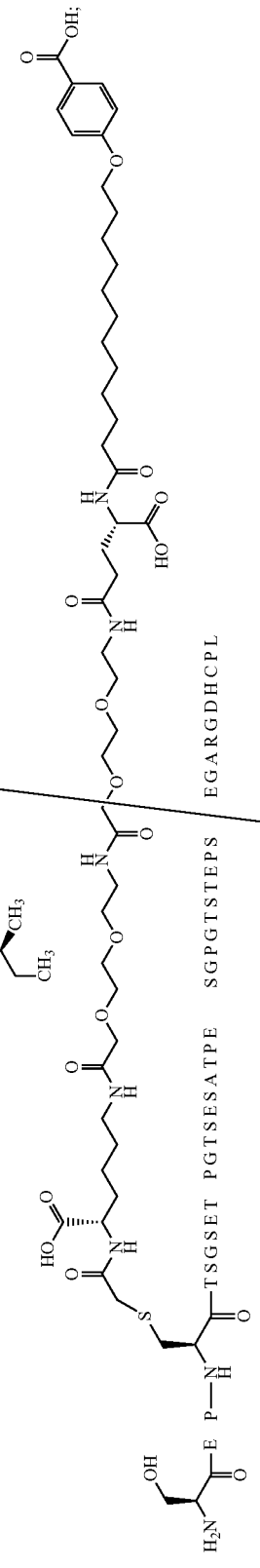
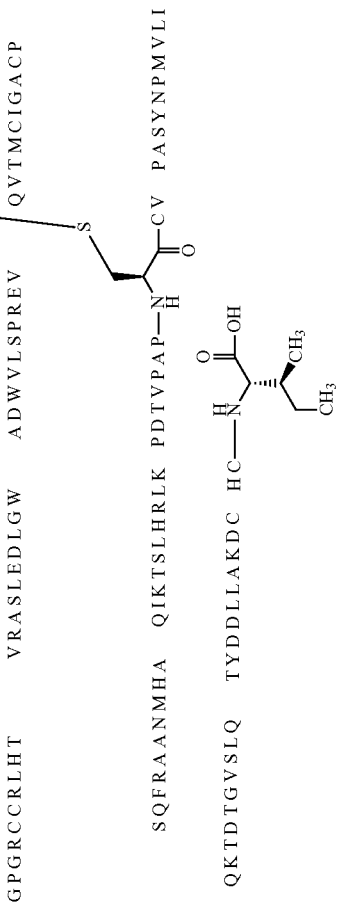
(Formula 20)
(SEQ ID NO: 288)

-continued
(Formula 21)
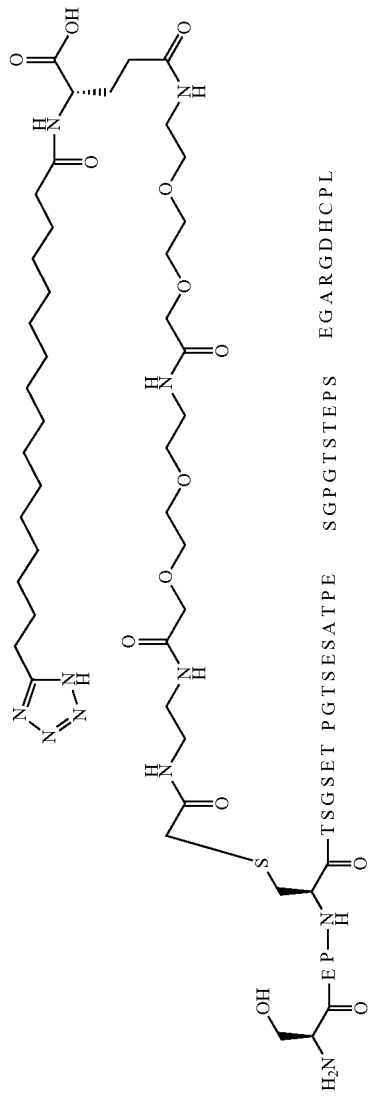
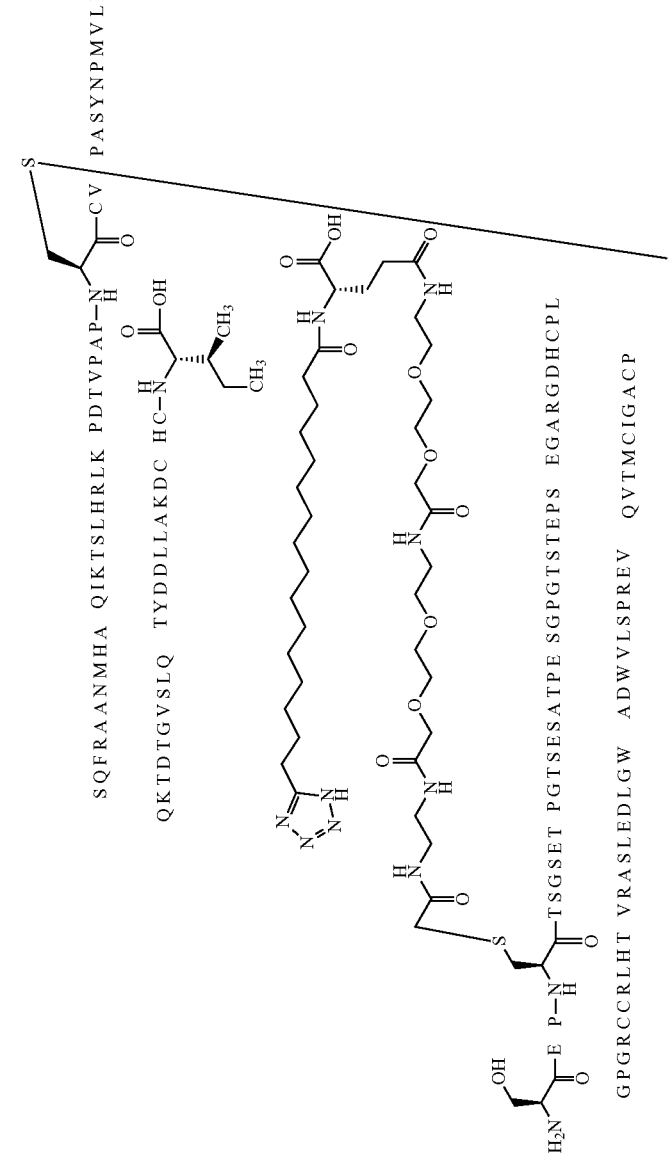

-continued
SQFRAANMHA QIKTSLHRLK PDTVPAP-CV PASYNPMVLI.
QKTDTGVSLQ TYDDLLAKDC HC-
(SEQ ID NO: 288)
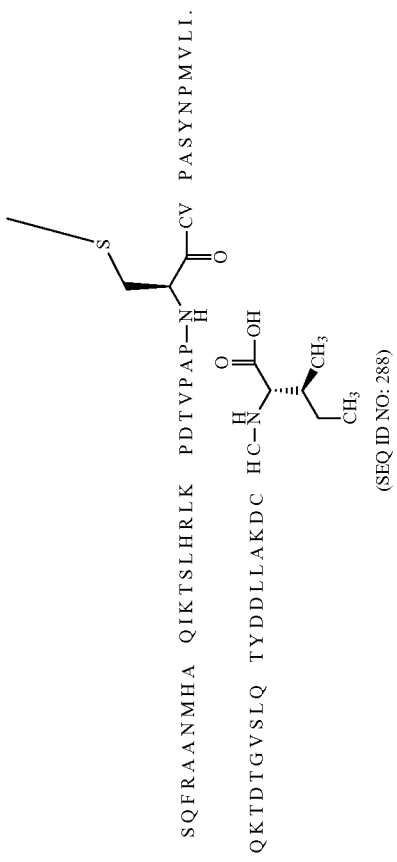
* * * * *

UNITED STATES PATENT AND TRADEMARK OFFICE
CERTIFICATE OF CORRECTION

PATENT NO. : 10,398,782 B2  
APPLICATION NO. : 15/986961  
DATED : September 3, 2019  
INVENTOR(S) : Xiang Gao et al.

Page 1 of 1

It is certified that error appears in the above-identified patent and that said Letters Patent is hereby corrected as shown below:

In the Claims

At Column 427, Claim number 12, Please change "TYDDLLARDC" to "TYDDLLAKDC"

At Column 441, Claim number 12, Please change "TYDDLLARDC" to "TYDDLLAKDC"

At Column 477/478, Claim number 20, Please place line "SQFRAANMHA QIKTSLHRLK PDTVPAP-NH O CVPASYNPMVLI" under the line "GPGRCCRLHT VRASLEDLGW ADWVLSPREV QVTMCIGACP"

At Column 489, Claim number 28, Please change "TYDDLLARDC" to "TYDDLLAKDC"

At Column 505, Claim number 28, Please change "TYDDLLARDC" to "TYDDLLAKDC"

At Column 506, Claim number 28, Please change "PGTSESAN" to "PGTSESA"

Signed and Sealed this  
Twenty-second Day of December, 2020

Andrei Iancu  
*Director of the United States Patent and Trademark Office*